US011591341B2

(12) United States Patent
Vendeville et al.

(10) Patent No.: US 11,591,341 B2
(45) Date of Patent: Feb. 28, 2023

(54) BICYCLIC AND TRICYCLIC COMPOUNDS

(71) Applicant: ALIGOS THERAPEUTICS, INC., South San Francisco, CA (US)

(72) Inventors: Sandrine Vendeville, Brussels (BE); Pierre Jean-Marie Bernard Raboisson, Wavre (BE); Yannick Debing, Bilzen (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 206 days.

(21) Appl. No.: 16/849,851

(22) Filed: Apr. 15, 2020

(65) Prior Publication Data

US 2020/0361947 A1    Nov. 19, 2020

Related U.S. Application Data

(60) Provisional application No. 62/835,301, filed on Apr. 17, 2019.

(51) Int. Cl.

| | |
|---|---|
| *C07D 487/04* | (2006.01) |
| *C07D 487/14* | (2006.01) |
| *C07D 491/22* | (2006.01) |
| *A61K 31/4985* | (2006.01) |
| *A61K 31/551* | (2006.01) |
| *A61P 31/20* | (2006.01) |
| *A61K 31/675* | (2006.01) |
| *A61K 31/683* | (2006.01) |
| *A61K 31/7068* | (2006.01) |
| *A61K 31/7072* | (2006.01) |
| *A61K 31/708* | (2006.01) |
| *A61K 38/21* | (2006.01) |

(52) U.S. Cl.
CPC ........ *C07D 487/14* (2013.01); *A61K 31/4985* (2013.01); *A61K 31/551* (2013.01); *A61K 31/675* (2013.01); *A61K 31/683* (2013.01); *A61K 31/708* (2013.01); *A61K 31/7068* (2013.01); *A61K 31/7072* (2013.01); *A61K 38/212* (2013.01); *A61P 31/20* (2018.01); *C07D 487/04* (2013.01); *C07D 491/22* (2013.01)

(58) Field of Classification Search
CPC .. C07D 487/04; C07D 487/14; C07D 491/22; A61K 31/4985; A61K 31/551; A61P 31/20
See application file for complete search history.

(56) References Cited

U.S. PATENT DOCUMENTS

| | | | |
|---|---|---|---|
| 2020/0147124 A1 | 5/2020 | Beigelman et al. | |
| 2022/0119395 A1 | 4/2022 | Vendeville et al. | |

FOREIGN PATENT DOCUMENTS

| | | |
|---|---|---|
| WO | WO 2008/017932 | 2/2008 |
| WO | WO 2016/168633 | 10/2016 |
| WO | WO 2017/011552 | 1/2017 |
| WO | WO 2018/219356 | 12/2018 |

OTHER PUBLICATIONS

CAS Registry No. 2386336-43-0; STN Entry Date Dec. 1, 2019.*
Second Written Opinion dated Mar. 11, 2021 for PCT Application No. PCT/US2020/028349, filed Apr. 15, 2020.
CAS Registry No. 1353500-80-7; STN Entry Date Jan. 18, 2012.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
Liang, "Hepatitis B: The Virus and Disease" Hepatology (2009) 49(S5):S13-S21.
International Search Report and Written Opinion dated Jul. 6, 2020 for PCT Application No. PCT/US2020/028349, filed Apr. 15, 2020.
International Preliminary Report on Patentability dated Aug. 3, 2021 for PCT Application No. PCT/US2020/028349, filed Apr. 15, 2020.

* cited by examiner

*Primary Examiner* — Brenda L Coleman
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

30 Claims, 1 Drawing Sheet
Specification includes a Sequence Listing.

The plate map of compound treatment

|   | 1 | 2 | 3 | 4 | 5 | 6 | 7 | 8 | 9 | 10 | 11 | 12 |
|---|---|---|---|---|---|---|---|---|---|----|----|----|
| A |   | High dose | | 4-fold dilution, 8 dilution points, duplicate | | | | | Low dose | | | |
| B | compound 1 | | | | | | | | | ETV(1μM) | 0.5%DMSO control | Blank |
| C | | | | | | | | | | | | |
| D | compound 2 | | | | | | | | | ETV(1μM) | 0.5%DMSO control | Blank |
| E | | | | | | | | | | | | |
| F | compound 3 | | | | | | | | | ETV(1μM) | 0.5%DMSO control | Blank |
| G | | | | | | | | | | | | |
| H |   | High dose | | 4-fold dilution, 8 dilution points, duplicate | | | | | Low dose | | | |

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic HBV-forward primer

<400> SEQUENCE: 1
gtgtctgcgg cgttttatca                                          20

<210> SEQ ID NO 2
<211> LENGTH: 21
<212> TYPE: DNA
<213> ORGANISM: Artificial Sequence
<220> FEATURE:
<223> OTHER INFORMATION: Synthetic HBV-reverse primer

<400> SEQUENCE: 2
gacaaacggg caacatacct t                                        21

<210> SEQ ID NO 3
<211> LENGTH: 28
<212> TYPE: DNA
<213> ORGANISM: Artificial Sequence
<220> FEATURE:
<223> OTHER INFORMATION: Synthetic HBV-probe
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 28

```
<223> OTHER INFORMATION: N=C-TAMRA

<400> SEQUENCE: 3
nctctkcatc ctgctgctat gcctcatn                                              28

<210> SEQ ID NO 4
<211> LENGTH: 20
<212> TYPE: DNA
<213> ORGANISM: Artificial Sequence
<220> FEATURE:
<223> OTHER INFORMATION: Synthetic HBV-forward primer

<400> SEQUENCE: 4
gtgtctgcgg cgttttatca                                                       20

<210> SEQ ID NO 5
<211> LENGTH: 21
<212> TYPE: DNA
<213> ORGANISM: Artificial Sequence
<220> FEATURE:
<223> OTHER INFORMATION: Synthetic HBV-reverse primer

<400> SEQUENCE: 5
gacaaacggg caacatacct t                                                     21

<210> SEQ ID NO 6
<211> LENGTH: 28
<212> TYPE: DNA
<213> ORGANISM: Artificial Sequence
<220> FEATURE:
<223> OTHER INFORMATION: Synthetic HBV probe
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 9
<223> OTHER INFORMATION: N=T-ZEN
<220> FEATURE:
<221> NAME/KEY: modified_base
<222> LOCATION: 28
<223> OTHER INFORMATION: N=C-3IABkFQ

<400> SEQUENCE: 6
nctctkcanc ctgctgctat gcctcatn                                              28
```

BICYCLIC AND TRICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/835,301, filed Apr. 17, 2019.

REFERENCE TO SEQUENCE LISTING

The present application is filed with a Sequence Listing in Electronic format. The Sequence Listing is provided as a file entitled ALIG025_replacement.txt, created Jul. 9, 2020, which is approximately 2 kb in size. The information in the electronic format of the sequence listing is incorporated herein by reference in its entirety.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

BRIEF DESCRIPTION OF THE DRAWINGS

The FIGURE shows the plate map of compound treatment for the HBV-DNA Antiviral Assay described herein.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis).

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium, alkyl, alkenyl, alkynyl, cycloalkyl, cycloalkenyl, aryl, heteroaryl, heterocyclyl, aryl (alkyl), heteroaryl(alkyl), (heterocyclyl)alkyl, hydroalkyl, hydroxy, alkoxyalkyl, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group, a di-substituted amino group, an unsubstituted C-amido($C_{1-3}$ alkyl), —O-(an unsubstituted $C_{1-4}$ alkyl)-OH, —O-(an unsubstituted $C_{1-4}$ alkyl)-(an unsubstituted alkoxy), —O-(an unsubstituted $C_{1-4}$ alkyl)-(an unsubstituted C-carboxy), —O—($C_{1-3}$ alkyl)-O-(an unsubstituted C-amido), —O-(an unsubstituted $C_{1-4}$ alkyl)-$NH_2$, —O-(an unsubstituted $C_{1-4}$ alkyl)-NH (an unsubstituted $C_{1-4}$ alkyl), —O-(an unsubstituted $C_{1-4}$ alkyl)-N (an unsubstituted $C_{1-4}$ alkyl)$_2$ and an unsubstituted —O-(an unsubstituted $C_{1-4}$ alkyl)-CN.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2, 3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group (e.g.,

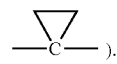

).

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, isobutoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by an alkoxy group. Exemplary alkoxyalkyl groups include but are not limited to, methoxymethyl, ethoxymethyl, methoxyethyl and ethoxyethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

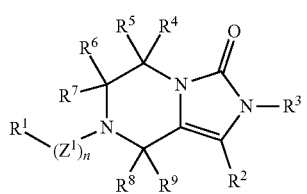

(I)

wherein: n can be 0 or 1; Z can be —C(=O)—, —NH—C(=O)—, —O—C(=O)—, —OCH$_2$C(=O)—, —CH=CHC(=O)— or —CH(CF$_3$)—; R$^1$ can be selected from an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^2$ can be selected from —C(=O)NR$^{10}$R$^{11}$, an optionally substituted cycloalkyl, an optionally substituted cycloalkenyl, an optionally substituted aryl, an optionally substituted heteroaryl, an optionally substituted heterocyclyl, an optionally substituted cycloalkyl(C$_{1-4}$ alkyl), an optionally substituted cycloalkenyl(C$_{1-4}$ alkyl), an optionally substituted aryl(C$_{1-4}$ alkyl), an optionally substituted heteroaryl(C$_{1-4}$ alkyl) and an optionally substituted heterocyclyl(C$_{1-4}$ alkyl); R$^3$ can be selected from hydrogen, an unsubstituted C$_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); or R$^2$ and R$^3$ can be taken together along with the atoms to which R$^2$ and R$^3$ are each attached to form an optionally substituted 6, 7 or 8 membered monocyclic heterocyclyl or an optionally substituted 9 to 14 membered spirocyclic heterocyclyl; R$^4$ and R$^5$ can be independently selected from hydrogen, an unsubstituted C$_{1-4}$ alkyl, an unsubstituted C$_{1-4}$ haloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^6$ and R$^7$ can be independently selected from hydrogen, an unsubstituted C$_{1-4}$ alkyl, an unsubstituted C$_{1-4}$ haloalkyl, an optionally substituted C$_{3-4}$ cycloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); or R$^4$ and R$^5$ can be taken together along with the carbon to which R$^4$ and R$^5$ are attached to form an optionally substituted monocyclic C$_{3-6}$ cycloalkyl or an optionally substituted 3 to 6 member monocyclic heterocyclyl; or R$^6$ and R$^7$ can be taken together along with the carbon to which R$^6$ and R$^7$ are attached to form an optionally substituted monocyclic C$_{3-6}$ cycloalkyl or an optionally substituted 3 to 6 member monocyclic heterocyclyl; or R$^4$ and R$^6$ can be taken together along with the carbons to which R$^4$ and R$^6$ are each attached to form an optionally monocyclic C$_{5-7}$ cycloalkyl or an optionally substituted 5 to 7 member monocyclic heterocyclyl; or R$^5$ and R$^7$ can be taken together along with the carbons to which R$^5$ and R$^7$ are each attached to form an optionally monocyclic C$_{5-7}$ cycloalkyl or an optionally substituted 5 to 7 member monocyclic heterocyclyl; R$^8$ and R$^9$ can be independently selected from hydrogen, an unsubstituted C$_{1-4}$ alkyl, an unsubstituted C$_{1-4}$ haloalkyl; or R$^8$ and R$^9$ are taken together along with the carbon to which R$^8$ and R$^9$ are attached to form an optionally substituted monocyclic C$_{3-4}$ cycloalkyl, an optionally substituted oxetane or an optionally substituted thietane; and R$^{10}$ and R$^{11}$ can be independently selected from hydrogen, an optionally substituted C$_{1-4}$ alkyl, an optionally substituted C$_{2-6}$ alkenyl, an optionally substituted C$_{2-6}$ alkynyl, an optionally substituted C$_{3-8}$ cycloalkyl, an optionally substituted C$_{3-8}$ cycloalkenyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); or R$^{10}$ and R$^{11}$ can be taken together along with the nitrogen to which R$^{10}$ and R$^{11}$ are attached to form an optionally substituted 4 to 8 member monocyclic heterocyclyl or an optionally substituted 7 to 12 member bicyclic heterocyclyl.

As provided herein, various groups can be attached to the piperazine ring of the 5,6,7,8-tetrahydroimidazo[1,5-a]pyrazin-3(2H)-one shown in Formula (I). In some embodiments, n can be 0; and R$^1$ can be selected from an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl) such that Formula (I), and pharmaceutically acceptable salts thereof can be Formula (Ia), or a pharmaceutically acceptable salt thereof. In other embodiments, n can be 1; Z$^1$ can be —C(=O)—, —NH—C(=O)— or —O—C(=O)—; and R$^1$ can be selected from an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl). As shown below, when Z$^1$ is —C(=O)—, —NH—C(=O)— or —O—C(=O)—, Formula (I) can be Formula (Ib), (Ic) or (Id), or a pharmaceutically acceptable salt thereof, respectively. In still other embodiments, when n can be 1; and Z$^1$ is —OCH$_2$C(=O)— or —CH=CHC(=O)—, Formula (I) can be Formula (Ie) and (If), respectively. In yet still other embodiments, when n can be 1; and Z$^1$ is —C(CF$_3$)—, Formula (I) can be Formula (Ig). In some embodiments, n can be 0; and R$^1$ can be

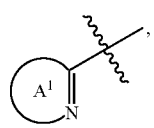

wherein Ring A$^1$ can be an optionally substituted bicyclic heteroaryl or an optionally substituted bicyclic heterocyclyl such that Formula (I), and pharmaceutically acceptable salts thereof can be Formula (Ih), or a pharmaceutically acceptable salt thereof. In some embodiments, R$^2$ and R$^3$ can be taken together along with the atoms to which R$^2$ and R$^3$ are each attached to form an optionally substituted 6, 7 or 8 membered monocyclic heterocyclyl or an optionally substituted 9 to 14 membered spirocyclic heterocyclyl to form a compound of Formula (Ii).

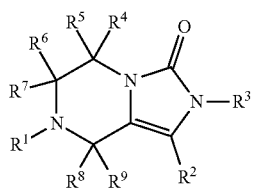
(Ia)

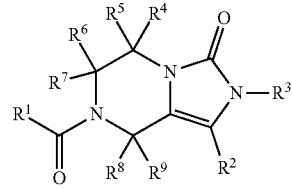
(Ib)

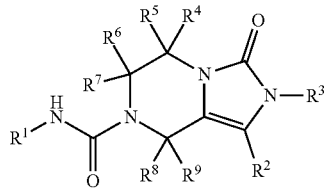
(Ic)

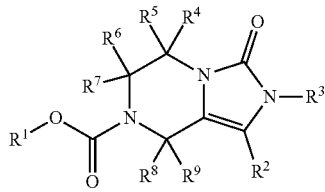
(Id)

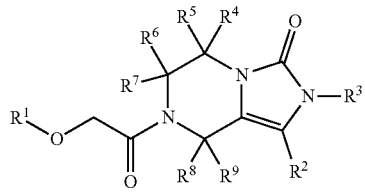
(Ie)

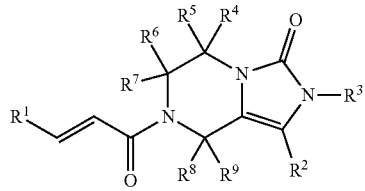
(If)

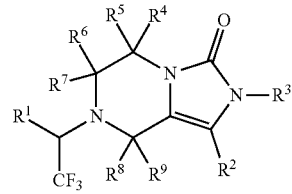
(Ig)

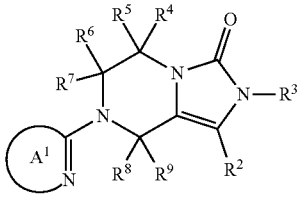
(Ih)

13

-continued

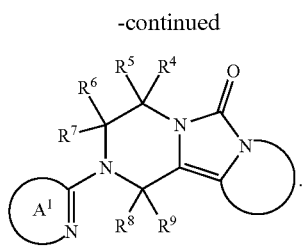

(Ii)

Various cyclic moieties can be present for $R^1$. In some embodiments, $R^1$ can be a carbocyclic moiety, for example an optionally substituted aryl. For example, $R^1$ can be an optionally substituted phenyl. In some embodiments, $R^1$ can be an unsubstituted phenyl. In other embodiments, $R^1$ can be a substituted phenyl. When $R^1$ is a substituted phenyl, the phenyl can be mono-substituted. The mono-substituted phenyl can be a para-substituted phenyl, a meta-substituted phenyl or an ortho-substituted phenyl. The substituted phenyl can be substituted by multiple moieties, such as 2, 3 or more than 3 times. For example, the substituted phenyl of $R^1$ can be di-substituted (such as a meta- and para-substituted phenyl). When more than one moiety is present, the moieties can be the same or different moieties can be different.

As described herein, $R^1$ can be a cyclic moiety, including a cyclic moiety that can include one or more heteroatoms in the ring(s). In some embodiments, $R^1$ can be an optionally substituted heteroaryl. The heteroaryl can be monocyclic or bicyclic. In some embodiments, $R^1$ can be an unsubstituted or a substituted monocyclic heteroaryl. For example, $R^1$ can be a 5-membered or 6-membered monocyclic heteroaryl. In other embodiments, $R^1$ can be an unsubstituted or a substituted bicyclic heteroaryl. The bicyclic heteroaryl can be a 9-membered or 10-membered heteroaryl. The heteroaryl can include one or more heteroatoms, such as N (nitrogen), O (oxygen) and/or S (sulfur). In some embodiments, $R^1$ can be an optionally substituted heterocyclyl. The heterocyclyl can be a monocyclic heterocyclyl or a bicyclic heterocyclyl. In some embodiments, $R^1$ can be an unsubstituted or a substituted monocyclic heterocyclyl, such as a 5-membered or 6-membered monocyclic heterocyclyl. In other embodiments, $R^1$ can be an unsubstituted or a substituted bicyclic heterocyclyl, including a 9-membered or 10-membered heterocyclyl. The number and types of heteroatoms that can be present in a heterocyclyl can vary. As an example, 1, 2, 3 or more than 3 heteroatoms, such as N (nitrogen), O (oxygen) and/or S (sulfur), can be present in a heterocyclyl of $R^1$.

In some embodiments, n can be 0; and $R^1$ can be

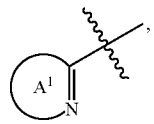

wherein Ring $A^1$ can be an optionally substituted bicyclic heteroaryl. In other embodiments, $R^1$ can be

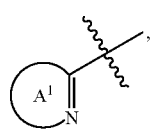

14 wherein Ring $A^1$ can be an optionally substituted bicyclic heterocyclyl. In some embodiments, Ring $A^1$ can be an optionally substituted nitrogen-containing, 9-membered bicyclic heteroaryl. In other embodiments, Ring $A^1$ can be an optionally substituted nitrogen-containing, 10-membered bicyclic heteroaryl. In still other embodiments, Ring $A^1$ can be an optionally substituted nitrogen-containing, 9-membered bicyclic heterocyclyl. In yet still other embodiments, Ring $A^1$ can be an optionally substituted nitrogen-containing, 10-membered bicyclic heterocyclyl.

In some embodiments, $R^1$ can be selected from an unsubstituted or a substituted [5,5] bicyclic heteroaryl, an unsubstituted or a substituted [5,6] bicyclic heteroaryl, an unsubstituted or a substituted [6,5] bicyclic heteroaryl, an unsubstituted or a substituted [6,6] bicyclic heteroaryl, an unsubstituted or a substituted [5,5] bicyclic heterocyclyl, an unsubstituted or a substituted [5,6] bicyclic heterocyclyl, an unsubstituted or a substituted [6,5] bicyclic heterocyclyl and an unsubstituted or a substituted [6,6] bicyclic heterocyclyl. In some embodiments, $R^1$ can be a nitrogen-containing, bicyclic heteroaryl. In other embodiments, $R^1$ can be a nitrogen-containing, bicyclic heterocyclyl. In some embodiments, $R^1$ can have the general structure

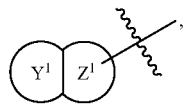

wherein Ring $Z^1$ indicates the point of attachment to the remaining portion of Formula (I); and wherein Ring $Y^1$ and Ring $Z^1$ can be independently selected from phenyl, furan, furazan, thiophene, phthalazine, pyrrole, oxazole, 1,2,3-oxadiazole, 1,2,4-oxadiazole, thiazole, 1,2,3-thiadiazole, 1,2,4-thiadiazole, imidazole, pyrazole, isoxazole, isothiazole, triazole, thiadiazole, tetrazole, pyridine, pyridazine, pyrimidine, pyrazine, 1,2,3-triazine, 1,2,4-triazine, 1,2,3,4-tetrazine, 2H-1,2-oxazine, hexahydro-1,3,5-triazine, imidazoline, imidazolidine, isoxazoline, isoxazolidine, oxazoline, oxazolidine, thiazoline, thiazolidine, morpholine, piperidine, piperazine, pyrrolidine, pyrazoline, pyrazolidine and thiamorpholine, wherein Ring $Y^1$ and Ring $Z^1$ can be each optionally substituted. In some embodiments, Ring $Y^1$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In some embodiments, Ring $Z^1$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In other embodiments, Ring $Z^1$ can be selected from an optionally substituted furan, an optionally substituted thiophene, an optionally substituted pyrrole, an optionally substituted oxazole, an optionally substituted thiazole, an optionally substituted imidazole, an optionally substituted pyrazole, an optionally substituted isoxazole and an optionally substituted isothiazole.

Various cyclic groups can be attached via a $C_{1-4}$ alkyl linker for $R^1$. In some embodiments, $R^1$ can be an optionally substituted aryl($C_{1-4}$ alkyl). An exemplary optionally substituted aryl($C_{1-4}$ alkyl) is an optionally substituted benzyl. In other embodiments, $R^1$ can be an optionally substituted heteroaryl($C_{1-4}$ alkyl). In still other embodiments, $R^1$ can be an optionally substituted heterocyclyl($C_{1-4}$ alkyl). Examples of heteroaryls and heterocyclyls are described herein, and include those of the previous paragraph. As described herein, the linker can include 1 to 4 carbons. In some embodiments, the $C_{1-4}$ alkyl linker for $R^1$ can be —$CH_2$—, —$CH_2CH_2$—, —$CH_2CH_2CH_2$— or —$CH_2CH_2CH_2CH_2$—. Further as described herein lower alkylene linker ($C_{1-4}$ alkyl linker) for $R^1$ can be substituted. Examples of substituents that can be present on a substituted lower alkylene linker ($C_{1-4}$ alkyl linker) for aryl($C_{1-4}$ alkyl), heteroaryl($C_{1-4}$ alkyl) and heterocyclyl($C_{1-4}$ alkyl) include an unsubstituted $C_{1-4}$ haloalkyl (such as $CF_3$).

As described herein, $R^1$ can be substituted. A variety of substituents can substitute the $R^1$ groups described herein. In some embodiments, $R^1$ can be substituted with one or more substituents selected from deuterium, halogen (such as F, Cl and/or Br), cyano, an unsubstituted $C_{1-6}$ alkyl (for example, methyl, ethyl, n-propyl, isopropyl, n-butyl, iso-butyl, sec-butyl, tert-butyl, pentyl (straight-changed or branched) and hexyl (straight-chained or branched)), an unsubstituted $C_{1-6}$ haloalkyl (such as —$CHF_2$, —$CH_2F$, —$CF_3$, —$CHClF$, —$CH_2Cl$, —$CHCl_2$, —$CCl_3$, —$CH_2CHF_2$, —$CH_2CH_2F$, —$CH_2CF_3$, —$CH_2CHClF$, —$CH_2CH_2Cl$, —$CH_2CHCl_2$, —$CH_2CCl_3$, —$CH(CH_3)CF_3$, —$CH(CH_3)CHF_2$, —$C(CH_3)_2CF_3$ and —$C(CH_3)_2CHF_2$), an unsubstituted $C_{1-6}$ alkoxy (for example, methoxy, ethoxy, isopropoxy, n-butoxy, sec-butoxy, isobutoxy, tert-butoxy, —O-(cyclopropyl), —O-(cyclobutyl) and —O-(oxetane)), an unsubstituted $C_{1-6}$ haloalkoxy (for example, —$OCHF_2$, —$OCH_2F$, —$OCF_3$, —$OCHClF$, —$OCH_2Cl$, —$OCHCl_2$, —$OCCl_3$, —$OCH_2CHF_2$, —$OCH_2CH_2F$, —$OCH_2CF_3$, —$OCH_2CHClF$, —$OCH_2CH_2Cl$, —$OCH_2CHCl_2$, —$OCH_2CCl_3$, —$OCH(CH_3)CF_3$, —$OCH(CH_3)CHF_2$, —$OC(CH_3)_2CF_3$, —$OC(CH_3)_2CHF_2$, —O(halo-substituted cyclopropyl) and —O(halo-substituted cyclobutyl)), an unsubstituted acyl (for example, —C(=O)—$C_{1-4}$ alkyl), an unsubstituted C-amido (such as —C(=O)$NH_2$ and —C(=O)NH—$C_{1-4}$ alkyl), an unsubstituted sulfonyl (such as —S(=O)$_2$—$C_4$ alkyl), an unsubstituted amino, a mono-substituted amine (for example, an mono-alkyl substituted amine) and a di-substituted amine (such as a di-alkyl substituted amine). In some embodiments, $R^1$ can be substituted with one or more substituents selected from halogen (such as F, Cl and/or Br), cyano and an unsubstituted $C_{1-6}$ alkyl (such as methyl).

The number of substituents present on a substituted $R^1$ group can vary. In some embodiments, $R^1$ is substituted with 1 substituent. In other embodiments, $R^1$ is substituted with 2 substituents. In still other embodiments, $R^1$ is substituted with 3 substituents.

Exemplary R groups include, but are not limited to, the following:

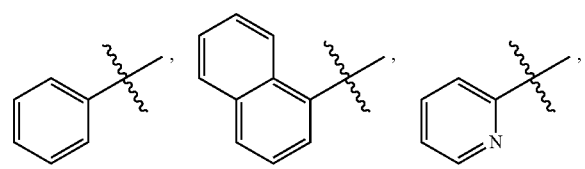

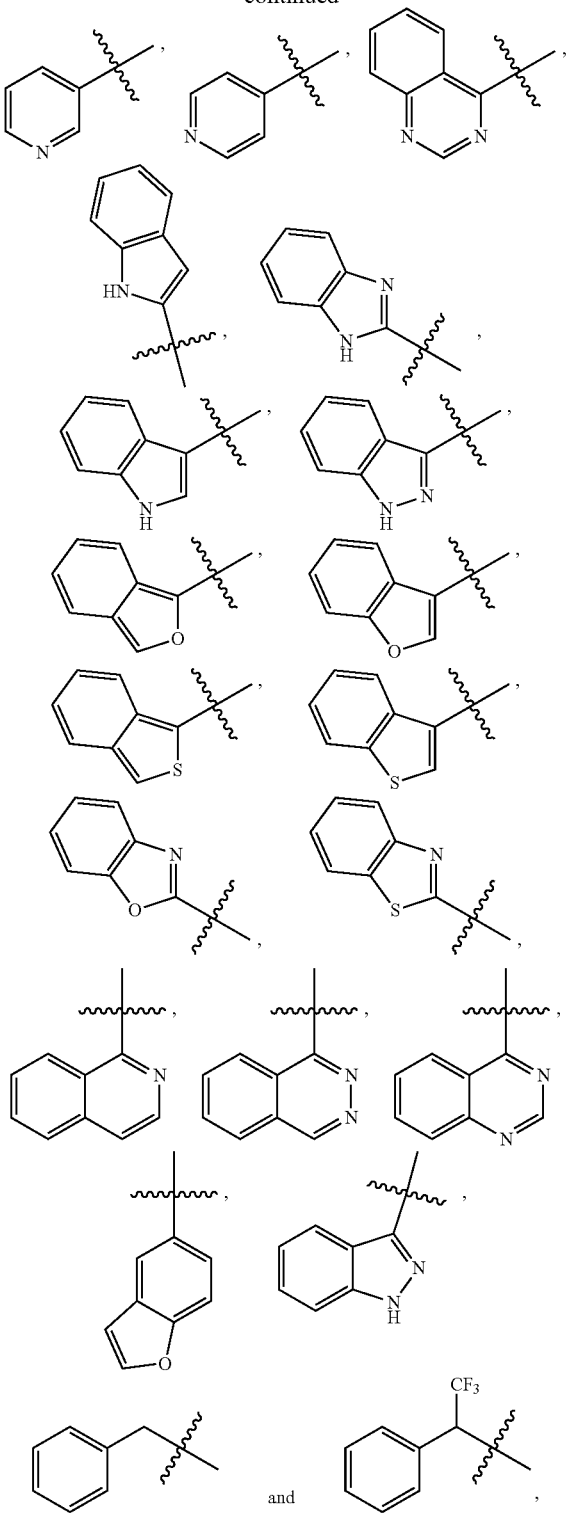

wherein each of these moieties can be unsubstituted or substituted.

As recited herein, $R^2$ can be an amido or a cyclic group. In some embodiments, $R^2$ can be —C(=O)$NR^{10}R^{11}$. In some embodiments, $R^{10}$ can be hydrogen. In other embodiments, $R^{10}$ can be an unsubstituted $C_{1-4}$ alkyl. In still other embodiments, $R^{10}$ can be a substituted $C_{1-4}$ alkyl. For example, R¹⁰ can be methyl, ethyl, n-propyl, iso-propyl, n-butyl, iso-butyl, sec-butyl or tert-butyl.

In some embodiments, R¹¹ can be hydrogen. In other embodiments, R¹¹ can be an unsubstituted $C_{1-6}$ alkyl, including an unsubstituted $C_{1-4}$ alkyl. In still other embodiments, R¹¹ can be a substituted $C_{1-8}$ alkyl, including a substituted $C_{1-4}$ alkyl. The unsubstituted or substituted $C_{1-6}$ alkyl can be methyl, ethyl, n-propyl, iso-propyl, n-butyl, iso-butyl, sec-butyl, tert-butyl, pentyl (branched or straight-chained), hexyl (branched or straight-chained), heptyl (branched or straight-chained) and octyl (branched or straight-chained). In yet still other embodiments, R¹¹ can be an optionally substituted $C_{2-6}$ alkenyl. In some embodiments, R¹¹ can be an optionally substituted $C_{2-6}$ alkynyl. When the alkyl of R¹¹ is substituted, the alkyl can be substituted with a cyclic group, such as an unsubstituted or a substituted $C_{3-6}$ cycloalkyl. For example, R¹¹ can be —CH₂(cyclopropyl), —CH(CH₃)(cyclopropyl), —CH₂(cyclobutyl), —CH(CH₃)(cyclobutyl), —CH₂(cyclopentyl), —CH(CH₃)(cyclopentyl), —CH₂(cyclohexyl) or —CH(CH₃)(cyclohexyl).

As described herein, R¹¹ can be various carbocyclic, heteroaryl or heterocyclic groups. In some embodiments, R¹¹ can be an optionally substituted $C_{3-8}$ cycloalkyl. In other embodiments, R¹¹ can be an optionally substituted $C_{3-10}$ cycloalkenyl. The optionally substituted $C_{3-8}$ cycloalkyl and the optionally substituted $C_{3-10}$ cycloalkenyl can be monocyclic or bicyclic (including fused bicyclic). In some embodiments, R¹¹ can be an optionally substituted aryl. For example, R¹¹ can be an unsubstituted or substituted phenyl. In still other embodiments, R¹¹ can be an optionally substituted heteroaryl. The heteroaryl for R¹¹ can be an optionally substituted monocyclic heteroaryl (such as an optionally substituted 5- or 6-membered monocyclic heteroaryl) or an optionally substituted bicyclic heteroaryl (for example, an optionally substituted 9- or 10-membered bicyclic heteroaryl). In some embodiments, R¹¹ can be an optionally substituted heterocyclyl.

A variety cyclic groups can be attached via a $C_{1-4}$ alkyl linker for R¹¹. In some embodiments, R¹¹ can be an optionally substituted aryl($C_{1-4}$ alkyl). As an example, R¹¹ can be an unsubstituted or a substituted benzyl, an unsubstituted or a substituted —CH(CH₃)(phenyl), an unsubstituted or a substituted —C(CH₃)₂(phenyl) or an unsubstituted or a substituted —C(spiro-connected cyclopropyl)(phenyl). As another example, R¹¹ can be an unsubstituted or a substituted —CH₂CH₂-phenyl. In other embodiments, R¹¹ can be an optionally substituted heteroaryl($C_{1-4}$ alkyl). In still other embodiments, R¹¹ can be an optionally substituted heterocyclyl($C_{1-4}$ alkyl). The heteroaryl of the optionally substituted heteroaryl($C_{1-4}$ alkyl) can be an optionally substituted monocyclic heteroaryl (such as a 5- or 6-membered heteroaryl) or an optionally substituted bicyclic heteroaryl (such as a 9- or 10-membered heteroaryl). The ($C_{1-4}$ alkyl) linker of an optionally substituted aryl($C_{1-4}$ alkyl), an optionally substituted heteroaryl($C_{1-4}$ alkyl) and/or an optionally substituted heterocyclyl($C_{1-4}$ alkyl) can be unsubstituted, such that the linker can be —CH₂—, —CH₂CH₂—, —CH₂CH₂CH₂— or —CH₂CH₂CH₂CH₂—. As provided below, the ($C_{1-4}$ alkyl) linker of an optionally substituted aryl($C_{1-4}$ alkyl), an optionally substituted heteroaryl($C_{1-4}$ alkyl) and/or an optionally substituted heterocyclyl($C_{1-4}$ alkyl) can be substituted.

Various heteroaryls can be present in an optionally substituted heteroaryl and/or an optionally substituted heteroaryl($C_4$ alkyl) of R¹¹, such as pyridine

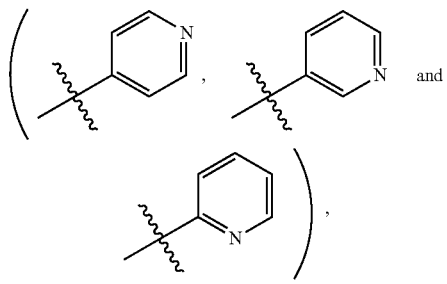

imidazole, oxazole, thiazole, pyridazine, pyrimidine, pyrazine, quinoline, quinoxaline, benzofuran, benzothiophene, benzoxazole, benzimidazole, indazole and benzo[1,2,5]oxadiazole, wherein each of the aforementioned moieties can be unsubstituted or substituted. Other examples of R¹¹ groups include cyclopropyl, cyclobutyl, cyclopentyl, cyclohexyl,

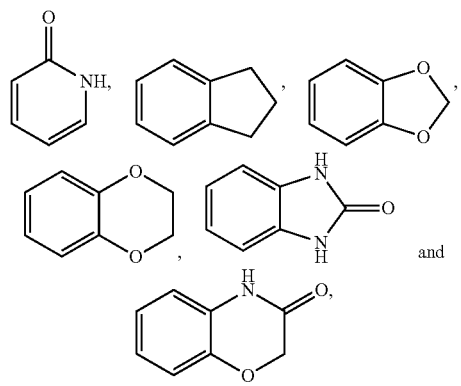

wherein each of the aforementioned moieties can be unsubstituted or substituted.

A variety of groups can be present when R¹¹ is substituted. For example, any of the groups listed for "optionally substituted" may be present on a substituted R¹¹ group along with any of those groups provided herein. In some embodiments, R¹¹ can be substituted with one or more moieties selected from halogen (such as F, Cl and Br), cyano, an unsubstituted $C_{1-4}$ alkyl (such as methyl, ethyl, n-propyl, isopropyl, n-butyl, iso-butyl and tert-butyl), an unsubstituted $C_{3-6}$ cycloalkyl, an unsubstituted $C_{1-4}$ alkoxy (for example, methoxy, ethoxy, isopropoxy, n-butoxy, sec-butoxy, isobutoxy, tert-butoxy, —O-(cyclopropyl), —O-(cyclobutyl) and —O-(oxetane)), an unsubstituted $C_{1-4}$ hydroxyalkyl (for example, —CH₂OH and —C(CH₃)₂OH), an unsubstituted $C_{1-4}$ alkoxyalkyl (for example, —CH₂OCH₃), an unsubstituted $C_{1-4}$ haloalkyl (such as —CHF₂, —CH₂F, —CF₃, —CHClF, —CH₂Cl, —CHCl₂, —CCl₃, —CH₂CHF₂, —CH₂CH₂F, —CH₂CF₃, —CH₂CHClF, —CH₂CH₂Cl, —CH₂CHCl₂, —CH₂CCl₃, —CH(CH₃)CF₃, —CH(CH₃)CHF₂, —C(CH₃)₂CF₃ and —C(CH₃)₂CHF₂), an unsubstituted $C_{1-4}$ haloalkoxy (for example, —OCHF₂, —OCH₂F, —OCF₃, —OCHClF, —OCH₂Cl, —OCHCl₂, —OCCl₃, —OCH₂CHF₂, —OCH₂CH₂F, —OCH₂CF₃, —OCH₂CHClF, —OCH₂CH₂Cl, —OCH₂CHCl₂, —OCH₂CCl₃, —OCH(CH₃)CF₃, —OCH(CH₃)CHF₂, —O(halo-substituted cyclopropyl) and —O(halo-substituted cyclobutyl)), an unsubstituted acyl (for example, —C(=O)H and —C(=O)CH₃), an unsubstituted C-carboxy (such as —C(=O)OH and —C(=O)OCH₃), an unsubstituted C-amido (for example, —C(=O)NH$_2$ and —C(=O)NH—C$_{1-4}$ alkyl), an unsubstituted C-carboxy (C$_{1-3}$ alkyl) (such as —CH$_2$C(=O)OH, —CH$_2$C(=O)OCH$_3$ and —CH$_2$C(=O)OCH$_2$CH$_3$), —O-(an unsubstituted C$_{1-4}$ alkyl)-(an unsubstituted C-carboxy) (such as —OCH$_2$—C(=O)OH, —OCH$_2$—C(=O)OCH$_3$ and —OCH$_2$—C(=O)OCH$_2$CH$_3$), an unsubstituted C-amido (C$_{1-3}$ alkyl) (for example, —CH$_2$C(=O)NH$_2$), —O—(C$_{1-3}$ alkyl)-O-(an unsubstituted C-amido) (such as —O-(an unsubstituted C$_{1-4}$ alkyl)-NH$_2$ (e.g., —OCH$_2$—C(=O)NH$_2$, —OCH(CH$_3$)—C(=O)NH$_2$ and —OC(CH$_3$)$_2$—C(=O)NH$_2$), —O-(an unsubstituted C$_{1-4}$ alkyl)-NH (an unsubstituted C$_{1-4}$ alkyl) (e.g., —OCH$_2$—C(=O)NH(CH$_3$)—OCH(CH$_3$)—C(=O)NH(CH$_3$) and —OC(CH$_3$)$_2$—C(=O)NH(CH$_3$)), —O-(an unsubstituted C$_{1-4}$ alkyl)-N (an unsubstituted C$_{1-4}$ alkyl)$_2$ (e.g., —OCH$_2$—C(=O)N(CH$_3$)$_2$, —OCH(CH$_3$)$_2$—C(=O)N(CH$_3$)$_2$ and —OC(CH$_3$)$_2$—C(=O)N(CH$_3$)$_2$)), an unsubstituted —O-(an unsubstituted C$_{1-4}$ alkyl)-CN (for example, —OCH$_2$CN), an unsubstituted sulfonyl (such as —S(=O)$_2$(an unsubstituted C$_{1-4}$ alkyl), an unsubstituted, a halogen-substituted or an unsubstituted C$_{1-4}$ alkyl substituted monocyclic 5-6 membered heteroaryl (such as an unsubstituted or a fluoro-substituted monocyclic 5-6 membered nitrogen-containing heteroaryl (e.g., pyridine, pyrimidine, pyrazine, pyridazine, 1,2,4-triazine, pyrazole, imidazole, 1,2,4-triazole, 1,2,3-triazole, oxazole, 1,2,4-oxadiazole and 1,3,4-oxadiazole))), an optionally substituted aryl(C$_{1-4}$ alkyl) (such as an optionally substituted benzyl) and an unsubstituted, a halogen-substituted or an unsubstituted C$_{1-4}$ alkyl monocyclic 5-6 membered heterocyclyl (such as oxetane, azetidine and pyrrolidine).

The number of moieties that can be present on a substituted R$^{11}$ can vary. The R$^{11}$ group can be mono-substituted. In other instances, R$^{11}$ group can be substituted with more than one moieties (such as two moieties) where the moieties can be the same or different. In some embodiments, R$^{11}$ can be substituted with one or more moieties selected from an unsubstituted halogen, C$_{1-4}$ alkoxy and an unsubstituted or a fluoro-substituted monocyclic 5-6 membered nitrogen-containing heteroaryl, including those described herein.

Further, as provided herein, the lower alkylene linker of an optionally substituted aryl(C$_{1-4}$ alkyl), an optionally substituted heteroaryl(C$_{1-4}$ alkyl) and an optionally substituted heterocyclyl(C$_{1-4}$ alkyl) can be substituted. Exemplary moieties that can be present on a lower alkylene linker include, but are not limited to, an unsubstituted C$_{1-4}$ alkyl (for example, —CH$_3$, —(CH$_2$)$_2$, —CH$_2$CH$_3$ and —CH(CH$_3$)$_2$), an unsubstituted C$_{3-4}$ cycloalkyl (an unsubstituted cyclopropyl and an unsubstituted cyclobutyl), an unsubstituted C$_{1-4}$ haloalkyl (such as —CHF$_2$ and —CF$_3$), an unsubstituted C$_{1-4}$ hydroxyalkyl (such as —CH$_2$OH), —C(=O)OH, —C(=O)NH$_2$, and/or by replacing both hydrogens on the same carbon with a cycloalkyl group. Depending on the groups present on the lower alkylene linker, a stereocenter can be present. In some embodiments, the stereocenter can be in the (R)-configuration. In other embodiments, the stereocenter can be in the (S)-configuration. In some embodiments, the substituted lower alkylene linker can be selected from —CH(CH$_3$)—, —C(CH$_3$)$_2$—, —CH(CH$_2$CH$_3$)—, —C(CH$_2$CH$_3$)$_2$—, —CH(CH(CH$_3$)$_2$)—, —C(CH(CH$_3$)$_2$)$_2$—, —CH (cyclopropyl)-, —CH(cyclobutyl)-, —CH(CH$_2$OH)—, —CH(C(=O)OH)— and

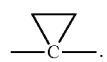

In some embodiments, R$^{10}$ can be hydrogen; and R$^{11}$ can be an unsubstituted or a substituted benzyl with an unsubstituted or a substituted methylene linker (for example, —CH$_2$— and —CH(CH$_3$)—). In other embodiments, R$^{10}$ can be hydrogen; and R$^{11}$ can be an unsubstituted or a substituted monocyclic heteroaryl, such as an unsubstituted or a substituted 5- to 6-membered nitrogen-containing heteroaryl. In other embodiments, R$^{10}$ can be hydrogen; and R$^{11}$ can be an unsubstituted or a substituted bicyclic heteroaryl, for example, an unsubstituted or a substituted 9- to 10-membered nitrogen-containing heteroaryl. Examples of suitable heteroaryls for R$^{11}$ are provided herein, and include pyridine, imidazole, oxazole, pyridazine, pyrimidine, pyrazine, quinoline, quinoxaline, benzoxazole, benzimidazole, indazole and benzo[1,2,5]oxadiazole.

In some embodiments, R$^{10}$ and R$^{11}$ can be taken together along with the nitrogen to which R$^{10}$ and R$^{11}$ are attached to form an optionally substituted 4 to 8 member monocyclic heterocyclyl. In other embodiments, R$^{10}$ and R$^{11}$ can be taken together along with the nitrogen to which R$^{10}$ and R$^{11}$ are attached to form an optionally substituted 7 to 12 member bicyclic heterocyclyl. The 4 to 8 member monocyclic heterocyclyl and/or 7 to 12 member bicyclic heterocyclyl can include one or more ring nitrogens.

A variety of saturated and unsaturated cyclic groups can be present for R$^2$. In some embodiments, R$^2$ can be an optionally substituted cycloalkyl. In other embodiments, R$^2$ can be an optionally substituted cycloalkenyl. For example, R$^2$ can be an unsubstituted monocyclic C$_{6-8}$ cycloalkyl, a substituted monocyclic C$_{6-8}$ cycloalkyl, an unsubstituted monocyclic C$_{6-8}$ cycloalkenyl or a substituted monocyclic C$_{6-8}$ cycloalkenyl. In still other embodiments, R$^2$ can be an optionally substituted aryl. The optionally substituted aryl can be an optionally substituted phenyl or an optionally substituted naphthyl. In yet still other embodiments, R$^2$ can be an optionally substituted heteroaryl. Exemplary heteroaryls include optionally substituted monocyclic heteroaryls (such as 5- and 6-membered heteroaryls) and optionally substituted bicyclic heteroaryls (such as 9- and 10-membered heteroaryls). In some embodiments, R$^2$ can be an optionally substituted heterocyclyl. Suitable heterocyclyls for R$^2$ include, but are not limited to, optionally substituted monocyclic heterocyclyls (for example, 5- and 6-membered heterocyclyls) and optionally substituted bicyclic heterocyclyls (for example, 9- and 10-membered heterocyclyls).

For R$^2$, the cycloalkyl, cycloalkenyl, aryl, heteroaryl and/or heterocyclyl can be connected via a C$_{1-4}$ alkyl linker. In some embodiments, R$^2$ can be an optionally substituted cycloalkyl(C$_{1-4}$ alkyl). In other embodiments, R$^2$ can be an optionally substituted cycloalkenyl(C$_{1-4}$ alkyl). The cycloalkyl portion of the optionally substituted cycloalkyl(C$_{1-4}$ alkyl) can be an unsubstituted monocyclic C$_{6-8}$ cycloalkyl or a substituted monocyclic C$_{6-8}$ cycloalkyl, and the cycloalkenyl portion of the optionally substituted cycloalkenyl(C$_{1-4}$ alkyl) can be an unsubstituted monocyclic C$_{6-8}$ cycloalkenyl or a substituted monocyclic C$_{6-8}$ cycloalkenyl. In still other embodiments, R$^2$ can be an optionally substituted aryl(C$_{1-4}$ alkyl). As an example, R$^2$ can be an optionally substituted benzyl. In some embodiments, R$^2$ can be an optionally substituted heteroaryl(C$_{1-4}$ alkyl). In other embodiments, R$^2$ can be an optionally substituted heterocyclyl(C$_{1-4}$ alkyl). The heteroaryl of the optionally substituted heteroaryl(C$_{1-4}$ alkyl) can be substituted or unsubstituted and/or monocyclic or bicyclic. In some embodiments, R$^2$ can be an optionally substituted 5-membered monocyclic heteroaryl(C$_{1-4}$ alkyl), an optionally substituted 6-membered monocyclic heteroaryl(C$_{1-4}$ alkyl), 9-membered bicyclic heteroaryl(C$_{1-4}$ alkyl), an optionally substituted 10-membered bicyclic heteroaryl($C_{1-4}$ alkyl). Likewise, the heterocyclyl of the optionally substituted heterocyclyl($C_{1-4}$ alkyl) can be substituted or unsubstituted and/or monocyclic or bicyclic. In other embodiments, $R^2$ can be an optionally substituted 5-membered monocyclic heterocyclyl($C_{1-4}$ alkyl), an optionally substituted 6-membered monocyclic heterocyclyl($C_{1-4}$ alkyl), 9-membered bicyclic heterocyclyl($C_{1-4}$ alkyl), an optionally substituted 10-membered bicyclic heterocyclyl ($C_{1-4}$ alkyl).

The optionally substituted heteroaryl, optionally substituted heterocyclyl, optionally substituted heteroaryl($C_{1-4}$ alkyl) and/or optionally substituted heterocyclyl($C_{1-4}$ alkyl) for $R^2$ can include at least one nitrogen in the ring(s). In some embodiments, the $C_{1-4}$ alkyl portion of the optionally substituted cycloalkyl($C_{1-4}$ alkyl), the optionally substituted cycloalkenyl($C_{1-4}$ alkyl), an optionally substituted aryl($C_{1-4}$ alkyl), the optionally substituted heteroaryl($C_{1-4}$ alkyl) and/or the optionally substituted heterocyclyl($C_{1-4}$ alkyl) for $R^2$ can be —$CH_2$—.

Examples of suitable $R^2$ groups include, but are not limited to, an unsubstituted or a substituted oxazole, an unsubstituted or a substituted imidazole, an unsubstituted or a substituted isoxazole, an unsubstituted or a substituted pyridine, an unsubstituted or a substituted pyrimidine, an unsubstituted or a substituted pyrazole, an unsubstituted or a substituted pyrazine, an unsubstituted or a substituted pyridazine, an unsubstituted or a substituted thiazole, an unsubstituted or a substituted oxadiazole (including an unsubstituted or a substituted 1,3,4-oxadiazole and an unsubstituted or a substituted 1,2,4-oxadiazole). Further examples of suitable $R^2$ groups include, but are not limited to, an unsubstituted or a substituted benzofuran, an unsubstituted or a substituted benzothiophene, an unsubstituted or a substituted indole and an unsubstituted or a substituted indazole.

Suitable $R^2$ groups include the following:

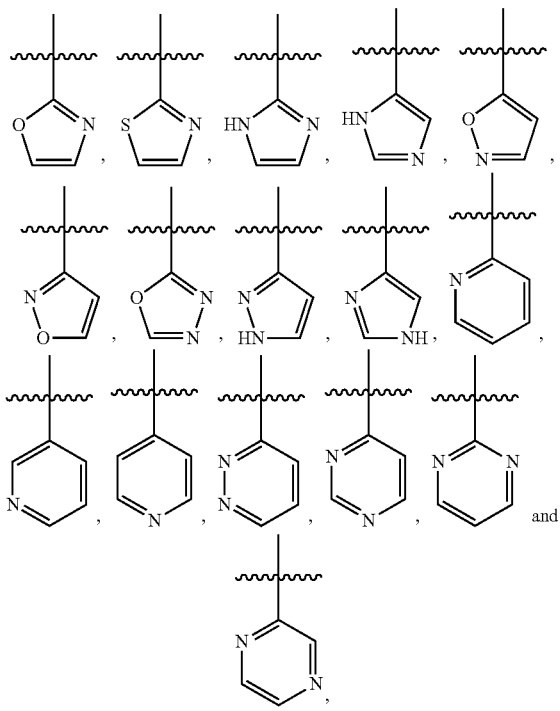

wherein each of the aforementioned rings can be unsubstituted or substituted; and when substituted, one or more hydrogens (including the hydrogen attached to the shown nitrogen) can be replaced with a substituent recited for "optionally substituted," and any of those provided herein. In some embodiments, each of the aforementioned examples of suitable $R^2$ groups can be substituted with one or more substituents provided in the paragraph below.

As provided herein, $R^2$ can be unsubstituted or substituted. When substituted $R^2$ can be substituted 1, 2 or 3 or more times. In some embodiments, $R^2$ can be substituted with one or more substituents independently selected from deuterium, halogen (for example, F, Cl and Br), cyano, an unsubstituted $C_{1-6}$ alkyl (such as methyl, ethyl, n-propyl, isopropyl, n-butyl, iso-butyl, sec-butyl, tert-butyl, pentyl (straight-changed or branched) and hexyl (straight-chained or branched), an unsubstituted $C_{1-6}$ haloalkyl (for example, —$CHF_2$, —$CH_2F$, —$CF_3$, —$CHClF$, —$CH_2Cl$, —$CHCl_2$, —$CCl_3$, —$CH_2CHF_2$, —$CH_2CH_2F$, —$CH_2CF_3$, —$CH_2CHClF$, —$CH_2CH_2Cl$, —$CH_2CHCl_2$, —$CH_2CCl_3$, —$CH(CH_3)CF_3$, —$CH(CH_3)CHF_2$, —$C(CH_3)_2CF_3$ and —$C(CH_3)_2CHF_2$), an unsubstituted $C_{1-6}$ alkoxy (for example, methoxy, ethoxy, isopropoxy, n-butoxy, sec-butoxy, isobutoxy, tert-butoxy, —O-(cyclopropyl), —O-(cyclobutyl) and —O-(oxetane)), an unsubstituted $C_{1-6}$ haloalkoxy (for example, —$OCHF_2$, —$OCH_2F$, —$OCF_3$, —$OCHClF$, —$OCH_2Cl$, —$OCHCl_2$, —$OCCl_3$, —$OCH_2CHF_2$, —$OCH_2CH_2F$, —$OCH_2CF_3$, —$OCH_2CHClF$, —$OCH_2CH_2Cl$, —$OCH_2CHCl_2$, —$OCH_2CCl_3$, —$OCH(CH_3)CF_3$, —$OCH(CH_3)CHF_2$, —$OC(CH_3)_2CF_3$, —$OC(CH_3)_2CHF_2$, —O(halo-substituted cyclopropyl) and —O(halo-substituted cyclobutyl)), an optionally substituted aryl (for example, an optionally substituted phenyl), an optionally substituted heteroaryl (such as an optionally substituted monocyclic heteroaryl, including a 5-membered and 6-membered monocyclic heteroaryls), an optionally substituted heterocyclyl (such as an optionally substituted monocyclic heteroaryl, including 4-membered, 5-membered and 6-membered monocyclic heterocyclyls), an optionally substituted aryl($C_{1-3}$ alkyl) (for example, an optionally substituted benzyl), an optionally substituted heteroaryl($C_{1-3}$ alkyl) (such as an optionally substituted monocyclic heteroaryl($C_{1-3}$ alkyl), including an optionally substituted 5-membered heteroaryl($C_{1-3}$ alkyl) and an optionally substituted 6-membered monocyclic heteroaryl($C_{1-3}$ alkyl)), an optionally substituted heterocyclyl ($C_{1-3}$ alkyl) (such as an optionally substituted monocyclic heterocyclyl($C_{1-3}$ alkyl), including an optionally substituted 5-membered heterocyclyl($C_{1-3}$ alkyl) and an optionally substituted 6-membered monocyclic heterocyclyl($C_{1-3}$ alkyl)), an unsubstituted $C_{1-6}$ alkoxy (for example, methoxy, ethoxy, isopropoxy, n-butoxy, sec-butoxy, isobutoxy and tert-butoxy), an unsubstituted acyl (such as —C(=O)—$C_{1-4}$ alkyl), an unsubstituted S-sulfonamido (such as —S(=O)$_2$NH$_2$ or —S(=O)$_2$NH—($C_4$ alkyl), an unsubstituted C-amido (such as —C(=O)NH$_2$ and —C(=O)NH—$C_{1-4}$ alkyl), an unsubstituted sulfonyl (such as —S(=O)$_2$—$C_{1-4}$ alkyl), an unsubstituted amino, a mono-substituted amine (for example, an mono-alkyl substituted amine) and a di-substituted amine (for example, a di-alkyl substituted amine). In some embodiments, including those of the previous paragraph, $R^2$ can be substituted with an unsubstituted or a substituted phenyl or an unsubstituted or a substituted benzyl. As an example, $R^2$ can be a 5- to 6-membered monocyclic nitrogen-containing heteroaryl, including an oxazole, an imidazole, an isoxazole, a pyridine, a pyrimidine, a pyrazole, a pyrazine and a pyridazine, and be substituted with an unsubstituted or a substituted phenyl or an unsubstituted or a substituted benzyl.

In some embodiments, $R^3$ can be hydrogen. In other embodiments, $R^3$ can be an unsubstituted $C_{1-4}$ alkyl (for example, methyl, ethyl, n-propyl, iso-propyl, n-butyl, iso-butyl, sec-butyl or tert-butyl). Additionally, various cyclic moieties can be present for $R^3$. The cyclic moieties for $R^3$ can be a saturated carbocyclyl or an unsaturated carbocyclyl. In some embodiments, $R^3$ can be an optionally substituted cycloalkyl. The optionally substituted cycloalkyl can be monocyclic or bicyclic. As examples, $R^3$ can be an optionally substituted monocyclic $C_{3-4}$ cycloalkyl or an optionally substituted monocyclic $C_{5-8}$ cycloalkyl. In other embodiments, $R^3$ can be an optionally substituted cycloalkenyl, such as an optionally substituted monocyclic $C_{5-8}$ cycloalkenyl and an optionally substituted bicyclic cycloalkenyl. In still other embodiments, $R^3$ can be an optionally substituted aryl. Exemplary optionally substituted aryls include, but are not limited to, an unsubstituted phenyl, a mono-substituted phenyl (such as a para-substituted phenyl, a meta-substituted phenyl and an ortho-substituted phenyl), a di-substituted phenyl (for example, a 2,3-di-substituted phenyl, a 2,4-di-substituted phenyl and a 3,4-di-substituted phenyl), and a tri-substituted phenyl.

The cyclic groups that can be present for $R^3$ can include heteroatoms. In some embodiments, $R^3$ can be an optionally substituted heteroaryl. The heteroaryl can be a monocyclic or a bicyclic heteroaryl. For example, $R^3$ can be an optionally substituted 5-membered, monocyclic heteroaryl, an optionally substituted 6-membered, monocyclic heteroaryl, an optionally substituted 9-membered, bicyclic heteroaryl or an optionally substituted 10-membered, bicyclic heteroaryl. In other embodiments, $R^3$ can be an optionally substituted heterocyclyl. The heterocyclyl for $R^3$ can be an optionally substituted monocyclic heterocyclyl (such as a 5-membered or 6-membered heterocyclyl) or an optionally substituted bicyclic heterocyclyl (such as a 9-membered or 10-membered heterocyclyl).

For $R^3$, a variety of cyclic groups can be connected via a $C_{1-4}$ alkyl linker. In some embodiments, $R^3$ can be an optionally substituted aryl($C_{1-4}$ alkyl), for example, an optionally substituted benzyl and an optionally substituted —(CH$_2$)$_2$-phenyl. In other embodiments, $R^3$ can be an optionally substituted heteroaryl($C_{1-4}$ alkyl). In still other embodiments, $R^3$ can be an optionally substituted heterocyclyl($C_{1-4}$ alkyl). As described herein, a heteroaryl and a heterocyclyl can be monocyclic or bicyclic. Exemplary $R^3$ groups that can be connected via a $C_{1-4}$ alkyl linker include, but are not limited to, an optionally substituted 5-membered, monocyclic heteroaryl, an optionally substituted 6-membered, monocyclic heteroaryl, an optionally substituted 9-membered, bicyclic heteroaryl, an optionally substituted 10-membered, bicyclic heteroaryl, an optionally substituted 5-membered, monocyclic heterocyclyl, an optionally substituted 6-membered, monocyclic heterocyclyl, an optionally substituted 9-membered, bicyclic heterocyclyl and an optionally substituted 10-membered, bicyclic heterocyclyl. In some embodiments, the $C_{1-4}$ alkyl linker can be —CH$_2$—, —CH$_2$CH$_2$—, —CH$_2$CH$_2$CH$_2$— or —CH$_2$CH$_2$CH$_2$CH$_2$—.

Examples of $R^3$ include —H, —CH$_3$, an unsubstituted or a substituted cyclopropyl, an unsubstituted or a substituted cyclobutyl, an unsubstituted or a substituted cyclopentyl, an unsubstituted or a substituted cyclohexyl, an unsubstituted or a substituted

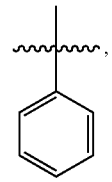

an unsubstituted or a substituted benzyl, an unsubstituted or a substituted —(CH$_2$)$_2$ (an unsubstituted or a substituted phenyl), an unsubstituted or a substituted pyridine (for example, an unsubstituted or a substituted

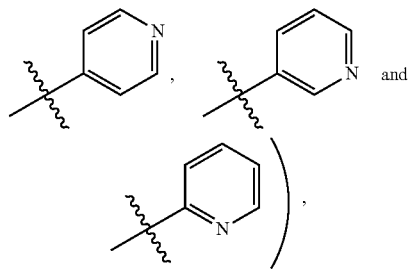 and an unsubstituted or a substituted pyrimidine (such as an unsubstituted or a substituted

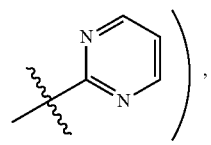

an unsubstituted or a substituted benzofuran, (such as an unsubstituted or a substituted

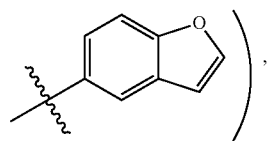

an unsubstituted or a substituted benzothiophene (for example, an unsubstituted or a substituted

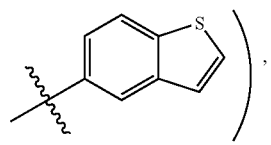

an unsubstituted or a substituted benzoxazole (for example, an unsubstituted or a substituted

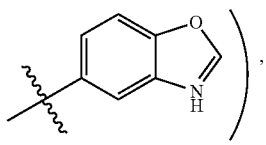, an unsubstituted or a substituted indole (such as an unsubstituted or a substituted

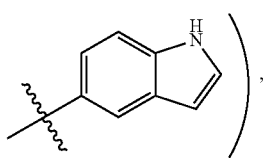, an unsubstituted or a substituted indazole (for example, an unsubstituted or a substituted

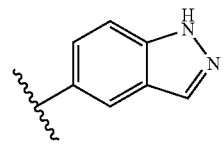 [SMILES: *c1ccc2[nH]ncc2c1]

and an unsubstituted or a substituted

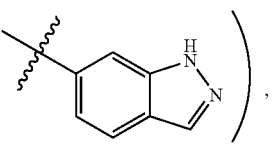, an unsubstituted or a substituted benzo[1,2,5]oxadiazole (such as an unsubstituted or a substituted

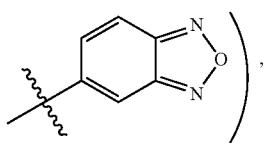, an unsubstituted or a substituted

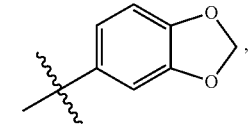 [SMILES: *c1ccc2c(c1)OCO2], an unsubstituted or a substituted

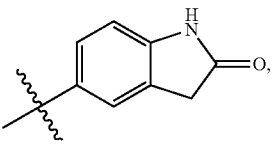 [SMILES: *c1ccc2c(c1)CC(=O)N2], an unsubstituted or a substituted

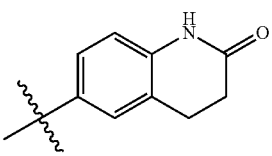 [SMILES: *c1ccc2c(c1)CCC(=O)N2], and an unsubstituted or a substituted.

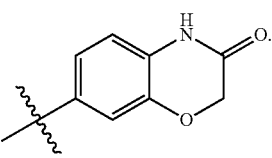 [SMILES: *c1ccc2c(c1)OCC(=O)N2]

When the $R^3$ group is substituted, a variety of substituents can be present. In some embodiments, $R^3$ can be substituted with one or more substituents independently selected from deuterium, halogen (such as F, Cl and/or Br), cyano, an unsubstituted $C_{1-6}$ alkyl (such as methyl, ethyl, n-propyl, isopropyl, n-butyl, iso-butyl, sec-butyl, tert-butyl, pentyl (straight-changed or branched) and hexyl (straight-chained or branched)), an optionally substituted aryl (for example, an optionally substituted phenyl), an optionally substituted heteroaryl (such as an optionally substituted monocyclic heteroaryl, including a 5-membered and 6-membered monocyclic heteroaryls (for example, an unsubstituted or a substituted pyrazole, an unsubstituted or a substituted imidazole, an unsubstituted or a substituted 1,2,3-triazole, an unsubstituted or a substituted 1,2,4-triazole and an unsubstituted or a substituted pyridine)), an optionally substituted heterocyclyl (such as an optionally substituted monocyclic heteroaryl, including 4-membered, 5-membered and 6-membered monocyclic heterocyclyls (for example, an unsubstituted or a substituted azetidine (e.g.,

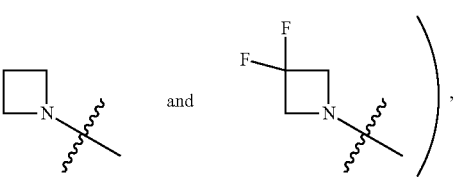

an unsubstituted or a substituted azetidinone, an unsubstituted or a substituted pyrrolidinine (e.g.,

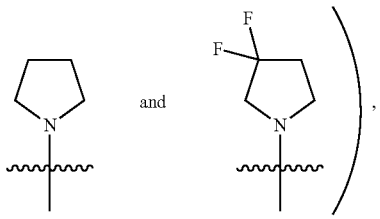

an unsubstituted or a substituted pyrrolidinone and an unsubstituted or a substituted morpholine), an optionally substituted aryl($C_{1-3}$ alkyl) (for example, an optionally substituted benzyl), an optionally substituted heteroaryl($C_{1-3}$ alkyl) (such as an optionally substituted monocyclic heteroaryl($C_{1-3}$ alkyl), including an optionally substituted 5-membered heteroaryl($C_{1-3}$ alkyl) and an optionally substituted 6-membered monocyclic heteroaryl($C_{1-3}$ alkyl)), an optionally substituted heterocyclyl($C_{1-3}$ alkyl) (such as an optionally substituted monocyclic heterocyclyl($C_{1-3}$ alkyl), including an optionally substituted 5-membered heterocyclyl($C_{1-3}$ alkyl) and an optionally substituted 6-membered monocyclic heterocyclyl($C_{1-3}$ alkyl)), an unsubstituted $C_{1-6}$ haloalkyl (for example, —$CHF_2$, —$CH_2F$, —$CF_3$, —CHClF, —$CH_2Cl$, —$CHCl_2$, —$CCl_3$, —$CH_2CHF_2$, —$CH_2CH_2F$, —$CH_2CF_3$, —$CH_2CHClF$, —$CH_2CH_2Cl$, —$CH_2CHCl_2$, —$CH_2CCl_3$, —CH($CH_3$)$CF_3$, —CH($CH_3$)$CHF_2$, —C($CH_3$)$_2CF_3$ and —C($CH_3$)$_2CHF_2$), an unsubstituted $C_{1-6}$ alkoxy (for example, methoxy, ethoxy, isopropoxy, n-butoxy, sec-butoxy, isobutoxy, tert-butoxy, —O-(cyclopropyl), —O-(cyclobutyl) and —O-(oxetane)), an unsubstituted $C_{1-6}$ haloalkoxy (for example, —$OCHF_2$, —$OCH_2F$, —$OCF_3$, —OCHClF, —$OCH_2Cl$, —$OCHCl_2$, —$OCCl_3$, —$OCH_2CHF_2$, —$OCH_2CH_2F$, —$OCH_2CF_3$, —$OCH_2CHClF$, —$OCH_2CH_2Cl$, —$OCH_2CHCl_2$, —$OCH_2CCl_3$, —OCH($CH_3$)$CF_3$, —OCH($CH_3$)$CHF_2$, —OC($CH_3$)$_2CF_3$, —OC($CH_3$)$_2CHF_2$, —O(halo-substituted cyclopropyl) and —O(halo-substituted cyclobutyl)), —O-(an unsubstituted $C_{1-4}$ alkyl)-OH (for example, —O($CH_2$)$_2$OH), —O-(an unsubstituted $C_{1-4}$ alkyl)-(an unsubstituted alkoxy) (such as —O($CH_2$)$_2OCH_3$), —O-(an unsubstituted $C_{1-4}$ alkyl)-(an unsubstituted C-carboxy) (such as —$OCH_2$—C(=O)OH, —$OCH_2$—C(=O)$OCH_3$ and —$OCH_2$—C(=O)$OCH_2CH_3$), —O-(an unsubstituted $C_{1-4}$ alkyl)-$NH_2$ (such as —$OCH_2$—C(=O)$NH_2$, —OC($CH_3$)—C(=O)$NH_2$ and —OC($CH_3$)$_2$—C(=O)$NH_2$), —O-(an unsubstituted $C_{1-4}$ alkyl)-NH (an unsubstituted $C_{1-4}$ alkyl) (such as —$OCH_2$—C(=O)NH($CH_3$), —OC($CH_3$)—C(=O)NH($CH_3$) and —OC($CH_3$)$_2$—C(=O)NH($CH_3$)), —O-(an unsubstituted $C_{1-4}$ alkyl)-N (an unsubstituted $C_{1-4}$ alkyl)$_2$ (such as —$OCH_2$—C(=O)N($CH_3$)$_2$, —OC($CH_3$)—C(=O)N($CH_3$)$_2$ and —OC($CH_3$)$_2$—C(=O)N($CH_3$)$_2$), an unsubstituted —O-(an unsubstituted $C_{1-4}$ alkyl)-CN (for example, —$OCH_2CN$), an unsubstituted acyl (such as —C(=O)—$C_{1-4}$ alkyl), an unsubstituted C-amido (such as —C(=O)$NH_2$ and —C(=O)NH—$C_{1-4}$ alkyl), an unsubstituted sulfenyl (for example, —S($C_{1-4}$ alkyl) (e.g., —$SCH_3$)), an unsubstituted sulfonyl (such as —S(=O)$_2$—$C_{1-4}$ alkyl), an unsubstituted S-sulfonamido (such as —S(=O)$_2NH_2$ and —S(=O)$_2$NH—$C_{1-4}$ alkyl), an unsubstituted amino, a mono-substituted amine (for example, an mono-alkyl substituted amine) and a di-substituted amine (for example, a di-alkyl substituted amine). In some embodiments, $R^3$ can be substituted with one or more substituents independently selected from halogen (such as F, $C_1$ and/or Br), cyano, an unsubstituted $C_{1-6}$ alkyl, an optionally substituted 5-membered and 6-membered monocyclic heteroaryl, an optionally substituted 4-membered, 5-membered and 6-membered monocyclic heterocyclyl, an unsubstituted $C_{1-6}$ haloalkyl, an unsubstituted $C_{1-6}$ alkoxy, an unsubstituted $C_{1-6}$ haloalkoxy, —O-(an unsubstituted $C_{1-4}$ alkyl)-OH, —O-(an unsubstituted $C_{1-4}$ alkyl)-(an unsubstituted alkoxy), —O-(an unsubstituted $C_{1-4}$ alkyl)-(an unsubstituted C-carboxy), —O-(an unsubstituted $C_{1-4}$ alkyl)-$NH_2$, —O-(an unsubstituted $C_{1-4}$ alkyl)-NH (an unsubstituted $C_{1-4}$ alkyl), —O-(an unsubstituted $C_{1-4}$ alkyl)-N (an unsubstituted $C_{1-4}$ alkyl)$_2$, an unsubstituted —O-(an unsubstituted $C_{1-4}$ alkyl)-CN, an unsubstituted C-amido, an unsubstituted sulfenyl, an unsubstituted sulfonyl, an unsubstituted S-sulfonamido, an unsubstituted amino, a mono-alkyl substituted amine) and a di-alkyl substituted amine). In some embodiments, $R^3$ can be substituted with one or more substituents independently selected from an unsubstituted $C_{1-6}$ alkoxy, an optionally substituted 5-membered and 6-membered monocyclic heteroaryl and an optionally substituted 4-membered, 5-membered and 6-membered monocyclic heterocyclyl.

When the $R^3$ group is substituted, the number of substituents present on a $R^3$ group can vary. For example, a $R^3$ group can be mono-substituted. Alternatively a $R^3$ group can be substituted with two or more substituents where each substituent can be independently chosen. In some embodiments, a $R^3$ group provided herein can be substituted with an unsubstituted $C_{1-4}$ alkoxy. In some embodiments, a $R^3$ group provided herein can be substituted with an unsubstituted or a substituted 5-membered and 6-membered monocyclic heteroaryl. For example, a $R^3$ group provided herein can be substituted with an unsubstituted pyrazole, an unsubstituted imidazole, an unsubstituted 1,2,3-triazole, an unsubstituted 1,2,4-triazole or an unsubstituted pyridine.

A third ring can be formed by taking $R^2$ and $R^3$ together. In some embodiments, $R^2$ and $R^3$ can be taken together along with the atoms to which $R^2$ and $R^3$ are each attached to form an optionally substituted 6-membered monocyclic heterocyclyl. In other embodiments, $R^2$ and $R^3$ can be taken together along with the atoms to which $R^2$ and $R^3$ are each attached to form an optionally substituted 7-membered monocyclic heterocyclyl. In still other embodiments, $R^2$ and $R^3$ can be taken together along with the atoms to which $R^2$ and $R^3$ are each attached to form an optionally substituted 8-membered monocyclic heterocyclyl. The 6-membered, 7-membered and/or 8-membered heterocyclyl formed by taking together $R^2$ and $R^3$ include one or more ring nitrogens and have one or more oxo groups attached. As an example, $R^2$ and $R^3$ can be taken together along with the atoms to which $R^2$ and $R^3$ are each attached to form the following, where "+" indicates the point of attachment to the nitrogen of $R^3$ and "*" indicates the point of attachment to carbon of $R^2$:

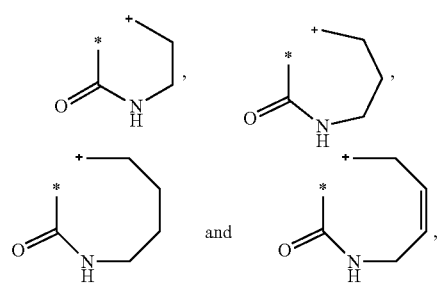

wherein each of the aforementioned rings can be unsubstituted or substituted; and when substituted, one or more hydrogens (including the hydrogen attached to the shown nitrogen) can be replaced with a substituent recited for "optionally substituted" and any of those provided herein, and/or 2 hydrogens on a single carbon can be taken together to form an unsubstituted 3- or 4-membered monocyclic cycloalkyl or an unsubstituted 3- or 4-membered monocyclic heterocyclyl (such as an unsubstituted or a substituted oxetane, an unsubstituted or a substituted thietane and an unsubstituted or a substituted azetidine). When the hydrogen on the nitrogen is replaced, the 6-membered, 7-membered and/or 8-membered heterocyclyl formed by taking together $R^2$ and $R^3$ include one or more ring nitrogens and have one or more oxo groups attached can be have the following structures:

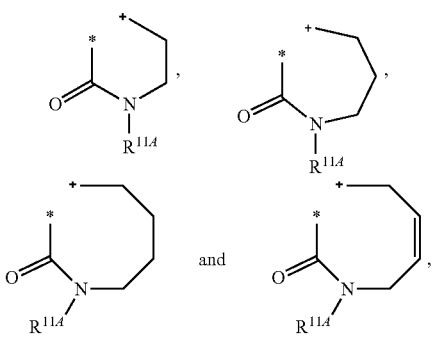

wherein each of the rings can be further substituted; and $R^{11A}$ can be selected from those groups described herein with respect to $R^{11}$. When $R^{11A}$ is not hydrogen, $R^{11A}$ can be an unsubstituted or a substituted $C_{1-4}$ alkyl or an unsubstituted or a substituted aryl($C_{1-4}$ alkyl) (such as an unsubstituted or a substituted benzyl), wherein the substituted $C_{1-4}$ alkyl can be substituted with an unsubstituted or a substituted $C_{3-6}$ cycloalkyl.

In some embodiments, the 6-, 7- or 8-membered monocyclic heterocyclyl formed by taking together $R^2$ and $R^3$ along with the atoms to which $R^2$ and $R^3$ are each attached can be substituted with one or more substituents independently selected from deuterium, halogen (for example, F, Cl and Br), hydroxy, hydroxy($C_{1-5}$ alkyl), cyano, an unsubstituted $C_{1-6}$ alkyl (such as methyl, ethyl, n-propyl, isopropyl, n-butyl, iso-butyl, sec-butyl, tert-butyl, pentyl (straight-changed or branched) and hexyl (straight-chained or branched)), an unsubstituted $C_{1-6}$ haloalkyl (for example, —CHF$_2$, —CH$_2$F, —CF$_3$, —CHClF, —CH$_2$Cl, —CHCl$_2$, —CCl$_3$, —CH$_2$CHF$_2$, —CH$_2$CH$_2$F, —CH$_2$CF$_3$, —CH$_2$CHClF, —CH$_2$CH$_2$Cl, —CH$_2$CHCl$_2$, —CH$_2$CCl$_3$, —CH(CH$_3$)CF$_3$, —CH(CH$_3$)CHF$_2$, —C(CH$_3$)$_2$CF$_3$ and —C(CH$_3$)$_2$CHF$_2$), an unsubstituted $C_{1-6}$ alkoxy (for example, methoxy, ethoxy, isopropoxy, n-butoxy, sec-butoxy, isobutoxy and tert-butoxy), an unsubstituted acyl (such as —C(═O)—$C_{1-4}$ alkyl), an unsubstituted C-amido (such as —C(═O)NH$_2$ and —C(═O)NH—$C_{1-4}$ alkyl), an unsubstituted sulfonyl (for example, —S(═O)$_2$—$C_{1-4}$ alkyl), an optionally substituted $C_{3-6}$ cycloalkyl($C_{1-3}$)alkyl (such as —CH$_2$-cyclopropyl), an optionally substituted aryl (such as an optionally substituted phenyl), an optionally substituted aryl($C_{1-3}$)alkyl (such as an optionally substituted benzyl), an optionally substituted heteroaryl($C_{1-3}$)alkyl (such as an optionally substituted monocyclic heteroaryl($C_{1-3}$ alkyl), including an optionally substituted 5-membered heteroaryl ($C_{1-3}$ alkyl) and an optionally substituted 6-membered monocyclic heteroaryl($C_{1-3}$ alkyl)), an optionally substituted heterocyclyl($C_{1-3}$)alkyl (such as an optionally substituted monocyclic heterocyclyl($C_{1-3}$ alkyl), including an optionally substituted 5-membered heterocyclyl($C_{1-3}$ alkyl) and an optionally substituted 6-membered monocyclic heterocyclyl ($C_{1-3}$ alkyl)), an unsubstituted amino, a mono-substituted amine (such as an mono-alkyl substituted amine) and a di-substituted amine (such as a di-alkyl substituted amine). In some embodiments, the 6-, 7- or 8-membered monocyclic heterocyclyl formed by taking together $R^2$ and $R^3$ along with the atoms to which $R^2$ and $R^3$ are each attached can be mono-substituted. In other embodiments, the 6-, 7- or 8-membered monocyclic heterocyclyl formed by taking together $R^2$ and $R^3$ along with the atoms to which $R^2$ and $R^3$ are each attached can be unsubstituted.

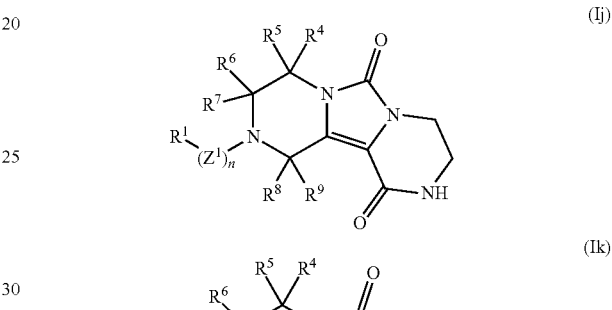
(Ij)

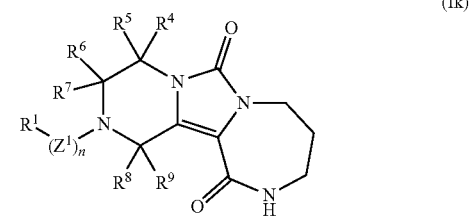
(Ik)

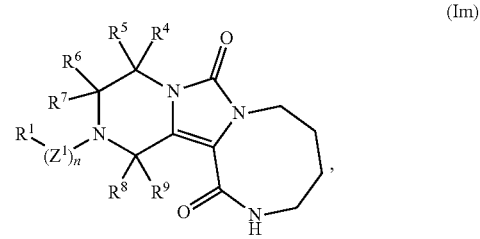
(Im)

wherein each of the aforementioned rings can be unsubstituted or substituted; and when substituted, one or more hydrogens (including the hydrogen attached to the shown nitrogen) can be replaced with a substituent recited for "optionally substituted," and any of those provided herein. When the hydrogen on the nitrogen is replaced of Formulae (Ij), (Ik) and (Im), a compound of Formula (I), or a pharmaceutically acceptable salt thereof can be

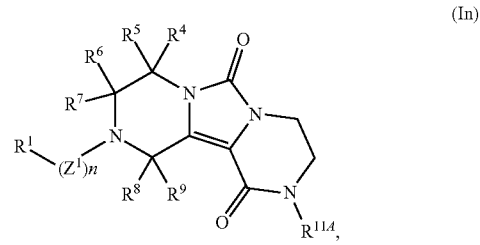
(In)

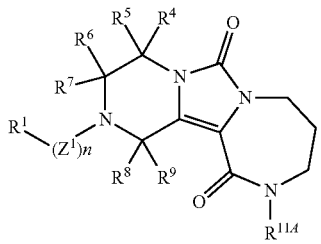
(Io)

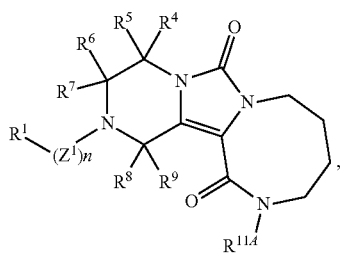
and
(Ip)

respectively, wherein $R^{11A}$ can be selected from those groups described herein with respect to $R^{11}$. In some embodiments, including those of this paragraph, the 6-membered, 7-membered and/or 8-membered heterocyclyls formed by taking together $R^2$ and $R^3$ can be unsubstituted. In other embodiments, including those of this paragraph, the 6-membered, 7-membered and/or 8-membered heterocyclyls formed by taking together $R^2$ and $R^3$ can be substituted 1, 2 or 3 times with a moiety independently selected from halogen, an unsubstituted $C_{1-4}$ alkyl, an unsubstituted $C_{2-4}$ alkenyl, hydroxy, an unsubstituted $C_{1-4}$ alkoxy, an unsubstituted $C_{1-4}$ hydroxyalkyl, an unsubstituted $C_{3-6}$ cycloalkyl $(C_{1-3})$alkyl (such as —$CH_2$-cyclopropyl) and an unsubstituted or a substituted aryl($C_1$ alkyl) (for example, an unsubstituted benzyl, —$CH(CH_3)$-phenyl and a methoxy-substituted benzyl). In some embodiments of Formula (Ij), (Ik) and/or (Im), n can be 0, such that $R^1$ can be directly attached to the heterocyclic rings. In other embodiments of Formula (Ij), (Ik) and/or (Im), n can be 1, and $Z^1$ can be —C(=O)—. In still other embodiments of Formula (Ij), (Ik) and/or (Im), n can be 1, and $Z^1$ can be —NH—C(=O)—. In yet still other embodiments of Formula (Ij), (Ik) and/or (Im), n can be 1, and Z can be —O—C(=O)—. When $R^{11A}$ is not hydrogen, in some embodiments, $R^{11A}$ can be an unsubstituted or a substituted $C_{1-4}$ alkyl or an unsubstituted or a substituted aryl($C_{1-4}$ alkyl) (such as an unsubstituted or a substituted benzyl), wherein the substituted $C_{1-4}$ alkyl can be substituted with an unsubstituted or a substituted $C_{3-6}$ cycloalkyl.

Examples of 6-membered, 7-membered and/or 8-membered heterocyclyls formed by taking together $R^2$ and $R^3$ include the following where "+" indicates the point of attachment to the nitrogen of $R^3$ and "*" indicates the point of attachment to carbon of $R^2$:

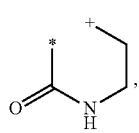 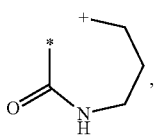 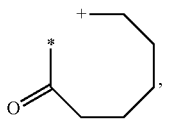

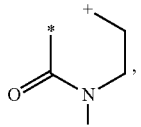
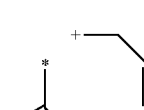
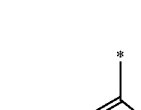
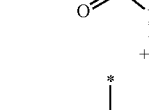
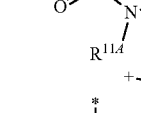
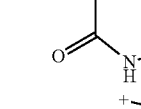
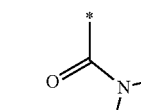
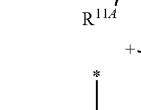
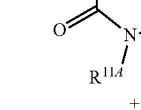
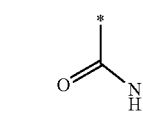
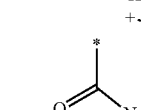
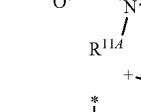
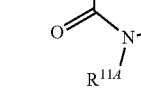
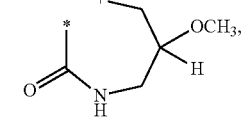

include moieties listed in the paragraph that describes "optionally substituted," and any of those provided herein, such as halogen, an unsubstituted $C_{1-4}$ alkyl, an unsubstituted $C_{1-4}$ alkoxy, an unsubstituted $C_{1-4}$ haloalkyl and an unsubstituted $C_{1-4}$ haloalkoxy (for example, —$OCF_3$, —$OCHF_2$ and —$OCH_2F$). In some embodiments, the 6-, 7- or 8-membered monocyclic heterocyclyl formed by taking together $R^2$ and $R^3$ along with the atoms to which $R^2$ and $R^3$ are each attached can be substituted with an unsubstituted benzyl. In some embodiments, the 6-, 7- or 8-membered monocyclic heterocyclyl formed by taking together $R^2$ and $R^3$ along with the atoms to which $R^2$ and $R^3$ are each attached can be substituted with a substituted benzyl (for example, (an unsubstituted $C_{1-4}$ alkoxy)-substituted benzyl).

In some embodiments, $R^2$ and $R^3$ can be taken together along with the atoms to which $R^2$ and $R^3$ are each attached to form an optionally substituted 9 to 14 membered spirocyclic heterocyclyl. For example, $R^2$ and $R^3$ can be taken together along with the atoms to which $R^2$ and $R^3$ are each attached to form an optionally substituted spiro[7.3]heterocyclyl or an optionally substituted spiro[8.3]heterocyclyl. In some embodiments, $R^2$ and $R^3$ can be taken together along with the atoms to which $R^2$ and $R^3$ are each attached to form an optionally substituted 9 to 14 membered spirocyclic heterocyclyl having the general structure

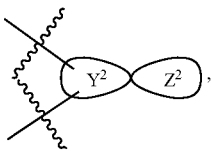

wherein Ring $Y^2$ can be a 7-membered or 8-membered heterocyclyl; and Ring $Z^2$ can be a 3-membered cycloalkyl, a 4-membered cycloalkyl or a 4-membered heterocyclyl. In some embodiments, Ring $Z^2$ can be an optionally substituted oxetane, an optionally substituted thietane, an optionally substituted thietane oxide or an optionally substituted thietane dioxide. Examples of $R^2$ and $R^3$ being taken together along with the atoms to which $R^2$ and $R^3$ are each attached to form an optionally substituted 9 to 14 membered spirocyclic heterocyclyl include

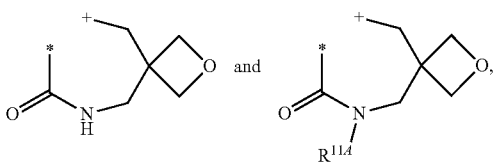

where "+" indicates the point of attachment to the nitrogen of $R^3$ and "*" indicates the point of attachment to carbon of $R^2$; and $R^{11A}$ can be $R^{11}$. In some embodiments, $R^{11A}$ can be an unsubstituted or a substituted $C_{1-4}$ alkyl or an unsubstituted or a substituted aryl($C_{1-4}$ alkyl) (such as an unsubstituted or a substituted benzyl), wherein the substituted $C_{1-4}$ alkyl can be substituted with an unsubstituted or a substituted $C_{3-6}$ cycloalkyl.

In addition to the groups described herein that can be attached to the piperazine ring of the 5,6,7,8-tetrahydroimidazo[1,5-a]pyrazin-3(2H)-one group of Formula (I), the piperazine ring can be further unsubstituted or substituted. In some embodiments, $R^4$ can be hydrogen. In other embodiments, $R^4$ can be an unsubstituted $C_{1-4}$ alkyl. For example, $R^4$ can be methyl, ethyl, n-propyl, iso-propyl, n-butyl, iso-butyl, sec-butyl and tert-butyl. In still other embodiments, $R^4$ can be an unsubstituted $C_{1-4}$ haloalkyl. Suitable unsubstituted $C_{1-4}$ haloalkyls are described herein, and include —CHF$_2$, —CH$_2$F, —CF$_3$, —CH$_2$Cl, —CHCl$_2$ and —CCl$_3$. In yet still other embodiments, $R^4$ can be an optionally substituted aryl (such as an optionally phenyl), an optionally substituted heteroaryl (such as an optionally substituted monocyclic heteroaryl) or an optionally substituted heterocyclyl (for example, an optionally substituted monocyclic heterocyclyl). The heteroaryl and heterocyclyl can include 3, 4, 5 or 6 ring(s) atoms. In some embodiments, $R^4$ can be an optionally substituted aryl($C_{1-4}$ alkyl), an optionally substituted heteroaryl($C_{1-4}$ alkyl) or an optionally substituted heterocyclyl($C_{1-4}$ alkyl).

In some embodiments, $R^5$ can be hydrogen. In other embodiments, $R^5$ can be an unsubstituted $C_{1-4}$ alkyl. In still other embodiments, $R^5$ can be an unsubstituted $C_{1-4}$ haloalkyl. Exemplary unsubstituted $C_{1-4}$ alkyls and unsubstituted $C_{1-4}$ haloalkyls are described herein and include those described with respect to $R^4$. In yet still other embodiments, $R^5$ can be an optionally substituted aryl, an optionally substituted heteroaryl or an optionally substituted heterocyclyl. In some embodiments, $R^5$ can be an optionally substituted aryl($C_{1-4}$ alkyl), an optionally substituted heteroaryl ($C_{1-4}$ alkyl) or an optionally substituted heterocyclyl($C_{1-4}$ alkyl). For example, $R^5$ can be an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl). In other embodiments, $R^4$ and $R^5$ can be taken together along with the carbon to which $R^4$ and $R^5$ are attached to form an optionally substituted monocyclic $C_{3-6}$ cycloalkyl or an optionally substituted 3 to 6 member monocyclic heterocyclyl. Exemplary monocyclic $C_{3-6}$ cycloalkyls and 3 to 6 member monocyclic heterocyclyls include, but are limited to, the following: cyclopropyl, cyclobutyl, cyclopentyl, cyclohexyl, oxetane, thietane, thietane oxide and thietane dioxide, each of the aforementioned can be optionally substituted.

In some embodiments, $R^6$ can be hydrogen. In other embodiments, $R^6$ can be halogen, such as F or Cl. In still other embodiments, $R^6$ can be an unsubstituted $C_{1-4}$ alkyl, such as those described herein. In yet still other embodiments, $R^6$ can be an unsubstituted $C_{1-4}$ haloalkyl, for example, —CHF$_2$, —CH$_2$F, —CF$_3$, —CH$_2$Cl, —CHCl$_2$ and —CCl$_3$. In some embodiments, $R^6$ can be an optionally substituted $C_{3-4}$ cycloalkyl (such as an unsubstituted or a substituted cyclopropyl and an unsubstituted or a substituted cyclobutyl). In other embodiments, $R^6$ can be an optionally substituted aryl, an optionally substituted heteroaryl or an optionally substituted heterocyclyl. In still other embodiments, $R^6$ can be an optionally substituted aryl($C_{1-4}$ alkyl), an optionally substituted heteroaryl($C_{1-4}$ alkyl) or an optionally substituted heterocyclyl($C_{1-4}$ alkyl). In yet still other embodiments, $R^6$ can be an optionally substituted phenyl, an optionally substituted monocyclic heteroaryl or an optionally substituted monocyclic heterocyclyl.

In some embodiments, $R^7$ can be hydrogen. In other embodiments, $R^6$ can be halogen, such as F or Cl. In still other embodiments, $R^7$ can be an unsubstituted $C_{1-4}$ alkyl. In yet still other embodiments, $R^7$ can be an unsubstituted $C_{1-4}$ haloalkyl. For example, $R^7$ can be methyl, ethyl, n-propyl, iso-propyl, n-butyl, iso-butyl, sec-butyl, tert-butyl, —CHF$_2$, —CH$_2$F, —CF$_3$, —CH$_2$Cl, —CHCl$_2$ and —CCl$_3$. In some embodiments, $R^7$ can be an optionally substituted $C_{3-4}$ cycloalkyl (such as an unsubstituted or a substituted cyclopropyl and an unsubstituted or a substituted cyclobutyl). In other embodiments, $R^7$ can be an optionally substituted aryl, an optionally substituted heteroaryl or an optionally substituted heterocyclyl. In still other embodiments, $R^7$ can be an optionally substituted aryl($C_{1-4}$ alkyl), an optionally substituted heteroaryl($C_{1-4}$ alkyl) or an optionally substituted heterocyclyl($C_4$ alkyl). Exemplary $R^7$ groups include, but are not limited to, an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl). In yet still other embodiments, $R^6$ and $R^7$ can be taken together along with the carbon to which $R^6$ and $R^7$ are attached to form an optionally substituted monocyclic $C_{3-6}$ cycloalkyl or an optionally substituted 3 to 6 member monocyclic heterocyclyl. For example, $R^6$ and $R^7$ can be taken together along with the carbon to which $R^6$ and $R^7$ are attached to form an optionally substituted cyclopropyl, an optionally substituted cyclobutyl, an optionally substituted cyclopentyl, an optionally substituted cyclohexyl, an optionally substituted oxetane, an optionally substituted thietane, an optionally substituted thietane oxide or an optionally substituted thietane dioxide.

In some embodiments, $R^4$ and $R^6$ can be taken together along with the carbons to which $R^4$ and $R^6$ are each attached to form an optionally substituted monocyclic $C_{5-7}$ cycloalkyl. In other embodiments, $R^4$ and $R^6$ can be taken together along with the carbons to which $R^4$ and $R^6$ are each attached to form an optionally substituted 5 to 7 member monocyclic heterocyclyl. In some embodiments, $R^5$ and $R^7$ can be taken together along with the carbons to which $R^5$ and $R^7$ are each attached to form an optionally monocyclic $C_{5-7}$ cycloalkyl. In other embodiments, $R^5$ and $R^7$ can be taken together along with the carbons to which $R^5$ and $R^7$ are each attached to form an optionally substituted 5 to 7 member monocyclic heterocyclyl. Exemplary 5 to 7 member monocyclic heterocyclyls include, but are not limited to, tetrahydrofuran, pyrrolidine, piperidine and tetrahydro-2H-pyran.

In some embodiments, $R^8$ can be hydrogen. In other embodiments, $R^8$ can be an unsubstituted $C_{1-4}$ alkyl. In still other embodiments, $R^8$ can be an unsubstituted $C_{1-4}$ haloalkyl. Suitable unsubstituted $C_{1-4}$ alkyls and unsubstituted $C_{1-4}$ haloalkyls include methyl, ethyl, n-propyl, iso-propyl, n-butyl, iso-butyl, sec-butyl, tert-butyl, —CHF$_2$, —CH$_2$F, —CF$_3$, —CH$_2$Cl, —CHCl$_2$ and —CCl$_3$.

In some embodiments, $R^9$ can be hydrogen. In other embodiments, $R^9$ can be an unsubstituted $C_{1-4}$ alkyl, such as methyl, ethyl, n-propyl, iso-propyl, n-butyl, iso-butyl, sec-butyl or tert-butyl. In still other embodiments, $R^9$ can be an unsubstituted $C_{1-4}$ haloalkyl, for example, —CHF$_2$, —CH$_2$F, —CF$_3$, —CH$_2$Cl, —CHCl$_2$ and —CCl$_3$. In some embodiments, $R^8$ and $R^9$ are taken together along with the carbon to which $R^8$ and $R^9$ are attached to form an unsubstituted monocyclic $C_{3-4}$ cycloalkyl. In other embodiments, $R^8$ and $R^9$ are taken together along with the carbon to which $R^8$ and $R^9$ are attached to form a substituted monocyclic $C_{3-4}$ cycloalkyl. In still other embodiments, $R^8$ and $R^9$ are taken together along with the carbon to which $R^8$ and $R^9$ are attached to form an unsubstituted oxetane or an unsubstituted thietane. In yet still other embodiments, $R^8$ and $R^9$ are taken together along with the carbon to which $R^8$ and $R^9$ are attached to form a substituted oxetane or a substituted thietane.

In some embodiments, $R^4$, $R^5$, $R^6$, $R^7$, $R^8$ and $R^9$ can be each hydrogen. In other embodiments, at least one of $R^4$, $R^5$, $R^6$, $R^7$, $R^8$ and $R^9$ can be a non-hydrogen group, such as those described herein in the previous paragraphs. In other embodiments, $R^4$, $R^5$, $R^6$ and $R^7$ can be each hydrogen, and $R^8$ and $R^9$ are taken together along with the carbon to which $R^8$ and $R^9$ are attached to form an optionally substituted monocyclic $C_{3-4}$ cycloalkyl, an optionally substituted oxetane or an optionally substituted thietane. When at one of $R^4$, $R^5$, $R^6$, $R^7$, $R^8$ and $R^9$ is a non-hydrogen group, at least one of $R^4$, $R^5$, $R^6$, $R^7$, $R^8$ and $R^9$ can be an unsubstituted $C_{1-4}$ alkyl (for example, methyl), an unsubstituted $C_{3-4}$ cycloalkyl or halogen (such as F or Cl). In some embodiments, $R^4$, $R^5$, $R^7$, $R^8$ and $R^9$ can be each hydrogen; and $R^6$ can be an unsubstituted $C_{1-4}$ alkyl (such as methyl), an unsubstituted $C_3\_4$ cycloalkyl or halogen (such as F or Cl). When at least one of $R^4$, $R^5$, $R^6$, $R^7$, $R^8$ and $R^9$ is a non-hydrogen group, a stereocenter may be formed. In some embodiments, the stereocenter that is formed can be in the (R)-configuration. In other embodiments, the stereocenter that is formed can be in the (S)-configuration.

In some embodiments, n can be 0 or 1; $Z^1$ can be —C(=O)—, —NH—C(=O)— and —O—C(=O)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ can be selected from —C(=O)$NR^{10}R^{11}$, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl); $R^3$ can be selected from hydrogen, an optionally substituted cycloalkyl, an optionally substituted cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); or $R^2$ and $R^3$ can be taken together along with the atoms to which $R^2$ and $R^3$ are each attached to form an optionally substituted 6, 7 or 8 membered monocyclic heterocyclyl or an optionally substituted 9 to 14 membered spirocyclic heterocyclyl; $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); or $R^4$ and $R^5$ can be taken together along with the carbon to which $R^4$ and $R^5$ are attached to form an optionally substituted monocyclic $C_{3-6}$ cycloalkyl or an optionally substituted 3 to 6 member monocyclic heterocyclyl; or $R^6$ and $R^7$ can be taken together along with the carbon to which $R^6$ and $R^7$ are attached to form an optionally substituted monocyclic $C_{3-6}$ cycloalkyl or an optionally substituted 3 to 6 member monocyclic heterocyclyl; or $R^4$ and $R^6$ can be taken together along with the carbons to which $R^4$ and $R^6$ are each attached to form an optionally monocyclic $C_{5-7}$ cycloalkyl or an optionally substituted 5 to 7 member monocyclic heterocyclyl; or $R^5$ and $R^7$ can be taken together along with the carbons to which $R^5$ and $R^7$ are each attached to form an optionally monocyclic $C_{5-7}$ cycloalkyl or an optionally substituted 5 to 7 member monocyclic heterocyclyl; $R^8$ and $R^9$ can be independently selected from hydrogen, an unsubstituted $C_{1-4}$ alkyl and an unsubstituted $C_{1-4}$ haloalkyl; or $R^8$ and $R^9$ can be taken together along with the carbon to which $R^8$ and $R^9$ are attached to form an optionally substituted monocyclic $C_{3-4}$ cycloalkyl, an optionally substituted oxetane or an optionally substituted thietane; and $R^{10}$ and $R^{11}$ can be independently selected from the hydrogen, an optionally substituted $C_{1-4}$ alkyl, an optionally substituted $C_{2-6}$ alkenyl, an optionally substituted $C_{2-6}$ alkynyl, an optionally substituted $C_{3-8}$ cycloalkyl, an optionally substituted $C_{3-8}$ cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); or $R^{10}$ and $R^{11}$ can be taken together along with the nitrogen to which $R^{10}$ and $R^{11}$ are attached to form an optionally substituted 4 to 8 member monocyclic heterocyclyl or an optionally substituted 7 to 12 member bicyclic heterocyclyl. In other embodiments, n can be 1; $Z^1$ can be —C(=O)—; $R^1$ can be an optionally substituted aryl or an optionally substituted heteroaryl; $R^2$ can be —C(=O)$NR^{10}R^{11}$; $R^3$ can be an optionally substituted aryl or an optionally substituted heteroaryl; $R^4$ and $R^5$ can be independently selected from hydrogen, an unsubstituted $C_{1-4}$ alkyl and an unsubstituted $C_{1-4}$ haloalkyl; $R^6$ and $R^7$ can be independently selected from hydrogen, an unsubstituted $C_{1-4}$ alkyl and an unsubstituted $C_{1-4}$ haloalkyl; $R^8$ and $R^9$ can be independently selected from hydrogen, an unsubstituted $C_{1-4}$ alkyl and an unsubstituted $C_{1-4}$ haloalkyl; and $R^{10}$ and $R^{11}$ can be independently selected from the hydrogen, an optionally substituted $C_{1-6}$ alkyl (including an optionally substituted $C_{1-4}$ alkyl), an optionally substituted $C_{2-6}$ alkenyl, an optionally substituted $C_{2-6}$ alkynyl, an optionally substituted $C_{3-8}$ cycloalkyl, an optionally substituted $C_{3-8}$ cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). In still other embodiments, n can be 1; $Z^1$ can be —NH—C(=O)—; $R^1$ can be an optionally substituted aryl or an optionally substituted heteroaryl; $R^2$ can be —C(=O)$NR^{10}R^{11}$; $R^3$ can be an optionally substituted aryl or an optionally substituted heteroaryl; $R^4$ and $R^5$ can be independently selected from hydrogen, an unsubstituted $C_{1-4}$ alkyl and an unsubstituted $C_{1-4}$ haloalkyl; $R^6$ and $R^7$ can be independently selected from hydrogen, an unsubstituted $C_{1-4}$ alkyl and an unsubstituted $C_{1-4}$ haloalkyl; $R^8$ and $R^9$ can be independently selected from hydrogen, an unsubstituted $C_{1-4}$ alkyl and an unsubstituted $C_{1-4}$ haloalkyl; and $R^{10}$ and $R^{11}$ can be independently selected from the hydrogen, an optionally substituted $C_{1-6}$ alkyl (including an optionally substituted $C_{1-4}$ alkyl), an optionally substituted $C_{2-6}$ alkenyl, an optionally substituted $C_{2-6}$ alkynyl, an optionally substituted $C_{3-8}$ cycloalkyl, an optionally substituted $C_{3-8}$ cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). In some embodiments, n can be 1; $Z^1$ can be —C(=O)—; $R^1$ can be an optionally substituted aryl or an optionally substituted heteroaryl; $R^2$ can be an optionally substituted heteroaryl; $R^3$ can be an optionally substituted aryl or an optionally substituted heteroaryl; $R^4$ and $R^5$ can be independently selected from hydrogen, an unsubstituted $C_{1-4}$ alkyl and an unsubstituted $C_{1-4}$ haloalkyl; $R^6$ and $R^7$ can be independently selected from hydrogen, an unsubstituted $C_{1-4}$ alkyl and an unsubstituted $C_{1-4}$ haloalkyl; $R^8$ and $R^9$ can be independently selected from hydrogen, an unsubstituted $C_{1-4}$ alkyl and an unsubstituted $C_{1-4}$ haloalkyl; and $R^{10}$ and $R^{11}$ can be independently selected from the hydrogen, an optionally substituted $C_{1-6}$ alkyl (including an optionally substituted $C_{1-4}$ alkyl), an optionally substituted $C_{2-6}$ alkenyl, an optionally substituted $C_{2-6}$ alkynyl, an optionally substituted $C_{3-8}$ cycloalkyl, an optionally substituted $C_{3-8}$ cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). In other embodiments, n can be 1; $Z^1$ can be —NH—C(=O)—; $R^1$ can be an optionally substituted aryl or an optionally substituted heteroaryl; $R^2$ can be an optionally substituted heteroaryl; $R^3$ can be an optionally substituted aryl or an optionally substituted heteroaryl; $R^4$ and $R^5$ can be independently selected from hydrogen, an unsubstituted $C_{1-4}$ alkyl and an unsubstituted $C_{1-4}$ haloalkyl; $R^6$ and $R^7$ can be independently selected from hydrogen, an unsubstituted $C_{1-4}$ alkyl and an unsubstituted $C_{1-4}$ haloalkyl; $R^8$ and $R^9$ can be independently selected from hydrogen, an unsubstituted $C_{1-4}$ alkyl and an unsubstituted $C_{1-4}$ haloalkyl; and $R^{10}$ and $R^{11}$ can be independently selected from the hydrogen, an optionally substituted $C_{1-6}$ alkyl (including an optionally substituted $C_{1-4}$ alkyl), an optionally substituted $C_{2-6}$ alkenyl, an optionally substituted $C_{2-6}$ alkynyl, an optionally substituted $C_{3-8}$ cycloalkyl, an optionally substituted $C_{3-8}$ cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). In still other embodiments, n can be 1; $Z^1$ can be —C(=O)—; $R^1$ can be an optionally substituted aryl or an optionally substituted heteroaryl; $R^2$ and $R^3$ can be taken together along with the atoms to which $R^2$ and $R^3$ are each attached to form an optionally substituted 6, 7 or 8 membered monocyclic heterocyclyl; $R^4$ and $R^5$ can be independently selected from hydrogen, an unsubstituted $C_{1-4}$ alkyl and an unsubstituted $C_{1-4}$ haloalkyl; $R^6$ and $R^7$ can be independently selected from hydrogen, an unsubstituted $C_{1-4}$ alkyl and an unsubstituted $C_{1-4}$ haloalkyl; $R^8$ and $R^9$ can be independently selected from hydrogen, an unsubstituted $C_{1-4}$ alkyl and an unsubstituted $C_{1-4}$ haloalkyl; and $R^{10}$ and $R^{11}$ can be independently selected from the hydrogen, an optionally substituted $C_{1-6}$ alkyl (including an optionally substituted $C_{1-4}$ alkyl), an optionally substituted $C_{2-6}$ alkenyl, an optionally substituted $C_{2-6}$ alkynyl, an optionally substituted $C_{3-8}$ cycloalkyl, an optionally substituted $C_{3-8}$ cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). In yet still other embodiments, n can be 1; $Z^1$ can be —NH—C(=O)—; $R^1$ can be an optionally substituted aryl or an optionally substituted heteroaryl; $R^2$ and $R^3$ can be taken together along with the atoms to which $R^2$ and $R^3$ are each attached to form an optionally substituted 6, 7 or 8 membered monocyclic heterocyclyl; $R^4$ and $R^5$ can be independently selected from hydrogen, an unsubstituted $C_{1-4}$ alkyl and an unsubstituted $C_{1-4}$ haloalkyl; $R^6$ and $R^7$ can be independently selected from hydrogen, an unsubstituted $C_{1-4}$ alkyl and an unsubstituted $C_{1-4}$ haloalkyl; $R^8$ and $R^9$ can be independently selected from hydrogen, an unsubstituted $C_{1-4}$ alkyl and an unsubstituted $C_{1-4}$ haloalkyl; and $R^{10}$ and $R^{11}$ can be independently selected from the hydrogen, an optionally substituted $C_{1-4}$ alkyl, an optionally substituted $C_{2-6}$ alkenyl, an optionally substituted $C_{2-6}$ alkynyl, an optionally substituted $C_{3-8}$ cycloalkyl, an optionally substituted $C_{3-8}$ cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl).

In some embodiments, a compound of Formula (I), or a pharmaceutically acceptable thereof, can be selected from Formula (Ia), Formula (Ib), Formula (Ic), Formula (Id), Formula (Ie), Formula (If), Formula (Ig) and Formula (Ih):

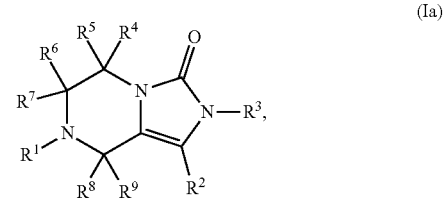

(Ia)

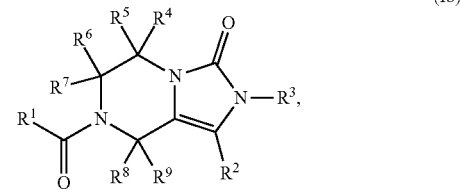

(Ib)

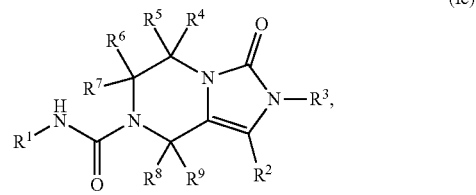

(Ic)

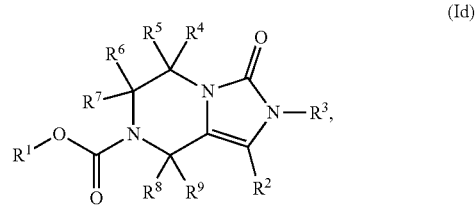

(Id)

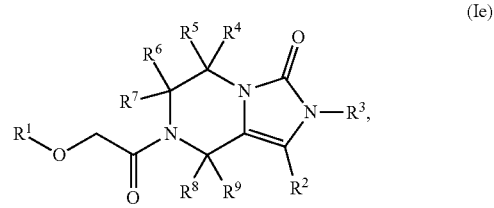

(Ie)

(If) 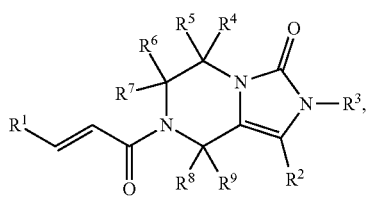

(Ig) 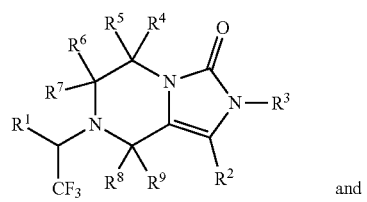

and (Ih) 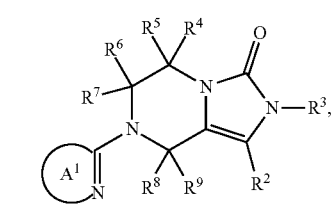

or a pharmaceutically acceptable salt of any of the foregoing. In other embodiments, a compound of Formula (I), or a pharmaceutically acceptable thereof, can be selected from Formula (Ii), Formula (Ij), Formula (Ik), Formula (Im), Formula (In), Formula (Jo) and Formula (Ip):

(Ii) 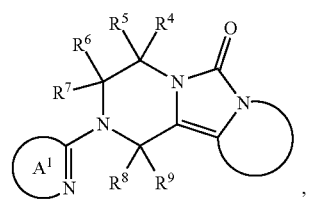

(Ij) 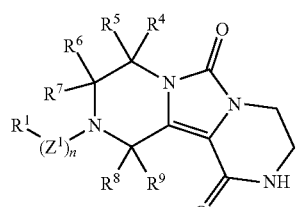

(Ik) 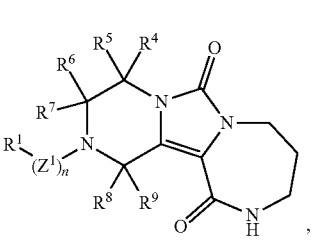

(Im) 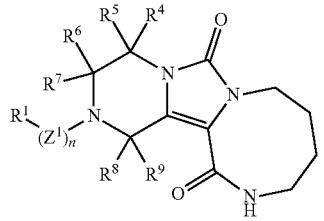

(In) 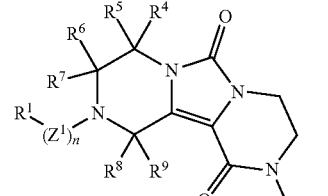

(Io) 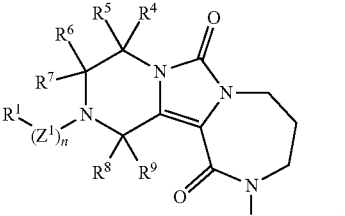

and (Ip) 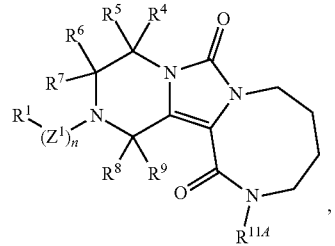

or a pharmaceutically acceptable salt of any of the foregoing. In some embodiments of this paragraph, $R^4$, $R^5$, $R^6$, $R^7$, $R^8$ and $R^9$ can be each hydrogen. In some embodiments of this paragraph, $R^3$ can be an unsubstituted or a substituted phenyl. In other embodiments, of this paragraph, $R^3$ can be an unsubstituted or a substituted benzyl. As provided herein the phenyl and/or the benzyl of $R^3$ can be substituted with one or more substituents independently selected from halogen, cyano, an unsubstituted $C_{1-6}$ alkyl, an optionally substituted 5-membered and 6-membered monocyclic heteroaryl, an optionally substituted 4-membered, 5-membered and 6-membered monocyclic heterocyclyls, an unsubstituted $C_{1-6}$ haloalkyl, an unsubstituted $C_{1-6}$ alkoxy, an unsubstituted $C_{1-6}$ haloalkoxy, —O-(an unsubstituted $C_{1-4}$ alkyl)-OH, —O-(an unsubstituted $C_{1-4}$ alkyl)-(an unsubstituted alkoxy), —O-(an unsubstituted $C_{1-4}$ alkyl)-(an unsubstituted C-carboxy), —O-(an unsubstituted $C_{1-4}$ alkyl)-NH$_2$, —O-(an unsubstituted $C_{1-4}$ alkyl)-NH (an unsubstituted $C_{1-4}$ alkyl), —O-(an unsubstituted $C_{1-4}$ alkyl)-N (an unsubstituted $C_{1-4}$ alkyl)$_2$, an unsubstituted —O-(an unsubstituted $C_{1-4}$ alkyl)-CN, an unsubstituted C-amido, an unsubstituted sulfenyl, an unsubstituted sulfonyl, an unsubstituted S-sulfonamido, an unsubstituted amino, a mono-alkyl substituted amine) and a di-alkyl substituted amine). In some embodiments of this paragraph, $R^1$ can be an unsubstituted or a substituted phenyl. The phenyl of $R^1$ can be substituted, for example, substituted with one or more substituents selected from halogen (such as F, Cl and/or Br), cyano and an unsubstituted $C_{1-6}$ alkyl (such as methyl).

Examples of compounds of Formula (I), including pharmaceutically acceptable salts thereof, are those provided in Table A, and compounds 1, 2, 3, 4, 5, 6, 7, 8, 9, 10, 11, 12, 13, 14 and 15 provided therein, including pharmaceutically acceptable salts thereof.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

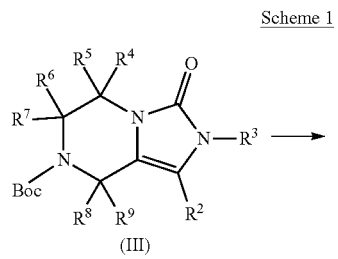

(III)

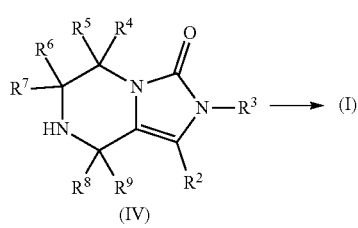

(IV)

Compounds of Formula (I), along with pharmaceutically acceptable salts thereof, can be prepared from an intermediate of Formula (III) by cleaving the Boc protecting group in acidic condition, for instance, by using HCl in a suitable solvent or by using cupper triflate to give an intermediate of Formula (IV). Compounds of Formula (I), and pharmaceutically acceptable salts thereof, can be obtained by methods know in the art. For instance, ureas of Formula (I) having $Z^1$ being —NH—C(=O)— and n=1, can be obtained by coupling Formula (IV) with a carbamate (for example, $R^1$NHC(=O)—OPh). Alternatively, acyls of Formula (I) having $Z^1$ being —C(=O)— and n=1, can be obtained by coupling Formula (IV) with an acyl chloride, such as an acyl chloride of the general formula $R^1$—C(=O)—Cl, or by using an acid (such as R—C(=O)—OH) in presence of a suitable coupling agent. Other $R^1$—$(Z^1)$n- group can be introduced by methods known in those skilled in the art.

Scheme 2

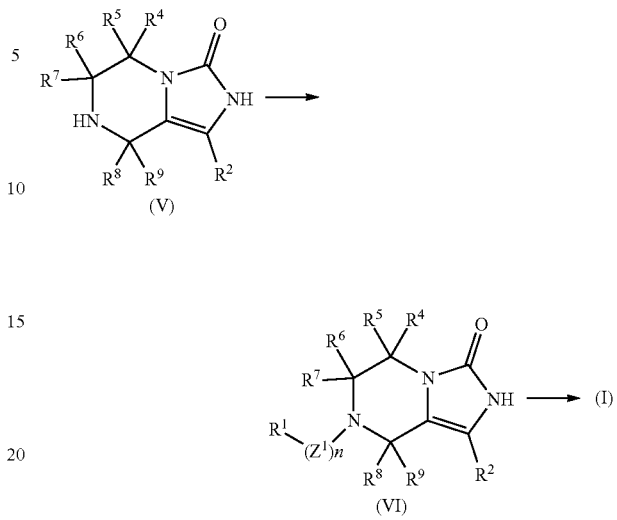

Alternatively, compounds of Formula (I), along with pharmaceutically acceptable salts thereof, can be prepared from an intermediate of Formula (V) following methods known to those skilled in the art as shown in Scheme 2. For instance, ureas of Formula (VI) having $Z^1$ being —NH—C(=O)— and n=1, can be obtained by coupling intermediate of Formula (V) with a carbamate, such as $R^1$NHC(=O)—OPh. Alternatively, an acyl of Formula (VI) having $Z^1$ being —C(=O)— and n=1, can be obtained by coupling Formula (V) with an acyl chloride of general formula $R^1$—C(=O)—$C_1$ or by using an acid of general formula $R^1$—C(=O)—OH in presence of a suitable coupling agent, such as EDCI/HOAT. Other $R^1$—$(Z^1)$n- groups can be introduced by methods known in the art. Compounds of Formula (I), along with pharmaceutically acceptable salts thereof, can be obtained from Formula (VI) by using an alkylating agent of general formula $R^3$—Halo, wherein Halo can be chloro, bromo or iodo, in presence of a suitable base (for example, potassium carbonate) in a suitable solvent. Alternatively, compounds of Formula (I), along with pharmaceutically acceptable salts thereof, can be obtained by a Mitsunobu reaction using an alcohol of general formula $R^3$—OH in a suitable solvent. Other compounds of Formula (I), along with pharmaceutically acceptable salts thereof, can be prepared using Formula (VI) using a boronic acid of general formula $R^3$—B(OH)$_2$, and a catalyst (such as Cu(AcO)$_2$) in presence of a base. Other compounds of Formula (I), along with pharmaceutically acceptable salts thereof, can be prepared from Formula (VI) using a halogenated aryl or heteroaryl $R^3$—Halo, where Halo can be iodo, bromo or chloro, in the presence of copper iodide, potassium carbonate and $N^1,N^2$-dimethylethane-1,2-diamine, in a solvent like DMSO under heating conditions. Other compounds of Formula (I), along with pharmaceutically acceptable salts thereof, can be prepared from Formula (VI) using a halogenated aryl or heteroaryl $R^3$—Halo, where Halo can be iodo, bromo or chloro, in the presence of a palladium catalyst such as Pd$_2$dba$_3$, a ligand such as Xantphos, a base (such as cesium carbonate) in a suitable solvent (for example, dioxane) under heating conditions. Other $R^3$ substituents can be introduced to Formula (VI) using methods known to those skilled the art.

Scheme 3

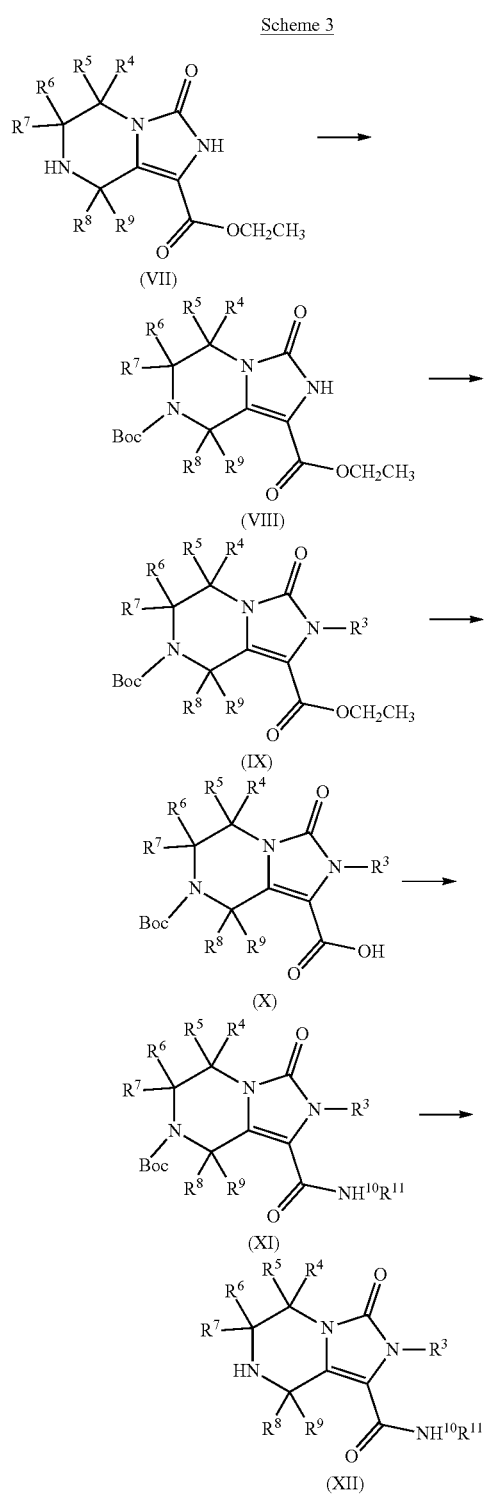

Compounds of Formula (I), and pharmaceutically acceptable salts thereof, wherein $R^2$ can be —C(=O)NR$^{10}$R$^{11}$ can be prepared as shown in Scheme 3. Intermediate of Formula (VII) can be protected using a Boc group to give a compound of Formula (VIII). The $R^3$ substituent can be introduced by method known in the art. For instance, intermediate of Formula (IX) can be obtained from an intermediate of Formula (VIII) by using an alkylating agent of general formula $R^3$—Halo, with Halo can be chloro, bromo or iodo, in presence of a base (for example, potassium carbonate) in a suitable solvent. Alternatively, Formula (IX) can be obtained by a Mitsunobu reaction using an alcohol of general formula $R^3$—OH in a suitable solvent. Other compounds of Formula (IX) can be prepared using Formula (VIII), a boronic acid of general formula $R^3$—B(OH)$_2$, and a catalyst (such as Cu(AcO)$_2$), in presence of a suitable base. Other compounds of Formula (IX) can be prepared from Formula (VIII) using a halogenated aryl or heteroaryl $R^3$—Halo, where Halo can be iodo, bromo or chloro, in the presence of copper iodide, potassium carbonate and N$^1$,N$^2$-dimethylethane-1,2-diamine, in a solvent like DMSO under heating conditions. Other compounds of Formula (IX) can be prepared from Formula (VIII) using a halogenated aryl or heteroaryl $R^3$—Halo, where Halo can be iodo, bromo or chloro, in the presence of a palladium catalyst such as Pd$_2$dba$_3$, a ligand such as Xantphos, a base like cesium carbonate in a suitable solvent like dioxane under heating conditions. Other methods known in the art to functionalize lactams can also be used. The ester of Formula (IX) can be saponified using lithium hydroxide or another suitable agent to give an intermediate of Formula (X). The coupling of Formula (X) with an amine of general formula HNR$^{10}$R$^{11}$ can be achieved using a coupling agent, such as EDCI/HOAT, in a suitable solvent to provide intermediate of Formula (XI). The Boc protecting group of Formula (XI) can be removed either by an acid (for example, HCl), by using cupper triflate or using other methods known in the art to obtain compound of Formula (XII). Compounds of Formula (I), along with pharmaceutically acceptable salts thereof, can be obtained from a compound of Formula (XII) following methods known in the art. For example, ureas (wherein Z$^1$ being —NH—C(=O)— and n=1) can be obtained by coupling Formula (XII) with a carbamate of general formula R$^1$NHC(=O)—OPh. Alternatively, acyls (wherein Z$^1$ being —C(=O)— and n=1) can be obtained by coupling Formula (XII) with an acyl chloride of general formula R$^1$—C(=O)—C$_1$ or by using an acid of general formula R—C(=O)—OH in presence of a suitable coupling agent (such as EDCI/HOAT). Other R$^1$—(Z$^1$)n- group can be introduced by methods known by those skilled in the art.

Scheme 4

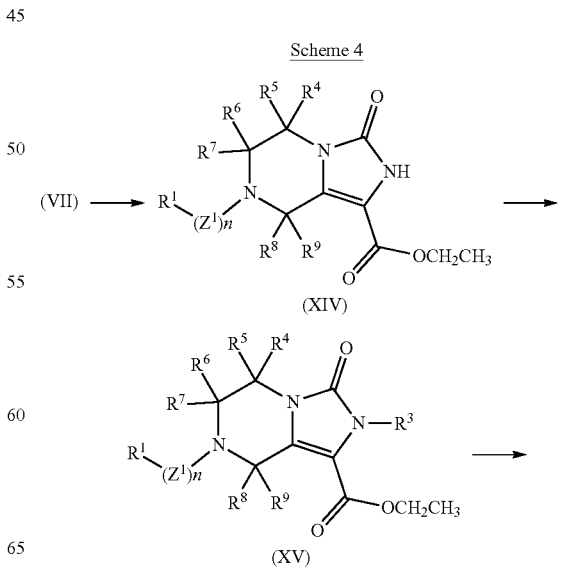

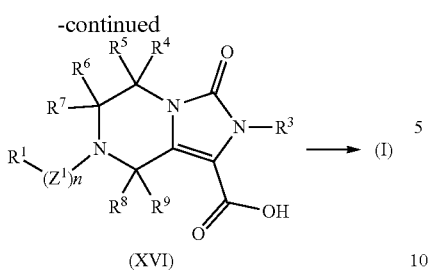

(XVI)

Alternatively, compounds of Formula (I), and pharmaceutically acceptable salts thereof, wherein $R^2$ can be —C(=O)NR$^{10}$R$^{11}$, can be synthesized following the procedure provided in Scheme 4. The intermediates of Formula (XIV) can be obtained from a compound of Formula (VII) following methods known in the art. For instance, ureas of Formula (XIV) having $Z^1$ being —NH—C(=O)— and n=1, can be obtained by coupling Formula (VII) with a carbamate of general formula R$^1$NHC(=O)—OPh. Alternatively, acyls of Formula (XIV) having $Z^1$ being —C(=O)— and n=1, can be obtained by coupling Formula (VII) with an acyl chloride of general formula R$^1$—C(=O)—Cl or by using an acid of general formula R$^1$—C(=O)—OH in presence of a suitable coupling agent (such as EDCI/HOAT). Other R$^1$—(Z$^1$)n- group can be introduced by methods known in the art. The R$^3$ substituent can be introduced by procedures known in the art. For instance, compounds of Formula (XV) can be obtained from Formula (XIV) by using an alkylating agent of general formula R$^3$—Halo, with Halo being chloro, bromo or iodo, in presence of a base (such as potassium carbonate) in a suitable solvent. Alternatively, Formula (XV) can be obtained by a Mitsunobu reaction using an alcohol of general formula R$^3$—OH in a suitable solvent. Other compounds of Formula (XV) can be prepared using Formula (XIV) using a boronic acid of general formula R$^3$—B(OH)$_2$, and a catalyst such as Cu(AcO)$_2$, in presence of a base. Other compounds of Formula (XV) can be prepared from Formula (XIV) using a halogenated aryl or heteroaryl R$^3$—Halo, where Halo can be iodo, bromo or chloro, in the presence of copper iodide, potassium carbonate and N$^1$,N$^2$-dimethylethane-1,2-diamine, in a solvent like DMSO under heating conditions. Other compounds of Formula (XV) can be prepared from Formula (XIV) using a halogenated aryl or heteroaryl R$^3$—Halo, where Halo can be iodo, bromo or chloro, in the presence of a palladium catalyst such as Pd$_2$dba$_3$, a ligand such as Xantphos, a base like cesium carbonate in a suitable solvent like dioxane under heating conditions. Other R$^3$ group can be introduced using known procedures for functionalization of lactams. Compounds of Formula (XV) can be saponified using lithium hydroxide or sodium hydroxide or another suitable agent to provide Formula (XVI). The coupling of an acid of Formula (XVI) with an amine of general formula HNR$^{10}$R$^{11}$ can be achieved using coupling agents, such as EDCI/HOAT, in a suitable solvent to give compounds of Formula (I), or a pharmaceutically acceptable salt thereof.

Scheme 5

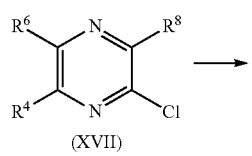

(XVII)

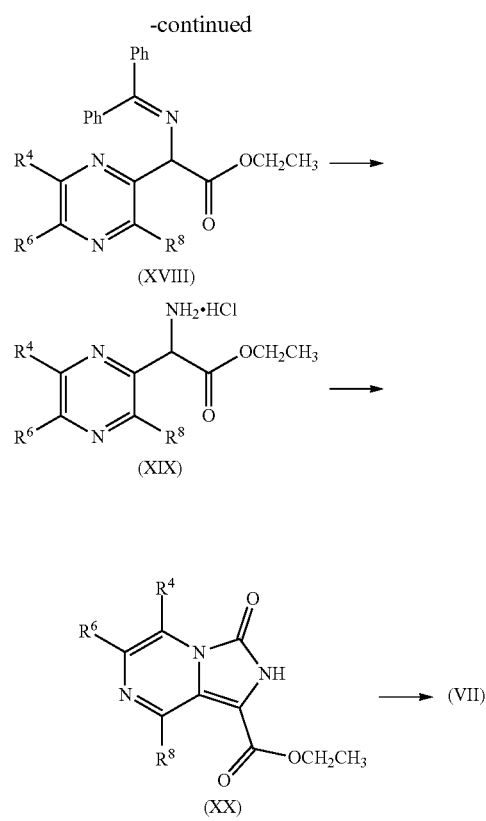

Compounds of Formula (VII) in which $R^5$, $R^7$ and $R^9$ are each hydrogen can be obtained starting from a pyrazine derivative of Formula (XVII). Formula (XVII) can be reacted with N-(diphenylmethylene)glycine ethyl ester in a suitable solvent in presence of a base (for example, potassium carbonate) to give a compound of Formula (XVIII). Deprotection of Formula (XVIII) can be accomplished in acidic conditions, for instance, in presence of HCl to give a compound of Formula (XIX). Formula (XIX) can be cyclized to a compound of Formula (XX), for example, using triphosgen in a suitable solvent (such as THF). The reduction of the pyrazine ring of Formula (XX) can be achieved by using an hydrogenation procedure in presence of a suitable catalyst (such as Pd/C) in a solvent (such as methanol) to afford a compound of Formula (VII). Compounds of Formula (I) as provided in Schemes 3 and 4 can be obtained from a compound of Formula (VII) in which $R^5$, $R^7$ and $R^9$ are each hydrogen as described herein. Alternatively, a compound of Formula (XX), in which $R^6$ is chloro, can be reacted first with an agent of general formula R$^3$—Halo, wherein Halo can be chloro, bromo or iodo, or general formula R$^3$—B(OH)$_2$, under the conditions reported for Scheme 2. The chloro can then be transformed to an alkyl or cycloalkyl, for example, methyl and cyclopropyl, using 2,4,6-trimethyl-1,3,5,2,4,6-trioxatriborinane and cyclopropyl boronic acid, respectively, in the presence of a catalyst like Pd(dppf)Cl$_2$, K$_2$CO$_3$ in dioxane, or Pd(OAc)$_2$ and SPhos in toluene/water respectively. The obtained derivative, where $R^6$ is methyl or cyclopropyl, can then be reduced under classical conditions like hydrogenation on Pd/C in ethanol, or using sodium borohydride in ethanol, to give a compound a Formula (XII), in which $R^6$ is methyl or cyclopropyl and $R^5$, $R^7$ and $R^9$ are each hydrogen.

Scheme 6

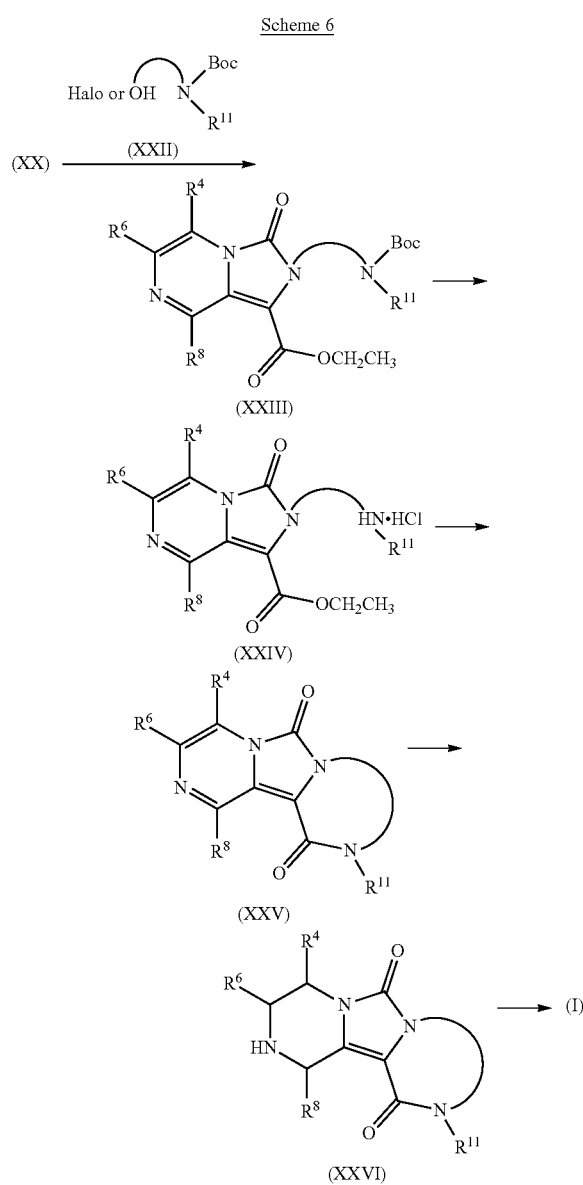

Compound of Formula (I), along with pharmaceutically acceptable salts thereof, in which $R^5$, $R^7$ and $R^9$ are each hydrogen, and $R^2$ and $R^3$ are taken together along with the atoms to which $R^2$ and $R^3$ are each attached to form an optionally substituted 6, 7 or 8 membered monocyclic heterocyclyl or an optionally substituted 9 to 14 membered spirocyclic heterocyclyl can be obtained following the route outlined in Scheme 6. The alkylation of the Formula (XX) with a chain of general Formula (XXII), where Halo represents chloro, bromo or iodo, can be achieved in presence of a base in a suitable solvent. Alternatively, a hydroxy derivative of Formula (XXII) can be coupled with Formula (XX) using a Mitsunobu reaction. Removal of the Boc protecting group from Formula (XXIII) can be achieved using an acid in a suitable solvent or cupper triflate to obtain a compound of Formula (XXIV). The cyclisation of Formula (XXIV) to provide a compound of Formula (XXV) can be achieved by heating a solution of Formula (XXIV) in a suitable solvent (such as methanol) in presence of a base (such as triethylamine). Alternatively, the ester of Formula (XXIV) can be saponified to the corresponding acid using lithium hydroxide or sodium hydroxide. After formation of the acid derivative, the corresponding acid compound can be cyclized to a compound of Formula (XXV) using an amide coupling reaction. Hydrogenation of Formula (XXV) in presence of a catalyst (for example, Pd/C) can provide a compound of Formula (XXVI). Compounds of Formula (I) can be obtained using methods know in the art. For example, compounds of Formula (I) having $Z^1$ being —NH—C(=O)— can be obtained by coupling Formula (XXVI) with a carbamate of general formula $R^1$NHC(=O)—OPh. Alternatively, compounds of Formula (I) having $Z^1$ being —C(=O)— can be obtained by coupling Formula (XXVI) with an acyl chloride of general formula $R^1$—C(=O)—Cl or by using an acid of general formula R—C(=O)—OH in presence of a suitable coupling agent. Other $R^1$—$(Z^1)$n-group can be introduced by methods known in the art.

Scheme 7

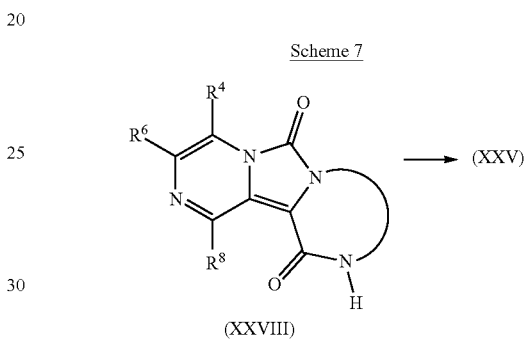

Alternatively, compound of Formula (I), along with pharmaceutically acceptable salts thereof, in which $R^5$, $R^7$ and $R^9$ are each hydrogen, and $R^2$ and $R^3$ are taken together along with the atoms to which $R^2$ and $R^3$ are each attached to form an optionally substituted 6, 7 or 8 membered monocyclic heterocyclyl or an optionally substituted 9 to 14 membered spirocyclic heterocyclyl, can prepared from Formula (XX) following a similar procedure as provided for Formula (XXV) in Scheme 6 using Formula (XXII) in which $R^{11}$ is a hydrogen. The conversion of a compound of Formula (XXVIII) to a compound of Formula (XXV), where $R^{11}$ is non-hydrogen, can be obtained by the alkylation of Formula (XXVIII) with a suitable alkylating agent of general formula ($R^{11}$—Halo) or via a Mitsunobu reaction using an alcohol of general formula ($R^{11}$—OH) as outlined in Scheme 7. Other $R^{11}$ groups can be introduced by methods known in the art for the functionalization of lactams.

Scheme 8

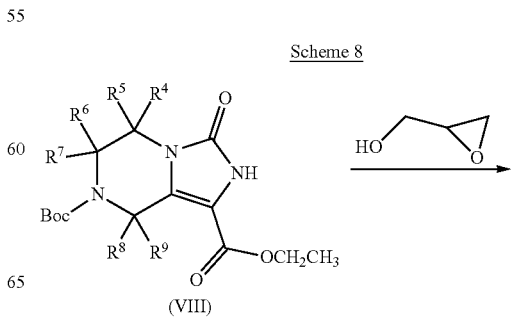

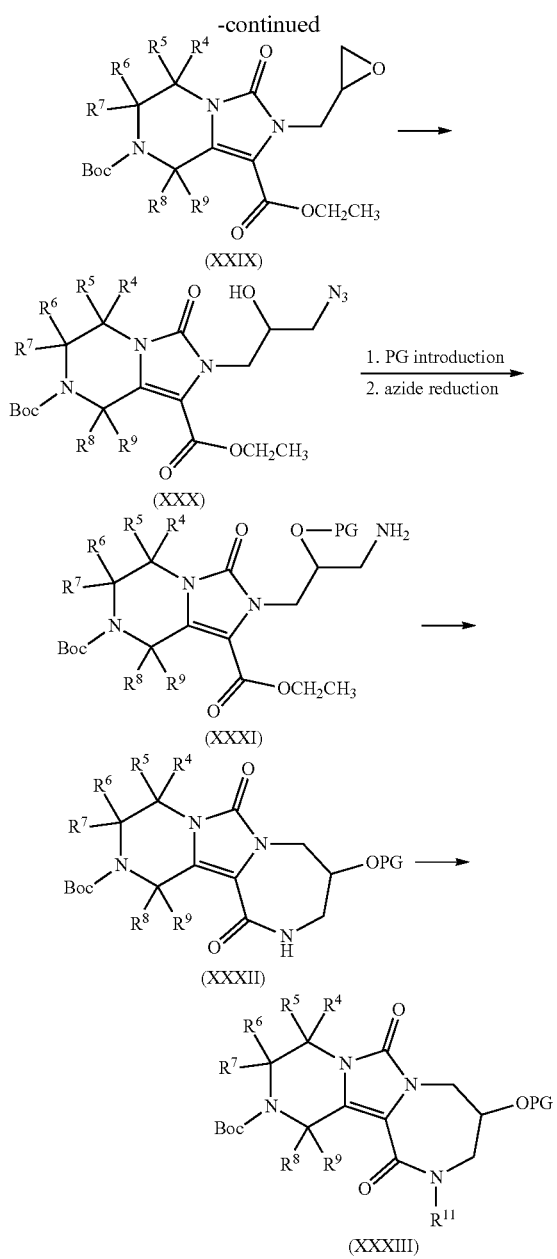

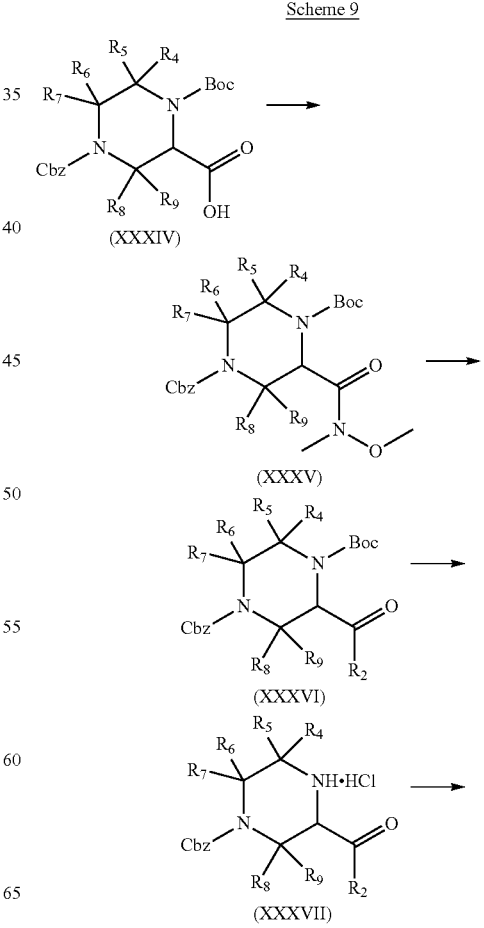

Compound of formula (XXXIII) can be prepared according to the synthetic pathway described in Scheme 8. A compound of formula (VIII) can be alkylated under Mitsunobu conditions with oxiran-2-ylmethanol to give the epoxide of Formula (XXIX), which can then be reacted with sodium azide to provide Formula (XXX). Protection of the secondary alcohol can be performed following conditions known in the art. A suitable protecting group can be, for example a silyl-based protecting group such as the TBDMS protecting group, introduced using TBDMSCl in presence of imidadazole in a suitable solvent (for example, DCM). Subsequently, the azido group can be reduced to the corresponding amine using conditions known in the art for the reduction of an azide, for example, the Staudinger reaction using triphenylphosphine in a solvent (such as THF/water), to provide a compound of Formula (XXXI). Cyclization can be achieved using a base (for example, triethylamine in MeOH) to give a compound of Formula (XXXII), which can further be alkylated to provide a compound of Formula (XXXIII), where $R^{11}$ is non-hydrogen, using alkylation methods known in the art. Exemplary conditions include using a suitable alkylating agent of general formula ($R^{11}$—Halo) in presence of a base (such as cesium carbonate). Other $R^{11}$ groups can be introduced by methods known in the art for the functionalization of lactams.

Scheme 9

Compound of Formula (I), along with pharmaceutically acceptable salts thereof, in which $R^5$, $R^7$ and $R^9$ are each hydrogen, and $R^2$ and $R^3$ are taken together along with the atoms to which $R^2$ and $R^3$ are each attached to form a substituted 7 membered monocyclic heterocyclyl, can be prepared from Formula (XXXIII) by following the 2-step procedure provided in Scheme 1, followed by deprotection of the alcohol under conditions known in the art. Additionally the obtained alcohol can be transformed to other groups of described herein, such as fluoro, using fluorinating agent (such as DAST), or alkylated using an alkyl halide in presence of a base, or another alcohol under Mitsunobu conditions, by applying methods known in the art for the transformation and alkylation of alcohols. The alcohol may also be deprotected and alkylated directly on a compound of formula (XXXIII), prior to performing the reactions described in Scheme 1 leading to the synthesis of a compound of Formula (I).

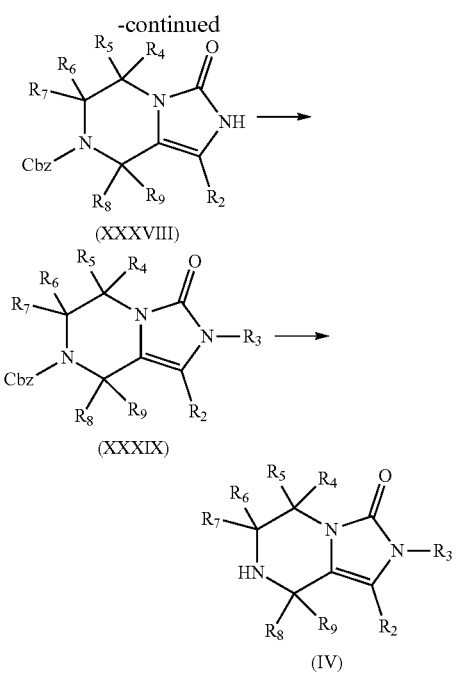

(XXXVIII)

(XXXIX)

(IV)

Compounds of Formula (IV) in which R² is an optionally substituted aryl or heteroaryl can be obtained starting from a bis-protected piperazine carboxylic acid of Formula (XXXIV) that can be reacted with N,O-dimethylhydroxylamine, in presence of coupling agents (for example, EDCI and HOBt) in presence of a base (e.g., trimethylamine), in an organic solvent (such as DMF), to give the Weinreb amide of Formula (XXXV). A Grignard reagent, R²—MgCl or R²—MgBr, which can be formed in situ by reacting a haloaryl or halo heteroaryl R²—Halo, where Halo can be Br or Cl, with for example isopropylmagnesium chloride in a solvent (such as THF), can then be reacted with a compound of Formula (XXXV) to give ketone of Formula (XXXVI). Removal of the Boc protecting group can be achieved under acidic conditions (such as with HCl in dioxane) to give a compound of Formula (XXXVII). Cyclization of Formula (XXXVII) using potassium cyanate in acetic acid/water gives bicycle of Formula (XXXVIII) in which R² is an optionally substituted aryl or heteroaryl. The R³ substituent can be introduced by procedures known in the art. For example, compounds of Formula (XXXIX) can be obtained from Formula (XXXVIII) by using an alkylating agent of general formula R³—Halo, with Halo being chloro, bromo or iodo, in presence of a base (such as potassium carbonate) in a suitable solvent.

Alternatively, Formula (XXXIX) can be obtained by a Mitsunobu reaction using an alcohol of general formula R³—OH in a suitable solvent. Other compounds of Formula (XXXIX) can be prepared from Formula (XXXVIII) using a boronic acid of general formula R³—B(OH)₂, and a catalyst such as Cu(AcO)₂, in presence of a base. Other compounds of Formula (XXXIX) can be prepared from Formula (XXXVIII) using a halogenated aryl or heteroaryl R³—Halo, where Halo can be iodo, bromo or chloro, in the presence of copper iodide, potassium carbonate and N¹,N²-dimethylethane-1,2-diamine, in a solvent (for example, DMSO) under heating conditions. Other compounds of Formula (XXXIX) can be prepared from Formula (XXXVIII) using a halogenated aryl or heteroaryl R³—Halo, where Halo can be iodo, bromo or chloro, in the presence of a palladium catalyst such as Pd₂dba₃, a ligand such as Xantphos, a base (such as cesium carbonate) in a suitable solvent (e.g., dioxane) under heating conditions. Other R³ group can be introduced using known procedures for functionalization of lactams. Deprotection of the Cbz protecting group can be performed using conditions known to the art to provide a compound of Formula (IV), in which R² is an optionally substituted aryl or heteroaryl.

Scheme 10

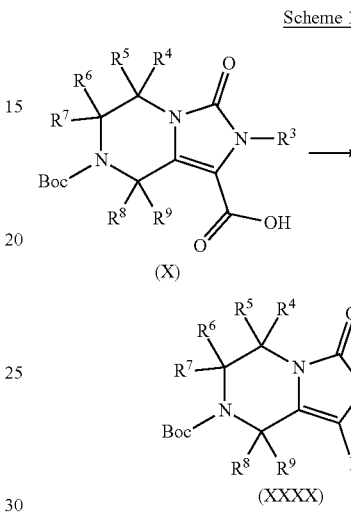

(X)

(XXXX)

(III)

A compound of Formula (X) can be reacted with iodine, in presence of a base (for example, sodium bicarbonate), in a solvent (such as MeOH/water), to give the iodo derivative of Formula (XXXX). A compound of Formula (XXXX) can react with a boronic acid of general formula R²—B(OH)₂, in presence of a palladium-based catalyst (such as Pd(dppf)Cl₂) and a base (e.g., potassium carbonate), in a solvent (such as dioxane/water), to give a compound of Formula (III), in which R² is an optionally substituted aryl or heteroaryl.

Scheme 11

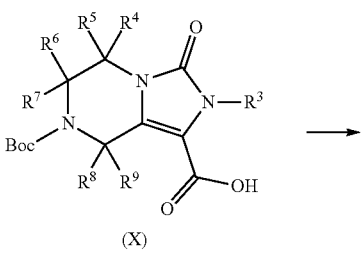

(X)

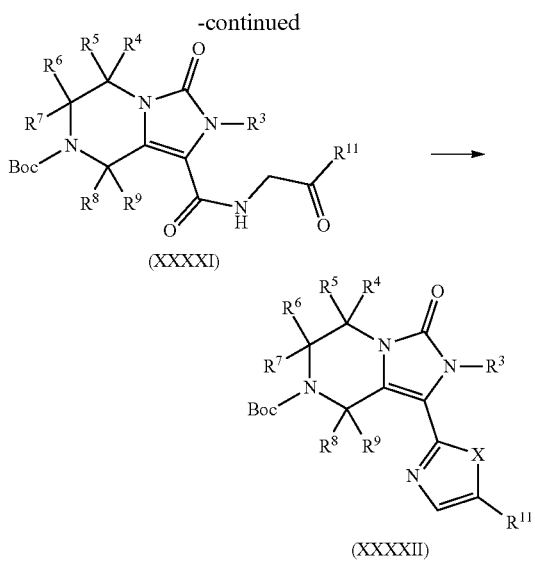

A compound of Formula (XXXXII), in which X can be —O— or —S—, and $R^{11}$ can be an optionally substituted aryl, heteroaryl or aryl($C_{1-4}$alkyl), can be obtained from a carboxylic acid of Formula (X). Coupling of a compound of Formula (X) with a ketoamide of general formula $R^{11}$—$COCH_2NH_2$, using coupling agents (such as TCFH) in presence of NMI in a suitable solvent (for example, acetonitrile), can provide a ketoamide of Formula (XXXXI). Cyclisation of a compound of Formula (XXXXI) using Burgess reagent in a solvent (such as THF), under heating conditions, can give a compound of Formula (XXXXII), in which X can be an oxygen and $R^{11}$ can be an optionally substituted aryl, heteroaryl or aryl($C_{1-4}$alkyl).

Alternatively, cyclisation of compound of Formula (XXXXI) using $P_2S_5$ in chloroform can give a compound of Formula (XXXXII), in which X can be a sulfur and $R^{11}$ can be an optionally substituted aryl, heteroaryl or aryl($C_{1-4}$alkyl). Compounds of Formula (XXXXII) can be treated as shown in Scheme 1 to give a compounds of Formula (I).

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction $<10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenanide and tenofovir disoproxil. However, some of the drawbacks associated with interferon treatment are the adverse side effects, the need for subcutaneous administration and high cost. Potential advantages of a compound of Formula (I) and/or (II), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels including STOPS™ compounds) an entry inhibitor and/or a small molecule immunomodulator. Examples of additional agents include recombinant interferon alpha 2b, IFN-(a, PEG-IFN-α-2a, lamivudine, telbivudine, adefovir dipivoxil, clevudine, entecavir, tenofovir aafenamide and tenofovir disoproxil. Examples of NAPs include, but are not limited to, REP 2139, REP 2165 and those STOPS™ compounds described in U.S. application Ser. No. 16/676,929, filed Nov. 7, 2019, which is hereby incorporated by reference for the purpose of describing the STOPS™ compounds provided therein.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Preparation of ethyl 3-oxo-2H-imidazo[1,5-a]pyrazine-1-carboxylate

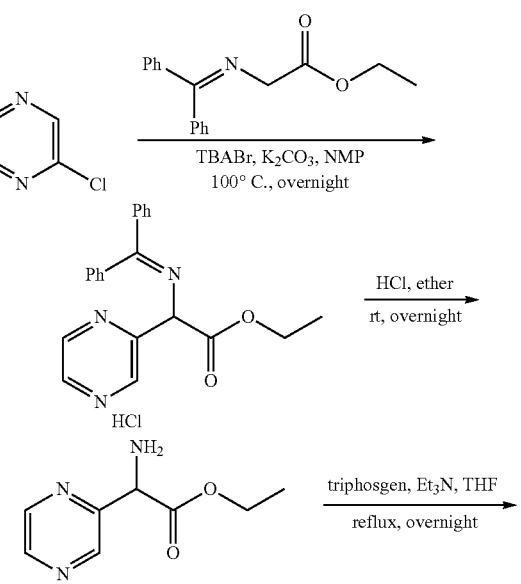

a) ethyl 2-[(diphenylmethylidene)amino]-2-(pyrazin-2-yl)acetate

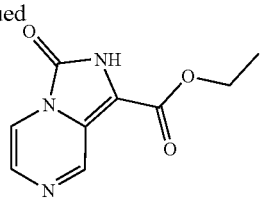

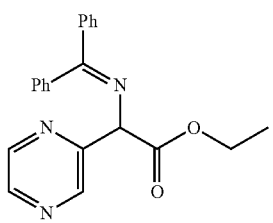 [SMILES: CCOC(=O)C(N=C(c1ccccc1)c1ccccc1)c1cnccn1]

A 1 μL three-neck round-bottom flask was charged with 2-chloropyrazine (60.0 g, 0.521 mol, 2.00 eq.), ethyl 2-[(diphenylmethylidene)amino]acetate (70.0 g, 0.262 mol, 1.00 eq.), N-methylpyrrolidone (600 mL), tetrabutylammonium bromide (84.4 g, 0.262 mol, 1.00 eq.) and potassium carbonate (109 g, 0.790 mol, 3.00 eq.). The mixture was stirred overnight at 100° C. under $N_2$ atmosphere. The solid was filtered off, and the filtrate was concentrated under reduced pressure. The residue was purified by silica gel column chromatography with ethyl acetate:petroleum ether (EA:PE) (1:10) to afford ethyl 2-[(diphenylmethylidene)amino]-2-(pyrazin-2-yl)acetate (54.0 g, 60% yield) as a yellow oil. LCMS (ESI, m/z): 346 [M+H]+, RT: 1.065 min. $^1$H NMR (400 MHz, DMSO-$d_6$) δ 8.87 (d, J=1.5 Hz, 1H), 8.63 (d, J=2.6 Hz, 1H), 8.59 (dd, J=2.6, 1.5 Hz, 1H), 7.63-7.41 (m, 8H), 7.24-7.14 (m, 2H), 5.28 (s, 1H), 4.15-4.04 (m, 2H), 1.11 (t, J=7.1 Hz, 3H).

b) ethyl 2-amino-2-(pyrazin-2-yl)acetate Hydrochloride

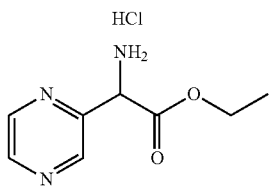

A 2 μL round-bottom flask was charged with ethyl 2-[(diphenylmethylidene)amino]-2-(pyrazin-2-yl)acetate (54.0 g, 156 mmol, 1.00 eq.), hydrochloric acid (187 mL, 187 mmol, 1.20 eq., 1 mol/L) and ether (800 mL). The solution was stirred for overnight at room temperature (rt). The mixture was diluted with water (500 mL), and extracted with ether (3×300 mL). The aqueous layer was concentrated under reduced pressure to afford ethyl 2-amino-2-(pyrazin-2-yl)acetate hydrochloride (33.0 g, 97% yield) as a brown solid. LCMS (ESI, m/z): 182 [M−HCl+H]+, RT: 0.366 min. $^1$H NMR (400 MHz, Methanol-$d_4$) δ 8.93 (d, J=1.5 Hz, 1H), 8.77-8.70 (m, 2H), 5.64 (s, 1H), 4.32 (qq, J=10.8, 7.1 Hz, 2H), 1.26 (t, J=7.1 Hz, 3H).

c) ethyl 3-oxo-2H-imidazo[1,5-a]pyrazine-1-carboxylate

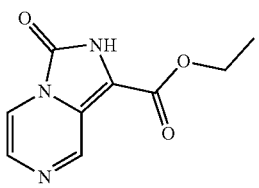

A 1 μL 3-necked round-bottom flask was charged with ethyl 2-amino-2-(pyrazin-2-yl)acetate hydrochloride (30.0 g, 137 mmol, 1.00 eq.), tetrahydrofuran (450 mL) and triethylamine (70.0 g, 690 mmol, 5.00 eq.). Triphosgene (14.3 g, 48.3 mmol, 0.35 eq.) in tetrahydrofuran (50 mL) was added dropwise with stirring at 0° C. under $N_2$ atmosphere. The solution was refluxed overnight and concentrated under reduced pressure. The residue was purified by trituration with ethyl acetate (100 mL) to afford ethyl 3-oxo-2H-imidazo[1,5-a]pyrazine-1-carboxylate (30.0 g, crude) as a yellow solid. LCMS (ESI, m/z): 208 [M+H]+, RT: 0.605 min. $^1$H NMR (400 MHz, Methanol-$d_4$) δ 9.08 (d, J=1.7 Hz, 1H), 7.72 (dd, J=5.1, 1.8 Hz, 1H), 7.42 (d, J=5.1 Hz, 1H), 4.43 (q, J=7.1 Hz, 2H), 1.43 (t, J=7.1 Hz, 3H).

Example 1

N-(3-chloro-4-fluorophenyl)-6,12-dioxo-1,3,4,8,9,10,11,12-octahydro-2H,6H-pyrazino[1',2':3,4]imidazo[1,5-a][1,4]diazepine-2-carboxamide (1)

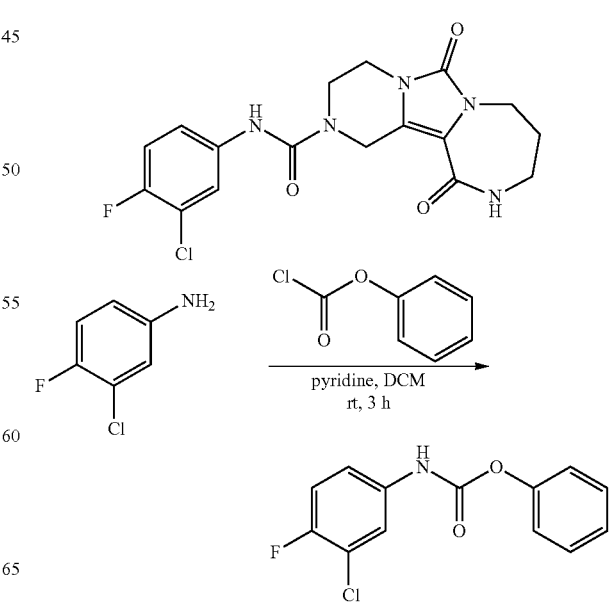

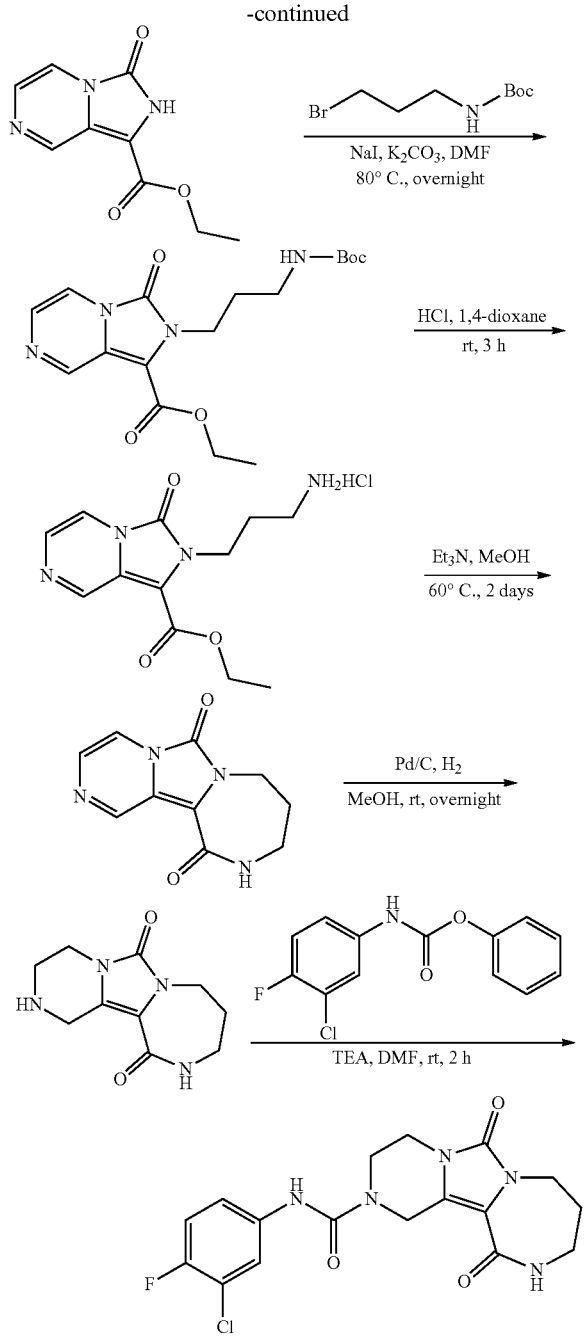

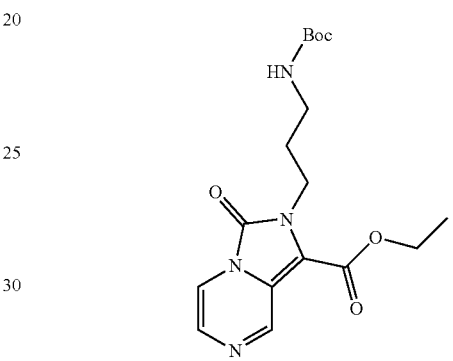

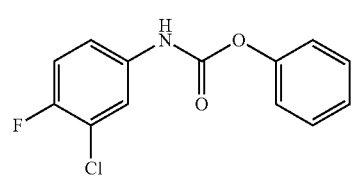 [SMILES: O=C(Nc1ccc(F)c(Cl)c1)Oc1ccccc1]

a) phenyl N-(3-chloro-4-fluorophenyl)carbamate

A 1 μL three-neck bottom-flask was charged with 3-chloro-4-fluoroaniline (30.0 g, 206 mmol, 1.00 eq.), pyridine (18.0 g, 228 mmol, 1.10 eq.) and dichloromethane (156 mL). Then phenyl chloroformate (35.5 g, 227 mmol, 1.10 eq.) was added at 0° C. The mixture was stirred for 3 h at rt, and the reaction quenched with water (200 mL). The mixture was extracted with dichloromethane (3×200 mL). The organic layers were combined, washed with water (3×100 mL), dried over anhydrous sodium sulfate, filtered and concentrated under reduced pressure. The residue was purified by silica gel column chromatography with EA:PE (1:7) to afford phenyl N-(3-chloro-4-fluorophenyl)carbamate (46.0 g, 84% yield) as a pink solid. LCMS (ESI, m/z): 266 [M+H]*, RT: 1.304 min. $^1$H NMR (300 MHz, DMSO-$d_6$) δ 10.47 (s, 1H), 7.73 (dd, J=6.7, 2.4 Hz, 1H), 7.51-7.34 (m, 4H), 7.34-7.18 (m, 3H).

b) ethyl 2-[3-[(tert-butoxycarbonyl)amino]propyl]-3-oxoimidazo[1,5-a]pyrazine-1-carboxylate A 500 mL round-bottom flask was charged with 3-oxo-2H-imidazo[1,5-a]pyrazine-1-carboxylate (17.0 g, 82.1 mmol, 1.00 eq.), tert-butyl N-(3-bromopropyl)carbamate (29.3 g, 123 mmol, 1.50 eq.), NaI (12.3 g, 82.1 mmol, 1.00 eq.), potassium carbonate (22.7 g, 164 mmol, 2.00 eq.) and N,N-dimethylformamide (200 mL). The mixture was stirred for overnight at 80° C., and the reaction was quenched with water (200 mL). The mixture was extracted with ethyl acetate (3×200 mL). The organic layers were combined, washed with brine (3×200 mL) and water (3×200 mL), dried over anhydrous sodium sulfate, filtered and concentrated under reduced pressure. The residue was purified by trituration with ethyl acetate (50 mL). The solid was collected by filtration and dried to afford ethyl 2-[3-[(tert-butoxycarbonyl)amino]propyl]-3-oxoimidazo[1,5-a]pyrazine-1-carboxylate (12.0 g, 40% yield) as a light yellow solid. LCMS (ESI, m/z): 365 [M+H]$^+$, RT: 0.720 min.

c) ethyl 2-(3-aminopropyl)-3-oxoimidazo[1,5-a]pyrazine-1-carboxylate hydrochloride

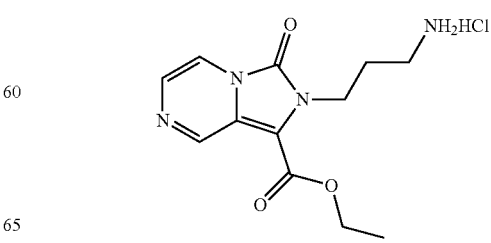

A 50 mL round-bottom flask was charged with ethyl 2-[3-[(tert-butoxycarbonyl)amino]propyl]-3-oxoimidazo[1,5-a]pyrazine-1-carboxylate (9.50 g, 26.1 mmol, 1.00 eq.) and hydrogen chloride (20.0 mL, 80.0 mmol, 3.07 eq., 4 M in 1,4-dioxane). The resulting solution was stirred for 4 h at rt and concentrated under reduced pressure to provide crude product ethyl 2-(3-aminopropyl)-3-oxoimidazo[1,5-a]pyrazine-1-carboxylate hydrochloride (8.00 g, crude) as a light yellow solid. LCMS (ESI, m/z): 265 [M−HCl+H]$^+$, RT: 0.523 min.

d) 4,7,9,13-tetraazatricyclo[7.5.0.0^[2,7]]tetradeca-1,3,5-triene-8,14-dione

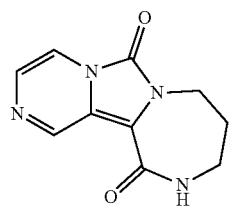 [SMILES: O=C1NCCCn2c1c1cnccn1c2=O]

A 250 mL round-bottom flask was charged with ethyl 2-(3-aminopropyl)-3-oxoimidazo[1,5-a]pyrazine-1-carboxylate hydrochloride (8.00 g, 26.1 mmol, 1.00 eq.), methanol (100 mL) and triethylamine (5.38 g, 53.2 mmol, 2.00 eq.). The solution was stirred for two days at 60° C. The solid was collected by filtration and dried under reduced pressure to provide 4,7,9,13-tetraazatricyclo[7.5.0.0^[2,7]]tetradeca-1,3,5-triene-8,14-dione (4.50 g, 79% yield) as a light yellow solid. LCMS (ESI, m/z): 219 [M+H]$^+$, RT: 0.520 min. e) 4,7,9,13-tetraazatricyclo[7.5.0.0^[2,7]]tetradec-1-ene-8,14-dione

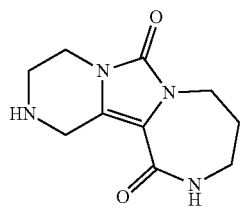 [SMILES: O=C1NCCCn2c1c1n(c2=O)CCNC1]

A 100 mL round-bottom flask was charged with 4,7,9,13-tetraazatricyclo[7.5.0.0^[2,7]]tetradeca-1,3,5-triene-8,14-dione (260 mg, 1.19 mmol, 1.00 eq.), 10% Pd/C (60.0 mg) and methanol (10 mL). The mixture was stirred overnight at rt under H$_2$ atmosphere (3 atm). The solid was filtrated off, and the filtrate was concentrated under reduced pressure to afford 4,7,9,13-tetraazatricyclo[7.5.0.0 ^[2,7]]tetradec-1-ene-8,14-dione (230 mg, 87% yield) as a light yellow solid. LCMS (ESI, m/z): 223 [M+H]$^+$, RT: 0.266 min.

f) N-(3-chloro-4-fluorophenyl)-8,14-dioxo-4,7,9,13-tetraazatricyclo[7.5.0.0^[2,7]]tetradec-1-ene-4-carboxamide

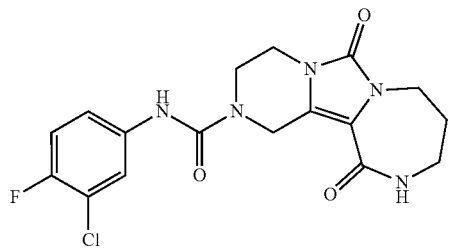 [SMILES: O=C1NCCCn2c1c1n(c2=O)CCN(C(=O)Nc2ccc(F)c(Cl)c2)C1]

A solution of 4,7,9,13-tetraazatricyclo[7.5.0.0 ^[2,7]]tetradec-1-ene-4-dione (230 mg, 1.03 mmol, 1.00 eq.), triethylamine (314 mg, 3.10 mmol, 3 eq.) and phenyl N-(3-chloro-4-fluorophenyl)carbamate (302 mg, 1.13 mmol, 1.10 eq.) in N,N-dimethylformamide (2.00 mL) was stirred for 2 h at rt. The reaction was quenched with water (20 mL). The mixture was extracted with ethyl acetate (3×50 mL). The organic layers were combined, washed with brine (3×50 mL) and water (3×50 mL), dried over anhydrous sodium sulfate, filtered and concentrated under reduced pressure. The crude product was purified by Prep-HPLC with the following gradient conditions: column: XBridge Prep C$_{18}$ OBD Column, 19×150 mm 5 m; Mobile Phase A: Water (10 mmol/L NH$_4$HCO$_3$), Mobile Phase B: ACN; Flow rate: 25 mL/min; Gradient: 16% B to 46% B in 7 min; 220 nm. Purification resulted in N-(3-chloro-4-fluorophenyl)-8,14-dioxo-4,7,9,13-tetraazatricyclo[7.5.0.0 ^[2,7]]tetradec-1-ene-4-carboxamide (172.4 mg, 42% yield) as a white solid. LCMS (ESI, m/z): 394 [M+H]$^+$, RT: 1.059 min. $^1$H NMR (400 MHz, DMSO-d$_6$) δ 9.04 (s, 1H), 7.84-7.64 (m, 2H), 7.41 (ddd, J=9.2, 4.5, 2.7 Hz, 1H), 7.31 (t, J=9.1 Hz, 1H), 4.75 (s, 2H), 3.79 (dt, J=19.2, 6.0 Hz, 4H), 3.61 (t, J=5.5 Hz, 2H), 3.18 (q, J=5.5 Hz, 2H), 1.91 (m, 2H).

Example 2

N-(3-chloro-4-fluorophenyl)-11-methyl-6,12-dioxo-1,3,4,8,9,10,11,12-octahydro-2H,6H-pyrazino[1',2':3,4]imidazo[1,5-a][1,4]diazepine-2-carboxamide (2)

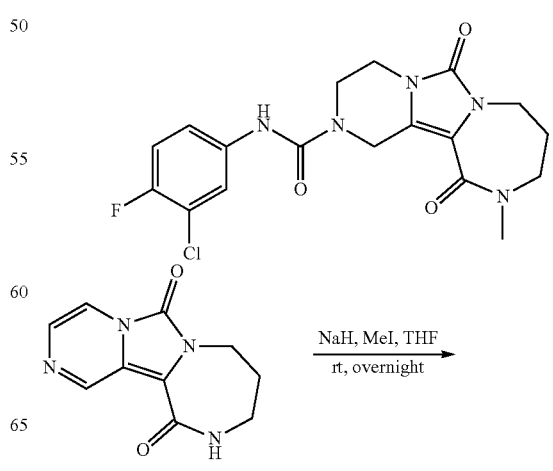

b) 13-methyl-4,7,9,13-tetraazatricyclo[7.5.0.0^[2,7]]
tetradec-1-ene-8,14-dione

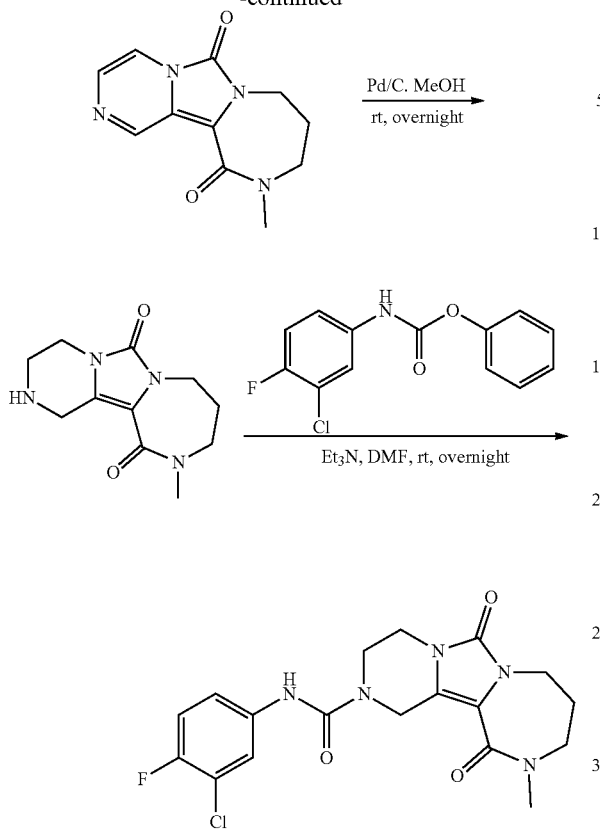

A 100 mL round-bottom flask was charged with 13-methyl-4,7,9,13-tetraazatricyclo[7.5.0.0^[2,7]]tetradeca-1,3,5-triene-8,14-dione (650 mg, 2.80 mmol, 1.00 eq.), 10% Pd/C (65.0 mg) and methanol (30 mL). The solution was stirred overnight at rt under H₂ atmosphere (3 atm). The solid was filtrated off, and the filter was concentrated under reduced pressure to provide 13-methyl-4,7,9,13-tetraazatricyclo[7.5.0.0^[2,7]]tetradec-1-ene-8,14-dione (660 mg, 99% yield) as a white solid. LCMS (ESI, m/z): 237 [M+H]⁺, RT: 0.365 min.

c) N-(3-chloro-4-fluorophenyl)-11-methyl-6,12-dioxo-1,3,4,8,9,10,11,12-octahydro-2H,6H-pyrazino[1',2':3,4]imidazo[1,5-a][1,4]diazepine-2-carboxamide a) 13-methyl-4,7,9,13-tetraazatricyclo[7.5.0.0^[2,7]]
tetradeca-1,3,5-triene-8,14-dione A 40 mL vial was charged with 4,7,9,13-tetraazatricyclo[7.5.0.0^[2,7]]tetradeca-1,3,5-triene-8,14-dione (1.00 g, 4.58 mmol, 1.00 eq.), tetrahydrofuran (20 mL) and NaH (0.275 g, 6.88 mmol, 1.50 eq., 60% in mineral). The solution was stirred 30 min at rt. Methyl iodide (0.780 g, 5.50 mmol, 1.20 eq.) was added. The solution was stirred overnight at rt, and the reaction was quenched with water (100 mL). The mixture was extracted with ethyl acetate (3×100 mL). The organic layers were combined, washed with brine (3×100 mL) and water (3×100 mL), dried over anhydrous sodium sulfate, filtered and concentrated under reduced pressure. The residue was trituration with EA:PE (1:1, 20 mL). The solid was collected by filtration and dried to afford 13-methyl-4,7,9,13-tetraazatricyclo[7.5.0.0^[2,7]]tetradeca-1,3,5-triene-8,14-dione (650 mg, 61% yield) as little yellow solid. LCMS (ESI, m/z): 233 [M+H]⁺, RT: 0.504 min.

A 40 mL vial was charged with 13-methyl-4,7,9,13-tetraazatricyclo[7.5.0.0^[2,7]]tetradec-1-ene-8,14-dione (200 mg, 0.846 mmol, 1.00 eq.), phenyl N-(3-chloro-4-fluorophenyl)carbamate (247 mg, 0.931 mmol, 1.10 eq.), triethylamine (257 mg, 2.54 mmol, 3.00 eq.) and N,N-dimethyl formamide (10 mL). The solution was stirred overnight at rt and diluted with ethyl acetate (100 mL). The mixture was washed with water (3×100 mL). The organic phase was dried over anhydrous sulfate, filtered and concentrated under reduced pressure. The crude product was purified by Prep-HPLC with the following conditions: Column: XBridge Prep OBD C₁₈ Column, 30×150 mm 5 m; Mobile Phase A: Water (10 mmol/L NH₄HCO₃+0.1% NH₃—H₂O), Mobile Phase B: ACN; Flow rate: 60 mL/min; Gradient: 20% B to 38% B in 7 min; 220 nm. Purification resulted in N-(3-chloro-4-fluorophenyl)-11-methyl-6,12-dioxo-1,3,4,8,9,10,11,12-octahydro-2H,6H-pyrazino[1',2':3,4]imidazo[1,5-a][1,4]diazepine-2-carboxamide (58.9 mg, 19% yield) as a white solid. LCMS (ESI, m/z): 408 [M+H]*, RT: 1.152 min. ¹H NMR (300 MHz, Chloroform-d) δ 7.57 (dd, J=6.5, 2.7 Hz, 1H), 7.25-7.17 (m, 1H), 7.08 (t, J=8.7 Hz, 1H), 6.77 (s, 1H), 4.84 (s, 2H), 3.93 (t, J=6.6 Hz, 4H), 3.81 (t, J=5.5 Hz, 2H), 3.53-3.41 (m, 2H), 3.10 (s, 3H), 2.20-2.17 (m, 2H).

Example 3

11-benzyl-N-(3-chloro-4-fluorophenyl)-6,12-dioxo-1,3,4,8,9,10,11,12-octahydro-2H,6H-pyrazino[1',2':3,4]imidazo[1,5-a][1,4]diazepine-2-carboxamide (3)

The title compound was prepared as a white solid according to the procedures of Example 2 a) to c) by substituting benzyl bromide for methyl iodide. LCMS (ESI, m/z): 484 [M+H]+, RT: 1.362 min. ¹H NMR (400 MHz, Chloroform-d) δ 7.58 (dd, J=6.6, 2.7 Hz, 1H), 7.43-7.30 (m, 5H), 7.27-7.21 (m, 1H), 7.09 (t, J=8.7 Hz, 1H), 6.84 (s, 1H), 4.88 (s, 2H), 4.68 (s, 2H), 4.00-3.90 (m, 4H), 3.82 (t, J=5.5 Hz, 2H), 3.44 (t, J=6.2 Hz, 2H), 1.95-1.75 (m, 2H).

Example 4

N-(3-chloro-4-fluorophenyl)-11-(4-methoxybenzyl)-6,12-dioxo-1,3,4,8,9,10,11,12-octahydro-2H,6H-pyrazino[1',2':3,4]imidazo[1,5-a][1,4]diazepine-2-carboxamide (4)

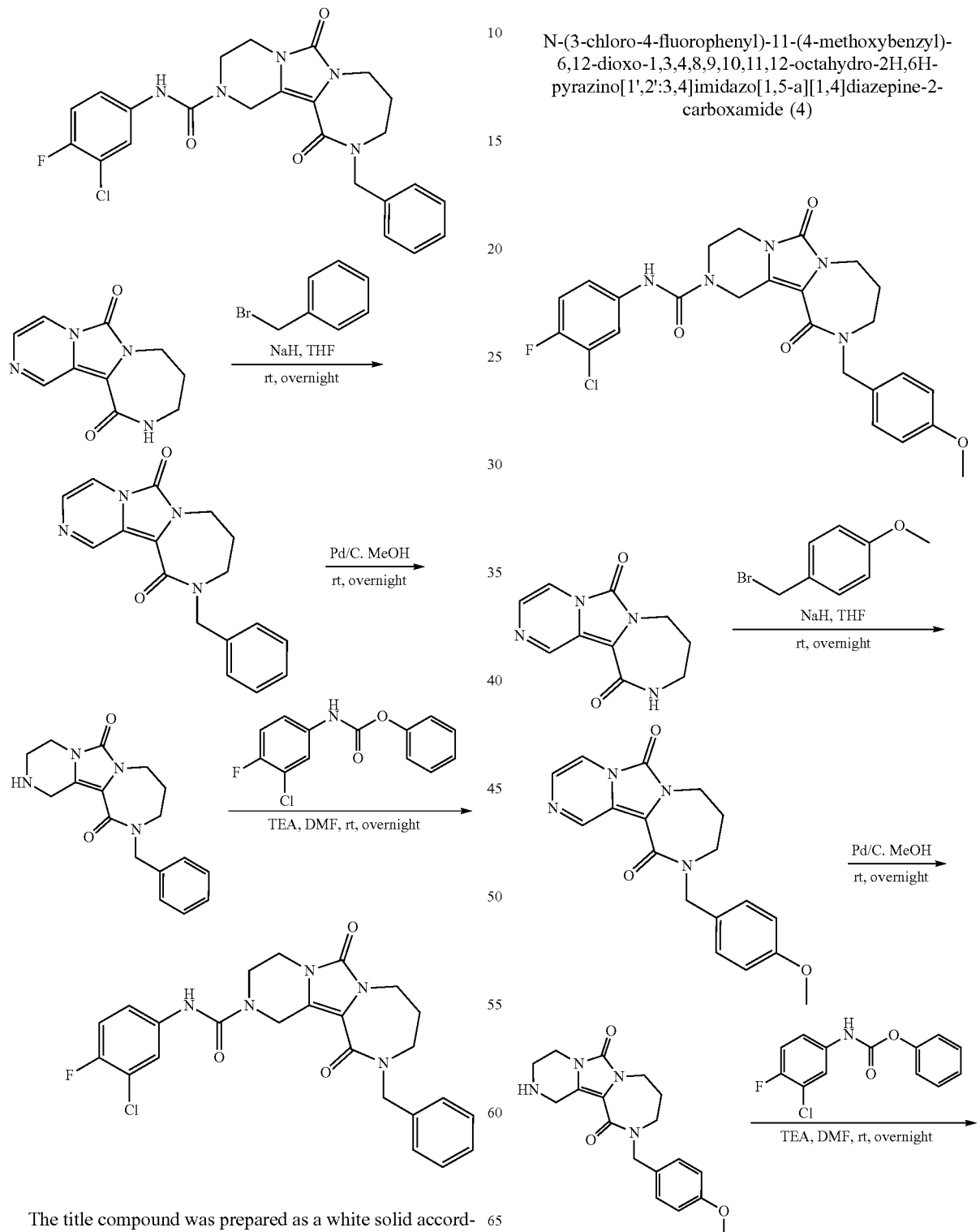

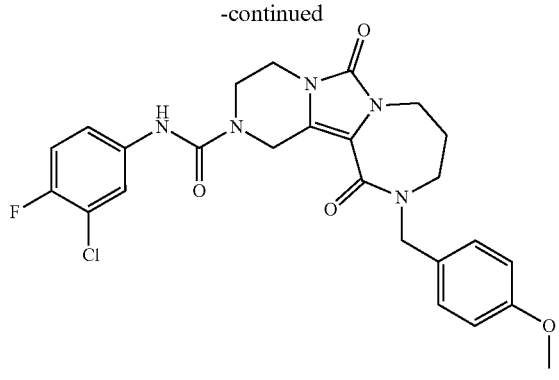

The title compound was prepared as a white solid according to the procedures of Example 2a) to c) by substituting 1-(bromomethyl)-4-methoxybenzene for methyliodide. LCMS (ES) m/z 514 [M+H], RT: 1.355 min. $^1$H NMR (400 MHz, Chloroform-d) δ 7.58 (dd, J=6.5, 2.6 Hz, 1H), 7.27-7.21 (m, 3H), 7.08 (t, J=8.8 Hz, 1H), 6.97-6.86 (m, 3H), 4.88 (s, 2H), 4.60 (s, 2H), 4.00-3.95 (m, 2H), 3.90-3.77 (m, 7H), 3.41 (t, J 6.2 Hz, 2H), 1.90-1.80 (m, 2H).

Example 5

4-(4-bromobenzoyl)-4,7,9,13-tetraazatricyclo[7.5.0.0^[2,7]]tetradec-1-ene-8,14-dione (5)

A 40 mL vial was charged with 4,7,9,13-tetraazatricyclo [7.5.0.0 ^[2,7]]tetradec-1-ene-8,14-dione (100 mg, 0.450 mmol, 1.00 eq.) and, 4-bromo-benzoyl chloride (118 mg, 0.540 mmol, 1.20 eq.), N,N-dimethyl formamide (5 mL) and N,N-diisopropylethylamine (174 mg, 1.35 mmol, 3.00 eq.). The mixture was stirred for 2 h at rt, and the reaction was quenched with water (30 mL). The solution was extracted with dichloromethane (3×50 mL). The organic layers were combined, washed with water (3×50 mL), dried over anhydrous sodium sulfate, filtered and concentrated under reduced pressure. The crude product was purified by Prep-HPLC with the following gradient conditions: Column: XBridge Prep OBD $C_{18}$ Column, 30×150 mm 5 m; Mobile Phase A: Water (10 mmol/L NH$_4$HCO$_3$+0.1% NH$_3$.H$_2$O), Mobile Phase B: ACN; Flow rate: 60 mL/min; Gradient: 13% B to 34% B in 7 min; 254 nm. Purification resulted in 4-(4-bromobenzoyl)-4,7,9,13-tetraazatricyclo[7.5.0.0^[2,7]] tetradec-1-ene-8,14-dione (30.1 mg, 16% yield) as a white solid. LCMS (ESI, m/z): 405 [M+H]$^+$, RT: 0.969 min. $^1$H NMR (300 MHz, DMSO-d$_6$) δ 7.86-7.55 (m, 3H), 7.45 (d, J=8.3 Hz, 2H), 4.82 (s, 2H), 3.94 (s, 1H), 3.76 (t, J=6.3 Hz, 5H), 3.18 (s, 2H), 1.92 (t, J=6.2 Hz, 2H).

Example 6

2-(4-bromo-3-fluorobenzoyl)-1,2,3,4,8,9,10,11-octahydro-6H,12H-pyrazino[1',2':3,4]imidazo[1,5-a][1,4]diazepine-6,12-dione (6)

A 40 mL vial was charged with 4,7,9,13-tetraazatricyclo [7.5.0.0 ^[2,7]]tetradec-1-ene-8,14-dione (100 mg, 0.450 mmol, 1.00 eq.), 4-bromo-3-fluorobenzoic acid (118 mg, 0.540 mmol, 1.20 eq.), 1-ethyl-3-(3-dimethylaminopropyl) carbodiimide hydrochloride (129 mg, 0.675 mmol, 1.50 eq.), 3H-[1,2,3]triazolo[4,5-b]pyridin-3-ol (91.9 mg, 0.675 mmol, 1.50 eq.), N,N-diisopropylethylamine (175 mg, 1.35 mmol, 3.00 eq.) and N,N-dimethylformamide (2 mL). The mixture was stirred for 2 h at rt, and the reaction was quenched with water (50 mL). The mixture was extracted with ethyl acetate (3×50 mL). The organic layers were combined, dried over anhydrous sodium sulfate, filtered and concentrated under reduced pressure. The residue was purified by Prep-HPLC with the following gradient conditions: Column: XBridge Prep OBD $C_{18}$ Column, 30×150 mm 5 m; Mobile Phase A: Water (10 mmol/L NH$_4$HCO$_3$+0.1% NH$_3$.H$_2$O), Mobile Phase B: ACN; Flow rate: 60 mL/min; Gradient: 13% B to 34% B in 7 min; 254 nm. Purification resulted in 4-(4-bromo-3-fluorobenzoyl)-4,7,9,13-tetraazatricyclo[7.5.0.0ˆ[2,7]]tetradec-1-ene-8,14-dione (33.0 mg, 17% yield) as a white solid. LCMS (ESI, m/z): 423 [M+H]+, RT: 0.951 min. ¹H NMR (300 MHz, DMSO-d₆) δ 7.89-7.49 (m, 3H), 7.29 (dd, J=8.2, 1.9 Hz, 1H), 4.77 (m, 2H), 3.95 (s, 1H), 3.80-3.75 (m, 2H), 3.65-3.55 (m, 3H), 3.18 (m, 2H), 1.92 (t, J=6.3 Hz, 2H).

Example 7

2-(4-bromo-3-chlorobenzoyl)-1,2,3,4,8,9,10,11-octahydro-6H,12H-pyrazino[1',2':3,4]imidazo[1,5-a][1,4]diazepine-6,12-dione (7)

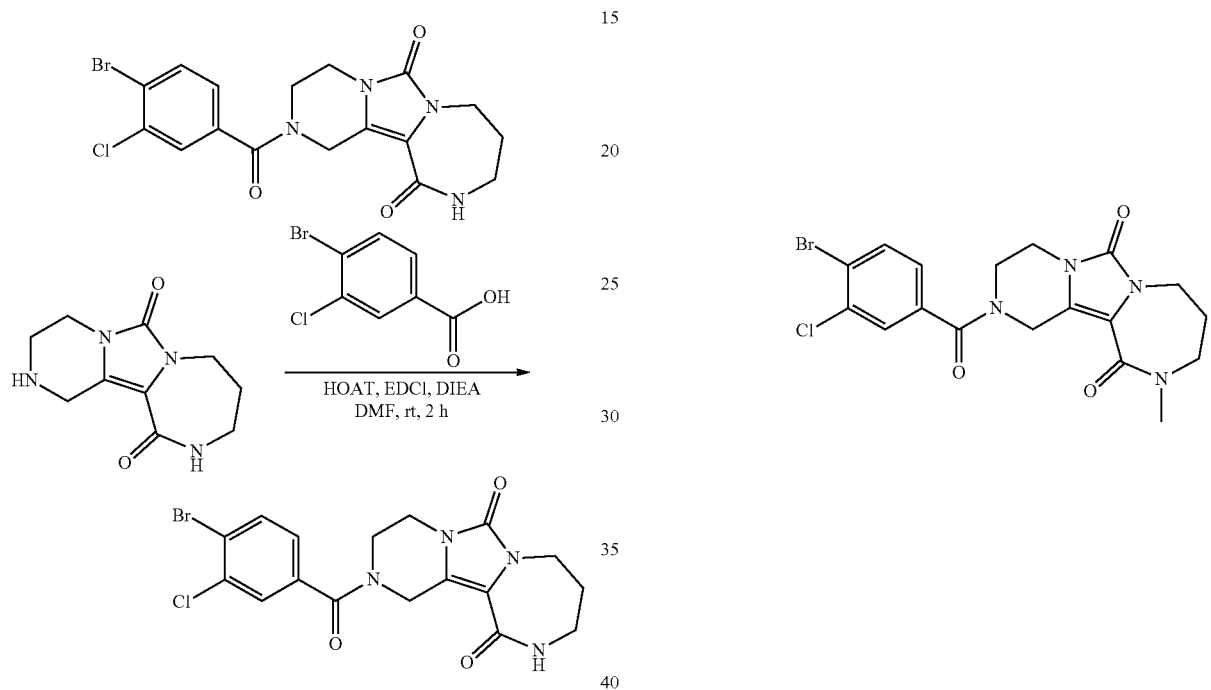

The title compound was prepared as a white solid according to the procedures of Example 6 by substituting 4-bromo-3-chlorobenzoic acid for 4-bromo-3-fluorobenzoic acid. LCMS (ESI, m/z): 439 [M+H]+, RT: 0.999 min. ¹H NMR (300 MHz, DMSO-d₆) δ 7.89 (d, J=8.2 Hz, 1H), 7.77 (d, J=1.9 Hz, 2H), 7.39 (dd, J=8.2, 2.0 Hz, 1H), 4.77 (m, 2H), 3.95 (s, 1H), 3.77 (s, 2H), 3.69-3.55 (m, 3H), 3.18 (s, 2H), 1.93 (d, J=6.4 Hz, 2H).

Example 8

2-(4-bromo-3-chlorobenzoyl)-11-methyl-1,2,3,4,8,9,10,11-octahydro-6H,12H-pyrazino[1',2':3,4]imidazo[1,5-a][1,4]diazepine-6,12-dione (8)

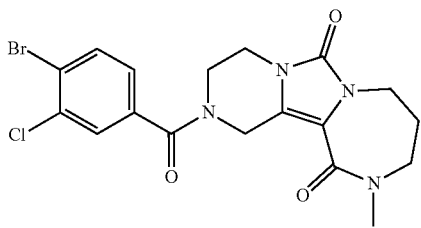

A 40 mL vial was charged with 13-methyl-4,7,9,13-tetraazatricyclo[7.5.0.0ˆ[2,7]]tetradec-1-ene-8,14-dione (200 mg, 0.846 mmol, 1.00 eq.), 4-bromo-3-chlorobenzoic acid (239 mg, 1.02 mmol, 1.20 eq.), 3H-[1,2,3]triazolo[4,5-b]pyridin-3-ol (173 mg, 1.27 mmol, 1.50 eq.), 1-ethyl-3-(3-dimethylaminopropyl)carbodiimide hydrochloride (243 mg, 1.27 mmol, 1.50 eq.), diisopropylethylamine (328 mg, 2.54 mmol, 3.00 eq.) and dimethylformamide (10 mL). The solution was stirred overnight at rt and diluted with ethyl acetate (100 mL). The mixture was washed with water (3×100 mL). The organic phase was dried over anhydrous sulfate, filtered and concentrated under reduced pressure. The residue was purified by Prep-HPLC with the following conditions: Column: XBridge Prep OBD C₁₈ Column, 30×150 mm 5 m; Mobile Phase A: Water (10 mmol/L, NH₄HCO₃+0.1% NH₃—H₂O), Mobile Phase B: ACN; Flow rate: 60 mL/min; Gradient: 20% B to 38% B in 7 min; 220 nm. Purification resulted in 4-(4-bromo-3-chlorobenzoyl)-13-methyl-4,7,9,13-tetraazatricyclo[7.5.0.0ˆ[2,7]]tetradec-1-ene-8,14-dione (60.1 mg, 16% yield) as a white solid. LCMS (ESI, m/z): 453 [M+H]+, RT: 1.078 min. ¹H NMR (300 MHz, Chloroform-d) δ 7.72 (d, J=8.2 Hz, 1H), 7.59 (d, J=2.0 Hz, 1H), 7.23 (dd, J=8.2, 2.0 Hz, 1H), 4.89 (s, 2H), 4.20-3.85 m, 4H), 3.80 (s, 2H), 3.43 (t, J=6.2 Hz, 2H), 3.06 (s, 3H), 2.14-1.97 (m, 2H).

Example 9

2-(4-bromo-3-chlorobenzoyl)-11-(4-methoxybenzyl)-1,2,3,4,8,9,10,11-octahydro-6H,12H-pyrazino[1',2':3,4]imidazo[1,5-a][1,4]diazepine-6,12-dione (9)

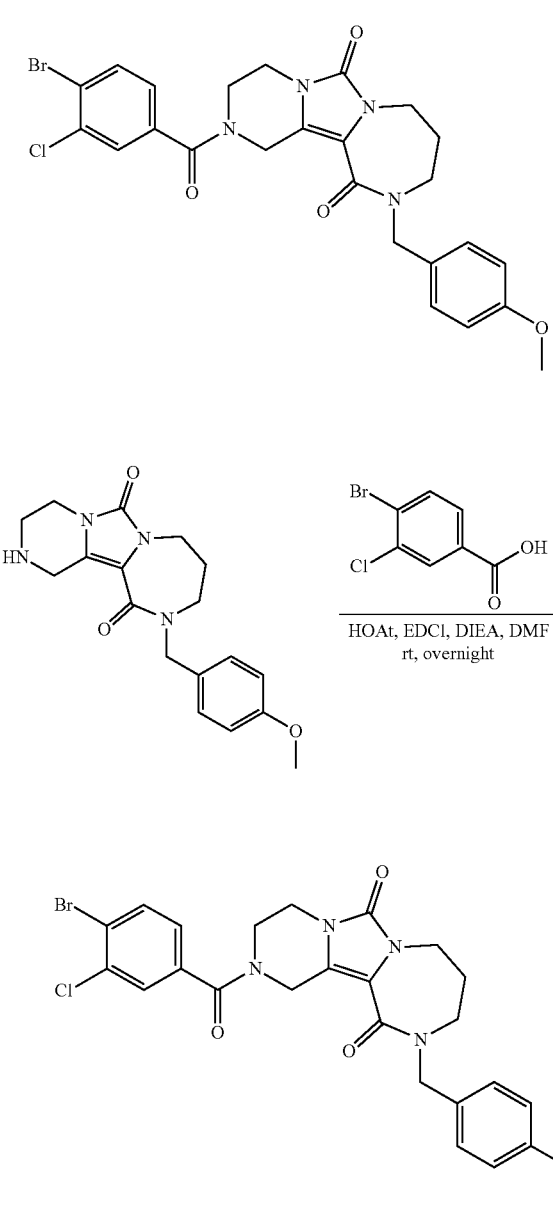

The title compound was prepared as a white solid according to the procedures of Example 8 by substituting 13-[(4-methoxyphenyl)methyl]-4,7,9,13-tetraazatricyclo[7.5.0.0^[2,7]]tetradec-1-ene-8,14-dione for 13-methyl-4,7,9,13-tetraazatricyclo[7.5.0.0 ^[2,7]]tetradec-1-ene-8,14-dione. LCMS (ES) m/z=559 [M+H]+, RT: 1.373 min. $^1$H NMR (400 MHz, Chloroform-d) δ 7.74 (d, J=8.2 Hz, 1H), 7.61 (d, J=2.0 Hz, 1H), 7.26-7.20 (m, 3H), 6.89 (d, J=8.7 Hz, 2H), 4.93 (s, 2H), 4.57 (s, 2H), 4.00 (s, 2H), 3.90-3.70 (m, 7H), 3.37 (t, J=6.2 Hz, 2H), 1.90-1.70 (m, 2H).

Example 10

N$^7$-(3-chloro-4-fluorophenyl)-3-oxo-2-phenyl-N1-(propan-2-yl)-2H,3H,5H,6H,7H,8H-imidazo[1,5-a]pyrazine-1,7-dicarboxamide (10)

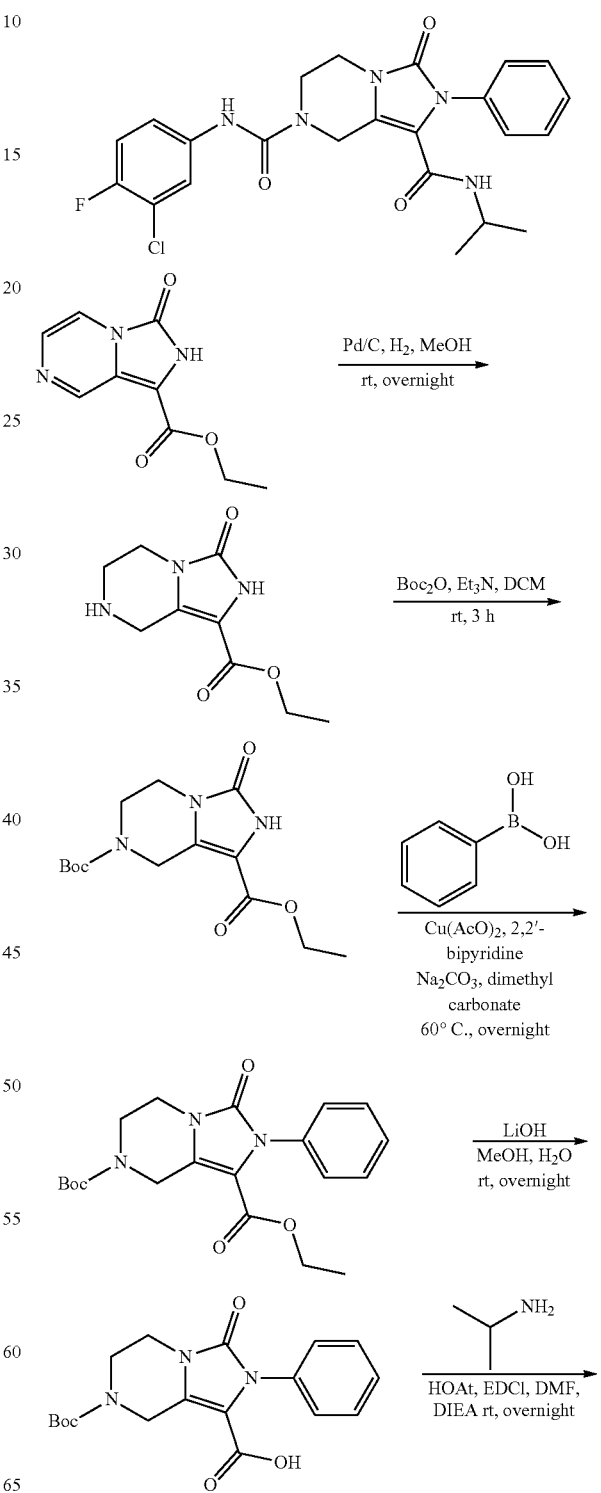

-continued

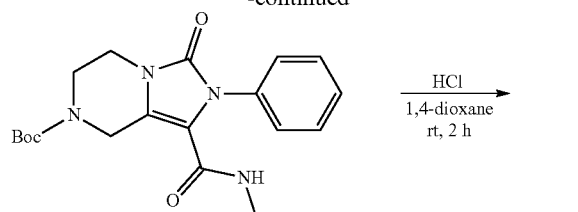

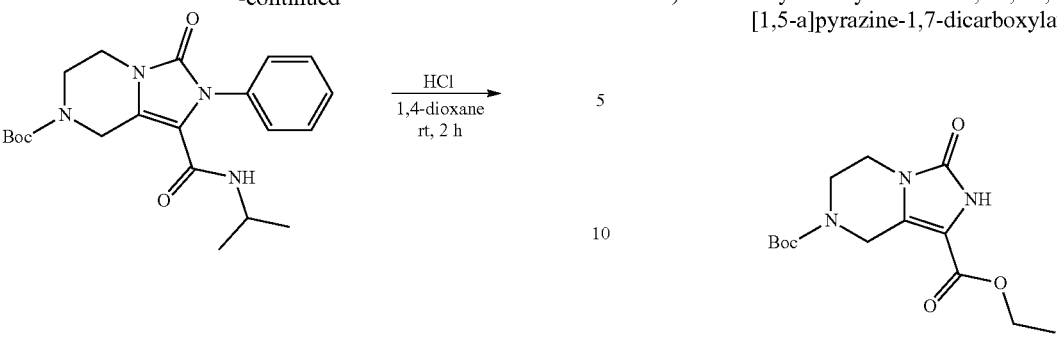

a) ethyl 3-oxo-2H,5H,6H,7H,8H-imidazo[1,5-a]pyrazine-1-carboxylate

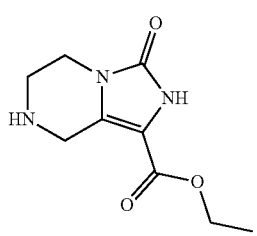

A 100 mL round-bottom flask was charged with ethyl 3-oxo-2H-imidazo[1,5-a]pyrazine-1-carboxylate (2.00 g, 9.65 mmol, 1.00 eq.), methanol (30 mL) and 10% Pd/C (200 mg). The mixture was stirred for overnight at rt under $H_2$ atmosphere (3 atm). The solid was filtrated off, and the filtrate was concentrated under reduced pressure to provide ethyl 3-oxo-2H,5H,6H,7H,8H-imidazo[1,5-a]pyrazine-1-carboxylate (2.00 g, 98% yield) as a light yellow solid. LCMS (ESI, m/z): 212 [M+H]$^+$, RT: 0.470 min.

b) 7-tert-butyl 1-ethyl 3-oxo-2H,5H,6H,8H-imidazo[1,5-a]pyrazine-1,7-dicarboxylate

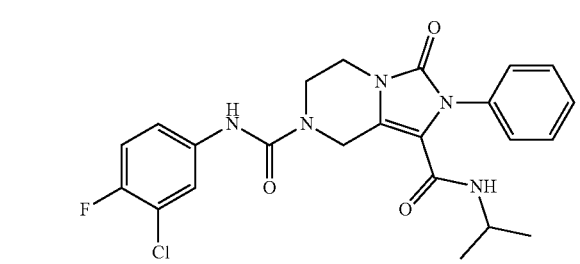

A 250 mL round-bottom flask was charged with ethyl 3-oxo-2H,5H,6H,7H,8H-imidazo[1,5-a]pyrazine-1-carboxylate (2.00 g, 9.47 mmol, 1.00 eq.), triethylamine (2.87 g, 28.5 mmol, 3.00 eq.) and dichloromethane (100 mL). Di-tert-butyl dicarbonate (2.48 g, 11.4 mmol, 1.20 eq.) in dichloromethane (20 mL) was added dropwise at rt. The mixture was stirred for 3 h at rt, and the reaction was quenched with water (100 mL). The mixture was extracted with dichloromethane (3×100 mL). The organic layers were combined, dried over anhydrous sodium sulfate, filtered and concentrated under reduced pressure. The residue was purified by silica gel column chromatography with EA:PE (9:1) to afford 7-tert-butyl 1-ethyl 3-oxo-2H,5H,6H,8H-imidazo[1,5-a]pyrazine-1,7-dicarboxylate (700 mg, 24% yield) as a light yellow solid. LCMS (ESI, m/z): 312 [M+H]$^+$, RT: 0.854 min. $^1$H NMR (400 MHz, Chloroform-d) δ 8.99 (s, 1H), 4.75 (s, 2H), 4.32 (q, J=7.1 Hz, 2H), 3.75 (dd, J=16.6, 5.3 Hz, 4H), 1.56-1.45 (m, 9H), 1.37 (t, J=7.1 Hz, 3H).

a) 7-tert-butyl 1-ethyl 3-oxo-2-phenyl-5H,6H,8H-imidazo[1,5-a]pyrazine-1,7-dicarboxylate

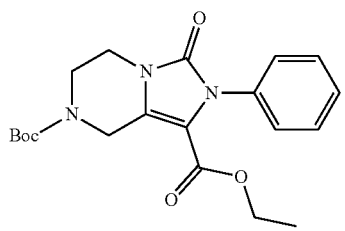 [SMILES: CCOC(=O)c1c2n(c(=O)n1-c1ccccc1)CCN(C(=O)OC(C)(C)C)C2]

A 100 mL round bottom flask was charged with 7-tert-butyl 1-ethyl 3-oxo-2H,5H,6H,8H-imidazo[1,5-a]pyrazine-1,7-dicarboxylate (500 mg, 1.61 mmol, 1.00 eq.), phenyl boronic acid (234 mg, 1.92 mmol, 1.20 eq.), 2,2'-bipyridyl (50.1 mg, 0.321 mmol, 0.20 eq.), dimethyl carbonate (20 mL), sodium carbonate (343 mg, 3.24 mmol, 2.00 eq.) and diacetoxycopper (58.0 mg, 0.321 mmol, 0.20 eq.). The solution was stirred overnight at 60° C. under oxygen atmosphere, and the reaction was quenched with water (100 mL). The solution was extracted with ethyl acetate (3×100 mL). The organic layers were combined, dried over anhydrous sodium sulfate, filtered and concentrated under reduced pressure. The residue was purified by silica gel column chromatography with EA:PE (1:2) to afford 7-tert-butyl 1-ethyl 3-oxo-2-phenyl-5H,6H,8H-imidazo[1,5-a]pyrazine-1,7-dicarboxylate (450 mg, 67% yield) as a white solid. LCMS (ESI, m/z): 388 [M+H]$^+$, RT: 0.691 min.

b) 7-(tert-butoxycarbonyl)-3-oxo-2-phenyl-5H,6H,8H-imidazo[1,5-a]pyrazine-1-carboxylic Acid

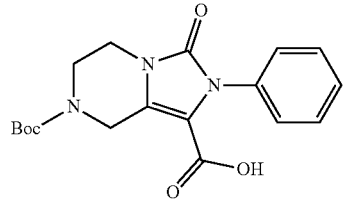 [SMILES: CC(C)(C)OC(=O)N1CCn2c(c(C(=O)O)n(-c3ccccc3)c2=O)C1]

A 50 round bottom flask was charged with 7-tert-butyl 1-ethyl 3-oxo-2-phenyl-5H,6H,8H-imidazo[1,5-a]pyrazine-1,7-dicarboxylate (450 mg, 1.16 mmol, 1.00 eq.), NaOH (92.9 mg, 2.32 mmol, 2 eq.), ethanol (10 mL) and water (1 mL). The solution was stirred overnight at rt, and the reaction was quenched by water (100 mL). The pH value of mixture was adjusted to about 4 with hydrochloric acid (1 mol/L). The mixture was extracted with ethyl acetate (3×100 mL). The organic layers were combined, dried over anhydrous sodium sulfate, filtered and concentrated under reduced pressure to provide 7-(tert-butoxycarbonyl)-3-oxo-2-phenyl-5H,6H,8H-imidazo[1,5-a]pyrazine-1-carboxylic acid (410 mg, 98% yield) as a white solid. LCMS (ESI, m/z): 360 [M+H]$^+$, RT: 0.818 min. $^1$H NMR (400 MHz, DMSO-d$_6$) δ 7.68-7.32 (m, 6H), 4.75 (s, 2H), 3.76-3.74 (m, 2H), 3.63-3.61 (m, 2H), 1.45 (s, 9H).

c) tert-butyl 1-(isopropylcarbamoyl)-3-oxo-2-phenyl-5H,6H,8H-imidazo[1,5-a]pyrazine-7-carboxylate

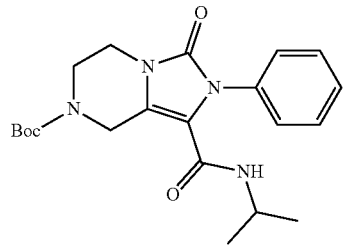 [SMILES: CC(C)NC(=O)c1c2n(c(=O)n1-c1ccccc1)CCN(C(=O)OC(C)(C)C)C2]

A 40 mL vial was charged with 7-(tert-butoxycarbonyl)-3-oxo-2-phenyl-5H,6H,8H-imidazo[1,5-a]pyrazine-1-carboxylic acid (210 mg, 0.584 mmol, 1.00 eq.), isopropylamine (41.4 mg, 0.701 mmol, 1.20 eq.), 3H-[1,2,3]triazolo[4,5-b]pyridin-3-ol (119 mg, 0.876 mmol, 1.50 eq.), 1-ethyl-3-(3-dimethylaminopropyl)carbodiimide hydrochloride (168 mg, 0.877 mmol, 1.50 eq.), N,N-diisopropylethylamine (302 mg, 2.33 mmol, 4.00 eq.) and N,N-dimethylformamide (10 mL). The solution was stirred overnight at rt, and the reaction was quenched with water (50 mL). The mixture was extracted with ethyl acetate (3×50 mL). The organic layers were combined, dried over anhydrous sodium sulfate, filtered and concentrated under reduced pressure. The residue was purified by silica gel column chromatography with EA:PE (2:5) to afford tert-butyl 1-(isopropylcarbamoyl)-3-oxo-2-phenyl-5H,6H,8H-imidazo[1,5-a]pyrazine-7-carboxylate (150 mg, 64% yield) as a colorless oil. LCMS (ESI, m/z): 401 [M+H]$^+$, RT: 0.961 min. $^1$H NMR (400 MHz, DMSO-d$_6$) δ 7.69-7.46 (m, 2H), 7.46-7.31 (m, 1H), 7.26-7.16 (m, 2H), 6.80 (s, 1H), 4.64 (s, 2H), 3.73-3.62 (m, 4H), 1.44 (s, 9H) 1.37-1.24 (m, 1H), 1.34-0.99 (m, 6H).

d) N-isopropyl-3-oxo-2-phenyl-5H,6H,7H,8H-imidazo[1,5-a]pyrazine-1-carboxamide

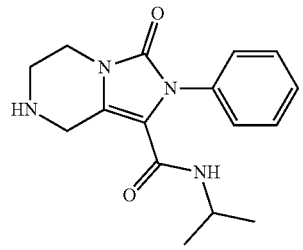 [SMILES: CC(C)NC(=O)c1c2n(c(=O)n1-c1ccccc1)CCNC2]

A 25-mL round-bottom flask was charged with tert-butyl 1-(isopropylcarbamoyl)-3-oxo-2-phenyl-5H,6H,8H-imidazo[1,5-a]pyrazine-7-carboxylate (150 mg, 0.375 mmol, 1.00 eq.), concentrated HCl (3 mL) and 1,4-dioxane (7 mL). The solution was stirred overnight at rt, and the reaction was quenched with water (50 mL). The pH value of the mixture was adjusted to about 10 with NaOH (1 mol/L). The mixture was extracted with dichloromethane (3×50 mL). The organic layers were combined, dried over anhydrous sodium sulfate, filtered and concentrated under reduced pressure afford N-isopropyl-3-oxo-2-phenyl-5H,6H,7H,8H-imidazo[1,5-a]pyrazine-1-carboxamide (100 mg, 89% yield) as an off-white solid. LCMS (ESI, m/z): 301 [M+H]$^+$, RT: 0.745 min.

e) N$^7$-(3-chloro-4-fluorophenyl)-3-oxo-2-phenyl-N$_1$-(propan-2-yl)-2H,3H,5H,6H,7H,8H-imidazo[1,5-a]pyrazine-1,7-dicarboxamide

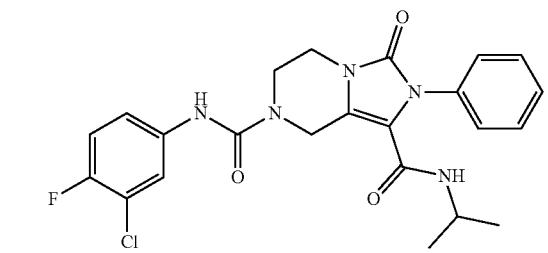 [SMILES: CC(C)NC(=O)c1c2n(c(=O)n1-c1ccccc1)CCN(C(=O)Nc1ccc(F)c(Cl)c1)C2]

A 25-mL round-bottom flask was charged with N-isopropyl-3-oxo-2-phenyl-5H,6H,7H,8H-imidazo[1,5-a]pyrazine-1-carboxamide (100 mg, 0.333 mmol, 1.00 eq.), phenyl N-(3-chloro-4-fluorophenyl)carbamate (97.2 mg, 0.366 mmol, 1.10 eq.), N,N-diisopropylethylamine (129 mg, 0.999 mmol, 3.00 eq.) and N,N-dimethylformamide (5 mL). The solution was stirred overnight at rt. The mixture was purified by Prep-HPLC with the following conditions: Column: XBridge Prep C$_{18}$ OBD Column, 19×150 mm 5 m; Mobile Phase A: Water (10 mmol/L NH$_4$HCO$_3$), Mobile Phase B: ACN; Flow rate: 25 mL/min; Gradient: 35% B to 55% B in 7 min; 220 nm. Purification resulted in N$^7$-(3-chloro-4-fluorophenyl)-3-oxo-2-phenyl-N1-(propan-2-yl)-2H,3H,5H,6H,7H,8H-imidazo[1,5-a]pyrazine-1,7-dicarboxamide (65.8 mg, 42% yield) as a white solid. LCMS (ESI, m/z): 472 [M+H]$^+$, RT: 2.772 min. $^1$H NMR (300 MHz, DMSO-d$_6$) δ 9.05 (s, 1H), 7.76-7.73 (m, 1H), 7.47-7.39 (m, 3H)7.39-7.21 (m, 5H), 4.76 (s, 2H), 3.89-3.84 (m, 3H), 3.69-3.66 (m, 2H), 0.98 (d, J=3.3 Hz, 6H). , Example 11
N[7]-(3-chloro-4-fluorophenyl)-N[1]-[(4-methoxyphenyl)methyl]-3-oxo-2-phenyl-2H,3H,5H,6H,7H,8H-imidazo[1,5-a]pyrazine-1,7-dicarboxamide (11)
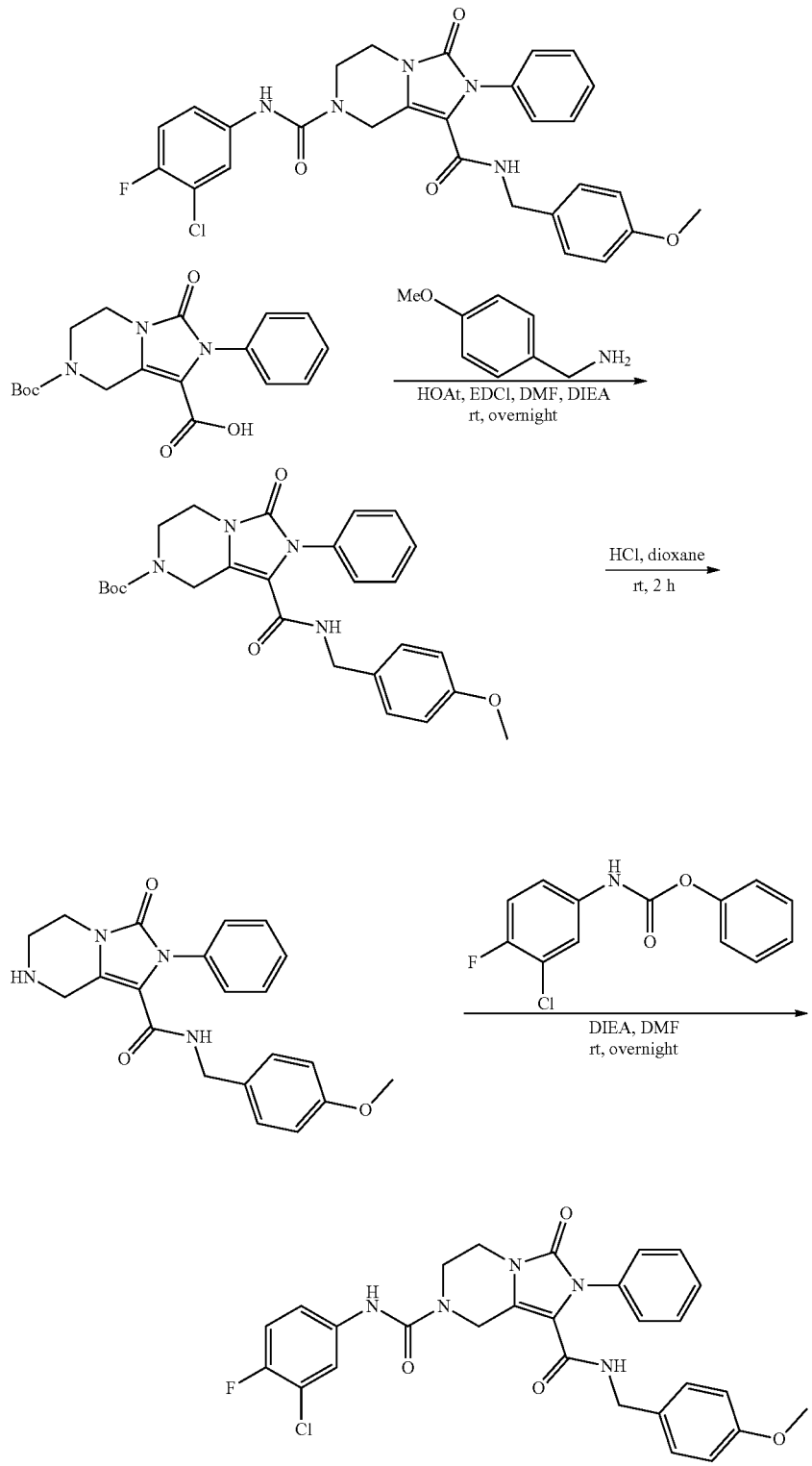

The title compound was prepared as a white solid according to the procedures of Example 10 e) to g) by substituting 4-methoxy-benzenemethanamine for isopropylamine. LCMS (ESI, m/z): 550 [M+H]+, RT: 3.093 min. ¹H NMR (300 MHz, DMSO-d₆) δ 9.04 (s, 1H), 7.99 (t, J=5.9 Hz, 1H), 7.75-7.72 (m, 1H), 7.44-7.36 (m, 3H), 7.35-7.25 (m, 2H), 7.25-7.17 (m, 2H), 7.04 (d, J=8.6 Hz, 2H), 6.85-6.76 (m, 2H), 4.78 (s, 2H), 4.22 (d, J=3.0 Hz, 2H), 3.88-3.85 (m, 2H), 3.72-3.67 (m, 5H).

Example 12

7-(4-bromo-3-chlorobenzoyl)-3-oxo-2-phenyl-N-(propan-2-yl)-2H,3H,5H,6H,7H,8H-imidazo[1,5-a]pyrazine-1-carboxamide (12)

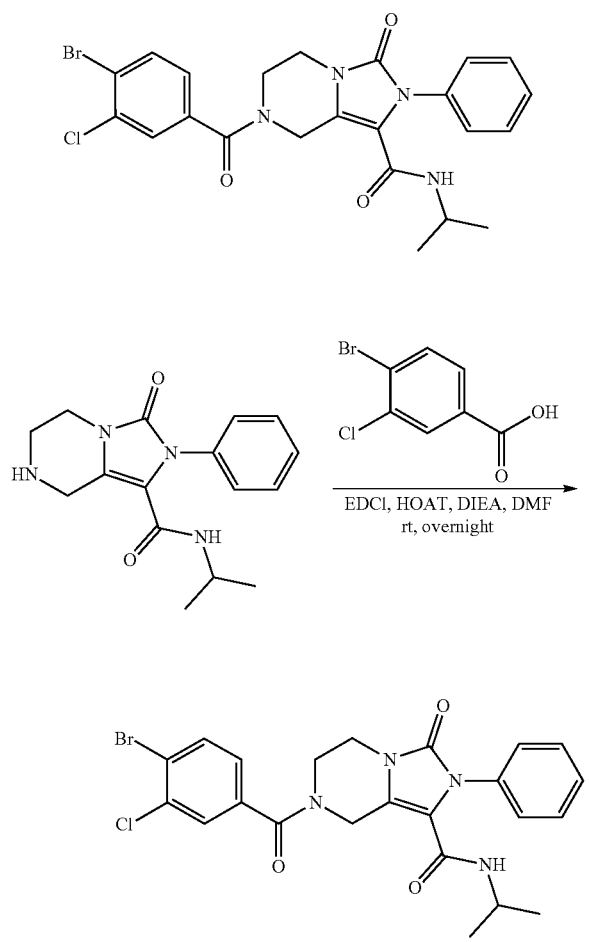

A 25-mL round-bottom flask was charged with N-isopropyl-3-oxo-2-phenyl-5H,6H,7H,8H-imidazo[1,5-a]pyrazine-1-carboxamide (220 mg, 0.732 mmol, 1.00 eq.), 4-bromo-3-chlorobenzoic acid (206 mg, 0.879 mmol, 1.20 eq.), 3H-[1,2,3]triazolo[4,5-b]pyridin-3-ol (149 mg, 1.09 mmol, 1.50 eq.), 1-ethyl-3-(3-dimethylaminopropyl)carbodiimide hydrochloride (210 mg, 1.09 mmol, 1.50 eq.), N,N-diisopropylethylamine (378 mg, 2.93 mmol, 4.00 eq.) and N,N-dimethylformamide (10 mL). The solution was stirred overnight at rt, and the reaction was quenched with water (10 mL). The mixture was extracted with dichloromethane (3×30 mL). The organic layers were combined, washed with brine (2×30 mL), dried over anhydrous sodium sulfate, filtered and concentrated under reduced pressure. The crude product was purified by Prep-HPLC with the following conditions: Column: Column: XBridge Shield RP₁₈ OBD Column, 30×150 mm 5 m; Mobile Phase A: Water (10 mmol/L NH₄HCO₃), Mobile Phase B: ACN; Flow rate: 60 mL/min; Gradient: 33% B to 47% B in 7 min; 220 nm. Purification resulted in 7-(4-bromo-3-chlorobenzoyl)-3-oxo-2-phenyl-N-(propan-2-yl)-2H,3H,5H,6H,7H,8H-imidazo[1,5-a]pyrazine-1-carboxamide (31.4 mg, 8% yield) as a white solid. LCMS (ESI, m/z): 517 [M+H]+, RT: 2.686 min. ¹H NMR (400 MHz, DMSO-d₆) δ 7.91-7.88 (m, 1H), 7.80-7.78 (m, 1H), 7.47-7.41 (m, 3H), 7.35-7.25 (m, 4H), 4.88 (s, 2H), 2.69 (m, 5H), 1.00-0.83 (m, 6H).

Example 13

7-(4-bromo-3-chlorobenzoyl)-N-[(4-methoxyphenyl)methyl]-3-oxo-2-phenyl-2H,3H,5H,6H,7H,8H-imidazo[1,5-a]pyrazine-1-carboxamide (13)

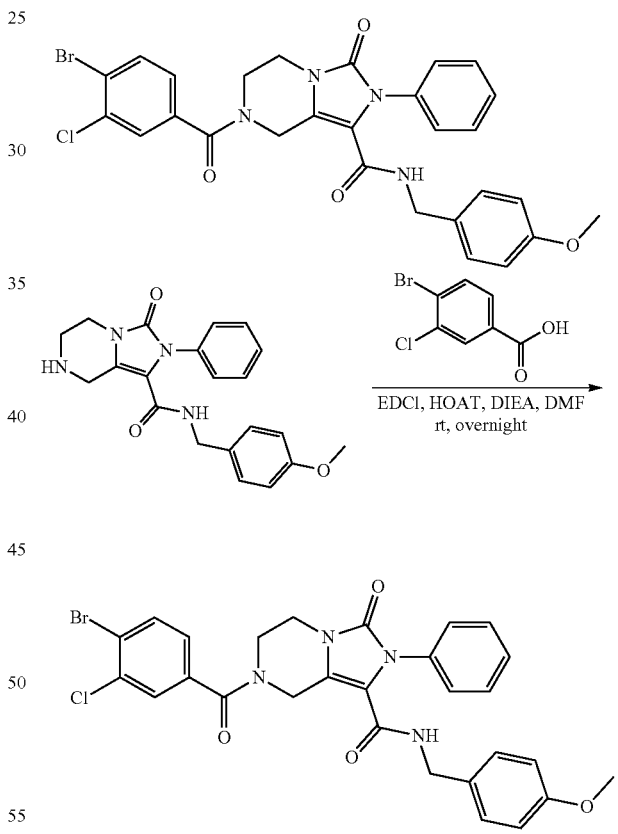

The title compound was prepared as a white solid according to the procedures of Example 12 by substituting N-[(4-methoxyphenyl)methyl]-3-oxo-2-phenyl-5H,6H,7H,8H-imidazo[1,5-a]pyrazine-1-carboxamide for N-isopropyl-3-oxo-2-phenyl-5H,6H,7H,8H-imidazo[1,5-a]pyrazine-1-carboxamide. LCMS (ESI, m/z): 595 [M+H]+, RT: 1.479 min. ¹H NMR (400 MHz, DMSO-d₆) δ 8.12 (s, 1H) 7.88 (d, J=4.2 Hz, 1H), 7.80 (s, 1H), 7.44-7.42 (m, 3H), 7.42-7.40 (m, 1H), 7.40-7.34 (m, 2H), 7.08 (s, 1H), 6.83 (m, 3H), 4.89-4.74 (m, 2H), 4.23-3.96 (m, 3H), 3.98-3.95 (m, 6H).

Example 14

2-benzyl-7-(4-bromo-3-chlorobenzoyl)-N-[(4-methoxyphenyl)methyl]-3-oxo-2H,3H,5H,6H,7H,8H-imidazo[1,5-a]pyrazine-1-carboxamide (14)

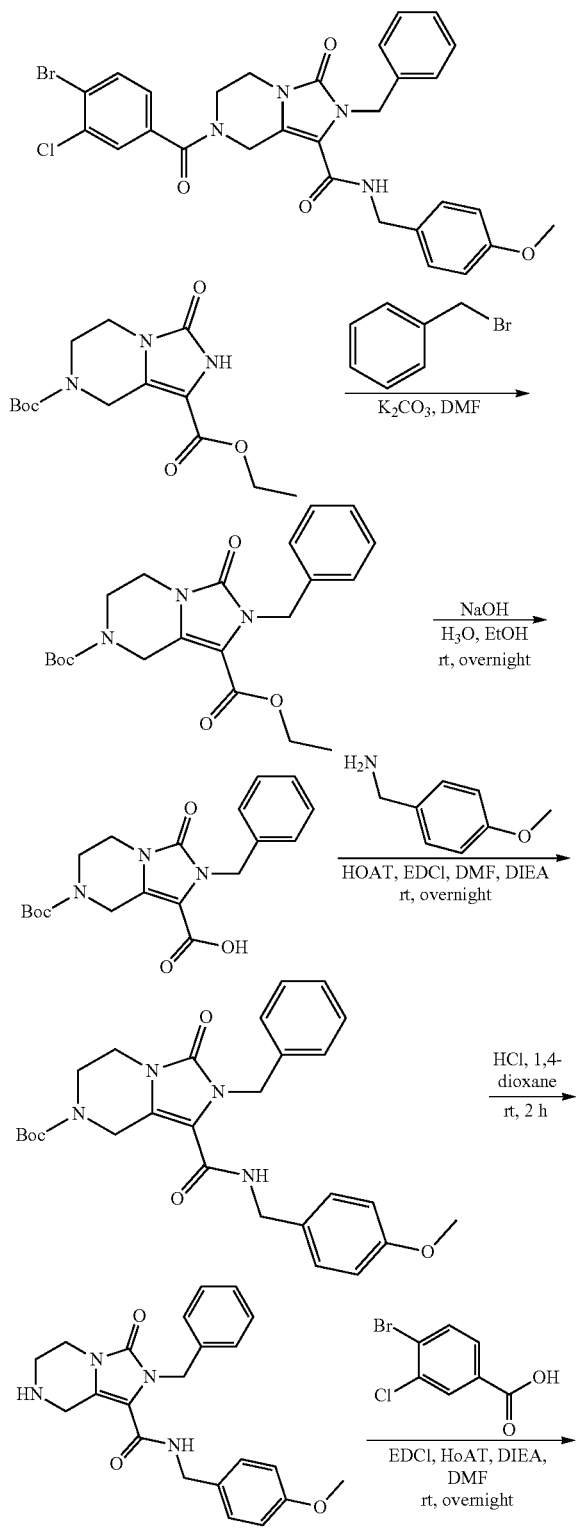

a) 7-tert-butyl 1-ethyl 2-benzyl-3-oxo-5H,6H,8H-imidazo[1,5-a]pyrazine-1,7-dicarboxylate A 100-mL round-bottom flask was charged with 7-tert-butyl 1-ethyl 3-oxo-2H,5H,6H,8H-imidazo[1,5-a]pyrazine-1,7-dicarboxylate (500 mg, 1.60 mmol, 1.00 eq.), benzyl bromide (329 mg, 1.927 mmol, 1.20 eq.), cesium carbonate (1.56 g, 4.818 mmol, 3.00 eq.) and N,N-dimethylformamide (10.00 mL). The solution was stirred overnight at rt, and the reaction was quenched with water (20 mL). The mixture was extracted with ethyl acetate (3×50 mL). The organic layers were combined, dried over anhydrous sodium sulfate, filtered and concentrated under reduced pressure. The residue was purified by silica gel column chromatography with EA:PE (2:5) to afford 7-tert-butyl 1-ethyl 2-benzyl-3-oxo-5H,6H,8H-imidazo[1,5-a]pyrazine-1,7-dicarboxylate (550 mg, 85% yield) as a yellow solid. LCMS (ESI, m/z): 402 [M+H]$^+$, RT: 1.144 min. $^1$H NMR (400 MHz, DMSO-d$_6$) δ 7.47-7.21 (m, 5H), 5.38 (s, 2H), 4.71 (s, 2H), 4.20-4.12 (m, 2H), 3.79-3.61 (m, 4H), 1.43 (s, 9H), 1.43-1.18 (m, 3H).

b) 2-benzyl-7-(tert-butoxycarbonyl)-3-oxo-5H,6H,8H-imidazo[1,5-a]pyrazine-1-Carboxylic Acid A 50-mL round-bottom flask was charged with 7-tert-butyl 1-ethyl 2-benzyl-3-oxo-5H,6H,8H-imidazo[1,5-a]pyrazine-1,7-dicarboxylate (450 mg, 1.12 mmol, 1.00 eq.), NaOH (89.7 mg, 2.24 mmol, 2.00 eq.), water (1 mL) and ethanol (5 mL). The solution was stirred overnight at rt, and the reaction was quenched with water (20 mL). The pH value of mixture was adjusted to about 4 with HCl (1 mol/L). The mixture was extracted with ethyl acetate (3×30 mL). The organic layers were combined, dried over anhydrous sodium sulfate, filtered concentrated to 2-benzyl-7-(tert-butoxycarbonyl)-3-oxo-5H,6H,8H-imidazo[1,5-a]pyrazine-1-carboxylic acid (410 mg, 98% yield) as a white solid. LCMS (ESI, m/z): 374 [M+H]+, RT: 0.943 min.

c) tert-butyl 2-benzyl-1-[[(4-methoxyphenyl)methyl]carbamoyl]-3-oxo-5H,6H,8H-imidazo[1,5-a]pyrazine-7-carboxylate

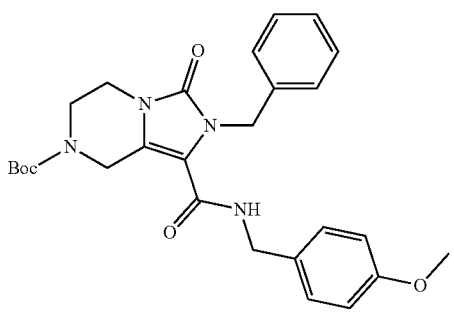 [SMILES: COc1ccc(CNC(=O)c2c3n(c(=O)n2Cc2ccccc2)CCN(C(=O)OC(C)(C)C)C3)cc1]

A 40 vial was charged with 2-benzyl-7-(tert-butoxycarbonyl)-3-oxo-5H,6H,8H-imidazo[1,5-a]pyrazine-1-carboxylic acid (410 mg, 1.09 mmol, 1.00 eq.), 4-methoxy-benzenemethanamine (180 mg, 1.31 mmol, 1.20 eq.), 3H-[1,2,3]triazolo[4,5-b]pyridin-3-ol (224 mg, 1.64 mmol, 1.50 eq.), 1-ethyl-3-(3-dimethylaminopropyl)carbodiimide hydrochloride (315 mg, 1.64 mmol, 1.50 eq.), N,N-diisopropylethylamine (567 mg, 4.39 mmol, 4.00 eq.) and N,N-dimethylformamide (10 mL). The solution was stirred overnight at rt, and the reaction was quenched with water (50 mL). The mixture was extracted with ethyl acetate (3×50 mL). The organic layers were combined, dried over anhydrous sodium sulfate, filtered and concentrated under reduced pressure. The residue was purified by silica gel column chromatography with EA:PE (1:1) to afford tert-butyl 2-benzyl-1-[[(4-methoxyphenyl)methyl]carbamoyl]-3-oxo-5H,6H,8H-imidazo[1,5-a]pyrazine-7-carboxylate (450 mg, 83% yield) as a white solid. LCMS (ESI, m/z): 493 [M+H]+, RT: 1.086 min. 1H NMR (400 MHz, Chloroform-d) δ 7.24-7.20 (m, 5H), 7.02-6.99 (m, 2H), 6.88-6.80 (m, 2H), 5.57 (s, 1H), 5.11 (s, 2H), 4.66 (s, 2H), 4.43-4.37 (m, 2H), 3.80 (s, 4H), 3.72 (s, 3H), 1.44 (s, 9H).

d) 2-benzyl-N-[(4-methoxyphenyl)methyl]-3-oxo-2H,3H,5H,6H,7H,8H-imidazo[1,5-a]pyrazine-1-carboxamide

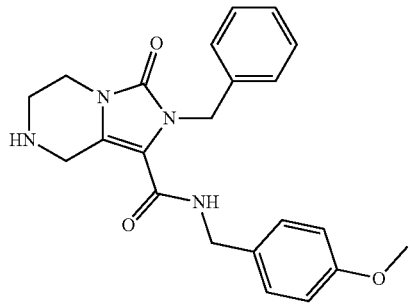 [SMILES: COc1ccc(CNC(=O)c2c3n(c(=O)n2Cc2ccccc2)CCNC3)cc1]

A 40 mL vial flask was charged with tert-butyl 2-benzyl-1-[[(4-methoxyphenyl)methyl]carbamoyl]-3-oxo-5H,6H,8H-imidazo[1,5-a]pyrazine-7-carboxylate (450 mg, 0.914 mmol, 1.00 eq.), concentrated HCl (5 mL) and 1,4-dioxane (10 mL). The solution was stirred 2 h at rt, and the reaction was quenched with water (50 mL). The pH value of the mixture was adjusted to about 10 with NaOH (1 mol/L). The mixture was extracted with dichloromethane (3×50 mL). The organic layers were combined, dried over anhydrous sodium sulfate, filtered and concentrated under reduced pressure afford 2-benzyl-N-[(4-methoxyphenyl)methyl]-3-oxo-2H,3H,5H,6H,7H,8H-imidazo[1,5-a]pyrazine-1-carboxamide (380 mg, 97% yield) as a white solid. LCMS (ESI, m/z): 393 [M+H]+, RT: 0.754 min.

e) 2-benzyl-7-(4-bromo-3-chlorobenzoyl)-N-[(4-methoxyphenyl)methyl]-3-oxo-2H,3H,5H,6H,7H,8H-imidazo[1,5-a]pyrazine-1-carboxamide

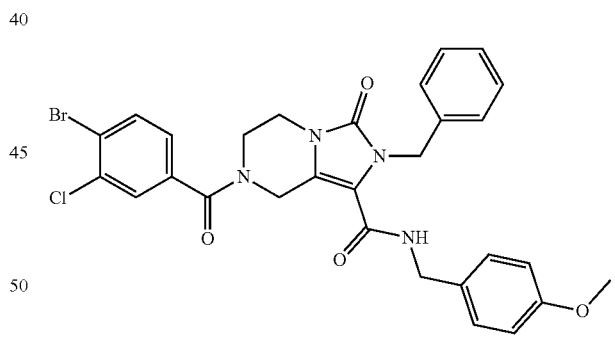

A 25-mL round-bottom flask was charged with 2-benzyl-N-[(4-methoxyphenyl)methyl]-3-oxo-5H,6H,7H,8H-imidazo[1,5-a]pyrazine-1-carboxamide (380 mg, 0.968 mmol, 1.00 eq.), 4-bromo-3-chlorobenzoic acid (273 mg, 1.16 mmol, 1.20 eq.), 3H-[1,2,3]triazolo[4,5-b]pyridin-3-ol (197 mg, 1.45 mmol, 1.50 eq.), 1-ethyl-3-(3-dimethylaminopropyl)carbodiimide hydrochloride (278 mg, 1.45 mmol, 1.50 eq.), N,N-diisopropylethylamine (500 mg, 3.87 mmol, 4.00 eq.) and N,N-dimethylformamide (10 mL). The solution was stirred overnight at rt. The mixture was purified by Prep-HPLC with the following conditions: Column: XBridge Shield RP18 OBD Column, 30×150 mm 5 m; Mobile Phase A: Water (10 mmol/L NH4HCO3), Mobile Phase B: ACN; Flow rate: 60 mL/min; Gradient: 40% B to 60% B in 7 min;

220 nm to afford 2-benzyl-7-(4-bromo-3-chlorobenzoyl)-N-[(4-methoxyphenyl)methyl]-3-oxo-2H,3H,5H,6H,7H,8H-imidazo[1,5-a]pyrazine-1-carboxamide (208 mg, 35% yield) as a white solid. LCMS (ESI, m/z): 609 [M+H]$^+$, RT: 1.452 min. $^1$H NMR (400 MHz, Chloroform-d) δ 7.70 (d, J=4.0 Hz, 1H), 7.57 (s, 1H), 7.26-7.24 (m, 3H), 7.20-7.15 (m, 3H), 6.95 (s, 2H), 6.81-6.79 (m, 2H), 5.58 (s, 1H), 5.06 (s, 2H), 4.87 (s, 2H), 4.27 (br, 2H), 3.99-3.81 (m, 7H).
Example 15
7-(4-bromo-3-chlorobenzoyl)-N-[(4-methoxyphenyl)methyl]-3-oxo-2-(2-phenylethyl)-5H,6H,8H-imidazo[1,5-a]pyrazine-1-carboxamide (15)
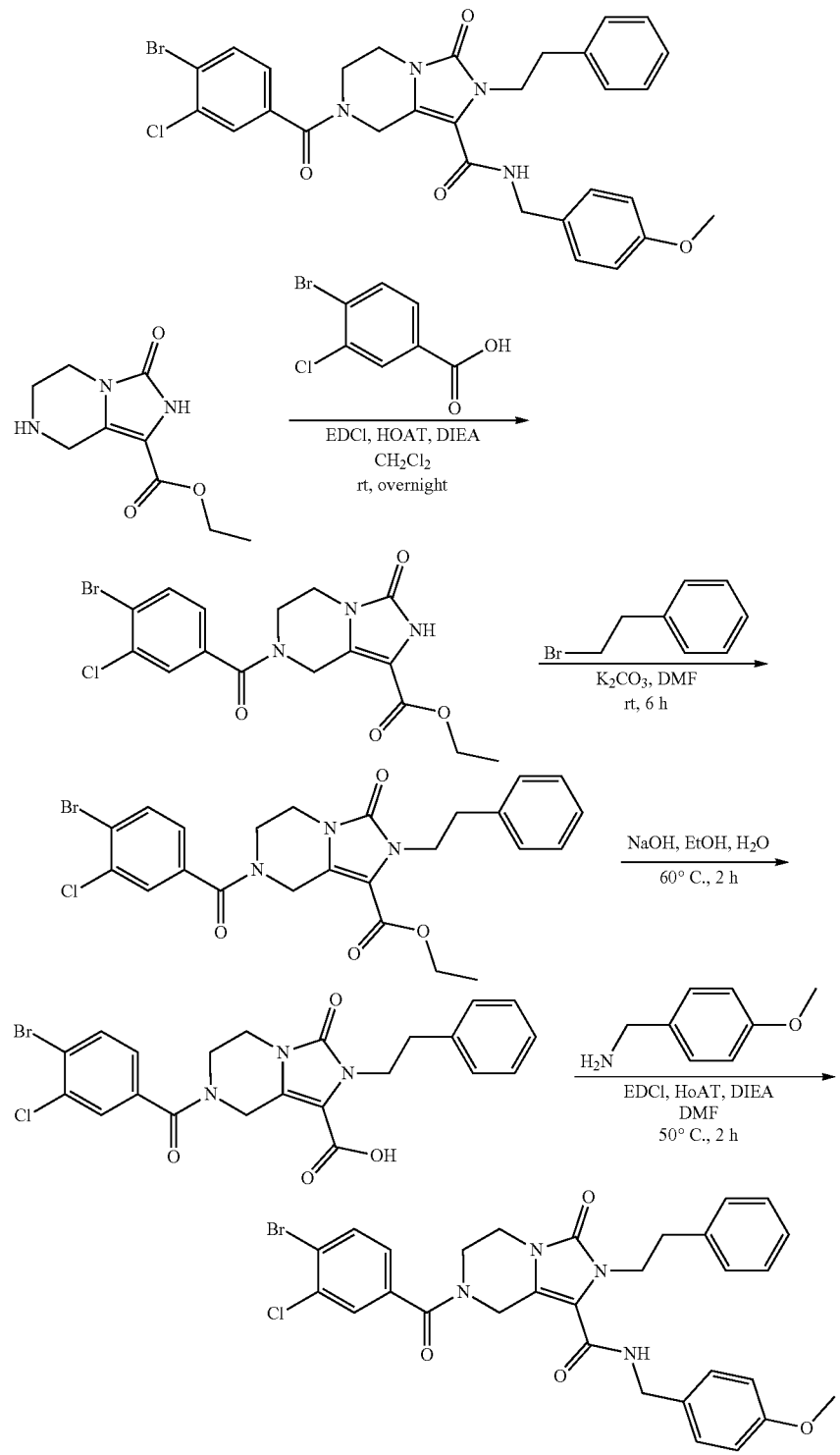

a) 7-(4-bromo-3-chlorobenzoyl)-3-oxo-2H,5H,6H, 8H-imidazo[1,5-a]pyrazine-1-carboxylate

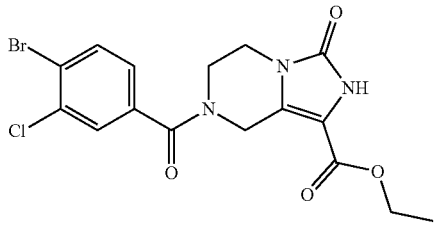 [SMILES: CCOC(=O)c1[nH]c(=O)n2c1CN(C(=O)c1ccc(Br)c(Cl)c1)CC2]

A 100-mL round-bottom flask was charged with 4-bromo-3-chlorobenzoic acid (268 mg, 1.14 mmol, 1.20 eq.), ethyl 3-oxo-2H,5H,6H,7H,8H-imidazo[1,5-a]pyrazine-1-carboxylate (500 mg, 0.947 mmol, 1.00 eq.), 3lH-[1,2,3]triazolo[4,5-b]pyridin-3-ol (193 mg, 1.42 mmol, 1.50 eq.), 1-ethyl-3-(3-dimethylaminopropyl)carbodiimide hydrochloride (272 mg, 1.42 mmol, 1.50 eq.), N,N-diisopropylethylamine (367 mg, 2.84 mmol, 3.00 eq.), N,N-dimethylformamide (5 mL). The solution was stirred overnight at rt, and the reaction was quenched with water (20 mL). The mixture was extracted with ethyl acetate (3×30 mL). The organic layers were combined, dried over anhydrous sodium sulfate, filtered and concentrated under reduced pressure. The residue was purified by silica gel column chromatography with EA:PE (1:4) to afford ethyl 7-(4-bromo-3-chlorobenzoyl)-3-oxo-2H,5H,6H,8H-imidazo[1,5-a]pyrazine-1-carboxylate (450 mg, 44% yield) as a white solid. LCMS (ESI, m/z): 428 [M+H]+, RT: 0.719 min.

b) ethyl 7-(4-bromo-3-chlorobenzoyl)-3-oxo-2-(2-phenylethyl)-5H,6H,8H-imidazo[1,5-a]pyrazine-1-carboxylate

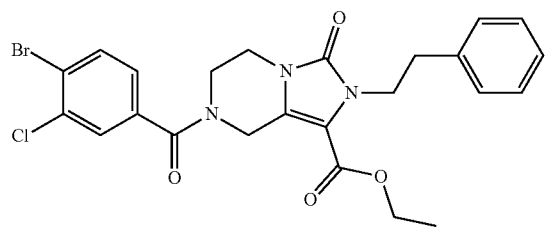 [SMILES: CCOC(=O)c1c2n(c(=O)n1CCc1ccccc1)CCN(C(=O)c1ccc(Br)c(Cl)c1)C2]

A 40 mL vial was charged with ethyl 7-(4-bromo-3-chlorobenzoyl)-3-oxo-2H,5H,6H,8H-imidazo[1,5-a]pyrazine-1-carboxylate (447 mg, 1.04 mmol, 1.00 eq.), potassium carbonate (288 mg, 2.09 mmol, 2.00 eq.), potassium iodide (1.73 mg, 0.010 mmol, 0.01 eq.) and N,N-dimethylformamide (1 mL). (2-bromoethyl)benzene (193 mg, 1.04 mmol, 1.00 eq.) was added dropwise at rt. The mixture was stirred for 6 h at rt, and the reaction was quenched with water (20 mL). The mixture was extracted with ethyl acetate (3×30 mL). The organic layers were combined, dried over anhydrous sodium sulfate, filtered and concentrated under reduced pressure to afford ethyl 7-(4-bromo-3-chlorobenzoyl)-3-oxo-2-(2-phenylethyl)-5H,6H,8H-imidazo[1,5-a]pyrazine-1-carboxylate (430 mg, 77% yield) as a light yellow oil. LCMS (ESI, m/z): 532 [M+H]+, RT: 0.743 min. 1H NMR (400 MHz, DMSO-d6) δ 7.95-7.84 (m, 2H), 7.77 (s, 1H), 7.41-7.35 (m, 1H), 7.33-7.25 (m, 2H), 7.22-7.16 (m, 2H), 4.33-4.21 (m, 1H), 4.09-4.01 (m, 4H), 3.62 (s, 2H), 3.32 (s, 1H), 2.80 (s, 2H), 2.80 (s, 1H), 2.72 (s, 1H), 1.36-1.17 (m, 3H).

c) 7-(4-bromo-3-chlorobenzoyl)-3-oxo-2-(2-phenylethyl)-5H,6H,8H-imidazo[1,5-a]pyrazine-1-carboxylic Acid

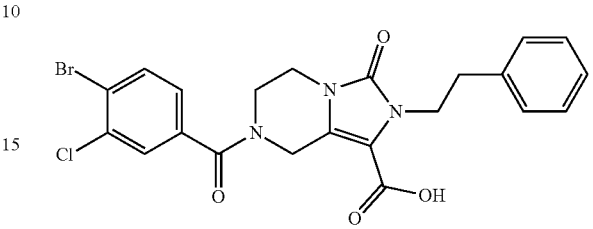

A 40 mL vial was charged with ethyl 7-(4-bromo-3-chlorobenzoyl)-3-oxo-2-(2-phenylethyl)-5H,6H,8H-imidazo[1,5-a]pyrazine-1-carboxylate (350 mg, 0.657 mmol, 1.00 eq.), ethanol (1 mL), water (1 mL) and NaOH (31.5 mg, 0.788 mmol, 1.20 eq.). The mixture was stirred for 2 h at 60° C., and the reaction was quenched with HCl (6 mL, 1 mol/L). The mixture was extracted with ethyl acetate (3×40 mL). The combined organic layers were washed with brine (20 mL), dried over anhydrous sodium sulfate, filtered and concentrated under reduced pressure to afford 7-(4-bromo-3-chlorobenzoyl)-3-oxo-2-(2-phenylethyl)-5H,6H,8H-imidazo[1,5-a]pyrazine-1-carboxylic acid (202 mg, 61% yield). LCMS (ESI, m/z): 504 [M+H]+, RT: 1.031 min. 1H NMR (300 MHz, DMSO-d6) δ 8.05-7.84 (m, 2H), 7.81-7.76 (m, 1H), 7.43-7.36 (m, 1H), 7.32-7.26 (m, 2H), 7.24-7.17 (m, 2H), 4.13-3.99 (m, 2H), 3.62 (s, 2H), 3.31 (s, 2H), 2.92-2.73 (m, 2H), 1.31-1.21 (m, 2H).

d) 7-(4-bromo-3-chlorobenzoyl)-N-[(4-methoxyphenyl)methyl]-3-oxo-2-(2-phenylethyl)-5H,6H,8H-imidazo[1,5-a]pyrazine-1-carboxamide

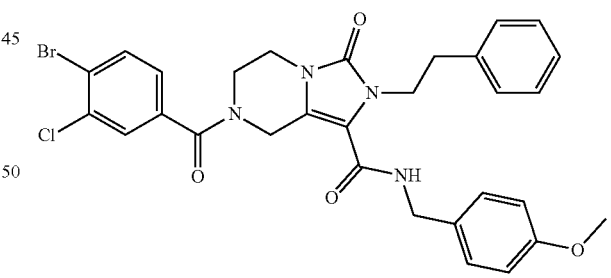

A 40 mL vial was charged with 7-(4-bromo-3-chlorobenzoyl)-3-oxo-2-(2-phenylethyl)-5H,6H,8H-imidazo[1,5-a]pyrazine-1-carboxylic acid (200 mg, 0.396 mmol, 1.00 eq.), 4-methoxy-benzenemethanamine (65.2 mg, 0.475 mmol, 1.20 eq.), 3H-[1,2,3]triazolo[4,5-b]pyridin-3-ol (80.9 mg, 0.594 mmol, 1.50 eq.), 1-ethyl-3-(3-dimethylaminopropyl)carbodiimide hydrochloride (114 mg, 0.594 mmol, 1.50 eq.), N,N-diisopropylethylamine (154 mg, 1.19 mmol, 3.00 eq.) and N,N-dimethylformamide (2 mL). The mixture was stirred for 2 h at 50° C., and the reaction was quenched with water (20 mL). The mixture was extracted with dichloromethane (4×50 mL). The combined organic layers were washed with brine (20 mL), dried over anhydrous sodium sulfate, filtered and concentrated under reduced pressure. The crude product was purified by Prep-HPLC with the following conditions: Column: YMC-Actus Triart C$_{18}$, 30×250 mm 5 μm; Mobile Phase A: Water (10 mmol/L NH$_4$HCO$_3$+0.1% NH$_3$.H$_2$O), Mobile Phase B: ACN; Flow rate: 60 mL/min; Gradient: 78% B to 88% B in 7 min; 220 nm. Purification resulted in 7-(4-bromo-3-chlorobenzoyl)-N-[(4-methoxyphenyl)methyl]-3-oxo-2-(2-phenylethyl)-5H,6H,8H-imidazo[1,5-a]pyrazine-1-carboxamide (91.0 mg, 37% yield) as a yellow solid. LCMS (ESI, m/z): 623 [M+H]$^+$, RT: 1.209 min. $^1$H NMR (400 MHz, Chloroform-d) δ 7.70 (d, J=8.2 Hz, 1H), 7.55 (d, J=2.0 Hz, 1H), 7.28-7.19 (m, 5H), 7.19-6.85 (m, 3H), 6.87 (d, J=8.2 Hz, 2H), 4.75 (s, 2H), 4.32 (s, 2H), 4.11 (s, 2H), 3.81-3.63 (m, 7H), 2.96 (t, J=7.3 Hz, 2H).

Example 16

13-benzyl-4-(4-bromo-3-chlorobenzoyl)-11-fluoro-4,7,9,13-tetraazatricyclo[7.5.0.0^[2,7]]tetradec-1-ene-8,14-dione (371 & 372)

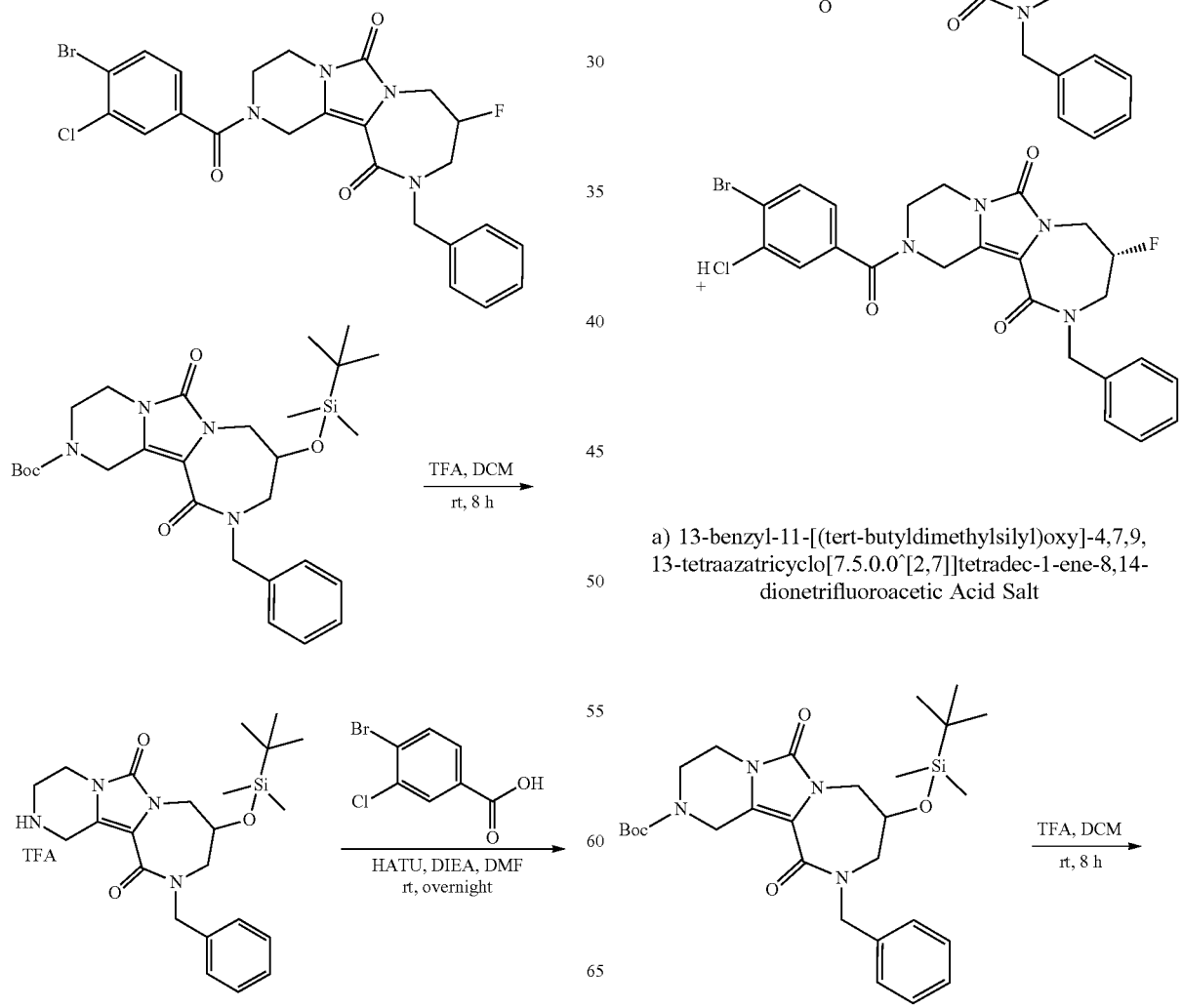

a) 13-benzyl-11-[(tert-butyldimethylsilyl)oxy]-4,7,9,13-tetraazatricyclo[7.5.0.0^[2,7]]tetradec-1-ene-8,14-dionetrifluoroacetic Acid Salt

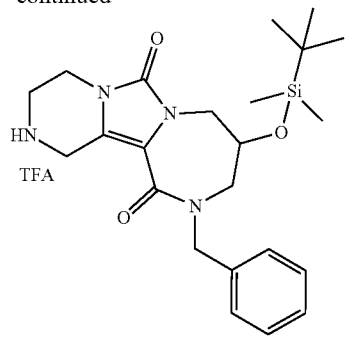

A 100 mL round bottom flask was charged with tert-butyl 13-benzyl-11-[(tert-butyldimethylsilyl)oxy]-8,14-dioxo-4,7,9,13-tetraazatricyclo[7.5.0.0^[2,7]]tetradec-1-ene-4-carboxylate (600 mg, 1.11 mmol, 1.00 eq.), synthesized as described in Example 17, trifluoroacetic acid (5.00 mL) and dichloromethane (50 mL). The resulting solution was stirred for 8 h at rt and concentrated under reduced pressure to provide 13-benzyl-11-[(tert-butyldimethylsilyl)oxy]-4,7,9,13-tetraazatricyclo[7.5.0.0^[2,7]]tetradec-1-ene-8,14-dione trifluoroacetic acid salt (700 mg, crude) as a light yellow solid. LCMS (ESI, m/z): 443 [M+H-TFA]+.

b) 13-benzyl-4-(4-bromo-3-chlorobenzoyl)-11-[(tert-butyldimethylsilyl)oxy]-4,7,9,13-tetraazatricyclo [7.5.0.0 ^[2,7]]tetradec-1-ene-8,14-dione

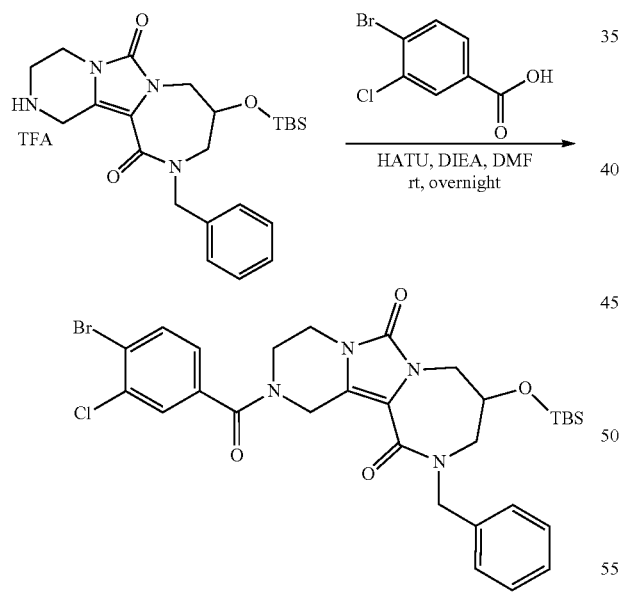

A 40 mL flask was charged with 13-benzyl-11-[(tert-butyldimethylsilyl)oxy]-4,7,9,13-tetraazatricyclo[7.5.0.0^[2,7]]tetradec-1-ene-8,14-dione trifluoroacetic acid salt (700 mg, 1.30 mmol, 1.00 eq.), 4-bromo-3-chlorobenzoic acid (335 mg, 1.42 mmol, 1.10 eq.), 2-(3H-[1,2,3]triazolo[4,5-b]pyridin-3-yl)-1,1,3,3-tetramethylisouronium (738 mg, 1.94 mmol, 1.50 eq.), N,N-diisopropylethylamine (502 mg, 3.88 mmol, 3.00 eq.) and N,N-dimethylformamide (20 mL). The solution was stirred overnight at rt and diluted with ethyl acetate (100 mL). The mixture was washed with water (3×50 mL). The organic layer was dried over anhydrous sodium sulfate, filtered and concentrated under reduced pressure. The residue was purified by silica gel column chromatography, eluted with petroleum ether:ethyl acetate (1:1) to afford 13-benzyl-4-(4-bromo-3-chlorobenzoyl)-11-[(tert-butyldimethylsilyl)oxy]-4,7,9,13-tetraazatricyclo[7.5.0.0 ^[2,7]]tetradec-1-ene-8,14-dione (500 mg, 58% yield) as a white solid. LCMS (ESI, m/z): 659 [M+H]+.

c) 13-benzyl-4-(4-bromo-3-chlorobenzoyl)-11-hydroxy-4,7,9,13-tetraazatricyclo[7.5.0.0 ^[2,7]]tetradec-1-ene-8,14-dione

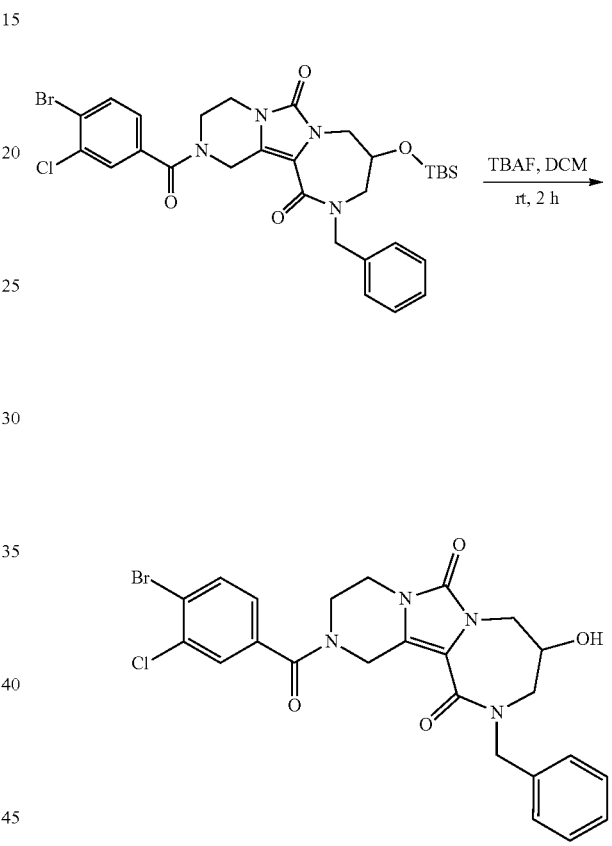

A 50 mL round bottom flask was charged with 13-benzyl-4-(4-bromo-3-chlorobenzoyl)-11-[(tert-butyldimethylsilyl)oxy]-4,7,9,13-tetraazatricyclo[7.5.0.0^[2,7]]tetradec-1-ene-8,14-dione (500 mg, 0.757 mmol, 1.00 eq.) and tetrahydrofuran (10 mL). Tetrabutylammoniumfluoride (1.50 mL, 1.50 mmol, 1.98 eq., 1 M in tetrahydroufuran) was added. The solution was stirred for 2 h at rt, and then diluted with ethyl acetate (100 mL). The mixture was washed with water (3×50 mL). The organic layer was dried over anhydrous sodium sulfate, filtered and concentrated under reduced pressure to obtain 13-benzyl-4-(4-bromo-3-chlorobenzoyl)-11-hydroxy-4,7,9,13-tetraazatricyclo [7.5.0.0^[2,7]]tetradec-1-ene-8,14-dione (300 mg, crude) as a white solid. LCMS (ESI, m/z): 545 [M+H]+.

d) 2 enantiomers of 13-benzyl-4-(4-bromo-3-chlorobenzoyl)-11-fluoro-4,7,9,13-tetraazatricyclo[7.5.0.0^[2,7]]tetradec-1-ene-8,14-dione(371 and 372)

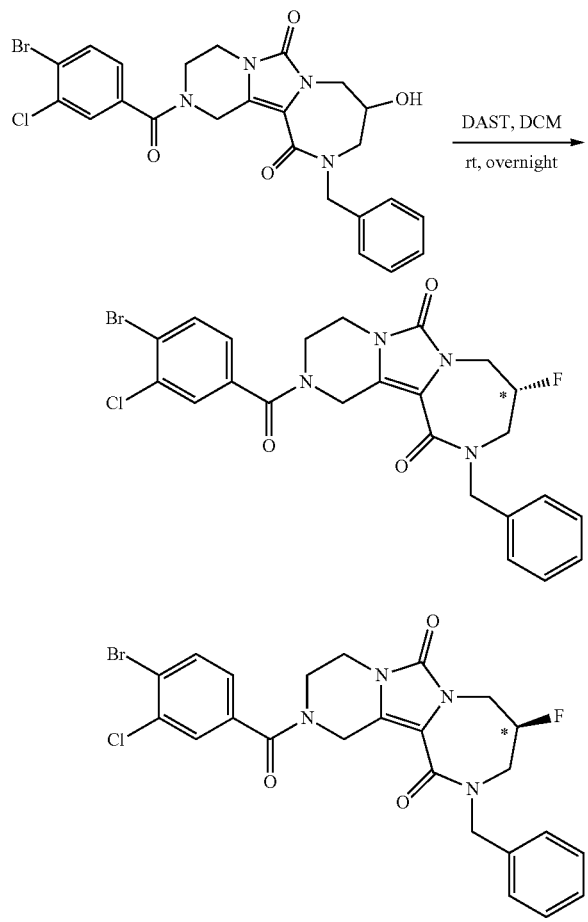

A 40 mL vial was charged with 13-benzyl-4-(4-bromo-3-chlorobenzoyl)-11-hydroxy-4,7,9,13-tetraazatricyclo[7.5.0.0^[2,7]]tetradec-1-ene-8,14-dione (80.0 mg, 0.147 mmol, 1.00 eq.) and dichloromethane (10 mL). The diethylaminosulfur trifluoride (47.2 mg, 0.293 mmol, 2.00 eq.) was added at 0° C. The solution was stirred overnight at rt. The reaction was quenched by water (20 mL). The mixture was extracted with dichloromethane (3×20 mL). The organic layers were combined, dried over anhydrous sodium sulfate, filtered and concentrated under reduced pressure. The crude product was purified by chiral-Prep-HPLC with the following conditions (Column: CHIRALPAK IF, 2×25 cm, 5 um; Mobile Phase A: MTBE (10 mm $NH_3$-MeOH)—HPLC, Mobile Phase B: EtOH—HPLC; Flow rate: 20 mL/min; Gradient: 50% B in 30 min; 220/254 nm to afford the 2 pure enantiomers of 13-benzyl-4-(4-bromo-3-chlorobenzoyl)-11-fluoro-4,7,9,13-tetraazatricyclo[7.5.0.0^[2,7]]tetradec-1-ene-8,14-dione. First enantiomer to elute: Compound 372, 10.7 mg, 13% yield as a white solid. LCMS (ESI, m/z): 547 [M+H]$^+$. $^1$H NMR (400 MHz, $CDCl_3$) δ 7.71 (d, J=8.2 Hz, 1H), 7.59 (d, J=2.0 Hz, 1H), 7.40-7.29 (m, 3H), 7.27 (s, 1H), 7.25-7.19 (m, 1H), 5.35 (d, J=15.0 Hz, 1H), 4.97 (d, J=14.3 Hz, 2H), 4.40 (d, J=6.6 Hz, 1H), 4.28 (d, J=6.6 Hz, 1H), 4.22-4.01 (m, 3H), 4.00-3.64 (m, 4H), 3.51 (dt, J=12.8, 3.7 Hz, 1H). Second enantiomer to elute: Compound 373, 10.7 mg, 13% yield as a white solid. LCMS (ESI, m/z): 547 [M+H]$^+$. $^1$H NMR (400 MHz, $CDCl_3$) 7.71 (d, J=8.2 Hz, 1H), 7.59 (d, J=2.0 Hz, 1H), 7.40-7.29 (m, 3H), 7.27 (s, 1H), 7.25-7.19 (m, 1H), 5.35 (d, J=15.0 Hz, 1H), 4.97 (d, J=14.3 Hz, 2H), 4.40 (d, J=6.6 Hz, 1H), 4.28 (d, J=6.6 Hz, 1H), 4.22-4.01 (m, 3H), 4.00-3.64 (m, 4H), 3.51 (dt, J=12.8, 3.7 Hz, 1H).

Example 17

Tert-butyl-13-benzyl-11-[(tert-butyldimethylsilyl)oxy]-8,14-dioxo-4,7,9,13-tetraazatricyclo[7.5.0.0^[2,7]]tetradec-1-ene-4-carboxylate (Intermediate 1)

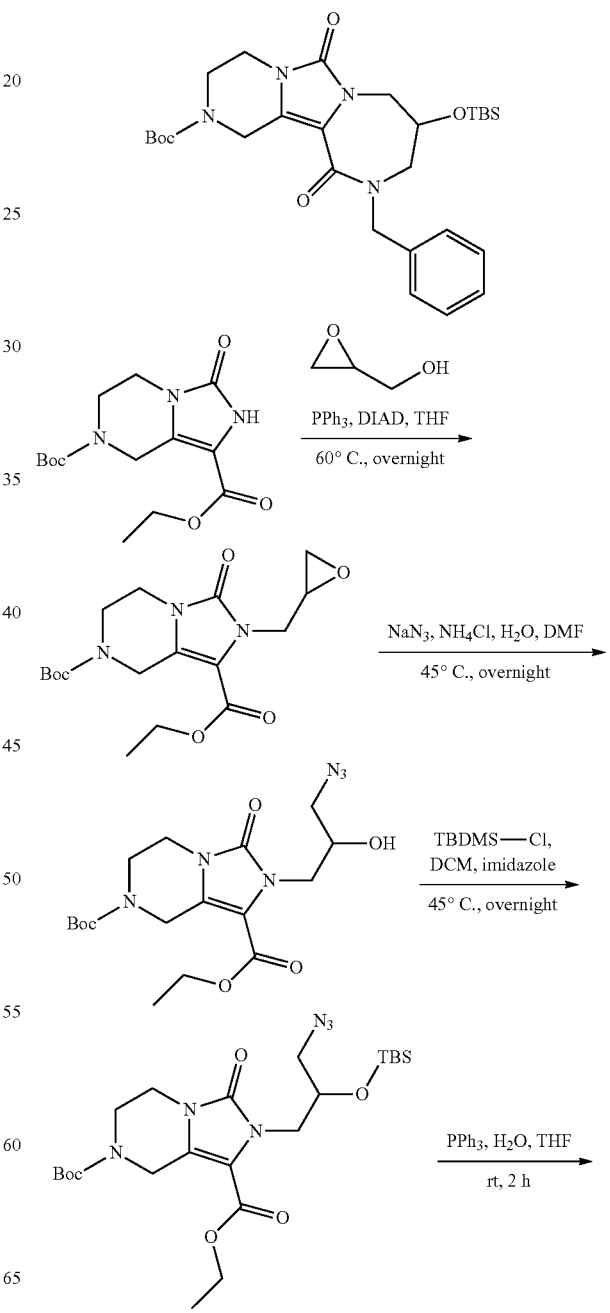

anhydrous sodium sulfate and concentrated under reduced pressure. The residue was purified by reverse flash chromatography, eluted with tetrahydrofuran:water (0.05% TFA) (1:1) to afford 7-tert-butyl-1-ethyl-2-(oxiran-2-ylmethyl)-3-oxo-5H,6H,8H-imidazo[1,5-a]pyrazine-1,7-dicarboxylate (2.10 g, 59% yield) as a light yellow oil. LCMS (ESI, m/z): 368 [M+H]⁺.

b) 7-tert-butyl-1-ethyl 2-(3-azido-2-hydroxypropyl)-3-oxo-5H,6H,8H-imidazo[1,5-a]pyrazine-1,7-dicarboxylate

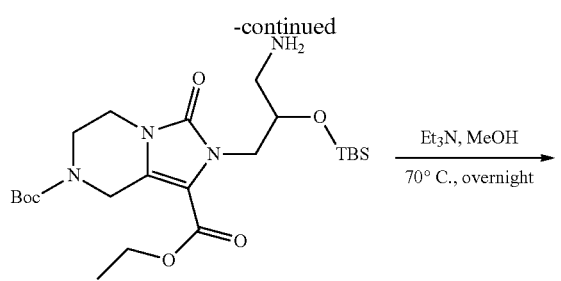

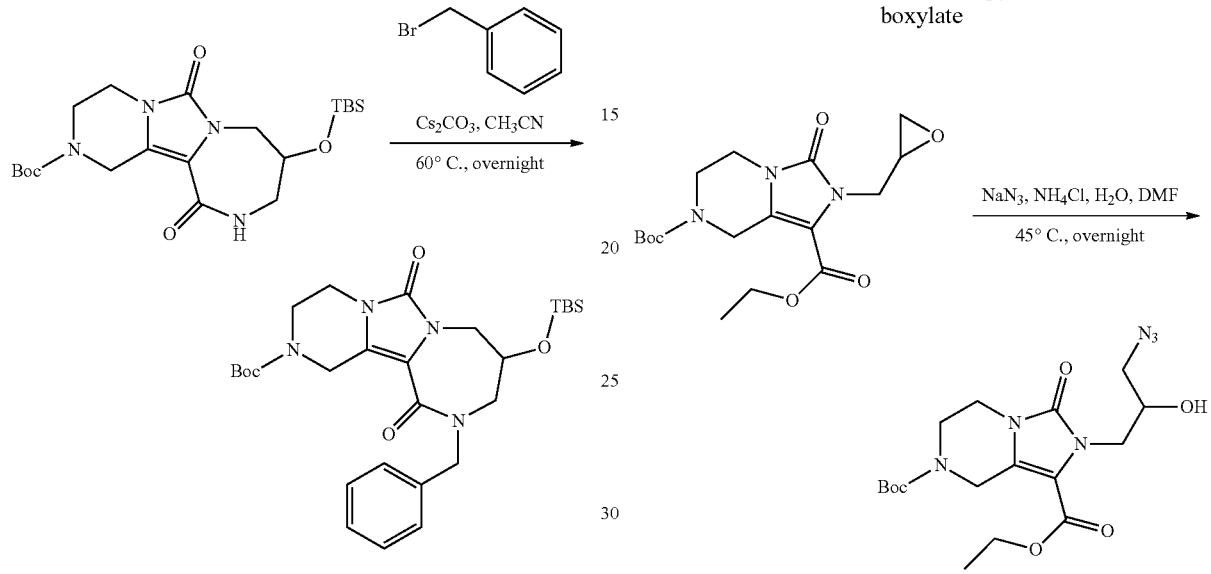

a) 7-tert-butyl 1-ethyl 2-(oxiran-2-ylmethyl)-3-oxo-5H,6H,8H-imidazo[1,5-a]pyrazine-1,7-dicarboxylate

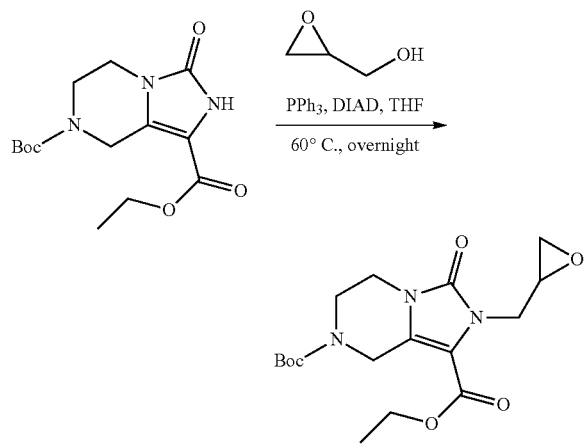

A 100 mL vial was charged with 7-tert-butyl-1-ethyl-3-oxo-2H,5H,6H,8H-imidazo[1,5-a]pyrazine-1,7-dicarboxylate (3.00 g, 9.60 mmol, 1.00 eq.), synthesized following the pathway of Example 10 (a) and (b), glycidol (1.50 g, 20.2 mmol, 2.10 eq.), triphenylphosphine (2.75 g, 10.4 mmol, 1.09 eq.), diisopropyl azodiformate (1.86 g, 10.6 mmol, 1.11 eq.) and tetrahydrofuran (50 mL). The mixture was stirred overnight at 60° C. under N₂ atmosphere, and the reaction was quenched with water (100 mL). The solution was extracted with ethyl acetate (3×100 mL). The organic layers were combined, washed with brine (2×100 mL), dried over anhydrous sodium sulfate and concentrated under reduced pressure. The residue was purified by silica gel column chromatography, eluted with ethyl acetate:petroleum ether (1:1) to afford 7-tert-butyl-1-ethyl-2-(3-azido-2-hydroxypropyl)-3-oxo-5H,6H,8H-imidazo[1,5-a]pyrazine-1,7-dicarboxylate (1.30 g, 3.53 mmol, 1.00 eq.), sodium azide (1.17 g, 17.9 mmol, 5.09 eq.), water (4 mL), ammonium chloride (0.390 g, 7.29 mmol, 2.06 eq.) and N,N-dimethylformamide (20 mL) was stirred overnight at 45° C., and the reaction was quenched with water (100 mL). The solution was extracted with ethyl acetate (3×100 mL). The organic layers were combined, washed with brine (2×100 mL), dried over anhydrous sodium sulfate and concentrated under reduced pressure. The residue was purified by silica gel column chromatography, eluted with ethyl acetate:petroleum ether (1:1) to afford 7-tert-butyl-1-ethyl-2-(3-azido-2-hydroxypropyl)-3-oxo-5H,6H,8H-imidazo[1,5-a]pyrazine-1,7-dicarboxylate (1.20 g, 83% yield) as a light yellow oil. LCMS (ESI, m/z): 411 [M+H]⁺.

c) 7-tert-butyl-1-ethyl-2-[3-azido-2-[(tert-butyldimethylsilyl)oxy]propyl]-3-oxo-5H,6H,8H-imidazo[1,5-a]pyrazine-1,7-dicarboxylate

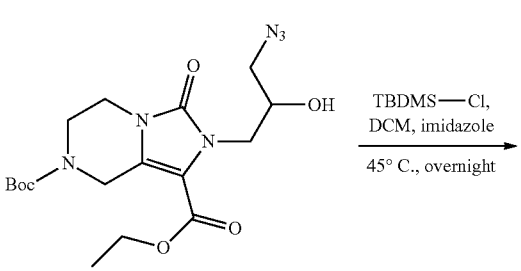

-continued

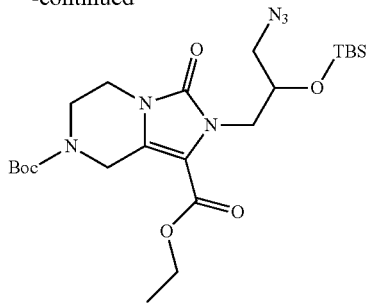

The mixture of 7-tert-butyl-1-ethyl-2-(3-azido-2-hydroxypropyl)-3-oxo-5H,6H,8H-imidazo[1,5-a]pyrazine-1,7-dicarboxylate (1.20 g, 2.92 mmol, 1.00 eq.), tert-butyldimethylsilyl chloride (0.900 g, 5.97 mmol, 2.04 eq.), imidazole (0.410 g, 6.02 mmol, 2.06 eq.) and dichloromethane (25 mL) was stirred overnight at 45° C. The reaction was quenched with water (100 mL). The solution was extracted with dichloromethane (3×100 mL). The organic layers were combined, washed with brine (2×100 mL), dried over anhydrous sodium sulfate and concentrated under reduced pressure. The residue was purified by silica gel column chromatography and eluted with ethyl acetate:petroleum ether (1:1) to afford 7-tert-butyl-1-ethyl-2-[3-azido-2-[(tert-butyldimethylsilyl)oxy]propyl]-3-oxo-5H,6H,8H-imidazo[1,5-a]pyrazine-1,7-dicarboxylate (1.00 g, 62% yield) as a light yellow oil. LCMS (ESI, m/z): 525 [M+H]$^+$.

d) 7-tert-butyl-1-ethyl-2-[3-amino-2-[(tert-butyldimethylsilyl)oxy]propyl]-3-oxo-5H,6H,8H-imidazo[1,5-a]pyrazine-1,7-dicarboxylate

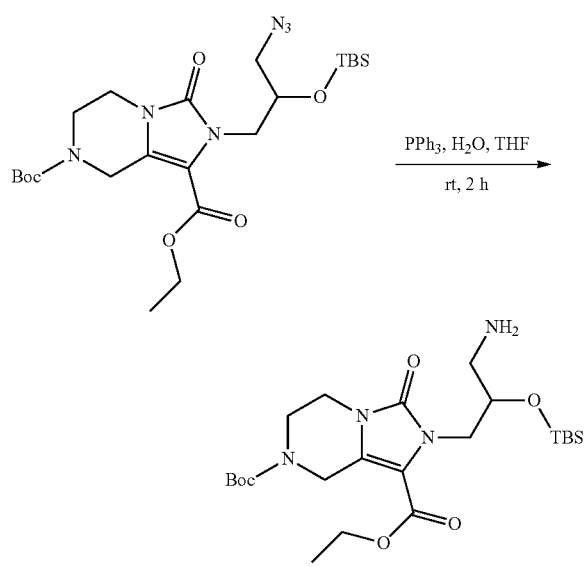

The mixture of 7-tert-butyl-1-ethyl-2-[3-azido-2-[(tert-butyldimethylsilyl)oxy]propyl]-3-oxo-5H,6H,8H-imidazo[1,5-a]pyrazine-1,7-dicarboxylate (1.00 g, 1.90 mmol, 1.00 eq.), triphenylphosphine (0.750 g, 2.85 mmol, 1.50 eq.), water (10 mL) and tetrahydrofuran (20 mL) was stirred for 2 h at rt. The reaction was quenched with water (50 mL). The solution was extracted with ethyl acetate (3×100 mL). The organic layers were combined, washed with brine (2×100 mL), dried over anhydrous sodium sulfate and concentrated under reduced pressure. The residue was purified by silica gel column chromatography, eluted with methanol:dichloromethane (1:10) to afford 7-tert-butyl-1-ethyl-2-[3-amino-2-[(tert-butyldimethylsilyl)oxy]propyl]-3-oxo-5H,6H,8H-imidazo[1,5-a]pyrazine-1,7-dicarboxylate (800 mg, 72% yield) as a light yellow oil. LCMS (ESI, m/z): 499 [M+H]$^+$.

e) tert-butyl 11-[(tert-butyldimethylsilyl)oxy]-8,14-dioxo-4,7,9,13-tetraazatricyclo[7.5.0.0^[2,7]]tetradec-1-ene-4-carboxylate

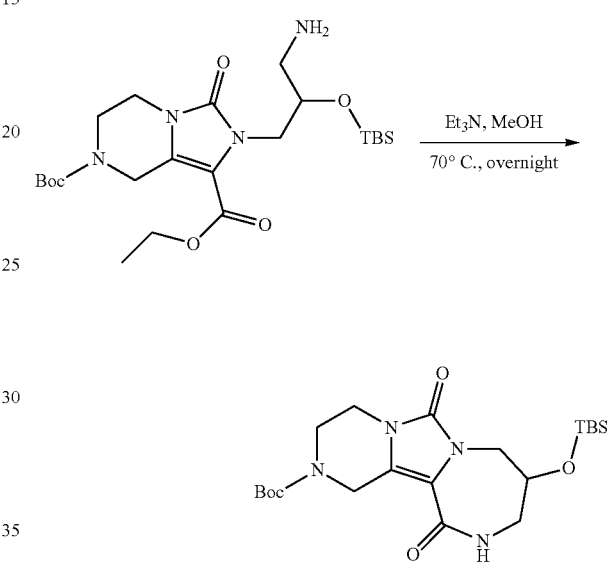

The mixture of 7-tert-butyl 1-ethyl 2-[3-amino-2-[(tert-butyldimethylsilyl)oxy]propyl]-3-oxo-5H,6H,8H-imidazo[1,5-a]pyrazine-1,7-dicarboxylate (500 mg, 1.00 mmol, 1.00 eq.), triethylamine (320 mg, 3.16 mmol, 3.15 eq.) and methanol (10 mL) was stirred overnight at 70° C. and concentrated under reduced pressure. The residue was purified by silica gel column chromatography, eluted with MeOH:dichloromethane (1:10) to afford tert-butyl 11-[(tert-butyldimethylsilyl)oxy]-8,14-dioxo-4,7,9,13-tetraazatricyclo[7.5.0.0^[2,7]]tetradec-1-ene-4-carboxylate (200 mg, 40% yield) as a white solid. LCMS (ESI, m/z): 453 [M+H]$^+$.

f) tert-butyl-13-benzyl-11-[(tert-butyldimethylsilyl)oxy]-8,14-dioxo-4,7,9,13-tetraazatricyclo[7.5.0.0^[2,7]]tetradec-1-ene-4-carboxylate

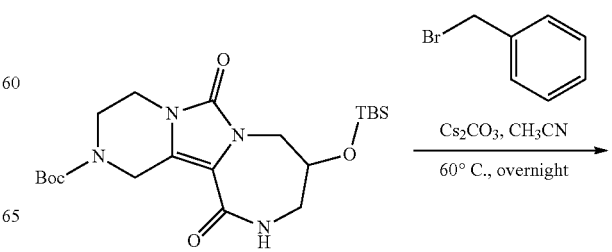

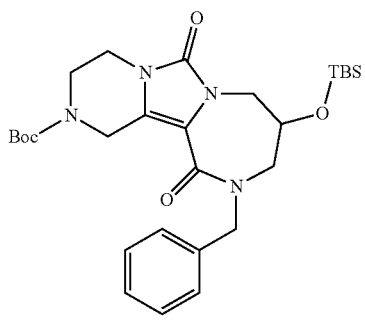

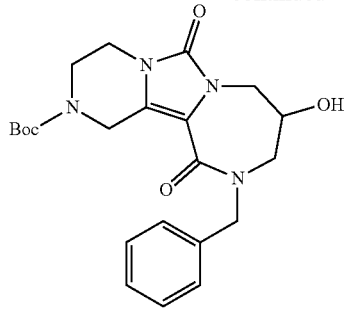

A 20 mL of vial was charged with tert-butyl-11-[(tert-butyldimethylsilyl)oxy]-8,14-dioxo-4,7,9,13-tetraazatricyclo[7.5.0.0^[2,7]]tetradec-1-ene-4-carboxylate (400 mg, 0.880 mmol, 1.00 eq.), benzyl bromide (180 mg, 1.05 mmol, 1.19 eq.), cesium carbonate (860 mg, 2.63 mmol, 2.99 eq.) and acetonitrile (20 mL). The mixture was stirred overnight at 60° C., and the reaction was quenched with water (50 mL). The solution was extracted with ethyl acetate (3×50 mL). The organic layers were combined, dried over anhydrous sodium sulfate and concentrated under vacuum. The residue was purified by silica gel column chromatography, eluted with MeOH:dichloromethane (1:10) to afford tert-butyl-13-benzyl-11-[(tert-butyldimethylsilyl)oxy]-8,14-dioxo-4,7,9,13-tetraazatricyclo[7.5.0.0^[2,7]]tetradec-1-ene-4-carboxylate (350 mg, 73% yield) as a light yellow solid. LCMS (ESI, m/z): 543 [M+H]⁺.

Example 18

Tert-butyl-13-benzyl-11-methoxy-8,14-dioxo-4,7,9,13-tetraazatricyclo[7.5.0.0^[2,7]]tetradec-1-ene-4-carboxylate (Intermediate 2)

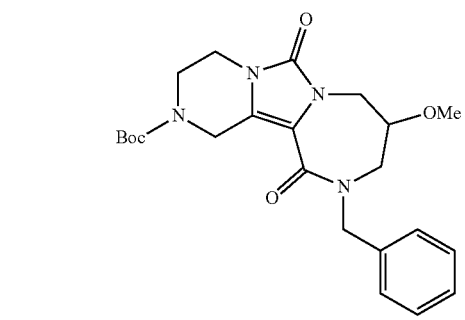

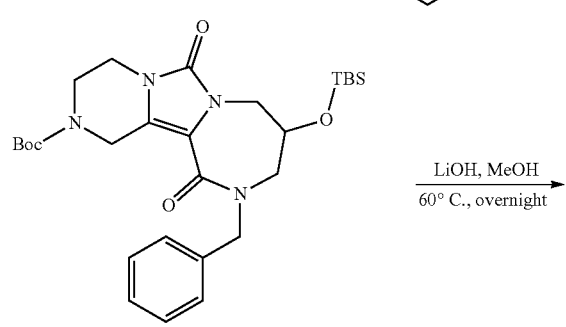

a) tert-butyl-13-benzyl-11-hydroxy-8,14-dioxo-4,7,9,13-tetraazatricyclo[7.5.0.0^[2,7]]tetradec-1-ene-4-carboxylate

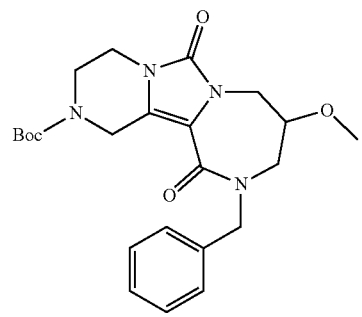

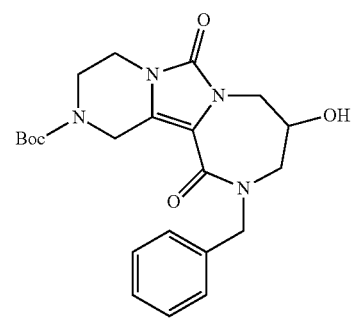

A 50 mL round bottom flask was charged with tert-butyl-13-benzyl-11-[(tert-butyldimethylsilyl)oxy]-8,14-dioxo-4,7,9,13-tetraazatricyclo[7.5.0.0^[2,7]]tetradec-1-ene-4-carboxylate (350 mg, 0.645 mmol, 1.00 eq.), lithium hydroxide (30.0 mg, 1.25 mmol, 1.94 eq.) and methanol (10 mL). The solution was stirred overnight at 60° C., and the reaction was quenched with water (50 mL). The mixture was extracted by ethyl acetate (3×50 mL), and the aqueous phase was collected. The pH value of the water layer was adjusted to 3 with hydrochloric acid (1 mol/L). The mixture was extracted with ethyl acetate (3×50 mL). The organic layers were combined, dried over anhydrous sulfate, filtered and concentrated under reduced pressure to provide tert-butyl-13-benzyl-11-hydroxy-8,14-dioxo-4,7,9,13-tetraazatricyclo [7.5.0.0^[2,7]]tetradec-1-ene-4-carboxylate (230 mg, 83% yield) as a light yellow solid. LCMS (ESI, m/z): 429 [M+H]+.

b) tert-butyl 13-benzyl-11-methoxy-8,14-dioxo-4,7, 9,13-tetraazatricyclo[7.5.0.0^[2,7]]tetradec-1-ene-4-carboxylate

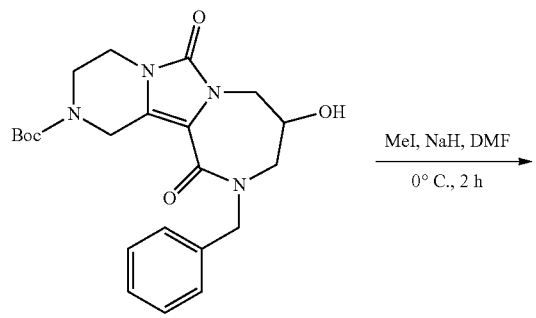

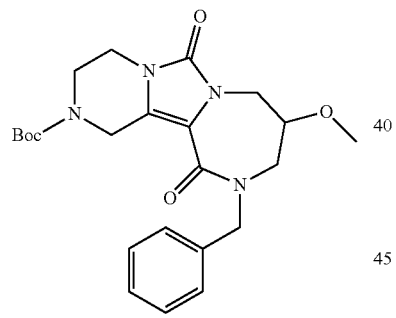

A 20 mL vial was charged with tert-butyl-13-benzyl-11-hydroxy-8,14-dioxo-4,7,9,13-tetraazatricyclo[7.5.0.0^[2,7]] tetradec-1-ene-4-carboxylate (230 mg, 0.537 mmol, 1.00 eq.) and N,N-dimethylformamide (10.0 mL). The sodium hydride (42.8 mg, 1.07 mmol, 2.00 eq., 60% dispersion in mineral oil) was added at 0° C. The solution was stirred for 0.5 h at 0° C. Iodomethane (152 mg, 1.07 mmol, 2.00 eq.) was then added. The solution was stirred for 2 h at 0° C., and the reaction was quenched with water (50 mL). The solution was extracted with ethyl acetate (3×50 mL). The organic layers were combined, dried over anhydrous sodium sulfate and concentrated under reduced pressure. The residue was purified by silica gel column chromatography and eluted with MeOH:dichloromethane (1:10) to afford tert-butyl-13-benzyl-11-methoxy-8,14-dioxo-4,7,9,13-tetraazatricyclo [7.5.0.0 ^[2,7]]tetradec-1-ene-4-carboxylate (100 mg, 42% yield) as a light yellow solid. LCMS (ESI, m/z): 443 [M+H]+.

Example 19

7-tert-butyl-1-ethyl-2-(4-methoxyphenyl)-6-methyl-3-oxo-5H,6H,8H-imidazo[1,5-a]pyrazine-1,7-dicarboxylate (Intermediate 3)

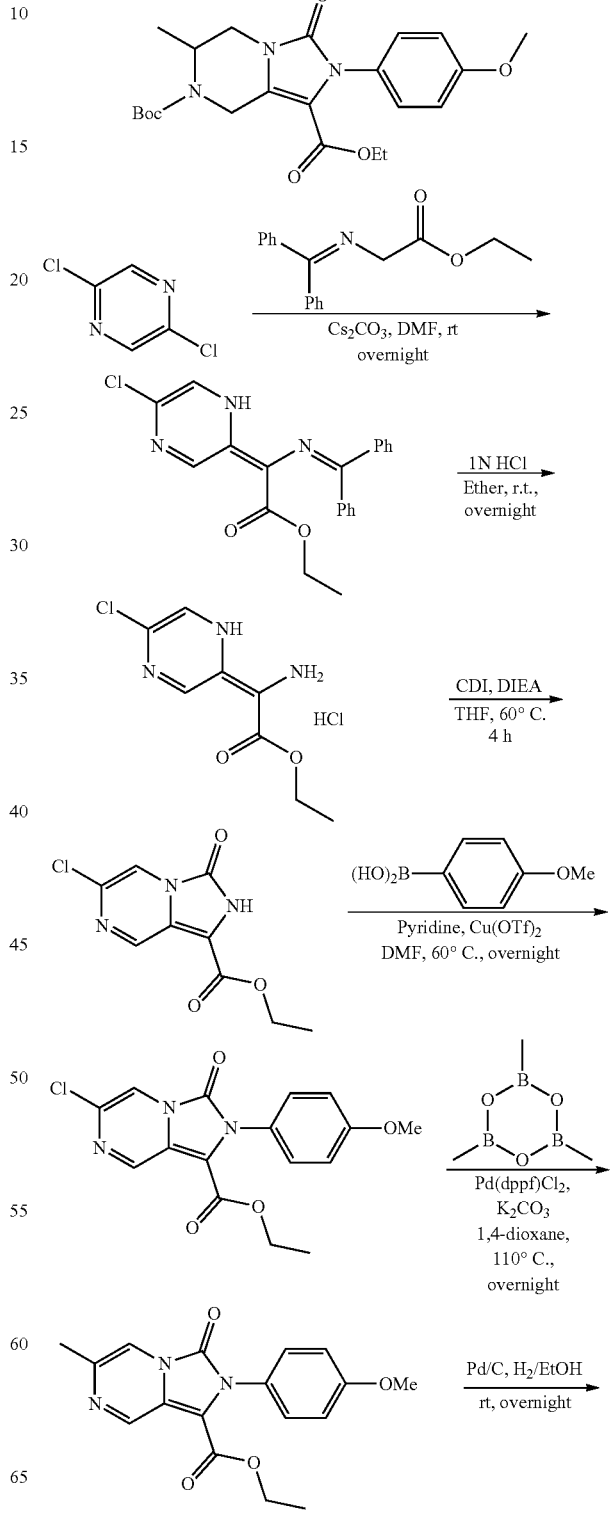

-continued

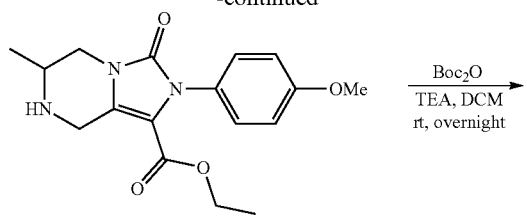

b) ethyl 2-amino-2-(5-chloropyrazin-2-yl)acetate Hydrochloric Acid Salt

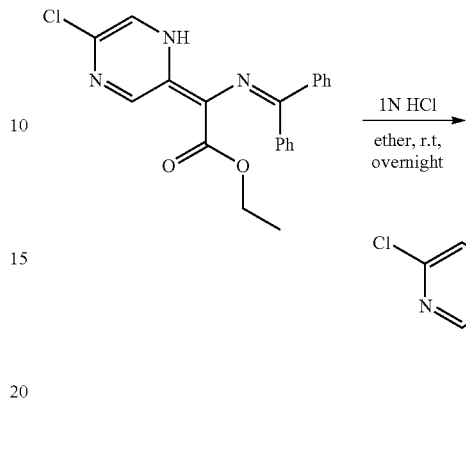

To a stirred solution of ethyl 2-(5-chloropyrazin-2-yl)-2-[(diphenylmethylidene) amino]acetate (40.0 g, 105 mmol, 1.00 eq.) in ether (400) was added 1N HCl (150 mL, 150 mmol, 1.42 eq.) at rt. The mixture was stirred overnight at rt and extracted with ether (2×20 mL). The combined water layers were concentrated under reduced pressure to afford ethyl 2-amino-2-(5-chloropyrazin-2-yl)acetate hydrochloric acid salt (20.0 g, crude) as white solid that was used directly into next step without further purification. LCMS (ESI, m/z): 216 [M+H−HCl]$^+$.

c) ethyl 6-chloro-3-oxo-2H-imidazo[1,5-a]pyrazine-1-carboxylate a) ethyl 2-(5-chloropyrazin-2-yl)-2-[diphenylmethylidene)amino]acetate

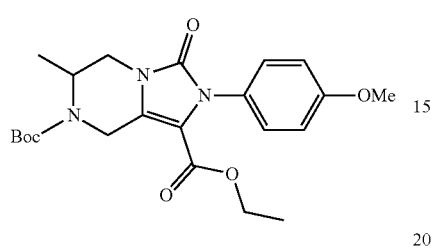

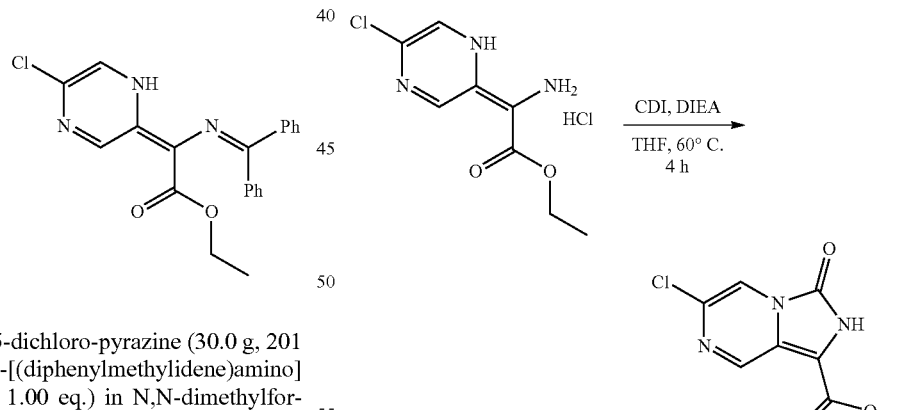

To a stirred solution of 2,5-dichloro-pyrazine (30.0 g, 201 mmol, 1.00 eq.) and ethyl 2-[(diphenylmethylidene)amino]acetate (53.8 g, 201 mmol, 1.00 eq.) in N,N-dimethylformamide (300 mL) was added cesium carbonate (65.6 g, 201 mmol, 1.00 eq.) at rt. The mixture was stirred overnight at rt, and the reaction was quenched with water (500 mL). The mixture was extracted with ethyl acetate (3×200 mL). The organic layers were combined, washed with water (3×100 mL), dried over anhydrous sodium sulfate, filtered and concentrated under reduced pressure. The residue was purified by silica gel column chromatography, eluted with 0-20% ethyl acetate in petroleum ether to afford ethyl 2-(5-chloropyrazin-2-yl)-2-[(diphenylmethylidene)amino]acetate (48.9 g, 64% yield) as a yellow solid. LCMS (ESI, m/z): 380 [M+H]$^+$.

To a stirred solution of ethyl 2-amino-2-(5-chloropyrazin-2-yl)acetate hydrochloric acid salt (19.0 g, 75.4 mmol, 1.00 eq.) in tetrahydrofuran (200 mL) was added N,N-diisopropylethylamine (30.8 g, 238 mmol, 3.16 eq.) and N,N'-carbonyldiimidazole (12.9 g, 79.3 mmol, 1.05 eq.) at 60° C. The mixture was stirred for 4 h at 60° C. and concentrated under reduced pressure. The residue was purified by silica gel column chromatography, eluted with 0-5% methanol in dichloromethane to afford ethyl 6-chloro-3-oxo-2H-imidazo

[1,5-a]pyrazine-1-carboxylate (11.0 g, 60% yield) as a yellow solid. LCMS (ESI, m/z): 242 [M+H]+.

d) ethyl 6-chloro-2-(4-methoxyphenyl)-3-oxoimidazo[1,5-a]pyrazine-1-carboxylate

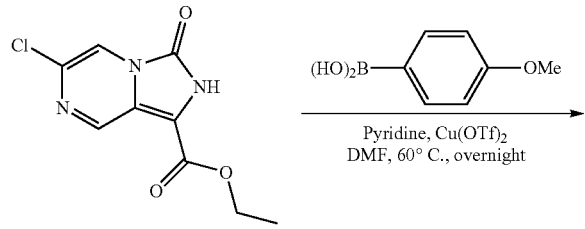

To a stirred mixture of ethyl 6-methyl-3-oxo-2H-imidazo[1,5-a]pyrazine-1-carboxylate (0.800 g, 3.62 mmol, 1.00 eq.) and 4-methoxyphenylboronic acid (0.659 g, 4.34 mmol, 1.20 eq.) in N,N-dimethylformamide (10 mL) was added pyridine (0.858 g, 10.8 mmol, 3.00 eq.) and copper (II) trifluoromethanesulfonate (1.31 g, 3.62 mmol, 1.00 eq.) at rt under oxygen atmosphere. The mixture was stirred overnight at 60° C., and the reaction was quenched with water (50 mL). The solid was filtered off, and the filtrate was extracted with ethyl acetate (3×100 mL). The combined organic layers were washed with water (3×100 mL), dried over anhydrous sodium sulfate, filtered and concentrated under reduced pressure. The residue was purified by silica gel column chromatography, eluted with petroleum ether: ethyl acetate (2:1) to afford ethyl 6-chloro-2-(4-methoxyphenyl)-3-oxoimidazo[1,5-a]pyrazine-1-carboxylate (800 mg, 69% yield) as a white solid. LCMS (ESI, m/z): 348 [M+H]+.

e) ethyl 2-(4-methoxyphenyl)-6-methyl-3-oxoimidazo[1,5-a]pyrazine-1-carboxylate

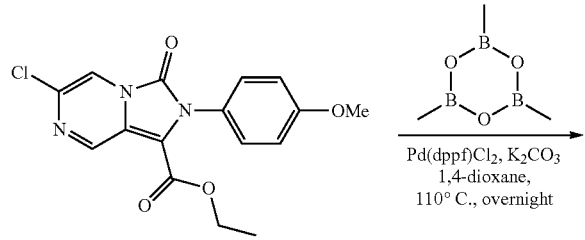

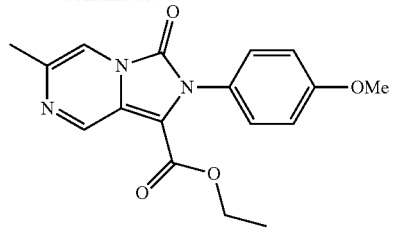

To a stirred mixture of ethyl 6-chloro-2-(4-methoxyphenyl)-3-oxoimidazo[1,5-a]pyrazine-1-carboxylate (0.660 g, 1.90 mmol, 1.00 eq.) and trimethyl-1,3,5,2,4,6-trioxatriborinane (1.43 g, 5.69 mmol, 3.00 eq., 50% in tetrahydrofuran) in 1,4-dioxane (10 mL) was added potassium carbonate (0.786 g, 5.69 mmol, 3.00 eq.) and [1,1'-bis(diphenylphosphino)ferrocene]dichloropalladium (0.138 g, 0.190 mmol, 0.10 eq.) under N2 atmosphere. The mixture was stirred overnight at 110° C., and the reaction was quenched with water (100 mL). The mixture was extracted with ethyl acetate (3×100 mL). The organic layers were combined, washed with water (3×50 mL), dried over anhydrous sodium sulfate, filtered and concentrated under reduced pressure. The residue was purified by silica gel column chromatography, eluted with 0-50% ethyl acetate in petroleum ether to afford ethyl 2-(4-methoxyphenyl)-6-methyl-3-oxoimidazo[1,5-a]pyrazine-1-carboxylate (520 mg, 84% yield) as a yellow solid. LCMS (ESI, m/z): 328 [M+H]+.

f) ethyl 2-(4-methoxyphenyl)-6-methyl-3-oxo-5H,6H,7H,8H-imidazo[1,5-a]pyrazine-1-carboxylate

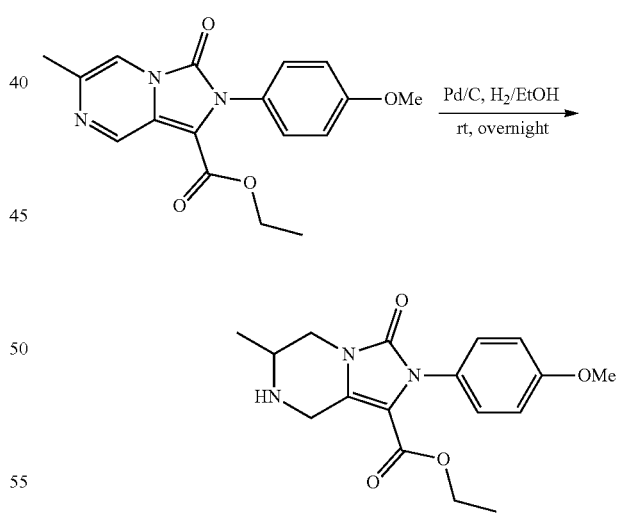

To a stirred mixture of ethyl 2-(4-methoxyphenyl)-6-methyl-3-oxoimidazo[1,5-a]pyrazine-1-carboxylate (520 mg, 1.53 mmol, 1.00 eq.) in ethanol (2 mL) was added 10% Pd/C (50 mg) at rt under 3 atm H2 atmosphere. The mixture was stirred overnight at rt. The solid was filtrated off, and the filtrate was concentrated under reduced pressure to afford ethyl 2-(4-methoxyphenyl)-6-methyl-3-oxo-5H,6H,7H,8H-imidazo[1,5-a]pyrazine-1-carboxylate (500 mg, crude) as a white solid. LCMS (ESI, m/z): 332 [M+H]+.

g) 7-tert-butyl 1-ethyl 2-(4-methoxyphenyl)-6-methyl-3-oxo-5H,6H,8H-imidazo[1,5-a]pyrazine-1,7-dicarboxylate

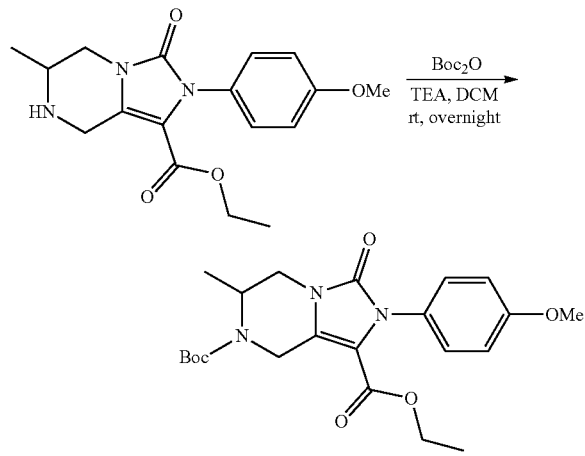

To a stirred solution of ethyl 2-(4-methoxyphenyl)-6-methyl-3-oxo-5H,6H,7H,8H-imidazo[1,5-a]pyrazine-1-carboxylate (500 mg, 1.50 mmol, 1.00 eq.) and di-tert-butyl dicarbonate (655 mg, 3.00 mmol, 2.00 eq.) in dichloromethane (10 mL) was added triethylamine (455 mg, 4.55 mmol, 3.00 eq.) at rt. The mixture was stirred overnight at rt and concentrated under reduced pressure. The residue was purified by silica gel column chromatography and eluted with 0-50% ethyl acetate in petroleum ether to afford 7-tert-butyl-1-ethyl-2-(4-methoxyphenyl)-6-methyl-3-oxo-5H,6H,8H-imidazo[1,5-a]pyrazine-1,7-dicarboxylate (500 mg, 77% yield) as a white solid. LCMS (ESI, m/z): 432 [M+H]⁺.

Example 20

13-benzyl-11-[(tert-butyldimethylsilyl)oxy]-5-methyl-4,7,9,13-tetraazatricyclo[7.5.0.0^[2,7]]tetradec-1-ene-8,14-dione (Intermediate 4)

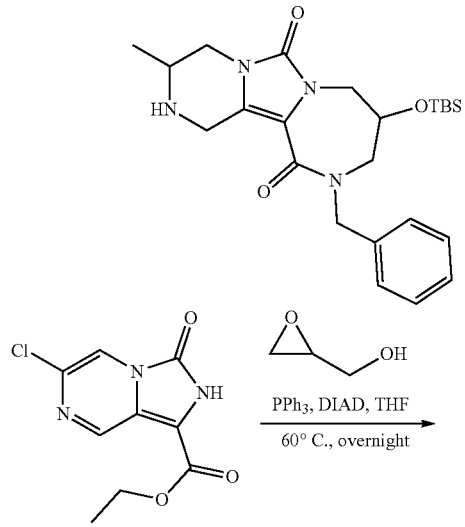

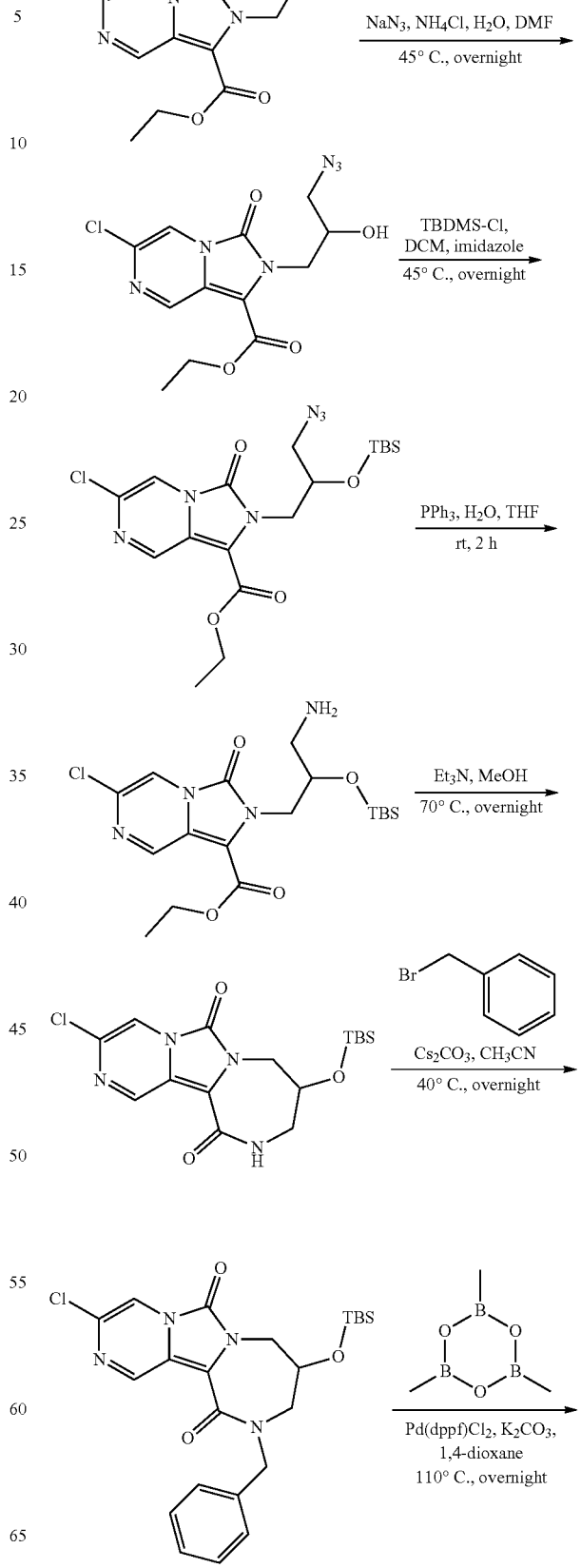

-continued

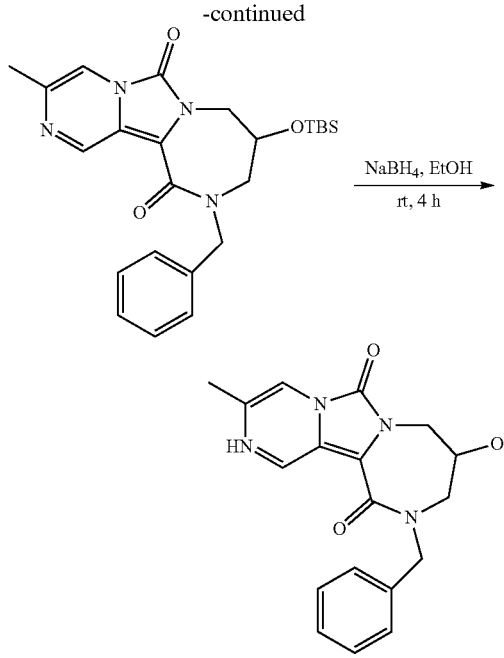

a) ethyl 6-chloro-2-(oxiran-2-ylmethyl)-3-oxoimidazo[1,5-a]pyrazine-1-carboxylate

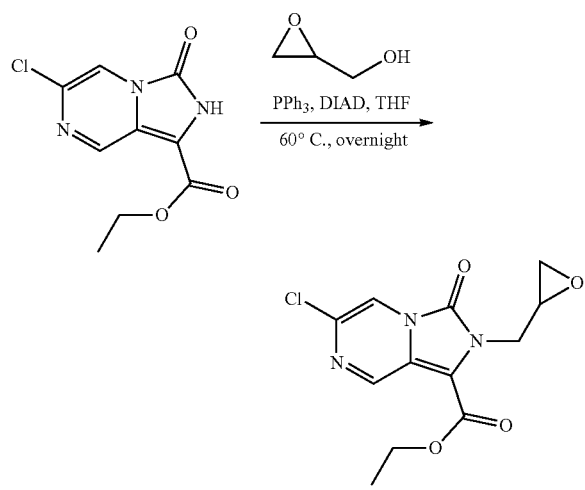

A 250 mL three necks bottle was charged with ethyl 6-chloro-3-oxo-2H-imidazo[1,5-a]pyrazine-1-carboxylate (4.00 g, 16.5 mmol, 1.00 eq.), glycidol (2.45 g, 33.1 mmol, 2.00 eq.), triphenylphosphine (4.78 g, 18.2 mmol, 1.10 eq.) and tetrahydrofuran (100 mL). Ciisopropyl azodiformate (5.02 g, 24.8 mmol, 1.50 eq.) was then added slowly at 0° C. under a N₂ atmosphere. The mixture was stirred overnight at 60° C., and the reaction was quenched with water (100 mL). The solution was extracted with ethyl acetate (3×100 mL). The organic layers were combined, dried over anhydrous sodium sulfate, filtered and concentrated under reduced pressure. The residue was purified by reverse flash chromatography with Cis column, eluted with tetrahydrofuran in water (0.05% TFA) (1:1) to afford ethyl 6-chloro-2-(oxiran-2-ylmethyl)-3-oxoimidazo[1,5-a]pyrazine-1-carboxylate (3.90 g, 79% yield) as a yellow solid. LCMS (ESI, m/z): 298 [M+H]⁺.

b) ethyl 2-(3-azido-2-hydroxypropyl)-6-chloro-3-oxoimidazo[1,5-a]pyrazine-1-carboxylate

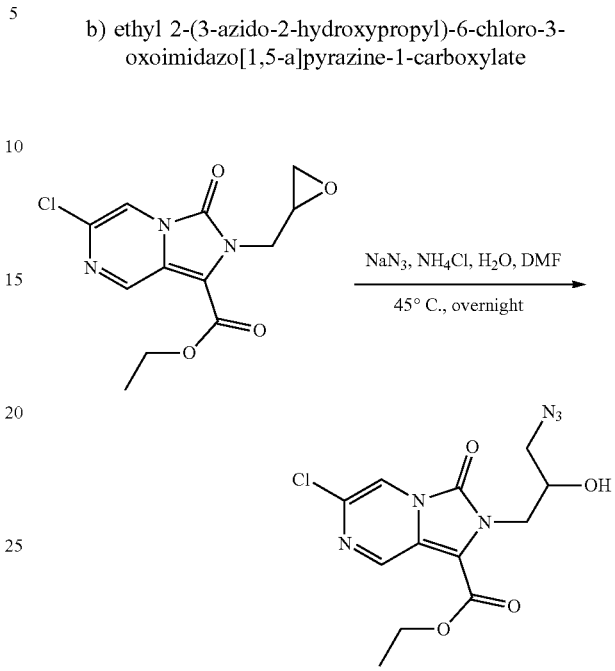

A 250 mL of round bottom flask was charged with ethyl 6-chloro-2-(oxiran-2-ylmethyl)-3-oxoimidazo[1,5-a]pyrazine-1-carboxylate (3.00 g, 10.0 mmol, 1.00 eq.), sodium azide (3.28 g, 50.4 mmol, 5.01 eq.), ammonium chloride (1.08 g, 20.1 mmol, 2.00 eq.), N,N-dimethylformamide (80 mL) and water (20 mL). The mixture was stirred overnight at 45° C., and the reaction was quenched with water (100 mL). The solution was extracted with ethyl acetate (3×100 mL). The organic layers were combined, washed with brine (2×100 mL), dried over anhydrous sodium sulfate, filtered and concentrated under reduced pressure. The residue was purified by silica gel column chromatography and eluted with ethyl acetate:petroleum ether (1:1) to afford ethyl 2-(3-azido-2-hydroxypropyl)-6-chloro-3-oxoimidazo[1,5-a]pyrazine-1-carboxylate (2.20 g, 64% yield) as a yellow solid. LCMS (ESI, m/z): 341 [M+H]⁺.

c) ethyl 2-[3-azido-2-[(tert-butyldimethylsilyl)oxy]propyl]-6-chloro-3-oxoimidazo[1,5-a]pyrazine-1-carboxylate

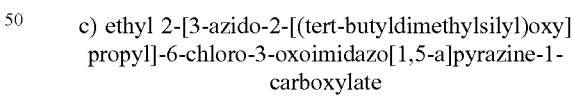

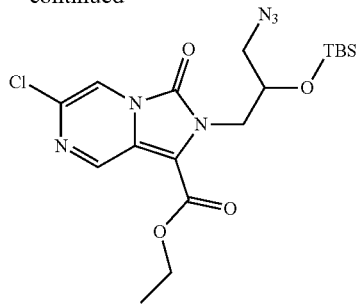

The mixture of ethyl 2-(3-azido-2-hydroxypropyl)-6-chloro-3-oxoimidazo[1,5-a]pyrazine-1-carboxylate (2.90 g, 8.51 mmol, 1.00 eq.), tert-butyldimethylsilyl chloride (2.57 g, 17.0 mmol, 2.00 eq.), imidazole (1.16 g, 17.0 mmol, 2.00 eq.) and dichloromethane (50 mL) was stirred overnight at 45° C. The reaction was quenched with water (100 mL), and the solution was extracted with dichloromethane (3×100 mL). The organic layers were combined, washed with water (2×100 mL), dried over anhydrous sodium sulfate, filtered and concentrated under reduced pressure. The residue was purified by silica gel column chromatography and eluted with ethyl acetate:petroleum ether (1:1) to afford ethyl 2-[3-azido-2-[(tert-butyldimethylsilyl)oxy]propyl]-6-chloro-3-oxoimidazo[1,5-a]pyrazine-1-carboxylate (2.30 g, 59% yield) as a light yellow oil. LCMS (ESI, m/z): 455 [M+H]⁺.

d) ethyl 2-[3-amino-2-[(tert-butyldimethylsilyl)oxy]propyl]-6-chloro-3-oxoimidazo[1,5-a]pyrazine-1-carboxylate

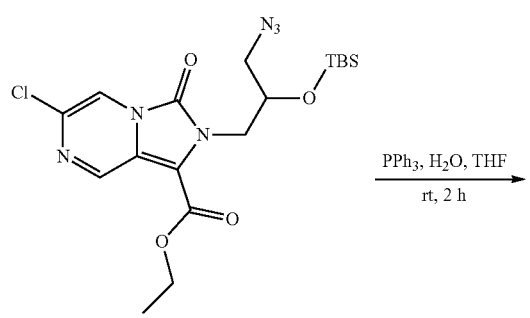

The mixture of ethyl 2-[3-azido-2-[(tert-butyldimethylsilyl)oxy]propyl]-6-chloro-3-oxoimidazo[1,5-a]pyrazine-1-carboxylate (3.10 g, 6.81 mmol, 1.00 eq.), triphenylphosphine (2.68 g, 10.2 mmol, 1.50 eq.), water (30 mL) and tetrahydrofuran (60 mL) was stirred at rt for 2 h. The reaction was quenched with water (100 mL). The solution was extracted with ethyl acetate (3×100 mL). The organic layers were combined, washed with water (2×100 mL), dried over anhydrous sodium sulfate, filtered and concentrated under reduced pressure. The residue was purified by silica gel column chromatography and eluted with methanol:dichloromethane (1:10) to afford ethyl 2-[3-amino-2-[(tert-butyldimethylsilyl)oxy]propyl]-6-chloro-3-oxoimidazo[1,5-a]pyrazine-1-carboxylate (1.70 g, 58% yield) as a yellow solid. LCMS (ESI, m/z): 429 [M+H]⁺.

e) 11-[(tert-butyldimethylsilyl)oxy]-5-chloro-4,7,9,13-tetraazatricyclo[7.5.0.0^[2,7]]tetradeca-1,3,5-triene-8,14-dione

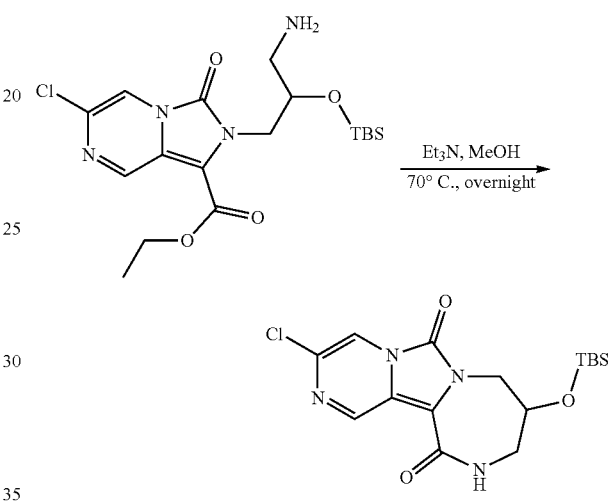

A 100 mL vial was charged with ethyl 2-[3-amino-2-[(tert-butyldimethylsilyl)oxy]propyl]-6-chloro-3-oxoimidazo[1,5-a]pyrazine-1-carboxylate (1.20 g, 2.79 mmol, 1.00 eq.), triethylamine (1.42 g, 14.0 mmol, 5.02 eq.) and methanol (50 mL). The mixture was stirred overnight at 70° C. and then concentrated under reduced pressure. The residue was purified by silica gel column chromatography, eluted with methanol:dichloromethane (1:10) to afford 11-[(tert-butyldimethylsilyl)oxy]-5-chloro-4,7,9,13-tetraazatricyclo[7.5.0.0^[2,7]]tetradeca-1,3,5-triene-8,14-dione (500 mg, 47% yield) as a brown solid. LCMS (ESI, m/z): 383 [M+H]⁺.

f) 13-benzyl-11-[(tert-butyldimethylsilyl)oxy]-5-chloro-4,7,9,13-tetraazatricyclo[7.5.0.0^[2,7]]tetradeca-1,3,5-triene-8,14-dione

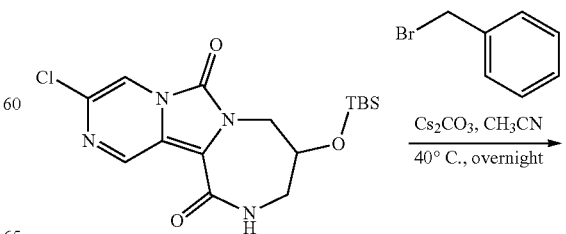

-continued

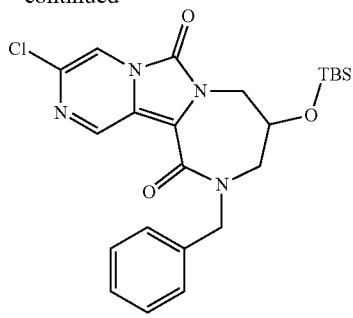

A 20 mL vial was charged with 11-[(tert-butyldimethylsilyl)oxy]-5-chloro-4,7,9,13-tetraazatricyclo[7.5.0.0^[2,7]]tetradeca-1,3,5-triene-8,14-dione (500 mg, 1.30 mmol, 1.00 eq.), benzyl bromide (445 mg, 2.60 mmol, 2.00 eq.), cesium carbonate (850 mg, 2.60 mmol, 2.00 eq.) and acetonitrile (20 mL). The mixture was stirred overnight at 40° C. The reaction was quenched by water (50 mL). The solution was extracted with ethyl acetate (3×50 mL). The organic layers were combined, washed with water (2×100 mL), dried over anhydrous sodium sulfate, filtered and concentrated under reduced pressure. The residue was purified by silica gel column chromatography and eluted with methanol:dichloromethane (1:10) to afford 13-benzyl-11-[(tert-butyldimethylsilyl)oxy]-5-chloro-4,7,9,13-tetraazatricyclo[7.5.0.0^[2,7]]tetradeca-1,3,5-triene-8,14-dione (245 mg, 40% yield) as a yellow solid. LCMS (ESI, m/z): 473 [M+H]$^+$.

g) 13-benzyl-11-[(tert-butyldimethylsilyl)oxy]-5-methyl-4,7,9,13-tetraazatricyclo[7.5.0.0^[2,7]]tetradeca-1,3,5-triene-8,14-dione

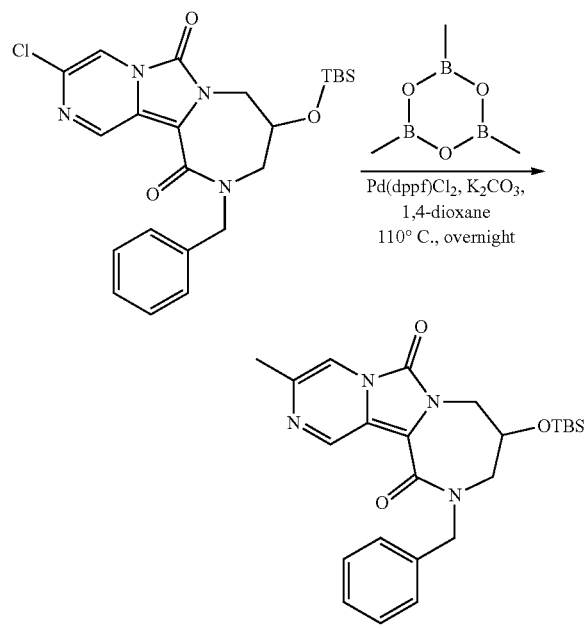

To a stirred solution of 13-benzyl-11-[(tert-butyldimethylsilyl)oxy]-5-chloro-4,7,9,13-tetraazatricyclo[7.5.0.0^[2,7]]tetradeca-1,3,5-triene-8,14-dione (250 mg, 0.528 mmol, 1.00 eq.) and [1,1'-bis(diphenylphosphino)ferrocene]dichloropalladium(II) (38.6 mg, 0.053 mmol, 0.10 eq.) in 1,4-dioxane (10 mL) was added potassium carbonate (220 mg, 1.58 mmol, 3.00 eq.) and trimethyl-1,3,5,2,4,6-trioxatriborinane (265 mg, 1.07 mmol, 2.00 eq., 50% in tetrahydrofuran) at rt under a N$_2$ atmosphere. The mixture was stirred overnight at 110° C. under N$_2$ atmosphere. The reaction was quenched with water (50 mL), and the solution was extracted with ethyl acetate (3×50 mL). The organic layers were combined, washed with water (2×50 mL), dried over anhydrous sodium sulfate, filtered and concentrated under reduced pressure. The residue was purified by silica gel column chromatography, eluted with ethyl acetate:hexane (1:1) to afford 13-benzyl-11-[(tert-butyldimethylsilyl)oxy]-5-methyl-4,7,9,13-tetraazatricyclo[7.5.0.0^[2,7]]tetradeca-1,3,5-triene-8,14-dione (180 mg, 77% yield) as a yellow solid. LCMS (ESI, m/z): 453 [M+H]$^+$.

h) 13-benzyl-11-[(tert-butyldimethylsilyl)oxy]-5-methyl-4,7,9,13-tetraazatricyclo[7.5.0.0^[2,7]]tetradec-1-ene-8,14-dione

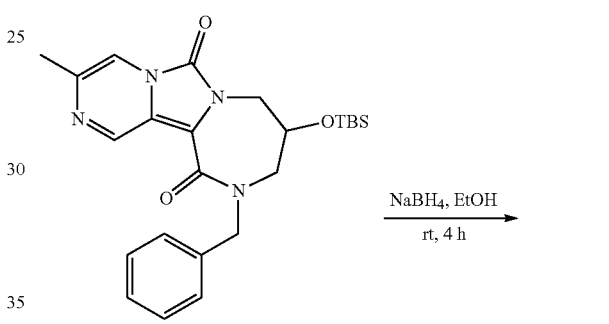

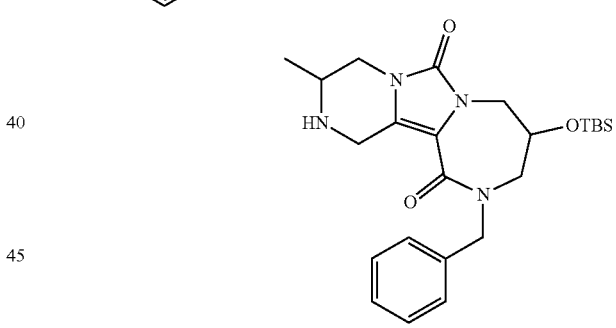

To a stirred solution of 13-benzyl-11-[(tert-butyldimethylsilyl)oxy]-5-chloro-4,7,9,13-tetraazatricyclo[7.5.0.0^[2,7]]tetradeca-1,3,5-triene-8,14-dione (180 mg, 0.398 mmol, 1.00 eq.) in ethanol (10 mL) was added sodium borohydride (75.0 mg, 1.99 mmol, 5.00 eq.) in portions at rt under a N$_2$ atmosphere. The mixture was stirred for 4 h at rt. The reaction was quenched with water (50 mL). The solution was extracted with ethyl acetate (3×50 mL). The organic layers were combined, washed with water (2×50 mL), dried over anhydrous sodium sulfate, filtered and concentrated under reduced pressure. The residue was purified by silica gel column chromatography and eluted with ethyl acetate:hexane (4:1) to afford 13-benzyl-11-[(tert-butyldimethylsilyl)oxy]-5-methyl-4,7,9,13-tetraazatricyclo[7.5.0.0^[2,7]]tetradec-1-ene-8,14-dione (150 mg, 83% yield) as an off-white solid. LCMS (ESI, m/z): 457 [M+H]$^+$.

Example 21

Tert-butyl-12-benzyl-8,13-dioxo-4,7,9,12-tetraazatricyclo[7.4.0.0^[2,7]]tridec-1-ene-4-carboxylate (Intermediate 5)

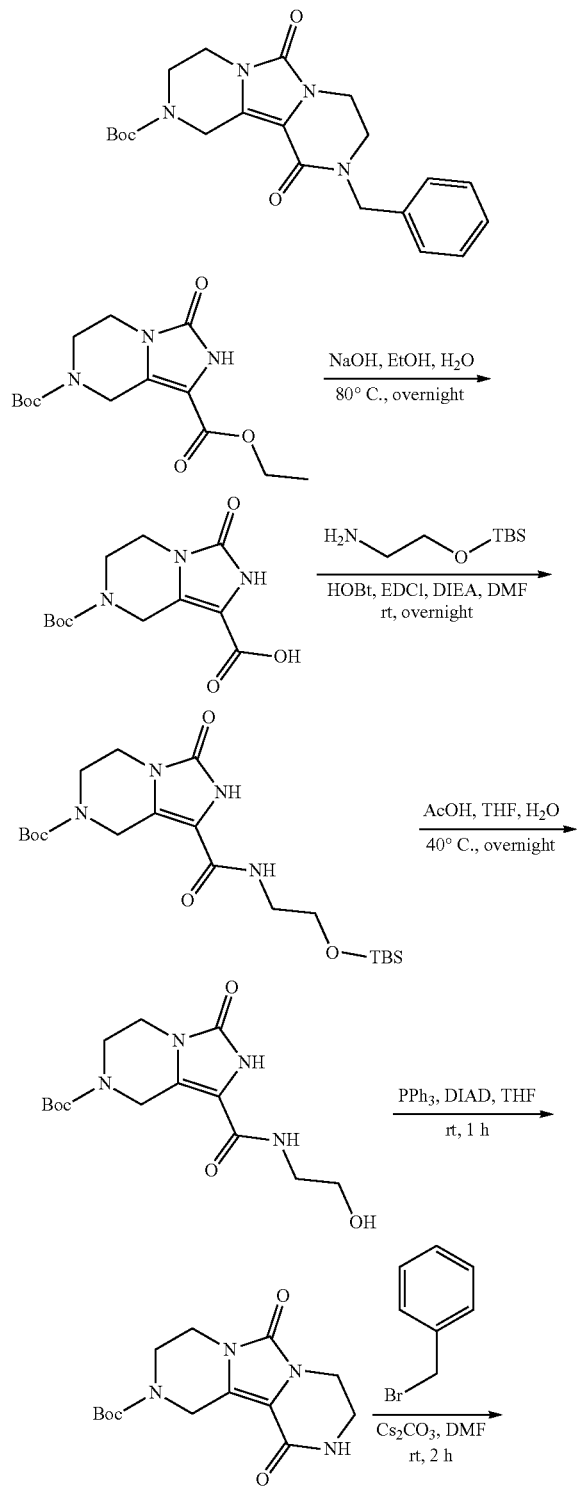

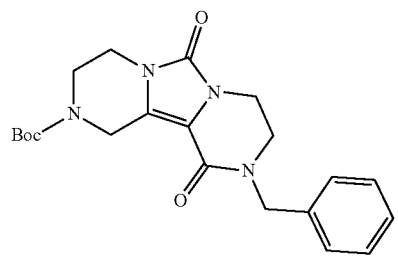

a) 7-(tert-butoxycarbonyl)-3-oxo-2,3,5,6,7,8-hexahydroimidazo[1,5-a]pyrazine-1-carboxylic Acid

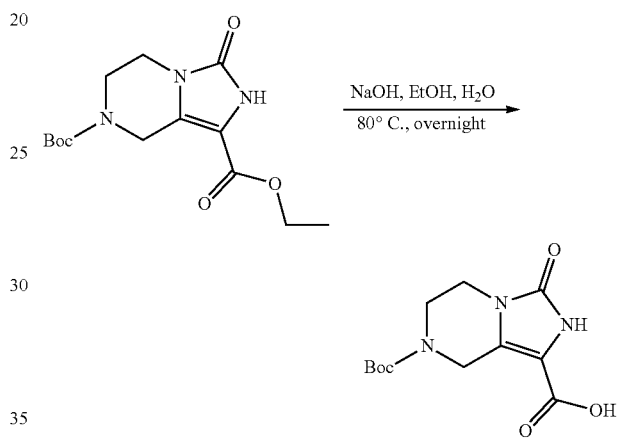

A 250 mL round bottom flask was charged with 7-(tert-butyl)-1-ethyl-3-oxo-2,5,6,8-tetrahydroimidazo[1,5-a]pyrazine-1,7(3H)-dicarboxylate (5.00 g, 16.1 mmol, 1.00 eq.), synthesized following the pathway of Example 10, steps (a) and (b), ethanol (50 mL), water (20 mL) and sodium hydroxide (1.28 g, 32.1 mmol, 2.00 eq.). The solution was stirred overnight at 80° C. The pH value of the mixture was adjusted to 7 with HCl (1 mol/L). The mixture was concentrated under reduced pressure to provide 7-(tert-butoxycarbonyl)-3-oxo-2,3,5,6,7,8-hexahydroimidazo[1,5-a]pyrazine-1-carboxylic acid (6.10 g, crude) as a white solid. LCMS (ESI, m/z): 284 [M+H]$^+$.

b) tert-butyl 1-([2-[(tert-butyldimethylsilyl)oxy]ethyl]carbamoyl)-3-oxo-2H,5H,6H,8H-imidazo[1,5-a]pyrazine-7-carboxylate

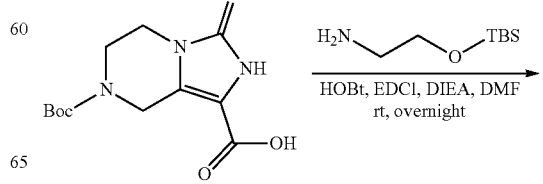

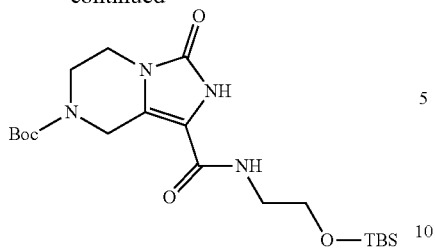

A 100 mL round bottom flask was charged with 7-(tert-butoxycarbonyl)-3-oxo-2H,5H,6H,8H-imidazo[1,5-a]pyrazine-1-carboxylic acid (2.00 g, 7.06 mmol, 1.00 eq.), (2-aminoethoxy)(tert-butyl)dimethylsilane (2.48 g, 14.1 mmol, 2.00 eq.), N,N-dimethylformamide (50 mL), hydroxybenzotriazole (1.15 g, 8.47 mmol, 1.20 eq.), 1-ethyl-3-(3-dimethylaminopropyl)carbodiimide hydrochloride (1.62 g, 8.47 mmol, 1.2 eq.) and N,N-diisopropylethylamine (4.56 g, 35.3 mmol, 5.00 eq.). The mixture was stirred overnight at rt. The reaction was quenched with water (100 mL). The mixture was extracted with ethyl acetate (3×100 mL). The organic layers were combined, washed with brine (1×200 mL) and water (1×100 mL), dried over anhydrous sodium sulfate, filtered and concentrated under reduced pressure. The residue was purified by silica gel column chromatography and eluted with dichloromethane:methanol (20:1) to afford tert-butyl 1-([2-[(tert-butyldimethylsilyl)oxy]ethyl]carbamoyl)-3-oxo-2H,5H,6H,8H-imidazo[1,5-a]pyrazine-7-carboxylate (0.650 g, 20% yield) as a yellow solid. LCMS (ESI, m/z): 441 [M+H]⁺.

c) tert-butyl 1-[(2-hydroxyethyl)carbamoyl]-3-oxo-2H,5H,6H,8H-imidazo[1,5-a]pyrazine-7-carboxylate

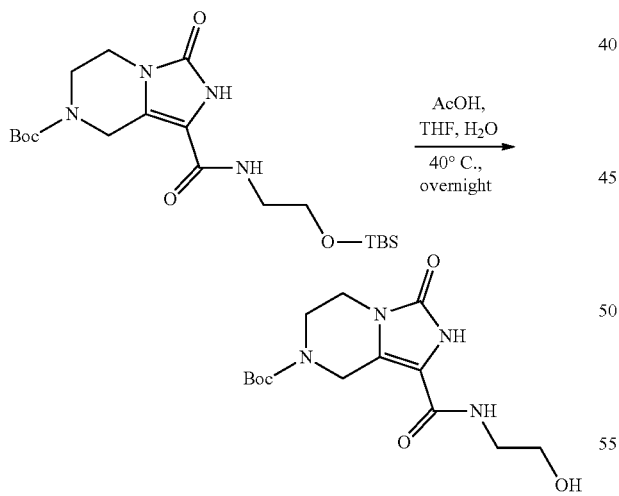

A 100 mL round bottom flask was charged with tert-butyl 1-([2-[(tert-butyldimethylsilyl)oxy]ethyl]carbamoyl)-3-oxo-2H,5H,6H,8H-imidazo[1,5-a]pyrazine-7-carboxylate (650 mg, 1.48 mmol, 1.00 eq.), tetrahydrofuran (16 mL), acetic acid (8 mL) and water (4 mL). The solution was stirred overnight at 40° C. and concentrated under reduced pressure. The residue was purified by reverse flash chromatography with the following conditions: column, C₁₈; mobile phase, acetonitrile in water, 5% to 20% gradient in 15 min; detector, UV 254 nm to provide tert-butyl 1-[(2-hydroxyethyl)carbamoyl]-3-oxo-2H,5H,6H,8H-imidazo[1,5-a]pyrazine-7-carboxylate (220 mg, 45% yield) as a white solid. LCMS (ESI, m/z): 327 [M+H]⁺.

d) tert-butyl 8,13-dioxo-4,7,9,12-tetraazatricyclo[7.4.0.0^[2,7]]tridec-1-ene-4-carboxylate

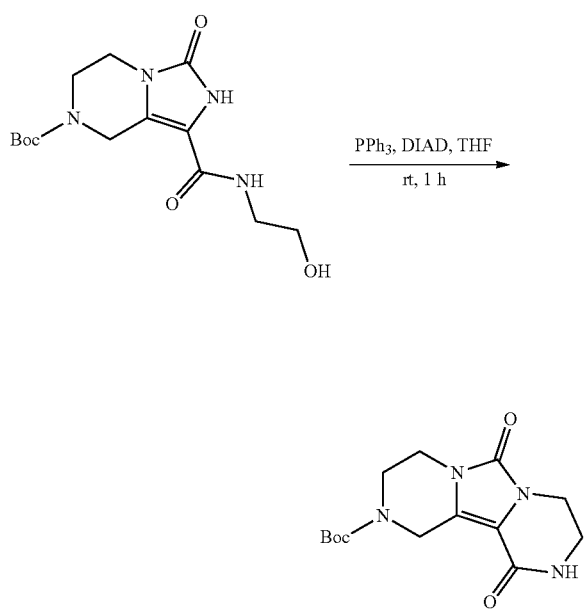

A 40 mL vial was charged with tert-butyl 1-[(2-hydroxyethyl)carbamoyl]-3-oxo-2H,5H,6H,8H-imidazo[1,5-a]pyrazine-7-carboxylate (220 mg, 0.674 mmol, 1.00 eq.), triphenylphosphine (354 mg, 1.35 mmol, 2.00 eq.) and tetrahydrofuran (10 mL). Diisopropyl azodicarboxylate (273 mg, 1.35 mmol, 2.00 eq.) was then added dropwise at 0° C. The solution was stirred for 1 h at rt. The mixture was concentrated under reduced pressure. The residue was purified by reverse flash chromatography with the following conditions: column, C₁₈; mobile phase, acetonitrile in water, 5% to 10% gradient in 15 min; detector, UV 254 nm to afford tert-butyl 8,13-dioxo-4,7,9,12-tetraazatricyclo[7.4.0.0^[2,7]]tridec-1-ene-4-carboxylate (150 mg, 72% yield) as a yellow solid. LCMS (ESI, m/z): 309 [M+H]⁺.

e) tert-butyl-12-benzyl-8,13-dioxo-4,7,9,12-tetraazatricyclo[7.4.0.0^[2,7]]tridec-1-ene-4-carboxylate

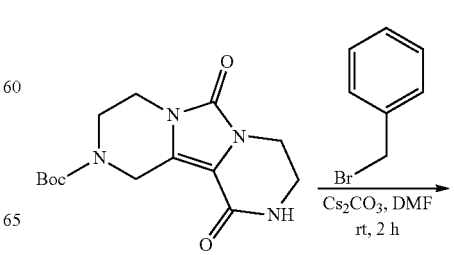

-continued

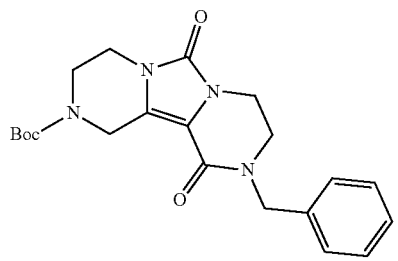 [SMILES: CC(C)(C)OC(=O)N1CCn2c(c3n(c2=O)CCN(Cc2ccccc2)C3=O)C1]

A 40 mL vial was charged with tert-butyl-8,13-dioxo-4,7,9,12-tetraazatricyclo[7.4.0.0^[2,7]]tridec-1-ene-4-carboxylate (200 mg, 0.649 mmol, 1.00 eq.), N,N-dimethylformamide (5 mL), cesium carbonate (422 mg, 1.30 mmol, 2.00 eq.) and benzyl bromide (133 mg, 0.778 mmol, 1.20 eq.). The solution was stirred for 2 h at rt. The solution was diluted with ethyl acetate (30 mL). The mixture was washed with water (3×10 mL), dried over anhydrous sodium sulfate, filtered and concentrated under reduced pressure. The residue was purified by silica gel column chromatography and eluted with petroleum ether:ethyl acetate (1:2) to afford tert-butyl-12-benzyl-8,13-dioxo-4,7,9,12-tetraazatricyclo[7.4.0.0^[2,7]]tridec-1-ene-4-carboxylate (120 mg, 46% yield) as a light yellow solid. LCMS (ESI, m/z): 399 [M+H]+.

Example 22

Tert-butyl-2-(4-methoxyphenyl)-3-oxo-1-phenyl-5H,6H,8H-imidazo[1,5-a]pyrazine-7-carboxylate (Intermediate 6)

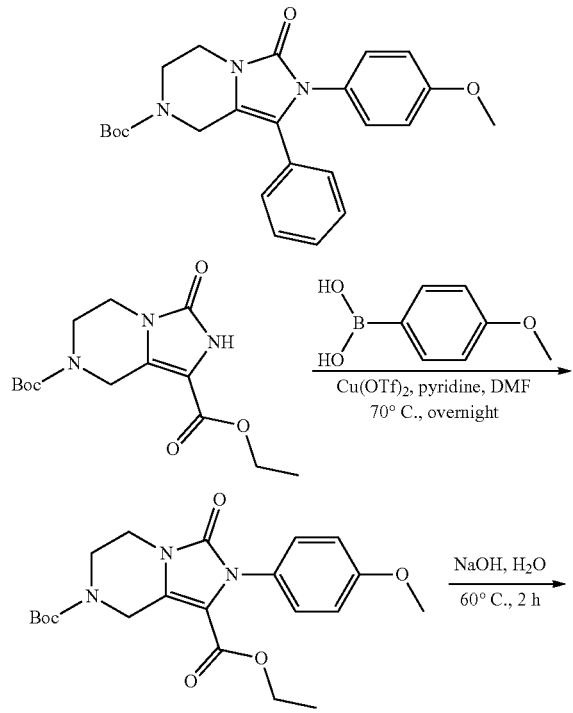

-continued

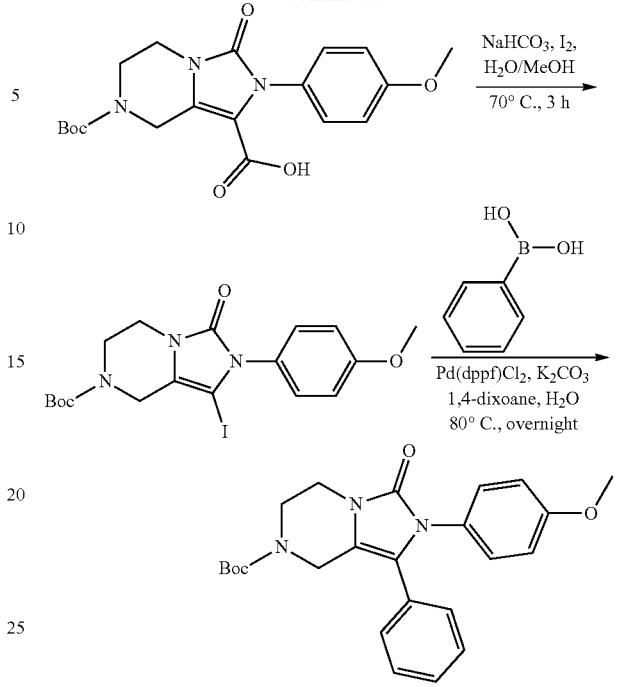

a) 7-tert-butyl-1-ethyl 2-(4-methoxyphenyl)-3-oxo-5H,6H,8H-imidazo[1,5-a]pyrazine-1,7-dicarboxylate

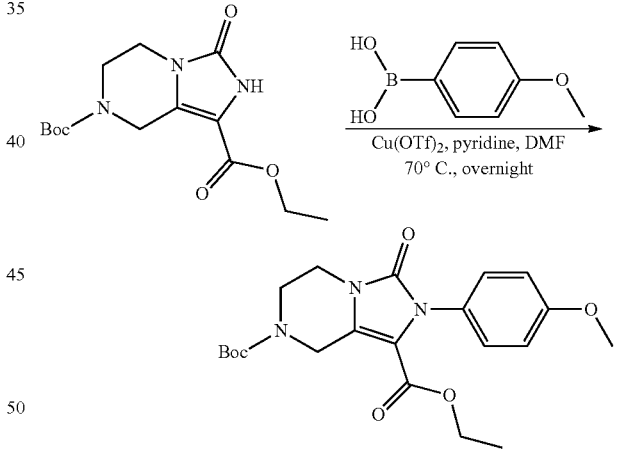

Into a 100 mL round-bottom flask were added 7-tert-butyl-1-ethyl 3-oxo-2H,5H,6H,8H-imidazo[1,5-a]pyrazine-1,7-dicarboxylate (3.00 g, 9.64 mmol, 1.00 eq.), synthetized following the pathway of Example 10, steps (a) and (b), 4-methoxyphenylboronic acid (1.76 g, 11.6 mmol, 1.20 eq.), pyridine (2.29 g, 28.9 mmol, 3.00 eq.), copper (II) trifluoromethanesulfonate (3.49 g, 9.64 mmol, 1.00 eq.) and N,N-dimethylformamide (30.0 mL) at rt. The mixture was stirred overnight at 70° C. under oxygen atmosphere. The reaction was quenched with water (40 mL). The mixture was extracted with ethyl acetate (3×100 mL). The organic layers were combined, washed with brine (2×50 mL), dried over anhydrous sodium sulfate, filtered and concentrated under reduced pressure. The residue was purified by silica gel column chromatography, eluted with petroleum ether:ethyl acetate (3:7) to afford 7-tert-butyl-1-ethyl 2-(4-methoxyphenyl)-3-oxo-5H,6H,8H-imidazo[1,5-a]pyrazine-1,7-dicarboxylate (2.80 g, 70% yield) as a light yellow solid. LCMS (ESI, m/z): 418 [M+H]+.

b) 7-(tert-butoxycarbonyl)-2-(4-methoxyphenyl)-3-oxo-5H,6H,8H-imidazo[1,5-a]pyrazine-1-carboxylic Acid

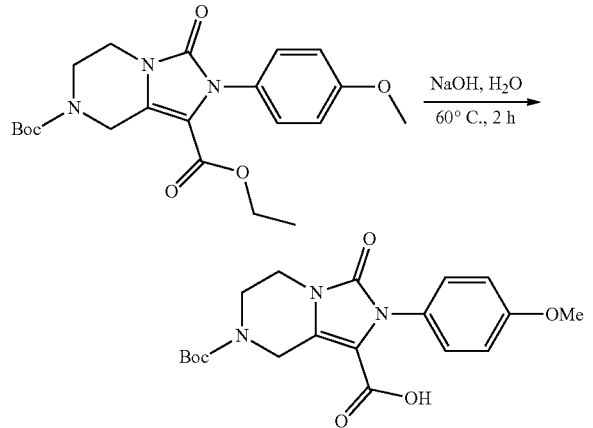

Into a 100 mL round-bottom flask were added 7-tert-butyl-1-ethyl 2-(4-methoxyphenyl)-3-oxo-5H,6H,8H-imidazo[1,5-a]pyrazine-1,7-dicarboxylate (2.80 g, 6.71 mmol, 1.00 eq.), ethanol (20 mL) and sodium hydroxide (0.400 g, 10.1 mmol, 1.50 eq.) in water (4 mL) at rt. The mixture was stirred for 2 h at 60° C. The mixture was concentrated under reduced pressure and diluted with water (20 mL). The pH value of the mixture was acidified to 3 with HCl (1 mol/L aq.). The mixture was extracted with ethyl acetate (3×100 mL). The organic layers were combined, washed with brine (2×50 mL), dried over anhydrous sodium sulfate, filtered and concentrated under reduced pressure to afford 7-(tert-butoxycarbonyl)-2-(4-methoxyphenyl)-3-oxo-5H,6H,8H-imidazo[1,5-a]pyrazine-1-carboxylic acid (2.40 g, 92% yield) as a light yellow solid. LCMS (ESI, m/z): 390 [M+H]+.

c) tert-butyl-1-iodo-2-(4-methoxyphenyl)-3-oxo-5H,6H,8H-imidazo[1,5-a]pyrazine-7-carboxylate

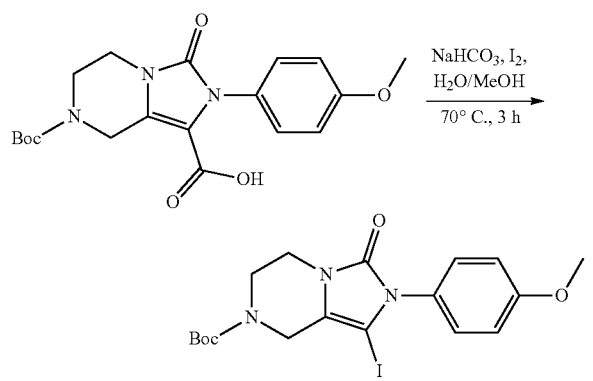

To a solution of 7-(tert-butoxycarbonyl)-2-(4-methoxyphenyl)-3-oxo-5H,6H,8H-imidazo[1,5-a]pyrazine-1-carboxylic acid (250 mg, 0.642 mmol, 1.00 eq.) and potassium iodide (319 mg, 1.93 mmol, 3.00 eq.) in methanol (8.00 mL) and water (2.00 mL) were added sodium bicarbonate (215 mg, 2.57 mmol, 4.00 eq.) and iodine (195 mg, 0.770 mmol, 1.20 eq.). The mixture was stirred for 3 h at 70° C. under a N2 atmosphere. The reaction was quenched with sat. sodium persulfate (2 mL, aq.). The mixture was extracted with dichloromethane (3×50 mL). The organic layers were combined, washed with water (3×30 mL), dried over anhydrous sodium sulfate, filtered and concentrated under reduced pressure to afford tert-butyl-1-iodo-2-(4-methoxyphenyl)-3-oxo-5H,6H,8H-imidazo[1,5-a]pyrazine-7-carboxylate (100 mg, crude) as an off-white solid. LCMS (ESI, m/z): 472 [M+H]+.

d) 2-(4-methoxyphenyl)-3-oxo-1-phenyl-5H,6H,8H-imidazo[1,5-a]pyrazine-7-carboxylate

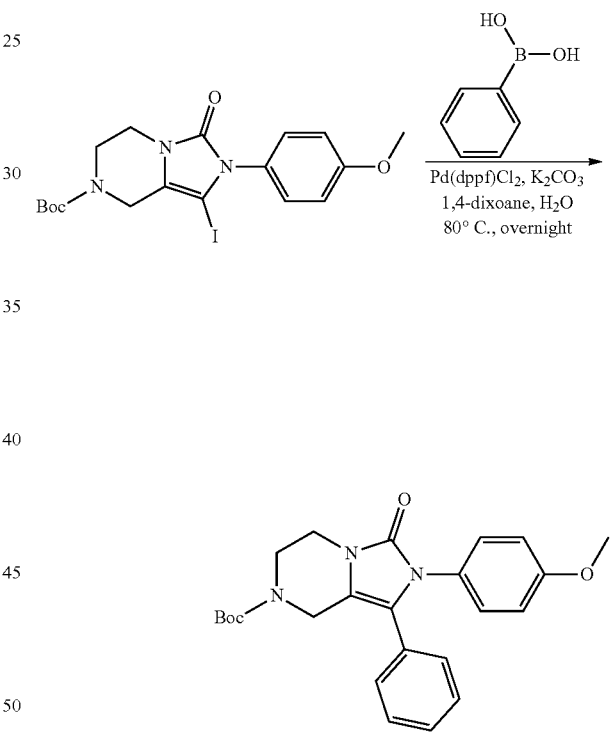

To a solution of tert-butyl-1-iodo-2-(4-methoxyphenyl)-3-oxo-5H,6H,8H-imidazo[1,5-a]pyrazine-7-carboxylate (100 mg, 0.212 mmol, 1.00 eq.) and phenyl boronic acid (38.0 mg, 0.318 mmol, 1.50 eq.) in 1,4-dioxane (2.5 mL) and water (0.5 mL) were added potassium carbonate (87.0 mg, 0.637 mmol, 3.00 eq.) and [1,1'-bis(diphenylphosphino)ferrocene]dichloropalladium(II) (31.0 mg, 0.042 mmol, 0.20 eq.). The mixture was stirred overnight at 80° C. under a N2 atmosphere and concentrated under reduced pressure. The residue was purified by Prep-TLC and eluted with petroleum ether:ethyl acetate (1:1) to afford tert-butyl-2-(4-methoxyphenyl)-3-oxo-1-phenyl-5H,6H,8H-imidazo[1,5-a]pyrazine-7-carboxylate (80 mg, 89% yield) as a white solid. LCMS (ESI, m/z): 422 [M+H]+.

Example 23

Tert-butyl-13-benzyl-11-methylidene-8,14-dioxo-4,7,9,13-tetraazatricyclo[7.5.0.0^[2,7]]tetradec-1-ene-4-carboxylate (Intermediate 7)

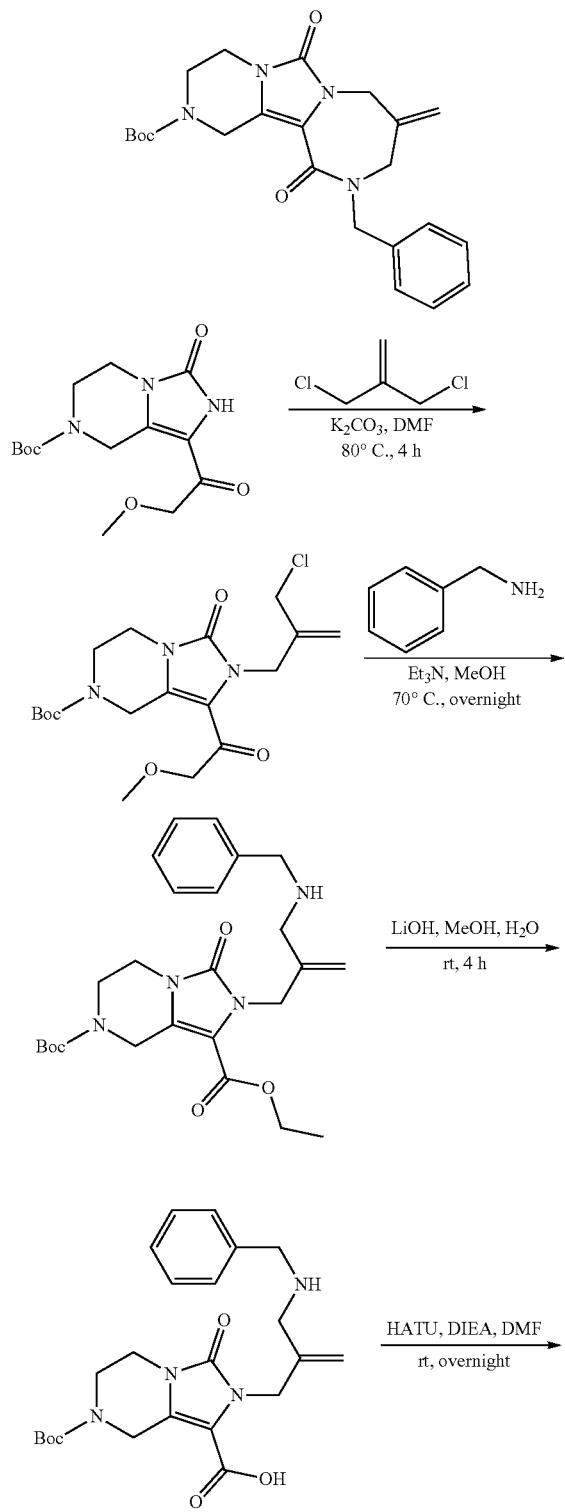

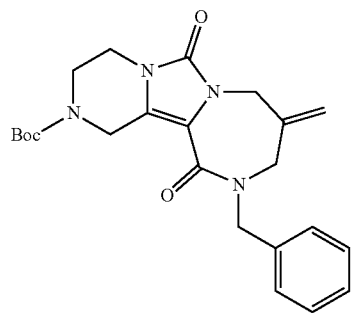

a) 7-tert-butyl-1-ethyl 2-[2-(chloromethyl)prop-2-en-1-yl]-3-oxo-5H,6H,8H-imidazo[1,5-a]pyrazine-1,7-dicarboxylate

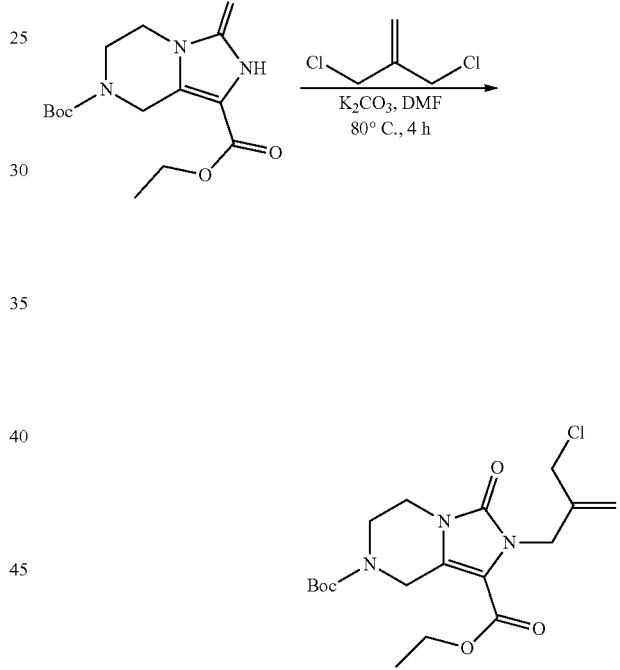

A mixture of 7-tert-butyl-1-ethyl-3-oxo-2H,5H,6H,8H-imidazo[1,5-a]pyrazine-1,7-dicarboxylate (1.00 g, 3.21 mmol, 1.00 eq.), synthesized as in Example 10, steps (a) and (b), 3-chloro-2-(chloromethyl)prop-1-ene (0.803 g, 6.42 mmol, 2.00 eq.), potassium carbonate (1.33 g, 9.63 mmol, 3.00 eq.) and N,N-dimethylformamide (50 mL) was stirred for 4 h at 80° C. To the mixture was added ethyl acetate (100 mL), and the mixture washed with water (3×100 mL). The organic layer was dried over anhydrous sodium sulfate, filtered and concentrated under reduced pressure. The residue was purified by silica gel column chromatography, eluted with ethyl acetate:petroleum ether (1:1) to provide 7-tert-butyl-1-ethyl-2-[2-(chloromethyl)prop-2-en-1-yl]-3-oxo-5H,6H,8H-imidazo[1,5-a]pyrazine-1,7-dicarboxylate (1.20 g, 93% yield) as a yellow solid. LCMS (ESI, m/z): 400 [M+H]$^+$.

b) 7-tert-butyl-1-ethyl-2-[2-[(benzylamino)methyl]prop-2-en-1-yl]-3-oxo-5H,6H,8H-imidazo[1,5-a]pyrazine-1,7-dicarboxylate

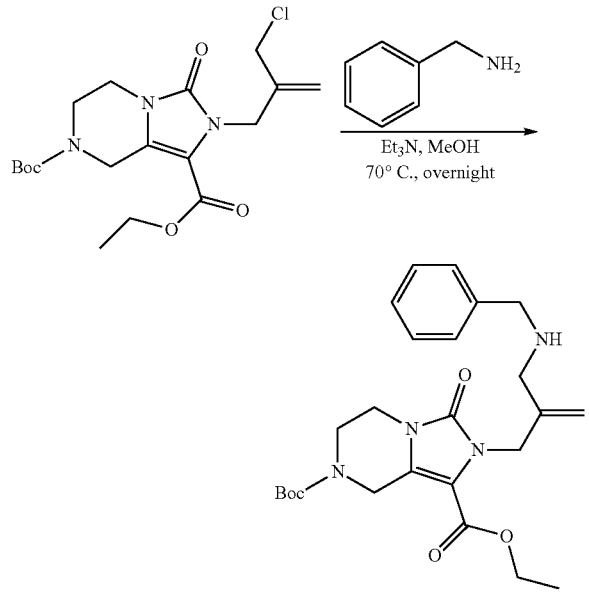

A mixture of 7-tert-butyl-1-ethyl-2-[2-(chloromethyl)prop-2-en-1-yl]-3-oxo-5H,6H,8H-imidazo[1,5-a]pyrazine-1,7-dicarboxylate (1.20 g, 3.00 mmol, 1.00 eq.), benzylamine (0.642 g, 6.00 mmol, 2.00 eq.), triethylamine (0.909 g, 9.00 mmol, 3.00 eq.) and methanol (50 mL) was stirred overnight at 70° C. and then concentrated under reduced pressure. The residue was purified by silica gel column chromatography and eluted with ethyl acetate:petroleum ether (3:1) to provide 7-tert-butyl-1-ethyl-2-[2-[(benzylamino)methyl]prop-2-en-1-yl]-3-oxo-5H,6H,8H-imidazo[1,5-a]pyrazine-1,7-dicarboxylate (950 mg, 67% yield) as a yellow solid. LCMS (ESI, m/z): 471 [M+H]$^+$.

c) 2-[2-[(benzylamino)methyl]prop-2-en-1-yl]-7-(tert-butoxycarbonyl)-3-oxo-5H,6H,8H-imidazo[1,5-a]pyrazine-1-carboxylic Acid

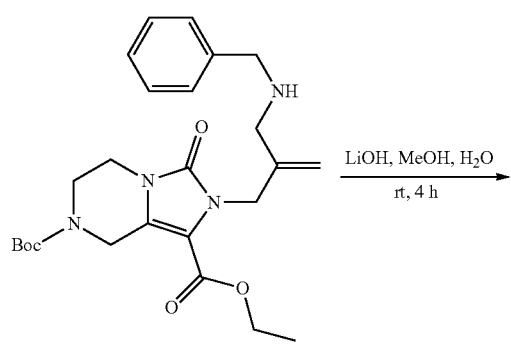

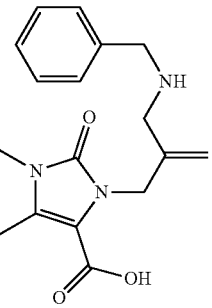

A mixture of 7-tert-butyl-1-ethyl-2-[2-[(benzylamino)methyl]prop-2-en-1-yl]-3-oxo-5H,6H,8H-imidazo[1,5-a]pyrazine-1,7-dicarboxylate (950 mg, 2.02 mmol, 1.00 eq.), lithium hydroxide (242 mg, 10.1 mmol, 5.00 eq.), methanol (40 mL) and water (10 mL) was stirred for 4 h at rt. The pH value of the mixture was neutralized to 7 with HCl (1.0 mol/L) and then concentrated under reduced pressure to afford crude 2-[2-[(benzylamino)methyl]prop-2-en-1-yl]-7-(tert-butoxycarbonyl)-3-oxo-5H,6H,8H-imidazo[1,5-a]pyrazine-1-carboxylic acid (800 mg, crude) as a yellow solid. LCMS (ESI, m/z): 443 [M+H]$^+$.

d) tert-butyl-13-benzyl-11-methylidene-8,14-dioxo-4,7,9,13-tetraazatricyclo[7.5.0.0 ^[2,7]]tetradec-1-ene-4-carboxylate

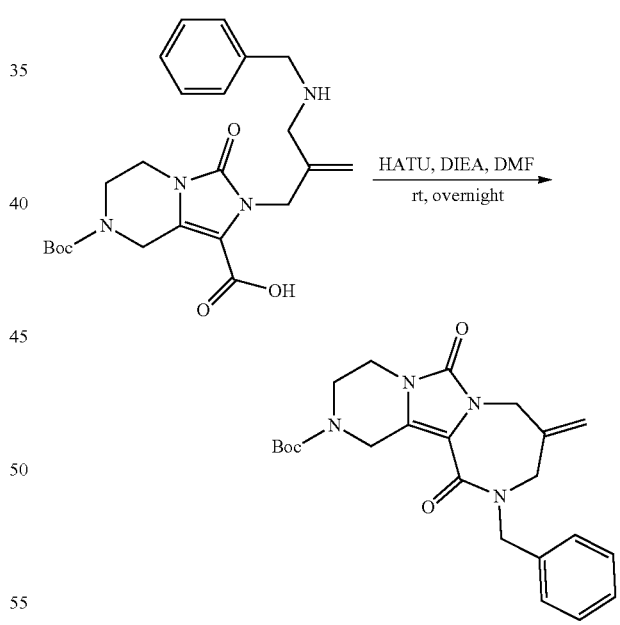

A mixture of 2-[2-[(benzylamino)methyl]prop-2-en-1-yl]-7-(tert-butoxycarbonyl)-3-oxo-5H,6H,8H-imidazo[1,5-a]pyrazine-1-carboxylic acid (0.800 g, 1.81 mmol, 1.00 eq.), 2-(7-azabenzotriazol-1-yl)-N,N,N',N'-tetramethyluronium hexafluorophospate (1.03 g, 2.71 mmol, 1.50 eq.), N,N-diisopropylethylamine (0.701 g, 5.43 mmol, 3.00 eq.) and N,N-dimethylformamide (50 mL) was stirred overnight at rt. To the mixture was added ethyl acetate (50 mL) and then the washed with water (3×50 mL). The organic layer was dried over anhydrous sodium sulfate, filtered and concentrated under reduced pressure. The residue was purified by silica gel column chromatography with ethyl acetate:petroleum ether (2:1) to afford tert-butyl-13-benzyl-11-methylidene-8,14-dioxo-4,7,9,13-tetraazatricyclo[7.5.0.0^[2,7]]tetradec-1-ene-4-carboxylate (400 mg, 52% yield) as a yellow solid. LCMS (ESI, m/z): 425 [M+H]⁺.

Example 24

Tert-butyl-13-benzyl-11-methyl-8,14-dioxo-4,7,9,13-tetraazatricyclo[7.5.0.0^[2,7]]tetradec-1-ene-4-carboxylate

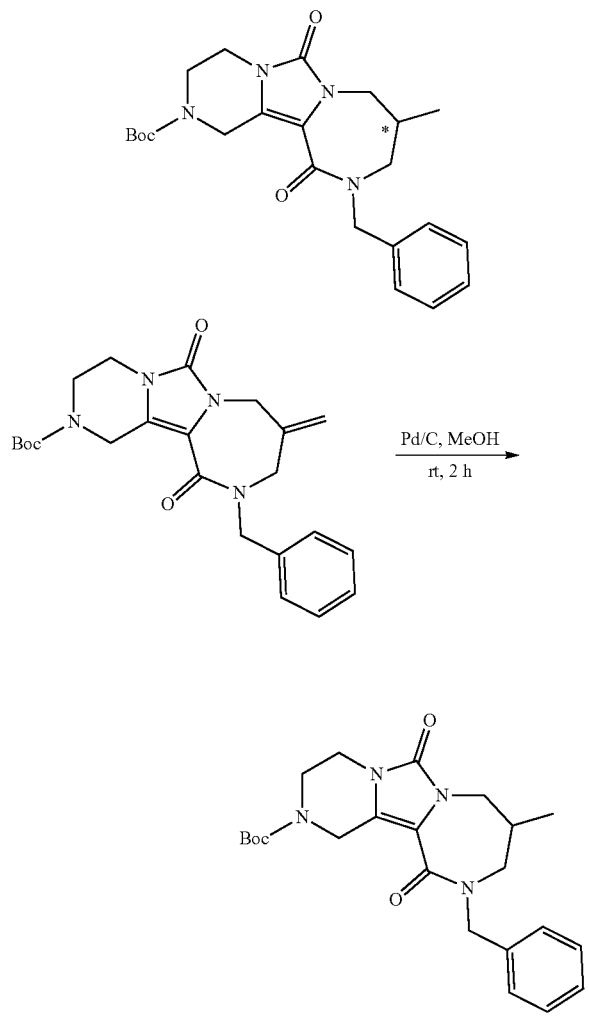

A 50 mL round bottom flask was charged with tert-butyl-13-benzyl-11-methylidene-8,14-dioxo-4,7,9,13-tetraazatricyclo[7.5.0.0 ^[2,7]]tetradec-1-ene-4-carboxylate (200 mg, 0.471 mmol, 1.00 eq.), 10% Pd/C (20 mg) and methanol (20 mL). The solution was stirred for 2 h at rt under 3 atm H₂ atmosphere. The solid was filtrated off, and the filtrate was concentrated under reduced pressure to provide tert-butyl-13-benzyl-11-methyl-8,14-dioxo-4,7,9,13-tetraazatricyclo[7.5.0.0^[2,7]]tetradec-1-ene-4-carboxylate (190 mg, 94% yield) as a white solid. LCMS (ESI, m/z): 427 [M+H]⁺.

Example 25

Tert-butyl-13-benzyl-11-(hydroxymethyl)-8,14-dioxo-4,7,9,13-tetraazatricyclo[7.5.0.0^[2,7]]tetradec-1-ene-4-carboxylate (Intermediate 8)

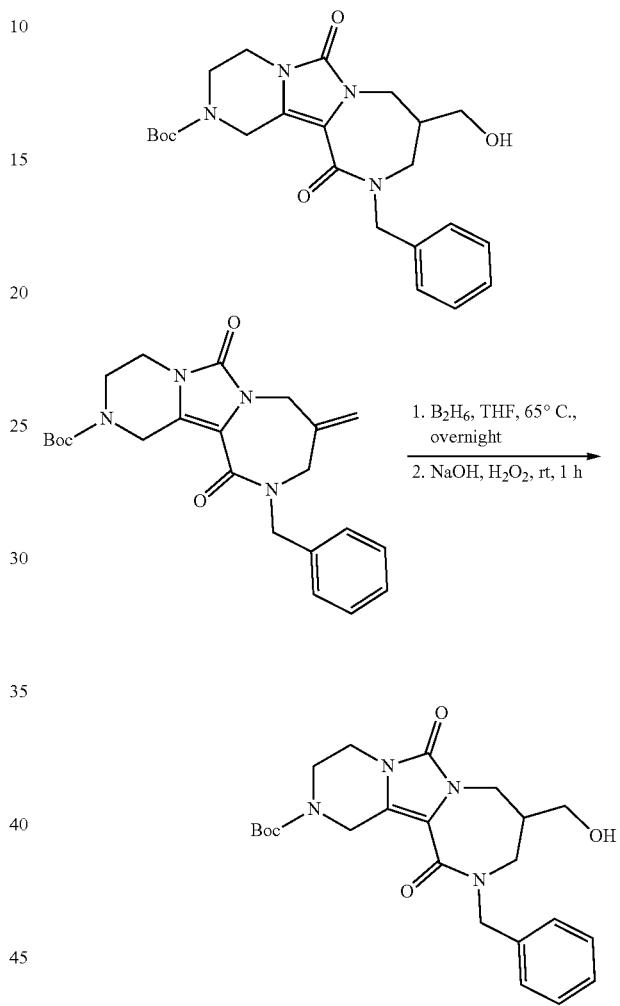

Borane (1.70 mL, 1.70 mmol, 4.00 eq., 1.0 mol/L in tetrahydrofuran) was added to a mixture of tert-butyl-13-benzyl-11-methylidene-8,14-dioxo-4,7,9,13-tetraazatricyclo[7.5.0.0^[2,7]]tetradec-1-ene-4-carboxylate (180 mg, 0.424 mmol, 1.00 eq.) and tetrahydrofuran (15 mL) at 0° C. under a N₂ atmosphere. The mixture was stirred overnight at 65° C. and then cooled to ice bath temperature. To the mixture was added sodium hydroxide (8.00 mL, 4.0 mol/L) followed by 30% hydrogen peroxide (0.70 mL). The mixture was stirred for additional 1 h at rt. The mixture was extracted with ethyl acetate (3×50 mL). The combined organic layers were dried over anhydrous sodium sulfate, filtered and concentrated under reduced pressure. The residue was purified by silica gel column chromatography with ethyl acetate:petroleum ether (4:1) to afford tert-butyl-13-benzyl-11-(hydroxymethyl)-8,14-dioxo-4,7,9,13-tetraazatricyclo[7.5.0.0^[2,7]]tetradec-1-ene-4-carboxylate (100 mg, 53% yield) as a yellow solid. LCMS (ESI, m/z): 443 [M+H]⁺.

Example 26

Tert-butyl (11Z)-14-[(4-methoxyphenyl)methyl]-8,15-dioxo-4,7,9,14-tetraazatricyclo[7.6.0.0^[2,7]]pentadeca-1,11-diene-4-carboxylate

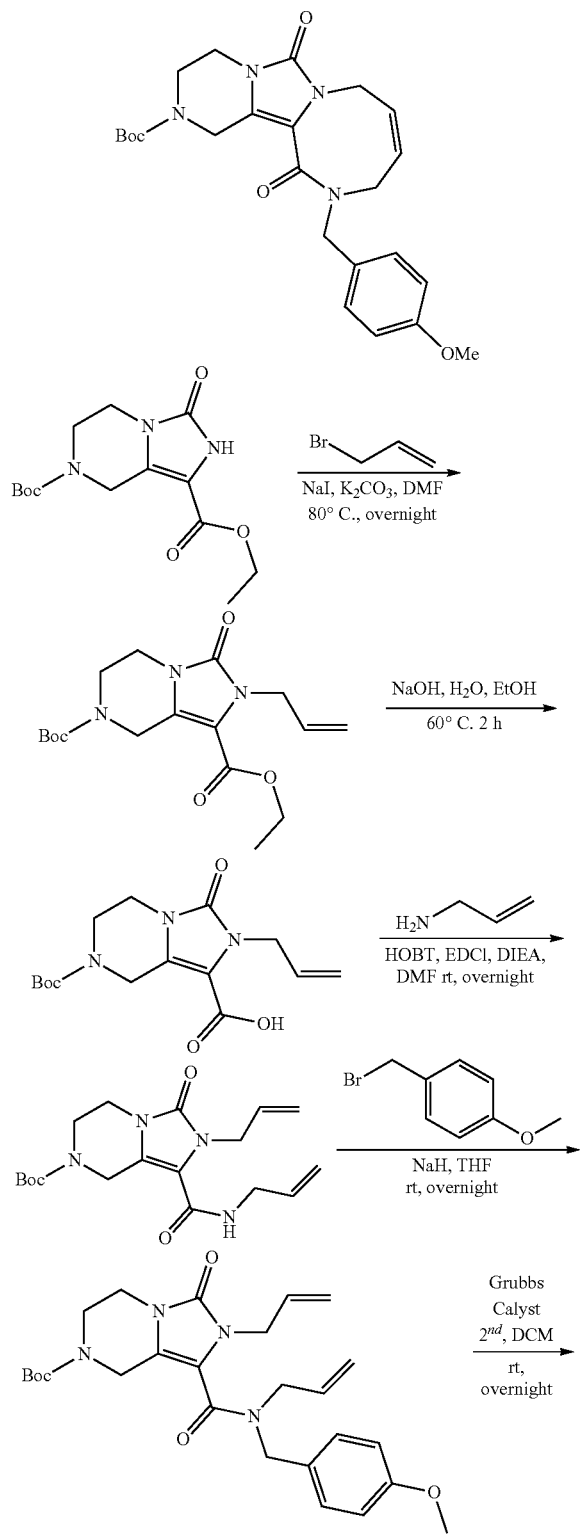

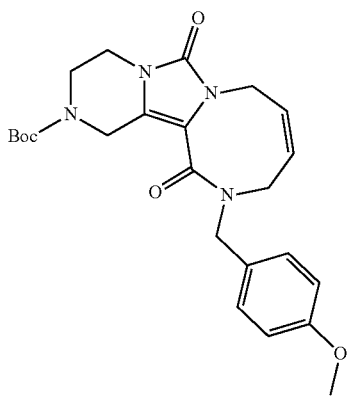 [SMILES: COc1ccc(CN2C/C=C\Cn3c(c4n(c3=O)CCN(C(=O)OC(C)(C)C)C4)C2=O)cc1]

a) 7-tert-butyl-1-ethyl 3-oxo-2-(prop-2-en-1-yl)-5H,6H,8H-imidazo[1,5-a]pyrazine-1,7-dicarboxylate

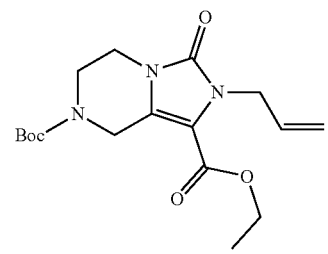

Into a 100 mL round-bottom flask were added 7-tert-butyl-1-ethyl 3-oxo-2H,5H,6H,8H-imidazo[1,5-a]pyrazine-1,7-dicarboxylate (2.00 g, 6.42 mmol, 1.00 eq.), allyl bromide (0.780 g, 6.42 mmol, 1.00 eq.), sodium iodide (0.190 g, 1.28 mmol, 0.200 eq.), potassium carbonate (2.66 g, 19.3 mmol, 3.00 eq.) and N,N-dimethylformamide (20.0 mL) at rt. The mixture was stirred overnight at 80° C., and the reaction was quenched with water (40 ml). The mixture was extracted with ethyl acetate (3×100 mL). The combined organic phased were washed with brine (2×50 mL), dried over anhydrous sodium sulfate, filtered and concentrated under reduced. The residue was purified by silica gel column chromatography and eluted with petroleum ether:ethyl acetate 1:1 to afford 7-tert-butyl-1-ethyl-3-oxo-2-(prop-2-en-1-yl)-5H,6H,8H-imidazo[1,5-a]pyrazine-1,7-dicarboxylate (1.60 g, 71% yield) as a light yellow oil. LCMS (ESI, m/z): 352 [M+H]$^+$.

b) 7-(tert-butoxycarbonyl)-3-oxo-2-(prop-2-en-1-yl)-5H,6H,8H-imidazo[1,5-a]pyrazine-1-carboxylic Acid

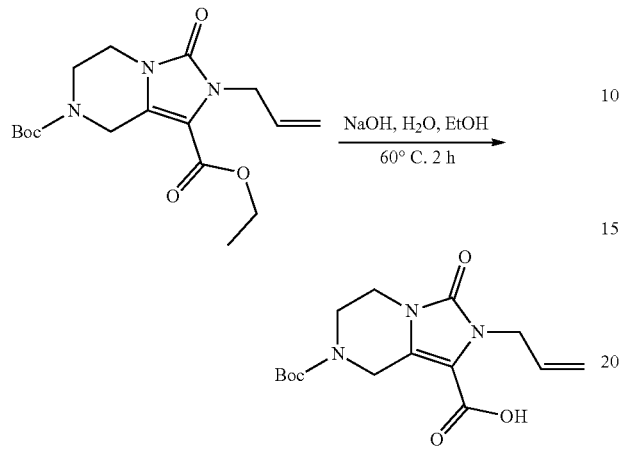

Into a 40 mL round-bottom flask were added 7-tert-butyl-1-ethyl-3-oxo-2-(prop-2-en-1-yl)-5H,6H,8H-imidazo[1,5-a]pyrazine-1,7-dicarboxylate (1.60 g, 4.55 mmol, 1.00 eq.), sodium hydroxide (0.270 g, 6.83 mmol, 1.50 eq.) in water (5 mL) and ethanol (15 mL) at rt. The mixture was stirred for 2 h at 60° C. and then concentrated under reduced pressure. The residue was dissolved in water (10 mL) and the pH value was acidified to 2 with HCl acid (1.00 mol/L aq.). The mixture was extracted with ethyl acetate (3×50 mL). The combined organic layers were washed with brine (2×40 mL), dried over anhydrous sodium sulfate, filtered and concentrated under reduced pressure to afford 7-(tert-butoxycarbonyl)-3-oxo-2-(prop-2-en-1-yl)-5H,6H,8H-imidazo[1,5-a]pyrazine-1-carboxylic acid (1.53 g, crude) as a light yellow solid. LCMS (ESI, m/z): 324 [M+H]$^+$.

c) tert-butyl-3-oxo-2-(prop-2-en-1-yl)-1-[(prop-2-en-1-yl)carbamoyl]-5H,6H,8H-imidazo[1,5-a]pyrazine-7-carboxylate

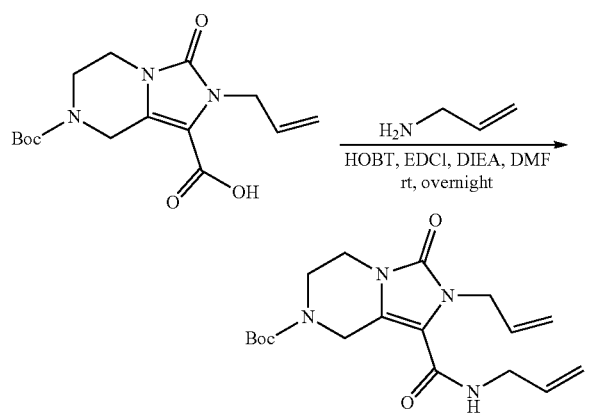

Into a 100 mL round-bottom flask were added 7-(tert-butoxycarbonyl)-3-oxo-2-(prop-2-en-1-yl)-5H,6H,8H-imidazo[1,5-a]pyrazine-1-carboxylic acid (1.53 g, 4.73 mmol, 1.00 eq.), allylamine (0.320 g, 5.68 mmol, 1.20 eq.), 1-hydroxybenzotriazole (0.770 g, 5.68 mmol, 1.20 eq.), N-(3-dimethylaminopropyl)-N'-ethylcarbodiimide (1.09 g, 5.68 mmol, 1.20 eq.), N,N-diisopropylethylamine (1.83 g, 14.2 mmol, 3.00 eq.) and N,N-dimethylformamide (15 mL) at rt. The mixture was stirred overnight at rt. The reaction was quenched with water (15 ml). The mixture was extracted with ethyl acetate (3×50 mL). The combined organic layers were washed with brine (2×20 mL), dried over anhydrous sodium sulfate, filtered and concentrated under reduced pressure. The residue was purified by silica gel column chromatography, eluted with petroleum ether:ethyl acetate (1:1) to afford tert-butyl-3-oxo-2-(prop-2-en-1-yl)-1-[(prop-2-en-1-yl)carbamoyl]-5H,6H,8H-imidazo[1,5-a]pyrazine-7-carboxylate (1.05 g, 61% yield) as a white solid. LCMS (ESI, m/z): 363 [M+H]$^+$.

d) tert-butyl-1-[[(4-methoxyphenyl)methyl](prop-2-en-1-yl)carbamoyl]-3-oxo-2-(prop-2-en-1-yl)-5H,6H,8H-imidazo[1,5-a]pyrazine-7-carboxylate

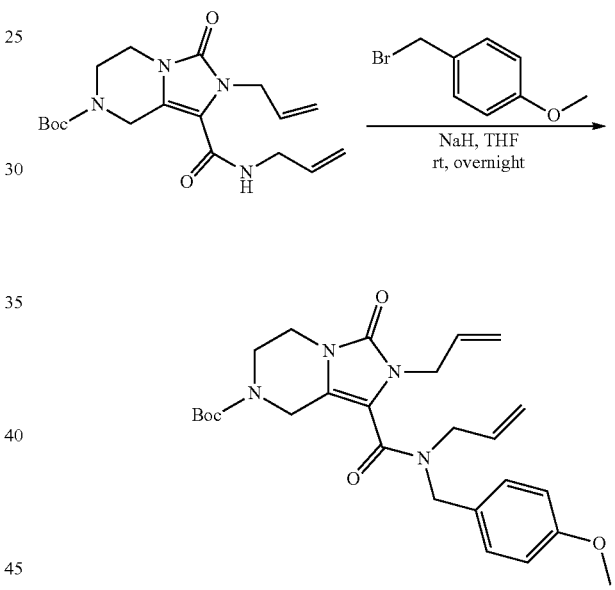

To a stirred solution of tert-butyl-3-oxo-2-(prop-2-en-1-yl)-1-[(prop-2-en-1-yl)carbamoyl]-5H,6H,8H-imidazo[1,5-a]pyrazine-7-carboxylate (1.05 g, 2.89 mmol, 1.00 eq.) in tetrahydrofuran (10 mL) was added NaH (0.170 g, 4.25 mmol, 1.47 equiv, 60% dispersion in mineral oil) at 0° C. The mixture was stirred for 20 min at rt. 1-(bromomethyl)-4-methoxybenzene (0.700 g, 3.48 mmol, 1.20 eq.) was added. The mixture was stirred overnight at rt. The reaction was quenched with water (20 mL). The mixture was extracted with ethyl acetate (3×50 mL). The organic layers were combined, washed with brine (2×40 mL), dried over anhydrous sodium sulfate, filtered and concentrated under reduced pressure. The residue was purified by silica gel column chromatography, eluted with petroleum ether:ethyl acetate (1:1) to afford tert-butyl-1-[[(4-methoxyphenyl)methyl](prop-2-en-1-yl)carbamoyl]-3-oxo-2-(prop-2-en-1-yl)-5H,6H,8H-imidazo[1,5-a]pyrazine-7-carboxylate (885 mg, 63% yield) as an off-white solid. LCMS (ESI, m/z): 483 [M+H]$^+$.

137 e) tert-butyl (11Z)-14-[(4-methoxyphenyl)methyl]-8,15-dioxo-4,7,9,14-tetraazatricyclo[7.6.0.0^[2,7]]pentadeca-1,11-diene-4-carboxylate

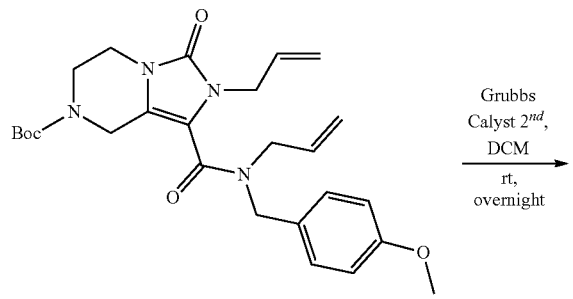

Into a 20 mL round-bottom flask were added tert-butyl-1-[[(4-methoxyphenyl)methyl](prop-2-en-1-yl)carbamoyl]-3-oxo-2-(prop-2-en-1-yl)-5H,6H,8H-imidazo[1,5-a]pyrazine-7-carboxylate (885 mg, 1.83 mmol, 1.00 eq.), Grubbs catalyst 2nd generation (77.8 mg, 0.0920 mmol, 0.05 eq.) and dichloromethane (10 mL) at rt. The mixture was stirred overnight at rt and then diluted with water (15 mL). The mixture was extracted with dichloromethane (3×40 mL). The combined organic layers were washed with brine (2×20 mL), dried over anhydrous sodium sulfate, filtered and concentrated under reduced pressure. The residue was purified by silica gel column chromatography, eluted with dichloromethane:methanol (10:1) to afford tert-butyl (11Z)-14-[(4-methoxyphenyl)methyl]-8,15-dioxo-4,7,9,14-tetraazatricyclo[7.6.0.0^[2,7]]pentadeca-1,11-diene-4-carboxylate (450 mg, 54% yield) as an off-white solid. LCMS (ESI, m/z): 455 [M+H]$^+$.

138

Example 27

Tert-butyl-14-[(4-methoxyphenyl)methyl]-8,15-dioxo-4,7,9,14-tetraazatricyclo[7.6.0.0^[2,7]]pentadec-1-ene-4-carboxylate (Intermediate 9)

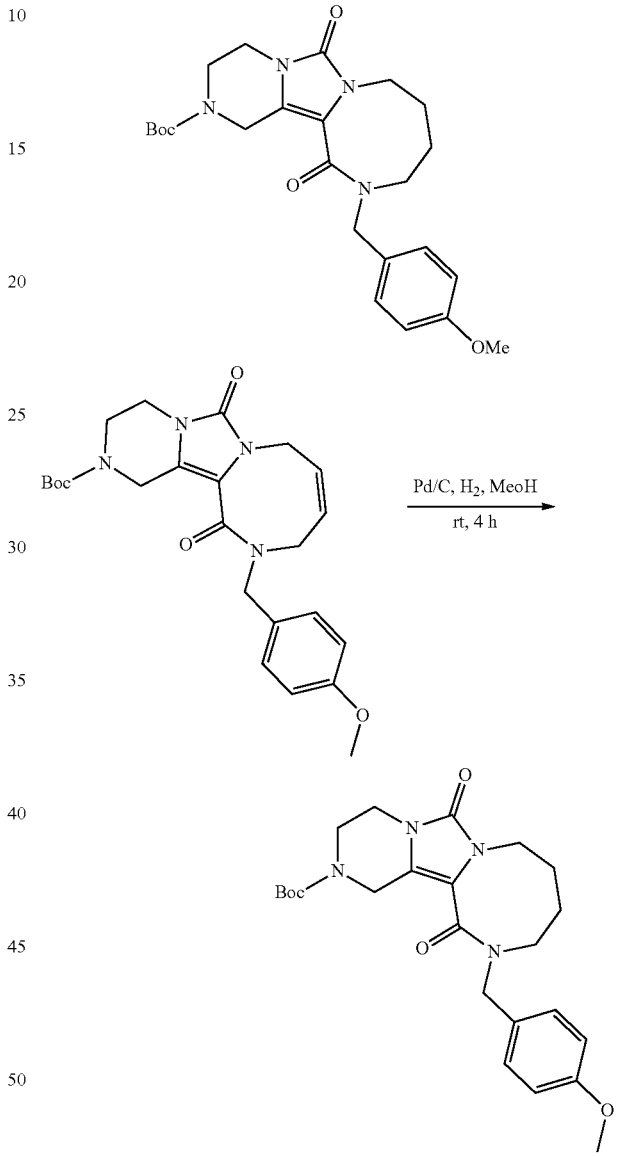

Into a 50 mL 2-necked round-bottom flask were added tert-butyl (11Z)-14-[(4-methoxyphenyl)methyl]-8,15-dioxo-4,7,9,14-tetraazatricyclo[7.6.0.0^[2,7]]pentadeca-1,11-diene-4-carboxylate (250 mg, 0.550 mmol, 1.00 eq.), methanol (10.0 mL) and 10% Pd/C (11.7 mg) at rt. The solution was stirred for 4 h at rt under 3 atm H$_2$ atmosphere. The solid was filtrated off, and the filtrate was concentrated under reduced pressure to provide tert-butyl-14-[(4-methoxyphenyl)methyl]-8,15-dioxo-4,7,9,14-tetraazatricyclo[7.6.0.0^[2,7]]pentadec-1-ene-4-carboxylate (220 mg, crude) as an off-white solid. LCMS (ESI, m/z): 457 [M+H]$^+$.

Example 28

Tert-butyl-13'-benzyl-8',14'-dioxo-4',7',9',13'-tetraazaspiro[oxetane-3,11'-tricyclo[7.5.0.0^[2,7]]tetradecan]-1'-ene-4'-carboxylate

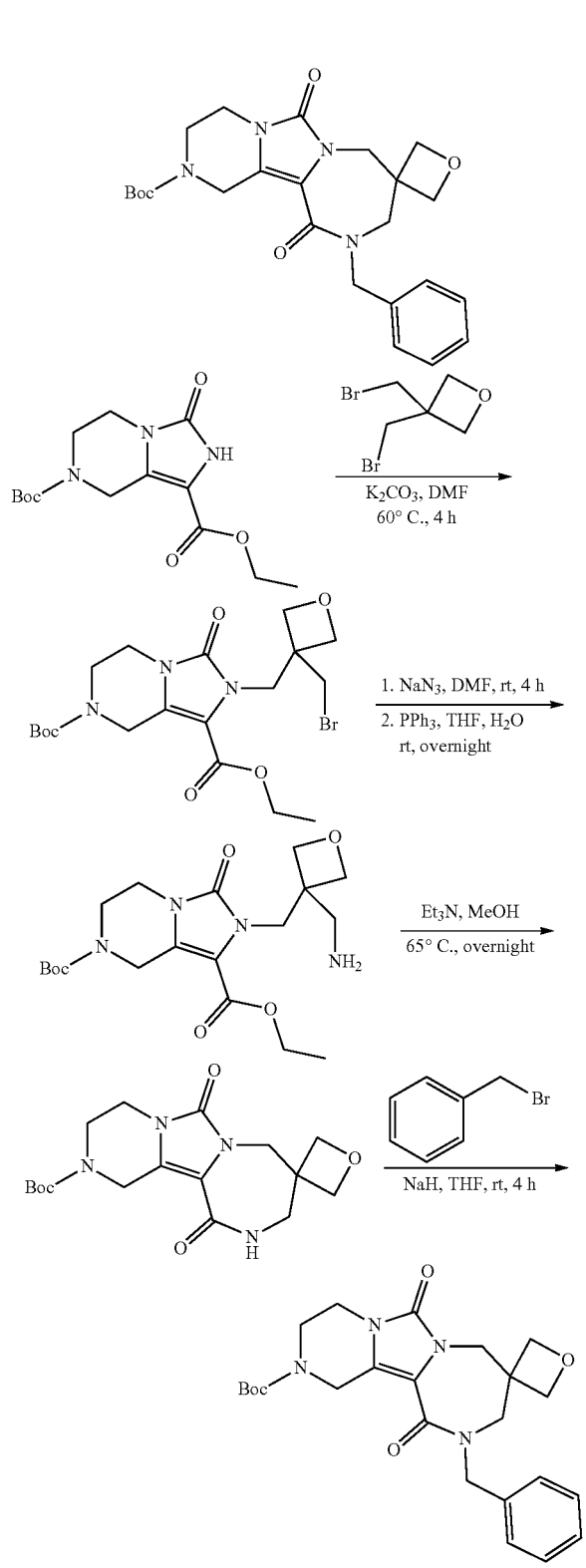

a) 7-tert-butyl 1-ethyl 2-[[3-(bromomethyl)oxetan-3-yl]methyl]-3-oxo-5H,6H,8H-imidazo[1,5-a]pyrazine-1,7-dicarboxylate

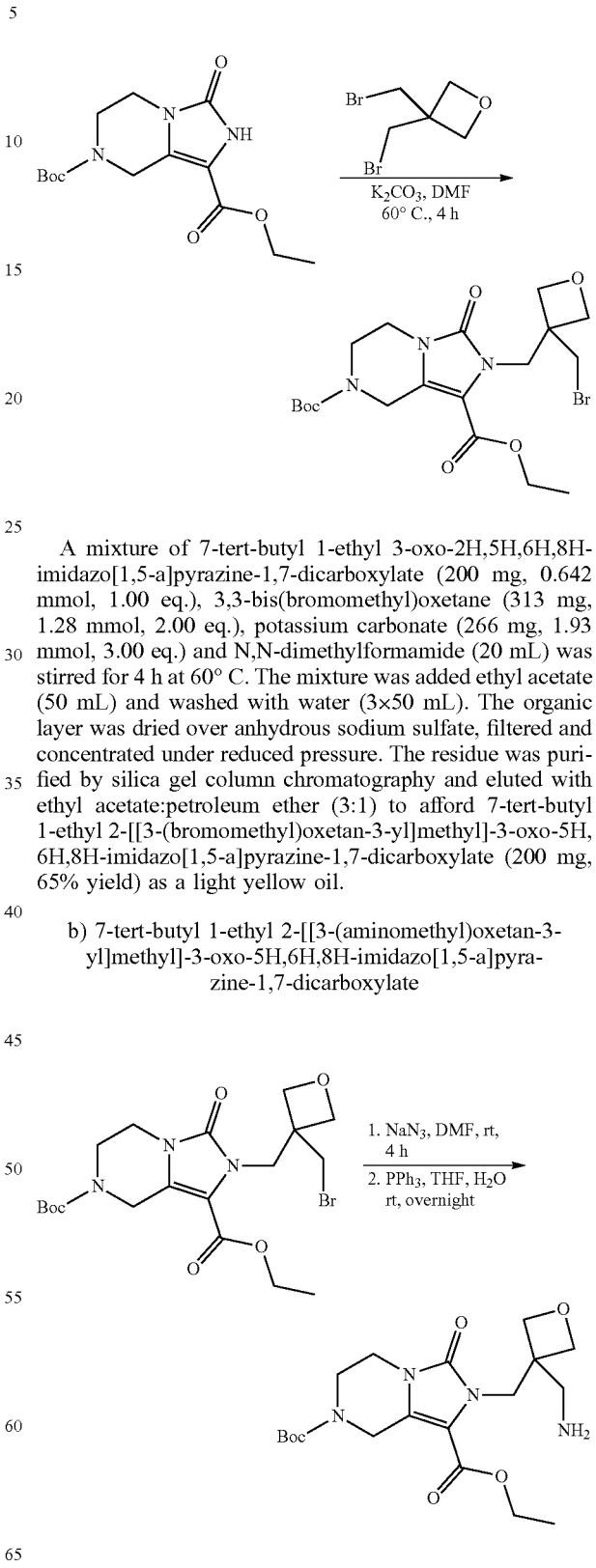

A mixture of 7-tert-butyl 1-ethyl 3-oxo-2H,5H,6H,8H-imidazo[1,5-a]pyrazine-1,7-dicarboxylate (200 mg, 0.642 mmol, 1.00 eq.), 3,3-bis(bromomethyl)oxetane (313 mg, 1.28 mmol, 2.00 eq.), potassium carbonate (266 mg, 1.93 mmol, 3.00 eq.) and N,N-dimethylformamide (20 mL) was stirred for 4 h at 60° C. The mixture was added ethyl acetate (50 mL) and washed with water (3×50 mL). The organic layer was dried over anhydrous sodium sulfate, filtered and concentrated under reduced pressure. The residue was purified by silica gel column chromatography and eluted with ethyl acetate:petroleum ether (3:1) to afford 7-tert-butyl 1-ethyl 2-[[3-(bromomethyl)oxetan-3-yl]methyl]-3-oxo-5H,6H,8H-imidazo[1,5-a]pyrazine-1,7-dicarboxylate (200 mg, 65% yield) as a light yellow oil.

b) 7-tert-butyl 1-ethyl 2-[[3-(aminomethyl)oxetan-3-yl]methyl]-3-oxo-5H,6H,8H-imidazo[1,5-a]pyrazine-1,7-dicarboxylate A mixture of 7-tert-butyl 1-ethyl 2-[[3-(bromomethyl)oxetan-3-yl]methyl]-3-oxo-5H,6H,8H-imidazo[1,5-a]pyrazine-1,7-dicarboxylate (200 mg, 0.422 mmol, 1.00 eq.), sodium azide (82.5 mg, 1.27 mmol, 3.00 eq.) and N,N-dimethylformamide (20 mL) was stirred for 4 h at rt. The mixture was added to ethyl acetate (50 mL) and washed with water (3×50 mL). The organic layer was dried over anhydrous sulfate, filtered and concentrated under reduced pressure to provide the crude product. Triphenylphosphine (221 mg, 0.844 mmol, 2.00 eq.) in tetrahydrofuran (10 mL) and water (10 mL) was added. The mixture was stirred overnight at rt. The mixture was extracted with ethyl acetate (3×50 mL). The combined organic layers were washed with water (3×50 mL), dried over anhydrous sodium sulfate, filtered and concentrated under reduced pressure. The residue was purified by silica gel column chromatography and eluted with methanol:dichloromethane (1:10) to afford 7-tert-butyl 1-ethyl 2-[[3-(aminomethyl)oxetan-3-yl]methyl]-3-oxo-5H,6H,8H-imidazo[1,5-a]pyrazine-1,7-dicarboxylate (120 mg, 69% yield) as a light yellow oil. LCMS (ESI, m/z): 411 [M+H]$^+$.

c) tert-butyl 8',14'-dioxo-4',7',9',13'-tetraazaspiro[oxetane-3,11'-tricyclo[7.5.0.0^[2,7]]tetradecan]-1'-ene-4'-carboxylate

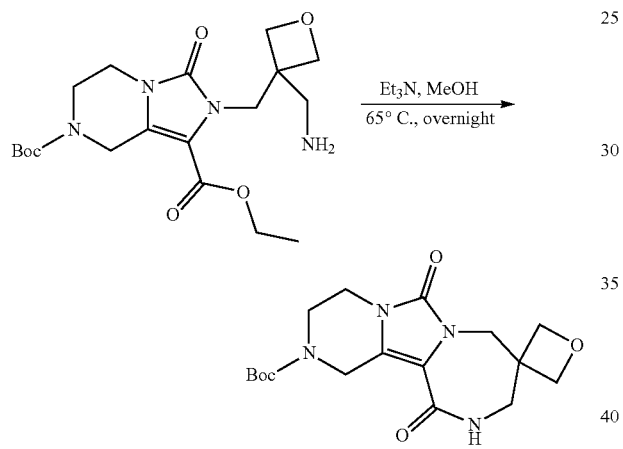

A mixture of with 7-tert-butyl 1-ethyl 2-[[3-(aminomethyl)oxetan-3-yl]methyl]-3-oxo-5H,6H,8H-imidazo[1,5-a]pyrazine-1,7-dicarboxylate (120 mg, 0.292 mmol, 1.00 eq.), triethylamine (88.7 mg, 0.877 mmol, 3.00 eq.) and methanol (10 mL) was stirred overnight at 65° C. The mixture was concentrated under reduced pressure to afford crude tert-butyl 8',14'-dioxo-4',7',9',13'-tetraazaspiro[oxetane-3,11'-tricyclo[7.5.0.0^[2,7]]tetradecan]-1'-ene-4'-carboxylate (70.0 mg, crude) as a light yellow solid. LCMS (ESI, m/z): 365 [M+H]$^+$.

d) tert-butyl 13'-benzyl-8',14'-dioxo-4',7',9',13'-tetraazaspiro[oxetane-3,11'-tricyclo[7.5.0.0^[2,7]]tetradecan]-1'-ene-4'-carboxylate

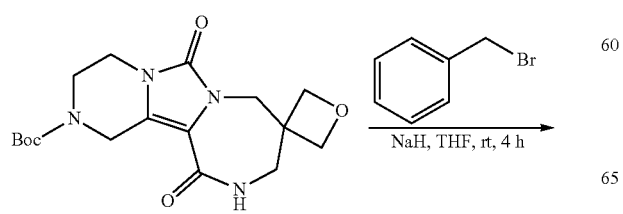

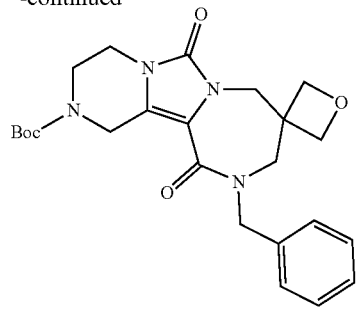

Sodium hydride (13.2 mg, 0.329 mmol, 2.00 eq., 60% dispersion in mineral oil) was added to a mixture of tert-butyl 8',14'-dioxo-4',7',9',13'-tetraazaspiro[oxetane-3,11'-tricyclo[7.5.0.0 ^[2,7]]tetradecan]-1'-ene-4'-carboxylate (60.0 mg, 0.165 mmol, 1.00 eq.) and tetrahydrofuran (10 mL) at 0° C. The mixture was stirred for 1 h at rt. Then to the mixture was added benzyl bromide (42.2 mg, 0.247 mmol, 1.50 eq.). The mixture was stirred for additional 4 h at rt. The reaction was quenched with water (10 mL). The mixture was extracted with ethyl acetate (3×30 mL). The combined organic layers were washed with brine (2×30 mL), dried over anhydrous sodium sulfate, filtered and concentrated under reduced pressure. The residue was purified by silica gel column chromatography, and eluted with ethyl acetate:petroleum ether (4:1) to afford tert-butyl-13'-benzyl-8',14'-dioxo-4',7',9',13'-tetraazaspiro[oxetane-3,11'-tricyclo[7.5.0.0^[2,7]]tetradecan]-1'-ene-4'-carboxylate (40.0 mg, 53% yield) as a yellow solid. LCMS (ESI, m/z): 455 [M+H]$^+$.

Example 29

Benzyl-2-(4-methoxyphenyl)-3-oxo-1-(pyridin-2-yl)-5H,6H,8H-imidazo[1,5-a]pyrazine-7-carboxylate (Intermediate 10)

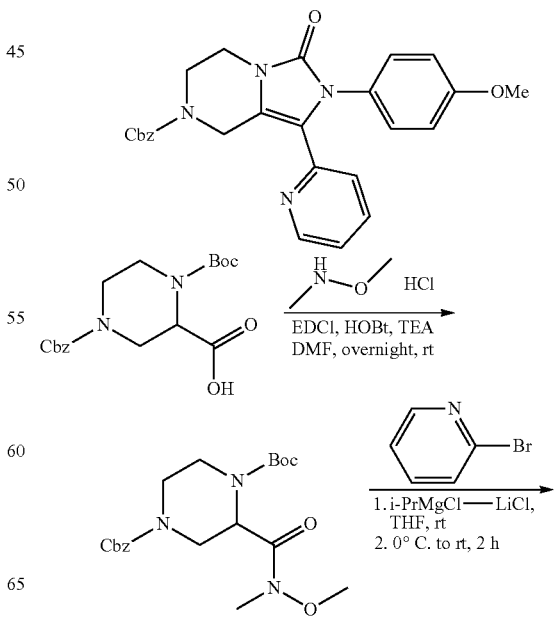

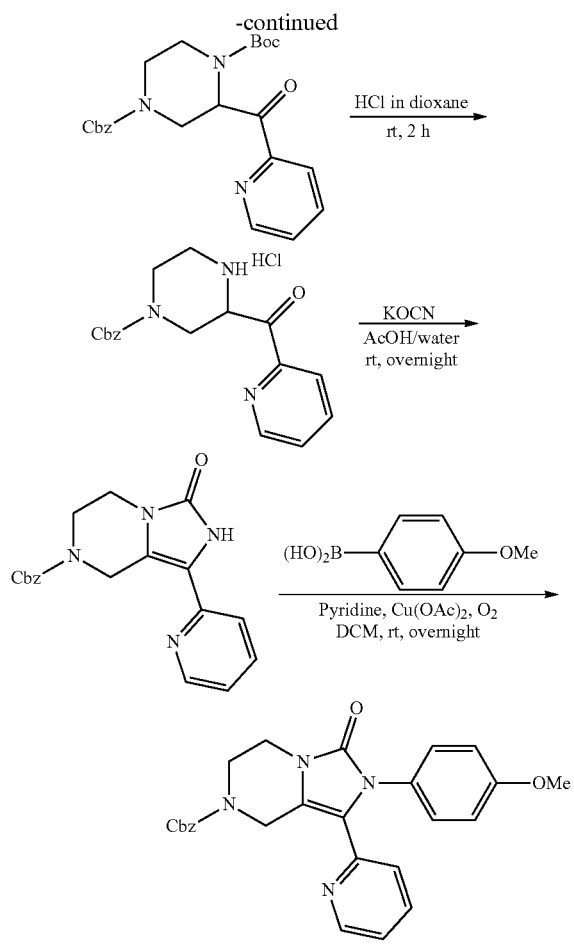

a) 4-benzyl 1-tert-butyl 2-[methoxy(methyl)carbamoyl]piperazine-1,4-dicarboxylate

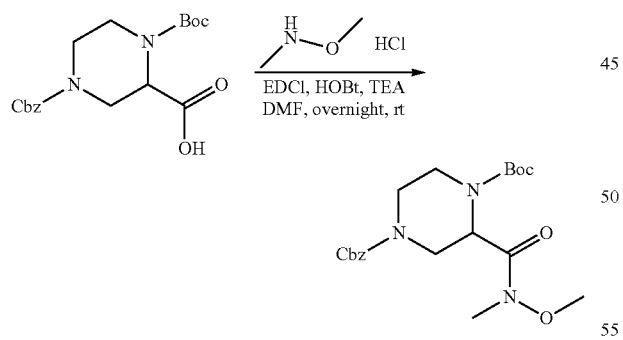

To a stirred mixture of 4-[(benzyloxy)carbonyl]-1-(tert-butoxycarbonyl)piperazine-2-carboxylic acid (3.10 g, 8.51 mmol, 1.00 eq.) and N,O-dimethylhydroxylamine (1.03 g, 17.0 mmol, 2.00 eq.) in N,N-dimethylformamide (31 mL) was added N'-(ethylkohlenstoffimidoyl)-N,N-dimethylpropan-1,3-diaminhydrochlorid (3.26 g, 17.0 mmol, 2.00 eq.), 1-hydroxy-7-azabenzotriazole (2.32 g, 17.0 mmol, 2.00 eq.) and triethylamine (7.09 mL, 70.1 mmol, 6.00 eq.) at rt. The mixture was stirred overnight at rt. The reaction was quenched with water (100 mL). The mixture was extracted with ethyl acetate (2×100 mL). The combined organic layers were washed with brine (2×30 mL), dried over anhydrous sodium sulfate, filtered and concentrated under reduced pressure. The residue was purified by silica gel column chromatography and eluted with petroleum ether:ethyl acetate (1:1) to afford 4-benzyl 1-tert-butyl 2-[methoxy(methyl)carbamoyl]piperazine-1,4-dicarboxylate (3.20 g, 92% yield) as a colorless oil. LCMS (ESI, m/z): 408 [M+H]$^+$.

b) 4-benzyl 1-tert-butyl 2-(pyridine-2-carbonyl)piperazine-1,4-dicarboxylate

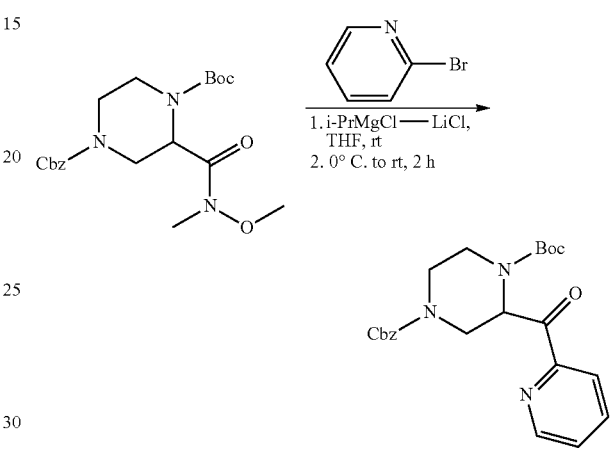

To a stirred solution of 2-bromopyridine (1.16 g, 7.36 mmol, 1.00 eq.) in tetrahydrofuran (6.00 mL) was added i-PrMgCl—LiCl (6.23 mL, 8.10 mmol, 1.10 eq., 1.30 M in THF) at rt under a N$_2$ atmosphere. The mixture was stirred overnight at rt under a N$_2$ atmosphere. To the mixture was added 4-benzyl 1-tert-butyl 2-[methoxy(methyl)carbamoyl]piperazine-1,4-dicarboxylate (3.10 g, 7.61 mmol, 1.03 eq.) dropwise at 0° C. The mixture was stirred for an additional overnight at rt. The reaction was quenched by with sat. ammonium chloride (10 mL, aq.) at 0° C. The mixture was extracted with ethyl acetate (2×50 mL). The combined organic layers were washed with brine (30 mL), dried over anhydrous sodium sulfate, filtered and concentrated under reduced pressure. The residue was purified by silica gel column chromatography and eluted with petroleum ether:ethyl acetate (1:1) to afford 4-benzyl 1-tert-butyl 2-(pyridine-2-carbonyl)piperazine-1,4-dicarboxylate (1.40 g, 45% yield) as a colorless oil. LCMS (ESI, m/z): 426 [M+H]$^+$.

c) benzyl 3-(pyridine-2-carbonyl)piperazine-1-carboxylate Hydrochloride Acid Salt

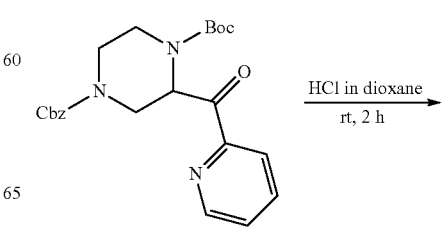

-continued

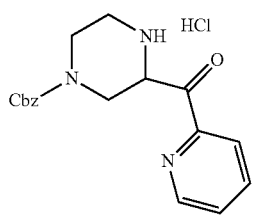

To a stirred solution of 4-benzyl 1-tert-butyl 2-(pyridine-2-carbonyl)piperazine-1,4-dicarboxylate (1.40 g, 3.29 mmol, 1.00 eq.) in 1.4-dioxane (12 mL) was added hydrogen chloride (4.11 mL, 4M in 1,4-dioxane) at rt under a N₂ atmosphere. The mixture was stirred for 2 h at rt. The precipitated solids were collected by filtration to afford benzyl 3-(pyridine-2-carbonyl)piperazine-1-carboxylate hydrochloride acid salt (1.10 g, crude) as a white solid. LCMS (ESI, m/z): 326 [M+H−HCl]⁺.

d) benzyl 3-oxo-1-(pyridin-2-yl)-2H,5H,6H,8H-imidazo [1,5-a]pyrazine-7-carboxylate

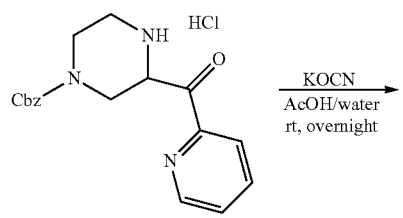

To a stirred solution of benzyl 3-(pyridine-2-carbonyl)piperazine-1-carboxylate hydrochloride acid salt (1.10 g, 3.04 mmol, 1.00 eq.) in acetic acid (4 mL) and water (16 mL) was added potassium cyanate (0.548 g, 6.76 mmol, 2.22 eq.) at rt. The mixture was stirred overnight at rt. The precipitated solids were collected by filtration, washed with water (10 mL) and dried to afford benzyl 3-oxo-1-(pyridin-2-yl)-2H,5H,6H,8H-imidazo[1,5-a]pyrazine-7-carboxylate (800 mg, 75% yield) as an off-white solid. LCMS (ESI, m/z): 351 [M+H]⁺.

e) benzyl 2-(4-methoxyphenyl)-3-oxo-1-(pyridin-2-yl)-5H,6H,8H-imidazo[1,5-a]pyrazine-7-carboxylate

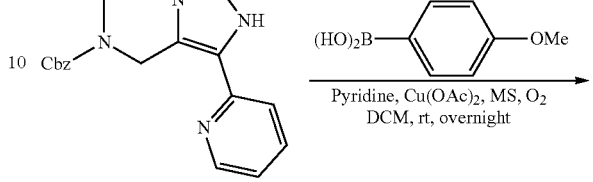

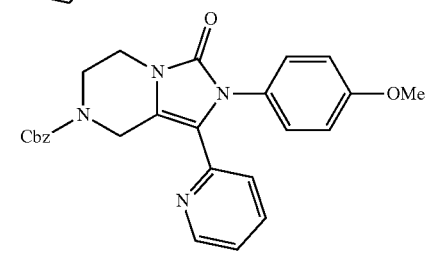

To a stirred mixture of benzyl 3-oxo-1-(pyridin-2-yl)-2H, 5H,6H,8H-imidazo[1,5-a]pyrazine-7-carboxylate (100 mg, 0.285 mmol, 1.00 eq.) and 4-methoxyphenylboronic acid (65.0 mg, 0.428 mmol, 1.50 eq.) in N,N-dimethylformamide (2.00 mL) was added pyridine (67.7 mg, 0.856 mmol, 3.00 eq.) and cupric acetate (103 mg, 0.285 mmol, 1.00 eq.) at rt under oxygen atmosphere. The mixture was stirred overnight at rt. The reaction was quenched with water (20 mL) at rt. The mixture was extracted with ethyl acetate (2×30 mL). The combined organic layers were washed with brine (2×20 mL), dried over anhydrous sodium sulfate filtered and concentrated under reduced pressure. The residue was purified by silica gel column chromatography and eluted with ethyl acetate to afford benzyl 2-(4-methoxyphenyl)-3-oxo-1-(pyridin-2-yl)-5H,6H,8H-imidazo[1,5-a]pyrazine-7-carboxylate as a white solid. LCMS (ESI, m/z): 457 [M+H]⁺.

Example 30

7-tert-butyl-1-ethyl-6-cyclopropyl-2-(4-methoxyphenyl)-3-oxo-5H,6H,8H-imidazo[1,5-a]pyrazine-1,7-dicarboxylate (Intermediate 11)

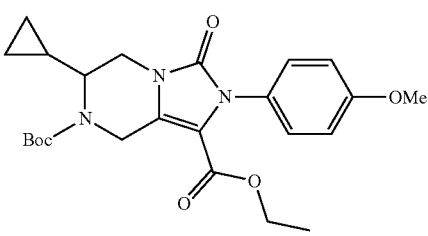

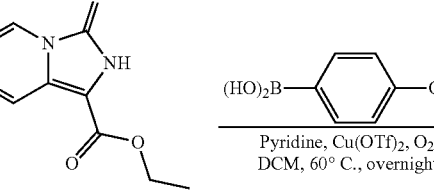

a) 7-tert-butyl 1-ethyl 2-(4-methoxyphenyl)-3-oxo-5H,6H,8H-imidazo[1,5-a]pyrazine-1,7-dicarboxylate

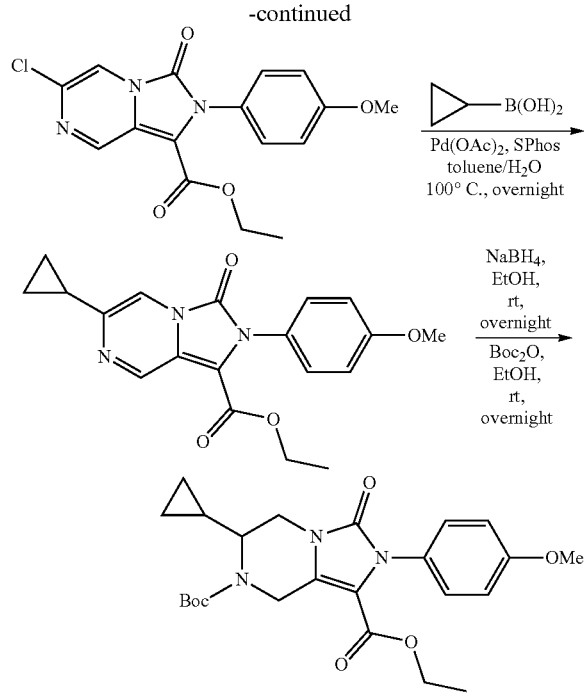

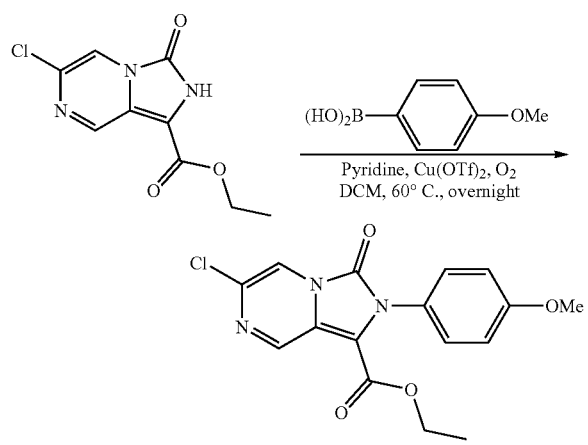

To a stirred mixture of ethyl 6-methyl-3-oxo-2H-imidazo[1,5-a]pyrazine-1-carboxylate (0.800 g, 3.62 mmol, 1.00 eq.) and 4-methoxyphenylboronic acid (0.659 g, 4.34 mmol, 1.20 eq.) in N,N-dimethylformamide (100 mL) was added pyridine (0.858 g, 10.8 mmol, 3.00 eq.), copper (II) trifluoromethanesulfonate (1.31 g, 3.62 mmol, 1.00 eq.) in portions at rt under oxygen atmosphere. The mixture was stirred overnight at 60° C. The reaction was quenched with water (50 mL). The solid was filtered off, and the filtrate was extracted with ethyl acetate (3×100 mL). The organic layers were combined, washed with water (3×100 mL), dried over anhydrous sodium sulfate, filtered and concentrated under reduced pressure. The residue was purified by silica gel column chromatography and eluted with petroleum ether: ethyl acetate (2:1) to afford 7-tert-butyl-1-ethyl-2-(4-methoxyphenyl)-3-oxo-5H,6H,8H-imidazo[1,5-a]pyrazine-1,7-dicarboxylate (800 mg, 69% yield) as a white solid. LCMS (ESI, m/z): 348 [M+H]⁺.

b) ethyl 6-cyclopropyl-2-(4-methoxyphenyl)-3-oxo-imidazo[1,5-a]pyrazine-1-carboxylate

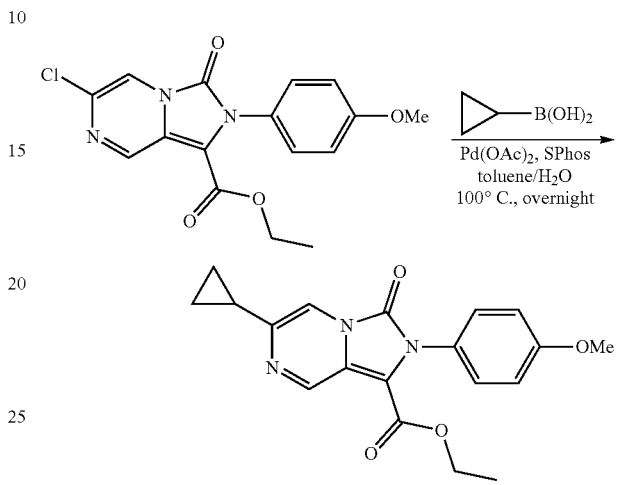

To a stirred solution of ethyl-6-chloro-2-(4-methoxyphenyl)-3-oxoimidazo[1,5-a]pyrazine-1-carboxylate (800 mg, 2.30 mmol, 1.00 eq.) and cyclopropylboronic acid (395 mg, 4.60 mmol, 2.00 eq.) in toluene (10 mL) and water (1 mL) was added palladium (II) acetate (51.0 mg, 0.230 mmol, 0.10 eq.), potassium phosphate (976 mg, 4.60 mmol, 2.00 eq.) and 2-dicyclohexylphosphino-2',6'-dimethoxy-1,1'-biphenyl (94.0 mg, 0.230 mmol, 0.10 eq.) under a N₂ atmosphere. The mixture was stirred overnight at 100° C. The reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by silica gel column chromatography and eluted with petroleum ether: ethyl acetate (2:1) to afford ethyl-6-cyclopropyl-2-(4-methoxyphenyl)-3-oxoimidazo[1,5-a]pyrazine-1-carboxylate (600 mg, 74% yield) as a yellow solid. LCMS (ESI, m/z): 354 [M+H]⁺.

c) 7-tert-butyl 1-ethyl 6-cyclopropyl-2-(4-methoxyphenyl)-3-oxo-5H,6H,8H-imidazo[1,5-a]pyrazine-1,7-dicarboxylate

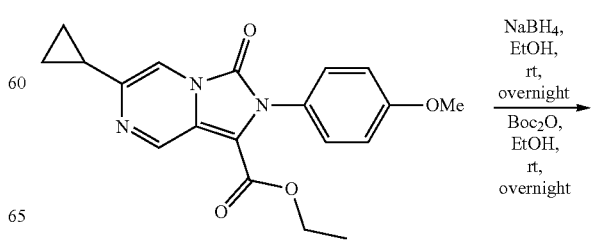

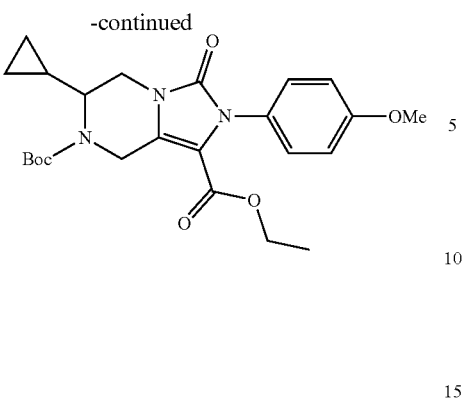

To a stirred mixture of ethyl 6-cyclopropyl-2-(4-methoxyphenyl)-3-oxoimidazo[1,5-a] pyrazine-1-carboxylate (0.500 g, 1.42 mmol, 1.00 eq.) in ethanol (10 mL) was added sodium borohydride (0.235 g, 6.23 mmol, 4.40 eq.) in portions at 0° C. The mixture was stirred overnight at rt. The reaction was quenched with water/ice (10 mL) at 0° C. Then the mixture was added sodium bicarbonate (0.587 g, 7.00 mmol, 5.00 eq.) and di-tert-butyl dicarbonate (1.50 g, 6.995 mmol, 5.00 eq.) in portions at rt. The mixture was stirred for an additional overnight at rt. The reaction was quenched with water (20 mL). The mixture was extracted with ethyl acetate (3×30 mL). The organic layers were combined, washed with water (3×30 mL), dried over anhydrous sodium sulfate, filtered and concentrated under reduced pressure. The residue was purified by Prep-TLC (petroleum ether: ethyl acetate, 1:1) to afford 7-tert-butyl-1-ethyl-6-cyclopropyl-2-(4-methoxyphenyl)-3-oxo-5H,6H,8H-imidazo[1,5-a] pyrazine-1,7-dicarboxylate (530 mg, 82% yield) as a colorless oil. LCMS (ESI, m/z): 458 [M+H]$^+$.

Example 31

Tert-butyl 1-(5-benzyloxazol-2-yl)-2-(4-methoxyphenyl)-3-oxo-2,5,6,8-tetrahydroimidazo[1,5-a]pyrazine-7 (3H)-carboxylate (Intermediate 12)

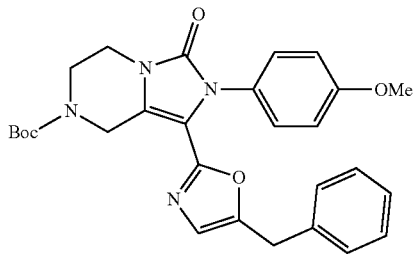 [SMILES: COc1ccc(-n2c(-c3ncc(Cc4ccccc4)o3)c3n(c2=O)CCN(C(=O)OC(C)(C)C)C3)cc1]

a) tert-butyl-2-(4-methoxyphenyl)-3-oxo-1-((2-oxo-3-phenylpropyl)carbamoyl)-2,5,6,8-tetrahydroimidazo[1,5-a]pyrazine-7(3H)-carboxylate

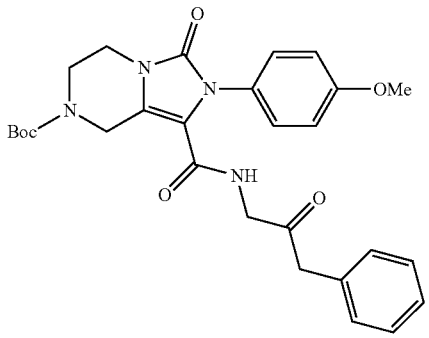 [SMILES: COc1ccc(-n2c(C(=O)NCC(=O)Cc3ccccc3)c3n(c2=O)CCN(C(=O)OC(C)(C)C)C3)cc1]

HATU (1.1 eq., 268.52 mg, 0.706 mmol), DIPEA (3.5 eq., 290.42 mg, 0.37 mL, 2.25 mmol) and 1-amino-3-phenylpropan-2-one hydrochloride (1.1 eq., 131.106 mg, 0.706 mmol) were added to a suspension of 7-(tert-butoxycarbonyl)-2-(4-methoxyphenyl)-3-oxo-2,3,5,6,7,8-hexahydroimidazo[1,5-a]pyrazine-1-carboxylic acid (1 eq., 250 mg, 0.64 mmol), synthesized following the pathway of Example 22, steps (a) and (b), in DCM (8 mL). The mixture was stirred at rt for 4 h and additional 1-amino-3-phenylpropan-2-one hydrochloride (0.5 eq., 59.59 mg, 0.32 mmol) was added. The mixture was further stirred at rt for 3 days. Sat. NaHCO$_3$(15 mL) was added, and the mixture was extracted with DCM (3×10 mL). The combined organic layers were dried over MgSO$_4$, filtered and evaporated to dryness. The crude mixture was purified by flash chromatography on silica gel (from 70 to 100% EtOAc in Cyclohexane) to give tert-butyl 2-(4-methoxyphenyl)-3-oxo-1-((2-oxo-3-phenylpropyl)carbamoyl)-2,5,6,8-tetrahydroimidazo[1,5-a]pyrazine-7(3H)-carboxylate (207 mg, 0.40 mmol, 62%) as a yellow gum. $^1$H NMR (DMSO, 400 MHz, 25° C.): 1.42 (s, 9H), 3.57-3.60 (m, 2H), 3.69-3.72 (m, 2H), 3.72 (s, 2H), 3.76 (s, 3H), 4.05 (d, J=5.6 Hz, 2H), 4.72 (br s, 2H), 6.95 (d, J=8.8 Hz, 2H), 7.14-7.32 (m, 7H), 7.46 (br s, 1H) ppm. LCMS: C$_{28}$H$_{32}$N$_4$O$_6$ [M+H]$^+$: 521.2.

b) tert-butyl 1-(5-benzyloxazol-2-yl)-2-(4-methoxyphenyl)-3-oxo-2,5,6,8-tetrahydroimidazo[1,5-a]pyrazine-7(3H)-carboxylate A mixture of tert-butyl 2-(4-methoxyphenyl)-3-oxo-1-((2-oxo-3-phenylpropyl)carbamoyl)-2,5,6,8-tetrahydroimidazo[1,5-a]pyrazine-7(3H)-carboxylate (1 eq., 270 mg, 0.39 mmol) and burgess reagent (3.67 eq., 345 mg, 1.45 mmol) in THF (2 mL) was heated at 80° C. under microwave irradiation for 30 min. The mixture was evaporated to dryness and purified by flash chromatography on silica gel (from 5 to 15% EtOAc in DCM) to give tert-butyl 2-(4-methoxyphenyl)-3-oxo-1-((2-oxo-3-phenylpropyl)carbamoyl)-2,5,6,8-tetrahydroimidazo[1,5-a]pyrazine-7(3H)-carboxylate (91 mg, 0.18 mmol, 46%) as a yellow solid. $^1$H NMR (DMSO, 400 MHz, 25° C.): 1.44 (s, 9H), 3.60-3.63 (m, 2H), 3.73-3.76 (m, 2H), 3.80 (s, 3H), 3.86 (s, 2H), 4.70 (s, 2H), 6.93-6.96 (m, 3H), 7.00-7.03 (m, 2H), 7.16 (d, J=8.8 Hz, 2H), 7.21-7.27 (m, 3H) ppm. LCMS: C$_{28}$H$_3$N$_4$O$_5$ [M+H]$^+$: 503.2.

Example 32

Tert-butyl-1-(5-benzyl-1,3,4-oxadiazol-2-yl)-2-(4-methoxyphenyl)-3-oxo-2,5,6,8-tetrahydroimidazo[1,5-a]pyrazine-7(3H)-carboxylate (Intermediate 13)

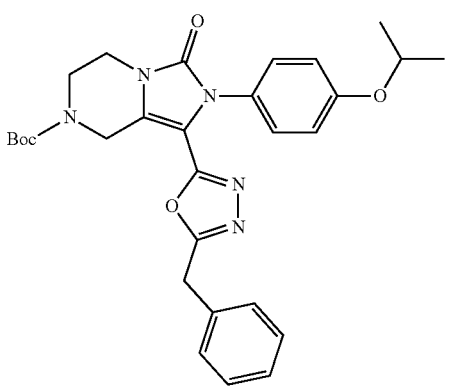 [SMILES: CC(C)Oc1ccc(-n2c(-c3nnc(Cc4ccccc4)o3)c3n(c2=O)CCN(C(=O)OC(C)(C)C)C3)cc1]

a) Tert-butyl 1-(hydrazinecarbonyl)-2-(4-isopropoxyphenyl)-3-oxo-2,5,6,8-tetrahydroimidazo[1,5-a]pyrazine-7(3H)-carboxylate

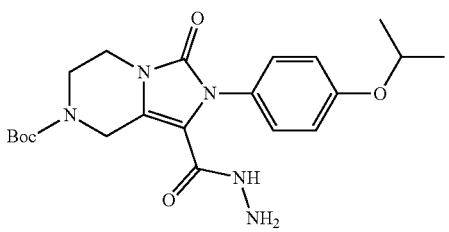 [SMILES: CC(C)Oc1ccc(-n2c(C(=O)NN)c3n(c2=O)CCN(C(=O)OC(C)(C)C)C3)cc1]

TCFH (2 eq., 201.63 mg, 0.72 mmol) was added to a suspension of the carboxylic acid (1 eq., 150 mg, 0.36 mmol), synthetized following the pathway described in Example 22, using 4-isopropyloxyphenylboronic acid instead of 4-methoxyphenylboronic acid in step (a), in MeCN (3.6 mL). N-methylimidazole (10 eq., 295.018 mg, 0.29 mL, 3.59 mmol) and hydrazine monohydrate (2 eq., 35.98 mg, 0.035 mL, 0.72 mmol) were then added. The mixture was stirred for 23 h at rt. The mixture was diluted with AcOEt (20 mL) and washed with sat. Na$_2$CO$_3$ (20 mL). The aqueous layer was extracted with AcOEt (3×20 mL). The combined organic layers were dried over magnesium sulfate, filtered and evaporated to dryness to afford crude title compound as a yellow oil, which was directly used in the next step. LCMS: C$_2$H$_{29}$N$_5$O$_5$ [M+H]$^+$: 432.

b) Tert-butyl-2-(4-isopropoxyphenyl)-3-oxo-1-(2-(2-phenylacetyl)hydrazine-1-carbonyl)-2,5,6,8-tetrahydroimidazo[1,5-a]pyrazine-7(3H)-carboxylate

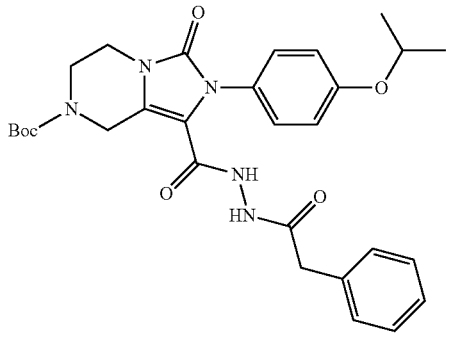 [SMILES: CC(C)Oc1ccc(-n2c(C(=O)NNC(=O)Cc3ccccc3)c3n(c2=O)CCN(C(=O)OC(C)(C)C)C3)cc1]

TCFH (2 eq., 716.58 mg, 2.55 mmol) was added to a solution of phenylacetic acid (1.2 eq., 208.63 mg, 0.19 mL, 1.53 mmol) in MeCN (16 mL). N-methylimidazole (10 eq., 1048.46 mg, 1.018 mL, 12.77 mmol) and tert-butyl 1-(hydrazinecarbonyl)-2-(4-isopropoxyphenyl)-3-oxo-2,5,6,8-tetrahydroimidazo[1,5-a]pyrazine-7(3H)-carboxylate (1 eq., 551 mg, 1.28 mmol) were added. The mixture was stirred for 2.5 h at rt. The mixture was diluted with dichloromethane (40 mL) and washed with 1M citric acid aq. (40 mL). The aqueous layer was extracted with dichloromethane (3×40 mL). The combined organic layers were dried over magnesium sulfate, filtered and evaporated to dryness. The crude product was purified by flash chromatography on silica gel (from 0% to 10% MeOH in DCM) to afford a solid, which was further purified by reverse phase chromatography (0.1% TFA in water/MeCN from 5% to 95% acetonitrile) to give title compound (140 mg, 0.26 mmol, 20%) as a yellow oil. $^1$H-NMR (DMSO, 400 MHz, 25° C.): 1.26 (d, J=6.1 Hz, 6H), 1.42 (s, 9H), 3.45 (s, 2H), 3.54-3.63 (m, 2H), 3.66-3.74 (m, 2H), 4.60 (hept, J=6.1 Hz, 1H), 4.74 (s, 2H), 6.91 (d, J=8.7 Hz, 2H), 7.13 (d, J=8.7 Hz, 2H), 7.18-7.34 (m, 5H), 9.61 (s, 1H), 10.15 (s, 1H) ppm. LCMS: C$_{29}$H$_{35}$N$_5$O$_6$ [M+H]$^+$: 550.

c) Tert-butyl-1-(5-benzyl-1,3,4-oxadiazol-2-yl)-2-(4-methoxyphenyl)-3-oxo-2,5,6,8-tetrahydroimidazo[1,5-a]pyrazine-7(3H)-carboxylate

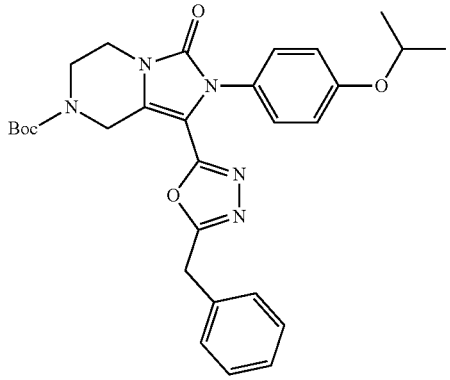 [SMILES: CC(C)Oc1ccc(-n2c(-c3nnc(Cc4ccccc4)o3)c3n(c2=O)CCN(C(=O)OC(C)(C)C)C3)cc1]

Burgess reagent (3.67 eq., 55.74 mg, 0.23 mmol) was added to a solution of tert-butyl-2-(4-isopropoxyphenyl)-3-oxo-1-(2-(2-phenylacetyl)hydrazine-1-carbonyl)-2,5,6,8-tetrahydroimidazo[1,5-a]pyrazine-7(3H)-carboxylate (1 eq., 35 mg, 0.064 mmol) in THF (3.5 mL). The mixture was heated for 30 min at 80° C. under microwave irradiation, and then evaporated to dryness. The crude product was purified by flash chromatography on silica gel (from 0% to 10% MeOH in DCM) to afford the title compound (25 mg, 0.048 mmol, 75%) as a white solid. $^1$H-NMR (DMSO, 400 MHz, 25° C.): 1.30 (d, J=5.9 Hz, 6H), 1.44 (s, 9H), 3.60-3.69 (m, 2H), 3.71-3.82 (m, 2H), 4.11 (s, 2H), 4.64 (hept, J=5.9 Hz, 1H), 4.71 (s, 2H), 6.92 (d, J=8.4 Hz, 2H), 7.05-7.13 (m, 2H), 7.16 (d, J=8.4 Hz, 2H), 7.20-7.34 (m, 3H) ppm. LCMS: $C_{29}H_{33}N_5O_5$ [M+H]$^+$: 532.

Example 33

1-(5-benzylthiazol-2-yl)-7-(4-bromo-3-chlorobenzoyl)-2-(4-isopropoxyphenyl)-5,6,7,8-tetrahydroimidazo[1,5-a]pyrazin-3(2H)-one (325)

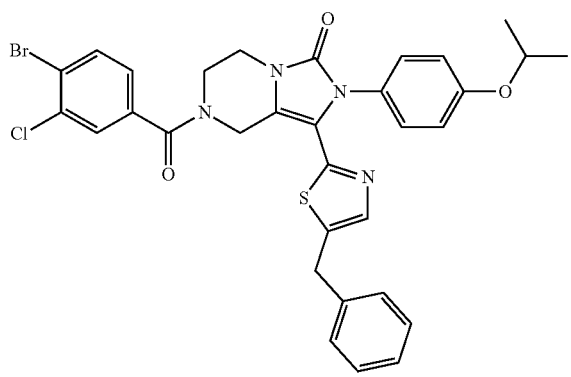 [SMILES: CC(C)Oc1ccc(-n2c(-c3ncc(Cc4ccccc4)s3)c3n(c2=O)CCN(C(=O)c2ccc(Br)c(Cl)c2)C3)cc1]

Phosphorus pentasulphide (1 eq., 13.3 mg, 0.060 mmol) was added to a suspension of tert-butyl 2-(4-isopropoxyphenyl)-3-oxo-1-((2-oxo-3-phenylpropyl)carbamoyl)-2,5,6,8-tetrahydroimidazo[1,5-a]pyrazine-7(3H)-carboxylate (1 eq., 33 mg, 0.0601 mmol), synthetized as described in example 31 (a), in CHCl$_3$ (2 mL). The mixture was stirred for 16 h at 65° C. The mixture was evaporated to dryness to afford 1-(5-benzylthiazol-2-yl)-2-(4-isopropoxyphenyl)-5,6,7,8-tetrahydroimidazo[1,5-a]pyrazin-3(2H)-one as a crude product, which was directly used as such in the next step.

HATU (1.1 eq., 39.3 mg, 0.10 mmol) was added to a suspension of 4-bromo-3-chlorobenzoic acid (1.2 eq., 26.5 mg, 0.11 mmol) in DCM (1.4 mL). A solution of the crude product from the previous step in DCM (1.4 mL) was added, followed by the addition of DIPEA (2.5 eq., 0.037 mL, 0.24 mmol). The mixture was stirred for 4 h at rt. Sat. Na$_2$CO$_3$ (20 mL) was added, and the aqueous layer was extracted with AcOEt (3×20 mL). The combined organic layers were dried with magnesium sulfate, filtered and concentrated to dryness. The crude product was purified by flash chromatography on silica gel (from 0% to 10% MeOH in DCM) to afford a yellow solid which was triturated in EtOH and Et$_2$O to the afford compound 325 (4.3 mg, 0.007 mmol, 7%) as a white solid. $^1$H-NMR (DMSO, 600 MHz, 80° C.): 1.31 (d, J=6.0 Hz, 6H), 3.72 (t, J=5.5 Hz, 2H), 3.86 (br. s., 2H), 4.04 (s, 2H), 4.63 (hept., J=6.0 Hz, 1H), 4.94 (s, 2H), 6.97 (d, J=8.6 Hz, 2H), 7.13 (d, J=7.5 Hz, 2H), 7.17-7.22 (m, 3H), 7.24-7.28 (m, 2H), 7.37-7.42 (m, 1H), 7.49 (s, 1H), 7.73 (s, 1H), 7.84 (d, J=8.2 Hz, 1H) ppm. LCMS: $C_{32}H_{28}ClBrN_4O_3S$ [M+H]$^+$: 663/665/667.

Example 34

Tert-butyl-1-((2-fluoro-4-(oxetan-3-yloxy)benzyl)carbamoyl)-3-oxo-2-(4-(2,2,2-trifluoroethoxy)phenyl)-2,5,6,8-tetrahydroimidazo[1,5-a]pyrazine-7(3H)-carboxylate (Intermediate 14)

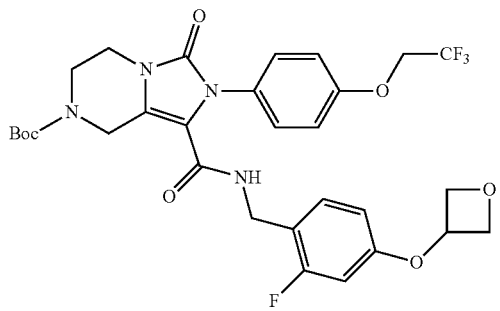 [SMILES: CC(C)(C)OC(=O)N1CCn2c(c(C(=O)NCc3ccc(OC4COC4)cc3F)n(-c3ccc(OCC(F)(F)F)cc3)c2=O)C1]

a) 4-(aminomethyl)-3-fluorophenol

Raney nickel (0.1 eq., 0.43 g, 0.048 mL, 3.65 mmol) was added to a solution of 2-fluoro-4-hydroxybenzonitrile (1 eq., 5 g, 36.47 mmol) in ammonia 7N in MeOH (200 mL). The mixture was purged with H$_2$ and stirred at rt for 5 h. The mixture was filtered through a pad of celite and evaporated to dryness to give 4-(aminomethyl)-3-fluorophenol (5.55 g, quant.) as a green solid, which was used without further purification. $^1$H-NMR (DMSO, 300 MHz, 25° C.): 3.74 (s, 2H), 6.46-6.56 (m, 2H), 7.12-7.17 (m, 1H).

b) Tert-butyl 1-((2-fluoro-4-hydroxybenzyl)carbamoyl)-3-oxo-2-(4-(2,2,2-trifluoroethoxy)phenyl)-2,5,6,8-tetrahydroimidazo[1,5-a]pyrazine-7(3H)-carboxylate

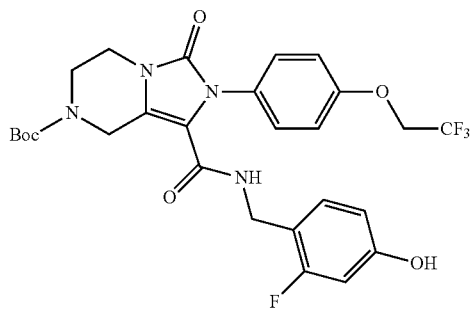 [SMILES: CC(C)(C)OC(=O)N1CCn2c(c(C(=O)NCc3ccc(O)cc3F)n(-c3ccc(OCC(F)(F)F)cc3)c2=O)C1]

The title compound was obtained using a general coupling procedure (870 mg, 1.5 mmol, 69%, colorless oil). ¹H-NMR (DMSO, 300 MHz, 25° C.): 1.43 (s, 9H), 3.54-3.63 (m, 2H), 3.64-3.75 (m, 2H), 4.18 (d, J=5.5 Hz, 2H), 4.63 (s, 2H), 4.77 (q, J=8.9 Hz, 2H), 6.44-6.55 (m, 2H), 6.95 (t, J=9.0 Hz, 1H), 7.07 (d, J=8.9 Hz, 2H), 7.18 (d, J=8.9 Hz, 2H), 7.72 (t, J=5.5 Hz, 1H), 9.75 (s, 1H) ppm. LCMS: $C_{27}H_{28}F_4N_4O_6$ [M+H]⁺: 581.

c) Oxetan-3-yl 4-methylbenzenesulfonate

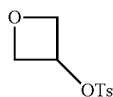

Tosyl chloride (2 eq., 2.57 g, 13.5 mmol) was added to a solution of oxetan-3-ol (1 eq., 0.5 g, 6.75 mmol) and Et₃N (4 eq., 3.75 mL, 27 mmol) in DCM (20 mL). The mixture was stirred at rt for 3 h. Sat. NaHCO₃ (50 mL) was added, and the aqueous layer was extracted with DCM (3×30 mL). The combined organic layers were dried with magnesium sulfate, filtered and evaporated to dryness. The crude product was purified by flash chromatography on silica gel (from 0% to 30% AcOEt in Cyclohexane) to afford oxetan-3-yl 4-methylbenzenesulfonate (1.21 g, 5.30 mmol, 79%) as a white solid. ¹H-NMR (CDCl₃, 400 MHz, 25° C.): 2.44 (s, 3H), 4.61-4.76 (m, 4H), 5.25-5.32 (m, 1H), 7.35 (d, J=8.2 Hz, 2H), 7.76 (d, J=8.2 Hz, 2H) ppm. LCMS: $C_{10}H_{12}O_4S$ [M+H]⁺: 229.

d) Tert-butyl-1-((2-fluoro-4-(oxetan-3-yloxy)benzyl)carbamoyl)-3-oxo-2-(4-(2,2,2-trifluoroethoxy)phenyl)-2,5,6,8-tetrahydroimidazo[1,5-a]pyrazine-7(3H)-carboxylate

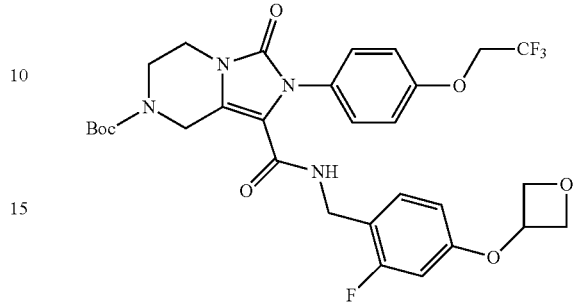

Oxetan-3-yl 4-methylbenzenesulfonate (5 eq., 589.78 mg, 2.58 mmol) was added to a solution of tert-butyl 1-((2-fluoro-4-hydroxybenzyl)carbamoyl)-3-oxo-2-(4-(2,2,2-trifluoroethoxy)phenyl)-2,5,6,8-tetrahydroimidazo[1,5-a]pyrazine-7(3H)-carboxylate (1 eq., 300 mg, 0.52 mmol) and K₂CO₃ (10 eq., 714.19 mg, 5.17 mmol) in DMF (10 mL) at rt. The mixture was heated at 50° C. for 4 days. Water (30 mL) was added, and the aqueous layer was extracted with AcOEt (3×30 mL). The combined organic layers were washed with brine (5×25 mL), dried with magnesium sulfate, filtered and concentrated to dryness. The crude product was purified by flash chromatography on silica gel (from 0% to 10% MeOH in DCM). The resulting solid was repurified by flash chromatography on silica gel (from 30% to 100% AcOEt in Cyclohexane) to afford the title compound (45 mg, 0.071 mmol, 14%) as a yellow oil. ¹H-NMR (DMSO, 400 MHz, 25° C.): 1.42 (s, 9H), 3.55-3.63 (m, 2H), 3.64-3.75 (m, 2H), 4.22 (d, J=5.5 Hz, 2H), 4.47-4.55 (m, 2H), 4.63 (s, 2H), 4.78 (q, J=8.8 Hz, 2H), 4.88-4.95 (m, 2H), 5.23-5.31 (m, 1H), 6.53-6.68 (m, 2H), 7.01-7.11 (m, 3H), 7.14-7.21 (m, 2H), 7.82-7.89 (m, 1H) ppm. LCMS: $C_3H_{32}F_4N_4O_7$ [M+H]⁺: 637.

Example 35

Compounds 16-483

Compounds 16-483 provided in Table A were synthetized using the intermediates and/or protocols of Examples 1-34, using methods and conditions known to those skilled in the art.

TABLE A

| Compound # | Structure | Name | NMR |
|---|---|---|---|
| 16 | 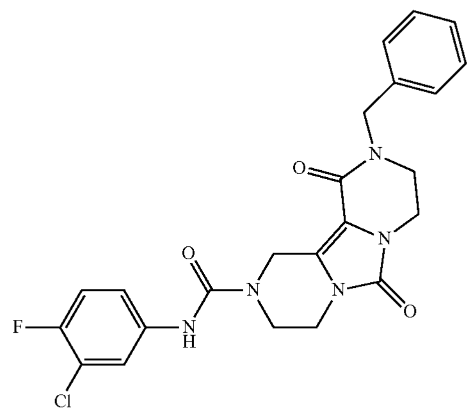 [SMILES: O=C(Nc1ccc(F)c(Cl)c1)N1CCn2c(c3n(c2=O)CCN(Cc2ccccc2)C3=O)C1] | 12-benzyl-N-(3-chloro-4-fluoro-phenyl)-8,13-dioxo-4,7,9,12-tetrazatricyclo[7.4.0.0^2,7]tridec-1-ene-4-carboxamide | 1H NMR (300 MHz, Methanol-d4) δ 7.60 (m, 1H), 7.37-7.20 (m, 6H), 7.25-7.09 (m, 1H), 5.33 (s, 2H), 4.33 (t, J = 9.4 Hz, 2H), 3.99-3.87 (m, 4H), 3.79 (t, J = 5.5 Hz, 2H), 3.32 (s, 2H). |
| 17 | 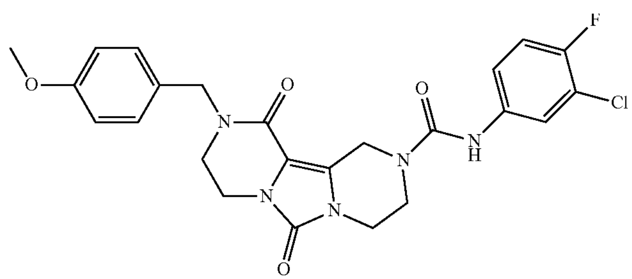 [SMILES: COc1ccc(CN2CCn3c(c4n(c3=O)CCN(C(=O)Nc3ccc(F)c(Cl)c3)C4)C2=O)cc1] | N-(3-chloro-4-fluoro-phenyl)-12-[(4-methoxyphenyl)methyl]-8,13-dioxo-4,7,9,12-tetrazatricyclo[7.4.0.0^2,7]tridec-1-ene-4-carboxamide | 1H NMR (400 MHz, DMSO-d6) δ 9.00 (s, 1H), 7.71 (dd, J = 6.8, 2.6 Hz, 1H), 7.43-7.37 (m, 1H), 7.30 (t, J = 9.1 Hz, 1H), 7.19 (d, J = 8.6 Hz, 2H), 6.84 (d, J = 6.5 Hz, 2H), 5.16 (s, 2H), 4.74 (s, 2H), 4.29 (t, J = 9.3 Hz, 2H), 3.89 (t, J = 9.3 Hz, 2H), 3.82 (t, J = 5.7 Hz, 2H), 3.70 (s, 3H), 3.63 (t, J = 5.4 Hz, 2H). |
| 18 | 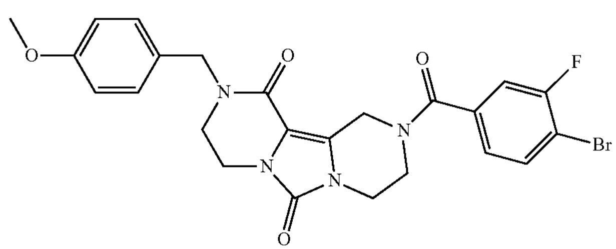 [SMILES: COc1ccc(CN2CCn3c(c4n(c3=O)CCN(C(=O)c3ccc(Br)c(F)c3)C4)C2=O)cc1] | 12-(4-bromo-3-fluoro-benzoyl)-4-[(4-methoxyphenyl)methyl]-4,7,9,12-tetrazatricyclo[7.4.0.0^2,7]tridec-1-ene-3,8-dione | 1H NMR (300 MHz, Methanol-d4) δ 7.78 (dd, J = 8.2, 6.9 Hz, 1H), 7.43 (dd, J = 8.9, 1.9 Hz, 1H), 7.32-7.14 (m, 3H), 6.89-6.79 (m, 2H), 5.26 (s, 2H), 4.91 (s, 2H), 4.32 (s, 2H), 3.72-3.95 (s, 9H). |

TABLE A-continued

| Compound # | Structure | Name | NMR |
|---|---|---|---|
| 19 | 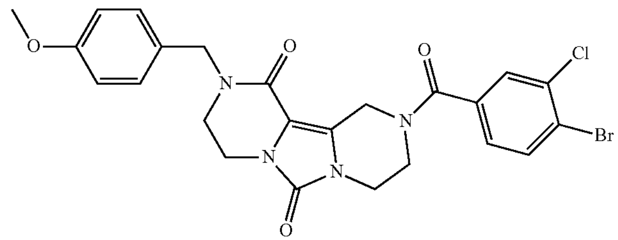 [SMILES: COc1ccc(CN2CCn3c(c4n(c3=O)CCN(C(=O)c3ccc(Br)c(Cl)c3)C4)C2=O)cc1] | 12-(4-bromo-3-chloro-benzoyl)-4-[(4-methoxyphenyl)methyl]-4,7,9,12-tetrazatricyclo[7.4.0.0^2,7]tridec-1-ene-3,8-dione | 1H NMR (300 MHz, Methanol-d4) δ 7.84 (d, J = 8.2 Hz, 1H), 7.71 (d, J = 2.0 Hz, 1H), 7.36 (dd, J = 8.2, 2.0 Hz, 1H), 7.24 (d, J = 8.6 Hz, 2H), 6.83 (d, J = 8.7 Hz, 2H), 5.26 (s, 2H), 4.98 (s, 2H), 4.39-4.28 (br, 2H), 4.08-3.73 (m, 9H). |
| 20 | 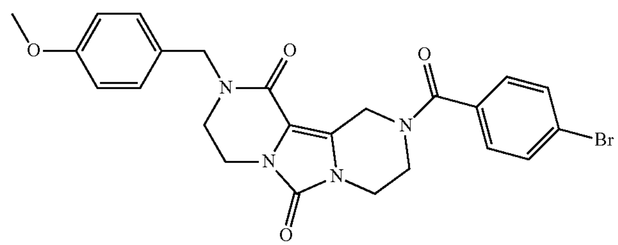 [SMILES: COc1ccc(CN2CCn3c(c4n(c3=O)CCN(C(=O)c3ccc(Br)cc3)C4)C2=O)cc1] | 12-(4-bromobenzoyl)-4-[(4-methoxyphenyl)methyl]-4,7,9,12-tetrazatricyclo[7.4.0.0^2,7]tridec-1-ene-3,8-dione | 1H NMR (300 MHz, Methanol-d4) δ 7.81-7.60 (m, 2H), 7.54-7.40 (m, 2H), 7.23 (d, J = 8.6 Hz, 2H), 6.95-6.73 (m, 2H), 5.26 (s, 2H), 4.93 (br, 2H) 4.31 (s, 2H), 3.94-3.74 (m, 9H). |
| 21 | 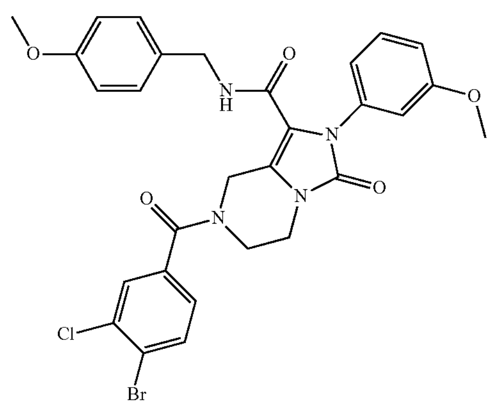 | 7-(4-bromo-3-chloro-benzoyl)-2-(3-methoxyphenyl)-N-[(4-methoxyphenyl)methyl]-3-oxo-6,8-dihydro-5H-imidazo[1,5-a]pyrazine-1-carboxamide | 1H NMR (400 MHz, DMSO-d6) δ 8.04 (br, 1H), 7.89 (d, J = 8.4 Hz, 1H), 7.79 (s, 1H), 7.42-7.40 (m, 1H), 7.32 (t, J = 8 Hz, 1H), 7.06 (s, 1H), 6.92 (t, J = 4.8 Hz, 1H), 6.89-6.78 (m, 4H), 4.88 (br, 2H), 4.23 (br, 2H), 4.11 (br, 1H), 3.66-3.73 (m, 9H). |

TABLE A-continued

| Compound # | Structure | Name | NMR |
|---|---|---|---|
| 22 | 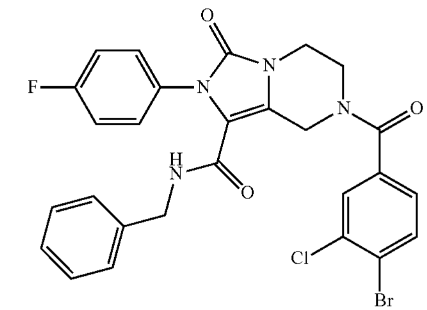 [SMILES: O=C(NCc1ccccc1)c1c2n(c(=O)n1-c1ccc(F)cc1)CCN(C(=O)c1ccc(Br)c(Cl)c1)C2] | N-benzyl-7-(4-bromo-3-chloro-benzoyl)-2-(4-fluorophenyl)-3-oxo-6,8-dihydro-5H-imidazo[1,5-a]pyrazine-1-carboxamide | 1H NMR (300 MHz, Chloroform-d) δ 7.72 (d, J = 8.2 Hz, 1H), 7.61 (s, 1H), 7.35-7.27 (m, 3H), 7.24 (dd, J = 4.7, 2.7 Hz, 3H), 7.07 (t, J = 8.4 Hz, 2H), 6.92 (s, 2H), 6.05 (s, 3H), 4.27 (d, J = 5.5 Hz, 2H), 4.02 (s, 2H), 3.83 (s, 2H). |
| 23 | 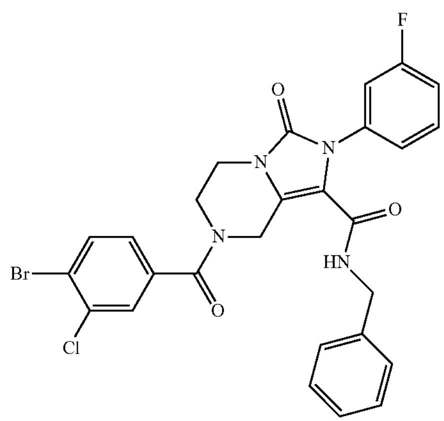 [SMILES: O=C(NCc1ccccc1)c1c2n(c(=O)n1-c1cccc(F)c1)CCN(C(=O)c1ccc(Br)c(Cl)c1)C2] | N-benzyl-7-(4-bromo-3-chloro-benzoyl)-2-(3-fluorophenyl)-3-oxo-6,8-dihydro-5H-imidazo[1,5-a]pyrazine-1-carboxamide | 1H NMR (400 MHz, Chloroform-d) δ 7.75 (d, J = 8.2 Hz, 1H), 7.64 (d, J = 2.0 Hz, 1H), 7.37 (td, J = 8.0, 5.9 Hz, 1H), 7.28-7.24 (m, 3H), 7.15-7.06 (m, 3H), 6.97 (s, 2H), 5.07 (s, 3H), 4.32 (s, 2H), 4.06 (s, 2H), 3.86 (s, 2H). |
| 24 | 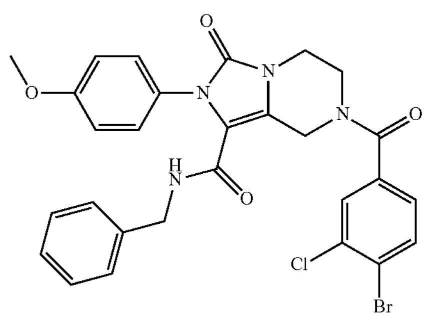 [SMILES: COc1ccc(-n2c(C(=O)NCc3ccccc3)c3n(c2=O)CCN(C(=O)c2ccc(Br)c(Cl)c2)C3)cc1] | N-benzyl-7-(4-bromo-3-chloro-benzoyl)-2-(4-methoxyphenyl)-3-oxo-6,8-dihydro-5H-imidazo[1,5-a]pyrazine-1-carboxamide | 1H NMR (300 MHz, Chloroform-d) δ 7.73 (d, J = 8.2 Hz, 1H), 7.63 (d, J = 1.9 Hz, 1H), 7.26-7.20 (m, 6H), 6.95-6.84 (m, 4H), 5.11 (d, J = 28.6 Hz, 3H), 4.26 (d, J = 5.3 Hz, 2H), 4.04 (s, 2H), 3.80-3.75 (m, 5H). |

TABLE A-continued

| Compound # | Structure | Name | NMR |
|---|---|---|---|
| 25 | 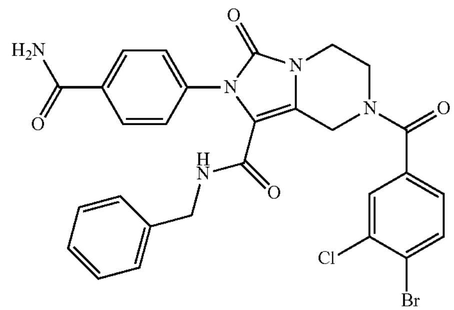 [SMILES: NC(=O)c1ccc(-n2c(C(=O)NCc3ccccc3)c3n(c2=O)CCN(C(=O)c2ccc(Br)c(Cl)c2)C3)cc1] | N-benzyl-7-(4-bromo-3-chlorobenzoyl)-2-(4-carbamoylphenyl)-3-oxo-6,8-dihydro-5H-imidazo[1,5-a]pyrazine-1-carboxamide | 1H NMR (300 MHz, Methanol-d4) δ 7.93 (d, J = 8.7 Hz, 2H), 7.88-7.77 (m, 1H), 7.72 (s, 1H), 7.41-7.34 (m, 3H), 7.24 (s, 3H), 7.11-7.00 (m, 2H), 4.97-4.89 (m, 2H), 4.33 (s, 2H), 3.92-3.81 (m, 2H), 3.26 (s, 1H), 3.09-2.99 (m, 1H). |
| 26 | 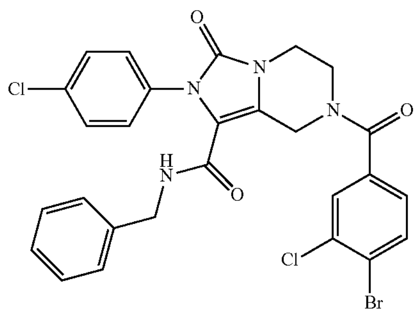 [SMILES: O=C(NCc1ccccc1)c1c2n(c(=O)n1-c1ccc(Cl)cc1)CCN(C(=O)c1ccc(Br)c(Cl)c1)C2] | N-benzyl-7-(4-bromo-3-chlorobenzoyl)-2-(4-chlorophenyl)-3-oxo-6,8-dihydro-5H-imidazo[1,5-a]pyrazine-1-carboxamide | 1H NMR (400 MHz, DMSO-d6) δ 8.32 (s, 1H), 7.88 (d, J = 8.2 Hz, 1H), 7.80 (s, 1H), 7.52-7.44 (m, 3H), 7.37-6.87 (m, 7H), 5.11-4.58 (m, 2H), 4.48-4.08 (m, 2H), 3.98 (s, 1H), 3.33 (s, 3H). |
| 27 | 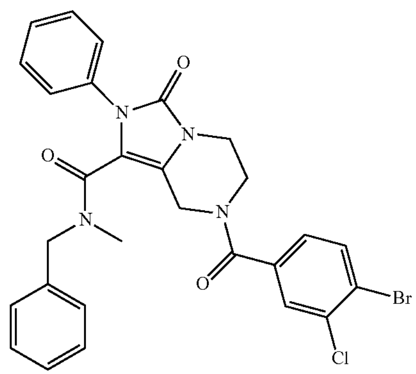 [SMILES: CN(Cc1ccccc1)C(=O)c1c2n(c(=O)n1-c1ccccc1)CCN(C(=O)c1ccc(Br)c(Cl)c1)C2] | N-benzyl-7-(4-bromo-3-chlorobenzoyl)-N-methyl-3-oxo-2-phenyl-6,8-dihydro-5H-imidazo[1,5-a]pyrazine-1-carboxamide | 1H NMR (300 MHz, Chloroform-d) δ 7.89-7.73 (m, 1H), 7.62-7.61 (m, 1H), 7.49-7.30 (m, 5H), 7.28-7.15 (m, 4H), 6.93 (s, 2H), 4.79 (s, 2H), 4.37 (br, 2H), 4.18-3.50 (m, 4H), 2.61 (s, 3H). |

TABLE A-continued

| Compound # | Structure | Name | NMR |
|---|---|---|---|
| 28 | 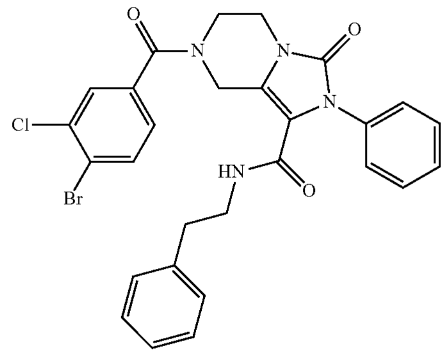 [SMILES: O=C(NCCc1ccccc1)c1c2n(c(=O)n1-c1ccccc1)CCN(C(=O)c1ccc(Br)c(Cl)c1)C2] | 7-(4-bromo-3-chloro-benzoyl)-3-oxo-2-phenyl-N-(2-phenylethyl)-6,8-dihydro-5H-imidazo[1,5-a]pyrazine-1-carboxamide | 1H NMR (300 MHz, Chloroform-d) δ 7.89-7.73 (m, 1H), 7.62-7.61 (m, 1H), 7.49-7.38 (m, 3H), 7.30-7.19 (m, 6H), 6.95-6.59 (s, 2H), 5.10 (s, 2H), 4.92-4.75 (m, 1H), 4.18 (s, 2H), 3.85 (s, 2H), 3.59-3.09 (m, 2H), 2.74-2.34 (m, 2H). |
| 29 | 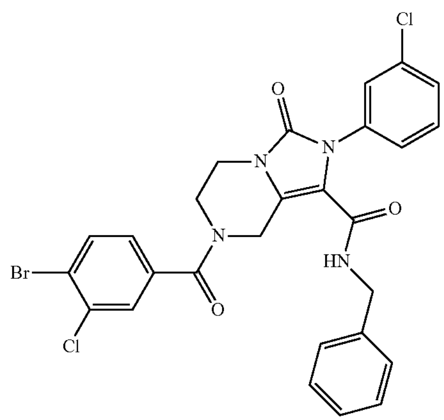 [SMILES: O=C(NCc1ccccc1)c1c2n(c(=O)n1-c1cccc(Cl)c1)CCN(C(=O)c1ccc(Br)c(Cl)c1)C2] | N-benzyl-7-(4-bromo-3-chloro-benzoyl)-2-(3-chlorophenyl)-3-oxo-6,8-dihydro-5H-imidazo[1,5-a]pyrazine-1-carboxamide | 1H NMR (400 MHz, Chloroform-d) δ 7.74 (d, J = 8.2 Hz, 1H), 7.52 (d, J = 1.9 Hz, 1H), 7.40-7.29 (m, 3H), 7.26-7.15 (m, 5H), 6.97 (s, 2H), 5.07 (s, 3H), 4.32 (s, 2H), 4.05 (s, 2H), 3.84 (s, 2H). |

TABLE A-continued

| Compound # | Structure | Name | NMR |
|---|---|---|---|
| 30 | 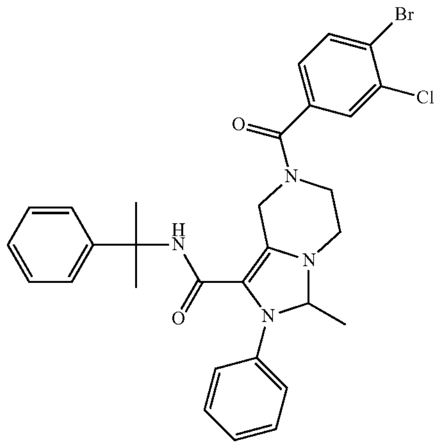 [SMILES: CC1N2CCN(C(=O)c3ccc(Br)c(Cl)c3)CC2=C(C(=O)NC(C)(C)c2ccccc2)N1c1ccccc1] | 7-(4-bromo-3-chloro-benzoyl)-N-(1-methyl-1-phenyl-ethyl)-3-oxo-2-phenyl-6,8-dihydro-5H-imidazo[1,5-a]pyrazine-1-carboxamide | 1H NMR (300 MHz, DMSO-d6) δ 7.91 (d, J = 8.2 Hz, 1H), 7.83 (s, 1H), 7.62 (s, 1H), 7.50-7.40 (m, 3H), 7.27 (s, 5H), 7.16 (s, 2H), 6.05 (s, 1H), 4.84 (d, J = 55.7 Hz, 2H), 4.01 (s, 1H), 3.70 (s, 3H), 1.39 (d, J = 45.3 Hz, 6H). |
| 31 | 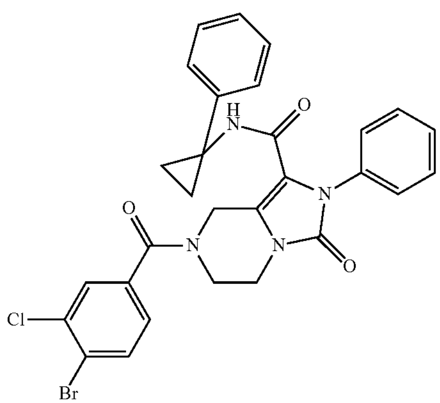 [SMILES: O=C(NC1(c2ccccc2)CC1)c1c2n(c(=O)n1-c1ccccc1)CCN(C(=O)c1ccc(Br)c(Cl)c1)C2] | 7-(4-bromo-3-chloro-benzoyl)-N-(1-phenylcyclopropyl)-3-oxo-2-phenyl-6,8-dihydro-5H-imidazo[1,5-a]pyrazine-1-carboxamide | 1H NMR (300 MHz, DMSO-d6) δ 8.42 (s, 1H), 7.90 (d, J = 8.2 Hz, 1H), 7.82 (d, J = 1.9 Hz, 1H), 7.44 (td, J = 6.7, 6.2, 3.1 Hz, 3H), 7.38-6.86 (m, 8H), 4.80 (m, 2H), 3.99 (s, 1H), 3.70 (s, 3H), 1.19-0.68 (m, 4H). |

TABLE A-continued

| Compound # | Structure | Name | NMR |
|---|---|---|---|
| 32 | 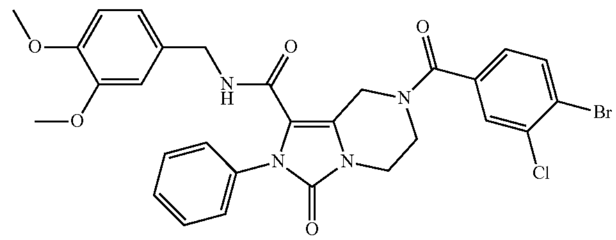 [SMILES: COc1ccc(CNC(=O)c2c3n(c(=O)n2-c2ccccc2)CCN(C(=O)c2ccc(Br)c(Cl)c2)C3)cc1OC] | 7-(4-bromo-3-chloro-benzoyl)-N-[(3,4-dimethoxyphenyl)methyl]-3-oxo-2-phenyl-6,8-dihydro-5H-imidazo[1,5-a]pyrazine-1-carboxamide | 1H NMR (400 MHz, DMSO-d6) δ 8.20 (s, 1H), 7.89 (d, J = 8.2 Hz, 1H), 7.80 (d, J = 1.9 Hz, 1H), 7.41 (dd, J = 8.8, 6.6 Hz, 3H), 7.34-7.29 (m, 1H), 7.27-7.22 (m, 2H), 6.77 (m, 3H), 4.91 (s, 2H), 4.24 (s, 2H), 3.72-3.30 (m, 10H). |
| 33 | 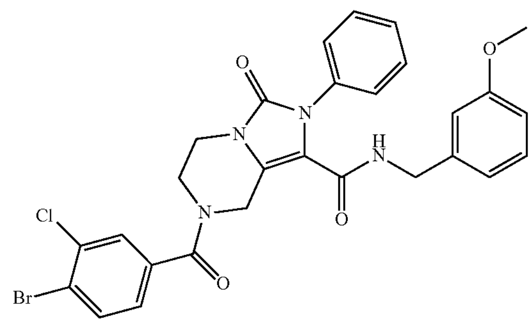 [SMILES: COc1cccc(CNC(=O)c2c3n(c(=O)n2-c2ccccc2)CCN(C(=O)c2ccc(Br)c(Cl)c2)C3)c1] | 7-(4-bromo-3-chloro-benzoyl)-N-[(3-methoxyphenyl)methyl]-3-oxo-2-phenyl-6,8-dihydro-5H-imidazo[1,5-a]pyrazine-1-carboxamide | 1H NMR (300 MHz, Chloroform-d) δ 7.74 (d, J = 8.2 Hz, 1H), 7.64 (d, J = 2.0 Hz, 1H), 7.51-7.40 (m, 3H), 7.39-7.32 (m, 2H), 7.26 (d, J = 2.0 Hz, 1H), 7.15 (t, J = 8.1 Hz, 1H), 6.83-6.71 (m, 1H), 6.47 (d, J = 6.6 Hz, 2H), 5.08 (s, 3H), 4.24 (d, J = 5.5 Hz, 2H), 4.05 (s, 2H), 3.86 (s, 2H), 3.78 (s, 3H). |
| 34 | 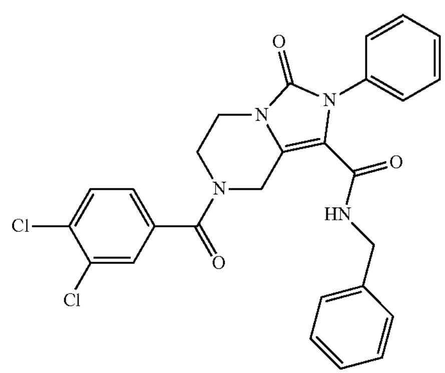 | N-benzyl-7-(3,4-dichlorobenzoyl)-3-oxo-2-phenyl-6,8-dihydro-5H-imidazo[1,5-a]pyrazine-1-carboxamide | 1H NMR (300 MHz, Chloroform-d) δ 7.65 (d, J = 2.0 Hz, 1H), 7.57 (d, J = 8.2 Hz, 1H), 7.52-7.40 (m, 3H), 7.40-7.32 (m, 3H), 7.27-7.20 (m, 3H), 6.90 (d, J = 5.6 Hz, 2H), 5.08 (s, 3H), 4.27 (d, J = 5.4 Hz, 2H), 4.05 (s, 2H), 3.86 (s, 2H). |

TABLE A-continued

| Compound # | Structure | Name | NMR |
|---|---|---|---|
| 35 | 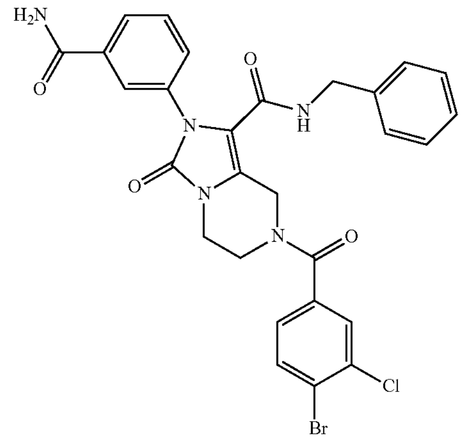 [SMILES: NC(=O)c1cccc(-n2c(C(=O)NCc3ccccc3)c3n(c2=O)CCN(C(=O)c2ccc(Br)c(Cl)c2)C3)c1] | N-benzyl-7-(4-bromo-3-chloro-benzoyl)-2-(3-carbamoylphenyl)-3-oxo-6,8-dihydro-5H-imidazo[1,5-a]pyrazine-1-carboxamide | 1H NMR (400 MHz, DMSO-d6) δ 8.25-8.06 (m, 2H), 7.89 (d, J = 8.4 Hz, 1H), 7.82-7.80 (m, 3H), 7.51-7.37 (m, 4H), 7.32-7.20 (m, 4H), 7.15 (br, 1H), 4.92-4.76 (m, 2H), 4.31-4.18 (m, 2H), 4.15-3.69 (m, 4H) |
| 36 | 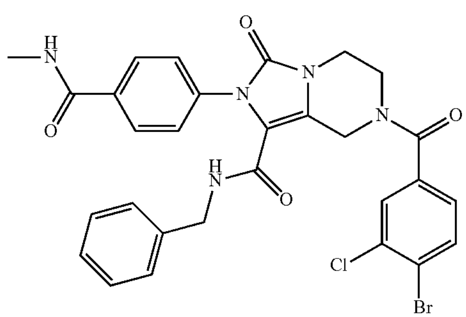 [SMILES: CNC(=O)c1ccc(-n2c(C(=O)NCc3ccccc3)c3n(c2=O)CCN(C(=O)c2ccc(Br)c(Cl)c2)C3)cc1] | N-benzyl-7-(4-bromo-3-chloro-benzoyl)-2-[4-(methylcarbamoyl)phenyl]-3-oxo-6,8-dihydro-5H-imidazo[1,5-a]pyrazine-1-carboxamide | 1H NMR (300 MHz, DMSO-d6) δ 8.48-7.89 (m, 2H), 7.87-7.79 (m, 4H), 7.43-7.29 (m, 4H), 7.11-6.92 (m, 4H), 4.90-4.75 (m, 2H), 4.33-4.22 (m, 2H), 4.00-3.91 (m, 1H), 3.78 (s, 3H), 2.80 (t, J = 12.9 Hz, 3H) |

TABLE A-continued

| Compound # | Structure | Name | NMR |
|---|---|---|---|
| 37 | 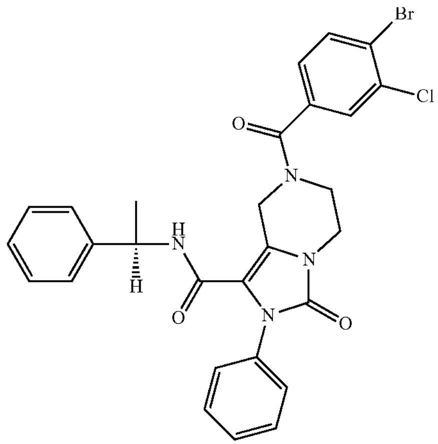 [SMILES: C[C@@H](NC(=O)c1c2n(c(=O)n1-c1ccccc1)CCN(C(=O)c1ccc(Br)c(Cl)c1)C2)c1ccccc1] | 7-(4-bromo-3-chloro-benzoyl)-3-oxo-2-phenyl-N-[rac-(1R)-1-phenylethyl]-6,8-dihydro-5H-imidazo[1,5-a]pyrazine-1-carboxamide | 1H NMR (300 MHz, Methanol-d4) δ 7.83 (d, J = 8.2 Hz, 1H), 7.73 (d, J = 2.0 Hz, 1H), 7.53-7.43 (m, 3H), 7.36 (ddd, J = 7.9, 3.2, 1.8 Hz, 3H), 7.30-7.20 (m, 3H), 7.05 (s, 2H), 4.97 (s, 2H), 4.84 (s, 1H), 3.82 (s, 4H), 1.39-1.15 (m, 3H). |
| 38 | 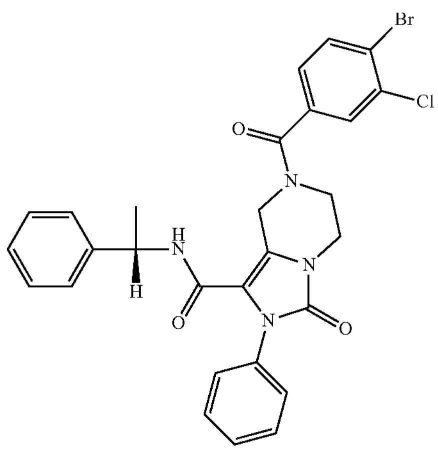 [SMILES: C[C@H](NC(=O)c1c2n(c(=O)n1-c1ccccc1)CCN(C(=O)c1ccc(Br)c(Cl)c1)C2)c1ccccc1] | 7-(4-bromo-3-chloro-benzoyl)-3-oxo-2-phenyl-N-[rac-(1S)-1-phenylethyl]-6,8-dihydro-5H-imidazo[1,5-a]pyrazine-1-carboxamide | 1H NMR (300 MHz, Methanol-d4) δ 7.83 (d, J = 8.2 Hz, 1H), 7.73 (d, J = 2.0 Hz, 1H), 7.53-7.43 (m, 3H), 7.36 (ddd, J = 7.9, 3.2, 1.8 Hz, 3H), 7.30-7.20 (m, 3H), 7.05 (s, 2H), 4.97 (s, 2H), 4.84 (s, 1H), 3.82 (s, 4H), 1.39-1.15 (m, 3H). |

TABLE A-continued

| Compound # | Structure | Name | NMR |
|---|---|---|---|
| 39 | 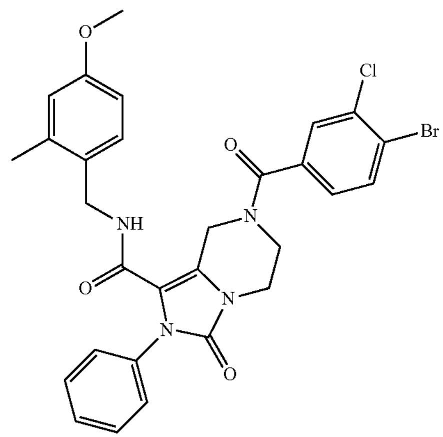 [SMILES: COc1ccc(CNC(=O)c2c3n(c(=O)n2-c2ccccc2)CCN(C(=O)c2ccc(Br)c(Cl)c2)C3)c(C)c1] | 7-(4-bromo-3-chloro-benzoyl)-N-[(4-methoxy-2-methyl-phenyl)methyl]-3-oxo-2-phenyl-6,8-dihydro-5H-imidazo[1,5-a]pyrazine-1-carboxamide | 1H NMR (400 MHz, DMSO-d6) δ 7.93-7.89 (m, 2H), 7.89-7.87 (m, 1H), 7.43-7.39 (m, 3H), 7.39-7.33 (m, 1H), 7.33-7.29 (m, 2H), 7.22-6.66 (m, 3H), 4.88-4.71 (m, 2H), 4.21-4.06 (m, 3H), 3.95-3.67 (m, 6H), 2.32-1.89 (m, 3H). |
| 40 | 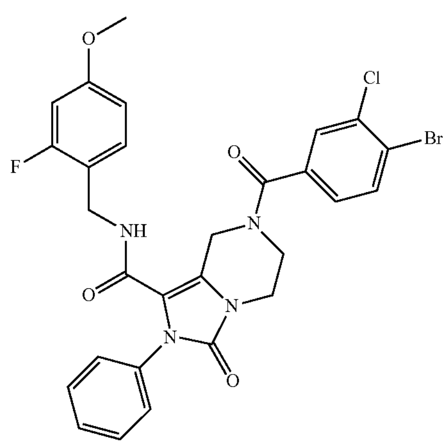 [SMILES: COc1ccc(CNC(=O)c2c3n(c(=O)n2-c2ccccc2)CCN(C(=O)c2ccc(Br)c(Cl)c2)C3)c(F)c1] | 7-(4-bromo-3-chloro-benzoyl)-N-[(2-fluoro-4-methoxy-phenyl)methyl]-3-oxo-2-phenyl-6,8-dihydro-5H-imidazo[1,5-a]pyrazine-1-carboxamide | 1H NMR (400 MHz, DMSO-d6) δ 8.09-8.03 (m, 1H), 7.99-7.96 (m, 1H), 7.89-7.72 (m, 1H), 7.57-7.41 (m, 3H), 7.39-7.33 (m, 1H), 7.33-7.29 (m, 2H), 7.20-7.07 (m, 1H), 7.00-6.56 (m, 2H), 4.94-4.74 (m, 2H), 4.33-4.08 (m, 2H), 3.98-3.34 (m, 7H). |

TABLE A-continued

| Compound # | Structure | Name | NMR |
|---|---|---|---|
| 41 | 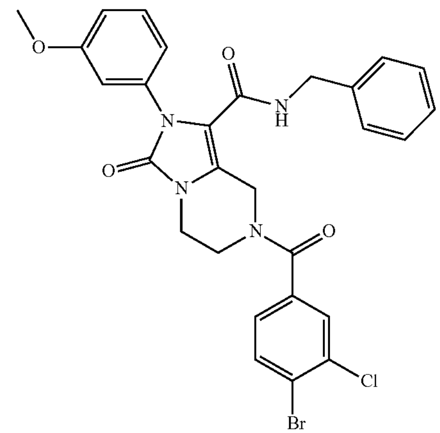 [SMILES: COc1cccc(-n2c(C(=O)NCc3ccccc3)c3n(c2=O)CCN(C(=O)c2ccc(Br)c(Cl)c2)C3)c1] | N-benzyl-7-(4-bromo-3-chlorobenzoyl)-2-(3-methoxyphenyl)-3-oxo-6,8-dihydro-5H-imidazo[1,5-a]pyrazine-1-carboxamide | 1H NMR (400 MHz, DMSO-d6) δ 8.15-7.80 (m, 3H), 7.49-7.37 (m, 1H), 7.37-7.05 (m, 5H), 6.97-6.87 (m, 1H), 6.85-6.74 (m, 2H), 4.83 (m, 2H), 4.26 (m, 2H), 3.95 (s, 1H), 3.73 (s, 3H), 3.67 (s, 2H), 3.31 (s, 2H). |
| 42 | 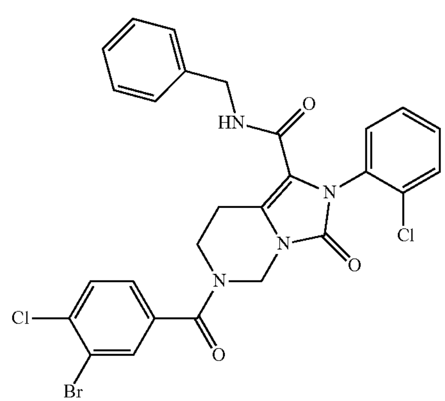 [SMILES: O=C(NCc1ccccc1)c1c2n(c(=O)n1-c1ccccc1Cl)CN(C(=O)c1ccc(Cl)c(Br)c1)CC2] | N-benzyl-7-(4-bromo-3-chlorobenzoyl)-2-(2-chlorophenyl)-3-oxo-6,8-dihydro-5H-imidazo[1,5-a]pyrazine-1-carboxamide | 1H NMR (400 MHz, DMSO-d6) δ 8.13 (s, 1H), 7.89 (d, J = 8.2 Hz, 1H), 7.81 (s, 1H), 7.57 (td, J = 4.7, 4.0, 2.6 Hz, 1H), 7.51-7.39 (m, 4H), 7.38-6.59 (m, 5H), 5.18-4.67 (m, 2H), 4.19 (d, J = 76.9 Hz, 2H), 3.71 (s, 4H). |

TABLE A-continued

| Compound # | Structure | Name | NMR |
|---|---|---|---|
| 43 | 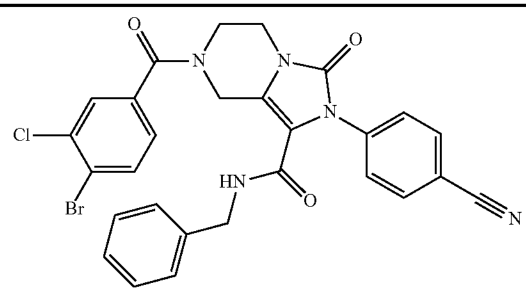 | N-benzyl-7-(4-bromo-3-chlorobenzoyl)-2-(4-cyanophenyl)-3-oxo-6,8-dihydro-5H-imidazo[1,5-a]pyrazine-1-carboxamide | 1H NMR (400 MHz, DMSO-d6) δ 8.79-8.11 (m, 1H), 7.89 (t, J = 7.2 Hz, 3H), 7.79 (s, 1H), 7.45-7.37 (m, 3H), 7.32-7.14 (m, 5H), 4.92 (br, 2H), 4.35 (br, 2H), 3.98 (br, 1H), 3.68 (s, 3H). |
| 44 | 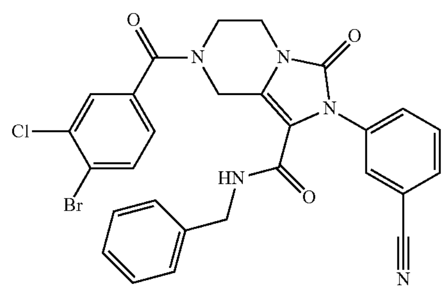 [SMILES: N#Cc1cccc(-n2c(C(=O)NCc3ccccc3)c3n(c2=O)CCN(C(=O)c2ccc(Br)c(Cl)c2)C3)c1] | N-benzyl-7-(4-bromo-3-chlorobenzoyl)-2-(3-cyanophenyl)-3-oxo-6,8-dihydro-5H-imidazo[1,5-a]pyrazine-1-carboxamide | 1H NMR (400 MHz, DMSO-d6) δ 8.59-7.98 (m, 1H), 7.87 (d, J = 8.4 Hz, 1H), 7.80-7.78 (m, 2H), 7.68 (s, 1H), 7.64-7.60 (m, 1H), 7.56-7.54 (m, 1H), 7.42-7.40 (m, 1H), 7.40-6.91 (m, 5H), 4.93 (br, 2H), 4.33 (br, 2H), 3.98 (br, 1H), 3.69 (s, 3H). |
| 45 | 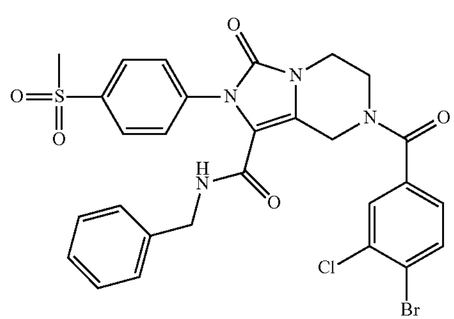 [SMILES: CS(=O)(=O)c1ccc(-n2c(C(=O)NCc3ccccc3)c3n(c2=O)CCN(C(=O)c2ccc(Br)c(Cl)c2)C3)cc1] | N-benzyl-7-(4-bromo-3-chlorobenzoyl)-2-(4-methylsulfonylphenyl)-3-oxo-6,8-dihydro-5H-imidazo[1,5-a]pyrazine-1-carboxamide | 1H NMR (400 MHz, DMSO-d6) δ 8.40 (m, 1H), 8.01-7.93 (m, 2H), 7.89 (d, J = 8.2 Hz, 1H), 7.80 (s, 1H), 7.48 (d, J = 8.4 Hz, 2H), 7.42 (d, J = 8.2 Hz, 1H), 7.27 (m, 5H), 4.86 (m, 2H), 4.36 (s, 2H), 4.00 (s, 1H), 3.70 (s, 3H), 3.25 (s, 3H). |

TABLE A-continued

| Compound # | Structure | Name | NMR |
|---|---|---|---|
| 46 | 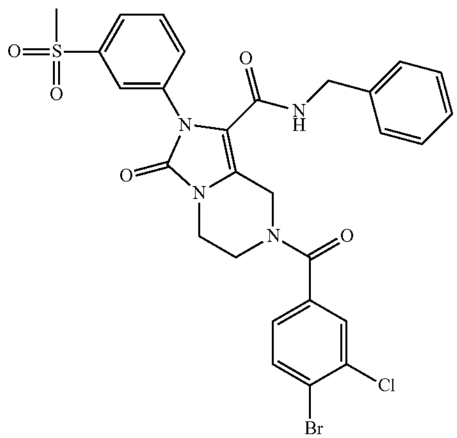 [SMILES: CS(=O)(=O)c1cccc(-n2c(C(=O)NCc3ccccc3)c3n(c2=O)CCN(C(=O)c2ccc(Br)c(Cl)c2)C3)c1] | N-benzyl-7-(4-bromo-3-chlorobenzoyl)-2-(3-methylsulfonylphenyl)-3-oxo-6,8-dihydro-5H-imidazo[1,5-a]pyrazine-1-carboxamide | 1H NMR (400 MHz, Chloroform-d) δ 7.97 (q, J = 1.5 Hz, 1H), 7.88 (ddd, J = 5.6, 3.0, 1.7 Hz, 1H), 7.74 (d, J = 8.2 Hz, 1H), 7.66-7.60 (m, 1H), 7.59-7.52 (m, 2H), 7.27 (d, J = 2.2 Hz, 4H), 7.01 (s, 2H), 5.32 (s, 1H), 5.03 (s, 2H), 4.33 (s, 2H), 4.02 (s, 2H), 3.80 (s, 2H), 2.99 (s, 3H). |
| 47 | 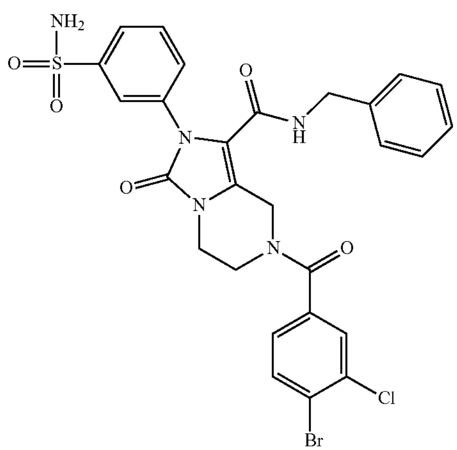 [SMILES: NS(=O)(=O)c1cccc(-n2c(C(=O)NCc3ccccc3)c3n(c2=O)CCN(C(=O)c2ccc(Br)c(Cl)c2)C3)c1] | N-benzyl-7-(4-bromo-3-chlorobenzoyl)-3-oxo-2-(3-sulfamoylphenyl)-6,8-dihydro-5H-imidazo[1,5-a]pyrazine-1-carboxamide | 1H NMR (400 MHz, DMSO-d6) δ 8.35 (br, 1H), 7.89 (d, J = 8.2 Hz, 1H), 7.85-7.69 (m, 3H), 7.61 (t, J = 8.1 Hz, 1H), 7.51 (s, 2H), 7.46-7.36 (m, 2H), 7.27 (m, 5H), 4.87 (m, 2H), 4.28 (m, 2H), 3.98 (br, 1H), 3.69 (s, 3H). |

TABLE A-continued

| Compound # | Structure | Name | NMR |
|---|---|---|---|
| 48 | 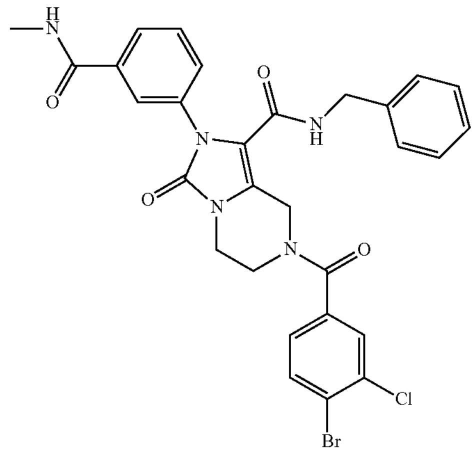 [SMILES: CNC(=O)c1cccc(-n2c(C(=O)NCc3ccccc3)c3n(c2=O)CCN(C(=O)c2ccc(Br)c(Cl)c2)C3)c1] | N-benzyl-7-(4-bromo-3-chlorobenzoyl)-2-[3-(methylcarbamoyl)phenyl]-3-oxo-6,8-dihydro-5H-imidazo[1,5-a]pyrazine-1-carboxamide | 1H NMR (400 MHz, DMSO-d6) δ 8.53 (d, J = 4.9 Hz, 1H), 8.38-7.86 (m, 2H), 7.85-7.54 (m, 3H), 7.52-7.48 (m, 1H), 7.43-7.37 (m, 2H), 7.34-6.82 (m, 5H), 5.18-4.52 (m, 2H), 4.31 (br, 2H), 3.99 (br, 1H), 3.69 (s, 3H), 2.81 (d, J = 4.5 Hz, 3H). |
| 49 | 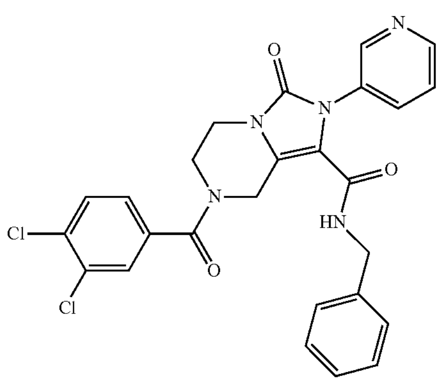 [SMILES: O=C(NCc1ccccc1)c1c2n(c(=O)n1-c1cccnc1)CCN(C(=O)c1ccc(Cl)c(Cl)c1)C2] | N-benzyl-7-(3,4-dichlorobenzoyl)-3-oxo-2-(3-pyridyl)-6,8-dihydro-5H-imidazo[1,5-a]pyrazine-1-carboxamide | 1H NMR (400 MHz, DMSO-d6) δ 8.57-8.08 (m, 3H), 7.83 (s, 1H), 7.76 (d, J = 8.3 Hz, 1H), 7.70-7.62 (m, 1H), 7.56-7.42 (m, 2H), 7.26 (m, 5H), 4.87 (m, 2H), 4.27 (m, 2H), 3.99 (s, 1H), 3.71 (s, 3H). |

TABLE A-continued

| Compound # | Structure | Name | NMR |
|---|---|---|---|
| 50 | 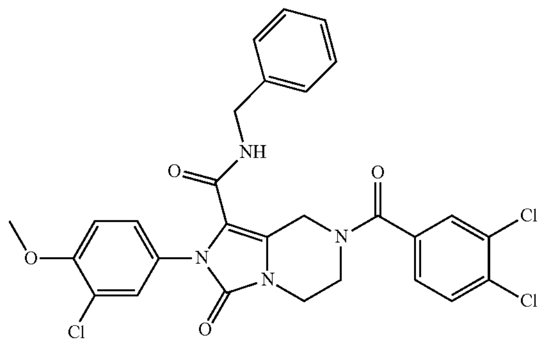 [SMILES: COc1ccc(-n2c(C(=O)NCc3ccccc3)c3n(c2=O)CCN(C(=O)c2ccc(Cl)c(Cl)c2)C3)cc1Cl] | N-benzyl-2-(3-chloro-4-methoxyphenyl)-7-(3,4-dichlorobenzoyl)-3-oxo-6,8-dihydro-5H-imidazo[1,5-a]pyrazine-1-carboxamide | 1H NMR (400 MHz, DMSO-d6) δ 8.14 (s, 1H), 7.86-7.79 (m, 1H), 7.76 (d, J = 8.2 Hz, 1H), 7.51 (d, J = 8.2 Hz, 1H), 7.48 (d, J = 8.2 Hz, 1H), 6.57 (m, 8H), 4.84 (m, 2H), 4.26 (m, 2H), 3.00 (s, 1H), 3.89 (s, 3H), 3.68 (s, 3H). |
| 51 | 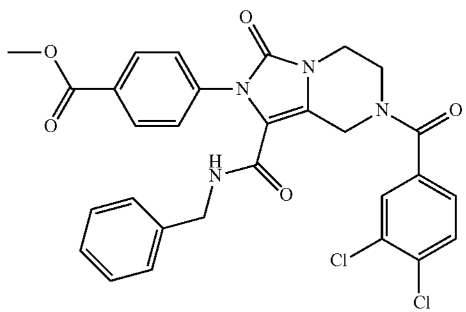 [SMILES: COC(=O)c1ccc(-n2c(C(=O)NCc3ccccc3)c3n(c2=O)CCN(C(=O)c2ccc(Cl)c(Cl)c2)C3)cc1] | N-benzyl-7-(3,4-dichlorobenzoyl)-2-(4-ethoxyphenyl)-3-oxo-6,8-dihydro-5H-imidazo[1,5-a]pyrazine-1-carboxamide | 1H NMR (300 MHz, DMSO-d6) δ 7.81 (s, 1H), 7.74 (d, J = 8.4 Hz, 1H), 7.52 (d, J = 8.4 Hz, 1H), 7.31-7.13 (m, 6H), 6.95 (d, J = 8.8 Hz, 3H), 4.88-4.76 (m, 2H), 4.27 (br, 2H), 4.07-3.94 (m, 2H), 3.66 (s, 3H), 1.34 (t, J = 7.0 Hz, 3H). |
| 52 | 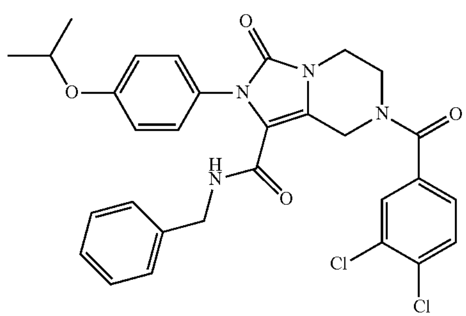 | N-benzoyl-7-(3,4-dichlorobenzoyl)-2-(4-isopropoxyphenyl)-3-oxo-6,8-dihydro-5H-imidazo[1,5-a]pyrazine-1-carboxamide | 1H NMR (300 MHz, DMSO-d6) δ 7.81 (s, 1H), 7.75 (d, J = 8.1 Hz, 1H), 7.52 (d, J = 8.1 Hz, 1H), 7.22-7.12 (m, 6H), 6.94 (d, J = 8.7 Hz, 3H), 4.89-4.73 (m, 2H), 4.64-4.56 (m, 1H), 4.27 (br, 2H), 3.95 (br, 1H), 3.66 (s, 3H), 1.27 (d, J = 6.0 Hz, 6H). |

TABLE A-continued

| Compound # | Structure | Name | NMR |
|---|---|---|---|
| 53 | 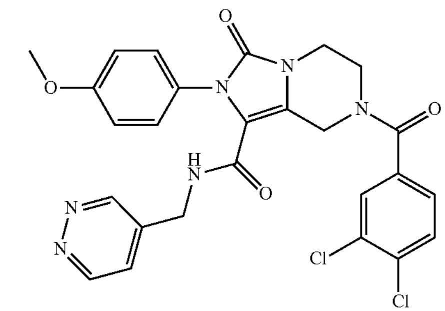 | 7-(3,4-dichlorobenzoyl)-2-(4-methoxyphenyl)-3-oxo-N-(pyridazin-4-ylmethyl)-6,8-dihydro-5H-imidazo[1,5-a]pyrazine-1-carboxamide | 1H-NMR (DMSO, 600 MHz, 80° C.): 3.66-3.73 (m, 2H); 3.81 (s, 3H); 3.82-3.90 (br. s, 2H); 4.27-4.36 (m, 2H); 4.87 (s, 2H); 6.97 (d, J = 8.8 Hz, 2H); 7.21 (d, J = 8.8 Hz, 2H); 7.27 (s, 1H); 7.43-7.58 (m, 2H); 7.73 (d, J = 8.1 Hz, 1H); 7.77 (s, 1H); 8.96 (s, 1H); 9.06 (d, J = 4.8 Hz, 1H) ppm. |
| 54 | 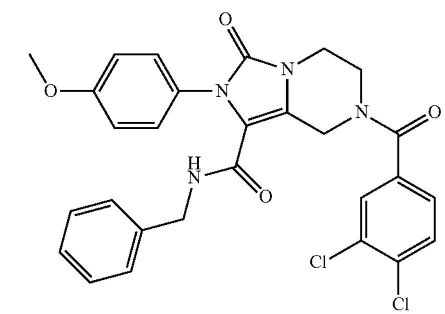 | N-benzyl-7-(3,4-dichlorobenzoyl)-2-(4-methoxyphenyl)-3-oxo-6,8-dihydro-5H-imidazo[1,5-a]pyrazine-1-carboxamide | 1H-NMR (DMSO, 600 MHz, 80° C.): 3.68 (t, J = 5.6 Hz, 2H); 3.79 (s, 3H); 3.80-3.88 (br. s., 2H); 4.25 (d, J = 5.7 Hz, 2H); 4.85 (s, 2H); 6.96 (d, J = 8.8 Hz, 2H); 7.04 (d, J = 5.7 Hz, 2H); 7.17-7.27 (m, 5H); 7.49 (dd, J = 8.2 Hz, 1.8 Hz, 1H); 7.71 (d, J = 8.3 Hz, 1H); 7.76 (d, J = 1.8 Hz, 1H) ppm. |
| 55 | 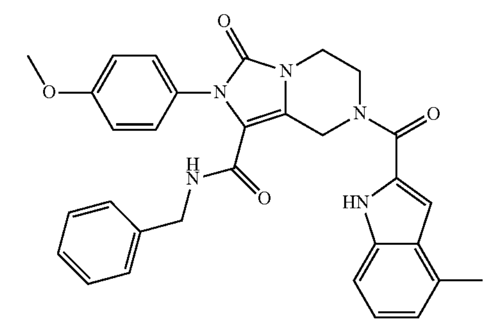 | N-benzyl-2-(4-methoxyphenyl)-7-(4-methyl-1H-indole-2-carbonyl)-3-oxo-6,8-dihydro-5H-imidazo[1,5-a]pyrazine-1-carboxamide | 1H-NMR (CDCl3, 400 MHz, 25° C.): 2.58 (s, 3H); 3.76 (s, 3H); 3.90 (t, J = 5.4 Hz, 2H); 4.21 (t, J = 4.9 Hz, 2H); 4.28 (d, J = 5.4 Hz, 2H), 5.15 (t, J = 4.9 Hz, 1H), 5.47 (s, 2H), 6.81-6.97 (m, 5H), 7.01 (br. s. 1H), 7.11-7.34 (m, 7H), 9.27 (s, 1H) ppm. |

TABLE A-continued

| Compound # | Structure | Name | NMR |
|---|---|---|---|
| 56 | 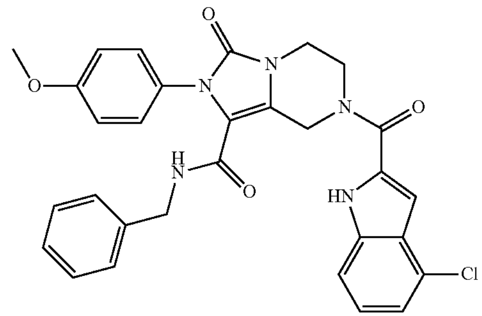 [SMILES: COc1ccc(-n2c(C(=O)NCc3ccccc3)c3n(c2=O)CCN(C(=O)c2cc4c(Cl)cccc4[nH]2)C3)cc1] | N-benzyl-7-(4-chloro-1H-indole-2-carbonyl)-2-(4-methoxyphenyl)-3-oxo-6,8-dihydro-H-imidazo[1,5-a]pyrazine-1-carboxamide | 1H-NMR (DMSO, 600 MHz, 80° C.): 3.77 (s, 3H); 3.79-3.88 (m, 2 H); 4.13 (br. s. 2H); 4.26 (d, J = 5.6 Hz, 2H); 5.10 (br. s. 2H); 6.89-6.99 (m, 3H); 7.05 (br. s. 2H); 7.10-7.20 (m, 5H); 7.23 (t, J = 8.0 Hz, 1H); 7.44 (d, J = 8.0 Hz, 1H); 7.79 (br. s. 1H); 12.07 (s, 1H) ppm. |
| 57 | 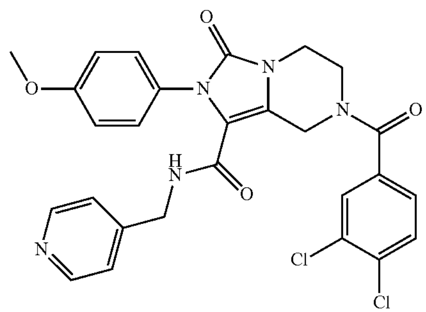 | 7-(3,4-dichlorobenzoyl)-2-(4-methoxyphenyl)-3-oxo-N-(4-pyridylmethyl)-6,8-dihydro-5H-imidazo[1,5-a]pyrazine-1-carboxamide | 1H-NMR (DMSO, 600 MHz, 80° C.): 3.70 (t, J = 5.5 Hz, 2H); 3.81 (s, 3H); 3.82-3.90 (br. s., 2H); 4.28 (d, J = 5.1 Hz, 2H); 4.87 (s, 2H); 6.98 (d, J = 8.8 Hz, 2H); 7.00-7.06 (br. s., 2H); 7.22 (d, J = 8.9 Hz, 2H); 7.49 (dd, J = 8.2 Hz, 1.8 Hz, 1H); 7.38-7.48 (br. s., 1H); 7.50 (dd, J = 8.1 Hz, 1.7 Hz, 1H); 7.72 (d, J = 8.2 Hz, 1H); 7.78 (d, J = 1.5 Hz, 1H); 8.43 (d, J = 5.3 Hz, 2H) ppm. |
| 58 | 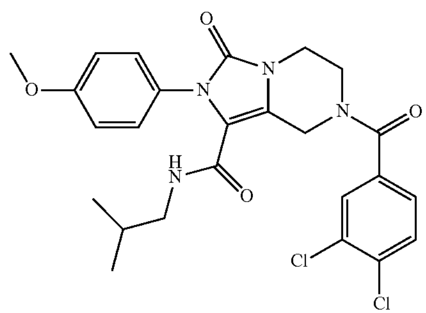 [SMILES: COc1ccc(-n2c(C(=O)NCC(C)C)c3n(c2=O)CCN(C(=O)c2ccc(Cl)c(Cl)c2)C3)cc1] | 7-(3,4-dichlorobenzoyl)-N-isobutyl-2-(4-methoxyphenyl)-3-oxo-6,8-dihydro-5H-imidazo[1,5-a]pyrazine-1-carboxamide | 1H-NMR (DMSO, 600 MHz, 80° C.): 0.66 (t, J = 5.9 Hz, 6H); 1.45-1.57 (m, 1H); 2.87 (t, J = 5.4 Hz, 2H); 3.68 (t, J = 5.5 Hz, 2H); 3.80 (s, 3H); 3.82-3.90 (br. s., 2H); 4.82 (s, 2H); 6.64-6.71 (m, 1H); 7.01 (d, J = 8.6 Hz, 2H); 7.22 (d, J = 8.9 Hz, 2H); 7.49 (d, J = 8.1 Hz, 1H); 7.72 (d, J = 8.2 Hz, 1H); 7.76 (s, 1H) ppm. |

TABLE A-continued

| Compound # | Structure | Name | NMR |
|---|---|---|---|
| 59 | 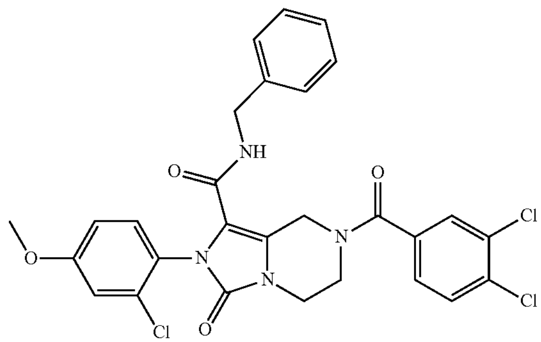 [SMILES: COc1ccc(-n2c(C(=O)NCc3ccccc3)c3n(c2=O)CCN(C(=O)c2ccc(Cl)c(Cl)c2)C3)c(Cl)c1] | N-benzyl-2-(2-chloro-4-methoxyphenyl)-7-(3,4-dichlorobenzoyl)-3-oxo-6,8-dihydro-5H-imidazo[1,5-a]pyrazine-1-carboxamide | 1H NMR (400 MHz, DMSO-d6) δ 7.91-7.82 (m, 1H), 7.75 (d, J = 8.4 Hz, 1H), 7.52 (d, J = 7.6 Hz, 1H), 7.34 (d, J = 8.8 Hz, 1H), 7.26 °C 7.13 (m, 5H), 6.99-6.93 (m, 2H), 5.01-4.86 (m, 2H), 4.33-4.24 (m, 2H), 4.12 (br, 1H), 3.81 (s, 3H), 3.69 (s, 3H). |
| 60 | 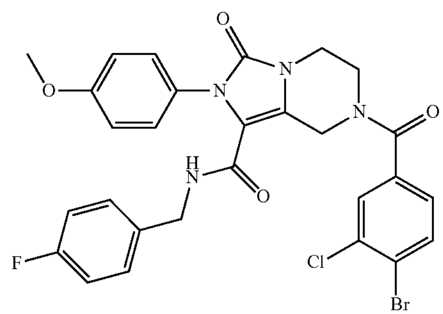 [SMILES: COc1ccc(-n2c(C(=O)NCc3ccc(F)cc3)c3n(c2=O)CCN(C(=O)c2ccc(Br)c(Cl)c2)C3)cc1] | 7-(4-bromo-3-chloro-benzoyl)-N-[(4-fluorophenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.68 (t, J = 5.5 Hz, 2H), 3.79 (s, 3H), 3.82-3.84 (m, 2H), 4.22 (d, J = 5.6 Hz, 2H), 4.84 (s, 2H), 6.95 (d, J = 8.6 Hz, 2H), 7.00-7.10 (m, 4H), 7.1-7.7.20 (m, 3H), 7.39 (d, J = 8.3 Hz, 1H), 7.74 (s, 1H), 7.85 (d, J = 8.3 Hz, 1H). |
| 61 | 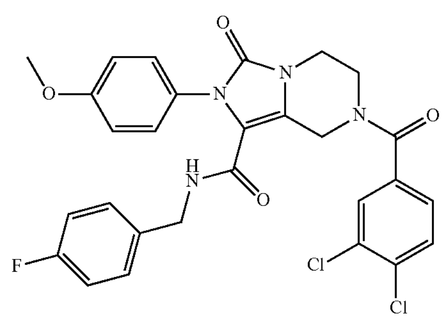 [SMILES: COc1ccc(-n2c(C(=O)NCc3ccc(F)cc3)c3n(c2=O)CCN(C(=O)c2ccc(Cl)c(Cl)c2)C3)cc1] | 7-(3,4-dichlorobenzoyl)-N-[(4-fluorophenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.68 (t, J = 5.4 Hz, 2H), 3.79 (s, 3H), 3.82-3.85 (m, 2H), 4.21 (d, J = 5.6 Hz, 2H), 4.84 (s, 2H), 6.95 (d, J = 8.6 Hz, 2H), 7.00-7.10 (m, 4H), 7.16-7.19 (m, 3H), 7.48 (d, J = 8.1 Hz, 1H), 7.71 (d, J = 8.3 Hz, 1H), 7.75 (s, 1H). |

TABLE A-continued

| Compound # | Structure | Name | NMR |
|---|---|---|---|
| 62 | 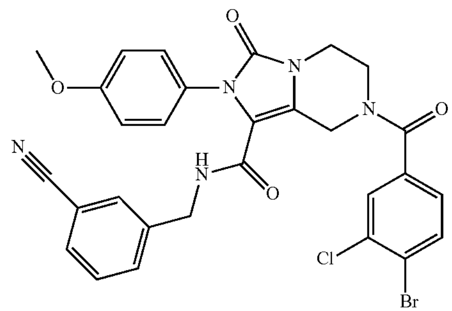 [SMILES: COc1ccc(-n2c(C(=O)NCc3cccc(C#N)c3)c3n(c2=O)CCN(C(=O)c2ccc(Br)c(Cl)c2)C3)cc1] | 7-(4-bromo-3-chloro-benzoyl)-N-[(3-cyanophenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.67-3.69 (m, 2H), 3.79 (s, 3H), 3.80-3.83 (m, 2H), 4.31 (d, J = 5.7 Hz, 2H), 4.85 (s, 2H), 6.95 (d, J = 8.2 Hz, 2H), 7.19 (d, J = 8.5 Hz, 2H), 7.31-7.53 (m, 5H), 7.66 (d, J = 7.3 Hz, 1H), 7.74 (s, 1H), 7.85 (d, J = 8.0 Hz, 1H). |
| 63 | 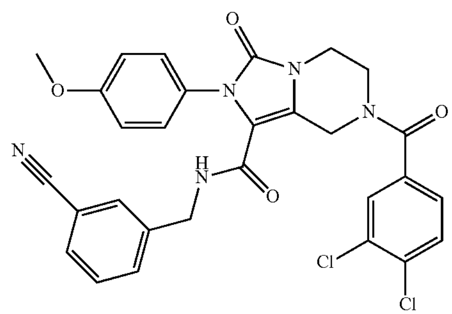 [SMILES: COc1ccc(-n2c(C(=O)NCc3cccc(C#N)c3)c3n(c2=O)CCN(C(=O)c2ccc(Cl)c(Cl)c2)C3)cc1] | N-[(3-cyanophenyl)methyl]-7-(3,4-dichlorobenzoyl)-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.3 Hz, 2H), 3.80 (s, 3H), 3.81-3.86 (m, 2H), 4.30 (d, J = 5.7 Hz, 2H), 4.85 (s, 2H), 6.96 (d, J = 8.4 Hz, 2H), 7.20 (d, J = 8.3 Hz, 2H), 7.30-7.55 (m, 5H), 7.66 (d, J = 7.4 Hz, 1H), 7.71 (d, J = 8.2 Hz, 1H), 7.75 (s, 1H). |
| 64 | 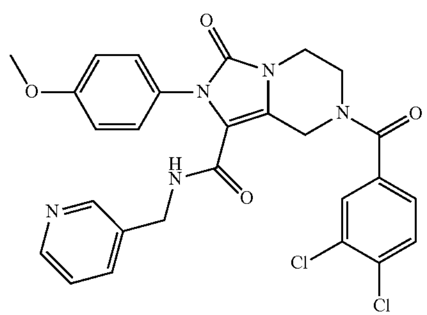 | 7-(3,4-dichlorobenzoyl)-2-(4-methoxyphenyl)-N-(3-pyridylmethyl)-6,8-dihydro-5H-imidazo[1,5-a]pyrazine-1-carboxamide | 1H-NMR (DMSO, 600 MHz, 80° C.): 3.65-3.72 (m, 2H), 3.80 (s, 3H), 3.80-3.91 (m, 2H), 4.28 (d, J = 5.2 Hz, 2H), 4.85 (s, 2H), 6.85 (d, J = 8.8 Hz, 2H), 7.18 (d, J = 8.8 Hz, 2H), 7.25 (dd, J = 7.7 Hz, 4.7 Hz, 1H), 7.29-7.39 (br. s. 1H), 7.40-7.46 (m, 1H), 7.49 (dd, J = 8.4 Hz, 2.0 Hz, 1H), 7.72 (dd, J = 8.2 Hz, 1H), 7.76 (d, J = 2.0 Hz, 1H), 8.33 (s, 1H), 8.44 (d, J = 4.8 Hz, 1H) ppm. |

TABLE A-continued

| Compound # | Structure | Name | NMR |
|---|---|---|---|
| 65 | 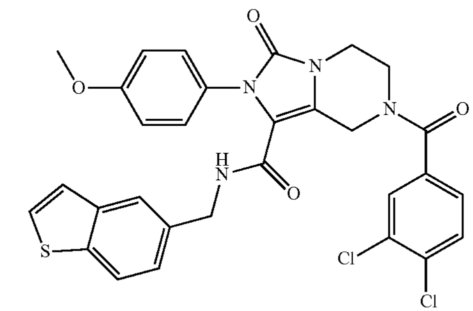 [SMILES: COc1ccc(-n2c(C(=O)NCc3ccc4occc4c3)c3n(c2=O)CCN(C(=O)c2ccc(Cl)c(Cl)c2)C3)cc1] | N-(benzothiophen-5-ylmethyl)-7-(3,4-dichlorobenzoyl)-2-(4-methoxyphenyl)-3-oxo-6,8-dihydro-5H-imidazo[1,5-a]pyrazine-1-carboxamide | 1H-NMR (DMSO, 600 MHz, 80° C.): 3.67-3.72 (m, 2H), 3.75 (s, 3H), 3.79-3.90 (br. s., 2H), 4.38 (d, J = 5.7 Hz, 2H), 4.89 (s, 2H), 6.94 (d, J = 8.8 Hz, 2H), 7.08 (d, J = 8.5 Hz, 1H), 7.21 (d, J = 8.8 Hz, 2H), 7.24-7.32 (br. s. 1H), 7.37 (d, J = 5.2 Hz, 1H), 7.50 (dd, J = 8.5 Hz, 1.9 Hz, 1H), 7.53 (s, 1H), 7.67-7.74 (m, 2H), 7.77 (d, J = 2.0 Hz, 1H), 7.85 (d, J = 8.3 Hz, 1H) ppm. |
| 66 | 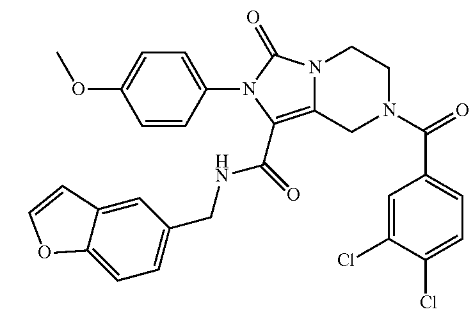 | N-(benzofuran-5-ylmethyl)-7-(3,4-dichlorobenzoyl)-2-(4-methoxyphenyl)-3-oxo-6,8-dihydro-5H-imidazo[1,5-a]pyrazine-1-carboxamide | 1H-NMR (DMSO, 600 MHz, 80° C.): 3.65-3.72 (m, 2H), 3.76 (s, 3H), 3.78-3.90 (m, 2H), 4.34 (d, J = 5.4 Hz, 2H), 4.87 (s, 3H), 6.86 (s, 1H), 6.94 (d, J = 8.9 Hz, 2H), 7.02 (d, J = 8.1 Hz, 1H), 7.12-7.26 (m, 3H), 7.30 (s, 1H), 7.43 (d, J = 8.4 Hz, 1H), 7.49 (dd, J = 8.2 Hz, 1.6 Hz, 1H), 7.71 (d, J = 1.6 Hz, 1H), 7.77 (d, J = 1.6 Hz, 1H), 7.91 (d, J = 1.9 Hz, 1H) ppm. |
| 67 | 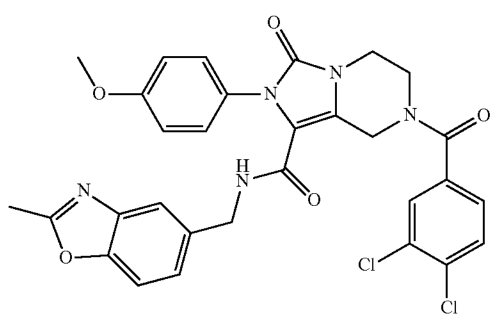 [SMILES: COc1ccc(-n2c(C(=O)NCc3ccc4oc(C)nc4c3)c3n(c2=O)CCN(C(=O)c2ccc(Cl)c(Cl)c2)C3)cc1] | 7-(3,4-dichlorobenzoyl)-2-(4-methoxyphenyl)-N-[(2-methyl-1,3-benzoxazol-5-yl)methyl]-3-oxo-6,8-dihydro-5H-imidazo[1,5-a]pyrazine-1-carboxamide | 1H-NMR (DMSO, 600 MHz, 80° C.): 2.61 (s, 3H), 3.66-3.72 (m, 2H), 3.78 (s, 3H), 3.80-3.89 (m, 2H), 4.34 (d, J = 5.8 Hz, 2H), 4.86 (s, 2H), 6.93 (d, J = 8.9 Hz, 2H), 7.04 (d, J = 8.1 Hz, 1H), 7.19 (d, J = 8.9 Hz, 2H), 7.22-7.30 (br. s. 1H), 7.34 (s, 1H), 7.47 (d, J = 8.4 Hz, 1H), 7.49 (dd, J = 8.2 Hz, 1.7 Hz, 1H), 7.71 (d, J = 8.2 Hz, 1H), 7.76 (d, J = 1.5 Hz, 1H) ppm. |

TABLE A-continued

| Compound # | Structure | Name | NMR |
|---|---|---|---|
| 68 | 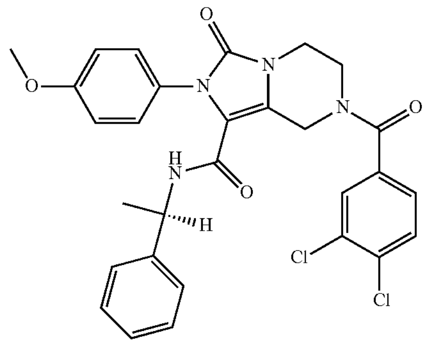 [SMILES: COc1ccc(-n2c(C(=O)N[C@H](C)c3ccccc3)c3n(c2=O)CCN(C(=O)c2ccc(Cl)c(Cl)c2)C3)cc1] | 7-(3,4-dichlorobenzoyl)-2-(4-methoxyphenyl)-3-oxo-N-[rac-(1R)-1-phenylethyl]-6,8-dihydro-5H-imidazo[1,5-a]pyrazine-1-carboxamide | 1H NMR (400 MHz, DMSO-d6, 80° C.): 1.22 (d, J = 6.8 Hz, 3H), 3.69 (t, J = 5.5 Hz, 2H), 3.81 (s, 3H), 3.85 (br s, 2H), 4.84-4.91 (m, 3H), 6.89 (d, J = 8.0 Hz, 1H), 6.98 (d, J = 8.6 Hz, 2H), 7.05 (d, J = 7.1 Hz, 2H), 7.20-7.25 (m, 5H), 7.49 (dd, J = 8.3 Hz, 1.8 Hz, 1H), 7.71 (d, J = 8.2 Hz, 1H), 7.76 (d, J = 1.9 Hz, 1H). |
| 69 | 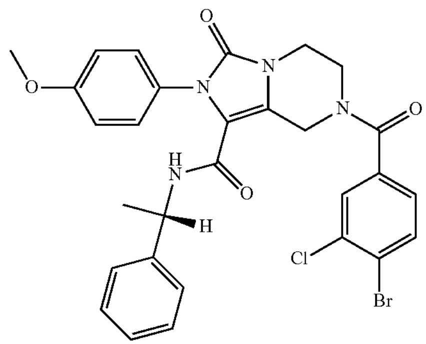 [SMILES: COc1ccc(-n2c(C(=O)N[C@@H](C)c3ccccc3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1S)-1-phenylethyl]-6,8-dihydro-5H-imidazo[1,5-a]pyrazine-1-carboxamide | 1H NMR (400 MHz, DMSO-d6, 80° C.): 1.21 (d, J = 6.9 Hz, 3H), 3.69 (t, J = 5.4 Hz, 2H), 3.80 (s, 3H), 3.82-3.87 (m, 2H), 4.84-4.90 (m, 3H), 6.88 (d, J = 7.5 Hz, 1H), 6.97 (d, J = 8.5 Hz, 2H), 7.05 (d, J = 7.1 Hz, 2H), 7.21-7.26 (m, 5H), 7.39 (d, J = 8.1 Hz, 1H), 7.74 (s, 1H), 7.85 (d, J = 8.1 Hz, 1H). |
| 70 | 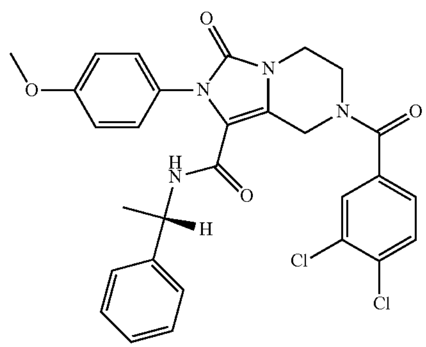 [SMILES: COc1ccc(-n2c(C(=O)N[C@@H](C)c3ccccc3)c3n(c2=O)CCN(C(=O)c2ccc(Cl)c(Cl)c2)C3)cc1] | 7-(3,4-dichlorobenzoyl)-2-(4-methoxyphenyl)-3-oxo-N-[rac-(1S)-1-phenylethyl]-6,8-dihydro-5H-imidazo[1,5-a]pyrazine-1-carboxamide | 1H NMR (400 MHz, DMSO-d6, 80° C.): 1.21 (d, J = 6.8 Hz, 3H), 3.69 (t, J = 5.5 Hz, 2H), 3.80 (s, 3H), 3.82-3.86 (m, 2H), 4.84-4.90 (m, 3H), 6.88 (d, J = 7.3 Hz, 1H), 6.97 (d, J = 8.5 Hz, 2H), 7.05 (d, J = 7.3 Hz, 2H), 7.21-7.24 (m, 5H), 7.48 (d, J = 8.3 Hz, 1H), 7.70 (d, J = 8.3 Hz, 1H), 7.76 (s, 1H). |

TABLE A-continued

| Compound # | Structure | Name | NMR |
|---|---|---|---|
| 71 | 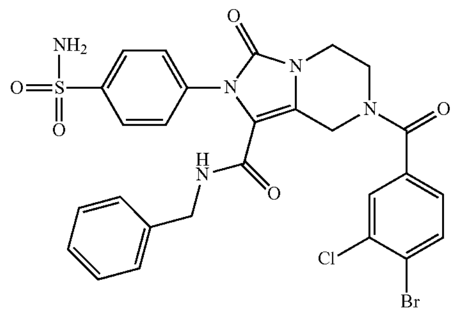 | N-benzyl-7-(4-bromo-3-chloro-benzoyl)-3-oxo-2-(4-sulfamoylphenyl)-6,8-dihydro-5H-imidazo[1,5-a]pyrazine-1-carboxamide | 1H NMR (400 MHz, Chloroform-d) δ 7.93 (d, J = 8.5 Hz, 2H), 7.75 (d, J = 8.2 Hz, 1H), 7.64 (s, 1H), 7.47 (d, J = 8.5 Hz, 2H), 7.28°C 7.26 (m, 6H), 6.98 (s, 2H), 5.05 (s, 2H), 4.86 (d, J = 6.7 Hz, 1H), 4.34 (s, 2H), 3.96 (m, 4H). |
| 72 | 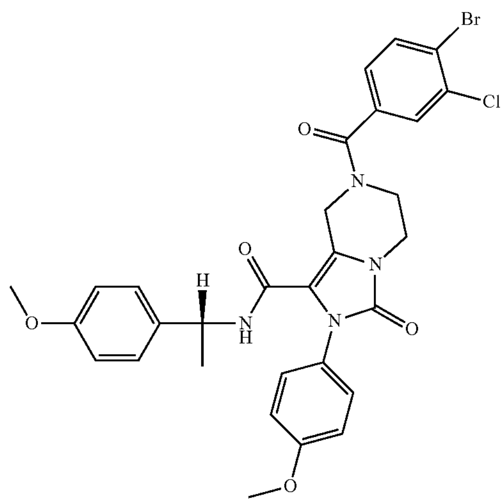 [SMILES: COc1ccc([C@@H](C)NC(=O)c2c3n(c(=O)n2-c2ccc(OC)cc2)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-1-(4-methoxyphenyl)ethyl]-6,8-dihydro-5H-imidazo[1,5-a]pyrazine-1-carboxamide | 1H NMR (400 MHz, Chloroform-d) δ 7.72 (d, J = 8.2 Hz, 1H), 7.63 (s, 1H), 7.29-7.22 (m, 3H), 7.01-6.94 (m, 2H), 6.83 (d, J = 8.4 Hz, 2H), 6.77 (d, J = 8.6 Hz, 2H), 5.15-4.92 (m, 3H), 4.87 (s, 1H), 4.06-3.76 (m, 10H), 1.19 (d, J = 6.8 Hz, 3H). |

TABLE A-continued

| Compound # | Structure | Name | NMR |
|---|---|---|---|
| 73 | 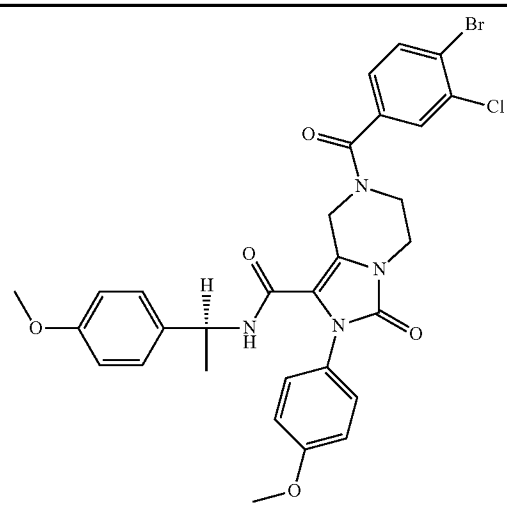 | 7-(4-bromo-3-chloro-benzoyl)-2-(4-methoxyphenyl)-3-oxo-N-[rac-(1S)-1-(4-methoxyphenyl)ethyl]-6,8-dihydro-5H-imidazo[1,5-a]pyrazine-1-carboxamide | 1H NMR (400 MHz, Chloroform-d) δ 7.72 (d, J = 8.2 Hz, 1H), 7.65-7.61 (m, 1H), 7.28-7.23 (m, 3H), 7.00-6.94 (m, 2H), 6.83 (d, J = 8.4 Hz, 2H), 6.77 (d, J = 8.7 Hz, 2H), 5.14 (d, J = 7.4 Hz, 1H), 5.03 (s, 2H), 4.87 (s, 1H), 4.06-3.76 (m, 10H), 1.32-1.08 (m, 3H). |
| 74 | 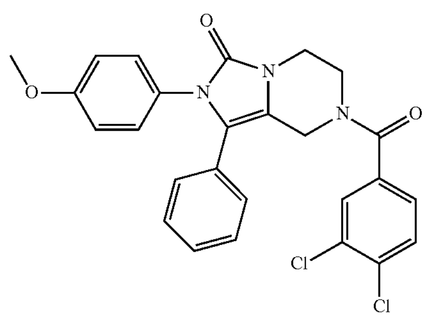 [SMILES: COc1ccc(-n2c(-c3ccccc3)c3n(c2=O)CCN(C(=O)c2ccc(Cl)c(Cl)c2)C3)cc1] | 7-(3,4-dichlorobenzoyl)-2-(4-methoxyphenyl)-1-phenyl-6,8-dihydro-5H-imidazo[1,5-a]pyrazin-3-one | 1H NMR (400 MHz, Chloroform-d) δ 7.58-7.52 (m, 2H), 7.29 (d, J = 8.3 Hz, 2H), 7.24 (s, 2H), 7.07 (d, J = 8.7 Hz, 2H), 6.98 (s, 2H), 6.83 (d, J = 8.8 Hz, 2H), 4.78 (s, 2H), 3.87-3.78 (m, 7H). |

TABLE A-continued

| Compound # | Structure | Name | NMR |
|---|---|---|---|
| 75 | 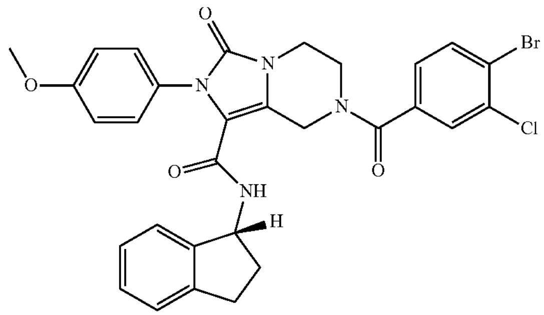 [SMILES: COc1ccc(-n2c(C(=O)N[C@@H]3CCc4ccccc43)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-indan-1-yl]-6,8-dihydro-5H-imidazo[1,5-a]pyrazine-1-carboxamide | 1H NMR (400 MHz, DMSO-d6) δ 7.90 (d, J = 8.2 Hz, 1H), 7.81 (d, J = 1.9 Hz, 1H), 7.60 (s, 1H), 7.42 (dd, J = 8.2, 2.0 Hz, 1H), 7.26-7.07 (m, 5H), 7.00 (d, J = 8.5 Hz, 3H), 5.33-4.68 (m, 3H), 4.00 (m, 1H), 3.80-3.62 (m, 6H), 2.78 (s, 2H), 2.40-2.12 (m, 1H), 1.88-1.39 (m, 1H). |
| 76 | 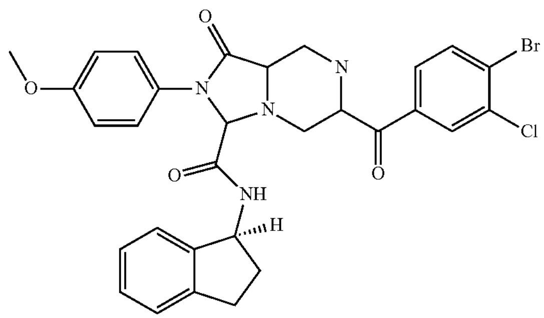 [SMILES: COc1ccc(N2C(=O)C3CNC(C(=O)c4ccc(Br)c(Cl)c4)CN3C2C(=O)N[C@H]2CCc3ccccc32)cc1] | 7-(4-bromo-3-chloro-benzoyl)-2-(4-methoxyphenyl)-3-oxo-N-[rac-(1S)-indan-1-yl]-6,8-dihydro-5H-imidazo[1,5-a]pyrazine-1-carboxamide | 1H NMR (400 MHz, DMSO-d6) δ 7.90 (d, J = 8.2 Hz, 1H), 7.81 (d, J = 2.0 Hz, 1H), 7.60 (s, 1H), 7.42 (dd, J = 8.2, 2.0 Hz, 1H), 7.32-7.07 (m, 5H), 7.00 (d, J = 8.5 Hz, 3H), 5.20 (m, 1H), 4.82 (m, 2H), 3.97 (s, 1H), 3.78 (s, 3H), 3.67 (s, 3H), 2.78 (s, 2H), 2.43-2.15 (m, 1H), 1.88-1.39 (m, 1H). |
| 77 | 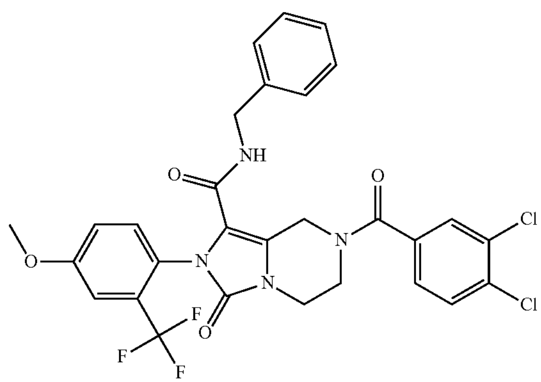 [SMILES: COc1ccc(-n2c(C(=O)NCc3ccccc3)c3n(c2=O)CCN(C(=O)c2ccc(Cl)c(Cl)c2)C3)c(C(F)(F)F)c1] | N-benzoyl-7-(3,4-dichlorobenzoyl)-2-[4-methoxy-2-(trifluoromethyl)phenyl]-3-oxo-6,8-dihydro-5H-imidazo[1,5-a]pyrazine-1-carboxamide | 1H NMR (400 MHz, DMSO-d6) δ 7.98 (s, 1H), 7.83 (s, 1H), 7.76 (d, J = 8.2 Hz, 1H), 7.52 (d, J = 8.2 Hz, 1H), 7.40 (d, J = 8.7 Hz, 1H), 7.35-7.24 (m, 3H), 7.19 (d, J = 21.8 Hz, 3H), 6.90 (s, 1H), 5.13-4.68 (m, 2H), 4.27 (m, 2H), 3.88 (s, 3H), 3.80-3.58 (m, 4H). |

TABLE A-continued

| Compound # | Structure | Name | NMR |
|---|---|---|---|
| 78 | 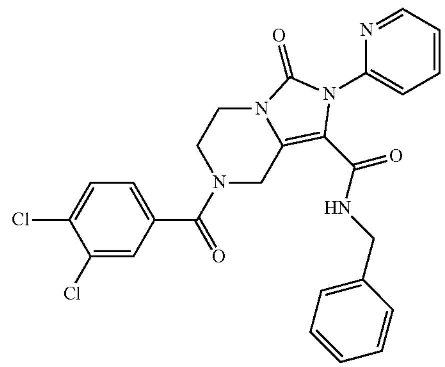 [SMILES: O=C(NCc1ccccc1)c1c2n(c(=O)n1-c1ccccn1)CCN(C(=O)c1ccc(Cl)c(Cl)c1)C2] | N-benzyl-7-(3,4-dichlorobenzoyl)-3-oxo-2-(2-pyridyl)-6,8-dihydro-5H-imidazo[1,5-a]pyrazine-1-carboxamide | 1H NMR (400 MHz, Chloroform-d) δ 8.61 (s, 1H), 8.12 (d, J = 4.8 Hz, 1H), 7.88 (td, J = 7.8, 2.0 Hz, 1H), 7.76 (d, J = 8.2 Hz, 1H), 7.65 (s, 1H), 7.56 (d, J = 8.2 Hz, 1H), 7.39 (m, 1H), 7.29-7.27 (m, 3H), 7.24-7.16 (m, 3H), 5.08 (s, 2H), 4.43 (s, 2H), 4.08-3.86 (m, 2H). |
| 79 | 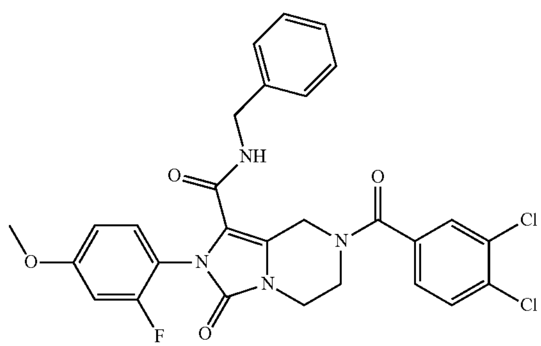 [SMILES: COc1ccc(-n2c(C(=O)NCc3ccccc3)c3n(c2=O)CCN(C(=O)c2ccc(Cl)c(Cl)c2)C3)c(F)c1] | N-benzyl-7-(3,4-dichlorobenzoyl)-2-(2-fluoro-4-methoxy-phenyl)-3-oxo-6,8-dihydro-5H-imidazo[1,5-a]pyrazine-1-carboxamide | 1H NMR (400 MHz, DMSO-d6) δ ppm 8.14 (s, 1H), 7.83 (s, 1H), 7.76 (d, J = 8.2 Hz, 1H), 7.52 (d, J = 8.3 Hz, 1H), 7.28 (dd, J = 20.1, 11.2 Hz, 5H), 6.96 (dd, J = 12.2, 2.7 Hz, 2H), 6.87-6.81 (m, 1H), 4.94 (s, 2H), 4.32 (s, 2H), 4.02-3.65 (m, 7H). |

TABLE A-continued

| Compound # | Structure | Name | NMR |
|---|---|---|---|
| 80 | 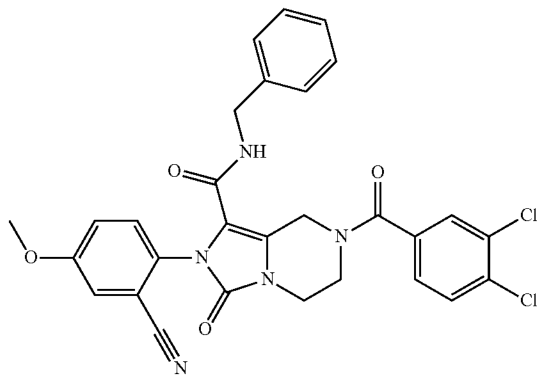 [SMILES: COc1ccc(-n2c(C(=O)NCc3ccccc3)c3n(c2=O)CCN(C(=O)c2ccc(Cl)c(Cl)c2)C3)c(C#N)c1] | N-benzyl-2-(2-cyano-4-methoxyphenyl)-7-(3,4-dichlorobenzoyl)-3-oxo-6,8-dihydro-5H-imidazo[1,5-a]pyrazine-1-carboxamide | 1H NMR (400 MHz, Chloroform-d) δ 7.65 (s, 1H), 7.56 (d, J = 8.2 Hz, 1H), 7.38-7.31 (m, 2H), 7.27 (d, J = 2.9 Hz, 3H), 7.17-7.08 (m, 2H), 7.02 (s, 2H), 5.09 (s, 1H), 4.99 (m, 2H), 4.33 (s, 2H), 3.90-3.84 (m, 7H) |
| 81 | 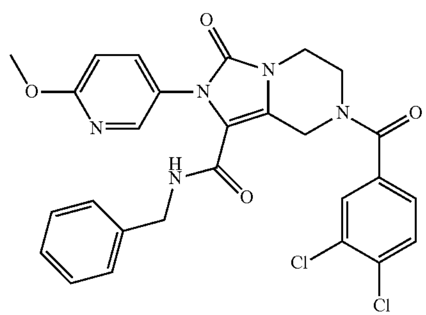 | N-benzoyl-7-(3,4-dichlorobenzoyl)-2-(6-methoxy-3-pyridyl)-3-oxo-6,8-dihydro-5H-imidazo[1,5-a]pyrazine-1-carboxamide | 1H NMR (400 MHz, Chloroform-d) δ 8.18 (d, J = 2.7 Hz, 1H), 7.65 (d, J = 1.9 Hz, 1H), 7.57 (d, J = 8.2 Hz, 1H), 7.51 (dd, J = 8.8, 2.7 Hz, 1H), 7.35 (dd, J = 8.3, 2.0 Hz, 1H), 7.30-7.23 (m, 3H), 6.97 (s, 2H), 6.77 (d, J = 8.8 Hz, 1H), 5.07 (s, 3H), 4.32-4.06 (m, 5H), 3.86 (s, 2H). |
| 82 | 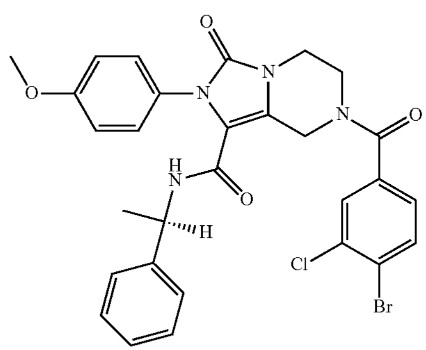 | 7-(4-bromo-3-chloro-benzoyl)-2-(4-methoxyphenyl)-3-oxo-N-[rac-(1R)-1-phenylethyl]-6,8-dihydro-5H-imidazo[1,5-a]pyrazine-1-carboxamide | 1H NMR (400 MHz, DMSO-d6, 80° C.): 1.22 (d, J = 7.0 Hz, 3H), 3.69 (d, J = 5.5 Hz, 2H), 3.80 (s, 3H), 3.85 (br s, 2H), 4.84-4.91 (m, 3H), 6.88 (d, J = 7.6 Hz, 1H), 6.98 (d, J = 8.6 Hz, 2H), 7.05 (d, J = 7.2 Hz, 2H), 7.20-7.26 (m, 5H), 7.39 (dd, J = 8.2 Hz, 1.6 Hz, 1H), 7.74 (d, J = 1.6 Hz, 1H), 7.85 (d, J = 8.2 Hz, 1H). |

TABLE A-continued

| Compound # | Structure | Name | NMR |
|---|---|---|---|
| 83 | 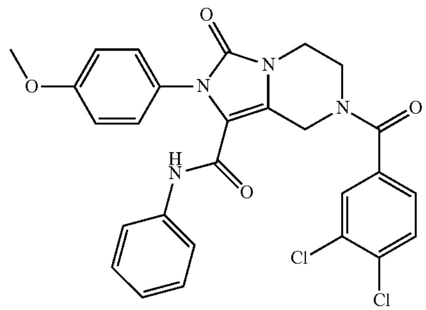 [SMILES: COc1ccc(-n2c(C(=O)Nc3ccccc3)c3n(c2=O)CCN(C(=O)c2ccc(Cl)c(Cl)c2)C3)cc1] | 7-(3,4-dichlorobenzoyl)-2-(4-methoxyphenyl)-3-oxo-N-phenyl-6,8-dihydro-5H-imidazo[1,5-a]pyrazine-1-carboxamide | 1H NMR (400 MHz, DMSO-d6, 80° C.): 3.73-3.76 (m, 2H), 3.81 (s, 3H), 3.85-3.88 (m, 2H), 4.91 (s, 2H), 7.02-7.08 (m, 3H), 7.25-7.33 (m, 6H), 7.51 (d, 2H = 7.8 Hz, 1H), 7.72 (d, J = 7.8 Hz, 1H) 7.78 (s, 1H), 9.00 (s, 1H) |
| 84 | 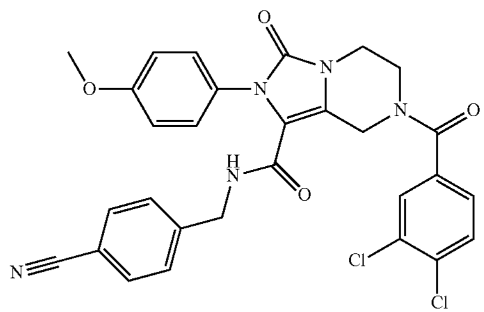 [SMILES: COc1ccc(-n2c(C(=O)NCc3ccc(C#N)cc3)c3n(c2=O)CCN(C(=O)c2ccc(Cl)c(Cl)c2)C3)cc1] | N-[(4-cyanophenyl)methyl]-7-(3,4-dichlorobenzoyl)-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.6 Hz, 2H), 3.80 (s, 3H), 3.81-3.86 (m, 2H), 4.32 (d, J = 6.0 Hz, 2H), 4.85 (s, 2H), 6.96 (d, J = 8.9 Hz, 2H), 7.19 (d, J = 8.9 Hz, 2H), 7.24 (d, J = 8.0 Hz, 2H), 7.41 (br s, 1H), 7.49 (dd, J = 8.2 Hz, 1.7 Hz, 1H), 7.67 (d, J = 8.0 Hz, 2H), 7.71 (d, J = 8.3 Hz, 1H), 7.76 (d, J = 1.7 Hz, 1H) |
| 85 | 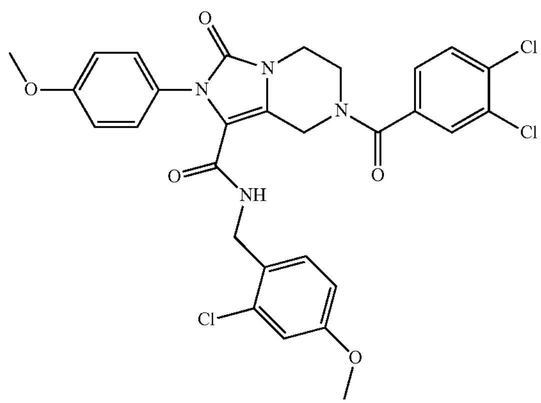 [SMILES: COc1ccc(-n2c(C(=O)NCc3ccc(OC)cc3Cl)c3n(c2=O)CCN(C(=O)c2ccc(Cl)c(Cl)c2)C3)cc1] | N-[(2-chloro-4-methoxyphenyl)methyl]-7-(3,4-dichlorobenzoyl)-2-(4-methoxyphenyl)-3-oxo-6,8-dihydro-5H-imidazo[1,5-a]pyrazine-1-carboxamide | 1H NMR (400 MHz, DMSO-d6, 80° C.): 3.66-3.70 (m, 2H), 3.79 (s, 3H), 3.80 (s, 3H), 3.84 (br s, 2H), 4.25 (d, J = 5.0 Hz, 2H), 4.87 (s, 2H), 6.80 (d, J = 7.7 Hz, 1H), 6.92-7.02 (m, 5H), 7.21 (d, J = 8.4 Hz, 2H), 7.50 (d, J = 8.4 Hz, 1H), 7.72 (d, J = 8.4 Hz, 1H), 7.77 (s, 1H). |

| Compound # | Structure | Name | NMR |
|---|---|---|---|
| 86 | 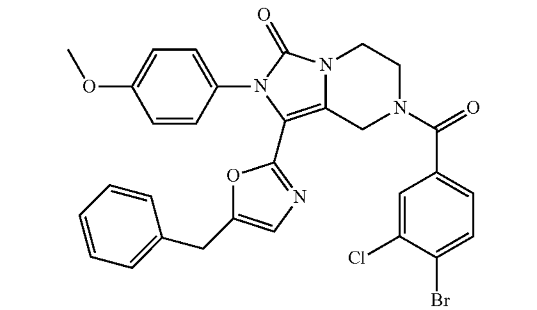 | 1-(5-benzoyloxazol-2-yl)-7-(4-bromo-3-chloro-benzoyl)-2-(4-methoxyphenyl)-6,8-dihydro-5H-imidazo[1,5-a]pyrazin-3-one | 1H NMR (400 MHz, DMSO-d6, 80° C.): 3.69-3.72 (m, 2H), 3.77-3.91 (m, 7H), 4.88 (s, 2H), 6.87 (s, 1H), 6.93 (d, J = 8.0 Hz, 2H), 7.00 (d, J = 6.8 Hz, 2H), 7.15 (d, J = 8.0 Hz, 2H), 7.19-7.29 (m, 3H), 7.41 (d, J = 8.2 Hz, 1H), 7.76 (s, 1H), 7.86 (d, J = 8.0 Hz, 1H). |
| 87 | 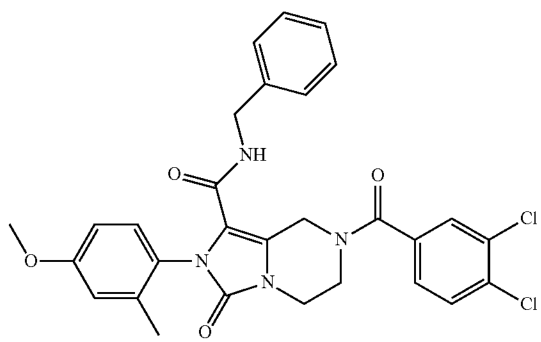 [SMILES: COc1ccc(-n2c(C(=O)NCc3ccccc3)c3n(c2=O)CCN(C(=O)c2ccc(Cl)c(Cl)c2)C3)c(C)c1] | N-benzyl-7-(3,4-dichlorobenzoyl)-2-(4-methoxy-2-methyl-phenyl)-3-oxo-6,8-dihydro-5H-imidazo[1,5-a]pyrazine-1-carboxamide | 1H NMR (400 MHz, DMSO-d6, 80° C.): 2.07 (s, 3H), 3.64-3.73 (m, 2H), 3.78 (s, 3H), 3.81-3.90 (m, 2H), 4.21 (s, 2H), 4.90 (s, 2H), 6.65 (br s, 1H), 6.79 (d, J = 8.6 Hz, 1H), 6.87 (s, 1H), 6.97-6.99 (m, 2H), 7.11 (d, J = 8.6 Hz, 1H), 7.15-7.27 (m, 3H), 7.50 (d, J = 8.1 Hz, 1H), 7.72 (d, J = 8.0 Hz, 1H), 7.77 (s, 1H). |
| 88 | 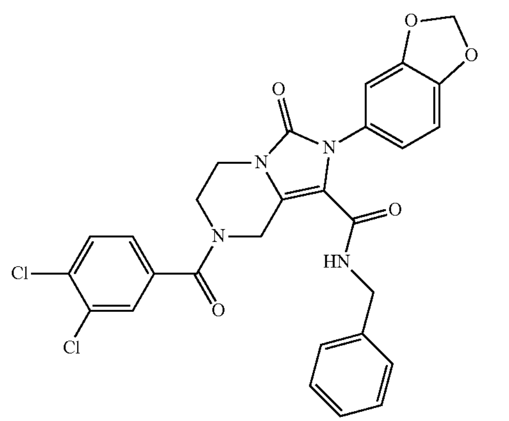 [SMILES: O=C(NCc1ccccc1)c1c2n(c(=O)n1-c1ccc3c(c1)OCO3)CCN(C(=O)c1ccc(Cl)c(Cl)c1)C2] | 2-(1,3-benzodioxol-5-yl)-N-benzyl-7-(3,4-dichlorobenzoyl)-3-oxo-6,8-dihydro-5H-imidazo[1,5-a]pyrazine-1-carboxamide | 1H NMR (400 MHz, DMSO-d6, 80° C.): 3.68 (t, J = 5.5 Hz, 2H), 3.83 (br s, 2H), 4.26 (d, J = 5.6 Hz, 2H), 4.85 (s, 2H), 6.05 (s, 2H), 6.72 (d, J = 8.3 Hz, 1H), 6.84 (s, 1H), 6.89 (d, J = 8.3 Hz, 1H), 7.06 (d, J = 7.0 Hz, 2H), 7.20-7.27 (m, 4H), 7.48 (d, J = 8.3 Hz, 1H), 7.70 (d, J = 8.3 Hz, 1H), 7.75 (s, 1H). |

TABLE A-continued

| Compound # | Structure | Name | NMR |
|---|---|---|---|
| 89 | 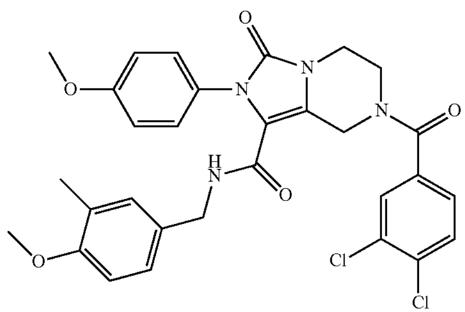 [SMILES: COc1ccc(-n2c(C(=O)NCc3ccc(OC)c(C)c3)c3n(c2=O)CCN(C(=O)c2ccc(Cl)c(Cl)c2)C3)cc1] | 7-(3,4-dichlorobenzoyl)-N-[(4-methoxy-3-methyl-phenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 2.12 (s, 3H), 3.69 (t, J = 5.5 Hz, 2H), 3.78 (s, 3H), 3.79 (s, 3H), 3.82-3.85 (m, 2H), 4.15 (d, J = 5.6 Hz, 2H), 4.87 (s, 2H), 6.78-6.85 (m, 3H), 6.95-6.98 (m, 3H), 7.20 (d, J = 8.8 Hz, 2H), 7.50 (dd, J = 8.2 Hz, 1.8 Hz, 1H), 7.72 (d, J = 8.1 Hz, 1H), 7.77 (d, J = 1.9 Hz, 1H). |
| 90 | 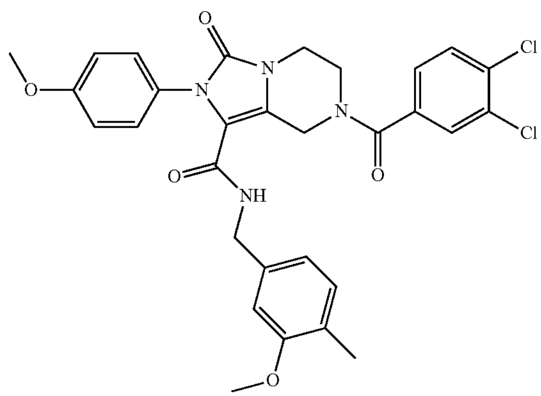 [SMILES: COc1ccc(-n2c(C(=O)NCc3ccc(C)c(OC)c3)c3n(c2=O)CCN(C(=O)c2ccc(Cl)c(Cl)c2)C3)cc1] | 7-(3,4-dichlorobenzoyl)-N-[(3-methoxy-4-methyl-phenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 2.12 (s, 3H), 3.68 (t, J = 5.6 Hz, 2H), 3.74 (s, 3H), 3.78 (s, 3H), 3.81-3.83 (m, 2H), 4.20 (d, J = 5.7 Hz, 2H), 4.87 (s, 2H), 6.51 (d, J = 7.4 Hz, 1H), 6.69 (s, 1H), 6.93 (d, J = 8.8 Hz, 2H), 6.98 (d, J = 7.67 Hz, 1H), 7.13 (br s, 1H), 7.19 (d, J = 8.8 Hz, 2H), 7.48 (dd, J = 8.3 Hz, 1.8 Hz, 1H), 7.71 (d, J = 8.2 Hz, 1H), 7.76 (d, J = 1.6 Hz, 1H). |
| 91 | 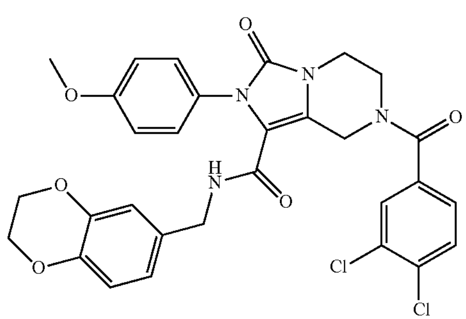 [SMILES: COc1ccc(-n2c(C(=O)NCc3ccc4c(c3)OCCO4)c3n(c2=O)CCN(C(=O)c2ccc(Cl)c(Cl)c2)C3)cc1] | 7-(3,4-dichlorobenzoyl)-N-(2,3-dihydro-1,4-benzodioxin-6-ylmethyl)-2-(4-methoxyphenyl)-3-oxo-6,8-dihydro-5H-imidazo[1,5-a]pyrazine-1-carboxamide | 1H-NMR (DMSO, 600 MHz, 80° C.): 3.65-3.72 (m, 2H), 3.81-3.87 (m, 1H), 4.08-4.16 (m, 2H), 4.19-4.26 (m, 4H), 4.86 (s, 2H); 6.46-6.52 (m, 2H), 6.55 (s, 1H), 6.70 (d, J = 8.3 Hz, 1H), 6.96 (d, J = 8.9 Hz, 2H); 6.99-7.10 (br. s, 1H), 7.19 (d, J = 8.8 Hz, 2H), 7.50 (dd, J = 8.3 Hz, 2.0 Hz, 1H), 7.72 (d, J = 8.2 Hz, 1H), 7.77 (d, J = 8.2 Hz, 1H) ppm. |

| Compound # | Structure | Name | NMR |
|---|---|---|---|
| 92 | 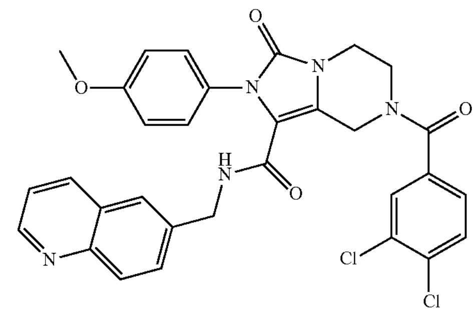 [SMILES: COc1ccc(-n2c(C(=O)NCc3ccc4ncccc4c3)c3n(c2=O)CCN(C(=O)c2ccc(Cl)c(Cl)c2)C3)cc1] | 7-(3,4-dichlorobenzoyl)-2-(4-methoxyphenyl)-3-oxo-N-(6-quinolylmethyl)-6,8-dihydro-5H-imidazo[1,5-a]pyrazine-1-carboxamide | 1H-NMR (DMSO, 600 MHz, 80° C.): 3.67-3.72 (m, 2H), 3.73 (s, 3H), 3.78-3.94 (m, 2H), 4.47 (d, J = 5.4 Hz, 2H), 4.91 (s, 2H), 6.94 (d, J = 8.8 Hz, 2H), 7.23 (d, J = 8.8 Hz, 2H), 7.32-7.54 (m, 4H), 7.59 (s, 1H), 7.70 (d, J = 8.2 Hz, 1H), 7.78 (d, J = 2.0 Hz, 1H), 7.92 (d, J = 8.7 Hz, 1H), 8.24 (d, J = 8.1 Hz, 1H), 8.87 (d, J = 4.2 Hz, 1.8 Hz, 1H) ppm. |
| 93 | 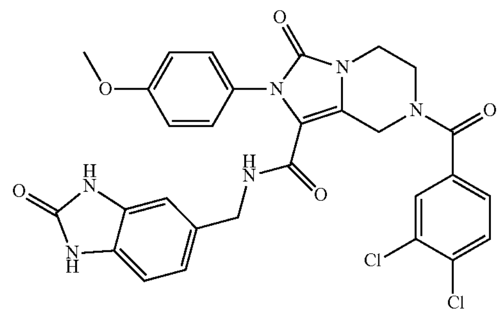 [SMILES: COc1ccc(-n2c(C(=O)NCc3ccc4[nH]c(=O)[nH]c4c3)c3n(c2=O)CCN(C(=O)c2ccc(Cl)c(Cl)c2)C3)cc1] | 7-(3,4-dichlorobenzoyl)-2-(4-methoxyphenyl)-3-oxo-N-[(2-oxo-1,3-dihydrobenzimidazol-5-yl)methyl]-6,8-dihydro-5H-imidazo[1,5-a]pyrazine-1-carboxamide | 1H-NMR (DMSO, 600 MHz, 80° C.): 3.68 (t, J = 5.5 Hz, 3H); 3.75 (s, 3H); 3.82 (br. s. 2H); 4.20 (d, J = 5.4 Hz, 2H); 4.85 (s, 2H); 6.60 (d, J = 8.0 Hz, 1H); 6.70 (d, J = 8.9 Hz, 1H); 6.78 (d, J = 8.0 Hz, 1H), 6.93 (d, J = 8.9 Hz, 2H), 7.01 (br. s, 1H); 7.17 (d, J = 8.9 Hz, 2H), 7.48 (dd, J = 8.2 Hz, 1.8 Hz, 1H), 7.70 (d, J = 8.2 Hz, 1H), 7.76 (d, J = 1.8 Hz, 1H), 10.26 (s, 2H) ppm. |
| 94 | 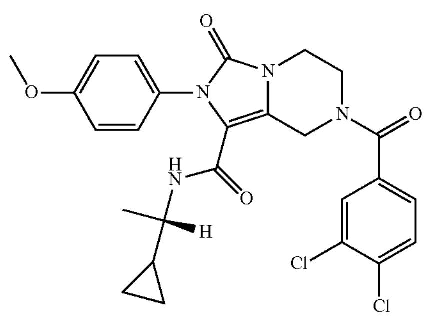 [SMILES: COc1ccc(-n2c(C(=O)N[C@@H](C)C3CC3)c3n(c2=O)CCN(C(=O)c2ccc(Cl)c(Cl)c2)C3)cc1] | 7-(3,4-dichlorobenzoyl)-2-(4-methoxyphenyl)-3-oxo-N-[rac-(1S)-1-cyclopropylethyl]-6,8-dihydro-5H-imidazo[1,5-a]pyrazine-1-carboxamide | 1H-NMR (DMSO, 600 MHz, 80° C.): −0.01-0.07 (m, 2H); 0.15-0.24 (m, 1H); 0.28-0.36 (m, 1H); 0.60-0.70 (m, 1H); 0.96 (d, J = 6.4 Hz, 3H); 3.28 (sext, J = 7.1 Hz, 1H); 3.69 (t, J = 5.5 Hz, 2H); 3.77-3.92 (m, 5H); 4.81 (br. s., 2H); 6.53 (d, J = 7.9 Hz, 1H), 7.02 (d, J = 9.0 Hz, 2H), 7.23 (d, J = 8.8 Hz, 2H), 7.49 (dd, J = 8.2 Hz, 1.9 Hz, 1H), 7.72 (d, J = 8.2 Hz, 1H), 7.76 (d, J = 1.9 Hz, 1H) ppm. |

TABLE A-continued

| Compound # | Structure | Name | NMR |
|---|---|---|---|
| 95 | 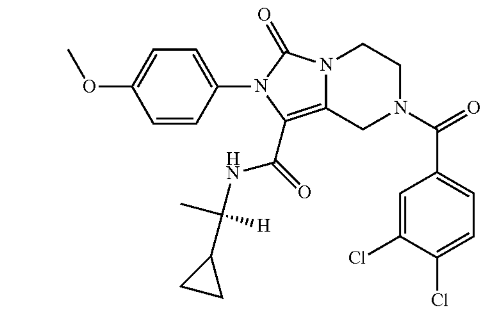 [SMILES: COc1ccc(-n2c(C(=O)N[C@H](C)C3CC3)c3n(c2=O)CCN(C(=O)c2ccc(Cl)c(Cl)c2)C3)cc1] | 7-(3,4-dichlorobenzoyl)-2-(4-methoxyphenyl)-3-oxo-N-[rac-(1R)-1-cyclopropylethyl]-6,8-dihydro-5H-imidazo[1,5-a]pyrazine-1-carboxamide | 1H-NMR (DMSO, 600 MHz, 80° C.): −0.02-0.08 (m, 2H), 0.15-0.25 (m, 1H), 0.29-0.35 (m, 1H), 0.60-0.69 (m, 1H), 0.96 (d, J = 6.4 Hz, 3H), 3.28 (sext, J = 7.1 Hz, 1H), 3.69 (t, J = 5.5 Hz, 2H), 3.78-3.91 (m, 5H), 4.82 (br. s., 2H), 6.53 (d, J = 7.9 Hz, 1H), 7.02 (d, J = 8.9 Hz, 2H), 7.23 (d, J = 8.9 Hz, 2H), 7.49 (dd, J = 8.2 Hz, 1.9 Hz, 1H), 7.72 (d, J = 8.2 Hz, 1H), 7.76 (d, J = 1.8 Hz, 1H) ppm. |
| 96 | 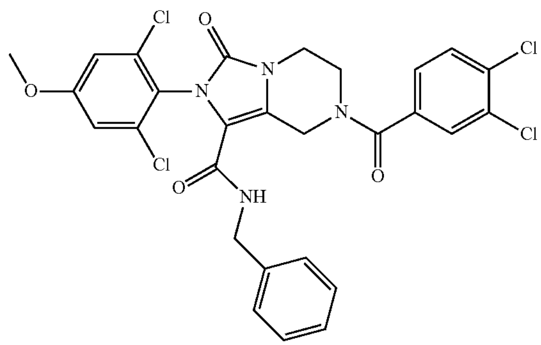 [SMILES: COc1cc(Cl)c(-n2c(C(=O)NCc3ccccc3)c3n(c2=O)CCN(C(=O)c2ccc(Cl)c(Cl)c2)C3)c(Cl)c1] | N-benzyl-7-(3,4-dichlorobenzoyl)-2-(2,6-dichloro-4-methoxy-phenyl)-3-oxo-6,8-dihydro-5H-imidazo[1,5-a]pyrazine-1-carboxamide | 1H NMR (400 MHz, DMSO-d6) δ 8.19 (s, 1H), 7.82 (s, 1H), 7.73 (d, J = 8.2 Hz, 1H), 7.51 (s, 1H), 7.19 (d, J = 12.8 Hz, 7H), 4.99 (s, 2H), 4.29 (s, 2H), 3.85-3.70 (m, 7H). |
| 97 | 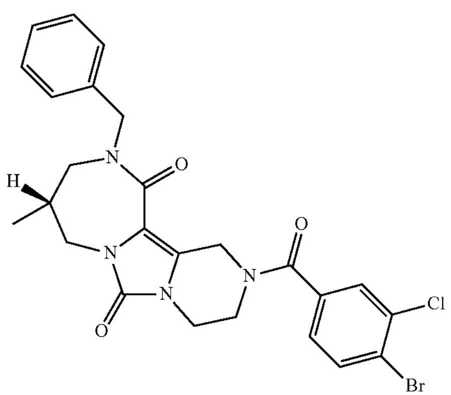 [SMILES: C[C@@H]1CN(Cc2ccccc2)C(=O)c2c3n(c(=O)n2C1)CCN(C(=O)c1ccc(Br)c(Cl)c1)C3] | rac-(11R)-13-benzyl-4-(4-bromo-3-chloro-benzoyl)-11-methyl-4,7,9,13-tetrazatricyclo[7.5.0.0 2,7]tetradec-1-ene-8,14-dione | 1H NMR (300 MHz, Chloroform-d) δ 7.74 (d, J = 8.2 Hz, 1H), 7.61 (d, J = 2.0 Hz, 1H), 7.43-7.32 (m, 3H), 7.30-7.20 (m, 3H), 4.91 (d, J = 14.6 Hz, 3H), 4.38 (d, J = 14.5 Hz, 1H), 4.25-3.71 (m, 5H), 3.64 (dd, J = 13.9, 4.6 Hz, 1H), 3.29 (dd, J = 15.0, 5.5 Hz, 1H), 3.07 (dd, J = 14.9, 8.3 Hz, 1H), 2.10-1.95 (m, 1H), 0.91 (d, J = 6.8 Hz, 3H). |

TABLE A-continued

| Compound # | Structure | Name | NMR |
|---|---|---|---|
| 98 | 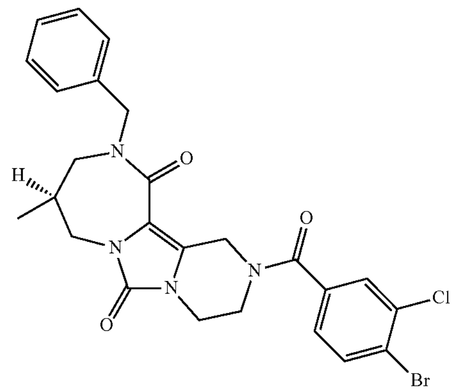 [SMILES: C[C@H]1CN(Cc2ccccc2)C(=O)c2c3n(c(=O)n2C1)CCN(C(=O)c1ccc(Br)c(Cl)c1)C3] | rac-((1S)-13-benzyl-4-(4-bromo-3-chloro-benzoyl)-11-methyl-4,7,9,13-tetrazatricyclo[7.5.0.0²,⁷]tetradec-1-ene-8,14-dione | 1H NMR (300 MHz, Chloroform-d) δ 7.74 (d, J = 8.2 Hz, 1H), 7.61 (d, J = 2.0 Hz, 1H), 7.43-7.32 (m, 3H), 7.30-7.20 (m, 3H), 4.91 (d, J = 14.6 Hz, 3H), 4.38 (d, J = 14.5 Hz, 1H), 4.25-3.71 (m, 5H), 3.64 (dd, J = 13.9, 4.6 Hz, 1H), 3.29 (dd, J = 15.0, 5.5 Hz, 1H), 3.07 (dd, J = 14.9, 8.3 Hz, 1H), 2.10-1.95 (m, 1H), 0.91 (d, J = 6.8 Hz, 3H). |
| 99 | 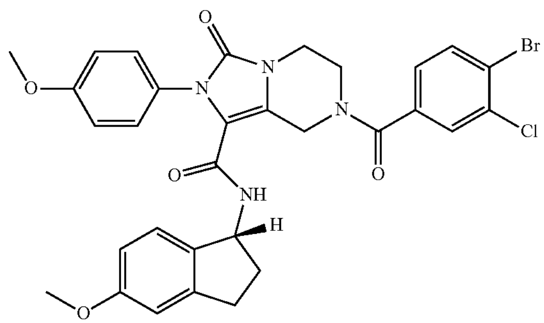 [SMILES: COc1ccc(-n2c(C(=O)N[C@@H]3CCc4cc(OC)ccc43)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-5-methoxyindazin-1-yl]-6,8-dihydro-5H-imidazo[1,5-a]pyrazine-1-carboxamide | 1H NMR (400 MHz, Chloroform-d) δ 7.75 (d, J = 8.2 Hz, 1H), 7.65 (s, 1H), 7.26-7.24 (m, 2H), 7.21-7.19 (d, J = 8.5 Hz, 2H), 6.89 (d, J = 8.5 Hz, 2H), 6.77 (d, J = 8.3 Hz, 1H), 6.69-6.65 (m, 1H), 5.15-5.00 (m, 3H), 4.07 (s, 2H), 3.86 (s, 2H), 3.79 (d, J = 4.9 Hz, 6H), 2.71 (q, J = 6.5, 5.7 Hz, 2H), 2.42 (s, 1H), 1.57-1.47 (m, 1H). |
| 100 | 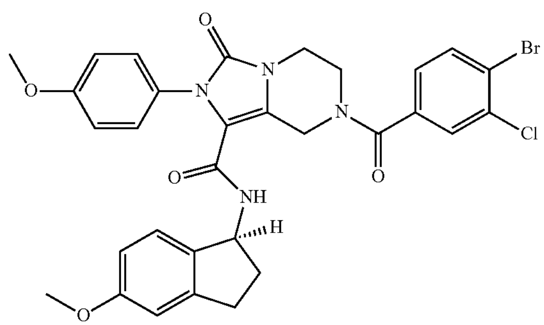 [SMILES: COc1ccc(-n2c(C(=O)N[C@H]3CCc4cc(OC)ccc43)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1S)-5-methoxyindazin-1-yl]-6,8-dihydro-5H-imidazo[1,5-a]pyrazine-1-carboxamide | 1H NMR (400 MHz, Chloroform-d) δ 7.75 (d, J = 8.2 Hz, 1H), 7.65 (s, 1H), 7.26-7.24 (m, 2H), 7.21-7.19 (d, J = 8.5 Hz, 2H), 6.89 (d, J = 8.5 Hz, 2H), 6.77 (d, J = 8.3 Hz, 1H), 6.69-6.65 (m, 1H), 5.15-5.00 (m, 3H), 4.07 (s, 2H), 3.86 (s, 2H), 3.79 (d, J = 4.9 Hz, 6H), 2.71 (q, J = 6.5, 5.7 Hz, 2H), 2.42 (s, 1H), 1.57-1.47 (m, 1H). |

TABLE A-continued

| Compound # | Structure | Name | NMR |
|---|---|---|---|
| 101 | 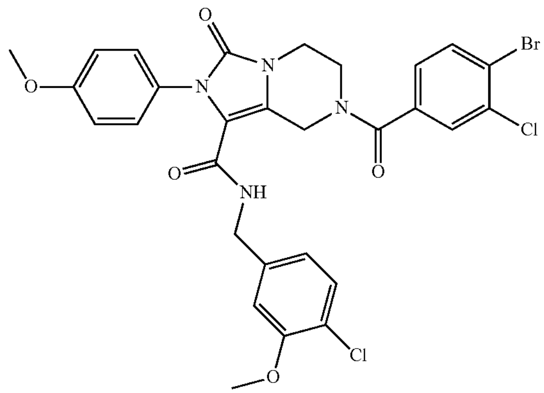 [SMILES: COc1ccc(-n2c(C(=O)NCc3ccc(Cl)c(OC)c3)c3n(c2=O)CCN(C(=O)c2ccc(Br)c(Cl)c2)C3)cc1] | 7-(4-bromo-3-chloro-benzoyl)-N-[(4-chloro-3-methoxy-phenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.68 (t, J = 5.0 Hz, 2H), 3.79 (s, 3H), 3.81 (s, 3H), 4.24 (d, J = 5.4 Hz, 2H), 4.69 (s, 2H), 6.63 (d, J = 7.9 Hz, 1H), 6.90-6.95 (m, 3H), 7.19 (d, J = 7.6 Hz, 2H), 7.25 (d, J = 7.9 Hz, 1H), 7.26 (br s, 1H), 7.39 (d, J = 8.3 Hz, 1H), 7.74 (s, 1H), 7.85 (d, J = 8.1 Hz, 1H). |
| 102 | 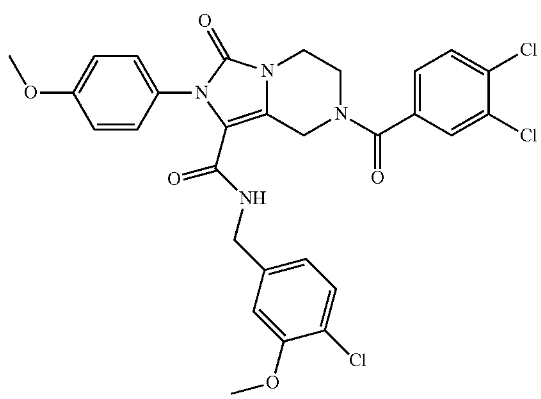 [SMILES: COc1ccc(-n2c(C(=O)NCc3ccc(Cl)c(OC)c3)c3n(c2=O)CCN(C(=O)c2ccc(Cl)c(Cl)c2)C3)cc1] | N-[(4-chloro-3-methoxy-phenyl)methyl]-7-(3,4-dichlorobenzoyl)-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.0 Hz, 2H), 3.78 (s, 3H), 3.81 (s, 3H), 3.80-3.83 (m, 2H), 4.24 (d, J = 5.4 Hz, 2H), 4.87 (s, 2H), 6.63 (d, J = 7.9 Hz, 1H), 6.90-6.95 (m, 3H), 7.19 (d, J = 7.9 Hz, 2H), 7.25 (d, J = 8.0 Hz, 1H), 7.26 (br s, 1H), 7.49 (d, J = 7.9 Hz, 1H), 7.71 (d, J = 8.5 Hz, 1H), 7.76 (s, 1H) |

TABLE A-continued

| Compound # | Structure | Name | NMR |
|---|---|---|---|
| 103 | 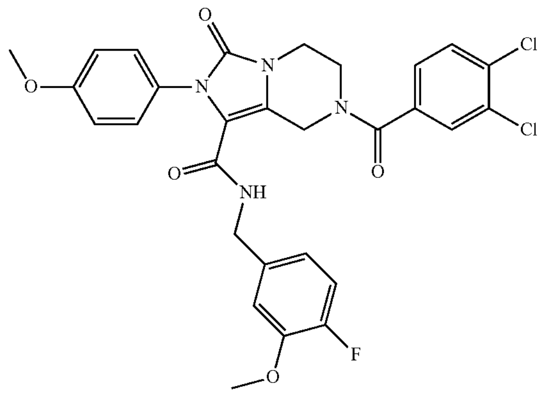 [SMILES: COc1ccc(-n2c(C(=O)NCc3ccc(F)c(OC)c3)c3n(c2=O)CCN(C(=O)c2ccc(Cl)c(Cl)c2)C3)cc1] | 7-(3,4-dichlorobenzoyl)-N-[(4-fluoro-3-methoxy-phenyl)methyl]-2-(4-methoxyphenyl)-3-oxo-6,8-dihydro-5H-imidazo[1,5-a]pyrazine-1-carboxamide | H NMR (400 MHz, DMSO-d6, 80° C.): 3.68 (t, J = 5.8 Hz, 2H), 3.78 (s, 3H), 3.80 (s, 3H), 3.81-3.84 (m, 2H), 4.21 (d, J = 5.6 Hz, 2H), 4.86 (s, 2H), 6.61-6.62 (m, 1H), 6.89-6.96 (m, 3H), 7.02 (dd, J = 11.5 Hz, 8.3 Hz, 1H), 7.18-7.21 (m, 3H), 7.48 (dd, J = 8.3 Hz, 1.8 Hz, 1H), 7.70 (d, J = 8.3 Hz, 1H), 7.75 (d, J = 1.5 Hz, 1H). |
| 104 | 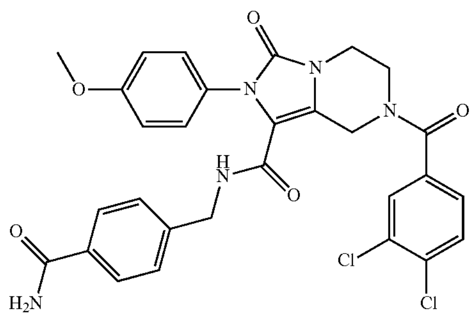 [SMILES: COc1ccc(-n2c(C(=O)NCc3ccc(C(N)=O)cc3)c3n(c2=O)CCN(C(=O)c2ccc(Cl)c(Cl)c2)C3)cc1] | N-[(4-carbamoylphenyl)methyl]-7-(3,4-dichlorobenzoyl)-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.2 Hz, 2H), 3.79 (s, 3H), 3.80-3.83 (m, 2H), 4.29 (d, J = 5.7 Hz, 2H), 4.87 (s, 2H), 6.96 (d, J = 8.7 Hz, 2H), 7.12 (d, J = 7.7 Hz, 2H), 7.20 (d, J = 8.7 Hz, 2H), 7.22-7.45 (m, 3H), 7.49 (d, J = 8.2 Hz, 1H), 7.71 (d, J = 8.2 Hz, 1H), 7.74-7.79 (m, 3H). |
| 105 | 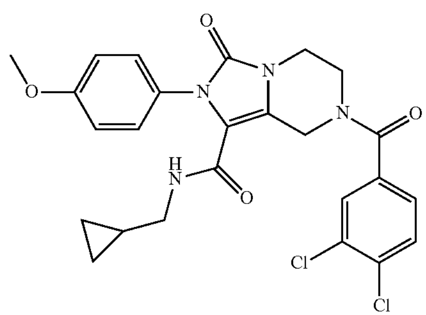 [SMILES: COc1ccc(-n2c(C(=O)NCC3CC3)c3n(c2=O)CCN(C(=O)c2ccc(Cl)c(Cl)c2)C3)cc1] | N-(cyclopropylmethyl)-7-(3,4-dichlorobenzoyl)-2-(4-methoxyphenyl)-3-oxo-6,8-dihydro-5H-imidazo[1,5-a]pyrazine-1-carboxamide | 1H-NMR (DMSO, 600 MHz, 80° C.): −0.08-0.05 (m, 2H); 0.22-0.34 (m, 2H); 0.67-0.76 (m, 1H); 2.93 (t, J = 6.0 Hz, 2H); 3.69 (t, J = 5.6 Hz, 2H); 3.81 (s, 3H); 3.84 (br. s., 2H); 4.84 (br. s., 2H); 6.67 (br. s., 1H); 7.01 (d, J = 8.9 Hz, 2H); 7.22 (d, J = 8.8 Hz, 2H); 7.49 (dd, J = 8.3 Hz, 2.0 Hz, 1H); 7.72 (d, J = 8.2 Hz, 1H); 7.76 (d, J = 1.9 Hz, 1H) ppm. |

TABLE A-continued

| Compound # | Structure | Name | NMR |
|---|---|---|---|
| 106 | 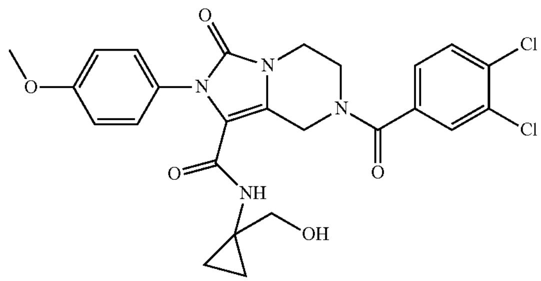 [SMILES: COc1ccc(-n2c(C(=O)NC3(CO)CC3)c3n(c2=O)CCN(C(=O)c2ccc(Cl)c(Cl)c2)C3)cc1] | 7-(3,4-dichlorobenzoyl)-N-[1-(hydroxymethyl)cyclopropyl]-2-(4-methoxyphenyl)-3-oxo-6,8-dihydro-5H-imidazo[1,5-a]pyrazine-1-carboxamide | 1H-NMR (DMSO, 600 MHz, 80° C.): 0.30-0.38 (m, 2H); 0.62-0.67 (m, 2H); 3.33-3.37 (m, 2H); 3.67 (t, J = 5.6 Hz, 2H); 3.78-3.86 (m, 5H); 4.30 (br. s., 1H); 4.80 (br. s., 2H); 6.94 (br. s., 1H); 7.00 (d, J = 8.9 Hz, 2H); 7.19 (d, J = 9.0 Hz, 2H); 7.48 (dd, J = 8.3 Hz, 1.9 Hz, 1H); 7.72 (d, J = 8.3 Hz, 1H); 7.76 (d, J = 1.9 Hz, 1H) ppm. |
| 107 | 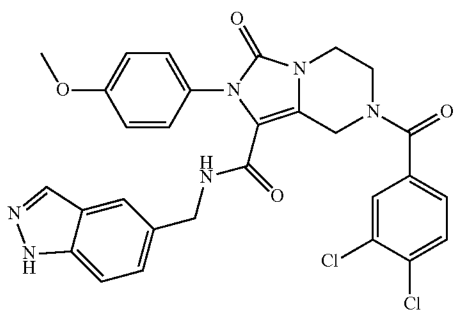 [SMILES: COc1ccc(-n2c(C(=O)NCc3ccc4[nH]ncc4c3)c3n(c2=O)CCN(C(=O)c2ccc(Cl)c(Cl)c2)C3)cc1] | 7-(3,4-dichlorobenzoyl)-N-(1H-indazol-5-ylmethyl)-2-(4-methoxyphenyl)-3-oxo-6,8-dihydro-5H-imidazo[1,5-a]pyrazine-1-carboxamide | 1H-NMR (DMSO, 600 MHz, 80° C.): 3.65-3.71 (m, 2H); 3.75 (s, 3H); 3.79-3.88 (m, 2H); 4.34 (d, J = 6.0 Hz, 2H); 4.88 (s, 2H); 6.93 (d, J = 8.8 Hz, 2H); 7.02-7.08 (m, 1H); 7.09-7.18 (m, 1H); 7.20 (d, J = 8.8 Hz, 2H); 7.37 (s, 1H); 7.42 (d, J = 8.6 Hz, 1H); 7.49 (dd, J = 8.3 Hz, 2.0 Hz, 1H); 7.70 (d, J = 8.1 Hz, 1H); 7.77 (d, J = 2.0 Hz, 1H); 7.96 (s, 1H), 12.79 (s, 1H) ppm. |
| 108 | 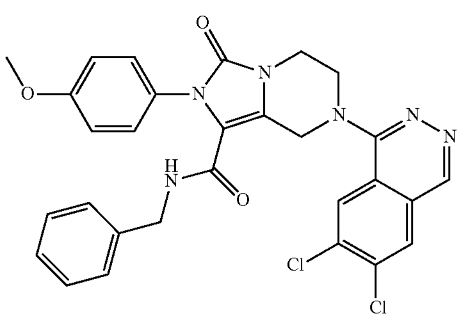 [SMILES: COc1ccc(-n2c(C(=O)NCc3ccccc3)c3n(c2=O)CCN(c2nncc4cc(Cl)c(Cl)cc24)C3)cc1] | N-benzyl-7-(6,7-dichloroquinazolin-4-yl)-2-(4-methoxyphenyl)-3-oxo-6,8-dihydro-5H-imidazo[1,5-a]pyrazine-1-carboxamide | 1H-NMR (DMSO, 400 MHz, 25° C.): 3.78 (s, 3H); 3.87-3.96 (m, 2H); 4.10-4.20 (m, 2H); 4.29 (d, J = 5.7 Hz, 2H); 5.09 (s, 2H); 6.97 (d, J = 8.5 Hz, 2H); 7.08-7.13 (m, 2H); 7.14-7.29 (m, 5H); 7.86-7.94 (m, 1H); 8.16 (s, 1H); 8.29 (s, 1H); 8.73 (s, 1H) ppm. |

TABLE A-continued

| Compound # | Structure | Name | NMR |
|---|---|---|---|
| 109 | 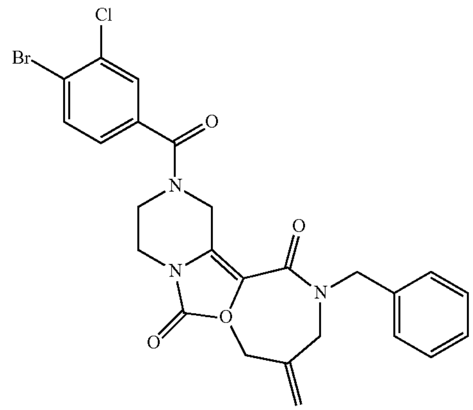 | 13-benzyl-4-(4-bromo-3-chlorobenzoyl)-11-methylene-4,7,9,13-tetrazatricyclo[7.5.0.0^2,7]tetradec-1-ene-8,14-dione | 1H NMR (400 MHz, DMSO-d6) δ 7.87 (d, J = 8.2 Hz, 1H), 7.76 (d, J = 2.0 Hz, 1H), 7.38 (dd, J = 8.2, 2.0 Hz, 1H), 7.29-7.10 (m, 5H), 4.96 (m, 2H), 4.83 (s, 1H); 4.57 (m, 3H), 4.40 (s, 2H), 3.91 (s, 3H), 3.62 (s, 3H). |
| 110 | 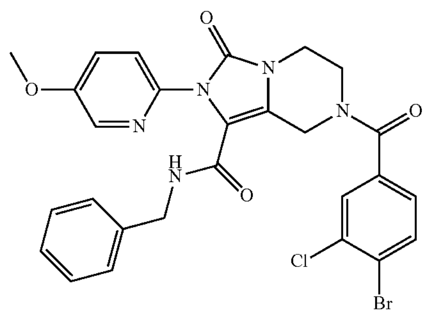 | N-benzyl-7-(4-bromo-3-chlorobenzoyl)-2-(5-methoxy-2-pyridyl)-3-oxo-6,8-dihydro-5H-imidazo[1,5-a]pyrazine-1-carboxamide | 1H NMR (400 MHz, Chloroform-d) δ 8.13 (s, 1H), 7.76-7.67 (m, 2H), 7.61 (d, J = 1.9 Hz, 1H), 7.55 (d, J = 8.9 Hz, 1H), 7.34 (dd, J = 8.9, 3.1 Hz, 1H), 7.33-7.27 (m, 3H), 7.26-7.20 (m, 1H), 7.10 (s, 2H), 5.03 (s, 2H), 4.37 (s, 2H), 4.02 (br, 2H), 3.81 (m, 5H) |
| 111 | 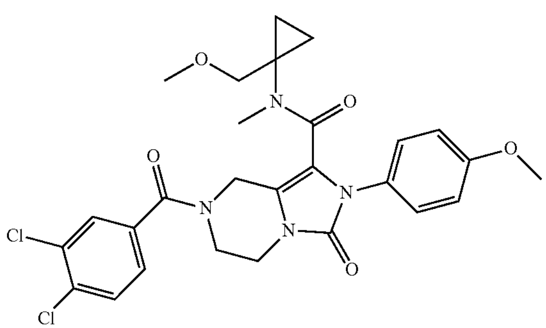 [SMILES: COCC1(N(C)C(=O)c2c3n(c(=O)n2-c2ccc(OC)cc2)CCN(C(=O)c2ccc(Cl)c(Cl)c2)C3)CC1] | 7-(3,4-dichlorobenzoyl)-N-[1-(methoxymethyl)cyclopropyl]-2-(4-methoxyphenyl)-N-methyl-3-oxo-6,8-dihydro-5H-imidazo[1,5-a]pyrazine-1-carboxamide | 1H-NMR (DMSO, 600 MHz, 80° C.): 0.48 (s, 2H), 0.72 (s, 2H), 2.74 (s, 3H), 3.18 (s, 3H), 3.35 (s, 2H), 3.64-3.70 (m, 2H), 3.79 (s, 3H), 3.82-3.91 (br. s., 2H), 4.57 (br. s., 2H), 6.98 (d, J = 9.0 Hz, 2H), 7.16 (d, J = 9.0 Hz, 2H), 7.49 (dd, J = 7.8 Hz, 1.4 Hz, 1H), 7.73 (d, J = 7.8 Hz, 1H), 7.78 (d, J = 1.4 Hz, 1H) ppm. |

TABLE A-continued

| Compound # | Structure | Name | NMR |
|---|---|---|---|
| 112 | 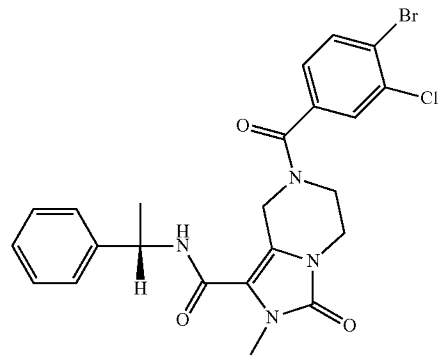 [SMILES: C[C@H](NC(=O)c1c2n(c(=O)n1C)CCN(C(=O)c1ccc(Br)c(Cl)c1)C2)c1ccccc1] | 7-(4-bromo-3-chloro-benzoyl)-2-methyl-3-oxo-N-[rac-(1S)-1-phenylethyl]-6,8-dihydro-5H-imidazo[1,5-a]pyrazine-1-carboxamide | 1H-NMR (DMSO, 600 MHz, 80° C.): 1.40 (br. s., 3H), 3.25 (s, 3H), 3.59-3.69 (m, 2H), 3.71-3.90 (m, 2H), 4.70-4.83 (m, 2H), 4.98-5.07 (m, 1H), 7.20-7.25 (m, 1H), 7.26-7.34 (m, 4H), 7.37 (dd, J = 8.0 Hz, 1.3 Hz, 1H), 7.72 (d, J = 1.3 Hz, 1H), 7.84 (d, J = 8.0 Hz, 1H), 7.92 (br. s., 1H) ppm. |
| 113 | 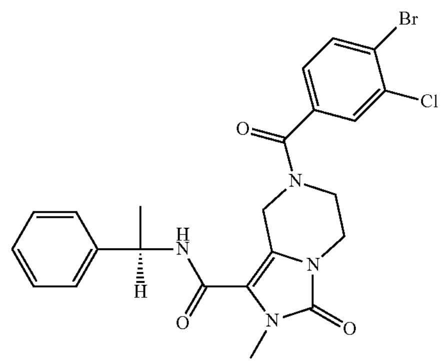 [SMILES: C[C@@H](NC(=O)c1c2n(c(=O)n1C)CCN(C(=O)c1ccc(Br)c(Cl)c1)C2)c1ccccc1] | 7-(4-bromo-3-chloro-benzoyl)-2-methyl-3-oxo-N-[rac-(1R)-1-phenylethyl]-6,8-dihydro-5H-imidazo[1,5-a]pyrazine-1-carboxamide | 1H-NMR (DMSO, 600 MHz, 80° C.): 1.40 (br. s., 3H), 3.25 (s, 3H), 3.59-3.69 (m, 2H), 3.71-3.90 (m, 2H), 4.70-4.83 (m, 2H), 4.98-5.07 (m, 1H), 7.20-7.25 (m, 1H), 7.26-7.34 (m, 4H), 7.37 (dd, J = 8.0 Hz, 1.3 Hz, 1H), 7.72 (d, J = 1.3 Hz, 1H), 7.84 (d, J = 8.0 Hz, 1H), 7.92 (br. s., 1H) ppm. |
| 114 | 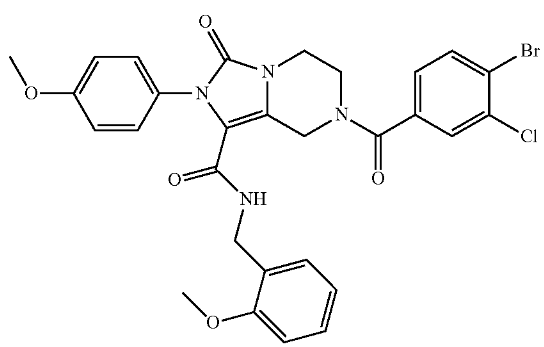 | 7-(4-bromo-3-chloro-benzoyl)-2-(4-methoxyphenyl)-N-[(2-methoxyphenyl)methyl]-3-oxo-6,8-dihydro-5H-imidazo[1,5-a]pyrazine-1-carboxamide | 1H-NMR (DMSO, 600 MHz, 80° C.): 3.65-3.69 (m, 2H), 3.72 (s, 3H), 3.80 (s, 3H), 3.81-3.89 (m, 2H), 4.22 (d, J = 4.5 Hz, 2H), 4.87 (s, 2H), 6.68-6.78 (br. s., 1H), 6.79-6.84 (m, 1H), 6.92 (d, J = 8.2 Hz, 2H), 6.97 (d, J = 8.9 Hz, 2H), 7.16-7.26 (m, 3H), 7.40 (d, J = 8.1 Hz, 1.4 Hz, 1H), 7.75 (d, J = 1.4 Hz, 1H), 7.86 (dd, J = 8.1 Hz, 1H) ppm. |

TABLE A-continued

| Compound # | Structure | Name | NMR |
|---|---|---|---|
| 115 | 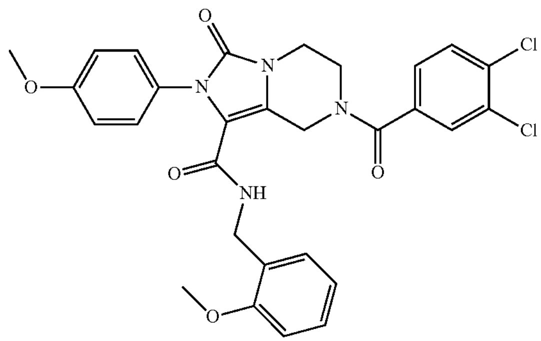 [SMILES: COc1ccc(-n2c(C(=O)NCc3ccccc3OC)c3n(c2=O)CCN(C(=O)c2ccc(Cl)c(Cl)c2)C3)cc1] | 7-(3,4-dichlorobenzoyl)-2-(4-methoxyphenyl)-N-[(2-methoxyphenyl)methyl]-3-oxo-6,8-dihydro-5H-imidazo[1,5-a]pyrazine-1-carboxamide | 1H-NMR (DMSO, 600 MHz, 80° C.): 3.65-3.70 (m, 2H), 3.72 (s, 3H), 3.80 (s, 3H), 3.81-3.90 (m, 2H), 4.22 (d, J = 4.8 Hz, 2H), 4.87 (s, 2H), 6.67-6.77 (br. s., 1H), 6.78-6.85 (m, 1H), 6.92 (d, J = 8.1 Hz, 2H), 6.97 (d, J = 9.0 Hz, 2H), 7.16-7.26 (m, 3H), 7.49 (d, J = 8.3 Hz, 1.3 Hz, 1H), 7.72 (d, J = 8.3 Hz, 1H), 7.77 (d, J = 1.3 Hz, 1H) ppm. |
| 116 | 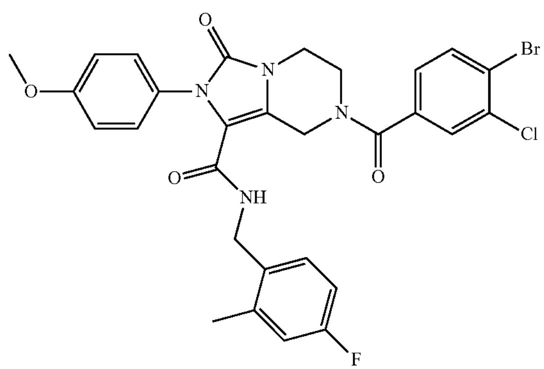 [SMILES: COc1ccc(-n2c(C(=O)NCc3ccc(F)cc3C)c3n(c2=O)CCN(C(=O)c2ccc(Br)c(Cl)c2)C3)cc1] | 7-(4-bromo-3-chloro-benzoyl)-N-[(4-fluoro-2-methyl-phenyl)methyl]-2-(4-methoxyphenyl)-3-oxo-6,8-dihydro-5H-imidazo[1,5-a]pyrazine-1-carboxamide | 1H-NMR (DMSO, 600 MHz, 80° C.): 2.14 (s, 3H); 3.65-3.70 (m, 2H); 3.78 (s, 3H); 3.83 (br. s., 2H); 4.14-4.23 (m, 2H); 4.84 (s, 2H); 6.79-6.86 (m, 1H); 6.89-6.99 (m, 5H); 7.18 (d, J = 8.6 Hz, 2H); 7.39 (d, J = 8.4 Hz, 1H); 7.74 (s, 1H); 7.86 (d, J = 8.3 Hz, 1H) ppm. |
| 117 | 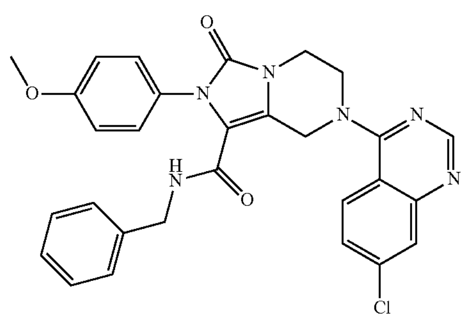 [SMILES: COc1ccc(-n2c(C(=O)NCc3ccccc3)c3n(c2=O)CCN(c2ncnc4cc(Cl)ccc24)C3)cc1] | N-benzyl-7-(7-chloroquinazolin-4-yl)-2-(4-methoxyphenyl)-3-oxo-6,8-dihydro-5H-imidazo[1,5-a]pyrazine-1-carboxamide | 1H-NMR (DMSO, 400 MHz, 25° C.): 3.78 (s, 3H), 3.84-4.00 (m, 2H), 4.05-4.19 (m, 2H), 4.28 (d, J = 6.1 Hz, 2H), 5.06 (s, 2H), 6.97 (d, J = 8.9 Hz, 2H), 7.07-7.14 (m, 2H), 7.15-7.31 (m, 5H), 7.58 (dd, J = 9.0 Hz, 2.3 Hz, 1H), 7.90 (t, J = 5.9 Hz, 1H), 7.90 (d, J = 2.3 Hz, 1H), 8.11 (d, J = 9.1 Hz, 1H), 8.73 (s, 1H) ppm. |

| Compound # | Structure | Name | NMR |
|---|---|---|---|
| 118 | 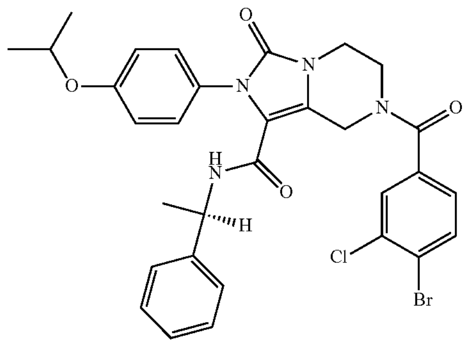 [SMILES: CC(C)Oc1ccc(-n2c(C(=O)N[C@H](C)c3ccccc3)c3n(c2=O)CCN(C(=O)c2ccc(Br)c(Cl)c2)C3)cc1] | 7-(4-bromo-3-chloro-benzoyl)-2-(4-isopropoxyphenyl)-3-oxo-N-[rac-(1R)-1-phenylethyl]-6,8-dihydro-5H-imidazo[1,5-a]pyrazine-1-carboxamide | 1H NMR (400 MHz, DMSO-d6, 80° C.): 1.20 (d, J = 6.9 Hz, 3H), 1.30 (d, J = 6.0 Hz, 6H), 3.68 (t, J = 5.5 Hz, 2H), 3.84 (br s, 2H), 4.61 (hept., J = 6.0 Hz, 1H), 4.80-4.93 (m, 3H), 6.82 (d, J = 7.4 Hz, 1H), 6.96 (d, J = 8.7 Hz, 2H), 7.05 (d, J = 7.2 Hz, 2H), 7.13-7.27 (m, 5H), 7.39 (dd, J = 8.2 Hz, 1.5 Hz, 1H), 7.74 (d, J = 1.4 Hz, 1H), 7.85 (d, J = 8.2 Hz, 1H). |
| 119 | 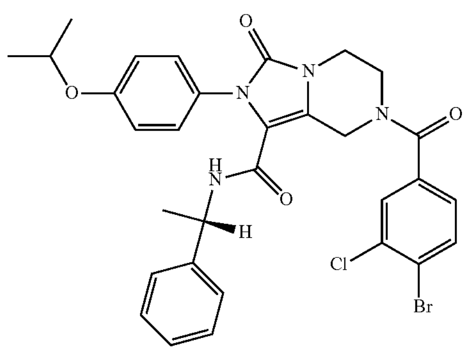 [SMILES: CC(C)Oc1ccc(-n2c(C(=O)N[C@@H](C)c3ccccc3)c3n(c2=O)CCN(C(=O)c2ccc(Br)c(Cl)c2)C3)cc1] | 7-(4-bromo-3-chloro-benzoyl)-2-(4-isopropoxyphenyl)-3-oxo-N-[rac-(1S)-1-phenylethyl]-6,8-dihydro-5H-imidazo[1,5-a]pyrazine-1-carboxamide | 1H NMR (400 MHz, DMSO-d6, 80° C.): 1.20 (d, J = 6.9 Hz, 3H), 1.30 (d, J = 6.0 Hz, 6H), 3.68 (t, J = 5.5 Hz, 2H), 3.84 (br s, 2H), 4.61 (hept., J = 6.0 Hz, 1H), 4.80-4.93 (m, 3H), 6.82 (d, J = 7.4 Hz, 1H), 6.96 (d, J = 8.7 Hz, 2H), 7.05 (d, J = 7.2 Hz, 2H), 7.13-7.27 (m, 5H), 7.39 (dd, J = 8.2 Hz, 1.5 Hz, 1H), 7.74 (d, J = 1.4 Hz, 1H), 7.85 (d, J = 8.2 Hz, 1H). |

| Compound # | Structure | Name | NMR |
|---|---|---|---|
| 120 | 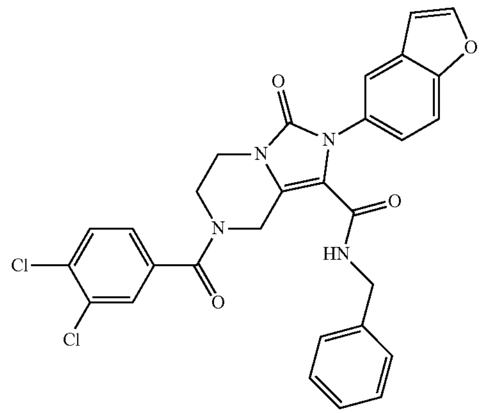 [SMILES: O=C(NCc1ccccc1)c1c2n(c(=O)n1-c1ccc3occc3c1)CCN(C(=O)c1ccc(Cl)c(Cl)c1)C2] | 2-(benzofuran-5-yl)-N-benzyl-7-(3,4-dichlorobenzoyl)-3-oxo-6,8-dihydro-5H-imidazo[1,5-a]pyrazine-1-carboxamide | 1H NMR (400 MHz, DMSO-d6, 80° C.): 3.70-3.73 (m, 2H), 3.86 (br s, 2H), 4.22 (d, J = 5.6 Hz, 2H), 4.88 (s, 2H), 6.96 (s, 3H), 7.15-7.21 (m, 4H), 7.26 (br s, 1H), 7.49 (d, J = 8.1 Hz, 1H), 7.58-7.60 (m, 2H), 7.71 (d, J = 8.3 Hz, 1H), 7.77 (s, 1H), 8.01 (s, 1H). |
| 121 | 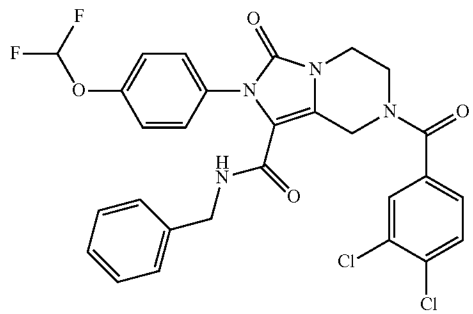 [SMILES: O=C(NCc1ccccc1)c1c2n(c(=O)n1-c1ccc(OC(F)F)cc1)CCN(C(=O)c1ccc(Cl)c(Cl)c1)C2] | N-benzyl-7-(3,4-dichlorobenzoyl)-2-[4-(difluoromethoxy)phenyl]-3-oxo-6,8-dihydro-5H-imidazo[1,5-a]pyrazine-1-carboxamide | 1H NMR (400 MHz, DMSO-d6, 80° C.): 3.71 (br s, 2H), 3.84 (br s, 2H), 4.28 (d, J = 5.7 Hz, 2H), 4.87 (s, 2H), 7.09-7.11 (m, 2H), 7.17 (t, J = 76 Hz, 1H), 7.19-7.29 (m, 5H), 7.32 (d, J = 8.0 Hz, 2H), 7.67 (br s, 1H) 7.71 (d, J = 8.0 Hz, 1H), 7.77 (s, 1H). |
| 122 | 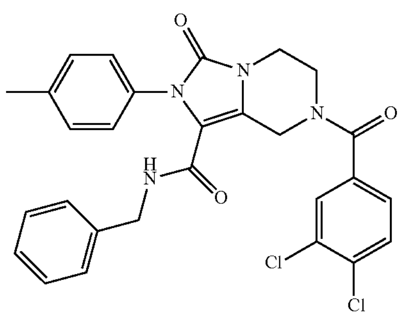 | N-benzyl-7-(3,4-dichlorobenzoyl)-3-oxo-2-(p-tolyl)-6,8-dihydro-5H-imidazo[1,5-a]pyrazine-1-carboxamide | 1H NMR (400 MHz, DMSO-d6, 80° C.): 2.34 (s, 3H), 3.69 (br s, 2H), 3.83 (d, J = 5.7 Hz, 2H), 4.25 (d, J = 5.7 Hz, 2H), 4.86 (s, 2H), 7.04 (d, J = 6.3 Hz, 2H), 7.14-7.26 (m, 7H), 7.32 (br s, 1H), 7.48 (d, J = 8.2 Hz, 1H), 7.71 (d, J = 8.2 Hz, 1H), 7.76 (s, 1H). |

TABLE A-continued

| Compound # | Structure | Name | NMR |
|---|---|---|---|
| 123 | 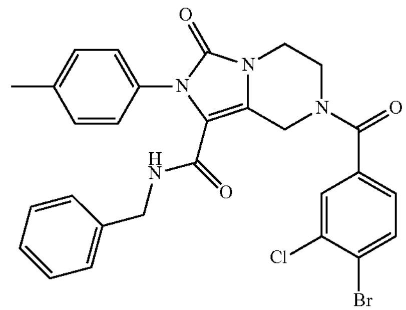 [SMILES: Cc1ccc(-n2c(C(=O)NCc3ccccc3)c3n(c2=O)CCN(C(=O)c2ccc(Br)c(Cl)c2)C3)cc1] | N-benzyl-7-(4-bromo-3-chloro-benzoyl)-3-oxo-2-(p-tolyl)-6,8-dihydro-5H-imidazo[1,5-a]pyrazine-1-carboxamide | 1H NMR (400 MHz, DMSO-d6, 80° C.): 2.36 (s, 3H), 3.71 (t, J = 5.3 Hz, 2H), 3.86 (br s, 2H), 4.27 (d, J = 5.4 Hz, 2H), 4.88 (s, 2H), 7.07 (d, J = 5.9 Hz, 2H), 7.19 (d, J = 8.4 Hz, 2H), 7.23 (d, J = 8.4 Hz, 2H), 7.24-7.29 (m, 3H), 7.34 (br s, 1H), 7.42 (d, J = 8.0 Hz, 1H), 7.77 (s, 1H), 7.87 (d, J = 7.8 Hz, 1H). |
| 124 | 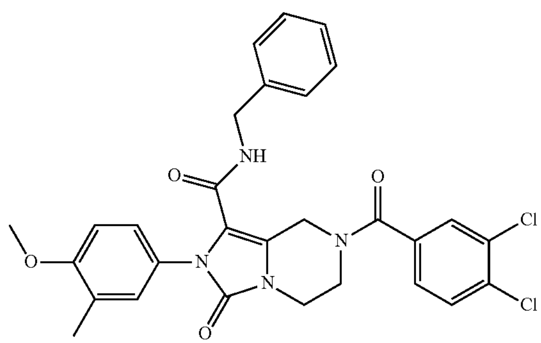 [SMILES: COc1ccc(-n2c(C(=O)NCc3ccccc3)c3n(c2=O)CCN(C(=O)c2ccc(Cl)c(Cl)c2)C3)cc1C] | N-benzyl-7-(3,4-dichlorobenzoyl)-2-(4-methoxy-3-methyl-phenyl)-3-oxo-6,8-dihydro-5H-imidazo[1,5-a]pyrazine-1-carboxamide | 1H NMR (400 MHz, DMSO-d6, 80° C.): 2.13 (s, 3H), 3.68 (t, J = 5.3 Hz, 2H), 3.82 (s, 3H), 3.82-3.84 (m, 2H), 4.24 (d, J = 5.2 Hz, 2H), 4.86 (s, 2H), 6.95 (d, J = 8.3 Hz, 1H), 7.01-7.05 (m, 4H), 7.09 (d, J = 8.4 Hz, 1H), 7.22-7.25 (m, 3H), 7.49 (d, J = 8.1 Hz, 1H), 7.71 (d, J = 8.2 Hz, 1H), 7.76 (s, 1H). |
| 125 | 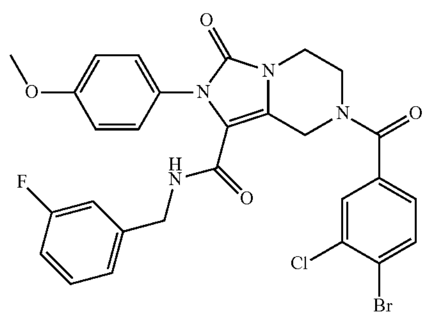 [SMILES: COc1ccc(-n2c(C(=O)NCc3cccc(F)c3)c3n(c2=O)CCN(C(=O)c2ccc(Br)c(Cl)c2)C3)cc1] | 7-(4-bromo-3-chloro-benzoyl)-N-[(3-fluorophenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.68 (t, J = 5.6 Hz, 2H), 3.79 (s, 3H), 3.82-3.84 (m, 2H), 4.26 (d, J = 5.8 Hz, 2H), 4.85 (s, 2H), 6.83 (d, J = 10.3 Hz, 1H), 6.89 (d, J = 7.6 Hz, 1H), 6.95 (d, J = 8.8 Hz, 2H), 6.98-7.03 (m, 1H), 7.20 (d, J = 8.9 Hz, 2H), 7.25-7.30 (m, 2H), 7.39 (dd, J = 8.1 Hz, 1.6 Hz, 1H), 7.74 (d, J = 1.6 Hz, 1H), 7.84 (d, J = 8.3 Hz, 1H). |

TABLE A-continued

| Compound # | Structure | Name | NMR |
|---|---|---|---|
| 126 | 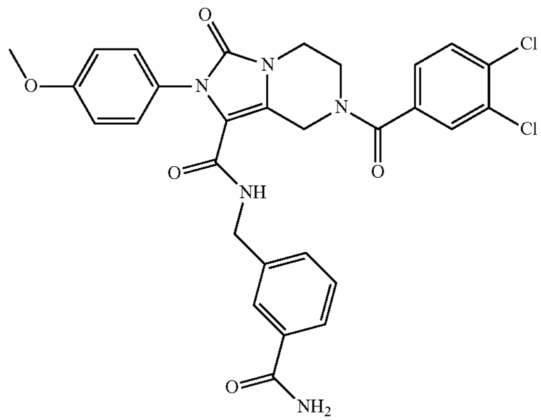 [SMILES: COc1ccc(-n2c(C(=O)NCc3cccc(C(N)=O)c3)c3n(c2=O)CCN(C(=O)c2ccc(Cl)c(Cl)c2)C3)cc1] | N-[(3-carbamoylphenyl)methyl]-7-(3,4-dichlorobenzoyl)-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.2 Hz, 2H), 3.78 (s, 3H), 3.83 (br s, 2H), 4.30 (d, J = 5.8 Hz, 2H), 4.87 (s, 2H), 6.94 (d, J = 8.4 Hz, 2H), 7.07-7.28 (m, 4H), 7.31 (t, J = 7.6 Hz, 1H), 7.49 (dd, J = 8.3 Hz, 1.8 Hz, 1H), 7.68 (br s, 1H), 7.67-7.76 (m, 4H). |
| 127 | 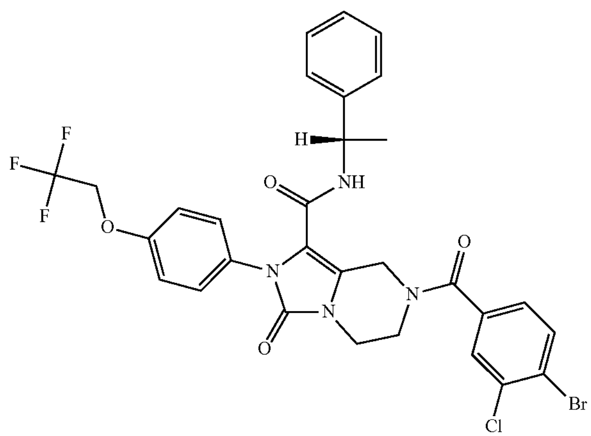 [SMILES: C[C@H](NC(=O)c1c2n(c(=O)n1-c1ccc(OCC(F)(F)F)cc1)CCN(C(=O)c1ccc(Br)c(Cl)c1)C2)c1ccccc1] | 7-(4-bromo-3-chloro-benzoyl)-3-oxo-N-[rac-(1S)-1-phenylethyl]-2-[4-(2,2,2-trifluoroethoxy)phenyl]-6,8-dihydro-5H-imidazo[1,5-a]pyrazine-1-carboxamide | 1H NMR (400 MHz, DMSO-d6, 80° C.): 1.24 (d, J = 6.8 Hz, 3H), 3.69 (t, J = 5.5 Hz, 2H), 3.84 (br s, 2H), 4.74 (q, J = 8.8 Hz, 2H), 4.79-4.93 (m, 3H), 7.04-7.15 (m, 5H), 7.17-7.23 (m, 5H), 7.39 (dd, J = 8.2 Hz, 1.7 Hz, 1H), 7.74 (d, J = 1.6 Hz, 1H), 7.85 (d, J = 8.2 Hz, 1H). |

TABLE A-continued

| Compound # | Structure | Name | NMR |
|---|---|---|---|
| 128 | 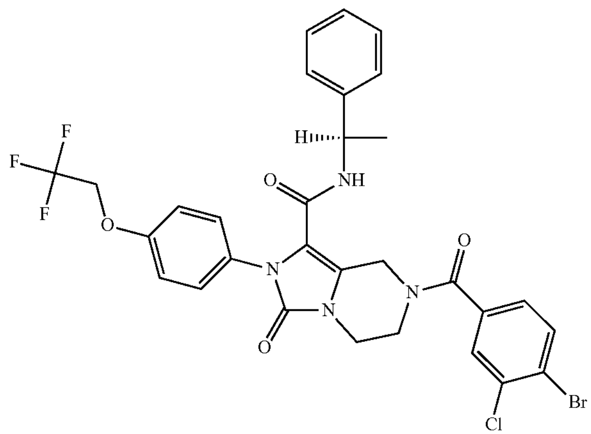 [SMILES: C[C@@H](NC(=O)c1c2n(c(=O)n1-c1ccc(OCC(F)(F)F)cc1)CCN(C(=O)c1ccc(Br)c(Cl)c1)C2)c1ccccc1] | 7-(4-bromo-3-chloro-benzoyl)-3-oxo-N-[rac-(1R)-1-phenylethyl]-2-[4-(2,2,2-trifluoroethoxy)phenyl]-6,8-dihydro-5H-imidazo[1,5-a]pyrazine-1-carboxamide | 1H NMR (400 MHz, DMSO-d6, 80° C.): 1.24 (d, J = 6.8 Hz, 3H), 3.69 (t, J = 5.5 Hz, 2H), 3.84 (br s, 2H), 4.74 (q, J = 8.8 Hz, 2H), 4.79-4.93 (m, 3H), 7.04-7.15 (m, 5H), 7.17-7.23 (m, 5H), 7.39 (dd, J = 8.2 Hz, 1.7 Hz, 1H), 7.74 (d, J = 1.6 Hz, 1H), 7.85 (d, J = 8.2 Hz, 1H). |
| 129 | 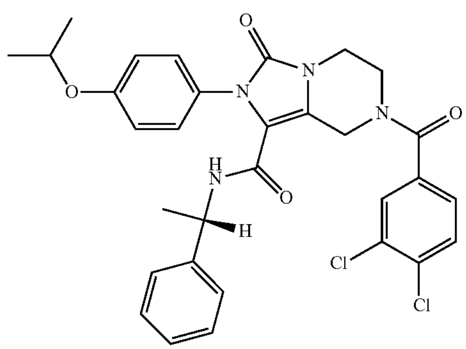 [SMILES: CC(C)Oc1ccc(-n2c(C(=O)N[C@@H](C)c3ccccc3)c3n(c2=O)CCN(C(=O)c2ccc(Cl)c(Cl)c2)C3)cc1] | 7-(3,4-dichlorobenzoyl)-2-(4-isopropoxyphenyl)-3-oxo-N-[rac-(1S)-1-phenylethyl]-6,8-dihydro-5H-imidazo[1,5-a]pyrazine-1-carboxamide | 1H NMR (400 MHz, DMSO-d6, 80° C.): 1.20 (d, J = 6.9 Hz, 3H), 1.30 (d, J = 6.0 Hz, 6H), 3.68 (t, J = 5.5 Hz, 2H), 3.84 (br s, 2H), 4.61 (hept., J = 6.0 Hz, 1H), 4.80-4.93 (m, 3H), 6.82 (d, J = 7.4 Hz, 1H), 6.96 (d, J = 8.7 Hz, 2H), 7.05 (d, J = 7.2 Hz, 2H), 7.13-7.30 (m, 5H), 7.48 (d, J = 8.2 Hz, 1H), 7.71 (d, J = 1.4 Hz, 1H), 7.76 (s, 1H) |

| Compound # | Structure | Name | NMR |
|---|---|---|---|
| 130 | 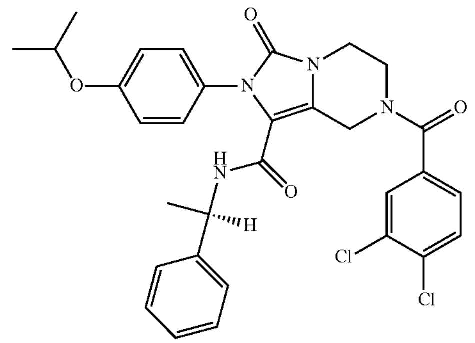 [SMILES: CC(C)Oc1ccc(-n2c(C(=O)N[C@H](C)c3ccccc3)c3n(c2=O)CCN(C(=O)c2ccc(Cl)c(Cl)c2)C3)cc1] | 7-(3,4-dichlorobenzoyl)-2-(4-isopropoxyphenyl)-3-oxo-N-[rac-(1R)-1-phenylethyl]-6,8-dihydro-5H-imidazo[1,5-a]pyrazine-1-carboxamide | 1H NMR (400 MHz, DMSO-d6, 80° C.): 1.20 (d, J = 6.9 Hz, 3H), 1.30 (d, J = 6.0 Hz, 6H), 3.68 (t, J = 5.5 Hz, 2H), 3.84 (br s, 2H), 4.61 (hept., J = 6.0 Hz, 1H), 4.80-4.93 (m, 3H), 6.82 (d, J = 7.4 Hz, 1H), 6.96 (d, J = 8.7 Hz, 2H), 7.05 (d, J = 7.2 Hz, 2H), 7.13-7.30 (m, 5H), 7.48 (d, J = 8.2 Hz, 1H), 7.71 (d, J = 1.4 Hz, 1H), 7.76 (s, 1H). |
| 131 | 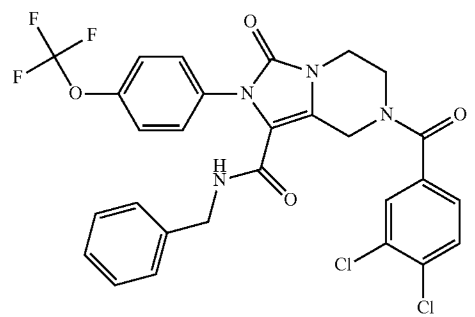 [SMILES: O=C(NCc1ccccc1)c1c2n(c(=O)n1-c1ccc(OC(F)(F)F)cc1)CCN(C(=O)c1ccc(Cl)c(Cl)c1)C2] | N-benzyl-7-(3,4-dichlorobenzoyl)-3-oxo-2-[4-(trifluoromethoxy)phenyl]-6,8-dihydro-5H-imidazo[1,5-a]pyrazine-1-carboxamide | 1H NMR (400 MHz, DMSO-d6, 80° C.): 3.70 (t, J = 5.6 Hz, 2H), 3.84 (br s, 2H), 4.28 (d, J = 5.7 Hz, 2H), 4.86 (s, 2H), 7.11 (d, J = 6.8 Hz, 2H), 7.16-7.30 (m, 3H), 7.34-7.39 (m, 4H), 7.48 (d, J = 8.2 Hz, 1H), 7.71 (d, J = 8.3 Hz, 1H), 7.76 (s, 1H), 7.79 (br s, 1H). |
| 132 | 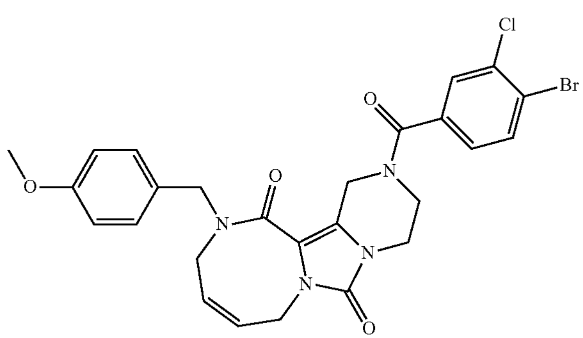 [SMILES: COc1ccc(CN2C/C=C\Cn3c(c4n(c3=O)CCN(C(=O)c3ccc(Br)c(Cl)c3)C4)C2=O)cc1] | (11Z)-4-(4-bromo-3-chloro-benzoyl)-14-[(4-methoxyphenyl)methyl]-4,7,9,14-tetrazatricyclo[7.6.0.0^2,7]pentadeca-1,11-diene-8,15-dione | 1H NMR (300 MHz, DMSO-d6) δ 7.90 (d, J = 8.1 Hz, 1H), 7.78 (d, J = 1.8 Hz, 1H), 7.41-7.32 (m, 1H), 7.29-7.13 (m, 2H), 6.89 (d, 2H), 5.83 (t, J = 13.8 Hz, 2H), 4.88-4.32 (m, 4H), 4.25 (s, 2H), 3.98 (s, 1H), 3.75 (s, 5H), 3.63 (s, 3H). |

TABLE A-continued

| Compound # | Structure | Name | NMR |
|---|---|---|---|
| 133 | 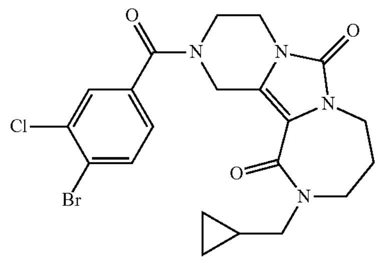 [SMILES: O=C(c1ccc(Br)c(Cl)c1)N1CCn2c(c3n(c2=O)CCCN(CC2CC2)C3=O)C1] | 4-(4-bromo-3-chloro-benzoyl)-13-(cyclopropylmethyl)-4,7,9,13-tetrazatricyclo[7.5.0.0^2,7]tetradec-1-ene-8,14-dione | 1H NMR (300 MHz, Chloroform-d) δ 7.72 (d, J = 8.2 Hz, 1H), 7.59 (d, J = 2.0 Hz, 1H), 7.23 (dd, J = 8.2, 2.0 Hz, 1H), 4.89 (s, 2H), 3.94 (t, J = 6.8 Hz, 4H), 3.80 (s, 2H), 3.51 (t, J = 6.3 Hz, 2H), 3.34 (d, J = 7.11 Hz, 2H), 2.13 (p, J = 6.6 Hz, 2H), 1.03 (s, 1H), 0.66-0.50 (m, 2H), 0.30 (d, J = 5.2 Hz, 2H). |
| 134 | 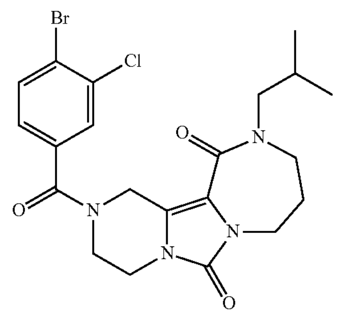 [SMILES: CC(C)CN1CCCn2c(c3n(c2=O)CCN(C(=O)c2ccc(Br)c(Cl)c2)C3)C1=O] | 4-(4-bromo-3-chloro-benzoyl)-13-isobutyl-4,7,9,13-tetrazatricyclo[7.5.0.0^2,7]tetradec-1-ene-8,14-dione | 1H NMR (300 MHz, Chloroform-d) δ 7.72 (d, J = 8.2 Hz, 1H), 7.59 (d, J = 1.9 Hz, 1H), 7.22 (dd, J = 8.2, 2.0 Hz, 1H), 4.88 (s, 2H), 3.94 (t, J = 6.9 Hz, 4H), 3.80 (s, 2H), 3.44 (t, J = 6.2 Hz, 2H), 3.29 (d, J = 7.4 Hz, 2H), 2.09 (p, J = 6.6 Hz, 2H), 1.96 (dt, J = 13.7, 6.9 Hz, 1H), 0.95 (d, J = 6.6 Hz, 6H). |
| 135 | 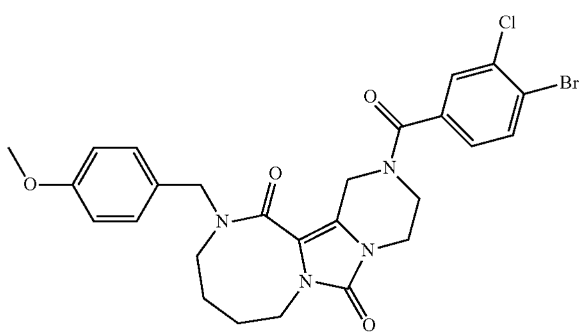 [SMILES: COc1ccc(CN2CCCCn3c(c4n(c3=O)CCN(C(=O)c3ccc(Br)c(Cl)c3)C4)C2=O)cc1] | 4-(4-bromo-3-chloro-benzoyl)-14-[(4-methoxyphenyl)methyl]-4,7,9,14-tetrazatricyclo[7.6.0.0^2,7]pentadec-1-ene-8,15-dione | 1H NMR (300 MHz, DMSO-d6) δ 7.90 (d, J = 8.1 Hz, 1H), 7.77 (s, 1H), 7.41-7.38 (m, 1H), 7.37-7.02 (m, 2H), 6.90 (br, 2H), 4.81-4.40 (m, 4H), 3.98 (br, 1H), 3.75 (s, 3H), 3.63 (br, 5H), 3.19 (s, 2H), 1.68 (m, 4H). |

TABLE A-continued

| Compound # | Structure | Name | NMR |
|---|---|---|---|
| 136 | 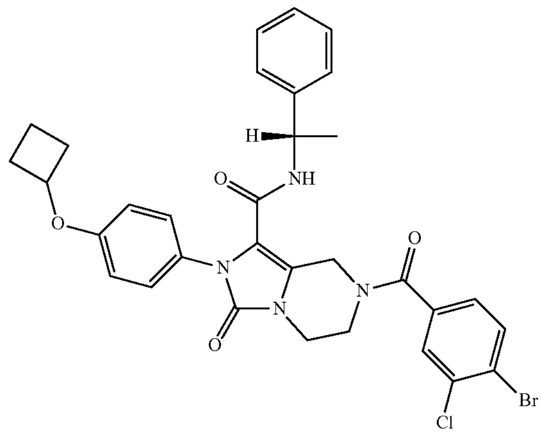 [SMILES: C[C@H](NC(=O)c1c2n(c(=O)n1-c1ccc(OC3CCC3)cc1)CCN(C(=O)c1ccc(Br)c(Cl)c1)C2)c1ccccc1] | 7-(4-bromo-3-chloro-benzoyl)-2-[4-(cyclobutoxy)phenyl]-3-oxo-N-[rac-(1S)-1-phenylethyl]-6,8-dihydro-5H-imidazo[1,5-a]pyrazine-1-carboxamide | 1H-NMR (DMSO, 600 MHz, 80° C.): 1.21 (d, J = 6.9 Hz, 3H), 1.63-1.74 (m, 1H), 1.79-1.89 (m, 1H), 2.02-2.13 (m, 2H), 2.43-2.49 (m, 2H), 3.64-3.74 (m, 2H), 3.78-3.95 (m, 2H), 4.72 (quint, J = 7.1 Hz, 1H), 4.79-4.92 (m, 3H), 6.85-6.93 (m, 3H), 7.06 (d, J = 6.8 Hz, 2H), 7.17-7.28 (m, 5H), 7.40 (dd, J = 8.2 Hz, 1.9 Hz, 1H), 7.65 (d, J = 1.9 Hz, 1H), 7.86 (dd, J = 8.2 Hz, 1H) ppm. |
| 137 | 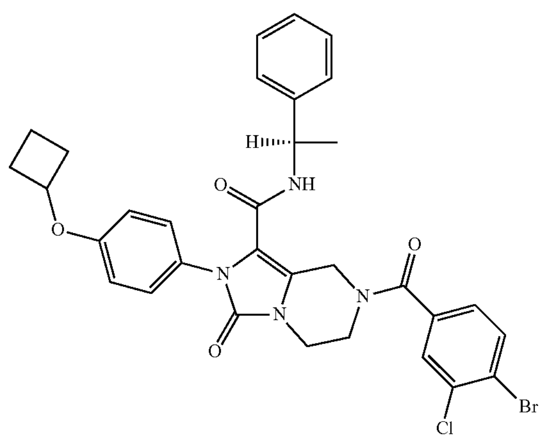 [SMILES: C[C@@H](NC(=O)c1c2n(c(=O)n1-c1ccc(OC3CCC3)cc1)CCN(C(=O)c1ccc(Br)c(Cl)c1)C2)c1ccccc1] | 7-(4-bromo-3-chloro-benzoyl)-2-[4-(cyclobutoxy)phenyl]-3-oxo-N-[rac-(1R)-1-phenylethyl]-6,8-dihydro-5H-imidazo[1,5-a]pyrazine-1-carboxamide | 1H-NMR (DMSO, 600 MHz, 80° C.): 1.21 (d, J = 6.9 Hz, 3H), 1.63-1.74 (m, 1H), 1.79-1.89 (m, 1H), 2.02-2.13 (m, 2H), 2.43-2.49 (m, 2H), 3.64-3.74 (m, 2H), 3.78-3.95 (m, 2H), 4.72 (quint, J = 7.1 Hz, 1H), 4.79-4.92 (m, 3H), 6.85-6.93 (m, 3H), 7.06 (d, J = 6.8 Hz, 2H), 7.17-7.28 (m, 5H), 7.40 (dd, J = 8.2 Hz, 1.9 Hz, 1H), 7.65 (d, J = 1.9 Hz, 1H), 7.86 (dd, J = 8.2 Hz, 1H) ppm. |

TABLE A-continued

| Compound # | Structure | Name | NMR |
|---|---|---|---|
| 138 | 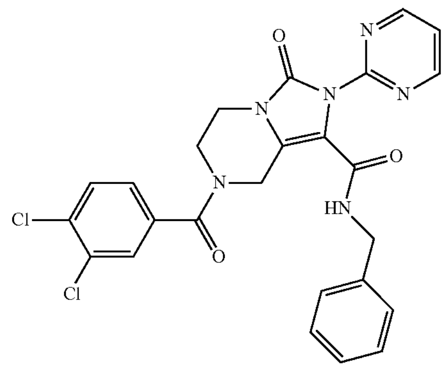 [SMILES: O=C(NCc1ccccc1)c1c2n(c(=O)n1-c1ncccn1)CCN(C(=O)c1ccc(Cl)c(Cl)c1)C2] | N-benzyl-7-(3,4-dichlorobenzoyl)-3-oxo-2-pyrimidin-2-yl-6,8-dihydro-5H-imidazo[1,5-a]pyrazine-1-carboxamide | 1H NMR (400 MHz, DMSO-d6, 80° C.): 3.86 (s, 4H), 4.38 (d, J = 6.3 Hz, 2H), 5.00 (s, 2H), 7.20-7.29 (m, 5H), 7.40 (t, J = 4.8 Hz, 1H), 7.48 (dd, J = 8.1 Hz, 1.1 Hz, 1H), 7.71 (d, J = 8.3 Hz, 1H), 7.75 (d, J = 1.1 Hz, 1H), 8.07 (br s, 1H), 8.72 (d, J = 4.8 Hz, 2H). |
| 139 | 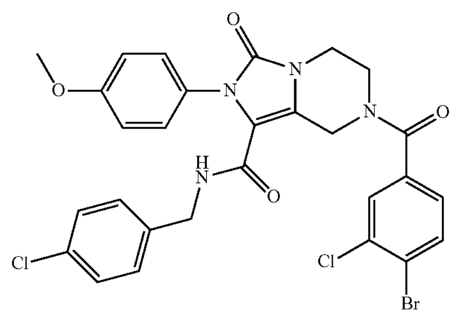 [SMILES: COc1ccc(-n2c(C(=O)NCc3ccc(Cl)cc3)c3n(c2=O)CCN(C(=O)c2ccc(Br)c(Cl)c2)C3)cc1] | 7-(4-bromo-3-chloro-benzoyl)-N-[(4-chlorophenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.6 Hz, 2H), 3.81 (s, 3H), 3.84 (br s, 2H), 4.24 (d, J = 5.6 Hz, 2H), 4.86 (s, 2H), 6.97 (d, J = 8.4 Hz, 2H), 7.08 (d, J = 8.0 Hz, 2H), 7.20 (d, J = 8.2 Hz, 2H), 7.25 (br s, 1H), 7.29 (d, J = 8.0 Hz, 2H), 7.41 (d, J = 8.2 Hz, 1H), 7.74 (s, 1H), 7.87 (d, J = 8.2 Hz, 1H). |
| 140 | 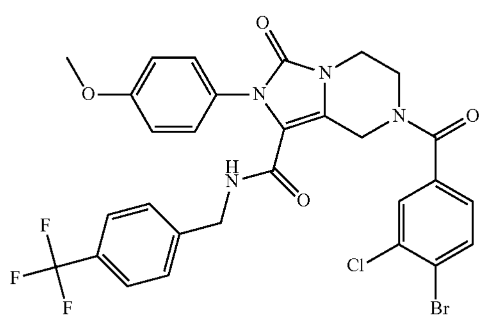 [SMILES: COc1ccc(-n2c(C(=O)NCc3ccc(C(F)(F)F)cc3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[[4-(trifluoromethyl)phenyl]methyl]-6,8-dihydro-5H-imidazo[1,5-a]pyrazine-1-carboxamide | 1H NMR (400 MHz, DMSO-d6, 80° C.): 3.70 (t, J = 4.8 Hz, 2H), 3.80 (s, 3H), 3.85 (br s, 2H), 4.35 (d, J = 5.6 Hz, 2H), 4.88 (s, 2H), 6.97 (d, J = 8.2 Hz, 2H), 7.21 (d, J = 8.6 Hz, 2H), 7.28 (d, J = 8.2 Hz, 2H), 7.37 (br s, 1H), 7.42 (d, J = 8.6 Hz, 1H), 7.59 (d, J = 7.7 Hz, 2H), 7.77 (s, 1H), 7.87 (d, J = 8.4 Hz, 1H). |

TABLE A-continued

| Compound # | Structure | Name | NMR |
|---|---|---|---|
| 141 | 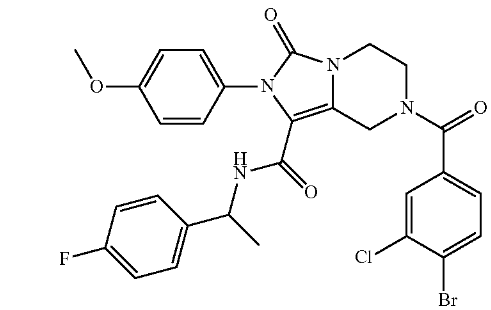 [SMILES: COc1ccc(-n2c(C(=O)NC(C)c3ccc(F)cc3)c3n(c2=O)CCN(C(=O)c2ccc(Br)c(Cl)c2)C3)cc1] | 7-(4-bromo-3-chloro-benzoyl)-N-[1-(4-fluorophenyl)ethyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 1.20 (d, J = 6.9 Hz, 3H), 3.68 (t, J = 5.5 Hz, 2H), 3.80 (s, 3H), 3.83 (br s, 2H), 4.82-4.86 (m, 3H), 6.91-7.12 (m, 8H), 7.19 (d, J = 8.9 Hz, 2H), 7.39 (dd, J = 8.1 Hz, 1.8 Hz, 1H), 7.74 (d, J = 1.8 Hz, 1H), 7.85 (d, J = 8.3 Hz, 1H). |
| 142 | 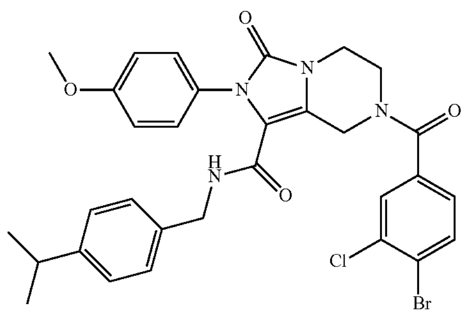 [SMILES: COc1ccc(-n2c(C(=O)NCc3ccc(C(C)C)cc3)c3n(c2=O)CCN(C(=O)c2ccc(Br)c(Cl)c2)C3)cc1] | 7-(4-bromo-3-chloro-benzoyl)-N-[(4-isopropylphenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 1.22 (d, J = 7.0 Hz, 6H), 2.88 (hept, J = 7.0 Hz, 1H), 3.69 (t, J = 5.3 Hz, 2H), 3.81 (s, 3H), 3.85 (br s, 2H), 4.21 (d, J = 5.3 Hz, 2H), 4.87 (s, 2H), 6.95-6.98 (m, 4H), 7.12 (d, J = 8.0 Hz, 2H), 7.13 (br s, 1H), 7.21 (d, J = 8.1 Hz, 2H), 7.42 (d, J = 8.1 Hz, 1H), 7.77 (s, 1H), 7.87 (d, J = 8.0 Hz, 1H). |
| 143 | 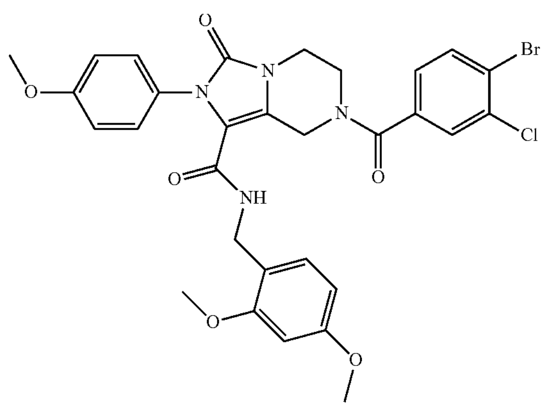 [SMILES: COc1ccc(-n2c(C(=O)NCc3ccc(OC)cc3OC)c3n(c2=O)CCN(C(=O)c2ccc(Br)c(Cl)c2)C3)cc1] | 7-(4-bromo-3-chloro-benzoyl)-N-[(2,4-dimethoxyphenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.65-3.68 (m, 2H), 3.69 (s, 3H), 3.76 (s, 3H), 3.79 (s, 3H), 3.82 (m, 2H), 4.12 (d, J = 5.5 Hz, 2H), 4.86 (s, 2H), 6.38 (dd, J = 8.3 Hz, 2.5 Hz, 1H), 6.47 (m, 2H), 6.83 (d, J = 8.1 Hz, 1H), 6.95 (d, J = 8.9 Hz, 2H), 7.18 (d, J = 8.9 Hz, 2H), 7.39 (dd, J = 9.8 Hz, 1.6 Hz, 1H), 7.74 (d, J = 1.5 Hz, 1H), 7.85 (d, J = 8.1 Hz, 1H). |

TABLE A-continued

| Compound # | Structure | Name | NMR |
|---|---|---|---|
| 144 | 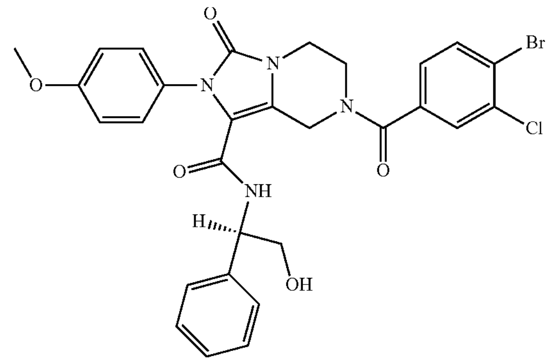 [SMILES: COc1ccc(-n2c(C(=O)N[C@@H](CO)c3ccccc3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-2-hydroxy-1-phenyl-ethyl]-6,8-dihydro-5H-imidazo[1,5-a]pyrazine-1-carboxamide | 1H NMR (400 MHz, DMSO-d6, 80° C.): 3.39-3.53 (m, 2H), 3.70 (t, J = 5.5 Hz, 2H), 3.82 (s, 3H), 3.86 (br s, 2H), 4.51 (t, J = 4.9 Hz, 1H), 4.80-4.84 (m, 1H) 4.88 (s, 2H), 6.79 (d, J = 7.4 Hz, 1H), 6.99-7.03 (m, 4H), 7.19-7.27 (m, 5H), 7.40 (dd, J = 8.3 Hz, 2.0 Hz, 1H), 7.75 (d, J = 1.4 Hz, 1H), 7.85 (d, J = 8.1 Hz, 1H). |
| 145 | 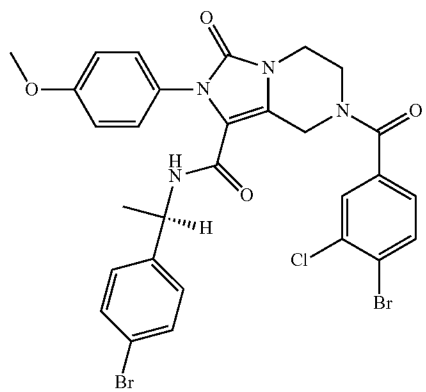 [SMILES: COc1ccc(-n2c(C(=O)N[C@H](C)c3ccc(Br)cc3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-1-(4-bromophenyl)ethyl]-6,8-dihydro-5H-imidazo[1,5-a]pyrazine-1-carboxamide | 1H NMR (400 MHz, DMSO-d6, 80° C.): 1.20 (d, J = 6.9 Hz, 3H), 3.68 (t, J = 5.6 Hz, 2H), 3.78 (s, 3H), 3.84 (br s, 2H), 4.79-4.85 (m, 3H), 6.96-6.99 (m, 3H), 7.03 (d, J = 8.3 Hz, 2H), 7.19 (d, J = 8.9 Hz, 2H), 7.38-7.43 (m, 3H), 7.74 (d, J = 1.6 Hz, 1H), 7.85 (d, J = 8.3 Hz, 1H). |

| Compound # | Structure | Name | NMR |
|---|---|---|---|
| 146 | 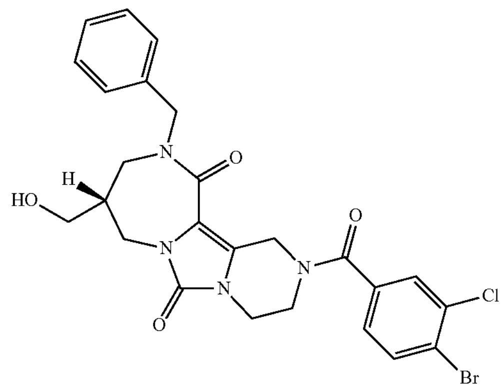 [SMILES: O=C(c1ccc(Br)c(Cl)c1)N1CCn2c(c3n(c2=O)C[C@H](CO)CN(Cc2ccccc2)C3=O)C1] | rac-(11R)-13-benzyl-4-(4-bromo-3-chloro-benzoyl)-11-(hydroxymethyl)-4,7,9,13-tetrazatricyclo[7.5.0.0^2,7]tetradec-1-ene-8,14-dione | 1H NMR (400 MHz, DMSO-d6) δ 7.87 (d, J = 8.2 Hz, 1H), 7.76 (d, J = 2.0 Hz, 1H), 7.44-7.12 (m, 6H), 4.90-4.55 (m, 4H), 4.39 (d, J = 15.5 Hz, 1H), 3.95 (s, 1H), 3.70-3.52 (m, J = 48.1 Hz, 6H), 3.12 (t, J = 11.2 Hz, 3H), 2.06 (m, 1H). |
| 147 | 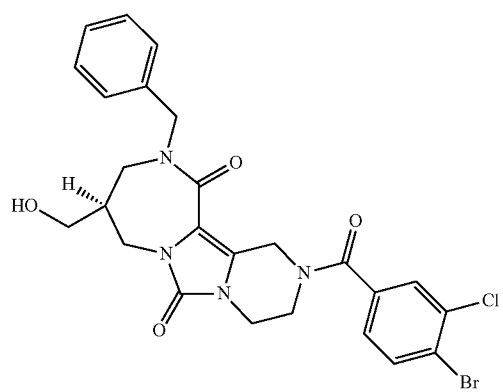 [SMILES: O=C(c1ccc(Br)c(Cl)c1)N1CCn2c(c3n(c2=O)C[C@@H](CO)CN(Cc2ccccc2)C3=O)C1] | rac-(11S)-13-benzyl-4-(4-bromo-3-chloro-benzoyl)-11-(hydroxymethyl)-4,7,9,13-tetrazatricyclo[7.5.0.0^2,7]tetradec-1-ene-8,14-dione | 1H NMR (400 MHz, DMSO-d6) δ 7.87 (d, J = 8.2 Hz, 1H), 7.76 (d, J = 2.0 Hz, 1H), 7.44-7.12 (m, 6H), 4.90-4.55 (m, 4H), 4.39 (d, J = 15.5 Hz, 1H), 3.95 (s, 1H), 3.70-3.52 (m, J = 48.1 Hz, 6H), 3.12 (t, J = 11.2 Hz, 3H), 2.06 (m, 1H). |

TABLE A-continued

| Compound # | Structure | Name | NMR |
|---|---|---|---|
| 148 | 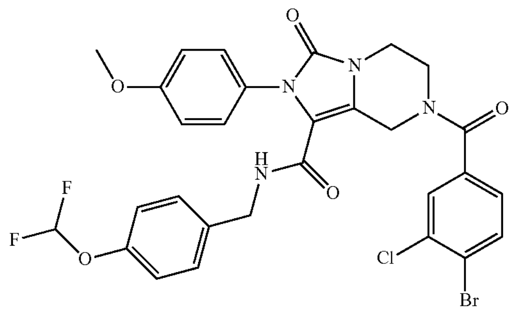 [SMILES: COc1ccc(-n2c(C(=O)NCc3ccc(OC(F)F)cc3)c3n(c2=O)CCN(C(=O)c2ccc(Br)c(Cl)c2)C3)cc1] | 7-(4-bromo-3-chloro-benzoyl)-N-[[4-(difluoromethoxy)phenyl]methyl]-2-(4-methoxyphenyl)-3-oxo-6,8-dihydro-5H-imidazo[1,5-a]pyrazine-1-carboxamide | 1H NMR (300 MHz, DMSO-d6) δ 7.90 (d, J = 8.1 Hz, 1H), 7.81 (d, J = 1.8 Hz, 1H), 7.44-7.41 (m, 1H), 7.20-6.95 (m, 8H), 4.99-4.71 (m, 2H), 4.28 (br, 2H), 3.78 (s, 3H), 3.68 (s, 3H), 3.32 (s, 3H). |
| 149 | 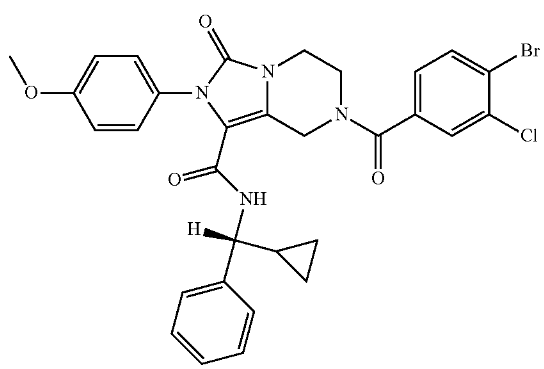 [SMILES: COc1ccc(-n2c(C(=O)N[C@@H](c3ccccc3)C3CC3)c3n(c2=O)CCN(C(=O)c2ccc(Br)c(Cl)c2)C3)cc1] | 7-(4-bromo-3-chloro-benzoyl)-2-(4-methoxyphenyl)-N-[rac-(R)-cyclopropyl(phenyl)methyl]-3-oxo-6,8-dihydro-5H-imidazo[1,5-a]pyrazine-1-carboxamide | 1H NMR (300 MHz, DMSO-d6) δ 7.89 (d, J = 8.1 Hz, 1H), 7.80 (d, J = 1.5 Hz, 2H), 7.42 (d, J = 8.3 Hz, 1H), 7.38-7.02 (m, 7H), 6.99 (d, J = 7.8 Hz, 2H), 4.99-4.62 (m, 2H), 4.27-3.89 (m, 2H), 3.78 (s, 3H), 3.68 (s, 3H), 1.05 –C 0.80 (m, 1H), 0.59-0.12 (m, 4H). |

TABLE A-continued

| Compound # | Structure | Name | NMR |
|---|---|---|---|
| 150 | 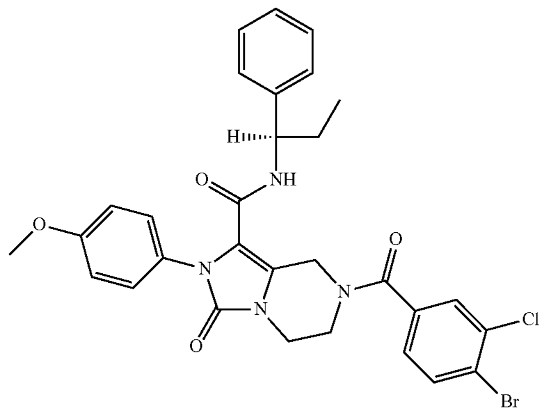 [SMILES: CC[C@@H](NC(=O)c1c2n(c(=O)n1-c1ccc(OC)cc1)CCN(C(=O)c1ccc(Br)c(Cl)c1)C2)c1ccccc1] | 7-(4-bromo-3-chloro-benzoyl)-2-(4-methoxyphenyl)-3-oxo-N-[rac-(1R)-1-phenylpropyl]-6,8-dihydro-5H-imidazo[1,5-a]pyrazine-1-carboxamide | 1H NMR (400 MHz, DMSO-d6) δ 7.85 (d, J = 8.2 Hz, 1H), 7.77 (d, J = 2.0 Hz, 1H), 7.52 (s, 1H), 7.38 (d, J = 8.2 Hz, 1H), 7.25-6.82 (m, 9H), 4.95-4.45 (m, 3H), 3.96 (s, 1H), 3.76-3.65 (m, 6H), 1.60-1.45 (m, 2H), 0.75-0.54 (m, 3H). |
| 151 | 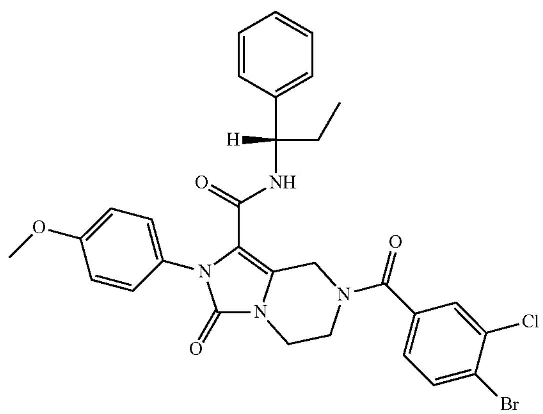 [SMILES: CC[C@H](NC(=O)c1c2n(c(=O)n1-c1ccc(OC)cc1)CCN(C(=O)c1ccc(Br)c(Cl)c1)C2)c1ccccc1] | 7-(4-bromo-3-chloro-benzoyl)-2-(4-methoxyphenyl)-3-oxo-N-[rac-(1S)-1-phenylpropyl]-6,8-dihydro-5H-imidazo[1,5-a]pyrazine-1-carboxamide | 1H NMR (400 MHz, DMSO-d6) δ 7.85 (d, J = 8.2 Hz, 1H), 7.77 (d, J = 1.9 Hz, 1H), 7.52 (s, 1H), 7.38 (d, J = 8.2 Hz, 1H), 7.33-7.05 (m, 6H), 6.92 (d, J = 7.8 Hz, 3H), 4.95-4.45 (m, 3H), 3.96 (s, 1H), 3.76-3.65 (m, 6H), 1.60-1.45 (m, 2H), 0.75-0.54 (m, 3H). |

TABLE A-continued

| Compound # | Structure | Name | NMR |
|---|---|---|---|
| 152 | 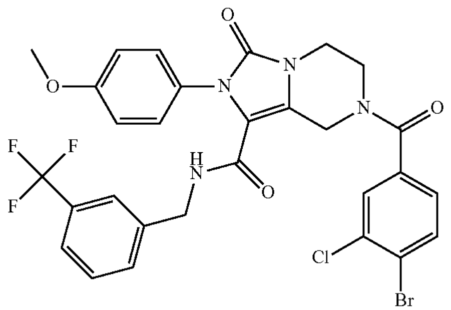 [SMILES: COc1ccc(-n2c(C(=O)NCc3cccc(C(F)(F)F)c3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[[3-(trifluoromethyl)phenyl]methyl]-6,8-dihydro-5H-imidazo[1,5-a]pyrazine-1-carboxamide | 1H NMR (400 MHz, DMSO-d6, 80° C.) 3.69 (t, J = 5.3 Hz, 2H), 3.79 (s, 3H), 3.83-3.85 (m, 2H) 4.35 (d, J = 5.5 Hz, 2H), 4.87 (s, 2H), 6.94 (d, J = 8.9 Hz, 2H), 7.19 (d, J = 8.9 Hz, 2H), 7.36-7.42 (m, 3H), 7.47-7.52 (m, 2H), 7.57 (d, J = 7.7 Hz, 1H), 7.75 (d, J = 1.7 Hz, 1H), |
| 153 | 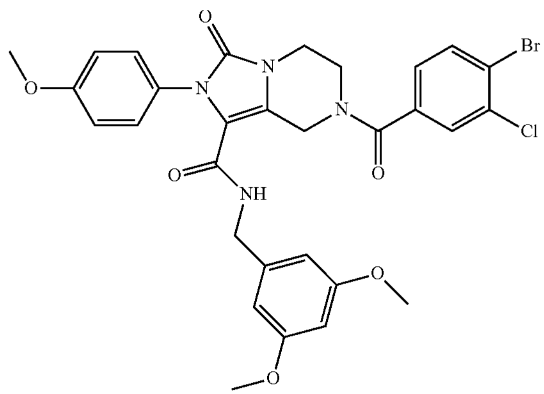 [SMILES: COc1ccc(-n2c(C(=O)NCc3cc(OC)cc(OC)c3)c3n(c2=O)CCN(C(=O)c2ccc(Br)c(Cl)c2)C3)cc1] | 7-(4-bromo-3-chloro-benzoyl)-N-[(3,5-dimethoxyphenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.7 Hz, 2H), 3.73 (s, 6H), 3.80 (s, 3H), 3.80-3.84 (m, 2H), 4.19 (d, J = 6.4 Hz, 2H), 4.89 (s, 2H), 6.28 (s, 2H), 6.36 (s, 1H), 6.94 (d, J = 8.7 Hz, 2H), 7.14 (br s, 1H), 7.21 (d, J = 8.5 Hz, 2H), 7.40 (dd, J = 8.5 Hz, 1.7 Hz, 1H), 7.75 (d, J = 1.6 Hz, 1H), 7.86 (d, J = 8.2 Hz, 1H). |
| 154 | 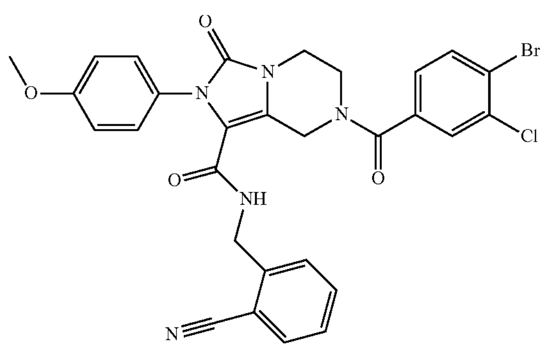 [SMILES: COc1ccc(-n2c(C(=O)NCc3ccccc3C#N)c3n(c2=O)CCN(C(=O)c2ccc(Br)c(Cl)c2)C3)cc1] | 7-(4-bromo-3-chloro-benzoyl)-N-[(2-cyanophenyl)methyl]-2-(4-methoxyphenyl)-3-oxo-6,8-dihydro-5H-imidazo[1,5-a]pyrazine-1-carboxamide | 1H-NMR (DMSO, 600 MHz, 80° C.): 3.65-3.73 (m, 2H), 3.80 (s, 3H), 3.81-3.88 (m, 2H), 4.41-4.45 (m, 2H), 4.87 (s, 2H), 6.96 (d, J = 9.0 Hz, 2H), 7.17-7.25 (m, 3H), 7.34-7.47 (m, 3H), 7.53-7.61 (m, 1H), 7.69-7.77 (m, 2H), 7.85 (d, J = 8.2 Hz, 1H) ppm. |

TABLE A-continued

| Compound # | Structure | Name | NMR |
|---|---|---|---|
| 155 | 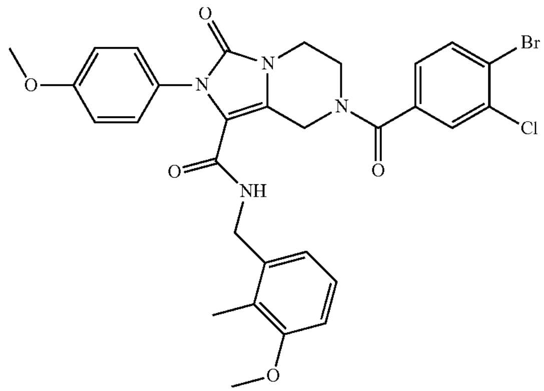 [SMILES: COc1ccc(-n2c(C(=O)NCc3cccc(OC)c3C)c3n(c2=O)CCN(C(=O)c2ccc(Br)c(Cl)c2)C3)cc1] | 7-(4-bromo-3-chloro-benzoyl)-N-[(3-methoxy-2-methyl-phenyl)methyl]-2-(4-methoxyphenyl)-3-oxo-6,8-dihydro-5H-imidazo[1,5-a]pyrazine-1-carboxamide | 1H-NMR (DMSO, 600 MHz, 80° C.): 1.97 (s, 3H), 3.65-3.72 (m, 2H), 3.79 (s, 6H), 3.80-3.88 (m, 2H), 4.16-4.26 (m, 2H), 4.86 (s, 2H), 6.51-6.61 (m, 1H), 6.76-6.87 (m, 2H), 6.93 (d, J = 8.4 Hz, 2H), 6.98-7.07 (m, 1H), 7.19 (d, J = 8.4 Hz, 2H), 7.37-7.43 (m, 1H), 7.72-7.76 (m, 1H), 7.86 (d, J = 8.2 Hz, 1H) ppm. |
| 156 | 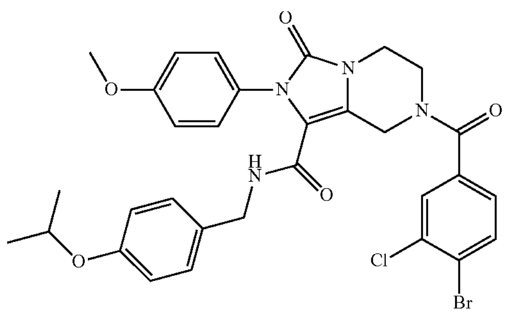 [SMILES: COc1ccc(-n2c(C(=O)NCc3ccc(OC(C)C)cc3)c3n(c2=O)CCN(C(=O)c2ccc(Br)c(Cl)c2)C3)cc1] | 7-(4-bromo-3-chloro-benzoyl)-N-(4-isopropoxyphenyl)-2-(4-methoxyphenyl)-3-oxo-6,8-dihydro-5H-imidazo[1,5-a]pyrazine-1-carboxamide | 1H-NMR (DMSO, 600 MHz, 80° C.): 1.27 (d, J = 6.0 Hz, 6H); 3.68 (t, J = 5.6 Hz, 2H); 3.79 (s, 3H); 3.83 (br. s, 2H); 4.16 (d, J = 4.9 Hz, 2H); 4.50-4.60 (m, 1H); 4.85 (s, 2H); 6.77 (d, J = 8.4 Hz, 2H); 6.96 (d, J = 8.9 Hz, 2H); 7.07 (br. s, 1H); 7.19 (d, J = 8.8 Hz, 2H); 7.41 (dd, J = 8.1 Hz, 1.6 Hz, 1H); 7.76 (d, J = 1.5 Hz, 1H); 7.87 (d, J = 8.2 Hz, 1H) ppm. |
| 157 | 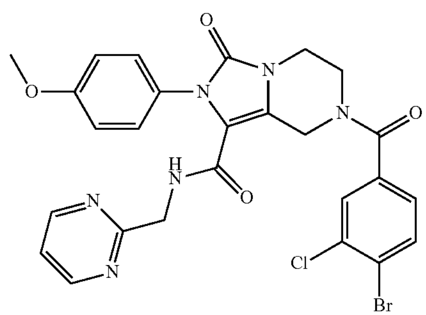 | 7-(4-bromo-3-chloro-benzoyl)-2-(4-methoxyphenyl)-3-oxo-N-(pyrimidin-2-ylmethyl)-6,8-dihydro-5H-imidazo[1,5-a]pyrazine-1-carboxamide | 1H-NMR (DMSO, 600 MHz, 80° C.): 3.70 (t, J = 5.4 Hz, 2H), 3.80 (s, 3H); 3.84 (br. s, 2H), 4.46 (d, J = 4.2 Hz, 2H), 4.99 (s, 2H), 7.00 (d, J = 8.8 Hz, 2H), 7.27 (d, J = 8.8 Hz, 2H), 7.31 (br. s, 1H), 7.34 (t, J = 4.8 Hz, 1H), 7.41 (d, J = 8.3 Hz, 1H), 7.75 (s, 1H), 7.85 (d, J = 8.1 Hz, 1H), 8.63 (d, J = 3.7 Hz, 2H) ppm. |

TABLE A-continued

| Compound # | Structure | Name | NMR |
|---|---|---|---|
| 158 | 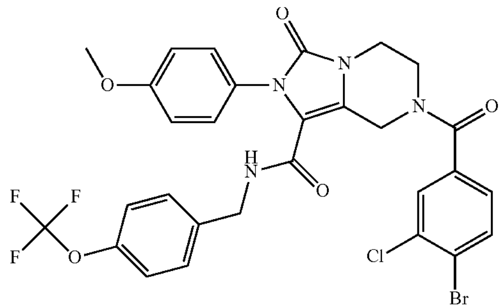 [SMILES: COc1ccc(-n2c(C(=O)NCc3ccc(OC(F)(F)F)cc3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[[4-(trifluoromethoxyphenyl]methyl]-6,8-dihydro-5H-imidazo[1,5-a]pyrazine-1-carboxamide | 1H NMR (300 MHz, DMSO-d6) δ 8.10-7.89 (m, 2H), 7.80 (s, 1H), 7.44 (d, J = 8.1 Hz, 1H), 7.37-7.10 (m, 5H), 6.98 (d, J = 8.4 Hz, 2H), 4.99-4.70 (m, 2H), 4.45-4.13 (m, 2H), 3.99 (s, 1H), 3.77 (s, 3H), 3.67 (s, 3H). |
| 159 | 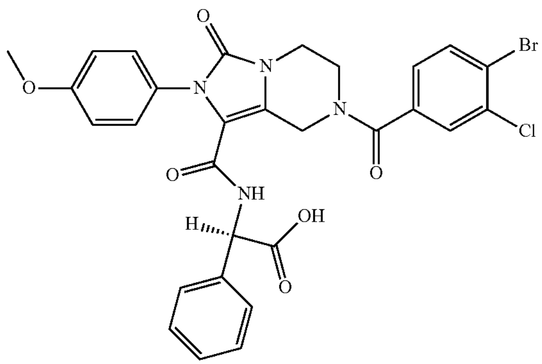 [SMILES: COc1ccc(-n2c(C(=O)N[C@@H](C(=O)O)c3ccccc3)c3n(c2=O)CCN(C(=O)c2ccc(Br)c(Cl)c2)C3)cc1] | rac-(2R)-2-[[[7-(4-bromo-3-chloro-benzoyl)-2-(4-methoxyphenyl)-3-oxo-6,8-dihydro-5H-imidazo[1,5-a]pyrazine-1-carbonyl]amino]-2-phenyl-acetic acid | 1H NMR (300 MHz, Methanol-d4) δ 7.84 (d, J = 8.1 Hz, 1H), 7.73 (s, 1H), 7.40-7.19 (m, 6H), 7.15-6.98 (m, 4H), 5.16 (s, 3H), 4.10 (s, 1H), 3.93-3.73 (m, 6H). |
| 160 | 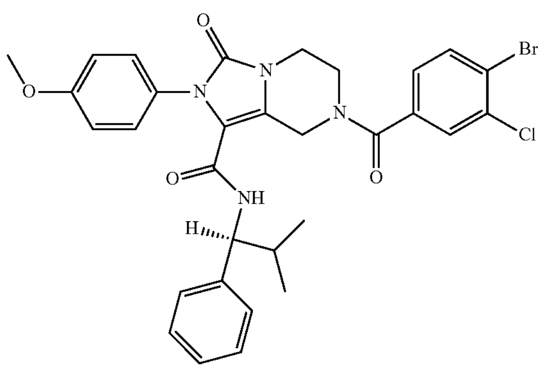 [SMILES: COc1ccc(-n2c(C(=O)N[C@H](c3ccccc3)C(C)C)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1S)-2-methyl-1-phenyl-propyl]-6,8-dihydro-5H-imidazo[1,5-a]pyrazine-1-carboxamide | 1H NMR (300 MHz, DMSO-d6) δ 7.83 (m, 2H), 7.48-6.80 (m, 11H), 5.03-4.31 (m, 3H), 4.00 (s, 1H), 3.72 (m, 6H), 1.92-1.65 (m, 1H), 0.80-0.40 (m, 6H). |

TABLE A-continued

| Compound # | Structure | Name | NMR |
|---|---|---|---|
| 161 | 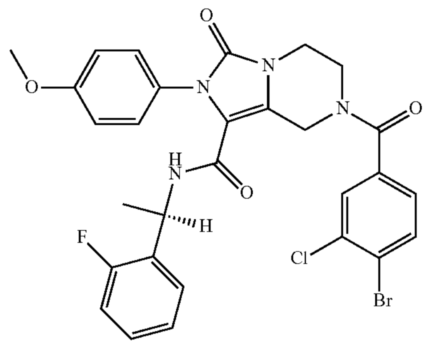 [SMILES: COc1ccc(-n2c(C(=O)N[C@H](C)c3ccccc3F)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-1-(2-fluorophenyl)ethyl]-6,8-dihydro-5H-imidazo[1,5-a]pyrazine-1-carboxamide | 1H NMR (400 MHz, DMSO-d6) δ 7.86 (d, J = 8.2 Hz, 1H), 7.78 (d, J = 1.9 Hz, 1H), 7.61 (s, 1H), 7.39 (dd, J = 8.2, 2.0 Hz, 1H), 7.25 (d, J = 7.2 Hz, 1H), 7.19-6.86 (m, 7H), 5.20-4.65 (m, 3H), 4.12-3.60 (m, 7H), 1.38-1.05 (m, 3H). |
| 162 | 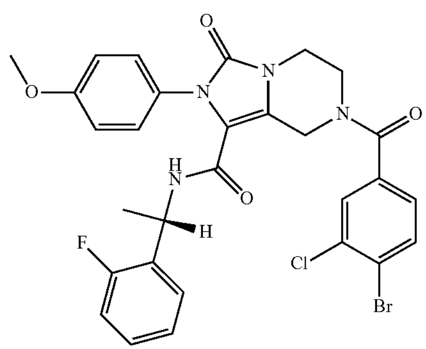 [SMILES: COc1ccc(-n2c(C(=O)N[C@@H](C)c3ccccc3F)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1S)-1-(2-fluorophenyl)ethyl]-6,8-dihydro-5H-imidazo[1,5-a]pyrazine-1-carboxamide | 1H NMR (400 MHz, DMSO-d6) δ 7.86 (d, J = 8.2 Hz, 1H), 7.78 (d, J = 1.9 Hz, 1H), 7.61 (s, 1H), 7.39 (dd, J = 8.2, 2.0 Hz, 1H), 7.25 (d, J = 7.2 Hz, 1H), 7.19-6.86 (m, 7H), 5.20-4.65 (m, 3H), 4.12-3.60 (m, 7H), 1.38-1.05 (m, 3H). |

TABLE A-continued

| Compound # | Structure | Name | NMR |
|---|---|---|---|
| 163 | 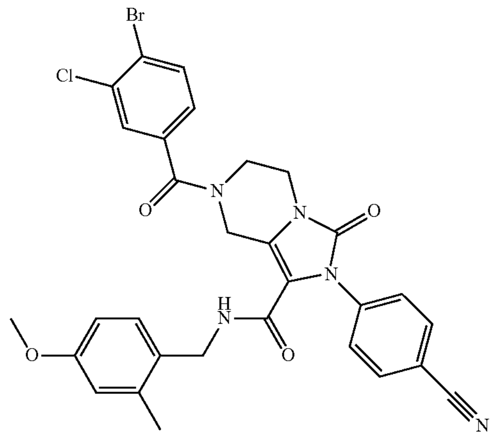 [SMILES: COc1ccc(CNC(=O)c2c3n(c(=O)n2-c2ccc(C#N)cc2)CCN(C(=O)c2ccc(Br)c(Cl)c2)C3)c(C)c1] | 7-(4-bromo-3-chloro-benzoyl)-2-(4-cyanophenyl)-N-[(4-methoxy-2-methyl-phenyl)methyl]-3-oxo-6,8-dihydro-5H-imidazo[1,5-a]pyrazine-1-carboxamide | 1H NMR (400 MHz, Chloroform-d) δ 7.73 (d, J = 8.4 Hz, 1H), 7.62-7.51 (m, 3H), 7.39 (d, J = 8.4 Hz, 2H), 7.28-7.20 (m, 1H), 6.80 (s, 1H), 6.70-6.58 (m, 2H), 5.08-4.83 (m, 2H), 4.30-4.13 (m, 2H), 4.12-3.90 (m, 2H), 3.88-3.70 (m, 5H), 2.05 (s, 3H). |
| 164 | 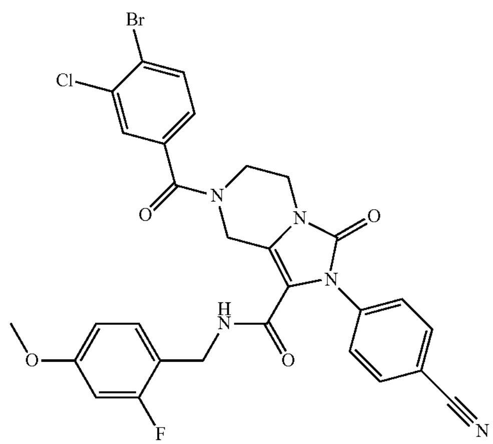 [SMILES: COc1ccc(CNC(=O)c2c3n(c(=O)n2-c2ccc(C#N)cc2)CCN(C(=O)c2ccc(Br)c(Cl)c2)C3)c(F)c1] | 7-(4-bromo-3-chloro-benzoyl)-2-(4-cyanophenyl)-N-[(2-fluoro-4-methoxy-phenyl)methyl]-3-oxo-6,8-dihydro-5H-imidazo[1,5-a]pyrazine-1-carboxamide | 1H NMR (400 MHz, Chloroform-d) δ 7.73 (d, J = 8.4 Hz, 1H), 7.69-7.51 (m, 3H), 7.39 (d, J = 8.4 Hz, 2H), 7.25-7.17 (m, 1H), 7.12-6.98 (m, 1H), 6.70-6.50 (m, 2H), 5.08-4.86 (m, 2H), 4.35-4.23 (m, 2H), 4.10-3.65 (m, 7H). |

TABLE A-continued

| Compound # | Structure | Name | NMR |
|---|---|---|---|
| 165 | 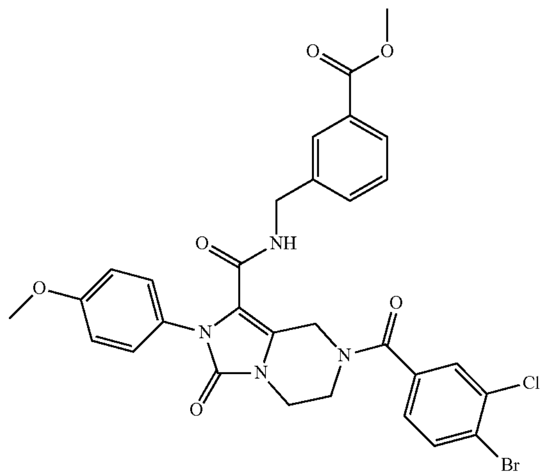 [SMILES: COC(=O)c1cccc(CNC(=O)c2c3n(c(=O)n2-c2ccc(OC)cc2)CCN(C(=O)c2ccc(Br)c(Cl)c2)C3)c1] | methyl 3-[[[7-(4-bromo-3-chloro-benzoyl)-2-(4-methoxyphenyl)-3-oxo-6,8-dihydro-5H-imidazo[1,5-a]pyrazine-1-carbonyl]amino]methyl]benzoate | 1H NMR (400 MHz, DMSO-d6, 80° C.): 3.71 (t, J = 5.4 Hz, 2H), 3.80 (s, 3H), 3.85 (br s, 2H), 3.90 (s, 3H), 4.34 (d, J = 5.7 Hz, 2H), 4.88 (s, 2H), 6.95 (d, J = 8.6 Hz, 2H), 7.21 (d, J = 8.6 Hz, 2H), 7.29-7.47 (m, 4H), 7.76 (br s, 2H), 7.81-7.91 (m, 2H) |
| 166 | 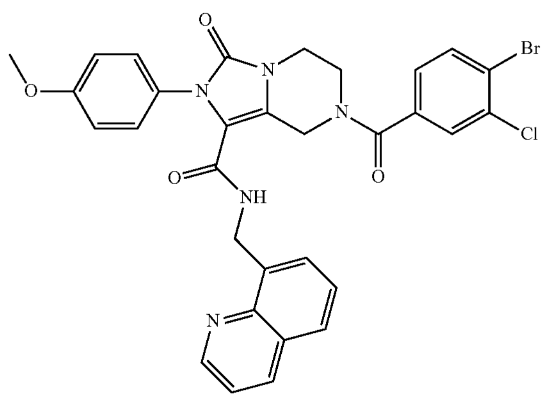 [SMILES: COc1ccc(-n2c(C(=O)NCc3cccc4cccnc34)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-(8-quinolylmethyl)-6,8-dihydro-5H-imidazo[1,5-a]pyrazine-1-carboxamide | 1H NMR (400 MHz, DMSO-d6, 80° C.): 3.66 (t, J = 5.4 Hz, 2H), 3.74 (s, 3H), 3.83 (br s, 2H), 4.83 (d, J = 5.6 Hz, 2H), 4.89 (s, 2H), 6.81 (d, J = 8.6 Hz, 2H), 6.96 (br s, 1H), 7.13 (d, J = 8.6 Hz, 2H), 7.38-7.53 (m, 4H), 7.74 (s, 1H), 7.84-7.86 (m, 2H), 8.32 (d, J = 8.3 Hz, 1H), 8.77 (d, J = 3.5 Hz, 1H). |

| Compound # | Structure | Name | NMR |
|---|---|---|---|
| 167 | 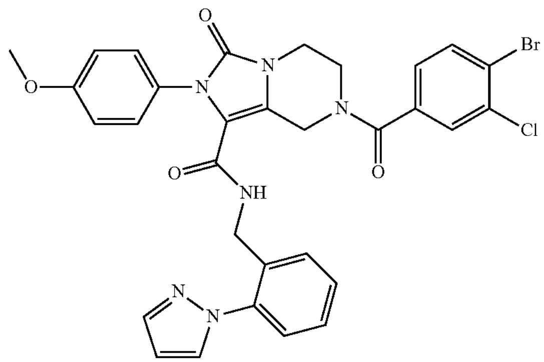 [SMILES: COc1ccc(-n2c(C(=O)NCc3ccccc3-n3cccn3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[(2-pyrazol-1-ylphenyl)methyl]-6,8-dihydro-5H-imidazo[1,5-a]pyrazine-1-carboxamide | 1H NMR (400 MHz, DMSO-d6, 80° C.): 3.67 (t, J = 5.4 Hz, 2H), 3.78 (s, 3H), 3.82 (br s, 2H), 4.18 (d, J = 5.3 Hz, 2H), 4.86 (s, 2H), 6.47 (s, 1H), 6.94 (d, J = 8.4 Hz, 2H), 7.02 (br s, 1H), 7.18-7.21 (m, 3H), 7.32-7.40 (m, 4H), 7.60 (s, 1H), 7.73 (s, 1H), 7.84 (d, J = 8.1 Hz, 1H), 7.94 (s, 1H). |
| 168 | 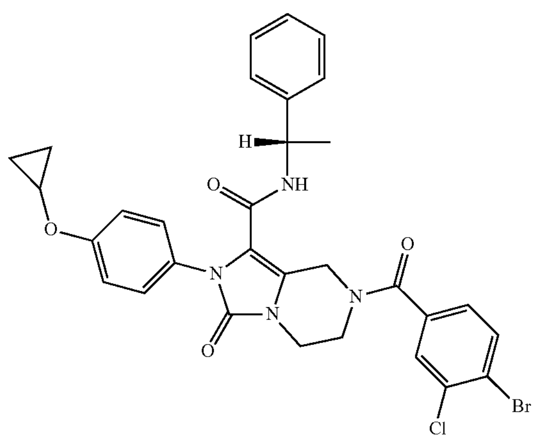 [SMILES: C[C@H](NC(=O)c1c2n(c(=O)n1-c1ccc(OC3CC3)cc1)CCN(C(=O)c1ccc(Br)c(Cl)c1)C2)c1ccccc1] | 7-(4-bromo-3-chloro-benzoyl)-2-[4-(cyclopropoxy)phenyl]-3-oxo-N-[rac-(1S)-1-phenylethyl]-6,8-dihydro-5H-imidazo[1,5-a]pyrazine-1-carboxamide | 1H NMR (400 MHz, DMSO-d6, 80° C.): 0.68 (m, 2H), 0.78-0.83 (m, 2H), 1.21 (d, J = 6.9 Hz, 3H), 3.69 (t, J = 5.5 Hz, 2H), 3.85-3.88 (m, 3H), 4.84-4.87 (m, 3H), 6.89 (d, J = 7.5 Hz, 1H), 7.05-7.10 (m, 4H), 7.20-7.24 (m, 5H), 7.39 (dd, J = 8.2, 2.1 Hz, 1H), 7.74 (d, J = 1.4 Hz, 1H), 7.85 (d, J = 8.1 Hz, 1H). |

TABLE A-continued

| Compound # | Structure | Name | NMR |
|---|---|---|---|
| 169 | 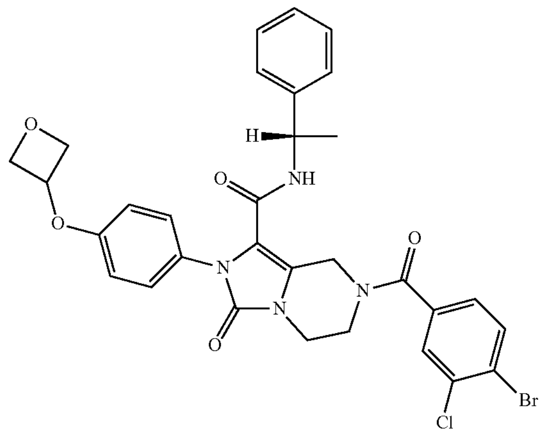 [SMILES: C[C@H](NC(=O)c1c2n(c(=O)n1-c1ccc(OC3COC3)cc1)CCN(C(=O)c1ccc(Br)c(Cl)c1)C2)c1ccccc1] | 7-(4-bromo-3-chloro-benzoyl)-2-[4-(oxetan-3-yloxy)phenyl]-3-oxo-N-[rac-(1S)-1-phenylethyl]-6,8-dihydro-5H-imidazo[1,5-a]pyrazine-1-carboxamide | 1H-NMR (DMSO, 600 MHz, 80° C.): 1.23 (d, J = 6.1 Hz, 3H), 3.66-3.72 (m, 2H), 3.78-3.92 (m, 2H), 4.54-4.60 (m, 2H), 4.78-4.91 (m, 3H), 4.94 (t, J = 6.6 Hz, 2H), 5.26-5.34 (m, 1H), 6.85 (d, J = 8.5 Hz, 2H), 7.01-7.11 (m, 3H), 7.19-7.30 (m, 5H), 7.40 (d, J = 8.3 Hz, 1H), 7.75 (s, 1H), 7.86 (d, J = 8.0 Hz, 1H) ppm. |
| 170 | 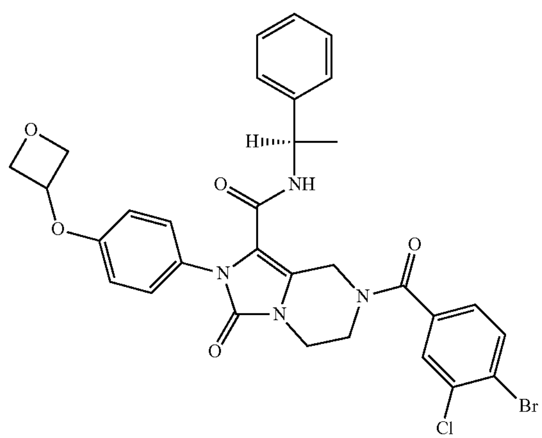 [SMILES: C[C@@H](NC(=O)c1c2n(c(=O)n1-c1ccc(OC3COC3)cc1)CCN(C(=O)c1ccc(Br)c(Cl)c1)C2)c1ccccc1] | 7-(4-bromo-3-chloro-benzoyl)-2-[4-(oxetan-3-yloxy)phenyl]-3-oxo-N-[rac-(1R)-1-phenylethyl]-6,8-dihydro-5H-imidazo[1,5-a]pyrazine-1-carboxamide | 1H-NMR (DMSO, 600 MHz, 80° C.): 1.23 (d, J = 6.1 Hz, 3H), 3.66-3.72 (m, 2H), 3.78-3.92 (m, 2H), 4.54-4.60 (m, 2H), 4.78-4.91 (m, 3H), 4.94 (t, J = 6.6 Hz, 2H), 5.26-5.34 (m, 1H), 6.85 (d, J = 8.5 Hz, 2H), 7.01-7.11 (m, 3H), 7.19-7.30 (m, 5H), 7.40 (d, J = 8.3 Hz, 1H), 7.75 (s, 1H), 7.86 (d, J = 8.0 Hz, 1H) ppm. |

TABLE A-continued

| Compound # | Structure | Name | NMR |
|---|---|---|---|
| 171 | 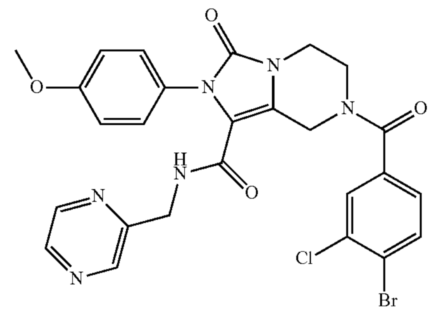 | 7-(4-bromo-3-chloro-benzoyl)-2-(4-methoxyphenyl)-3-oxo-N-(pyrazin-2-ylmethyl)-6,8-dihydro-5H-imidazo[1,5-a]pyrazine-1-carboxamide | 1H-NMR (DMSO, 600 MHz, 80° C.): 3.70 (t, J = 5.4 Hz, 2H); 3.81 (s, 3H); 3.84 (br. s., 2H); 4.43 (d, J = 5.3 Hz, 2H); 4.91 (s, 2H); 6.97 (d, J = 8.9 Hz, 2H); 7.23 (d, J = 8.9 Hz, 2H); 7.41 (d, J = 8.5 Hz, 1H); 7.42 (br. s., 1H); 7.75 (s, 1H); 7.86 (d, J = 8.1 Hz, 1H); 8.37-8.47 (m, 2H); 8.49 (s, 1H) ppm. |
| 172 | 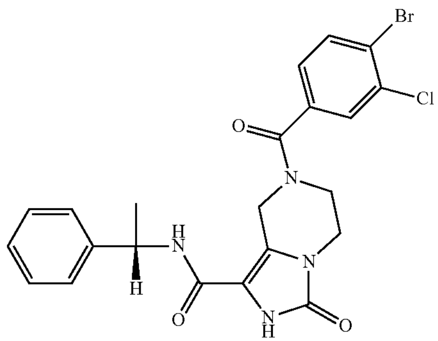 [SMILES: C[C@H](NC(=O)c1[nH]c(=O)n2c1CN(C(=O)c1ccc(Br)c(Cl)c1)CC2)c1ccccc1] | 7-(4-bromo-3-chloro-benzoyl)-3-oxo-N-[rac-(1R)-1-phenylethyl]-2,5,6,8-tetrahydroimidazo[1,5-a]pyrazine-1-carboxamide | 1H-NMR (DMSO, 600 MHz, 80° C.): 1.43 (d, J = 6.9 Hz, 3H); 3.58 (t, J = 5.3 Hz, 2H); 3.69-3.89 (m, 2H); 4.70-4.88 (m, 2H); 5.00-5.10 (m, 1H); 7.22-7.28 (m, 1H); 7.31-7.38 (m, 5H); 7.61 (d, J = 7.7 Hz, 1H); 7.71 (s, 1H); 7.84 (d, J = 8.0 Hz, 1H); 10.20 (s, 1H) ppm. |
| 173 | 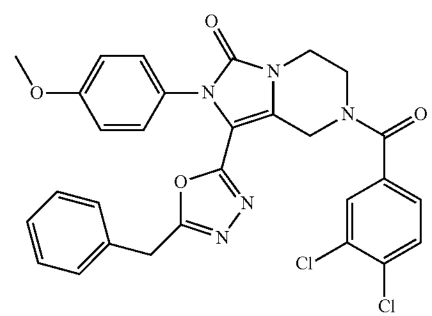 [SMILES: COc1ccc(-n2c(-c3nnc(Cc4ccccc4)o3)c3n(c2=O)CCN(C(=O)c2ccc(Cl)c(Cl)c2)C3)cc1] | 1-(5-benzoyl-1,3,4-oxadiazol-2-yl)-7-(3,4-dichlorobenzoyl)-2-(4-methoxyphenyl)-6,8-dihydro-5H-imidazo[1,5-a]pyrazin-3-one | 1H-NMR (DMSO, 600 MHz, 80° C.): 3.73 (t, J = 5.5 Hz, 2H); 3.82 (s, 3H); 3.88 (br. s., 2H); 4.09 (s, 2H); 4.89 (s, 2H); 6.95 (d, J = 8.9 Hz, 2H); 7.04-7.11 (m, 2H); 7.18 (d, J = 8.9 Hz, 2H); 7.23-7.31 (m, 3H); 7.51 (dd, J = 8.3 Hz, J = 2.0 Hz, 1H); 7.73 (d, J = 8.2 Hz, 1H); 7.78 (d, J = 1.9 Hz, 1H) ppm. |

| Compound # | Structure | Name | NMR |
|---|---|---|---|
| 174 | 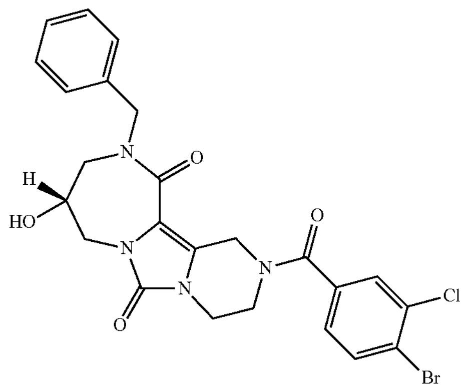 [SMILES: O=C(c1ccc(Br)c(Cl)c1)N1CCn2c(c3n(c2=O)C[C@H](O)CN(Cc2ccccc2)C3=O)C1] | rac-(11R)-13-benzyl-4-(4-bromo-3-chloro-benzoyl)-11-hydroxy-4,7,9,13-tetrazatricyclo[7.5.0.0^2,7]tetradec-1-ene-8,14-dione | 1H NMR (300 MHz, DMSO-d6) δ 7.88 (d, J = 8.2 Hz, 1H), 7.77 (d, J = 1.9 Hz, 1H), 7.48-7.12 (m, 6H), 5.30 (s, 1H), 4.90-4.60 (m, 3H), 4.28 (s, 1H), 4.00-3.65 (m, 4H), 3.65-3.55 (m, 3H), 3.30-3.20 (m, 1H), 3.13 (dd, J = 14.9, 7.1 Hz, 1H). |
| 175 | 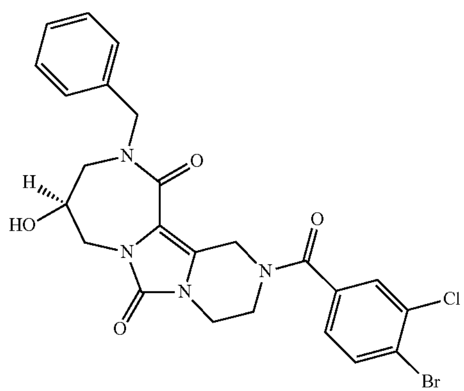 [SMILES: O=C(c1ccc(Br)c(Cl)c1)N1CCn2c(c3n(c2=O)C[C@@H](O)CN(Cc2ccccc2)C3=O)C1] | rac-(11S)-13-benzyl-4-(4-bromo-3-chloro-benzoyl)-11-hydroxy-4,7,9,13-tetrazatricyclo[7.5.0.0^2,7]tetradec-1-ene-8,14-dione | 1H NMR (300 MHz, DMSO-d6) δ 7.88 (d, J = 8.2 Hz, 1H), 7.77 (d, J = 1.9 Hz, 1H), 7.48-7.12 (m, 6H), 5.30 (s, 1H), 4.90-4.60 (m, 3H), 4.28 (s, 1H), 4.00-3.75 (m, 3H), 3.70-3.55 (m, 4H), 3.30-3.20 (m, 1H), 3.13 (dd, J = 14.9, 7.1 Hz, 1H). |

TABLE A-continued

| Compound # | Structure | Name | NMR |
|---|---|---|---|
| 176 | 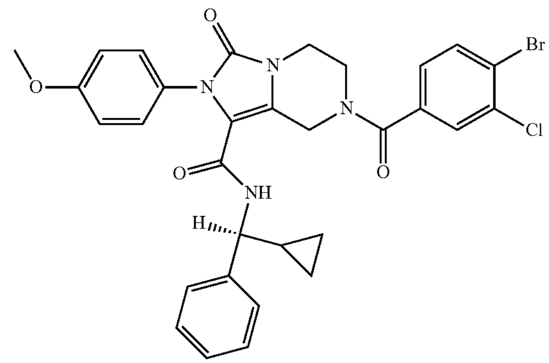 [SMILES: COc1ccc(-n2c(C(=O)N[C@H](c3ccccc3)C3CC3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(S)-cyclopropyl(phenyl)methyl]-6,8-dihydro-5H-imidazo[1,5-a]pyrazine-1-carboxamide | 1H NMR (300 MHz, DMSO-d6) δ 7.88 (d, J = 8.2 Hz, 1H), 7.78 (d, J = 12.6 Hz, 2H), 7.42 (d, J = 8.3 Hz, 1H), 7.35-7.05 (m, 7H), 6.98 (d, J = 7.9 Hz, 2H), 5.05-4.65 (m, 2H), 4.30-3.95 (m, 2H), 3.78 (s, 3H), 3.69 (s, 3H), 1.04-0.80 (m, 1H), 0.58-0.38 (m, 4H). |
| 177 | 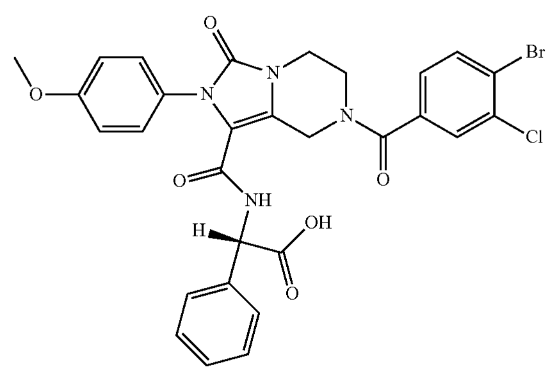 [SMILES: COc1ccc(-n2c(C(=O)N[C@H](C(=O)O)c3ccccc3)c3n(c2=O)CCN(C(=O)c2ccc(Br)c(Cl)c2)C3)cc1] | rac-(2S)-2-[[7-(4-bromo-3-chloro-benzoyl)-2-(4-methoxyphenyl)-3-oxo-6,8-dihydro[1,5-a]pyrazine-1-carbonyl]amino]-2-phenyl-acetic acid | 1H NMR (300 MHz, Methanol-d4) δ 7.84 (d, J = 8.4 Hz, 1H), 7.73 (s, 1H), 7.42-7.23 (m, 6H), 7.07 (d, J = 7.5 Hz, 4H), 5.49-4.98 (m, 3H), 4.09 (s, 1H), 3.86 (m, 6H). |

TABLE A-continued

| Compound # | Structure | Name | NMR |
|---|---|---|---|
| 178 | 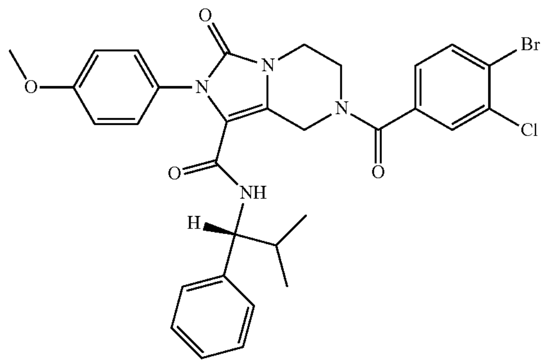 [SMILES: COc1ccc(-n2c(C(=O)N[C@@H](c3ccccc3)C(C)C)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-2-methyl-1-phenyl-propyl]-6,8-dihydro-5H-imidazo[1,5-a]pyrazine-1-carboxamide | 1H NMR (300 MHz, DMSO-d6) δ 7.86 (d, J = 22.5 Hz, 2H), 7.49-6.82 (m, 11H), 5.05-4.35 (m, 3H), 4.00 (s, 1H), 3.86-3.55 (m, 6H), 1.99-1.65 (m, 1H), 0.66 (d, J = 37.2 Hz, 6H). |
| 179 | 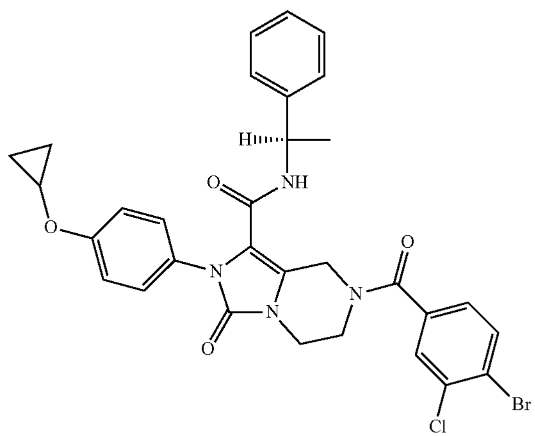 [SMILES: C[C@@H](NC(=O)c1c2n(c(=O)n1-c1ccc(OC3CC3)cc1)CCN(C(=O)c1ccc(Br)c(Cl)c1)C2)c1ccccc1] | 7-(4-bromo-3-chloro-benzoyl)-2-[4-(cyclopropoxy)phenyl]-3-oxo-N-[(1R)-1-phenylethyl]-6,8-dihydro-5H-imidazo[1,5-a]pyrazine-1-carboxamide | 1H NMR (400 MHz, DMSO-d6, 80° C.): 0.68 (m, 2H), 0.81 (m, 2H), 1.21 (d, J = 6.8 Hz, 3H), 3.69 (t, J = 5.5 Hz, 2H), 3.85-3.88 (m, 3H), 4.84-4.89 (m, 3H), 6.90 (d, J = 7.4 Hz, 1H), 7.06-7.10 (m, 4H), 7.18-7.26 (m, 5H), 7.39 (d, J = 8.1 Hz, 1H), 7.74 (s, 1H), 7.85 (d, J = 8.1 Hz, 1H). |

TABLE A-continued

| Compound # | Structure | Name | NMR |
|---|---|---|---|
| 180 | 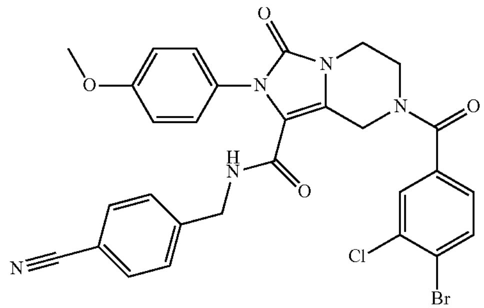 | 7-(4-bromo-3-chloro-benzoyl)-N-[(4-cyanophenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.4 Hz, 2H), 3.80 (s, 3H), 3.81-3.86 (m, 2H), 4.32 (d, J = 5.6 Hz, 2H), 4.85 (s, 2H), 6.96 (d, J = 8.4 Hz, 2H), 7.19 (d, J = 8.4 Hz, 2H), 7.25 (d, J = 7.5 Hz, 2H), 7.40 (d, J = 8.1 Hz, 2H), 7.67 (d, J = 7.9 Hz, 2H), 7.74 (s, 1H), 7.86 (d, J = 8.1 Hz, 1H) |
| 181 | 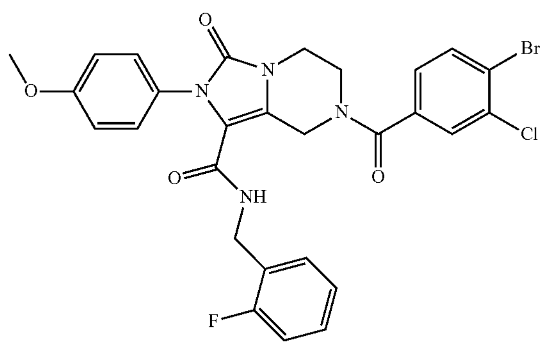 [SMILES: COc1ccc(-n2c(C(=O)NCc3ccccc3F)c3n(c2=O)CCN(C(=O)c2ccc(Br)c(Cl)c2)C3)cc1] | 7-(4-bromo-3-chloro-benzoyl)-N-[(2-fluorophenyl)methyl]-2-(4-methoxyphenyl)-3-oxo-6,8-dihydro-5H-imidazo[1,5-a]pyrazine-1-carboxamide | 1H NMR (400 MHz, DMSO-d6, 80° C.): 3.69 (t, J = 5.6 Hz, 2H), 3.80 (s, 3H), 3.85 (br s, 2H), 4.30 (d, J = 5.7 Hz, 2H), 4.86 (s, 2H), 6.96 (d, J = 8.9 Hz, 2H), 7.06-7.11 (m, 3H), 7.15 (br s, 1H), 7.20 (d, J = 8.8 Hz, 2H), 7.26-7.32 (m, 1H), 7.40 (dd, J = 8.3 Hz, 1.7 Hz, 1H), 7.75 (d, J = 1.7 Hz, 1H), 7.86 (d, J = 8.4 Hz, 1H) |
| 182 | 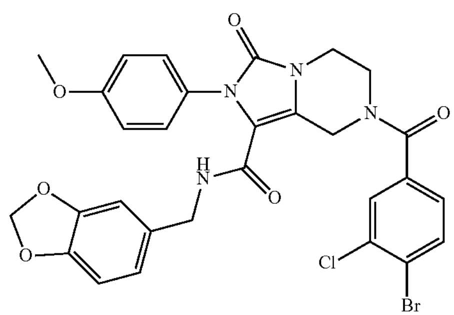 [SMILES: COc1ccc(-n2c(C(=O)NCc3ccc4c(c3)OCO4)c3n(c2=O)CCN(C(=O)c2ccc(Br)c(Cl)c2)C3)cc1] | N-(1,3-benzodioxol-5-ylmethyl)-7-(4-bromo-3-chloro-benzoyl)-2-(4-methoxyphenyl)-3-oxo-6,8-dihydro-5H-imidazo[1,5-a]pyrazine-1-carboxamide | 1H NMR (400 MHz, DMSO-d6, 80° C.): 3.68 (t, J = 5.4 Hz, 2H), 3.79 (s, 3H), 3.81-3.89 (m, 2H), 4.14 (d, J = 5.7 Hz, 2H), 4.85 (s, 2H), 5.96 (s, 2H), 6.53 (d, J = 8.0 Hz, 1H), 6.58 (s, 1H), 6.74 (d, J = 8.0 Hz, 1H), 6.95 (d, J = 8.8 Hz, 2H), 7.05 (br s, 1H), 7.19 (d, J = 8.4 Hz, 2H), 7.40 (dd, J = 8.2 Hz, 1.2 Hz, 1H), 7.74 (s, 1H), 7.85 (d, J = 8.3 Hz, 1H) |

TABLE A-continued

| Compound # | Structure | Name | NMR |
|---|---|---|---|
| 183 | 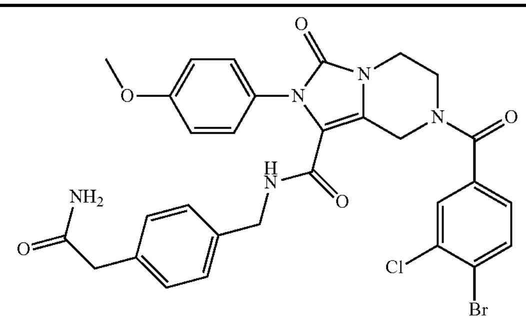 | N-[[4-(2-amino-2-oxoethyl)phenyl]methyl]-7-(4-bromo-3-chloro-benzoyl)-2-(4-methoxyphenyl)-3-oxo-6,8-dihydro-5H-imidazo[1,5-a]pyrazine-1-carboxamide | 1H NMR (400 MHz, DMSO-d6, 80° C.): 3.37 (s, 2H), 3.68 (t, J = 5.4 Hz, 2H), 3.80 (s, 3H), 3.81-3.86 (m, 2H), 4.22 (d, J = 5.3 Hz, 2H), 4.86 (s, 2H), 6.58 (br s, 2H), 6.92-6.99 (m, 4H), 7.11-7.24 (m, 5H), 7.40 (d, J = 8.2 Hz, 2H), 7.75 (s, 1H), 7.86 (d, J = 8.1 Hz, 1H) |
| 184 | 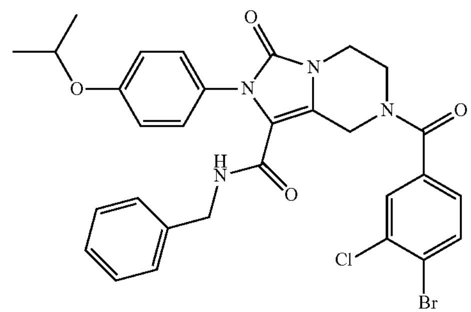 [SMILES: CC(C)Oc1ccc(-n2c(C(=O)NCc3ccccc3)c3n(c2=O)CCN(C(=O)c2ccc(Br)c(Cl)c2)C3)cc1] | N-benzyl-7-(4-bromo-3-chloro-benzoyl)-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.29 (d, J = 6.0 Hz, 6H), 3.68 (t, J = 5.3 Hz, 2H), 3.83 (br s, 2H), 4.25 (d, J = 5.6 Hz, 2H), 4.58 (hept, J = 6.0 Hz, 1H), 4.85 (s, 2H), 6.92 (d, J = 8.7 Hz, 2H), 7.04 (d, J = 6.2 Hz, 2H), 7.09-7.28 (m, 6H), 7.39 (d, J = 8.3 Hz, 1H), 7.74 (br s, 1H), 7.85 (d, J = 8.3 Hz, 1H) |
| 185 | 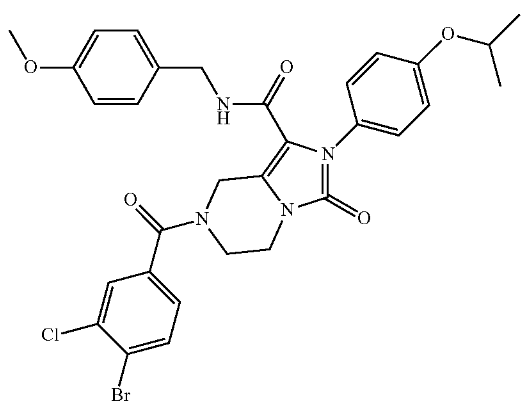 | 7-(4-bromo-3-chloro-benzoyl)-2-(4-isopropoxyphenyl)-N-[(4-methoxyphenyl)methyl]-3-oxo-6,8-dihydro-5H-imidazo[1,5-a]pyrazine-1-carboxamide | 1H NMR (400 MHz, DMSO-d6, 80° C.): 1.30 (d, J = 5.9 Hz, 6H), 3.69 (t, J = 5.4 Hz, 2H), 3.76 (s, 3H), 3.84 (br s, 2H), 4.18 (d, J = 5.9 Hz, 2H), 4.59 (hept, J = 6.0 Hz, 1H), 4.86 (s, 2H), 6.81 (d, J = 8.7 Hz, 2H), 6.92-7.01 (m, 5H), 7.18 (d, J = 8.7 Hz, 2H), 7.41 (dd, J = 8.2 Hz, 1.7 Hz, 1H), 7.76 (d, J = 1.7 Hz, 1H), 7.87 (d, J = 8.1 Hz, 1H) |

TABLE A-continued

| Compound # | Structure | Name | NMR |
|---|---|---|---|
| 186 | 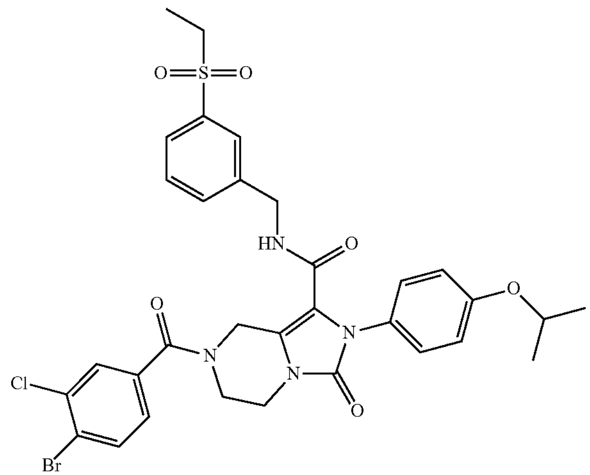 [SMILES: CCS(=O)(=O)c1cccc(CNC(=O)c2c3n(c(=O)n2-c2ccc(OC(C)C)cc2)CCN(C(=O)c2ccc(Br)c(Cl)c2)C3)c1] | 7-(4-bromo-3-chloro-benzoyl)-N-[(3-ethylsulfonylphenyl)methyl]-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.13 (t, J = 7.4 Hz, 3H), 1.28 (d, J = 6.0 Hz, 6H), 3.22 (q, J = 7.4 Hz, 2H), 3.68 (t, J = 5.3 Hz, 2H), 3.82 (br s, 2H), 4.37 (d, J = 5.9 Hz, 2H), 4.57 (hept, J = 6.0 Hz, 1H), 4.86 (s, 2H), 6.92 (d, J = 8.0 Hz, 2H), 7.17 (d, J = 8.0 Hz, 2H), 7.35-7.49 (m, 3H), 7.54 (t, J = 7.6 Hz, 1H), 7.70 (s, 1H), 7.71-7.77 (m, 2H), 7.85 (d, J = 8.5 Hz, 1H) |
| 187 | 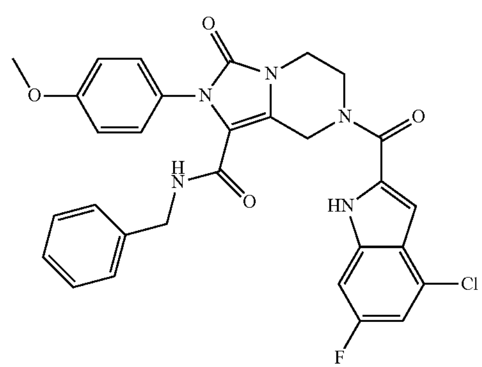 [SMILES: COc1ccc(-n2c(C(=O)NCc3ccccc3)c3n(c2=O)CCN(C(=O)c2cc4c(Cl)cc(F)cc4[nH]2)C3)cc1] | N-benzyl-7-(4-chloro-6-fluoro-1H-indole-2-carbonyl)-2-(4-methoxyphenyl)-3-oxo-6,8-dihydro-5H-imidazo[1,5-a]pyrazine-1-carboxamide | 1H-NMR (DMSO, 300 MHz, 25° C.): 3.73-3.86 (m, 5H); 4.12 (br. s, 2H); 4.26 (d, J = 5.3 Hz, 2H); 5.09 (br. s, 2H); 6.90-7.00 (m, 3H); 7.02-7.10 (m, 2H); 7.10-7.29 (m, 8H); 7.80 (br. s., 1H); 12.15 (br. s, 1H) ppm. |

| Compound # | Structure | Name | NMR |
|---|---|---|---|
| 188 | 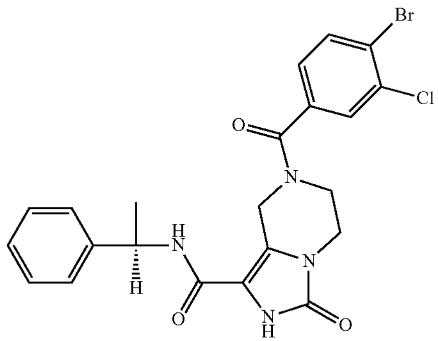 [SMILES: C[C@@H](NC(=O)c1[nH]c(=O)n2c1CN(C(=O)c1ccc(Br)c(Cl)c1)CC2)c1ccccc1] | 7-(4-bromo-3-chloro-benzoyl)-3-oxo-N-[rac-(1R)-1-phenylethyl]-2,5,6,8-tetrahydroimidazo[1,5-a]pyrazine-1-carboxamide | 1H-NMR (DMSO, 600 MHz, 80° C.): 1.43 (d, J = 6.9 Hz, 3H); 3.58 (t, J = 5.3 Hz, 2H); 3.69-3.89 (m, 2H); 4.70-4.88 (m, 2H); 5.00-5.10 (m, 1H); 7.22-7.28 (m, 1H); 7.31-7.38 (m, 5H); 7.61 (d, J = 7.7 Hz, 1H); 7.71 (s, 1H); 7.84 (d, J = 8.0 Hz, 1H); 10.20 (s, 1H) ppm. |
| 189 | 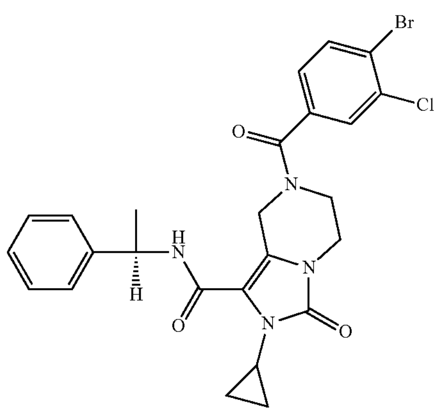 [SMILES: C[C@@H](NC(=O)c1c2n(c(=O)n1C1CC1)CCN(C(=O)c1ccc(Br)c(Cl)c1)C2)c1ccccc1] | 7-(4-bromo-3-chloro-benzoyl)-2-cyclopropyl-3-oxo-N-[rac-(1R)-1-phenylethyl]-6,8-dihydro-5H-imidazo[1,5-a]pyrazine-1-carboxamide | 1H-NMR (DMSO, 600 MHz, 80° C.): 0.76-0.91 (m, 4H); 1.46 (d, J = 6.9 Hz, 3H); 2.99-3.05 (m, 1H); 3.58 (t, J = 5.6 Hz, 2H); 3.72-3.83 (m, 2H); 4.70 (s, 2H); 5.09 (m, 1H); 7.24 (t, J = 7.3 Hz, 1H); 7.27-7.39 (m, 5H); 7.55-7.63 (m, 1H); 7.66 (d, J = 1.4 Hz, 1H); 7.80 (d, J = 8.2 Hz, 1H) ppm. |

| Compound # | Structure | Name | NMR |
|---|---|---|---|
| 190 | 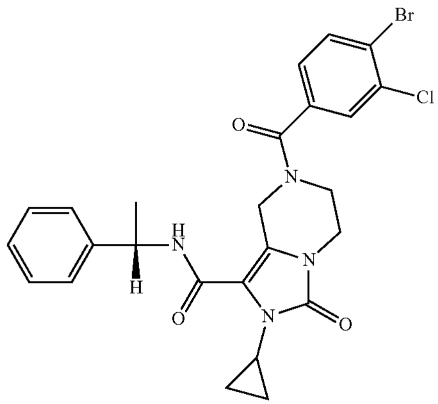 [SMILES: C[C@H](NC(=O)c1c2n(c(=O)n1C1CC1)CCN(C(=O)c1ccc(Br)c(Cl)c1)C2)c1ccccc1] | 7-(4-bromo-3-chloro-benzoyl)-2-cyclopropyl-3-oxo-N-[rac-(1S)-1-phenylethyl]-6,8-dihydro-5H-imidazo[1,5-a]pyrazine-1-carboxamide | 1H-NMR (DMSO, 600 MHz, 80° C.): 0.76-0.91 (m, 4H); 1.46 (d, J = 6.9 Hz, 3H); 2.99-3.05 (m, 1H); 3.58 (t, J = 5.6 Hz, 2H); 3.72-3.83 (m, 2H); 4.70 (s, 2H); 5.09 (m, 1H); 7.24 (t, J = 7.3 Hz, 1H); 7.27-7.39 (m, 5H); 7.55-7.63 (m, 1H); 7.66 (d, J = 1.4 Hz, 1H), 7.80 (d, J = 8.2 Hz, 1H) ppm. |
| 191 | 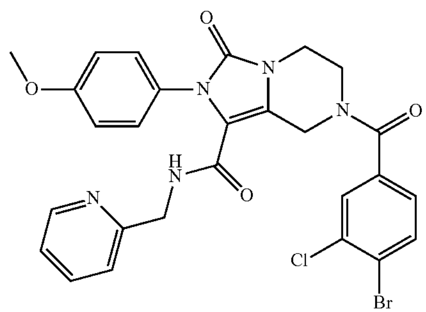 | 7-(4-bromo-3-chloro-benzoyl)-2-(4-methoxyphenyl)-3-oxo-N-(2-pyridylmethyl)-6,8-dihydro-5H-imidazo[1,5-a]pyrazine-1-carboxamide | 1H-NMR (DMSO, 600 MHz, 80° C.): 3.71 (t, J = 5.5 Hz, 2H); 3.81 (s, 3H); 3.87 (t, J = 5.5 Hz, 2H); 4.36 (d, J = 5.3 Hz, 2H); 4.92 (s, 2H); 6.98 (d, J = 8.6 Hz, 3H); 7.09 (d, J = 7.8 Hz, 1H); 7.20 (m, 1H); 7.25 (d, J = 8.6 Hz, 2H); 7.39 (dd, J = 8.0 Hz, 1.5 Hz, 1H), 7.65 (td, J = 7.7 Hz, 1.4 Hz, 1H), 7.70-7.73 (m, 1H), 7.83 (d, J = 8.3 Hz, 1H), 8.36 (d, J = 4.3 Hz, 1H) ppm. |
| 192 | 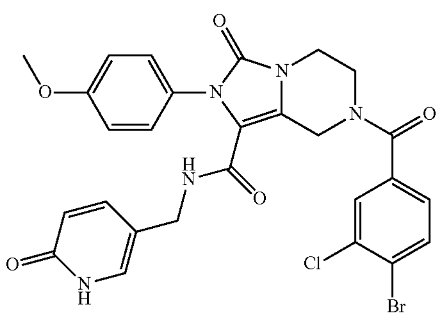 [SMILES: COc1ccc(-n2c(C(=O)NCc3ccc(=O)[nH]c3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[(6-oxo-1H-pyridin-3-yl)methyl]-6,8-dihydro-5H-imidazo[1,5-a]pyrazine-1-carboxamide | 1H-NMR (DMSO, 600 MHz, 80° C.): 3.69 (t, J = 5.5 Hz, 2H); 3.81 (s, 3H); 3.81-3.87 (m, 2H); 3.97 (d, J = 5.5 Hz, 2H); 4.85 (s, 2H); 6.23 (d, J = 10.0 Hz, 1H); 6.69 (br. s., 1H); 6.96 (d, J = 8.9 Hz, 2H); 7.05-7.14 (m, 2H); 7.19 (d, J = 8.9 Hz, 2H), 7.38 (dd, J = 8.0, 1.9 Hz, 1H), 7.68-7.73 (m, 1H), 7.84 (d, J = 8.1 Hz, 1H), 10.82 (br. s., 1H) ppm. |

TABLE A-continued

| Compound # | Structure | Name | NMR |
|---|---|---|---|
| 193 | 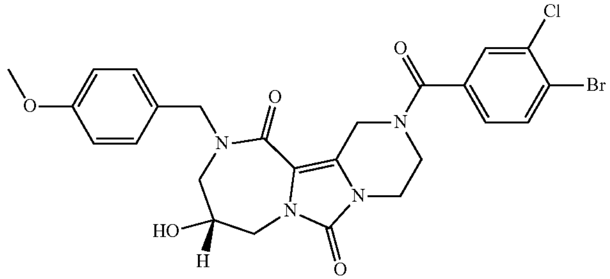 [SMILES: COc1ccc(CN2C[C@@H](O)Cn3c(c4n(c3=O)CCN(C(=O)c3ccc(Br)c(Cl)c3)C4)C2=O)cc1] | rac-(11R)-4-(4-bromo-3-chlorobenzoyl)-11-hydroxy-13-[(4-methoxyphenyl)methyl]-4,7,9,13-tetrazatricyclo[7.5.0.0^2,7]tetradec-1-ene-8,14-dione | 1H NMR (400 MHz, Chloroform-d) δ 7.71 (d, J = 8.2 Hz, 1H), 7.58 (d, J = 1.9 Hz, 1H), 7.24-7.15 (m, 3H), 6.92-6.82 (m, 2H), 4.90 (s, 2H), 4.77 (d, J = 14.3 Hz, 1H), 4.33 (d, J = 14.3 Hz, 1H), 4.13-3.64 (m, 11H), 3.43 (dd, J = 15.2, 4.9 Hz, 1H), 3.26 (dd, J = 15.1, 6.4 Hz, 1H). |
| 194 | 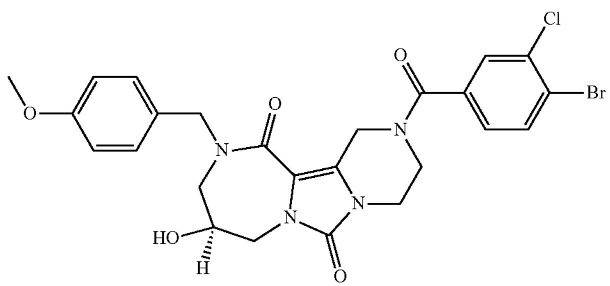 [SMILES: COc1ccc(CN2C[C@H](O)Cn3c(c4n(c3=O)CCN(C(=O)c3ccc(Br)c(Cl)c3)C4)C2=O)cc1] | rac-(11S)-4-(4-bromo-3-chlorobenzoyl)-11-hydroxy-13-[(4-methoxyphenyl)methyl]-4,7,9,13-tetrazatricyclo[7.5.0.0^2,7]tetradec-1-ene-8,14-dione | 1H NMR (400 MHz, Chloroform-d) δ 7.71 (d, J = 8.2 Hz, 1H), 7.57 (d, J = 1.9 Hz, 1H), 7.21 (dd, J = 8.1, 2.0 Hz, 3H), 6.91-6.84 (m, 2H), 4.90 (s, 2H), 4.79 (d, J = 14.3 Hz, 1H), 4.31 (d, J = 14.4 Hz, 1H), 4.13-3.66 (m, 11H), 3.42 (dd, J = 15.2, 5.0 Hz, 1H), 3.26 (dd, J = 15.1, 6.4 Hz, 1H). |
| 195 | 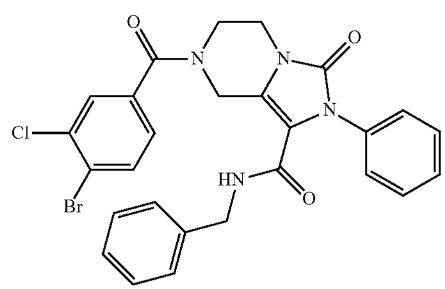 [SMILES: O=C(NCc1ccccc1)c1c2n(c(=O)n1-c1ccccc1)CCN(C(=O)c1ccc(Br)c(Cl)c1)C2] | N-benzyl-7-(4-bromo-3-chlorobenzoyl)-3-oxo-2-phenyl-6,8-dihydro-5H-imidazo[1,5-a]pyrazine-1-carboxamide | 1H NMR (400 MHz, DMSO-d6, 80° C.): 3.39-3.72 (m, 2H), 3.84-3.87 (m, 2H), 4.26 (d, J = 5.4 Hz, 2H), 4.86 (s, 2H), 7.06 (d, J = 6.8 Hz, 2H), 7.19-7.42 (m, 10H), 7.73 (s, 1H), 7.84 (d, J = 8.1 Hz, 1H) |

TABLE A-continued

| Compound # | Structure | Name | NMR |
|---|---|---|---|
| 196 | 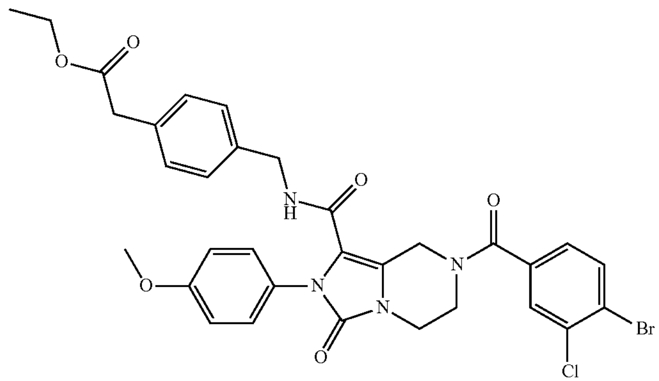 [SMILES: CCOC(=O)Cc1ccc(CNC(=O)c2c3n(c(=O)n2-c2ccc(OC)cc2)CCN(C(=O)c2ccc(Br)c(Cl)c2)C3)cc1] | ethyl 2-[4-[[[7-(4-bromo-3-chloro-benzoyl)-2-(4-methoxyphenyl)-3-oxo-6,8-dihydro-5H-imidazo[1,5-a]pyrazine-1-carbonyl]amino]methyl]phenyl]acetate | 1H NMR (400 MHz, DMSO-d6, 80° C.): 1.20 (t, J = 7.1 Hz, 3H), 3.60 (s, 2H), 3.68 (t, J = 5.5 Hz, 2H), 3.79 (s, 3H), 3.83 (br s, 2H), 4.10 (q, J = 7.1 Hz, 2H), 4.23 (d, J = 5.7 Hz, 2H), 4.86 (s, 2H), 6.89-7.04 (m, 4H), 7.14 (d, J = 8.0 Hz, 2H), 7.17-7.26 (m, 3H), 7.40 (d, J = 8.2 Hz, 1H), 7.75 (s, 1H), 7.86 (d, J = 8.1 Hz, 1H) |
| 197 | 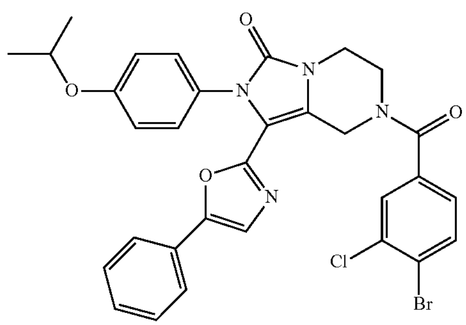 [SMILES: CC(C)Oc1ccc(-n2c(-c3ncc(-c4ccccc4)o3)c3n(c2=O)CCN(C(=O)c2ccc(Br)c(Cl)c2)C3)cc1] | 7-(4-bromo-3-chloro-benzoyl)-2-(4-isopropoxyphenyl)-1-(5-phenyloxazol-2-yl)-6,8-dihydro-5H-imidazo[1,5-a]pyrazin-3-one | 1H NMR (400 MHz, DMSO-d6, 80° C.): 1.34 (d, J = 5.7 Hz, 6H), 3.76 (t, J = 5.0 Hz, 2H), 3.92 (br s, 2H), 4.67 (hept, J = 5.9 Hz, 1H), 5.01 (s, 2H), 7.03 (d, J = 8.4 Hz, 2H), 7.19-7.39 (m, 7H), 7.45 (d, J = 8.0 Hz, 1H), 7.58 (s, 1H), 7.79 (s, 1H), 7.88 (d, J = 8.1 Hz, 1H) |
| 198 | 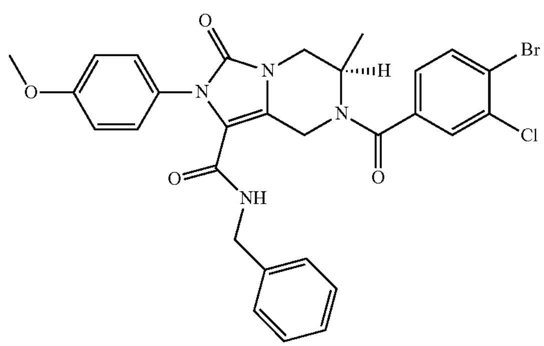 [SMILES: COc1ccc(-n2c(C(=O)NCc3ccccc3)c3n(c2=O)C[C@@H](C)N(C(=O)c2ccc(Br)c(Cl)c2)C3)cc1] | rac-(6R)-N-benzyl-7-(4-bromo-3-chloro-benzoyl)-2-(4-methoxyphenyl)-6-methyl-3-oxo-6,8-dihydro-5H-imidazo[1,5-a]pyrazine-1-carboxamide | 1H NMR (400 MHz, Chloroform-d) δ 7.71 (d, J = 8.2 Hz, 1H), 7.58 (d, J = 2.0 Hz, 1H), 7.25-7.18 (m, 6H), 6.94-6.84 (m, 4H), 5.16 (s, 2H), 4.63 (d, J = 19.2 Hz, 1H), 4.26 (qd, J = 14.7, 5.2 Hz, 2H), 3.86 (d, J = 12.8 Hz, 1H), 3.78 (s, 3H), 3.71 (d, J = 12.6 Hz, 1H), 1.40 (d, J = 7.0 Hz, 3H). |

TABLE A-continued

| Compound # | Structure | Name | NMR |
|---|---|---|---|
| 199 | 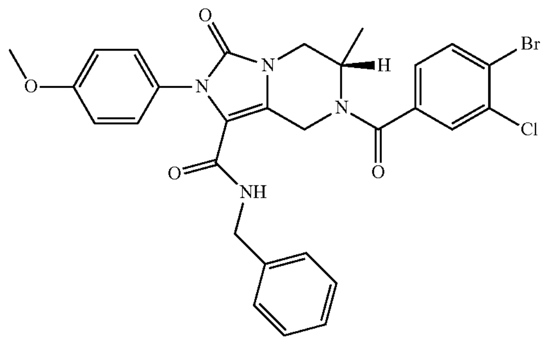 [SMILES: COc1ccc(-n2c(C(=O)NCc3ccccc3)c3n(c2=O)C[C@H](C)N(C(=O)c2ccc(Br)c(Cl)c2)C3)cc1] | rac-(6S)-N-benzyl-7-(4-bromo-3-chloro-benzoyl)-2-(4-methoxyphenyl)-6-methyl-3-oxo-6,8-dihydro-5H-imidazo[1,5-a]pyrazine-1-carboxamide | 1H NMR (400 MHz, Chloroform-d) δ 7.71 (d, J = 8.2 Hz, 1H), 7.58 (d, J = 2.0 Hz, 1H), 7.25-7.18 (m, 6H), 6.94-6.84 (m, 4H), 5.16 (s, 2H), 4.63 (d, J = 19.2 Hz, 1H), 4.26 (qd, J = 14.7, 5.2 Hz, 2H), 3.86 (d, J = 12.8 Hz, 1H), 3.78 (s, 3H), 3.71 (d, J = 12.6 Hz, 1H), 1.40 (d, J = 7.0 Hz, 3H). |
| 200 | 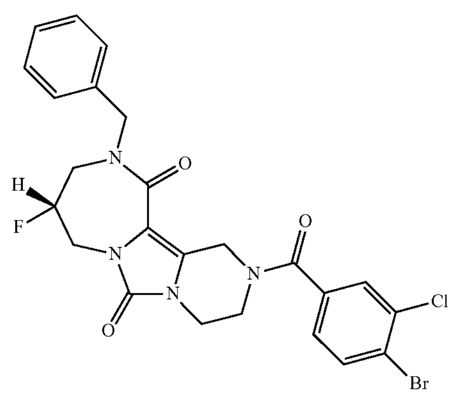 [SMILES: O=C(c1ccc(Br)c(Cl)c1)N1CCn2c(c3n(c2=O)C[C@H](F)CN(Cc2ccccc2)C3=O)C1] | rac-(11R)-13-benzyl-4-(4-bromo-3-chloro-benzoyl)-11-fluoro-4,7,9,13-tetrazatricyclo[7.5.0.0²,⁷]tetradec-1-ene-8,14-dione | 1H NMR (400 MHz, Chloroform-d) δ 7.71 (d, J = 8.2 Hz, 1H), 7.59 (d, J = 2.0 Hz, 1H), 7.40 °C 7.29 (m, 3H), 7.27 (s, 1H), 7.25-7.19 (m, 2H), 5.35 (d, J = 15.0 Hz, 1H), 4.97 (d, J = 14.3 Hz, 2H), 4.40 (d, J = 6.6 Hz, 1H), 4.28 (d, J = 6.6 Hz, 1H), 4.22-4.01 (m, 3H), 4.00-3.64 (m, 4H), 3.51 (dt, J = 12.8, 3.7 Hz, 1H). |

TABLE A-continued

| Compound # | Structure | Name | NMR |
|---|---|---|---|
| 201 | 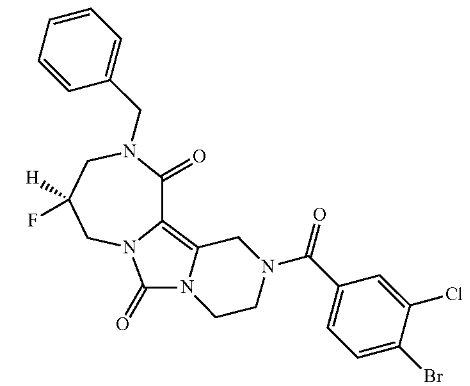 [SMILES: O=C(c1ccc(Br)c(Cl)c1)N1CCn2c(c3n(c2=O)C[C@@H](F)CN(Cc2ccccc2)C3=O)C1] | rac-(11S)-13-benzyl-4-(4-bromo-3-chloro-benzoyl)-11-fluoro-4,7,9,13-tetrazatricyclo[7.5.0.0^2,7]tetradec-1-ene-8,14-dione | 1H NMR (400 MHz, Chloroform-d) δ 7.71 (d, J = 8.2 Hz, 1H), 7.59 (d, J = 2.0 Hz, 1H), 7.40 ·C 7.29 (m, 3H), 7.27 (s, 1H), 7.25-7.19 (m, 2H), 5.35 (d, J = 15.0 Hz, 1H), 4.97 (d, J = 14.3 Hz, 2H), 4.40 (d, J = 6.6 Hz, 1H), 4.28 (d, J = 6.6 Hz, 1H), 4.22-4.01 (m, 3H), 4.00-3.64 (m, 4H), 3.51 (dt, J = 12.8, 3.7 Hz, 1H). |
| 202 | 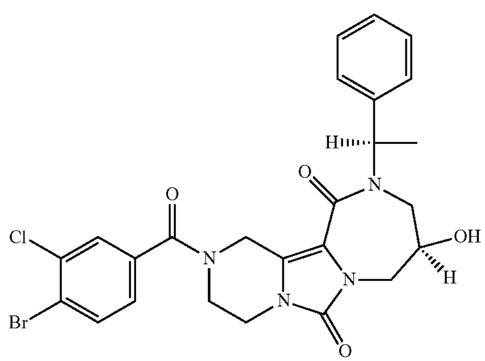 [SMILES: C[C@H](c1ccccc1)N1C[C@@H](O)Cn2c(c3n(c2=O)CCN(C(=O)c2ccc(Br)c(Cl)c2)C3)C1=O] | (11RS)-4-(4-bromo-3-chloro-benzoyl)-11-hydroxy-13-[(1R)-1-phenylethyl]-4,7,9,13-tetrazatricyclo[7.5.0.0^2,7]tetradec-1-ene-8,14-dione | 1H NMR (400 MHz, Chloroform-d) δ 7.74 (d, J = 8.2 Hz, 1H), 7.60 (d, J = 1.9 Hz, 1H), 7.43-7.30 (m, 5H), 7.24 (dd, J = 8.2, 2.0 Hz, 1H), 5.72 (s, 1H), 4.91 (d, J = 16.5 Hz, 2H), 4.24-3.65 (m, 5H), 3.56 (d, J = 14.5 Hz, 1H), 3.39-3.18 (m, 3H), 3.01 (dd, J = 13.3, 7.1 Hz, 1H), 1.57 (d, J = 6.9 Hz, 3H). |

TABLE A-continued

| Compound # | Structure | Name | NMR |
|---|---|---|---|
| 203 | 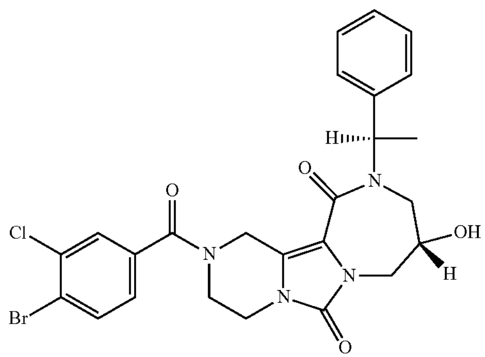 [SMILES: C[C@H](c1ccccc1)N1C[C@H](O)Cn2c(c3n(c2=O)CCN(C(=O)c2ccc(Br)c(Cl)c2)C3)C1=O] | (11SR)-4-(4-bromo-3-chloro-benzoyl)-11-hydroxy-13-[(1R)-1-phenylethyl]-4,7,9,13-tetrazatricyclo[7.5.0.0^2,7]tetradec-1-ene-8,14-dione | 1H NMR (400 MHz, Chloroform-d) δ 7.73 (d, J = 8.2 Hz, 1H), 7.60 (d, J = 2.0 Hz, 1H), 7.38 (dt, J = 19.4, 7.7 Hz, 5H), 7.23 (dd, J = 8.2, 2.0 Hz, 1H), 5.84 (s, 1H), 4.94 (s, 2H), 4.18 (t, J = 5.9 Hz, 1H), 4.05-3.84 (m, 4H), 3.78 (s, 2H), 3.36 (dd, J = 15.5, 5.5 Hz, 1H), 3.05 (dd, J = 15.4, 7.0 Hz, 1H), 2.33 (s, 1H), 1.58 (d, J = 7.1 Hz, 3H). |
| 204 | 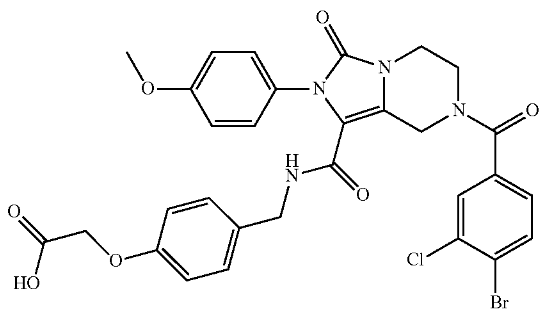 [SMILES: COc1ccc(-n2c(C(=O)NCc3ccc(OCC(=O)O)cc3)c3n(c2=O)CCN(C(=O)c2ccc(Br)c(Cl)c2)C3)cc1] | 2-[4-[[[7-(4-bromo-3-chloro-benzoyl)-2-(4-methoxyphenyl)-3-oxo-6,8-dihydro-5H-imidazo[1,5-a]pyrazine-1-carbonyl]amino]methyl]phenoxy]acetic acid | 1H NMR (400 MHz, Chloroform-d) δ 7.72 (d, J = 7.6 Hz, 1H), 7.62 (s, 1H), 7.29-7.12 (m, 3H), 6.97-6.81 (m, 4H), 6.80-6.69 (m, 2H), 5.24-4.95 (m, 2H), 4.56 (s, 2H), 4.17 (s, 2H), 3.80 (d, J = 18.6 Hz, 6H), 3.30 (br. 3H). |
| 205 | 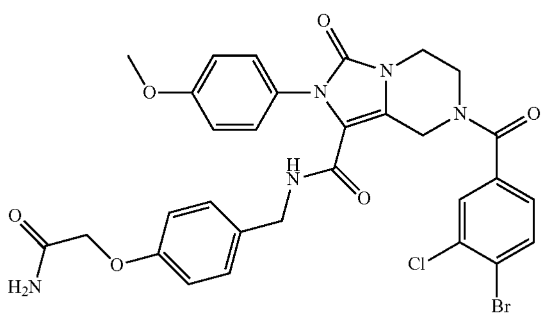 | N-[[4-(2-amino-2-oxo-ethoxy)phenyl]methyl]-7-(4-bromo-3-chloro-benzoyl)-2-(4-methoxyphenyl)-3-oxo-6,8-dihydro-5H-imidazo[1,5-a]pyrazine-1-carboxamide | 1H NMR (300 MHz, Chloroform-d) δ 7.73 (d, J = 8.4 Hz, 1H), 7.62 (s, 1H), 7.27-7.20 (m, 3H), 6.90-6.87 (m, 4H), 6.80 (d, J = 9.0 Hz, 2H), 6.52 (s, 1H), 5.69 (s, 1H), 5.10-5.05 (m, 3H), 4.48 (s, 2H), 4.20 (d, J = 4.8 Hz, 2H), 4.05 (s, 2H), 3.81 (s, 5H). |

| Compound # | Structure | Name | NMR |
|---|---|---|---|
| 206 | 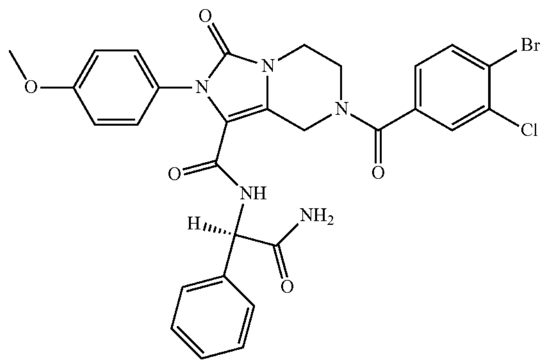 [SMILES: COc1ccc(-n2c(C(=O)N[C@@H](C(N)=O)c3ccccc3)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-amino-2-oxo-1-phenyl-ethyl]-6,8-dihydro-5H-imidazo[1,5-a]pyrazine-1-carboxamide | 1H NMR (400 MHz, Chloroform-d) δ 7.75-7.68 (m, 1H), 7.67-7.52 (m, 1H), 7.32-7.27 (m ,5H), 7.26-7.19 (m, 1H), 7.01 (d, J = 8.8 Hz, 4H), 6.24 (s, 1H), 5.49-5.21 (m, 3H), 4.96 (s, 2H), 4.09-3.75 (m, 7H). |
| 207 | 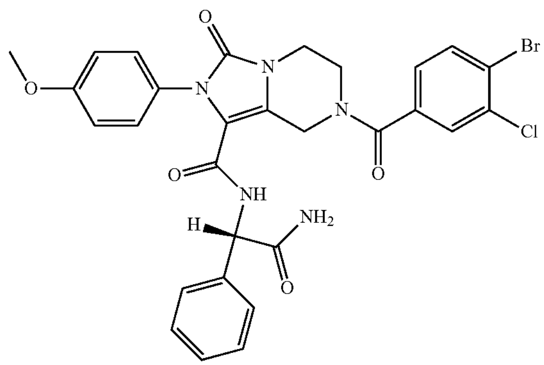 | 7-(4-bromo-3-chloro-benzoyl)-2-(4-methoxyphenyl)-3-oxo-N-[rac-(1S)-amino-2-oxo-1-phenyl-ethyl]-6,8-dihydro-5H-imidazo[1,5-a]pyrazine-1-carboxamide | 1H NMR (300 MHz, DMSO-d6) δ 7.88 (d, J = 8.1 Hz, 1H), 7.78 (s, 1H), 7.55 (br, 1H), 7.42-7.38 (m, 1H), 7.28 (d, J = 8.7 Hz, 5H), 7.14 (s, 1H), 7.05 (d, J = 9 Hz, 3H), 5.28 (s, 1H), 4.98-4.65 (m, 2H), 4.04 (s, 1H), 3.80 (s, 3H), 3.66 (s, 3H). |
| 208 | 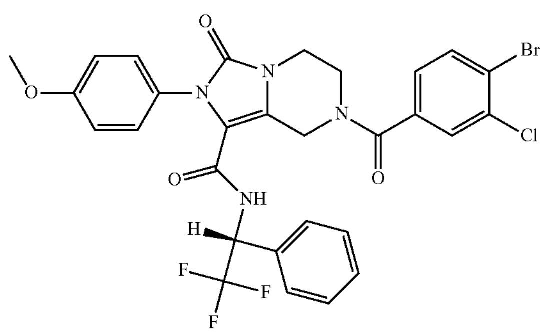 [SMILES: COc1ccc(-n2c(C(=O)N[C@H](c3ccccc3)C(F)(F)F)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-2,2,2-trifluoro-1-phenyl-ethyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.61 (d, J = 2.0 Hz, 1H), 7.37-7.23 (m, 8H), 7.11-7.04 (m, 2H), 6.86 (d, J = 7.4 Hz, 2H), 5.69 (d, J = 9.3 Hz, 1H), 5.55 (s, 1H), 5.04 (s, 2H), 4.01 (s, 1H), 3.90 (s, 3H), 3.85 (s, 2H). |

| Compound # | Structure | Name | NMR |
|---|---|---|---|
| 209 | 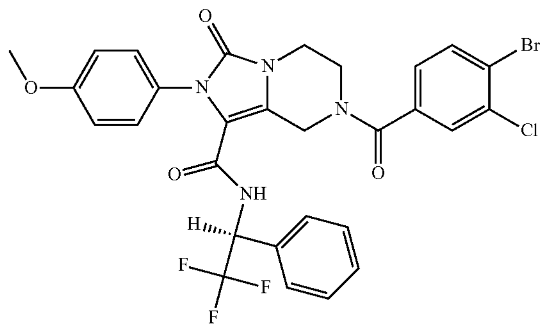 [SMILES: COc1ccc(-n2c(C(=O)N[C@@H](c3ccccc3)C(F)(F)F)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1S)-2,2,2-trifluoro-1-phenyl-ethyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.61 (d, J = 2.0 Hz, 1H), 7.37-7.23 (m, 7H), 7.11-7.04 (m, 2H), 6.86 (d, J = 7.4 Hz, 2H), 5.69 (d, J = 9.3 Hz, 1H), 5.55 (s, 1H), 5.04 (s, 2H), 4.01 (s, 1H), 3.90 (s, 3H), 3.85 (s, 2H). |
| 210 | 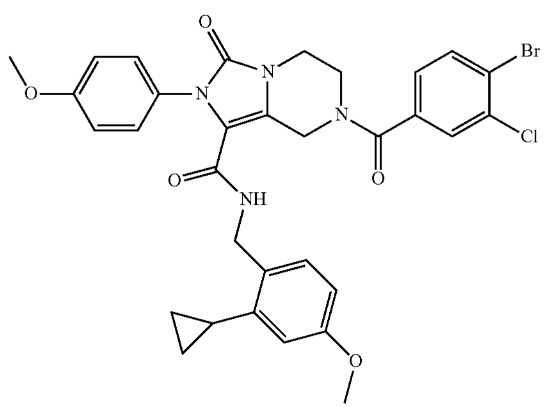 [SMILES: COc1ccc(-n2c(C(=O)NCc3ccc(OC)cc3C3CC3)c3n(c2=O)CCN(C(=O)c2ccc(Br)c(Cl)c2)C3)cc1] | 7-(4-bromo-3-chloro-benzoyl)-N-[(2-cyclopropyl-4-methoxyphenyl)methyl]-2-(4-methoxyphenyl)-3-oxo-6,8-dihydro-5H-imidazo[1,5-a]pyrazine-1-carboxamide | 1H NMR (400 MHz, DMSO-d6) δ 7.87 (d, J = 8.4 Hz, 1H), 7.79 (d, J = 1.6 Hz, 1H), 7.42-7.40 (m, 2H), 7.41 (d, J = 6.8 Hz, 2H), 7.18-6.80 (m, 3H), 6.70-6.50 (m, 1H), 6.45 (s, 1H), 5.00-4.60 (m, 2H), 4.50-4.10 (m, 2H), 4.05-3.60 (m, 10H), 1.90-1.50 (m, 1H), 1.00-0.70 (m, 2H), 0.65-0.45 (m, 2H). |

TABLE A-continued

| Compound # | Structure | Name | NMR |
|---|---|---|---|
| 211 | 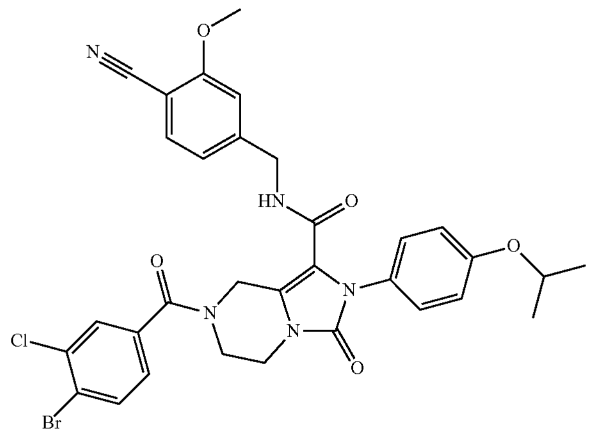 [SMILES: COc1cc(CNC(=O)c2c3n(c(=O)n2-c2ccc(OC(C)C)cc2)CCN(C(=O)c2ccc(Br)c(Cl)c2)C3)ccc1C#N] | 7-(4-bromo-3-chloro-benzoyl)-N-[(4-cyano-3-methoxy-phenyl)methyl]-2-(4-isopropxoyphenyl)-3-oxo-6,8-dihydro-5H-imidazo[1,5-a]pyrazine-1-carboxamide | 1H-NMR (DMSO, 600 MHz, 80° C.): 1.29 (d, J = 6.0 Hz, 6H); 3.68 (t, J = 5.5 Hz, 2H); 3.82 (br. s., 2H); 3.88 (s, 3H); 4.32 (d, J = 5.2 Hz, 2H); 4.58 (hept., J = 6.0 Hz, 1H); 4.87 (s, 2H); 6.76 (d, J = 7.3 Hz, 1H); 6.91 (d, J = 8.8 Hz, 2H); 7.00 (s, 1H); 7.17 (d, J = 8.8 Hz, 2H); 7.39 (br. s., 1H); 7.40 (dd, J = 8.2 Hz, 1.8 Hz, 1H); 7.54 (d, J = 7.8 Hz, 1H); 7.75 (d, J = 1.9 Hz, 1H); 7.86 (d, J = 8.2 Hz, 1H) ppm. |
| 212 | 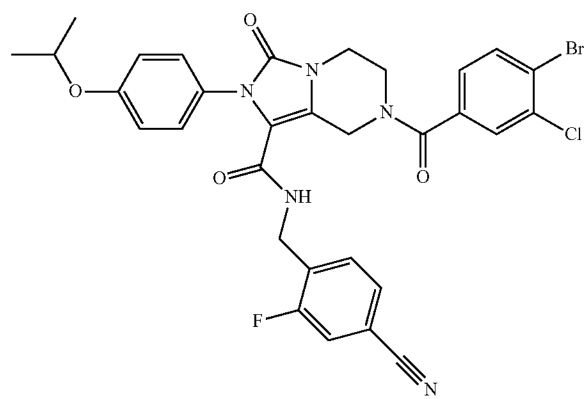 [SMILES: CC(C)Oc1ccc(-n2c(C(=O)NCc3ccc(C#N)cc3F)c3n(c2=O)CCN(C(=O)c2ccc(Br)c(Cl)c2)C3)cc1] | 7-(4-bromo-3-chloro-benzoyl)-N-[(4-cyano-2-fluoro-phenyl)methyl]-2-(4-isopropoxyphenyl)-3-oxo-6,8-dihydro-5H-imidazo[1,5-a]pyrazine-1-carboxamide | 1H-NMR (DMSO, 600 MHz, 80° C.): 1.29 (d, J = 6.0 Hz, 6H); 3.68 (t, J = 5.4 Hz, 2H); 3.82 (br. s., 2H); 4.35 (d, J = 4.4 Hz, 2H); 4.59 (hept., J = 6.0 Hz, 1H); 4.84 (s, 2H); 6.92 (d, J = 8.9 Hz, 2H); 7.15 (d, J = 8.9 Hz, 2H); 7.23-7.25 (m, 1H); 7.34 (br. s., 1H); 7.40 (dd, J = 8.2 Hz, 1.8 Hz, 1H); 7.53 (d, J = 7.8 Hz, 1H); 7.66 (d, J = 9.9 Hz, 1H); 7.74 (d, J = 1.8 Hz, 1H), 7.86 (d, J = 8.2 Hz, 1H) ppm. |

TABLE A-continued

| Compound # | Structure | Name | NMR |
|---|---|---|---|
| 213 | 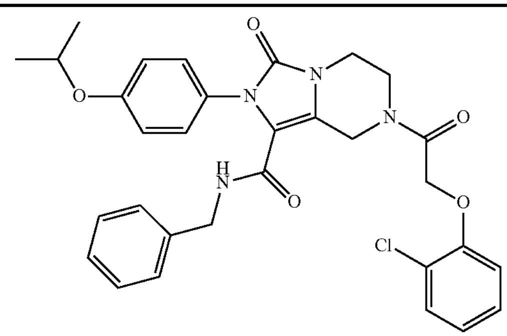 | N-benzoyl-7-[2-(2-chlorophenoxy)acetyl]-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.31 (d, J = 6.0 Hz, 6H), 3.72 (br s, 2H), 3.92 (t, J = 5.3 Hz, 2H), 4.29 (d, J = 5.6 Hz, 2H), 4.60 (hept, J = 5.9 Hz, 1H), 4.86 (s, 2H), 5.03 (s, 2H), 6.93 (d, J = 8.0 Hz, 2H), 7.00 (t, J = 5.4 Hz, 1H), 7.09-7.31 (m, 10H), 7.44 (d, J = 8.0 Hz, 1H). |
| 214 | 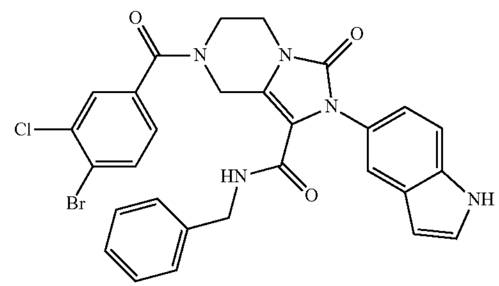 | N-benzoyl-7-(4-bromo-3-chloro-benzoyl)-2-(1H-indol-5-yl)-3-oxo-6,8-dihydro-5H-imidazo[1,5-a]pyrazine-1-carboxamide | 1H NMR (400 MHz, DMSO-d6, 80° C.): 3.70 (t, J = 5.6 Hz, 2H), 3.86 (br s, 2H), 4.18 (d, J = 5.6 Hz, 2H), 4.90 (s, 2H), 6.47 (s, 1H), 6.69 (br s, 1H), 6.84 (d, J = 7.1 Hz, 2H), 7.00 (dd, J = 8.6, 1.6 Hz, 1H), 7.07-7.15 (m, 3H), 7.40-7.44 (m, 3H), 7.51 (s, 1H), 7.76 (d, J = 1.5 Hz, 1H), 7.86 (d, J = 8.3 Hz, 1H), 1.11 (s, 1H). |
| 215 | 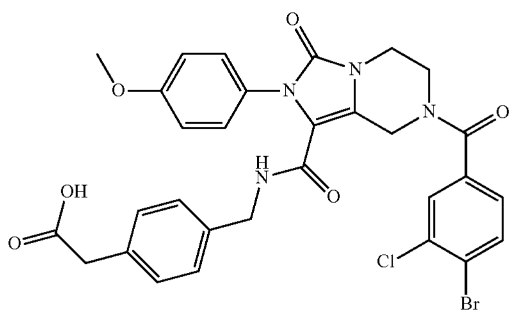 [SMILES: COc1ccc(-n2c(C(=O)NCc3ccc(CC(=O)O)cc3)c3n(c2=O)CCN(C(=O)c2ccc(Br)c(Cl)c2)C3)cc1] | 2-[4-[[[7-(4-bromo-3-chloro-benzoyl)-2-(4-methoxyphenyl)-3-oxo-6,8-dihydro-5H-imidazo[1,5-a]pyrazine-1-carbonyl]amino]methyl]phenyl]acetic acid | 1H NMR (400 MHz, DMSO-d6, 80° C.): 3.52 (s, 2H), 3.68 (t, J = 5.4 Hz, 2H), 3.79 (s, 3H), 3.83 (br s, 2H), 4.22 (d, J = 5.5 Hz, 2H), 4.86 (s, 2H), 6.92-7.02 (m, 4H), 7.10-7.24 (m, 5H), 7.40 (d, J = 8.4 Hz, 1H), 7.75 (s, 1H), 7.86 (d, J = 8.2 Hz, 1H), 11.93 (br s, 1H) |

TABLE A-continued

| Compound # | Structure | Name | NMR |
|---|---|---|---|
| 216 | 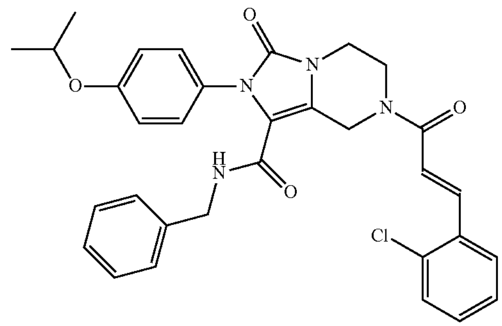 [SMILES: CC(C)Oc1ccc(-n2c(C(=O)NCc3ccccc3)c3n(c2=O)CCN(C(=O)/C=C/c2ccccc2Cl)C3)cc1] | N-benzyl-7-[(E)-3-(2-chloropehnyl)prop-2-enoyl]-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.29 (d, J = 6.0 Hz, 6H), 3.71 (t, J = 5.3 Hz, 2H), 4.06 (t, J = 5.8 Hz, 2H), 4.30 (d, J = 5.8 Hz, 2H), 4.59 (hept, J = 6.0 Hz, 1H), 4.96 (s, 2H), 6.91 (d, J = 8.5 Hz, 2H), 7.11 (d, J = 7.3 Hz, 2H), 7.17-7.30 (m, 7H), 7.41-7.43 (m, 2H), 7.51-7.53 (m, 1H), 7.86 (d, J = 15.5 Hz, 1H), 7.93 (br s, 1H). |
| 217 | 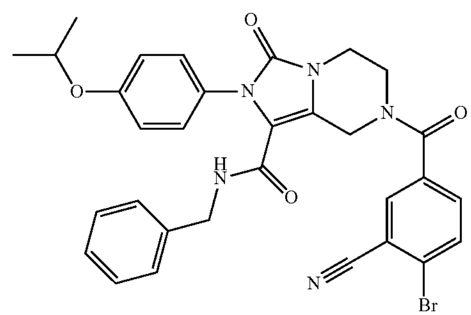 [SMILES: CC(C)Oc1ccc(-n2c(C(=O)NCc3ccccc3)c3n(c2=O)CCN(C(=O)c2ccc(Br)c(C#N)c2)C3)cc1] | N-benzyl-7-(4-bromo-3-cyanobenzoyl)-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.29 (d, J = 6.0 Hz, 6H), 3.69 (t, J = 5.5 Hz, 2H), 3.82 (br s, 2H), 4.25 (d, J = 5.6 Hz, 2H), 4.58 (hept, J = 6.1 Hz, 1H), 4.85 (s, 2H), 6.92 (d, J = 8.8 Hz, 2H), 7.04 (d, J = 6.8 Hz, 2H), 7.16-7.24 (m, 6H), 7.74 (dd, J = 8.3, 2.1 Hz, 1H), 7.96 (d, J = 8.4 Hz, 1H), 8.06 (s, 1H). |
| 218 | 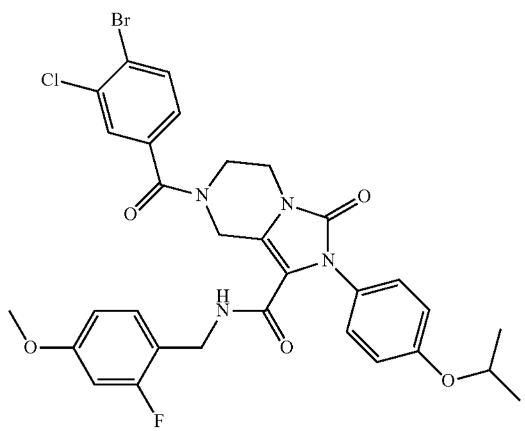 [SMILES: COc1ccc(CNC(=O)c2c3n(c(=O)n2-c2ccc(OC(C)C)cc2)CCN(C(=O)c2ccc(Br)c(Cl)c2)C3)c(F)c1] | 7-(4-bromo-3-chloro-benzoyl)-N-[(2-fluoro-4-methoxy-phenyl)methyl]-2-(4-isopropoxyphenyl)-3-oxo-6,8-dihydro-5H-imdiazo[1,5-a]pyrazine-1-carboxamide | 1H NMR (400 MHz, DMSO-d6, 80° C.): 1.30 (d, J = 6.0 Hz, 6H), 3.69 (t, J = 5.4 Hz, 2H), 3.78 (s, 3H), 3.84 (br s, 2H), 4.21 (d, J = 5.3 Hz, 2H), 4.59 (hept, J = 6.1 Hz, 1H), 4.85 (s, 2H), 6.61-6.74 (m, 2H), 6.86-7.04 (m, 4H), 7.16 (d, J = 8.6 Hz, 2H), 7.40 (d, J = 8.2 Hz, 1H), 7.75 (s, 1H), 7.87 (d, J = 8.2 Hz, 1H) |

TABLE A-continued

| Compound # | Structure | Name | NMR |
|---|---|---|---|
| 219 | 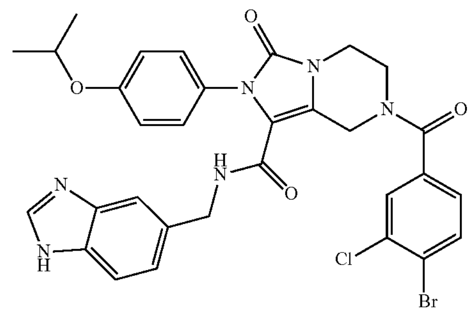 [SMILES: CC(C)Oc1ccc(-n2c(C(=O)NCc3ccc4[nH]cnc4c3)c3n(c2=O)CCN(C(=O)c2ccc(Br)c(Cl)c2)C3)cc1] | N-(1H-benzimidazol-5-ylmethyl)-7-(4-bromo-3-chloro-benzoyl)-2-(4-isopropoxyphenyl)-3-oxo-6,8-dihydro-5H-imidazo[1,5-a]pyrazine-1-carboxamide | 1H-NMR (DMSO, 600 MHz, 80° C.): 1.25 (d, J = 6.1 Hz, 6H); 3.69 (t, J = 5.3 Hz, 2H); 3.83 (s, 2H); 4.35 (d, J = 5.3 Hz, 2H); 4.51 (m, J = 6.0 Hz, 1H); 4.88 (s, 2H); 6.89 (d, J = 8.6 Hz, 2H); 7.03 (br. s, 1H); 7.18 (d, J = 8.6 Hz, 2H); 7.35 (s, 1H); 7.40 (d, J = 8.1 Hz, 1H); 7.45 (d, J = 8.1 Hz, 1H); 7.75 (s, 1H); 7.85 (d, J = 8.1 Hz, 1H); 8.10 (s, 1H); 12.09 (br. s, 1H) ppm. |
| 220 | 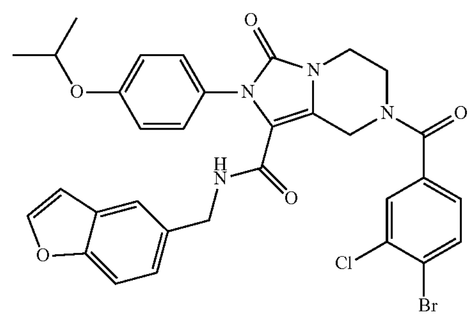 [SMILES: CC(C)Oc1ccc(-n2c(C(=O)NCc3ccc4occc4c3)c3n(c2=O)CCN(C(=O)c2ccc(Br)c(Cl)c2)C3)cc1] | N-(benzofuran-5-ylmethyl)-7-(4-bromo-3-chloro-benzoyl)-2-(4-isopropoxyphenyl)-3-oxo-6,8-dihydro-5H-imidazo[1,5-a]pyrazine-1-carboxamide | 1H-NMR (DMSO, 600 MHz, 80° C.): 1.26 (d, J = 5.9 Hz, 6H); 3.68 (t, J = 5.4 Hz, 2H); 3.83 (s, 2H); 4.34 (d, J = 5.3 Hz, 2H); 4.53 (m, J = 6.0 Hz, 1H); 4.87 (s, 2H); 6.86 (s, 1H); 6.89 (d, J = 8.4 Hz, 2H); 7.0 (d, J = 8.3 Hz, 1H); 7.07 (br. s, 1H); 7.18 (d, J = 8.4 Hz, 2H); 7.30 (s, 1H); 7.41 (dd, J = 14.4 Hz, 8.3 Hz, 2H); 7.74 (s, 1H); 7.84 (d, J = 8.3 Hz, 1H); 7.89 (s, 1H) ppm. |
| 221 | 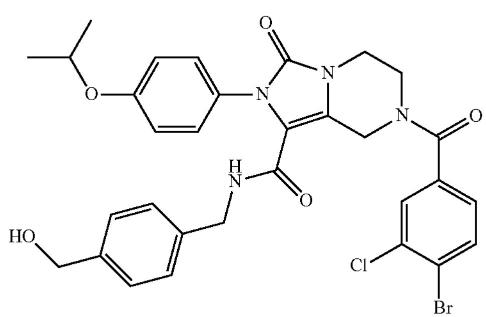 [SMILES: CC(C)Oc1ccc(-n2c(C(=O)NCc3ccc(CO)cc3)c3n(c2=O)CCN(C(=O)c2ccc(Br)c(Cl)c2)C3)cc1] | 7-(4-bromo-3-chloro-benzoyl)-N-[[4-(hydroxymethyl)phenyl]methyl]-2-(4-isopropoxyphenyl)-3-oxo-6,8-dihydro-5H-imidazo[1,5-a]pyrazine-1-carboxamide | 1H-NMR (DMSO, 600 MHz, 80° C.): 1.30 (d, J = 6.0 Hz, 6H); 3.68 (t, J = 5.5 Hz, 2H); 3.82 (br. s., 2H); 4.23 (d, J = 5.7 Hz, 2H); 4.48 (d, J = 3.3 Hz, 2H); 4.59 (hept, J = 6.0 Hz, 1H); 4.82 (br. s., 1H); 4.86 (s, 2H); 6.93 (d, J = 8.7 Hz, 2H); 6.99 (d, J = 7.3 Hz, 2H); 7.08 (br. s., 1H); 7.14-7.23 (m, 4H); 7.37-7.42 (m, 1H); 7.75 (s, 1H); 7.86 (d, J = 8.3 Hz, 1H) ppm. |

TABLE A-continued

| Compound # | Structure | Name | NMR |
|---|---|---|---|
| 222 | 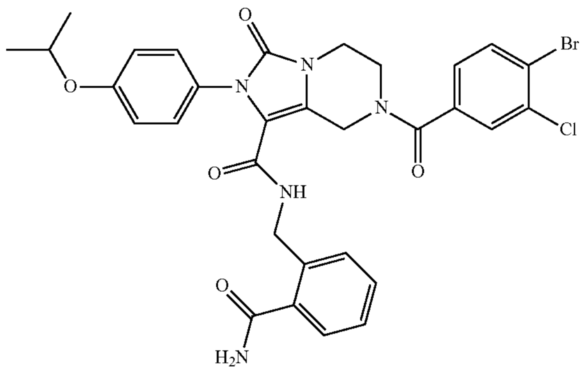 [SMILES: CC(C)Oc1ccc(-n2c(C(=O)NCc3ccccc3C(N)=O)c3n(c2=O)CCN(C(=O)c2ccc(Br)c(Cl)c2)C3)cc1] | 7-(4-bromo-3-chloro-benzoyl)-N-[(2-carbamoylphenyl)methyl]-2-(4-isopropoxyphenyl)-3-oxo-6,8-dihydro-5H-imidazo[1,5-a]pyrazine-1-carboxamide | 1H-NMR (DMSO, 600 MHz, 80° C.): 1.30 (d, J = 6.0 Hz, 6H); 3.67 (t, J = 5.6 Hz, 2H); 3.83 (br. s., 2H); 4.39 (d, J = 5.4 Hz, 2H); 4.58 (hept, J = 6.0 Hz, 1H); 4.86 (s, 2H); 6.89 (d, J = 8.7 Hz, 2H); 6.99-7.09 (m, 2H); 7.14 (d, J = 8.7 Hz, 2H); 7.25-7.33 (m, 2H), 7.39 (d, J = 8.3 Hz, 1H), 7.44 (d, J = 7.3 Hz, 1H), 7.74 (s, 1H), 7.85 (d, J = 8.1 Hz, 1H) ppm. |
| 223 | 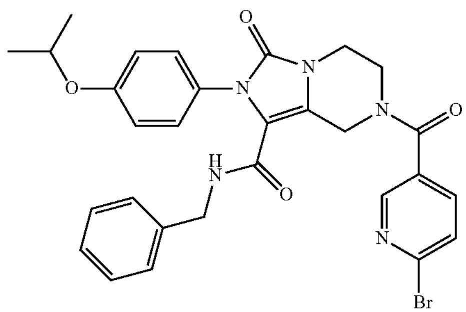 [SMILES: CC(C)Oc1ccc(-n2c(C(=O)NCc3ccccc3)c3n(c2=O)CCN(C(=O)c2ccc(Br)nc2)C3)cc1] | N-benzyl-7-(6-bromopyridine-3-carbonyl)-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.29 (d, J = 6.0 Hz, 6H), 3.70 (t, J = 5.5 Hz, 2H), 3.85 (br s, 2H), 4.25 (d, J = 5.6 Hz, 2H), 4.58 (hept, J = 6.1 Hz, 1H), 4.87 (s, 2H), 6.92 (d, J = 8.8 Hz, 2H), 7.04 (d, J = 6.8 Hz, 1H), 7.16-7.25 (m, 6H), 7.73 (d, J = 8.3, 1H), 7.87 (dd, J = 8.1, 2.1 Hz, 1H), 8.53 (d, J = 2.0 Hz, 1H). |
| 224 | 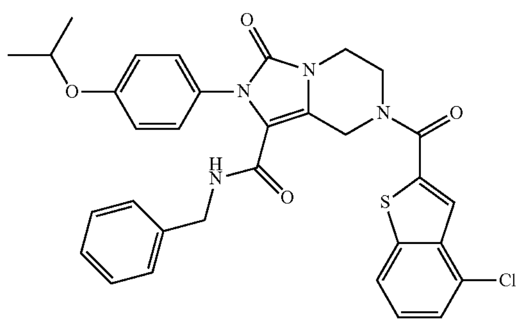 [SMILES: CC(C)Oc1ccc(-n2c(C(=O)NCc3ccccc3)c3n(c2=O)CCN(C(=O)c2cc4c(Cl)cccc4s2)C3)cc1] | N-benzyl-7-(4-chlorobenzothiophene-2-carbonyl)-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.31 (d, J = 6.1 Hz, 6H), 3.78 (t, J = 5.6 Hz, 2H), 4.08 (t, J = 5.6 Hz, 2H), 4.26 (d, J = 6.1 Hz, 2H), 4.60 (hept, J = 6.3 Hz, 1H), 5.07 (s, 2H), 6.94 (d, J = 8.6 Hz, 2H), 7.04-7.06 (m, 2H), 7.18-7.24 (m, 6H), 7.50 (t, J = 7.9 Hz, 1H), 7.56 (d, J = 7.6 Hz, 1H), 7.83 (s, 1H), 8.05 (d, J = 7.9 Hz, 1H) |

TABLE A-continued

| Compound # | Structure | Name | NMR |
|---|---|---|---|
| 225 | 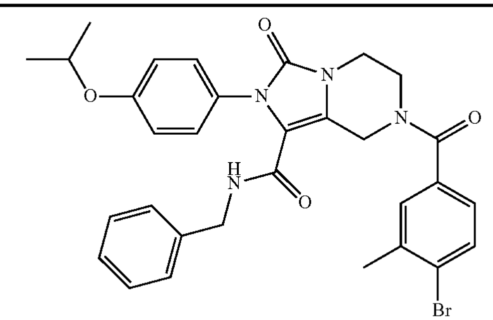 | N-benzoyl-7-(4-bromo-3-methyl-benzoyl)-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.31 (d, J = 5.9 Hz, 6H), 2.42 (s, 3H), 3.69 (t, J = 5.2 Hz, 2H), 3.85 (br s, 2H), 4.26 (d, J = 5.6 Hz, 2H), 4.60 (hept, J = 5.9 Hz, 1H), 4.87 (s, 2H), 6.93 (d, J = 8.1 Hz, 2H), 7.05 (d, J = 6.5 Hz, 2H), 7.13-7.30 (m, 7H), 7.48 (s, 1H), 7.68 (d, J = 8.2 Hz, 1H). |
| 226 | 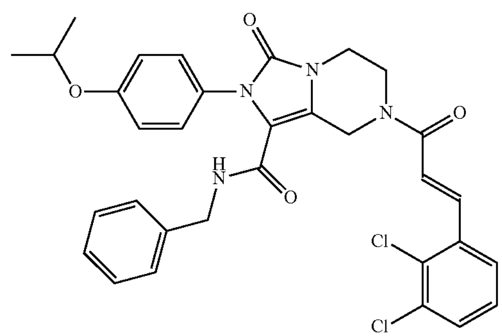 [SMILES: CC(C)Oc1ccc(-n2c(C(=O)NCc3ccccc3)c3n(c2=O)CCN(C(=O)/C=C/c2cccc(Cl)c2Cl)C3)cc1] | N-benzyl-7-[(E)-3-(2,3-dichlorophenyl)prop-2-enoyl]-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.31 (d, J = 6.0 Hz, 6H), 3.71 (t, J = 5.1 Hz, 2H), 4.06 (br s, 2H), 4.30 (d, J = 5.7 Hz, 2H), 4.59 (hept, J = 6.0 Hz, 1H), 4.96 (s, 2H), 6.92 (d, J = 8.4 Hz, 2H), 7.10 (d, J = 7.1 Hz, 2H), 7.14-7.35 (m, 7H), 7.43 (t, J = 7.9 Hz, 1H), 7.66 (d, J = 7.8 Hz, 1H), 7.85 (d, J = 15.4 Hz, 1H), 7.90 (d, J = 7.1 Hz, 1H). |
| 227 | 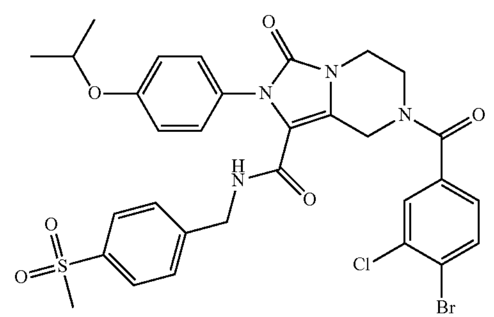 [SMILES: CC(C)Oc1ccc(-n2c(C(=O)NCc3ccc(S(C)(=O)=O)cc3)c3n(c2=O)CCN(C(=O)c2ccc(Br)c(Cl)c2)C3)cc1] | 7-(4-bromo-3-chloro-benzoyl)-2-(4-isopropoxyphenyl)-N-[(4-methylsulfonyl)phenyl)methyl]-3-oxo-6,8-dihydro-5H-imidazo[1,5-a]pyrazine-1-carboxamide | 1H NMR (400 MHz, DMSO-d6, 80° C.): 1.31 (d, J = 5.8 Hz, 6H), 3.15 (s, 3H), 3.70 (t, J = 5.2 Hz, 2H), 3.84 (br s, 2H), 4.37 (d, J = 5.4 Hz, 2H), 4.60 (hept, J = 6.2 Hz, 1H), 4.88 (s, 2H), 6.95 (d, J = 8.9 Hz, 2H), 7.20 (d, J = 8.9 Hz, 2H), 7.31 (d, J = 7.9 Hz, 2H), 7.38 (br s, 1H), 7.42 (dd, J = 7.9 Hz, 1.4 Hz, 1H), 7.76 (d, J = 1.5 Hz, 1H), 7.82 (d, J = 8.3 Hz, 2H), 7.87 (d, J = 8.3 Hz, 1H). |

| Compound # | Structure | Name | NMR |
|---|---|---|---|
| 228 | 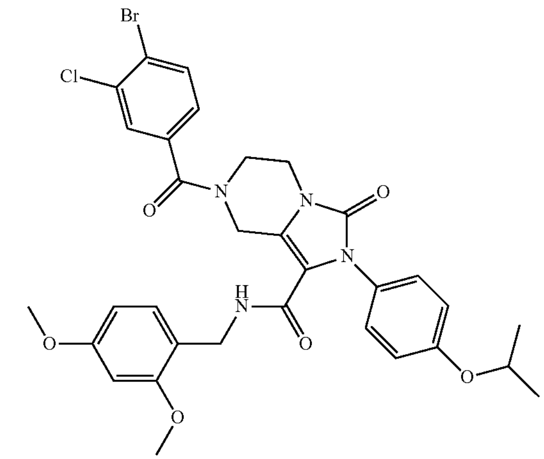 [SMILES: COc1ccc(CNC(=O)c2c3n(c(=O)n2-c2ccc(OC(C)C)cc2)CCN(C(=O)c2ccc(Br)c(Cl)c2)C3)c(OC)c1] | 7-(4-bromo-3-chloro-benzoyl)-N-[(2,4-dimethoxyphenyl)methyl]-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.30 (d, J = 5.9 Hz, 6H), 3.67 (t, J = 5.5 Hz, 2H), 3.70 (s, 3H), 3.75 (s, 3H), 3.82 (br s, 2H), 4.13 (d, J = 5.4 Hz, 2H), 4.59 (hept, J = 6.0 Hz, 1H), 4.86 (s, 2H), 6.38 (d, J = 8.3 Hz, 1H), 6.47 (s, 1H), 6.50 (br s, 1H), 6.83 (d, J = 8.3 Hz, 1H), 6.93 (d, J = 8.7 Hz, 2H), 7.17 (d, J = 8.7 Hz, 2H), 7.39 (d, J = 8.2 Hz, 1H), 7.74 (s, 1H), 7.85 (d, J = 8.1 Hz, 1H). |
| 229 | 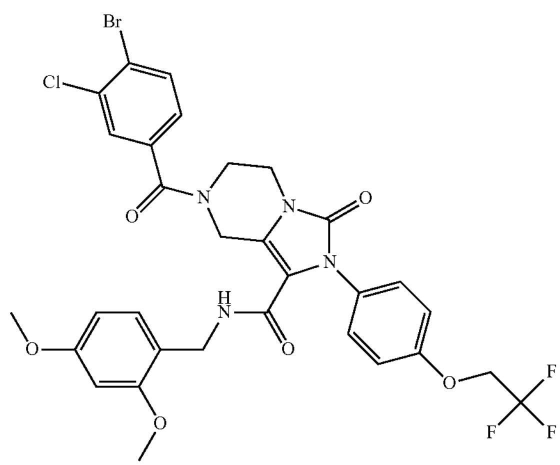 [SMILES: COc1ccc(CNC(=O)c2c3n(c(=O)n2-c2ccc(OCC(F)(F)F)cc2)CCN(C(=O)c2ccc(Br)c(Cl)c2)C3)c(OC)c1] | 7-(4-bromo-3-chloro-benzoyl)-N-[(2,4-dimethoxyphenyl)methyl]-3-oxo-2-[4-(2,2,2-trifluoroethoxy)phenyl]-6,8-dihydro-5H-imidazo[1,5-a]pyrazine-1-carboxamide | 1H NMR (400 MHz, DMSO-d6, 80° C.): 3.67 (t, J = 5.4 Hz, 2H), 3.71 (s, 3H), 3.75 (s, 3H), 3.82 (br s, 2H), 4.14 (d, J = 5.4 Hz, 2H), 4.72 (q, J = 8.8 Hz, 2H), 4.86 (s, 2H), 6.39 (d, J = 8.4 Hz, 1H), 6.48 (s, 1H), 6.74 (br s, 1H), 6.84 (d, J = 8.0 Hz, 1H), 7.09 (d, J = 8.6 Hz, 2H), 7.23 (d, J = 8.6 Hz, 2H), 7.39 (d, J = 8.3 Hz, 1H), 7.74 (s, 1H), 7.85 (d, J = 8.3 Hz, 1H). |

TABLE A-continued

| Compound # | Name | Structure | NMR |
|---|---|---|---|
| 230 | 7-(4-bromo-3-chloro-benzoyl)-3-oxo-N-(8-quinolylmethyl)-2-[4-(2,2,2-trifluoroethoxy)phenyl]-6,8-dihydro-5H-imidazo[1,5-a]pyrazine-1-carboxamide | 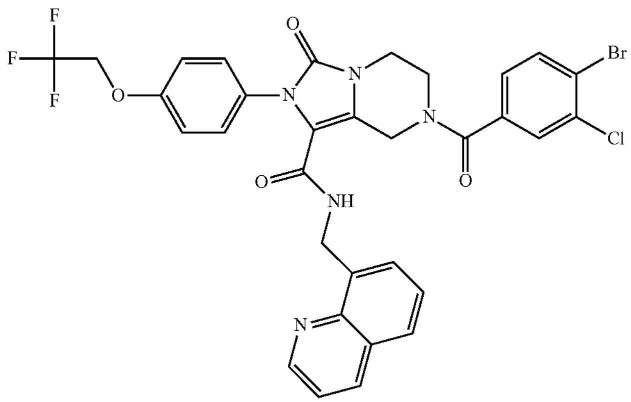 | 1H NMR (400 MHz, DMSO-d6, 80° C.): 3.66 (t, J = 5.3 Hz, 2H), 3.83 (br s, 2H), 4.67 (q, J = 8.9 Hz, 2H), 4.85 (d, J = 5.6 Hz, 2H), 4.89 (s, 2H), 6.96 (d, J = 8.6 Hz, 2H), 7.16 (br s, 1H), 7.20 (d, J = 8.6, 2H), 7.38-7.53 (m, 4H), 7.74 (s, 1H), 7.83-7.86 (m, 2H), 8.32 (d, J = 8.3 Hz, 1H), 8.79 (d, J = 2.6 Hz, 1H). |
| 231 | 7-(4-bromo-3-chloro-benzoyl)-3-oxo-N[(2-pyrazol-1-ylphenyl)methyl]-2-[4-(2,2,2-trifluoroethoxy)phenyl]-6,8-dihydro-5H-imidazo[1,5-a]pyrazine-1-carboxamide | 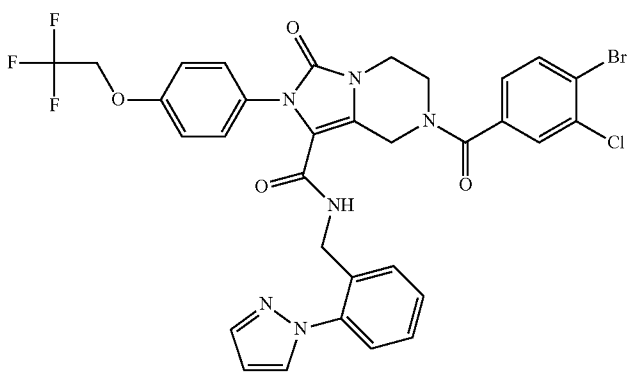 [SMILES: O=C(NCc1ccccc1-n1cccn1)c1c2n(c(=O)n1-c1ccc(OCC(F)(F)F)cc1)CCN(C(=O)c1ccc(Br)c(Cl)c1)C2] | 1H NMR (400 MHz, DMSO-d6, 80° C.): 3.67 (t, J = 5.4 Hz, 2H), 3.83 (br s, 2H), 4.19 (d, J = 5.8 Hz, 2H), 4.70 (q, J = 8.9 Hz, 2H), 4.86 (s, 2H), 6.46 (s, 1H), 7.08 (d, J = 8.8 Hz, 2H), 7.18 (br s, 1H), 7.21-7.24 (m, 3H), 7.31-7.39 (m, 4H), 7.62 (s, 1H), 7.73 (s, 1H), 7.83 (d, J = 8.1 Hz, 1H), 7.95 (s, 1H). |

| Compound # | Structure | Name | NMR |
|---|---|---|---|
| 232 | 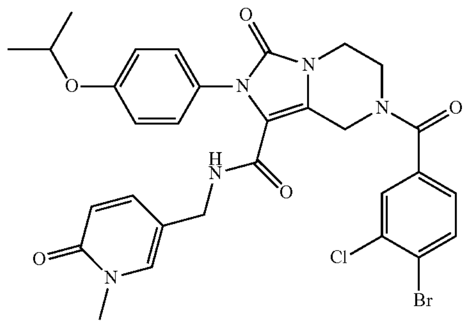 [SMILES: CC(C)Oc1ccc(-n2c(C(=O)NCc3ccc(=O)n(C)c3)c3n(c2=O)CCN(C(=O)c2ccc(Br)c(Cl)c2)C3)cc1] | 7-(4-bromo-3-chloro-benzoyl)-2-(4-isopropoxyphenyl)-N-[(1-methyl-6-oxo-3-pyridyl)methyl]-3-oxo-6,8-dihydro-5H-imidazo[1,5-a]pyrazine-1-carboxamide | 1H-NMR (DMSO, 600 MHz, 80° C.): 1.29 (d, J = 6.0 Hz, 6H); 3.36 (s, 3H); 3.67 (t, J = 5.3 Hz, 2H); 3.74-3.90 (m, 2H); 3.97 (d, J = 5.1 Hz, 2H); 4.59 (hept, J = 6.0 Hz, 1H); 4.84 (s, 2H); 6.28 (d, J = 9.4 Hz, 1H); 6.92 (d, J = 8.8 Hz, 2H); 6.95-7.13 (m, 2H); 7.16 (d, J = 8.9 Hz, 2H); 7.32-7.38 (m, 1H); 7.40 (d, J = 8.3 Hz, 1H); 7.73-7.76 (m, 1H); 7.86 (d, J = 8.1 Hz, 1H) ppm. |
| 233 | 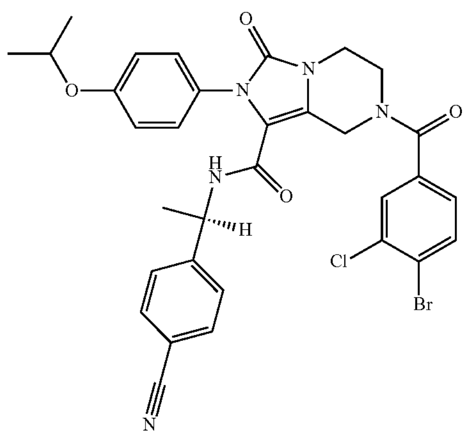 [SMILES: CC(C)Oc1ccc(-n2c(C(=O)N[C@H](C)c3ccc(C#N)cc3)c3n(c2=O)CCN(C(=O)c2ccc(Br)c(Cl)c2)C3)cc1] | 7-(4-bromo-3-chloro-benzoyl)-2-(4-isopropoxyphenyl)-3-oxo-N-[rac-(1R)-1-(4-cyanophenyl)ethyl]-6,8-dihydro-5H-imidazo[1,5-a]pyrazine-1-carboxamide | 1H-NMR (DMSO, 600 MHz, 80° C.): 1.22 (d, J = 7.0 Hz, 3H); 1.30 (d, J = 6.1 Hz, 6H); 3.65-3.74 (m, 2H); 3.85 (br s, 2H); 4.61 (hept, J = 6.1 Hz, 1H); 4.82 (s, 2H); 4.88-4.97 (m, 1H); 6.95 (d, J = 8.8 Hz, 2H); 7.11 (br. s, 1H); 7.19 (d, J = 8.8 Hz, 2H); 7.29 (d, J = 7.7 Hz, 2H); 7.40 (dd, J = 8.2 Hz, 1.6 Hz, 1H); 7.68 (d, J = 8.2 Hz, 2H); 7.75 (d, J = 1.6 Hz, 1H); 7.86 (d, J = 8.2 Hz, 1H) ppm. |

TABLE A-continued

| Compound # | Structure | Name | NMR |
|---|---|---|---|
| 234 | 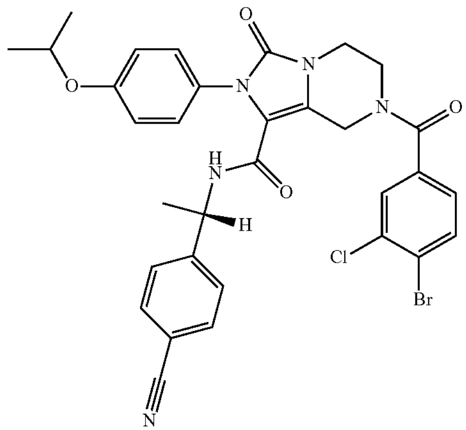 [SMILES: CC(C)Oc1ccc(-n2c(C(=O)N[C@@H](C)c3ccc(C#N)cc3)c3n(c2=O)CCN(C(=O)c2ccc(Br)c(Cl)c2)C3)cc1] | 7-(4-bromo-3-chloro-benzoyl)-2-(4-isopropoxyphenyl)-3-oxo-N-[rac-(1S)-1-(4-cyanophenyl)ethyl]-6,8-dihydro-5H-imidazo[1,5-a]pyrazine-1-carboxamide | 1H-NMR (DMSO, 600 MHz, 80° C.): 1.22 (d, J = 7.0 Hz, 3H); 1.30 (d, J = 6.1 Hz, 6H); 3.65-3.74 (m, 2H); 3.85 (br. s, 2H); 4.61 (hept, J = 6.1 Hz, 1H); 4.82 (s, 2H); 4.88-4.97 (m, 1H); 6.95 (d, J = 8.8 Hz, 2H); 7.11 (br. s, 1H); 7.19 (d, J = 8.8 Hz, 2H); 7.29 (d, J = 7.7 Hz, 2H); 7.40 (dd, J = 8.2 Hz, 1.6 Hz, 1H); 7.68 (d, J = 8.2 Hz, 2H); 7.75 (d, J = 1.6 Hz, 1H); 7.86 (d, J = 8.2 Hz, 1H) ppm. |
| 235 | 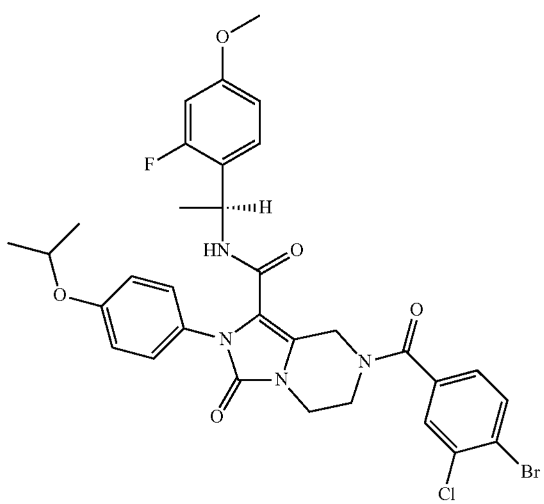 [SMILES: COc1ccc([C@H](C)NC(=O)c2c3n(c(=O)n2-c2ccc(OC(C)C)cc2)CCN(C(=O)c2ccc(Br)c(Cl)c2)C3)c(F)c1] | 7-(4-bromo-3-chloro-benzoyl)-2-(4-isopropoxyphenyl)-3-oxo-N-[rac-(1S)-1-(2-fluoro-4-methoxy-phenyl)ethyl]-6,8-dihydro-5H-imidazo[1,5-a]pyrazine-1-carboxamide | 1H-NMR (DMSO, 600 MHz, 80° C.): 1.19 (d, J = 7.0 Hz, 3H), 1.30 (d, J = 6.1 Hz, 6H), 3.67-3.71 (m, 2H), 3.76 (s, 3H), 3.79-3.92 (m, 2H), 4.61 (hept, J = 6.1 Hz, 1H), 4.84 (s, 2H), 4.98-5.05 (m, 1H), 6.92-6.70 (m, 2H), 6.74-6.79 (m, 1H), 6.93-7.00 (m, 3H), 7.19 (d, J = 8.8 Hz, 2H), 7.40 (dd, J = 7.0 Hz, 1H), 7.74 (s, 1H), 7.86 (d, J = 8.0 Hz, 1H) ppm. |

| Compound # | Structure | Name | NMR |
|---|---|---|---|
| 236 | 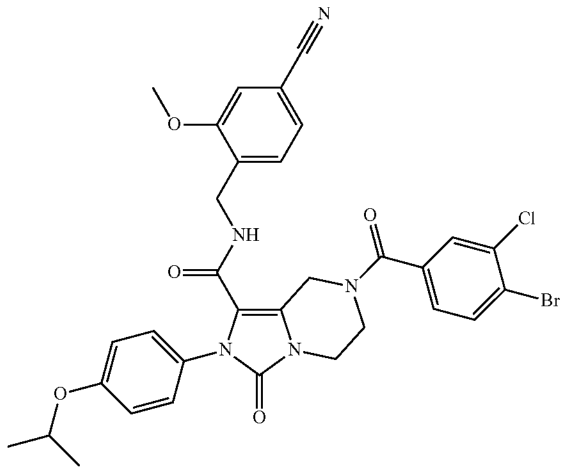 [SMILES: COc1cc(C#N)ccc1CNC(=O)c1c2n(c(=O)n1-c1ccc(OC(C)C)cc1)CCN(C(=O)c1ccc(Br)c(Cl)c1)C2] | 7-(4-bromo-3-chloro-benzoyl)-N-[(4-cyano-2-methoxy-phenyl)methyl]-2-(4-isopropoxyphenyl)-3-oxo-6,8-dihydro-5H-imidazo[1,5-a]pyrazine-1-carboxamide | 1H-NMR (DMSO, 600 MHz, 80° C.): 1.31 (d, J = 6.0 Hz, 6H), 3.65-3.71 (m, 2H), 3.78-3.89 (m, 5H), 4.26 (d, J = 5.87 Hz, 2H), 4.60 (hept, J = 6.0 Hz, 1H), 4.86 (s, 2H), 6.92-7.01 (m, 3H), 7.04-7.09 (m, 1H), 7.18 (d, J = 8.9 Hz, 2H), 7.25 (d, J = 7.6 Hz, 1H), 7.35 (d, J = 1.3 Hz, 1H), 7.41 (dd, J = 8.2 Hz, 2.0 Hz, 1H), 7.75 (d, J = 2.0 Hz, 1H), 7.86 (d, J = 8.2 Hz, 1H) ppm. |
| 237 | 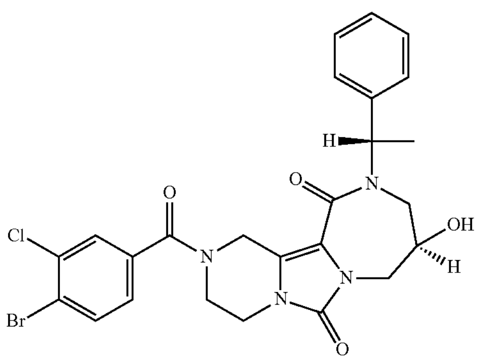 [SMILES: C[C@@H](c1ccccc1)N1C[C@@H](O)Cn2c(c3n(c2=O)CCN(C(=O)c2ccc(Br)c(Cl)c2)C3)C1=O] | (11RS)-2-(4-bromo-3-chloro-benzoyl)-11-hydroxy-13-[(1S)-1-phenylethyl]-4,7,9,13-tetrazatricyclo[7.5.0.0²,⁷]tetradec-1-ene-8,14-dione | 1H NMR (400 MHz, Chloroform-d) δ 7.74 (d, J = 8.2 Hz, 1H), 7.60 (d, J = 2.0 Hz, 1H), 7.37 (dt, J = 15.3, 7.5 Hz, 5H), 7.24 (dd, J = 8.3, 2.0 Hz, 1H), 5.72 (s, 1H), 4.91 (d, J = 16.4 Hz, 2H), 4.19-3.64 (m, 5H), 3.58 (d, J = 14.6 Hz, 1H), 3.39-3.21 (m, 2H), 3.01 (dd, J = 13.9, 7.7 Hz, 2H), 1.58 (d, J = 6.9 Hz, 3H). |

TABLE A-continued

| Compound # | Structure | Name | NMR |
|---|---|---|---|
| 238 | 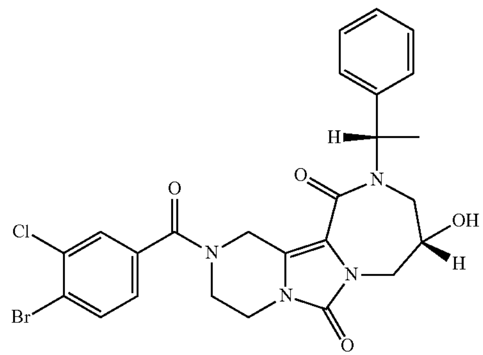 [SMILES: C[C@@H](c1ccccc1)N1C[C@H](O)Cn2c(c3n(c2=O)CCN(C(=O)c2ccc(Br)c(Cl)c2)C3)C1=O] | (11SR)-4-(4-bromo-3-chloro-benzoyl)-11-hydroxy-13-[(1S)-1-phenylethyl]-4,7,9,13-tetrazatricyclo[7.5.0.0 2,7]tetradec-1-ene-8,14-dione | 1H NMR (400 MHz, Chloroform-d) δ 7.73 (dd, J = 8.2, 1.4 Hz, 1H), 7.60 (d, J = 1.9 Hz, 1H), 7.47-7.30 (m, 5H), 7.23 (dd, J = 8.3, 1.7 Hz, 1H), 5.84 (s, 1H), 4.94 (s, 2H), 4.27-3.63 (m, 7H), 3.36 (d, J = 15.3 Hz, 1H), 3.13-2.98 (m, 1H), 2.43-1.87 (m, 1H), 1.58 (d, J = 7.1 Hz, 3H). |
| 239 | 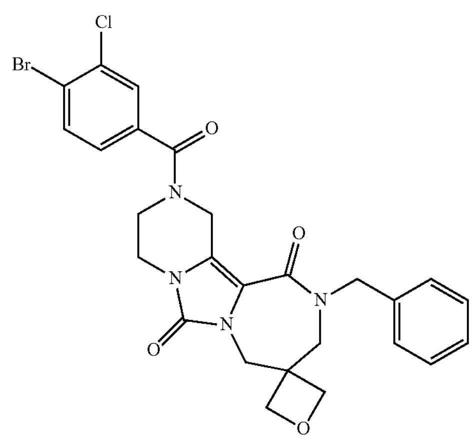 [SMILES: O=C(c1ccc(Br)c(Cl)c1)N1CCn2c(c3n(c2=O)CC2(COC2)CN(Cc2ccccc2)C3=O)C1] | 13-benzyl-4-(4-bromo-3-chloro-benzoyl)spiro[4,7,9,13-tetrazatricyclo[7.5.0.0 2,7]tetradec-1-ene-11,3'-oxetane]-8,14-dione | 1H NMR (400 MHz, Chloroform-d) δ 7.74 (dd, J = 8.2, 1.0 Hz, 1H), 7.60 (s, 1H), 7.43-7.30 (m, 3H), 7.28-7.18 (m, 3H), 4.92 (s, 2H), 4.63 (s, 2H), 4.25-3.69 (m, 10H), 3.57 (s, 2H). |

TABLE A-continued

| Compound # | Structure | Name | NMR |
|---|---|---|---|
| 240 | 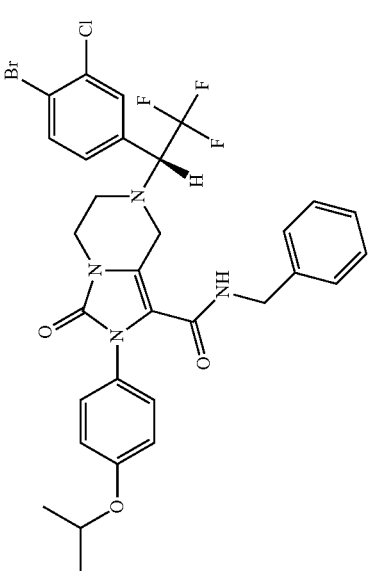 | N-benzyl-2-(4-isopropoxyphenyl)-3-oxo-7-[rac-(1R)-1-(4-bromo-3-chlorophenyl)-2,2,2-trifluoro-ethyl]-6,8-dihydro-5H-imidazo[1,5-a]pyrazine-1-carboxamide | 1H NMR (400 MHz, Chlorofom-d) δ 7.67 (d, J = 8.4 Hz, 1H), 7.55 (d, J = 2.0 Hz, 1H), 7.26-7.14 (m, 6H), 6.99-6.89 (m, 2H), 6.89-6.80 (m, 2H), 5.18 (t, J = 5.2 Hz, 1H), 4.53-4.41 (m, 1H), 4.39-4.18 (m, 5H), 3.72 (t, J = 5.4 Hz, 2H), 3.21-3.09 (m, 1H), 2.92-2.77 (m, 1H), 1.31 (d, J = 6.0 Hz, 6H). |
| 241 | 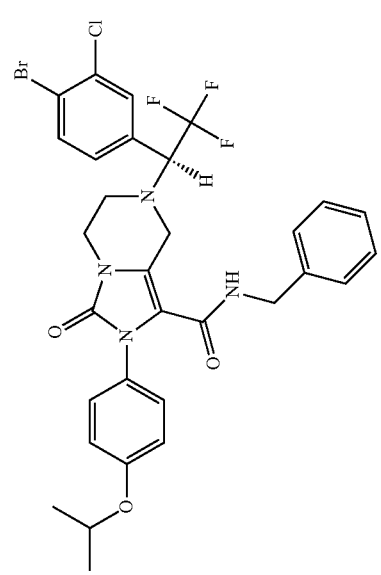 | N-benzyl-2-(4-isopropoxyphenyl)-3-oxo-7-[rac-(1S)-1-(4-bromo-3-chlorophenyl)-2,2,2-trifluoro-ethyl]-6,8-dihydro-5H-imidazo[1,5-a]pyrazine-1-carboxamide | 1H NMR (400 MHz, Chlorofom-d) δ 7.67 (d, J = 8.4 Hz, 1H), 7.55 (d, J = 2.0 Hz, 1H), 7.26-7.14 (m, 6H), 6.99-6.89 (m, 2H), 6.89-6.80 (m, 2H), 5.18 (t, J = 5.2 Hz, 1H), 4.53-4.41 (m, 1H), 4.39-4.18 (m, 5H), 3.72 (t, J = 5.4 Hz, 2H), 3.21-3.09 (m, 1H), 2.92-2.77 (m, 1H), 1.31 (d, J = 6.0 Hz, 6H). |

| Compound # | Structure | Name | NMR |
|---|---|---|---|
| 242 | 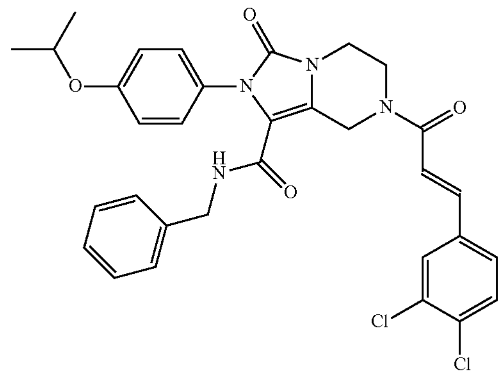 [SMILES: CC(C)Oc1ccc(-n2c(C(=O)NCc3ccccc3)c3n(c2=O)CCN(C(=O)/C=C/c2ccc(Cl)c(Cl)c2)C3)cc1] | N-benzyl-7-[(E)-3-(3,4-dichlorophenyl)prop-2-enoyl]-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.29 (d, J = 6.0 Hz, 6H), 3.70 (t, J = 5.4 Hz, 2H), 4.06 (t, J = 4.6 Hz, 2H), 4.30 (d, J = 5.8 Hz, 2H), 4.59 (hept, J = 6.0 Hz, 1H), 4.94 (s, 2H), 6.91 (d, J = 8.6 Hz, 2H), 7.10 (d, J = 7.4 Hz, 2H), 7.17-7.35 (m, 7H), 7.51 (d, J = 15.5 Hz, 1H), 7.64-7.69 (m, 2H), 8.04 (s, 1H). |
| 243 | 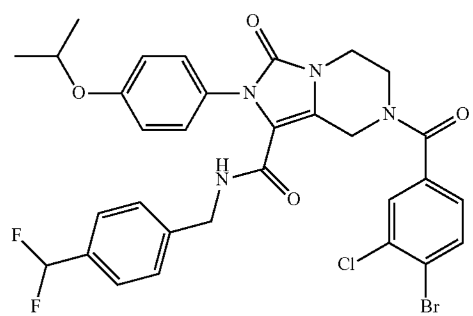 [SMILES: CC(C)Oc1ccc(-n2c(C(=O)NCc3ccc(C(F)F)cc3)c3n(c2=O)CCN(C(=O)c2ccc(Br)c(Cl)c2)C3)cc1] | 7-(4-bromo-3-chloro-benzoyl)-N-[[4-(difluoromethyl)phenyl]methyl]-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.28 (d, J = 6.0 Hz, 6H), 3.68 (t, J = 5.5 Hz, 2H), 3.83 (br s, 2H), 4.30 (d, J = 5.6 Hz, 2H), 4.57 (hept, J = 6.1 Hz, 1H), 4.86 (s, 2H), 6.92 (d, J = 8.0 Hz, 2H), 6.93 (t, J = 55.5 Hz, 1H), 7.17-7.19 (m, 4H), 7.26 (br s, 1H), 7.39-7.44 (m, 3H), 7.75 (s, 1H), 7.85 (d, J = 8.3 Hz, 1H). |

TABLE A-continued

| Compound # | Structure | Name | NMR |
|---|---|---|---|
| 244 | 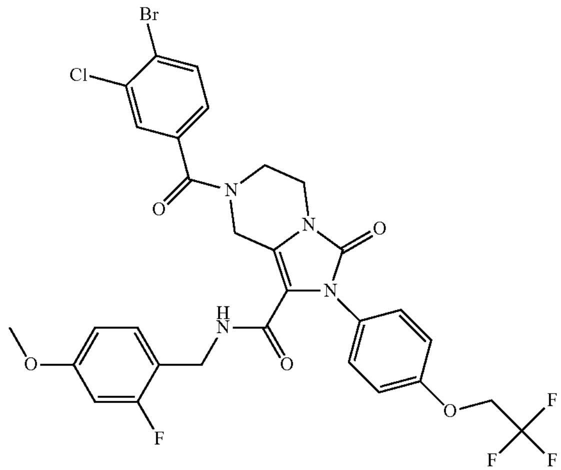 [SMILES: COc1ccc(CNC(=O)c2c3n(c(=O)n2-c2ccc(OCC(F)(F)F)cc2)CCN(C(=O)c2ccc(Br)c(Cl)c2)C3)c(F)c1] | 7-(4-bromo-3-chloro-benzoyl)-N-[(2-fluoro-4-methoxy-phenyl)methyl]-3-oxo-2-[4-(2,2,2-trifluoroethoxy)phenyl]-6,8-dihydro-5H-imidazo[1,5-a]pyrazine-1-carboxamide | 1H NMR (400 MHz, DMSO-d6, 80° C.): 3.69 (t, J = 5.5 Hz, 2H), 3.78 (s, 3H), 3.84 (t, J = 5.4 Hz, 2H), 4.22 (d, J = 6.1 Hz, 2H), 4.73 (q, J = 9.0 Hz, 2H), 4.85 (s, 2H), 6.68 (t, J = 11.3 Hz, 2H), 7.00 (t, J = 8.1 Hz, 1H), 7.09 (d, J = 8.1 Hz, 2H), 7.23 (d, J = 8.1 Hz, 3H), 7.40 (d, J = 8.0 Hz, 1H), 7.76 (s, 1H), 7.87 (d, J = 8.0 Hz, 1H) |
| 245 | 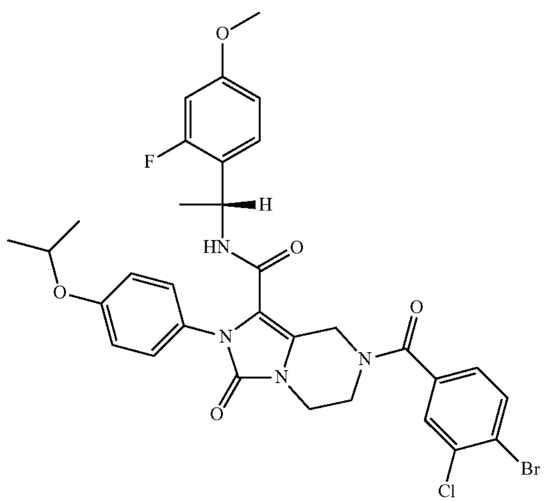 [SMILES: COc1ccc([C@@H](C)NC(=O)c2c3n(c(=O)n2-c2ccc(OC(C)C)cc2)CCN(C(=O)c2ccc(Br)c(Cl)c2)C3)c(F)c1] | 7-(4-bromo-3-chloro-benzoyl)-2-(4-isopropoxyphenyl)-3-oxo-N-[rac-(1R)-1-(2-fluoro-4-methoxy-phenyl)ethyl]-6,8-dihydro-5H-imidazo[1,5-a]pyrazine-1-carboxamide | 1H-NMR (DMSO, 600 MHz, 80° C.): 1.19 (d, J = 7.0 Hz, 3H), 1.30 (d, J = 6.1 Hz, 6H), 3.67-3.71 (m, 2H), 3.76 (s, 3H), 3.79-3.92 (m, 2H), 4.61 (hept, J = 6.1 Hz, 1H), 4.84 (s, 2H), 4.98-5.05 (m, 1H), 6.92-6.70 (m, 2H), 6.74-6.79 (m, 1H), 6.93-7.00 (m, 3H), 7.19 (d, J = 8.8 Hz, 2H), 7.40 (dd, J = 7.0 Hz, 1H), 7.74 (s, 1H), 7.86 (d, J = 8.0 Hz, 1H) ppm. |

TABLE A-continued

| Compound # | Name | Structure | NMR |
|---|---|---|---|
| 246 | 7-(4-bromo-3-chloro-benzoyl)-N-[(4-methoxy-2-methyl-phenyl)methyl]-3-oxo-2-[4-(2,2,2-trifluoroethoxy)phenyl]-6,8-dihydro-5H-imidazo[1,5-a]pyrazine-1-carboxamide | 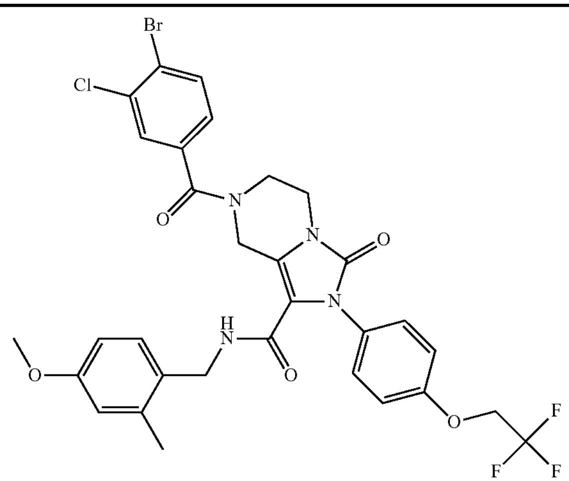 | 1H-NMR (DMSO, 600 MHz, 80° C.): 2.11 (s, 3H), 3.65-3.71 (m, 2H), 3.73 (s, 3H), 3.80-3.87 (m, 2H), 4.17 (d, J = 4.9 Hz, 2H), 4.92 (q, J = 8.9 Hz, 2H), 4.84 (s, 2H), 6.63 (dd, J = 8.3 Hz, 1.9 Hz, 1H), 6.69 (d, J = 2.2 Hz, 1H), 6.84-6.90 (m, 1H), 7.00-7.05 (m, 1H), 7.08 (d, J = 8.7 Hz, 2H), 7.23 (d, J = 8.7 Hz, 2H), 7.40 (d, J = 8.2 Hz, 1.6 Hz, 1H), 7.75 (s, 1H), 7.86 (d, J = 8.2 Hz, 1H) ppm. |
| 247 | 7-(4-bromo-3-chloro-benzoyl)-2-(4-methoxycyclohexyl)-3-oxo-N-[rac-(1S)-1-phenylethyl]-6,8-dihydro-5H-imidazo[1,5-a]pyrazine-1-carboxamide | 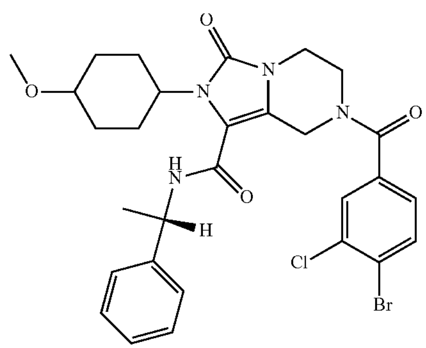 [SMILES: COC1CCC(n2c(C(=O)N[C@@H](C)c3ccccc3)c3n(c2=O)CCN(C(=O)c2ccc(Br)c(Cl)c2)C3)CC1] | 1H-NMR (DMSO, 600 MHz, 80° C.): 1.49 (d, J = 7.0 Hz, 3H), 1.57-1.78 (m, 6H), 1.85-1.96 (m, 2H), 3.26 (s, 3H), 3.28-3.32 (m, 1H), 3.75-3.89 (m, 4H), 4.82-4.93 (m, 3H), 5.06-5.13 (m, 1H), 7.21-7.25 (m, 1H), 7.29-7.43 (m, 6H), 7.72 (d, J = 1.7 Hz, 1H), 7.85 (d, J = 8.0 Hz, 1H) ppm. |

| Compound # | Structure | Name | NMR |
|---|---|---|---|
| 248 | 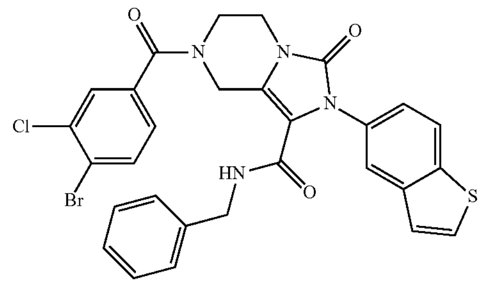 [SMILES: O=C(NCc1ccccc1)c1c2n(c(=O)n1-c1ccc3sccc3c1)CCN(C(=O)c1ccc(Br)c(Cl)c1)C2] | 2-(benzothiophen-5-yl)-N-benzoyl-7-(4-bromo-3-chloro-benzoyl)-3-oxo-6,8-dihydro-5H-imidazo[1,5-a]pyrazine-1-carboxamide | 1H-NMR (DMSO, 600 MHz, 80° C.): 3.72 (t, J = 5.5 Hz, 2H); 3.85 (br. s.., 2H); 4.23 (d, J = 5.5 Hz, 2H); 4.89 (s, 2H); 6.93-7.00 (m, 2H); 7.12-7.19 (m, 3H); 7.25 (dd, J = 8.5 Hz, .16 Hz, 1H); 7.39-7.43 (m, 1H); 7.43-7.48 (br. s., 1H); 7.45 (d, J = 5.5 Hz, 1H); 7.74-7.78 (m, 1H); 7.80 (d, J = 1.6 Hz, 1H); 7.82 (d, J = 5.5 Hz, 1H); 7.86 (d, J = 8.2 Hz, 1H); 8.00 (d, J = 8.6 Hz, 1H) ppm. |
| 249 | 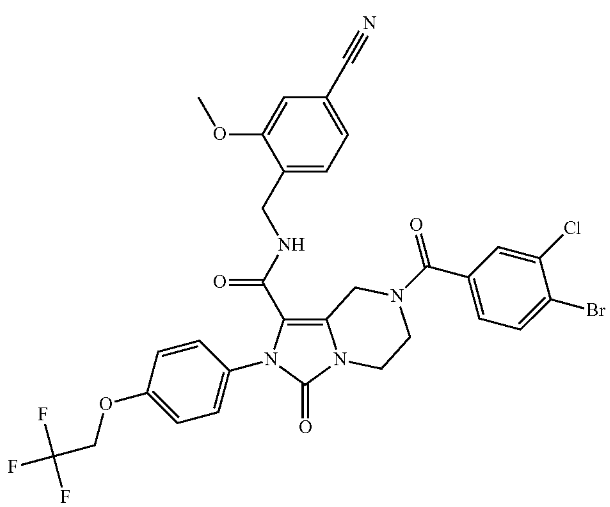 [SMILES: COc1cc(C#N)ccc1CNC(=O)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-N-[(4-cyano-2-methoxy-phenyl)methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.69 (t, J = 5.5 Hz, 2H); 3.82 (s, 5H); 4.27 (d, J = 5.5 Hz, 2H); 4.75 (q, J = 8.8 Hz, 2H); 4.85 (s, 2H); 7.04-7.10 (m, 1H); 7.11 (d, J = 8.6 Hz, 2H); 7.15-7.30 (m, 4H); 7.36 (s, 1H); 7.40 (d, J = 8.3 Hz, 1H); 7.75 (s, 1H); 7.86 (d, J = 8.3 Hz, 1H) ppm. |

TABLE A-continued

| Compound # | Structure | Name | NMR |
|---|---|---|---|
| 250 | 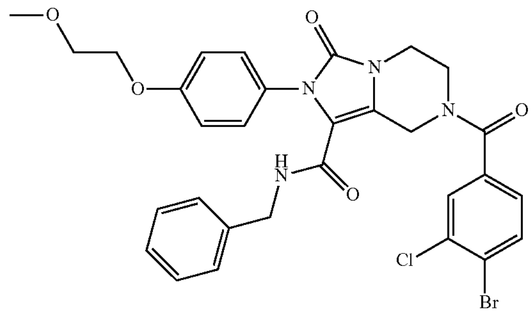 [SMILES: COCCOc1ccc(-n2c(C(=O)NCc3ccccc3)c3n(c2=O)CCN(C(=O)c2ccc(Br)c(Cl)c2)C3)cc1] | N-benzyl-7-(4-bromo-3-chloro-benzoyl)-2-[4-(2-methoxyethoxy)phenyl]-3-oxo-6,8-dihydro-5H-imidazo[1,5-a]pyrazine-1-carboxamide | 1H NMR (300 MHz, Chloroform-d) δ 7.73 (t, J = 4.1 Hz, 1H), 7.64 (d, J = 1.8 Hz, 1H), 7.26 °C 7.20 (m, 6H), 6.94 (d, J = 9 Hz, 4H), 5.14 (s, 1H), 5.04 (s, 2H), 4.25 (d, J = 4.5 Hz, 2H), 4.08-4.05 (m, 4H), 3.83 (s, 2H), 3.77-3.74 (m, 2H), 3.46 (s, 3H). |
| 251 | 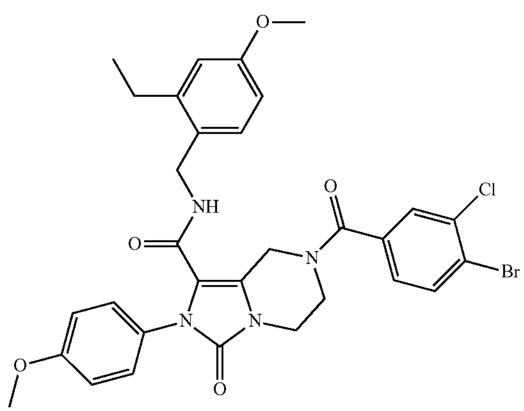 [SMILES: CCc1cc(OC)ccc1CNC(=O)c1c2n(c(=O)n1-c1ccc(OC)cc1)CCN(C(=O)c1ccc(Br)c(Cl)c1)C2] | 7-(4-bromo-3-chloro-benzoyl)-N-[(2-ethyl-4-methoxy-phenyl)methyl]-2-(4-methoxyphenyl)-3-oxo-6,8-dihydro-5H-imidazo[1,5-a]pyrazine-1-carboxamide | 1H NMR (400 MHz, DMSO-d6, ppm) δ 7.88 (d, J = 8.0 Hz, 1H), 7.80 (d, J = 2.0 Hz, 1H), 7.43-7.41 (m, 1H), 7.15 (d, J = 8.8 Hz, 2H), 6.94 (d, J = 8.8 Hz, 2H), 6.70-6.64 (m, 3H), 4.89-4.75 (m, 2H), 4.22-3.95 (m, 3H), 3.77-3.60 (m, 10H), 2.50-2.34 (m, 1H), 1.14-1.09 (m, 3H). |

TABLE A-continued

| Compound # | Structure | Name | NMR |
|---|---|---|---|
| 252 | 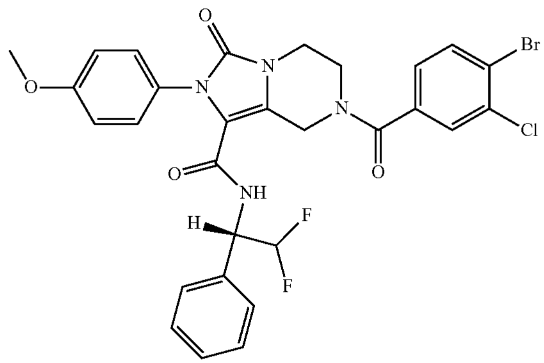 [SMILES: COc1ccc(-n2c(C(=O)N[C@@H](c3ccccc3)C(F)F)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1S)-2,2-difluoro-1-phenyl-ethyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.63 (d, J = 2.0 Hz, 1H), 7.40-7.29 (m, 4H), 7.28-7.22 (m, 2H), 7.11-7.02 (m, 2H), 6.85 (d, J = 7.1 Hz, 2H), 6.02-5.55 (m, 2H), 5.25 (q, J = 13.1 Hz, 1H), 5.04 (s, 2H), 4.09 (s, 2H), 3.91-3.75 (m, 5H). |
| 253 | 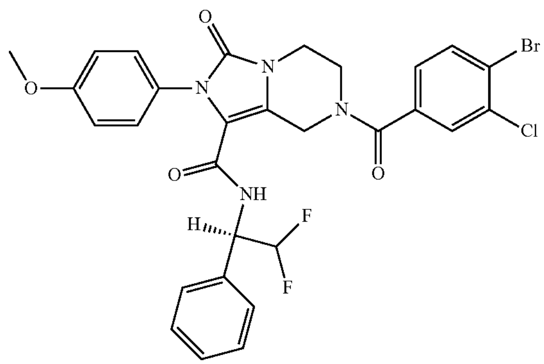 [SMILES: COc1ccc(-n2c(C(=O)N[C@H](c3ccccc3)C(F)F)c3n(c2=O)CCN(C(=O)c2ccc(Br)c(Cl)c2)C3)cc1] | 7-(4-bromo-3-chloro-benzoyl)-2-(4-methoxyphenyl)-3-oxo-N-[rac-(1R)-2,2-difluoro-1-phenyl-ethyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.63 (d, J = 2.0 Hz, 1H), 7.40-7.29 (m, 4H), 7.28-7.22 (m, 2H), 7.11-7.02 (m, 2H), 6.85 (d, J = 7.1 Hz, 2H), 6.02-5.55 (m, 2H), 5.25 (q, J = 13.1 Hz, 1H), 5.04 (s, 1H), 4.09 (s, 2H), 3.91-3.75 (m, 5H). |
| 254 | 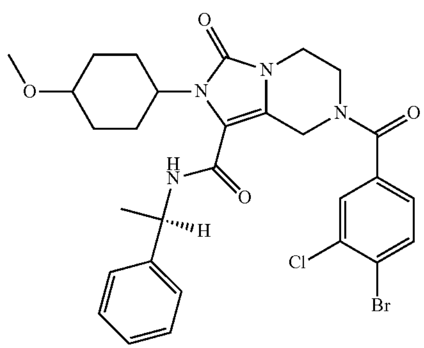 [SMILES: COC1CCC(n2c(C(=O)N[C@H](C)c3ccccc3)c3n(c2=O)CCN(C(=O)c2ccc(Br)c(Cl)c2)C3)CC1] | 7-(4-bromo-3-chloro-benzoyl)-2-(4-methoxycyclohexyl)-3-oxo-N-[rac-(1R)-1-phenylethyl]-6,8-dihydro-5H-imidazo[1,5-a]pyrazine-1-carboxamide | 1H-NMR (DMSO, 600 MHz, 80° C.): 1.49 (d, J = 7.0 Hz, 3H), 1.57-1.78 (m, 6H), 1.85-1.96 (m, 2H), 3.26 (s, 3H), 3.28-3.32 (m, 1H), 3.75-3.89 (m, 4H), 4.82-4.93 (m, 3H), 5.06-5.13 (m, 1H), 7.21-7.25 (m, 1H), 7.29-7.43 (m, 6H), 7.72 (d, J = 1.7 Hz, 1H), 7.85 (d, J = 8.0 Hz, 1H) ppm. |

TABLE A-continued

| Compound # | Structure | Name | NMR |
|---|---|---|---|
| 255 | 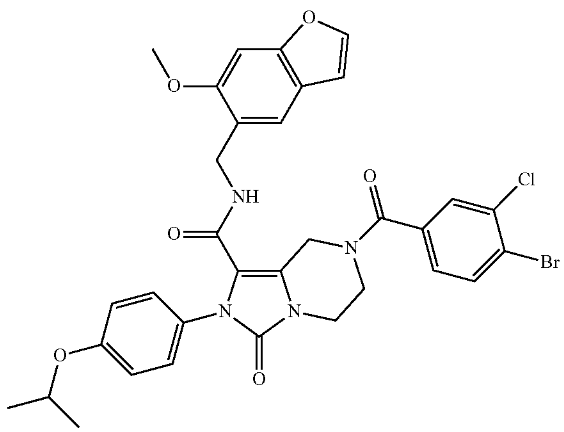 [SMILES: COc1cc2occc2cc1CNC(=O)c1c2n(c(=O)n1-c1ccc(OC(C)C)cc1)CCN(C(=O)c1ccc(Br)c(Cl)c1)C2] | 7-(4-bromo-3-chloro-benzoyl)-2-(4-isopropoxyphenyl)-N-[(6-methoxybenzofuran-5-yl)methyl]-3-oxo-6,8-dihydro-5H-imidazo[1,5-a]pyrazine-1-carboxamide | 1H-NMR (DMSO, 600 MHz, 80° C.): 1.27 (d, J = 6.1 Hz, 6H), 3.64-3.70 (m, 2H), 3.78 (s, 3H), 3.80-3.86 (m, 2H), 4.28 (d, J = 5.7 Hz, 2H), 4.55 (hept, J = 6.1 Hz, 1H), 4.89 (s, 2H), 6.63 (br. s., 1H), 6.79 (s, 1H), 6.93 (d, J = 9.0 Hz, 2H), 7.13-7.22 (m, 4H), 7.40 (dd, J = 8.5 Hz, 1.5 Hz, 1H), 7.74 (s, 1H), 7.79 (d, J = 1.8 Hz, 1H), 7.85 (d, J = 8.2 Hz, 1H) ppm. |
| 256 | 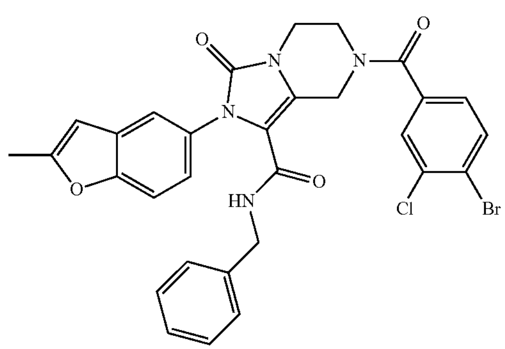 [SMILES: Cc1cc2cc(-n3c(C(=O)NCc4ccccc4)c4n(c3=O)CCN(C(=O)c3ccc(Br)c(Cl)c3)C4)ccc2o1] | N-benzyl-7-(4-bromo-3-chloro-benzoyl)-2-(2-methylbenzofuran-6-yl)-3-oxo-6,8-dihydro-5H-imidazo[1,5-a]pyrazine-1-carboxamide | 1H-NMR (DMSO, 600 MHz, 80° C.): 2.48 (s, 3H), 3.69-3.73 (m, 2H), 3.85 (s, 2H), 4.22 (d, J = 5.8 Hz, 2H), 4.88 (s, 2H), 6.57 (s, 1H), 6.93-6.99 (m, 2H), 7.08-7.14 (m, 2H), 7.14-7.20 (m, 3H), 7.41 (dd, J = 8.4 Hz, 1.4 Hz, 1H), 7.44 (d, J = 1.8 Hz, 1H), 7.48 (d, J = 8.6 Hz, 1H), 7.76 (s, 1H), 7.86 (d, J = 8.2 Hz, 1H) ppm. |

TABLE A-continued

| Compound # | Structure | Name | NMR |
|---|---|---|---|
| 257 | 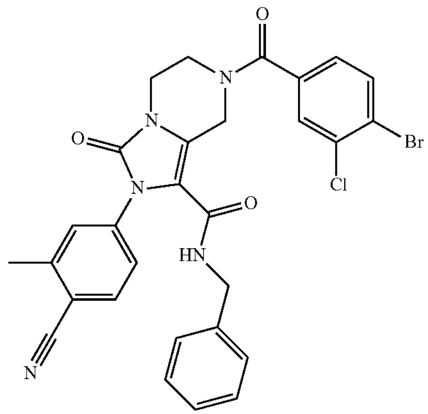 [SMILES: Cc1cc(-n2c(C(=O)NCc3ccccc3)c3n(c2=O)CCN(C(=O)c2ccc(Br)c(Cl)c2)C3)ccc1C#N] | N-benzyl-7-(4-bromo-3-chloro-benzoyl)-2-(4-cyano-3-methyl-phenyl)-3-oxo-6,8-dihydro-5H-imidazo[1,5-a]pyrazine-1-carboxamide | 1H-NMR (DMSO, 600 MHz, 80° C.): 2.44 (s, 3H); 3.68-3.73 (m, 2H); 3.83 (br. s., 2H); 4.29 (d, J = 5.6 Hz, 2H); 4.86 (s, 2H); 7.13 (m, 2H), 7.21-7.33 (m, 5H); 7.39 (dd, J = 8.1 Hz, 1.6 Hz, 1H); 7.70-7.77 (m, 2H); 7.85 (d, J = 8.1 Hz, 1H); 7.90 (br. s, 1H) ppm. |
| 258 | 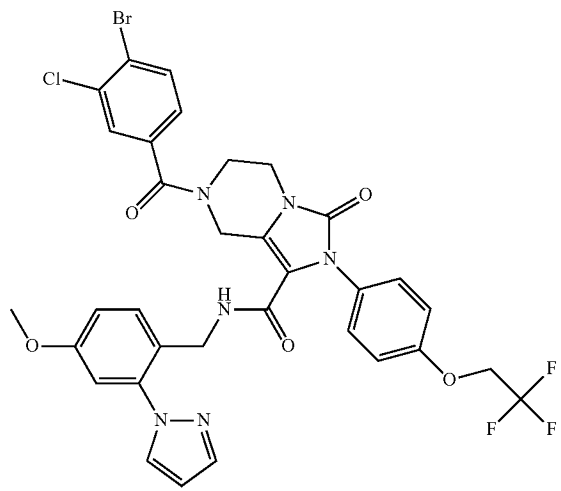 [SMILES: COc1ccc(CNC(=O)c2c3n(c(=O)n2-c2ccc(OCC(F)(F)F)cc2)CCN(C(=O)c2ccc(Br)c(Cl)c2)C3)c(-n2cccn2)c1] | 7-(4-bromo-3-chloro-benzoyl)-N-[(4-methoxy-2-pyrazol-1-yl-phenyl)methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.67 (t, J = 5.5 Hz, 2H); 3.81 (s, 3H); 3.82 (br. s., 2H); 4.11 (d, J = 5.6 Hz, 2H); 4.69 (q, J = 8.8 Hz, 2H); 4.86 (s, 2H); 6.43-6.48 (m, 1H); 6.88-6.94 (m, 2H); 7.03 (br. s., 1H); 7.07 (d, J = 8.8 Hz, 2H); 7.15 (d, J = 8.1 Hz, 1H); 7.22 (d, J = 8.8 Hz, 2H); 7.39 (dd, J = 8.1 Hz, 1.2 Hz, 1H); 7.59 (s, 1H); 7.73 (d, J = 1.2 Hz, 1H); 7.84 (d, J = 8.3 Hz, 1H); 7.97 (d, J = 1.6 Hz, 1H) ppm. |

TABLE A-continued

| Compound # | Structure | Name | NMR |
|---|---|---|---|
| 259 | 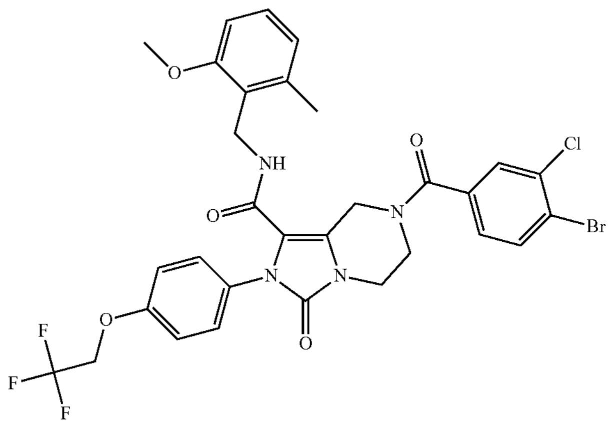 [SMILES: COc1cccc(C)c1CNC(=O)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-N-[(2-methoxy-6-methyl-phenyl)methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 2.20 (s, 3H); 3.65 (br. s., 2H); 3.66 (s, 3H); 3.81 (br. s., 2H); 4.25 (d, J = 5.0 Hz, 2H); 4.70 (q, J = 8.8 Hz, 2H); 4.82 (s, 2H); 6.28 (br. s., 1H); 6.70-6.77 (m, 2H); 7.05 (d, J = 8.7 Hz, 2H); 7.11 (t, J = 8.0 Hz, 1H); 7.21 (d, J = 8.6 Hz, 2H); 7.37 (d, J = 8.2 Hz, 1H); 7.72 (s, 1H); 7.84 (d, J = 8.3 Hz, 1H) ppm. |
| 260 | 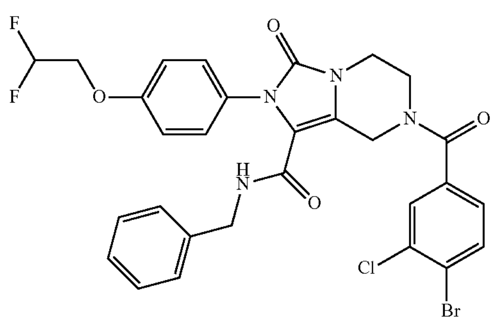 [SMILES: O=C(NCc1ccccc1)c1c2n(c(=O)n1-c1ccc(OCC(F)F)cc1)CCN(C(=O)c1ccc(Br)c(Cl)c1)C2] | N-benzyl-7-(4-bromo-3-chloro-benzoyl)-2-[4-(2,2-difluoroethoxy)phenyl]-3-oxo-6,8-dihydro-5H-imidazo[1,5-a]pyrazine-1-carboxamide | 1H NMR (400 MHz, DMSO-d6, 80° C.): 3.68 (t, J = 5.5 Hz, 2H), 3.83 (br s, 2H), 4.25 (d, J = 5.6 Hz, 2H), 4.32 (td, J = 14.6 Hz, 3.3 Hz, 2H), 4.85 (s, 2H), 6.35 (t, J = 54.8 Hz, 1H), 7.03-7.06 (m, 4H), 7.21-7.27 (m, 5H), 7.31-7.34 (m, 1H), 7.39 (d, J = 8.3 Hz, 1H), 7.74 (s, 1H), 7.85 (d, J = 8.3 Hz, 1H). |

| Compound # | Structure | Name | NMR |
|---|---|---|---|
| 261 | 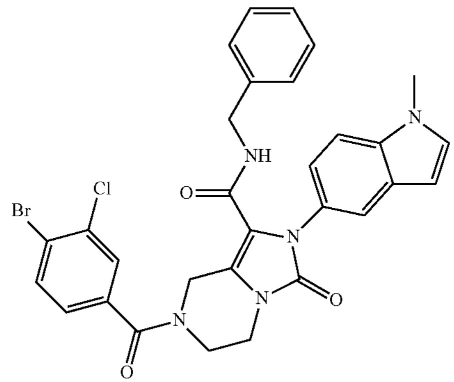 [SMILES: Cn1ccc2cc(-n3c(C(=O)NCc4ccccc4)c4n(c3=O)CCN(C(=O)c3ccc(Br)c(Cl)c3)C4)ccc21] | N-benzoyl-7-(4-bromo-3-chloro-benzoyl)-2-(1-methylindol-5-yl)-3-oxo-6,8-dihydro-5H-imidazo[1,5-a]pyrazine-1-carboxamide | 1H NMR (400 MHz, DMSO-d6, 80° C.): 3.70 (t, J = 5.5 Hz, 2H), 3.82 (s, 3H), 3.86 (br s, 2H), 4.17 (d, J = 5.4 Hz, 2H), 4.89 (s, 2H), 6.47 (d, J = 2.6 Hz, 1H), 6.72 (br s, 1H), 6.85 (d, J = 7.0 Hz, 2H), 7.04-7.16 (m, 4H), 7.38 (d, J = 2.8 Hz, 1H), 7.42 (t, J = 8.6 Hz, 2H), 7.50 (s, 1H), 7.76 (s, 1H), 7.86 (d, J = 8.1 Hz, 1H). |
| 262 | 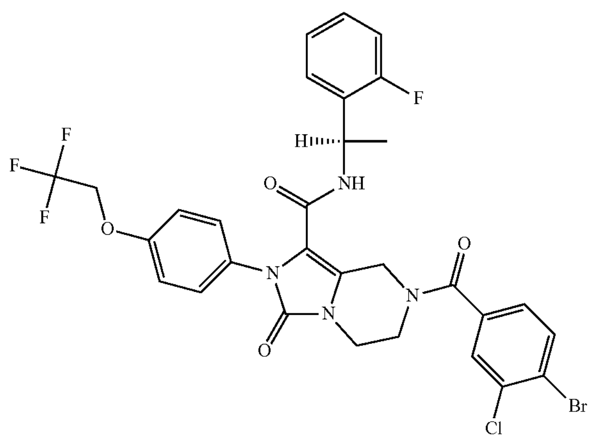 [SMILES: C[C@@H](NC(=O)c1c2n(c(=O)n1-c1ccc(OCC(F)(F)F)cc1)CCN(C(=O)c1ccc(Br)c(Cl)c1)C2)c1ccccc1F] | 7-(4-bromo-3-chloro-benzoyl)-3-oxo-N-[rac-(1R)-1-(2-fluorophenyl)ethyl]-2-[4-(2,2,2-trifluoroethoxy)phenyl]-6,8-dihydro-5H-imidazo[1,5-a]pyrazine-1-carboxamide | 1H NMR (400 MHz, DMSO-d6, 80° C.): 1.24 (d, J = 6.8 Hz, 3H), 3.69 (t, J = 5.5 Hz, 2H), 3.84 (br s, 2H), 4.73 (q, J = 8.8 Hz, 2H), 4.83 (s, 2H), 5.07-5.13 (m, J = 5.1 Hz, 1H), 7.00-7.19 (m, 6H), 7.21-7.30 (m, 3H), 7.39 (dd, J = 8.2 Hz, 1.1 Hz, 1H), 7.74 (s, 1H), 7.85 (d, J = 8.2 Hz, 1H). |

TABLE A-continued

| Compound # | Structure | Name | NMR |
|---|---|---|---|
| 263 | 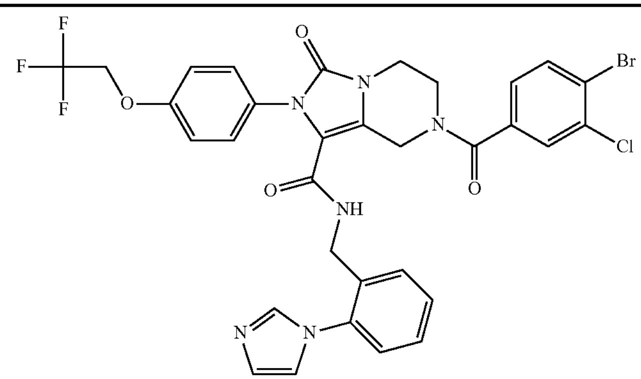 | 7-(4-bromo-3-chloro-benzoyl)-N-[(2-imidazol-1-ylphenyl)methyl]-3-oxo-2-[4-(2,2,2-trifluoroethoxy)phenyl]-6,8-dihydro-5H-imidazo[1,5-a]pyrazine-1-carboxamide | 1H NMR (400 MHz, DMSO-d6, 80° C.): 3.69 (t, J = 5.5 Hz, 2H), 3.82 (br s, 2H), 4.08 (d, J = 5.6 Hz, 2H), 4.73 (q, J = 8.9 Hz, 2H), 4.84 (s, 2H), 7.08 (d, J = 7.8 Hz, 2H), 7.11 (s, 1H), 7.17 (br s, 1H), 7.23 (s, 1H), 7.25-7.28 (m, 3H), 7.33-7.43 (m, 4H), 7.69 (s, 1H), 7.71-7.74 (m, 1H), 7.84 (d, J = 8.1 Hz, 1H). |
| 264 | 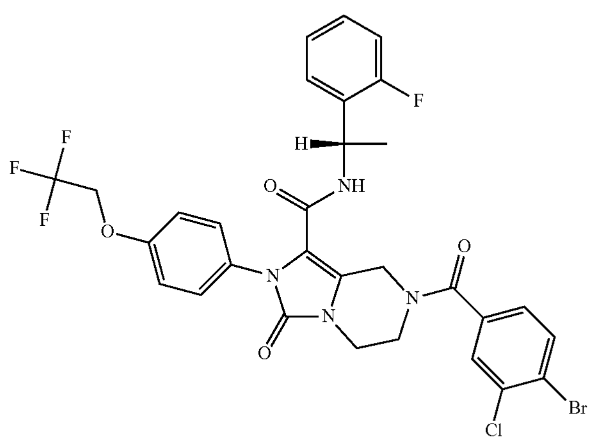 [SMILES: C[C@H](NC(=O)c1c2n(c(=O)n1-c1ccc(OCC(F)(F)F)cc1)CCN(C(=O)c1ccc(Br)c(Cl)c1)C2)c1ccccc1F] | 7-(4-bromo-3-chloro-benzoyl)-3-oxo-N-[rac-(1S)-1-(2-fluorophenyl)ethyl]-2-[4-(2,2,2-trifluoroethoxy)phenyl]-6,8-dihydro5H-imidazo[1,5-a]pyrazine-1-carboxamide | 1H NMR (400 MHz, DMSO-d6, 80° C.): 1.24 (d, J = 6.5 Hz, 3H), 3.69 (t, J = 5.1 Hz, 2H), 3.84 (br s, 2H), 4.73 (q, J = 8.6 Hz, 2H), 4.83 (s, 2H), 5.07-5.13 (m, J = 6.9 Hz, 1H), 7.04-7.15 (m, 6H), 7.24-7.26 (m, 3H), 7.39 (d, J = 8.1 Hz, 1H), 7.74 (s, 1H), 7.84 (d, J = 8.1 Hz, 1H). |

| Compound # | Structure | Name | NMR |
|---|---|---|---|
| 265 | 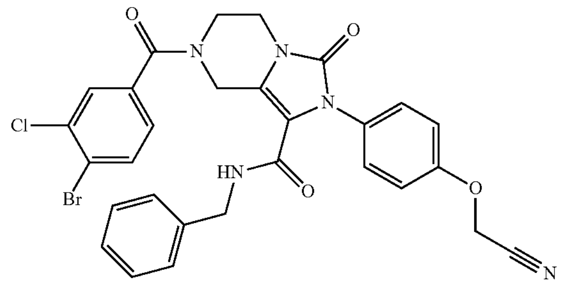 [SMILES: N#CCOc1ccc(-n2c(C(=O)NCc3ccccc3)c3n(c2=O)CCN(C(=O)c2ccc(Br)c(Cl)c2)C3)cc1] | N-benzyl-7-(4-bromo-3-chloro-benozyl)-2-[4-(cyanomethoxy)phenyl]-3-oxo-6,8-dihydro-5H-imidazo[1,5-a]pyrazine-1-carboxamide | 1H NMR (400 MHz, DMSO-d6, 80° C.): 3.70 (t, J = 4.0 Hz, 2H), 3.84 (s, 2H), 4.27 (d, J = 4.8 Hz, 2H), 4.87 (s, 2H), 5.15 (s, 2H), 7.08-7.12 (m, 4H), 7.2-3-7.29 (m, 5H), 7.41 (d, J = 8.0 Hz, 1H), 7.49 (br s, 1H) 7.76 (s, 1H), 7.87 (d, J = 8.4 Hz, 1H). |
| 266 | 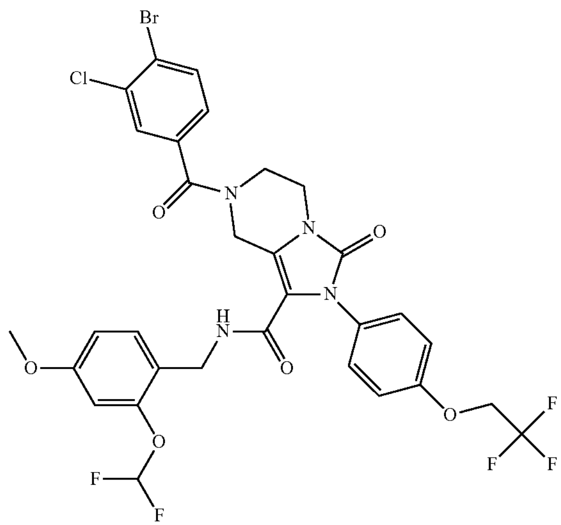 [SMILES: COc1ccc(CNC(=O)c2c3n(c(=O)n2-c2ccc(OCC(F)(F)F)cc2)CCN(C(=O)c2ccc(Br)c(Cl)c2)C3)c(OC(F)F)c1] | 7-(4-bromo-3-chloro-benzoyl)-N-[[2-(difluoromethoxy)-4-methoxy-phenyl]methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.67-3.72 (m, 2H), 3.78 (s, 3H), 3.81-3.87 (m, 2H), 4.22 (d, J = 5.8 Hz, 2H), 4.71 (q, J = 8.8 Hz, 2H), 4.86 (s, 2H), 6.69-6.74 (m, 2H), 6.94-7.04 (m, 2H), 7.02 (t, J = 74.0 Hz, 1H), 7.09 (d, J = 9.0 Hz, 2H), 7.25 (d, J = 9.0 Hz, 2H), 7.40 (dd, J = 8.3 Hz, 2.0 Hz, 1H), 7.74 (d, J = 1.9 Hz, 1H), 7.85 (d, J = 8.2 Hz, 1H) ppm. |

TABLE A-continued

| Compound # | Structure | Name | NMR |
|---|---|---|---|
| 267 | 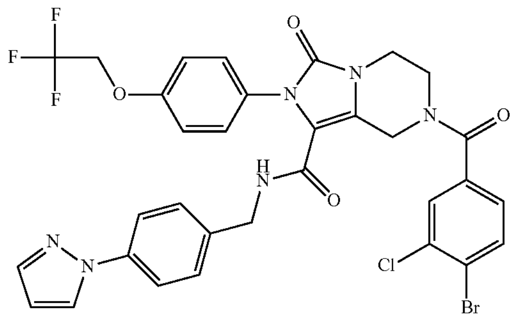 [SMILES: O=C(NCc1ccc(-n2cccn2)cc1)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-3-oxo-N-[(4-pyrazol-1-ylphenyl)methyl]-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.70 (dd, J = 6.0 Hz, 5.3 Hz, 2H), 3.81-3.87 (m, 2H), 4.30 (d, J = 5.3 Hz, 2H), 4.70 (q, J = 8.8 Hz, 2H), 4.87 (s, 2H), 6.51 (dd, J = 2.2 Hz, 1.9 Hz, 1H), 7.10 (d, J = 9.0 Hz, 2H), 7.20 (d, J = 8.1 Hz, 1H), 7.26 (d, J = 9.0 Hz, 2H), 7.40 (dd, J = 8.1 Hz, 1.8 Hz, 1H), 7.40 (br. s., 1H), 7.67-7.72 (m, 3H), 7.74 (d, J = 2.0 Hz, 1H), 7.85 (d, J = 8.2 Hz, 1H), 8.32 (d, J = 2.4 Hz, 1H) ppm. |
| 268 | 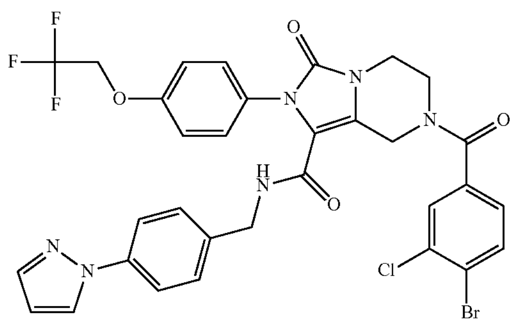 [SMILES: O=C(NCc1ccc(-n2cccn2)cc1)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-N-[(4-imidazol-1-ylphenyl)methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.70 (t, J = 5.6 Hz, 2H); 3.80-3.87 (m, 2H); 4.30 (d, J = 5.7 Hz, 2H); 4.71 (q, J = 8.8 Hz, 2H); 4.87 (s, 2H); 7.10 (d, J = 8.8 Hz, 3H); 7.21 (d, J = 8.1 Hz, 2H); 7.25 (d, J = 8.8 Hz, 2H), 7.40 (dd, J = 8.2 Hz, 2.0 Hz, 1H); 7.43 (br. s., 1H); 7.48 (d, J = 8.5 Hz, 2H); 7.59 (t, J = 1.3 Hz, 1H), 7.74 (d, J = 2.0 Hz, 1H), 7.85 (d, J = 8.2 Hz, 1H), 8.07-8.11 (m, 1H) ppm. |
| 269 | 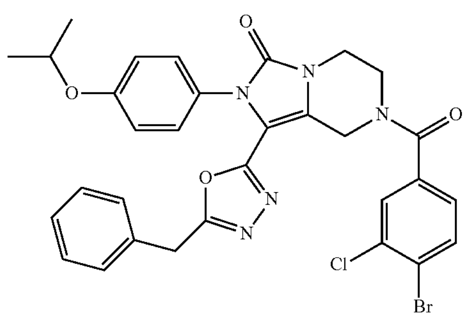 | 1-(5-benzoyl-1,3,4-oxadiazol-2-yl)-7-(4-bromo-3-chloro-benzoyl)-2-(4-isopropoxyphenyl)-6,8-dihdyro-5H-imidazo[1,5-a]pyrazin-3-one | 1H-NMR (DMSO, 600 MHz, 80° C.): 1.32 (d, J = 6.0 Hz, 6H); 3.73 (t, J = 5.6 Hz, 2H); 3.84-3.92 (m, 2H); 4.08 (s, 2H); 4.62 (hept., J = 6.0 Hz, 1H); 4.89 (s, 2H); 6.92 (d, J = 8.9 Hz, 2H); 7.09 (d, J = 7.1 Hz, 2H); 7.16 (d, J = 8.9 Hz, 2H); 7.22-7.33 (m, 3H); 7.41 (dd, J = 8.2 Hz, 2.0 Hz, 1H); 7.76 (d, J = 2.0 Hz, 1H); 7.86 (d, J = 8.2 Hz, 1H) ppm. |

TABLE A-continued

| Compound # | Structure | Name | NMR |
|---|---|---|---|
| 270 | 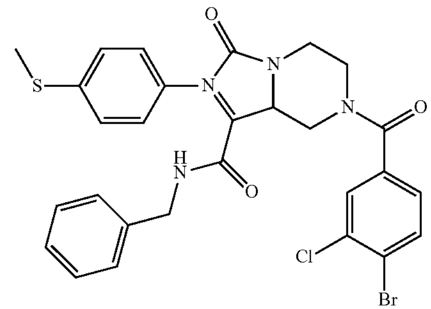 | N-benzyl-7-(4-bromo-3-chlorobenzoyl)-2-(4-methylsulfanoylphenyl)-3-oxo-6,8-dihydro-5H-imidazo[1,5-a]pyrazine-1-carboxamide | 1H NMR (400 MHz, Chloroform-d) δ 7.71 (d, J = 8.2 Hz, 1H), 7.62 (d, J = 1.9 Hz, 1H), 7.25-7.15 (m, 8H), 6.89 (s, 2H), 5.20-4.90 (m, 3H), 4.27 (s, 2H), 4.15-3.70 (m, 4H), 2.46 (s, 3H). |
| 271 | 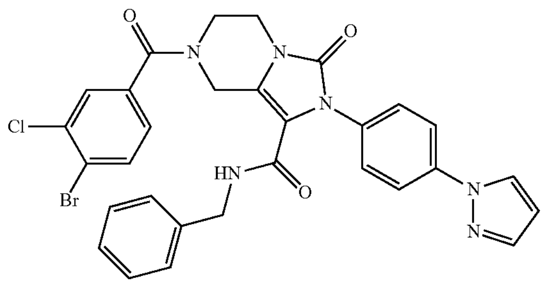 [SMILES: O=C(NCc1ccccc1)c1c2n(c(=O)n1-c1ccc(-n3cccn3)cc1)CCN(C(=O)c1ccc(Br)c(Cl)c1)C2] | N-benzyl-7-(4-bromo-3-chlorobenzoyl)-3-oxo-2-(4-pyrazol-1-ylphenyl)-6,8-dihydro-5H-imidazo[1,5-a]pyrazine-1-carboxamide | 1H NMR (300 MHz, Chloroform-d) δ 7.91 (d, J = 2.6 Hz, 1H), 7.83-7.71 (m, 4H), 7.65 (d, J = 2.0 Hz, 1H), 7.42 (d, J = 8.7 Hz, 2H), 7.26 (d, J = 2.0 Hz, 1H), 7.15 (t, J = 32 Hz, 3H), 6.94 (s, 2H), 6.59-6.50 (m, 1H), 5.08-4.90 (m, 3H), 4.29 (s, 2H), 4.06 (s, 2H), 3.87 (s, 2H). |
| 272 | 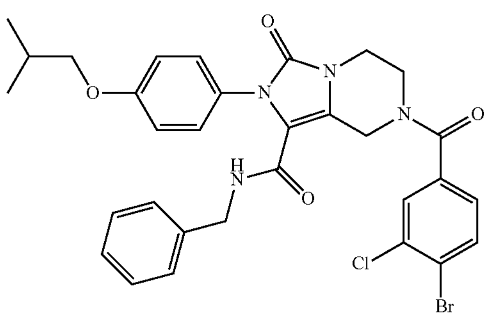 [SMILES: CC(C)COc1ccc(-n2c(C(=O)NCc3ccccc3)c3n(c2=O)CCN(C(=O)c2ccc(Br)c(Cl)c2)C3)cc1] | N-benzyl-7-(4-bromo-3-chlorobenzoyl)-2-(4-isobutoxyphenyl)-3-oxo-6,8-dihydro-5H-imidazo[1,5-a]pyrazine-1-carboxamide | 1H NMR (300 MHz, Chloroform-d) δ 7.72 (d, J = 8.1 Hz, 1H), 7.62 (d, J = 1.5 Hz, 1H), 7.26-7.19 (m, 6H), 6.98-6.81 (m, 4H), 5.17 (s, 1H), 5.04 (s, 2H), 4.25 (d, J = 4.8 Hz, 2H), 4.06 (s, 2H), 3.83 (s, 2H), 3.68 (d, J = 6.6 Hz, 2H), 2.13-2.04 (m, 1H), 1.05 (d, J = 6.6 Hz, 6H). |

TABLE A-continued

| Compound # | Structure | Name | NMR |
|---|---|---|---|
| 273 | 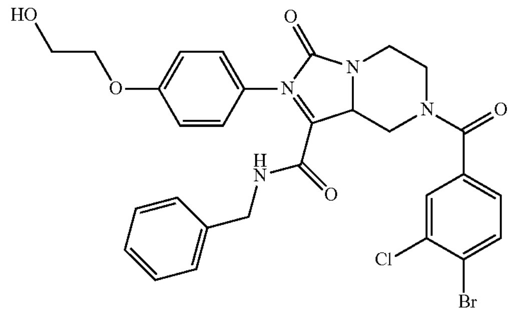 | N-benzyl-7-(4-bromo-3-chloro-benzoyl)-2-[4-(2-hydroxyethoxy)phenyl]-3-oxo-6,8-dihydro-5H-imidazo[1,5-a]pyrazine-1-carboxamide | 1H NMR (300 MHz, Methanol-d4) δ 7.84 (d, J = 8.2 Hz, 1H), 7.74 (s, 1H), 7.41-7.30 (m, 1H), 7.29-7.12 (m, 5H), 6.96 (d, J = 8.7 Hz, 4H), 5.02 (br, 2H), 4.41-3.69 (m, 10H). |
| 274 | 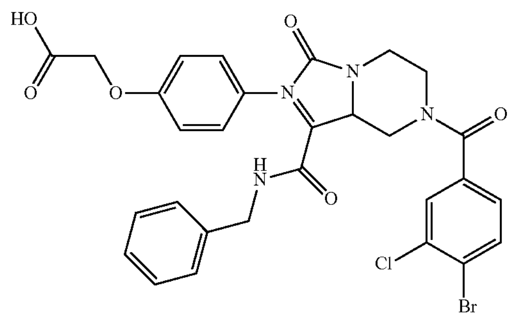 | 2-[4-[1-(benzoylcarbamoyl)-7-(4-bromo-3-chloro-benzoyl)-3-oxo-6,8-dihydro-5H-imidazo[1,5-a]pyrazin-2-yl]phenoxy]acetic acid | 1H NMR (300 MHz, DMSO-d6) δ 13.03 (s, 1H), 8.12-7.60 (m, 3H), 7.42 (d, J = 6.9 Hz, 1H), 7.33-7.21 (m, 3H), 7.19-7.07 (m, 3H), 7.01-6.81 (m, 3H), 4.89 (s, 1H), 4.70 (s, 3H), 4.30-3.85 (m, 3H), 3.66 (s, 3H). |
| 275 | 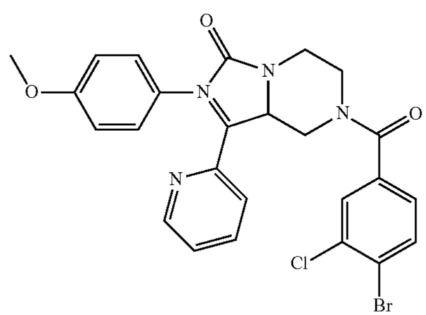 | 7-(4-bromo-3-chloro-benzoyl)-2-(4-methoxyphenyl)-1-(2-pyridyl)-6,8-dihydro-5H-imidazo[1,5-a]pyrazin-3-one | 1H NMR (400 MHz, Chloroform-d) δ 8.54 (s, 1H), 7.69 (d, J = 8.4 Hz, 1H), 7.59 (s, 1H), 7.39 (s, 1H), 7.23 (s, 1H), 7.21-7.15 (m, 2H), 7.04 (s, 1H), 6.95-6.89 (m, 2H), 6.54 (s, 1H), 5.07 (s, 2H), 4.20-3.75 (s, 7H). |

TABLE A-continued

| Compound # | Structure | Name | NMR |
|---|---|---|---|
| 276 | 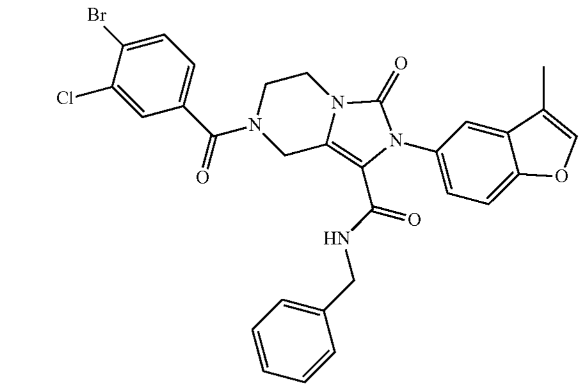 [SMILES: Cc1coc2ccc(-n3c(C(=O)NCc4ccccc4)c4n(c3=O)CCN(C(=O)c3ccc(Br)c(Cl)c3)C4)cc12] | N-benzyl-7-(4-bromo-3-chloro-benzoyl)-2-(3-methylbenzofuran-5-yl)-3-oxo-6,8-dihydro-5H-imidazo[1,5-a]pyrazine-1-carboxamide | 1H-NMR (DMSO, 600 MHz, 80° C.): 2.19 (s, 3H), 3.72 (dd, J = 5.6 Hz, 5.4 Hz, 2H), 3.82-3.90 (m, 2H), 4.23 (d, J = 5.8 Hz, 2H), 4.90 (s, 2H), 6.91-6.98 (m, 2H), 7.07 (br. s., 1H), 7.13-7.19 (m, 3H), 7.22 (dd, J = 8.6 H, 2.2 Hz, 1H), 7.41 (dd, J = 8.3 Hz 2.0 Hz, 1H), 7.51 (d, J = 2.2 Hz, 1H), 7.54 (d, J = 8.6 Hz, 1H), 7.76 (d, J = 2.0 Hz, 1H), 7.78 (d, J = 1.3 Hz, 1H), 7.86 (d, J = 8.2 Hz, 1H) ppm. |
| 277 | 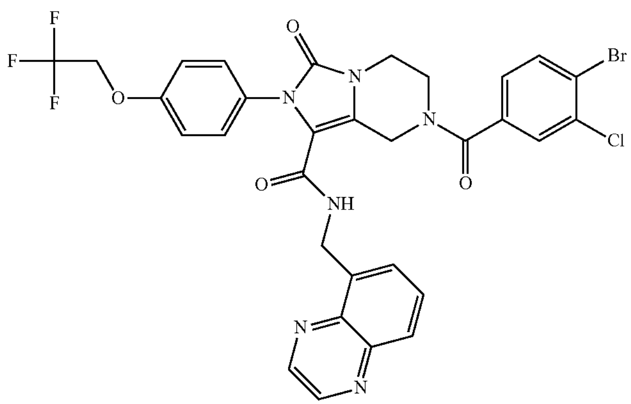 [SMILES: O=C(NCc1cccc2nccnc12)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-3-oxo-N-(quinoxalin-5-ylmethyl)-2-[4-(2,22,-trifluoroethoxy)phenyl]-6,8-dihydro-5H-imidazo[1,5-a]pyrazine-1-carboxamide | 1H-NMR (DMSO, 600 MHz, 80° C.): 3.68 (t, J = 5.6 Hz, 2H); 3.77-3.88 (m, 2H); 4.68 (q, J = 8.8 Hz, 2H); 4.84-4.91 (m, 4H); 6.97 (d, J = 9.0 Hz, 2H); 7.14 (br. s., 1H); 7.20 (d, J = 9.0 Hz, 2H); 7.38 (dd, J = 8.3 Hz, 1.9 Hz, 1H); 7.53 (d, J = 7.0 Hz, 1H); 7.70-7.76 (m, 2H); 7.84 (d, J = 8.2 Hz, 1H); 7.98 (d, J = 8.4 Hz, 1H); 8.84 (d, J = 1.5 Hz, 1H); 8.93 (d, J = 1.7 Hz, 1H) ppm. |
| 278 | 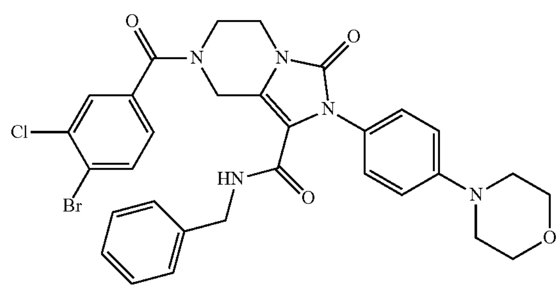 [SMILES: O=C(NCc1ccccc1)c1c2n(c(=O)n1-c1ccc(N3CCOCC3)cc1)CCN(C(=O)c1ccc(Br)c(Cl)c1)C2] | N-benzyl-7-(4-bromo-3-chloro-benzoyl)-2-(4-morpholinophenyl)-3-oxo-6,8-dihydro-5H-imidazo[1,5-a]pyrazine-1-carboxamide | 1H NMR (400 MHz, DMSO-d6) δ 7.90-7.60 (m, 2H), 7.43-7.42 (m, 1H), 7.40-6.96 (m, 9H), 4.91-4.70 (m, 2H), 4.30-3.95 (m, 3H), 3.76-3.68 (m, 7H), 3.20-3.14 (m, 4H). |

TABLE A-continued

| Compound # | Structure | Name | NMR |
|---|---|---|---|
| 279 | 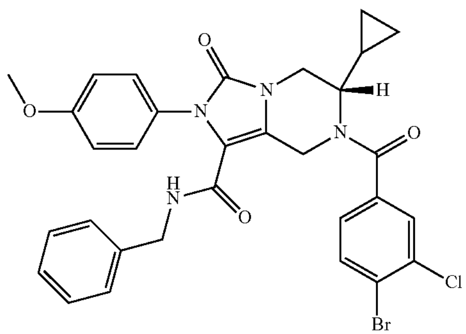 [SMILES: COc1ccc(-n2c(C(=O)NCc3ccccc3)c3n(c2=O)C[C@H](C2CC2)N(C(=O)c2ccc(Br)c(Cl)c2)C3)cc1] | rac-(6S)-N-benzyl-7-(4-bromo-3-chloro-benzoyl)-6-cyclopropyl-2-(4-methoxyphenyl)-3-oxo-6,8-dihydro-5H-imidazo[1,5-a]pyrazine-1-carboxamide | 1H NMR (400 MHz, Chloroform-d) δ 7.70 (d, J = 8.2 Hz, 1H), 7.57 (s, 1H), 7.27-7.17 (m, 6H), 6.93-6.85 (m, 4H), 5.35-5.10 (m, 2H), 4.85 (s, 1H), 4.30 (dd, J = 14.7, 5.5 Hz, 1H), 4.21 (dd, J = 14.7, 5.1 Hz, 1H), 4.11 (d, J = 12.6 Hz, 1H), 3.78-3.71 (m, 4H), 1.22 (s, 1H), 0.69 (s, 2H), 0.46 (s, 2H). |
| 280 | 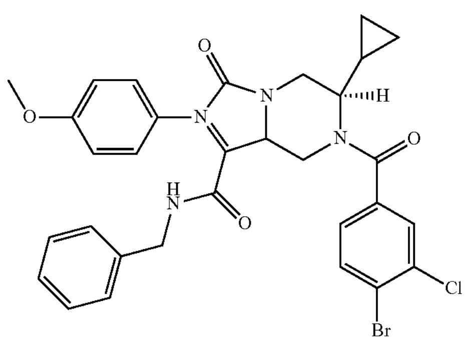 | rac-(6R)-N-benzyl-7-(4-bromo-3-chloro-benzoyl)-6-cyclopropyl-2-(4-methoxyphenyl)-3-oxo-6,8-dihydro-5H-imidazo[1,5-a]pyrazine-1-carboxamide | 1H NMR (400 MHz, Chloroform-d) δ 7.70 (d, J = 8.1 Hz, 1H), 7.60-7.55 (m, 1H), 7.27-7.18 (m, 6H), 6.93-6.86 (m, 4H), 5.35-5.10 (m, 2H), 4.85 (s, 1H), 4.30-4.21 (m, 2H), 4.11 (d, J = 12.6 Hz, 1H), 3.78 (s, 3H), 3.73 (dd, J = 12.7, 4.8 Hz, 1H), 1.22 (s, 1H), 0.72-0.65 (m, 2H), 0.46 (s, 2H). |

TABLE A-continued

| Compound # | Structure | Name | NMR |
|---|---|---|---|
| 281 | 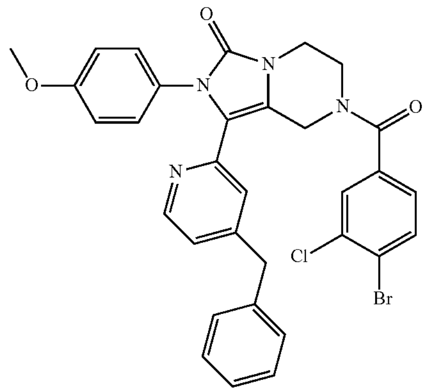 [SMILES: COc1ccc(-n2c(-c3cc(Cc4ccccc4)ccn3)c3n(c2=O)CCN(C(=O)c2ccc(Br)c(Cl)c2)C3)cc1] | 1-(4-benzoyl-2-pyridyl)-7-(4-bromo-3-chloro-benzoyl)-2-(4-methoxyphenyl)-6,8-dihydro-5H-imidazo[1,5-a]pyrazin-3-one | 1H NMR (400 MHz, Chloroform-d) δ 8.37 (s, 1H), 7.73-7.61 (m, 1H), 7.58 (d, J = 1.2 Hz, 1H), 7.26-7.18 (m, 4H), 7.11-7.02 (m, 2H), 6.90-6.79 (m, 5H), 6.34 (s, 1H), 5.03 (s, 2H), 4.11-3.75 (m, 8H), 3.65 (s, 2H). |
| 282 | 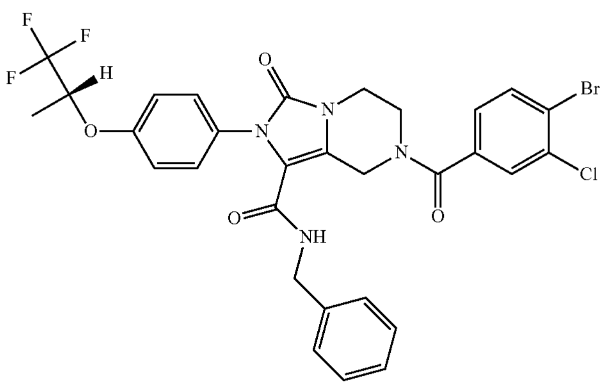 [SMILES: C[C@@H](Oc1ccc(-n2c(C(=O)NCc3ccccc3)c3n(c2=O)CCN(C(=O)c2ccc(Br)c(Cl)c2)C3)cc1)C(F)(F)F] | N-benzyl-7-(4-bromo-3-chloro-benozyl)-3-oxo-2-[4-[rac-(1R)-2,2,2-trifluoro-1-methyl-ethoxy]phenyl]-6,8-dihydro-5H-imidazo[1,5-a]pyrazine-1-carboxamide | 1H NMR (300 MHz, Chloroform-d) δ 7.73 (d, J = 8.4 Hz, 1H), 7.62 (s, 1H), 7.26-7.18 (m, 6H), 6.95 (d, J = 8.7 Hz, 4H), 5.05 (s, 3H), 4.52-4.48 (m, 1H), 4.27 (d, J = 3.9 Hz, 2H), 4.03 (s, 2H), 3.83 (s, 2H), 1.50 (d, J = 6.3 Hz, 3H). |

TABLE A-continued

| Compound # | Structure | Name | NMR |
|---|---|---|---|
| 283 | 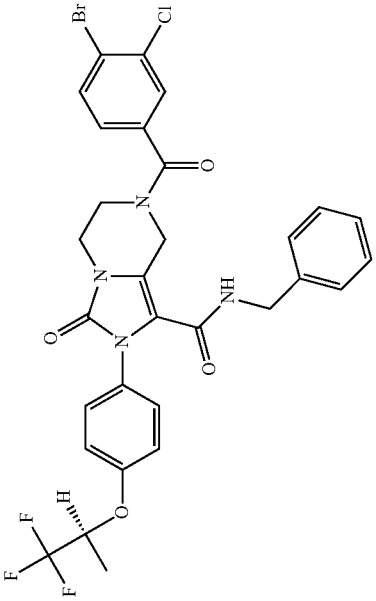 | N-benzyl-7-(4-bromo-3-chloro-benozyl)-3-oxo-2-[4-[rac-(1S)-2,2,2-trifluoro-1-methyl-ethoxy]phenyl]-6,8-dihydro-5H-imidazo[1,5-a]pyrazine-1-carboxamide | 1H NMR (300 MHz, Chloroform-d) δ 7.73 (d, J = 8.4 Hz, 1H), 7.62 (s, 1H), 7.26-7.18 (m, 6H), 6.95 (d, J = 8.7 Hz, 4H), 5.05 (s, 3H), 4.52-4.48 (m, 1H), 4.27 (d, J = 3.9 Hz, 2H), 4.03 (s, 2H), 3.83 (s, 2H), 1.50 (d, J = 6.3 Hz, 3H). |
| 284 | 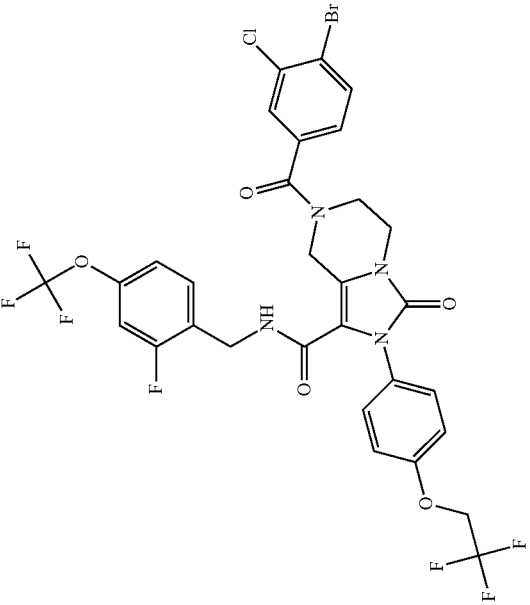 | 7-(4-bromo-3-chloro-benzoyl)-N-[[2-fluoro-4-(trifluoromethoxy)phenyl]methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.67-3.73 (m, 2H), 3.84 (br. s. 2H), 4.31 (d, J = 4.9 Hz, 2H), 4.72 (q, J = 8.6 Hz, 2H), 4.86 (s, 2H), 7.08 (d, J = 8.1 Hz, 3H), 7.15-7.26 (m, 4H), 7.34-7.43 (m, 2H), 7.75 (s, 1H), 7.86 (d, J = 8.7 Hz, 1H) ppm. |

TABLE A-continued

| Compound # | Structure | Name | NMR |
|---|---|---|---|
| 285 | 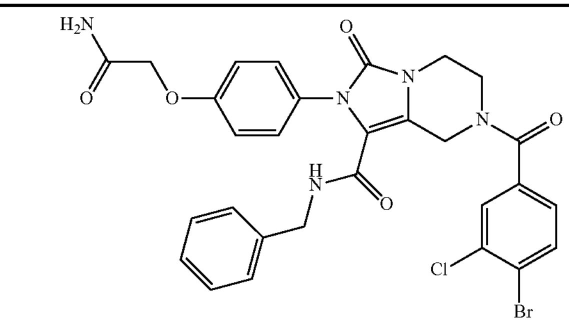 | 2-[4-(2-amino-2-oxo-ethoxy)phenyl]-N-benzyl-7-(4-bromo-3-chloro-benzoyl)-3-oxo-6,8-dihydro-5H-imidazo[1,5-a]pyrazine-1-carboxamide | 1H NMR (400 MHz, DMSO-d6, 80° C.): 3.68 (t, J = 5.6 Hz, 2H), 3.83 (t, J = 5.6 Hz, 2H), 4.25 (d, J = 5.6 Hz, 2H), 4.44 (s, 2H), 4.85 (s, 2H), 6.99 (d, J = 8.8 Hz, 2H), 7.05 (d, J = 7.1 Hz, 2H), 7.11-7.34 (m, 8H), 7.39 (dd, J = 8.3 Hz, 2.2 Hz, 1H), 7.74 (d, J = 1.8 Hz, 1H), 7.84 (d, J = 8.1 Hz, 1H). |
| 286 | 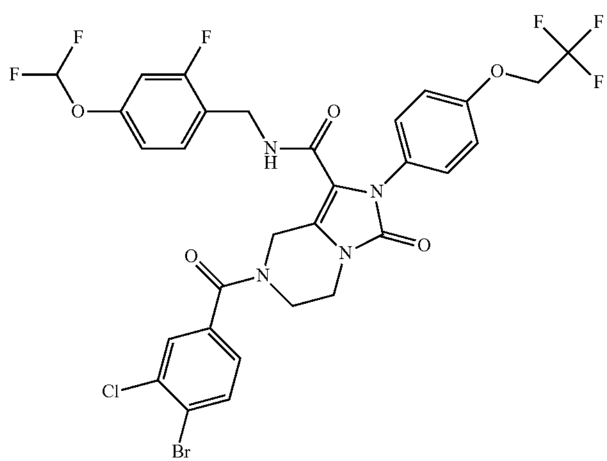 [SMILES: O=C(NCc1ccc(OC(F)F)cc1F)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-N-[[4-(difluoromethoxy)-2-fluoro-phenyl]methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.69 (t, J = 5.2 Hz, 2H); 3.83 (br. s., 2H); 4.27 (d, J = 5.2 Hz, 2H); 4.71 (q, J = 8.8 Hz, 2H); 4.85 (s, 2H); 6.92 (d, J = 8.6 Hz, 1H); 6.98 (d, J = 10.7 Hz, 1H); 7.08 (d, J = 8.6 Hz, 2H); 7.11-7.17 (m, 1H); 7.14 (t, J = 73.8 Hz, 1H); 7.23 (d, J = 8.6 Hz, 2H); 7.32 (br. s., 1H); 7.39 (d, J = 8.3 Hz, 1H); 7.74 (s, 1H); 7.85 (d, J = 8.3 Hz, 1H) ppm. |

TABLE A-continued

| Compound # | Structure | Name | NMR |
|---|---|---|---|
| 287 | 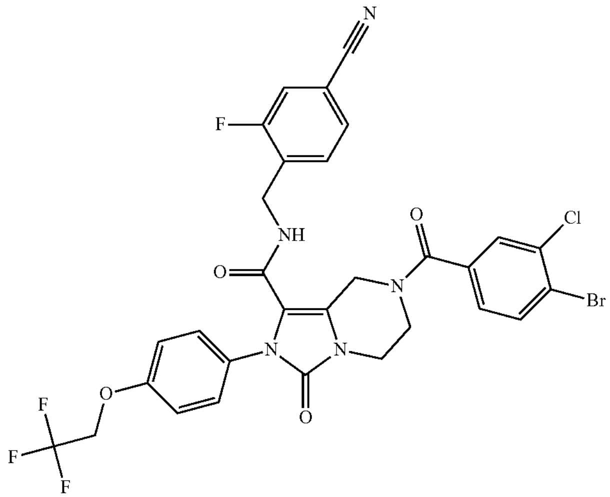 [SMILES: N#Cc1ccc(CNC(=O)c2c3n(c(=O)n2-c2ccc(OCC(F)(F)F)cc2)CCN(C(=O)c2ccc(Br)c(Cl)c2)C3)c(F)c1] | 7-(4-bromo-3-chloro-benzoyl)-N-[(4-cyano-2-fluoro-phenyl)methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.65-3.72 (m, 2H); 3.83 (br. s, 2H); 4.35 (d, J = 4.7 Hz, 2H); 4.73 (q, J = 8.6 Hz, 2H); 4.84 (s, 2H); 7.09 (d, J = 7.5 Hz, 2H); 7.23 (d, J = 7.5 Hz, 2H); 7.25-7.31 (m, 1H); 7.39 (d, J = 8.2 Hz, 1H); 7.47 (br. s, 1H); 7.53 (d, J = 7.7 Hz, 1H); 7.64 (d, J = 9.8 Hz, 1H); 7.73 (s, 1H); 7.85 (d, J = 8.2 Hz, 1H) ppm. |
| 288 | 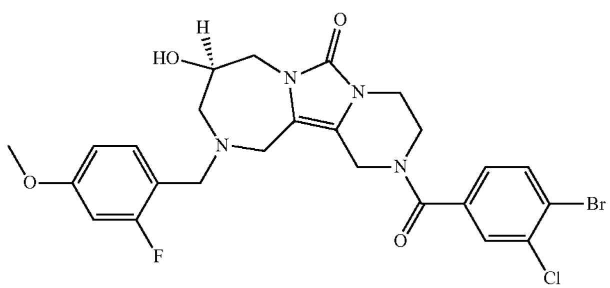 [SMILES: COc1ccc(CN2Cc3c4n(c(=O)n3C[C@H](O)C2)CCN(C(=O)c2ccc(Br)c(Cl)c2)C4)c(F)c1] | rac-(11R)-4-(4-bromo-3-chloro-benzoyl)-13-[(2-fluoro-4-methoxy-phenyl)methyl]-11-hydroxy-4,7,9,13-tetrazatricyclo[7.5.0.0 2,7]tetradec-1-ene-8,14-dione | 1H NMR (300 MHz, Chloroform-d) δ 7.73 (d, J = 8.2 Hz, 1H), 7.60 (d, J = 1.9 Hz, 1H), 7.23 (d, J = 8.0 Hz, 2H), 6.68 (dd, J = 15.5, 10.5 Hz, 2H), 4.91 (d, J = 13.7 Hz, 3H), 4.34 (d, J = 14.6 Hz, 1H), 4.14-3.66 (m, 10H), 3.54-3.23 (m, 2H). |
| 289 | 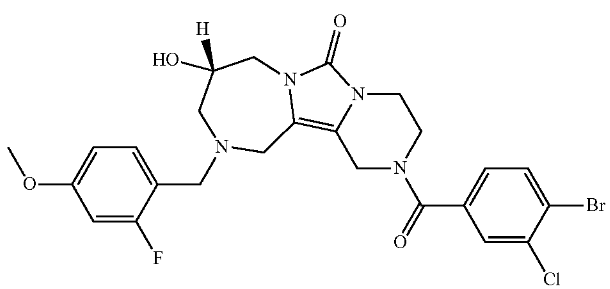 [SMILES: COc1ccc(CN2Cc3c4n(c(=O)n3C[C@@H](O)C2)CCN(C(=O)c2ccc(Br)c(Cl)c2)C4)c(F)c1] | rac-(11S)-4-(4-bromo-3-chloro-benzoyl)-13-[(2-fluoro-4-methoxy-phenyl)methyl]-11-hydroxy-4,7,9,13-tetrazatricyclo[7.5.0.0 2,7]tetradec-1-ene-8,14-dione | 1H NMR (300 MHz, Chloroform-d) δ 7.73 (d, J = 8.2 Hz, 1H), 7.60 (d, J = 2.0 Hz, 1H), 7.23 (dd, J = 8.2, 2.0 Hz, 2H), 6.75-6.60 (m, 2H), 4.91 (d, J = 14.2 Hz, 3H), 4.34 (d, J = 14.5 Hz, 1H), 4.11-3.66 (m, 10H), 3.48 (dd, J = 15.1, 5.2 Hz, 1H), 3.31 (dd, J = 15.1, 7.2 Hz, 1H). |

| Compound # | Structure | Name | NMR |
|---|---|---|---|
| 290 | 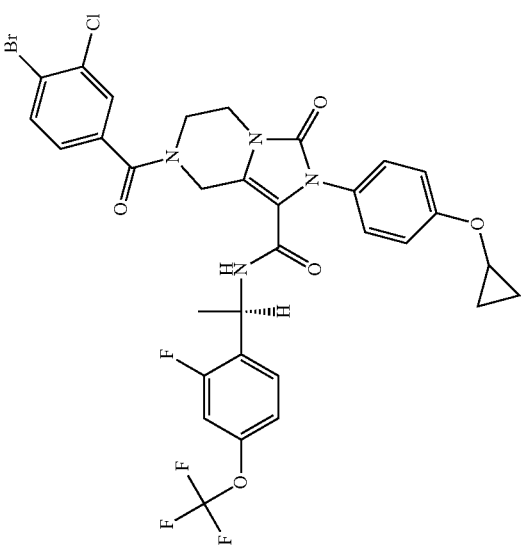 | 7-(4-bromo-3-chloro-benzoyl)-2-[4-(cyclopropoxy)phenyl]-3-oxo-N-[rac-(1R)-1-[2-fluoro-4-(trifluoromethoxy)phenyl]ethyl]-6,8-dihydro-5H-imidazo[1,5-a]pyrazine-1-carboxamide | 1H NMR (300 MHz, Chloroform-d) δ 7.71 (d, J = 8.4 Hz, 1H), 7.59 (s, 1H), 7.29-7.10 (m, 5H), 7.01-6.80 (m, 3H), 5.37 (d, J = 8.1 Hz, 1H), 5.21-4.85 (m, 3H), 4.15-3.70 (m, 5H), 1.17 (d, J = 6.9 Hz, 3H), 0.83 (d, J = 10.8 Hz, 4H). |
| 291 | 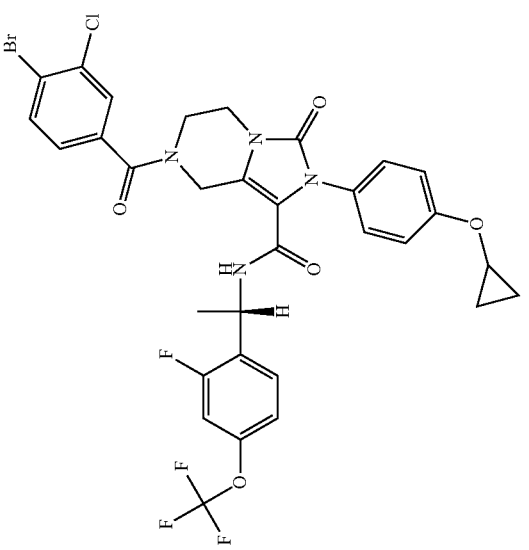 | 7-(4-bromo-3-chloro-benzoyl)-2-[4-(cyclopropoxy)phenyl]-3-oxo-N-[rac-(1S)-1-[2-fluoro-4-(trifluoromethoxy)phenyl]ethyl]-6,8-dihydro-5H-imidazo[1,5-a]pyrazine-1-carboxamide | 1H NMR (300 MHz, Chloroform-d) δ 7.71 (d, J = 8.4 Hz, 1H), 7.59 (s, 1H), 7.30 (s, 2H), 7.25-7.12 (m, 3H), 7.02-6.81 (m, 3H), 5.37 (d, J = 8.1 Hz, 1H), 5.21-4.85 (m, 3H), 4.27-3.71 (m, 5H), 1.16 (d, J = 6.9 Hz, 3H), 0.91-0.70 (m, 4H). |

TABLE A-continued
| Compound # | Structure | Name | NMR |
|---|---|---|---|
| 292 | 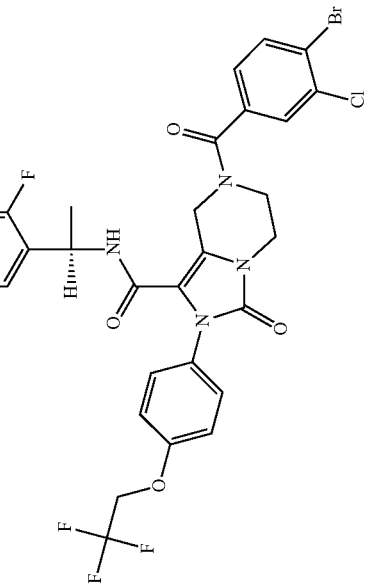 | 7-(4-bromo-3-chloro-benzoyl)-3-oxo-N-[rac-(1R)-1-[2-fluoro-4-(trifluoromethoxy)phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.73 (d, J = 7.5 Hz, 1H), 7.59 (s, 1H), 7.38-7.29 (m, 2H), 7.25-7.18 (m, 1H), 7.10-6.97 (m, 3H), 6.96-6.80 (m, 2H), 5.31 (d, J = 7.8 Hz, 1H), 5.19-4.88 (m, 3H), 4.49-4.32 (m, 2H), 4.19-3.89 (m, 2H), 3.82 (s, 2H), 1.21 (d, J = 6.9 Hz, 3H). |

TABLE A-continued

| Compound # | Structure | Name | NMR |
|---|---|---|---|
| 293 | 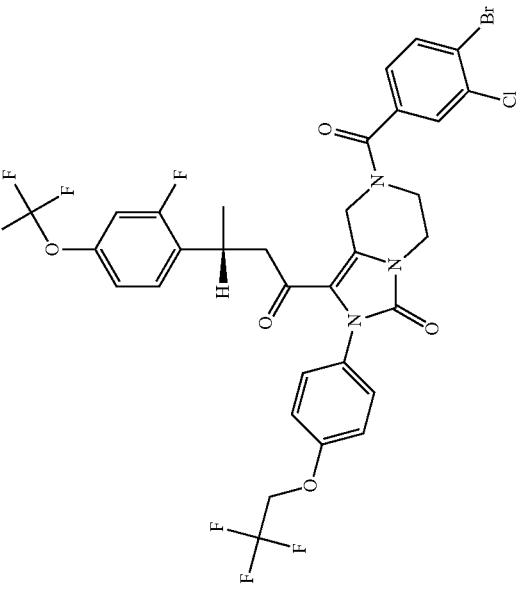 | 7-(4-bromo-3-chloro-benzoyl)-3-oxo-N-[rac-(1S)-1-[2-[4-(trifluoromethoxy)phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.73 (d, J = 7.5 Hz, 1H), 7.59 (s, 1H), 7.38-7.29 (m, 2H), 7.25-7.18 (m, 1H), 7.10-6.97 (m, 3H), 6.96-6.80 (m, 2H), 5.31 (d, J = 7.8 Hz, 1H), 5.19-4.88 (m, 3H), 4.49-4.32 (m, 2H), 4.19-3.89 (m, 2H), 3.82 (s, 2H), 1.21 (d, J = 6.9 Hz, 3H). |
| 294 | 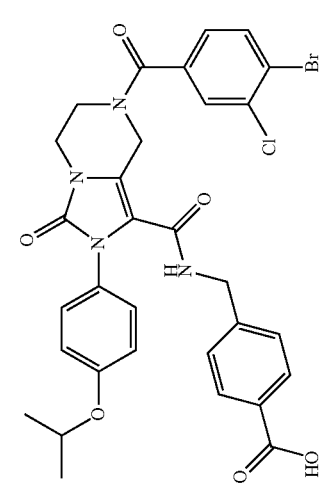 | 4-[[[[7-(4-bromo-3-chloro-benzoyl)-2-(4-isopropoxyphenyl)-3-oxo-6,8-dihydro-5H-imidazo[1,5-a]pyrazine-1-carbonyl]amino]methyl]benzoic acid | 1H-NMR (DMSO, 600 MHz, 80° C.): 1.29 (d, J = 6.0 Hz, 6H); 3.69 (t, J = 5.3 Hz, 2H); 3.80-3.89 (m, 2H); 4.32 (d, J = 5.7 Hz, 2H); 4.57 (hept, J = 6.0 Hz, 1H); 4.87 (s, 2H); 6.92 (d, J = 8.4 Hz, 2H); 7.09-7.17 (m, 3H); 7.19 (d, J = 8.5 Hz, 2H), 7.40 (d, J = 8.2 Hz, 1H); 7.74 (s, 1H); 7.80-7.87 (m, 3H); 12.34 (br. s., 1H) ppm. |

TABLE A-continued

| Compound # | Structure | Name | NMR |
|---|---|---|---|
| 295 | 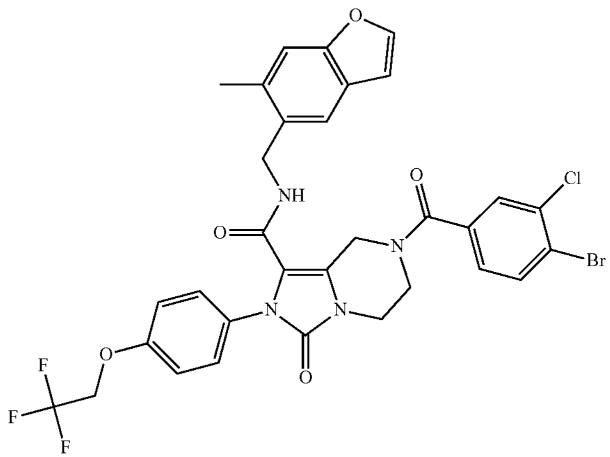 [SMILES: Cc1cc2occc2cc1CNC(=O)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-N-[(6-methylbenzofuran-5-yl)methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 2.25 (s, 3H); 3.69 (t, J = 5.4 Hz, 2H); 3.79-3.87 (m, 2H); 4.32 (d, J = 5.2 Hz, 2H); 4.65 (q, J = 8.8 Hz, 2H); 4.87 (s, 2H); 6.80 (s, 1H); 7.03 (br. s., 1H); 7.06 (d, J = 8.5 Hz, 2H); 7.21-7.28 (m, 3H); 7.31 (s, 1H); 7.39 (d, J = 8.3 Hz, 1H); 7.73 (s, 1H); 7.80 (s, 1H); 7.83 (d, J = 8.2 Hz, 1H) ppm. |
| 296 | 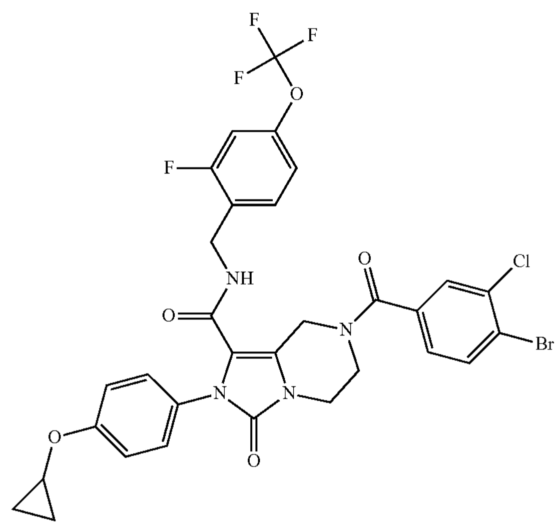 [SMILES: O=C(NCc1ccc(OC(F)(F)F)cc1F)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-N-[[2-fluoro-4-(trifluoromethoxy)phenyl]methyl]-3-oxo-6,8-dihydro-5H-imidazo[1,5-a]pyrazine-1-carboxamide | 1H NMR (400 MHz, DMSO-d6, 80° C.): 0.67-0.69 (m, 2H), 0.78-0.81 (m, 2H), 3.68 (t, J = 5.5 Hz, 2H), 3.82-3.86 (m, 3H), 4.29 (d, J = 5.5 Hz, 2H), 4.85 (s, 2H), 7.04-7.09 (m, 3H), 7.17-7.28 (m, 5H), 7.39 (dd, J = 8.3, 0.9 Hz, 1H), 7.74 (s, 1H), 7.85 (d, J = 8.3 Hz, 1H). |

TABLE A-continued

| Compound # | Structure | Name | NMR |
|---|---|---|---|
| 297 | 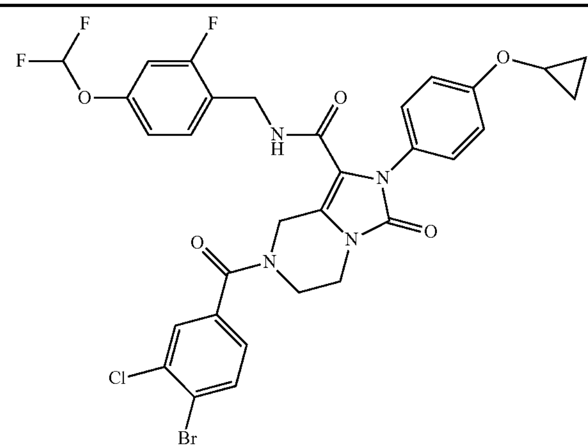 | 7-(4-bromo-3-chloro-benzoyl)-2-[4-(cyclopropoxy)phenyl]-N-[[4-(difluoromethoxy)-2-fluorophenyl]methyl]-3-oxo-6,8-dihydro-5H-imidazo[1,5-a]pyrazine-1-carboxamide | 1H NMR (400 MHz, DMSO-d6, 80° C.): 0.66-0.69 (m, 2H), 0.78-0.81 (m, 2H), 3.68 (t, J = 5.8 Hz, 2H), 3.81-3.85 (m, 3H), 4.26 (d, J = 5.5 Hz, 2H), 4.85 (s, 2H), 6.91 (dd, J = 8.4, 1.6 Hz, 1H), 6.97-7.01 (m, 1H), 7.05-7.07 (m, 2H), 7.13 (t, J = 8.5 Hz, 1H), 7.15-7.20 (m, 4H), 7.39 (dd, J = 8.1, 1.8 Hz, 1H), 7.74 (d, J = 1.8 Hz, 1H), 7.85 (d, J = 8.3 Hz, 1H). |
| 298 | 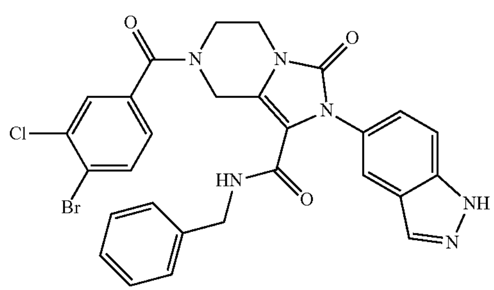 [SMILES: O=C(NCc1ccccc1)c1c2n(c(=O)n1-c1ccc3[nH]ncc3c1)CCN(C(=O)c1ccc(Br)c(Cl)c1)C2] | N-benzyl-7-(4-bromo-3-chlorobenzoyl)-2-(1H-indazol-5-yl)-3-oxo-6,8-dihydro-5H-imidazo[1,5-a]pyrazine-1-carboxamide | 1H NMR (400 MHz, DMSO-d6, 80° C.): 3.71 (t, J = 5.5 Hz, 2H), 3.86 (br s, 2H), 4.21 (d, J = 5.7 Hz, 2H), 4.89 (s, 2H), 6.92 (d, J = 6.8 Hz, 2H), 7.07-7.20 (m, 4H), 7.23 (dd, J = 8.8 Hz, 2H), 7.41 (dd, J = 8.2 Hz, 1.9 Hz, 1H), 7.55 (d, J = 8.7 Hz, 1H), 7.69 (d, J = 1.7 Hz, 1H), 7.76 (d, J = 1.9 Hz, 1H), 7.86 (d, J = 8.3 Hz, 1H), 8.08 (s, 1H), 13.0 (br s, 1H). |

| Compound # | Structure | Name | NMR |
|---|---|---|---|
| 299 | 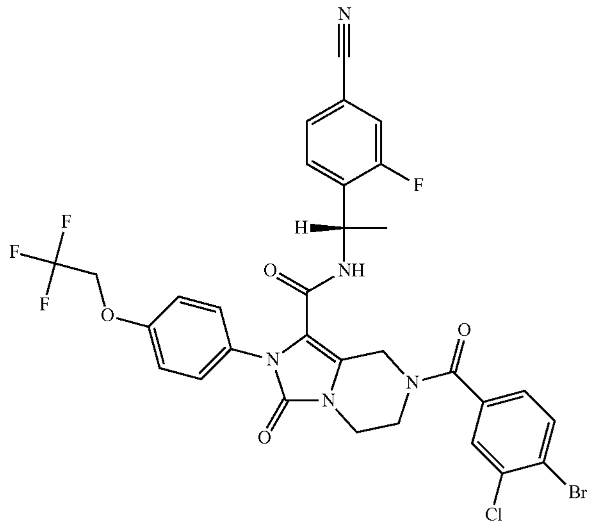 [SMILES: C[C@H](NC(=O)c1c2n(c(=O)n1-c1ccc(OCC(F)(F)F)cc1)CCN(C(=O)c1ccc(Br)c(Cl)c1)C2)c1ccc(C#N)cc1F] | 7-(4-bromo-3-chloro-benzoyl)-3-oxo-N-[rac-(1R)-1-(4-cyano-2-fluorophenyl)-1-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.71 (d, J = 8.1 Hz, 1H), 7.60 (d, J = 1.9 Hz, 1H), 7.38 (d, J = 8.6 Hz, 3H), 7.27-7.20 (m, 2H), 7.13 (d, J = 8.5 Hz, 3H), 5.31 (d, J = 7.6 Hz, 1H), 5.18 (m, 1H), .5.10-4.83 (m, 2H), 4.46 (q, J = 8.0 Hz, 2H), 4.18-3.79 (m, 4H), 1.18 (d, J = 6.9 Hz, 3H). |
| 300 | 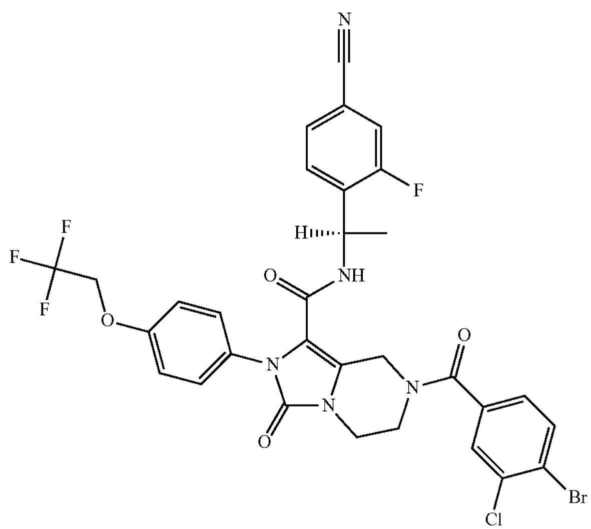 [SMILES: C[C@@H](NC(=O)c1c2n(c(=O)n1-c1ccc(OCC(F)(F)F)cc1)CCN(C(=O)c1ccc(Br)c(Cl)c1)C2)c1ccc(C#N)cc1F] | 7-(4-bromo-3-chloro-benzoyl)-3-oxo-N-[rac-(1S)-1-(4-cyano-2-fluorophenyl)-1-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.71 (d, J = 8.2 Hz, 1H), 7.60 (d, J = 2.0 Hz, 1H), 7.42-7.34 (m, 3H), 7.27-7.20 (m, 2H), 7.17-7.08 (m, 3H), 5.30 (d, J = 7.6 Hz, 1H), 5.22-4.86 (m, 3H), 4.46 (q, J = 8.0 Hz, 2H), 4.17-3.79 (m, 4H), 1.18 (d, J = 7.0 Hz, 3H). |

TABLE A-continued

| Compound # | Structure | Name | NMR |
|---|---|---|---|
| 301 | 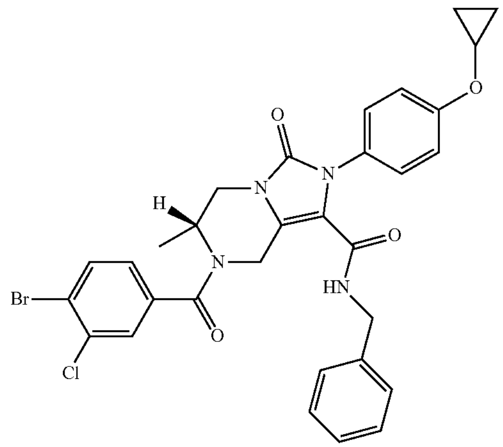 [SMILES: C[C@@H]1Cn2c(c(C(=O)NCc3ccccc3)n(-c3ccc(OC4CC4)cc3)c2=O)CN1C(=O)c1ccc(Br)c(Cl)c1] | rac-(6R)-N-benzyl-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | 1H NMR (300 MHz, Chloroform-d) δ 7.74 (d, J = 8.2 Hz, 1H), 7.60 (d, J = 2.0 Hz, 1H), 7.28-7.19 (m, 6H), 7.12-7.02 (m, 2H), 6.94 (s, 2H), 5.61-5.04 (m, 3H), 4.66 (d, J = 19.1 Hz, 1H), 4.40-4.16 (m, 2H), 3.89 (d, J = 12.8 Hz, 1H), 3.79-3.64 (m, 2H), 1.42 (d, J = 7.0 Hz, 3H), 0.79 (m, 4H). |
| 302 | 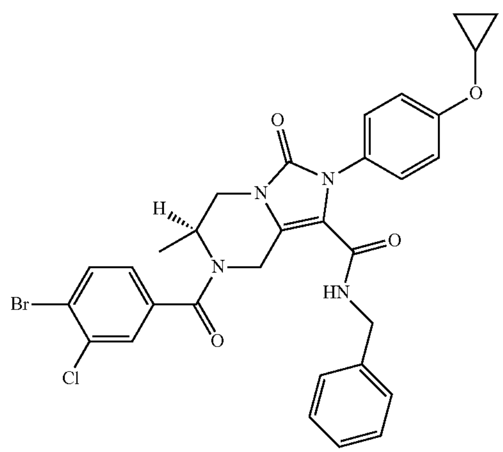 [SMILES: C[C@H]1Cn2c(c(C(=O)NCc3ccccc3)n(-c3ccc(OC4CC4)cc3)c2=O)CN1C(=O)c1ccc(Br)c(Cl)c1] | rac-(6S)-N-benzyl-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | 1H NMR (300 MHz, Chloroform-d) δ 7.74 (d, J = 8.2 Hz, 1H), 7.60 (d, J = 2.0 Hz, 1H), 7.28-7.19 (m, 6H), 7.12-7.02 (m, 2H), 6.94 (s, 2H), 5.61-5.04 (m, 3H), 4.66 (d, J = 19.1 Hz, 1H), 4.40-4.16 (m, 2H), 3.89 (d, J = 12.8 Hz, 1H), 3.79-3.64 (m, 2H), 1.42 (d, J = 7.0 Hz, 3H), 0.79 (m, 4H). |

TABLE A-continued

| Compound # | Name | Structure | NMR |
|---|---|---|---|
| 303 | N-[[4-(2-amino-2-oxo-ethoxy)-2-fluoro-phenyl]methyl]-7-(4-bromo-3-chloro-benzoyl)-3-oxo-2-[4-(2,2,2-trifluoroethoxy)phenyl]-6,8-dihydro-5H-imidazo[1,5-a]pyrazine-1-carboxamide | 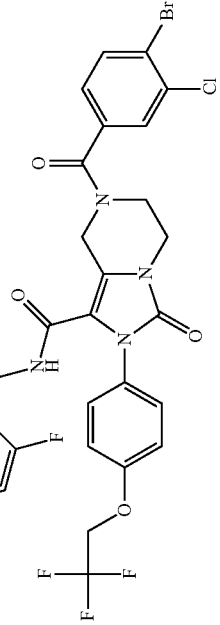 | 1H-NMR (DMSO, 600 MHz, 80° C.): 3.67-3.71 (m, 2H), 3.83 (br. s, 2H), 4.22 (d, J = 5.1 Hz, 2H), 4.38 (s, 2H), 4.72 (q, J = 8.6 Hz, 2H), 4.85 (s, 2H), 6.68-6.78 (m, 2H), 7.03 (t, J = 8.3 Hz, 1H), 7.06-7.28 (m, 7H), 7.40 (dd, J = 8.2 Hz, 1.0 Hz, 1H), 7.74 (s, 1H), 7.86 (d, J = 8.1 Hz, 1H) ppm. |
| 304 | 7-(4-bromo-3-chloro-benzoyl)-3-oxo-N-[[2-(1,2,4-triazol-1-yl)phenyl]methyl]-2-[4-(2,2,2-trifluoroethoxy)phenyl]-6,8-dihydro-5H-imidazo[1,5-a]pyrazine-1-carboxamide | 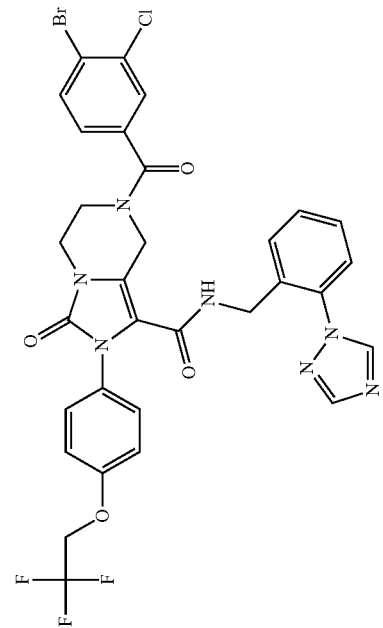 | 1H-NMR (DMSO, 600 MHz, 80° C.): 3.66-3.72 (m, 2H), 3.83 (br. s, 2H), 4.18 (d, J = 5.6 Hz, 2H), 4.72 (q, J = 8.7 Hz, 2H), 4.86 (s, 2H), 7.09 (d, J = 8.3 Hz, 2H), 7.17 (br. s., 1H), 7.24 (d, J = 8.3 Hz, 2H), 7.26-7.29 (m, 1H), 7.37-7.47 (m, 4H), 7.73 (s, 1H), 7.84 (d, J = 8.2 Hz, 1H), 8.10 (s, 1H), 8.73 (s, 1H) ppm. |

TABLE A-continued

| Compound # | Structure | Name | NMR |
|---|---|---|---|
| 305 | 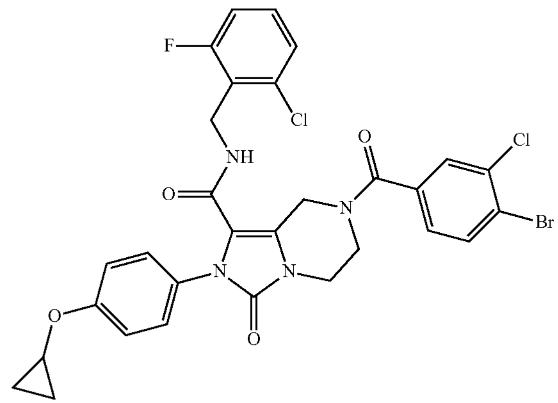 [SMILES: O=C(NCc1c(F)cccc1Cl)c1c2n(c(=O)n1-c1ccc(OC3CC3)cc1)CCN(C(=O)c1ccc(Br)c(Cl)c1)C2] | 7-(4-bromo-3-chloro-benzoyl)-N-[(2-chloro-6-fluoro-phenyl)methyl]-2-[4-(cyclopropoxy)phenyl]-3-oxo-6,8-dihydro-5H-imidazo[1,5-a]pyrazine-1-carboxamide | 1H NMR (400 MHz, DMSO-d6, 80° C.): 0.65-0.71 (m, 2H), 0.78-0.83 (m, 2H), 3.67 (t, J = 5.6 Hz, 2H), 3.78-3.87 (m, 3H), 4.39 (d, J = 5.0 Hz, 2H), 4.82 (s, 2H), 6.81 (t, J = 4.7 Hz, 1H), 7.00-7.06 (m, 2H), 7.12 (t, J = 9.0 Hz, 1H), 7.15-7.20 (m, 2H), 7.24 (d, J = 8.2 Hz, 1H), 7.32-7.40 (m, 2H), 7.73 (d, J = 1.9 Hz, 1H), 7.84 (d, J = 8.2 Hz, 1H). |
| 306 | 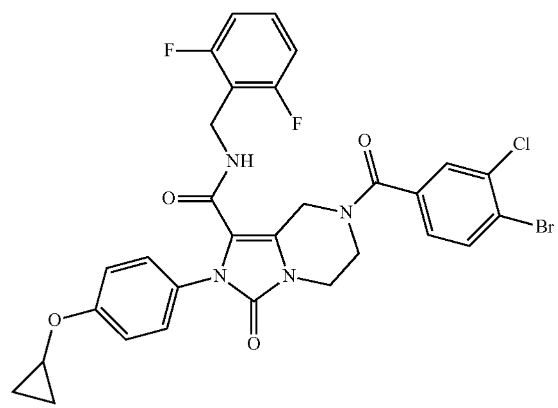 [SMILES: O=C(NCc1c(F)cccc1F)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-N-[(2,6-difluorophenyl)methyl]-3-oxo-6,8-dihydro-5H-imidazo[1,5-a]pyrazine-1-carboxamide | 1H NMR (400 MHz, DMSO-d6, 80° C.): 0.68-0.70 (m, 2H), 0.80-0.82 (m, 1H), 3.67 (t, J = 5.5 Hz, 2H), 3.82-34.86 (m, 3H), 4.31 (d, J = 5.1 Hz, 2H), 4.81 (s, 2H), 6.95-7.03 (m, 5H), 7.15 (d, J = 8.8 Hz, 2H), 7.32-7.39 (m, 2H), 7.73 (d, J = 1.4 Hz, 1H), 7.84 (d, J = 8.3 Hz, 1H). |

TABLE A-continued

| Compound # | Structure | Name | NMR |
|---|---|---|---|
| 307 | 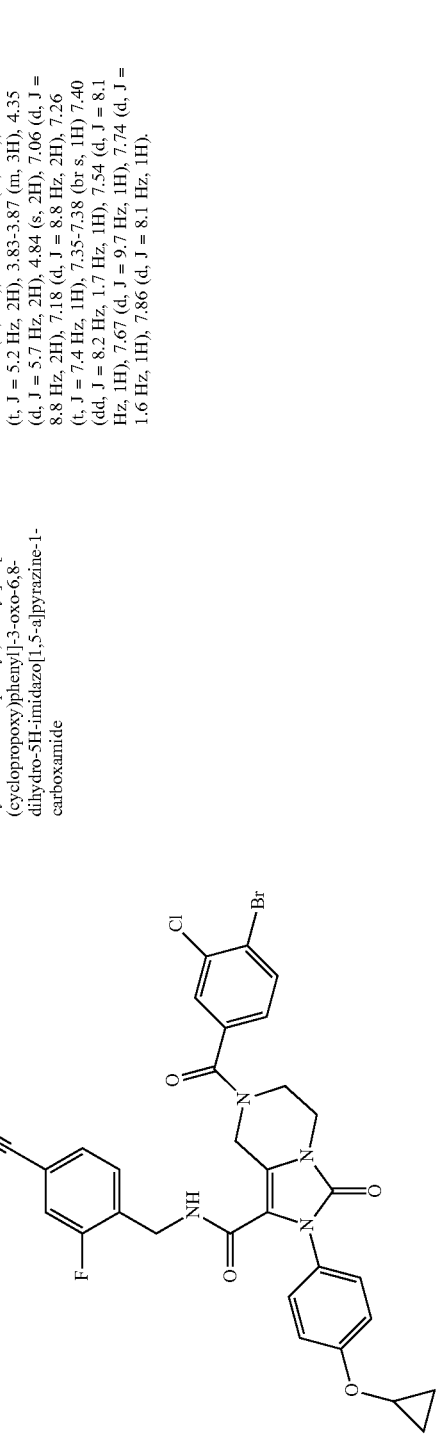 | 7-(4-bromo-3-chloro-benzoyl-N-[(4-cyano-2-fluoro-phenyl)methyl]-2-[4-(cyclopropoxy)phenyl]-3-oxo-6,8-dihydro-5H-imidazo[1,5-a]pyrazine-1-carboxamide | 1H NMR (400 MHz, DMSO-d6, 80° C.): 0.68-0.70 (m, 2H), 0.80-0.82 (m, 2H), 3.69 (t, J = 5.2 Hz, 2H), 3.83-3.87 (m, 3H), 4.35 (d, J = 5.7 Hz, 2H), 4.84 (s, 2H), 7.06 (d, J = 8.8 Hz, 2H), 7.18 (d, J = 8.8 Hz, 2H), 7.26 (t, J = 7.4 Hz, 1H), 7.35-7.38 (br s, 1H) 7.40 (dd, J = 8.2 Hz, 1.7 Hz, 1H), 7.54 (d, J = 8.1 Hz, 1H), 7.67 (d, J = 9.7 Hz, 1H), 7.74 (d, J = 1.6 Hz, 1H), 7.86 (d, J = 8.1 Hz, 1H). |
| 308 | 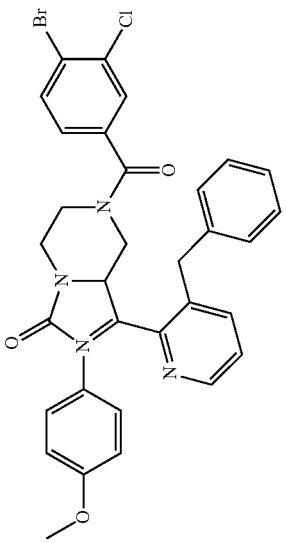 | 1-(3-benzyl-2-pyridyl)-7-(4-bromo-3-chloro-benzoyl)-2-(4-methoxyphenyl)-6,8-dihydro-5H-imidazo[1,5-a]pyrazin-3-one | 1H NMR (400 MHz, Chloroform-d) δ 8.56 (s, 1H), 7.69 (d, J = 8.0 Hz, 1H), 7.53 (d, J = 2.0 Hz, 1H), 7.43 (s, 1H), 7.16 (ddd, J = 12.9, 10.6, 8.4 Hz, 7H), 6.91-6.67 (m, 4H), 4.57 (m, 1H), 4.15-3.34 (m, 10H). |

| Compound # | Structure | Name | NMR |
|---|---|---|---|
| 309 | 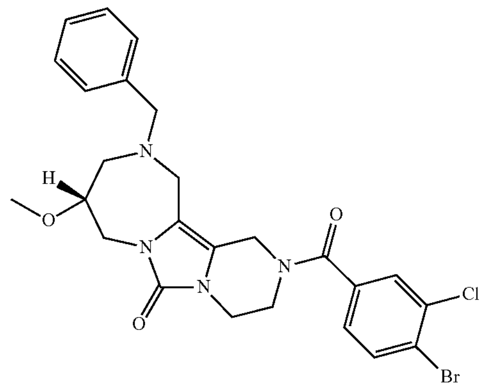 [SMILES: CO[C@@H]1CN(Cc2ccccc2)Cc2c3n(c(=O)n2C1)CCN(C(=O)c1ccc(Br)c(Cl)c1)C3] | rac-(11R)-13-benzyl-4-(4-bromo-3-chloro-benzoyl)-11-methoxy-4,7,9,13-tetrazatricyclo[7.5.0.0^2,7]tetradec-1-ene-8,14-dione | 1H NMR (300 MHz, Chloroform-d) δ 7.74 (d, J = 8.2 Hz, 1H), 7.60 (dd, J = 2.0 Hz, 1H), 7.42-7.29 (m, 5H), 7.23 (dd, J = 8.2, 2.0 Hz, 1H), 5.06 (d, J = 14.5 Hz, 1H), 4.93 (s, 2H), 4.23 (d, J = 14.6 Hz, 1H), 4.00 (dd, J = 14.3, 5.6 Hz, 2H), 3.91-3.72 (m, 4H), 3.61-3.50 (m, 1H), 3.37 (d, J = 5.0 Hz, 2H), 3.32 (s, 3H). |
| 310 | 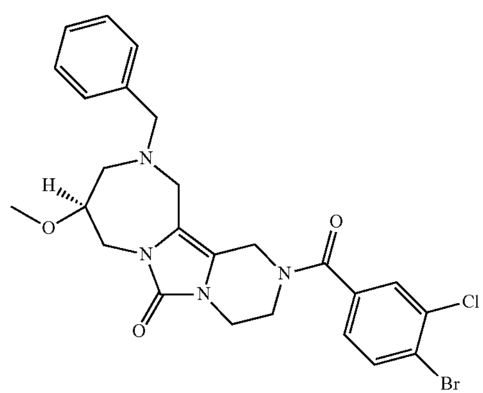 [SMILES: CO[C@H]1CN(Cc2ccccc2)Cc2c3n(c(=O)n2C1)CCN(C(=O)c1ccc(Br)c(Cl)c1)C3] | rac-(11S)-13-benzyl-4-(4-bromo-3-chloro-benzoyl)-11-methoxy-4,7,9,13-tetrazatricyclo[7.5.0.0^2,7]tetradec-1-ene-8,14-dione | 1H NMR (300 MHz, Chloroform-d) δ 7.74 (d, J = 8.2 Hz, 1H), 7.60 (dd, J = 2.0 Hz, 1H), 7.42-7.29 (m, 5H), 7.23 (dd, J = 8.2, 2.0 Hz, 1H), 5.06 (d, J = 14.5 Hz, 1H), 4.93 (s, 2H), 4.23 (d, J = 14.6 Hz, 1H), 4.00 (dd, J = 14.3, 5.6 Hz, 2H), 3.91-3.72 (m, 4H), 3.61-3.50 (m, 1H), 3.37 (d, J = 5.0 Hz, 2H), 3.32 (s, 3H). |

TABLE A-continued

| Compound # | Structure | Name | NMR |
|---|---|---|---|
| 311 | 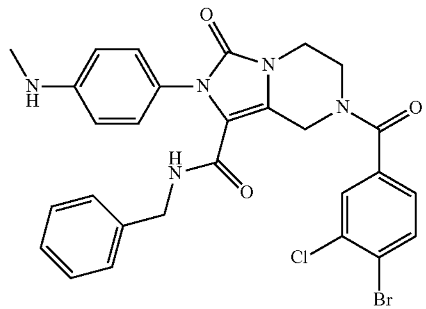 [SMILES: CNc1ccc(-n2c(C(=O)NCc3ccccc3)c3n(c2=O)CCN(C(=O)c2ccc(Br)c(Cl)c2)C3)cc1] | N-benzyl-7-(4-bromo-3-chlorobenzoyl)-2-[4-(methylamino)phenyl]-3-oxo-6,8-dihydro-5H-imidazo[1,5-a]pyrazine-1-carboxamide | 1H NMR (400 MHz, DMSO-d6) δ 7.88 (t, J = 4.0 Hz, 1H), 7.79 (d, J = 1.2 Hz, 1H), 7.41 (d, J = 6.8 Hz, 1H), 7.32-7.21 (m, 4H), 7.10-6.90 (m, 4H), 6.54 (d, J = 8.8 Hz, 2H), 5.92 (s, 1H), 4.90-4.75 (m, 2H), 4.28-4.16 (m, 2H), 3.97-3.83 (m, 1H), 3.86-3.65 (m, 3H), 2.74 (s, 3H). |
| 312 | 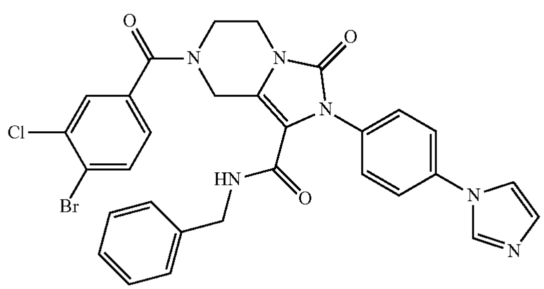 [SMILES: O=C(NCc1ccccc1)c1c2n(c(=O)n1-c1ccc(-n3ccnc3)cc1)CCN(C(=O)c1ccc(Br)c(Cl)c1)C2] | N-benzyl-7-(4-bromo-3-chlorobenzoyl)-2-[4-(imidazol-1-yl)phenyl]-3-oxo-6,8-dihydro-5H-imidazo[1,5-a]pyrazine-1-carboxamide | 1H NMR (300 MHz, DMSO-d6) δ 8.27 (t, J = 1.2 Hz, 1H), 7.88 (d, J = 8.2 Hz, 1H), 7.82-7.74 (m, 2H), 7.70 (d, J = 8.7 Hz, 2H), 7.39 (dd, J = 17.9, 8.3 Hz, 3H), 7.30-7.20 (m, 4H), 7.15-6.90 (m, 3H), 5.05-4.70 (m, 2H), 4.42-4.10 (m, 2H), 4.00-3.60 (m, 4H). |

| Compound # | Structure | Name | NMR |
|---|---|---|---|
| 313 | 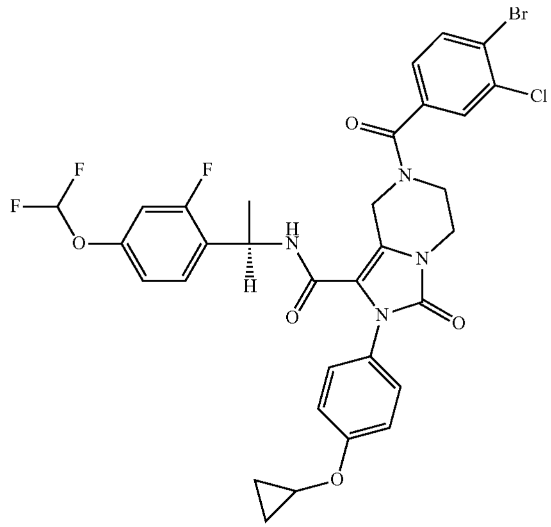 [SMILES: C[C@@H](NC(=O)c1c2n(c(=O)n1-c1ccc(OC3CC3)cc1)CCN(C(=O)c1ccc(Br)c(Cl)c1)C2)c1ccc(OC(F)F)cc1F] | 7-(4-bromo-3-chloro-benzoyl)-2-[4-(cyclopropoxy)phenyl]-3-oxo-N-[rac-(1R)-1-[4-(difluoromethoxy)-2-fluoro-phenyl]ethyl]-6,8-dihydro-5H-imidazo[1,5-a]pyrazine-1-carboxamide | 1H NMR (400 MHz, Chloroform-d) δ 7.70 (d, J = 8.0 Hz, 1H), 7.59 (d, J = 1.6 Hz, 1H), 7.30-7.29 (m, 1H), 7.26-7.25 (m, 1H), 7.23-7.20 (m, 1H), 7.20-7.10 (m, 2H), 6.98-6.88 (m, 1H), 6.83-6.71 (m, 2H), 6.48 (m, 1H), 5.33 (d, J = 8.0 Hz, 1H), 5.15-4.88 (m, 3H), 4.21-3.60 (m, 5H), 1.15 (d, J = 6.8 Hz, 3H), 0.89-0.71 (m, 4H). |
| 314 | 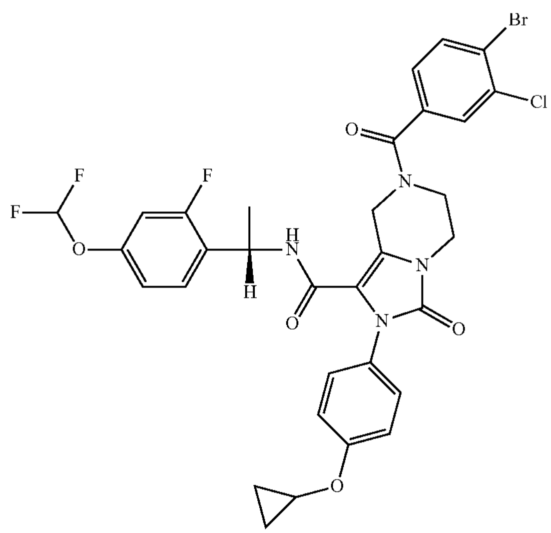 [SMILES: C[C@H](NC(=O)c1c2n(c(=O)n1-c1ccc(OC3CC3)cc1)CCN(C(=O)c1ccc(Br)c(Cl)c1)C2)c1ccc(OC(F)F)cc1F] | 7-(4-bromo-3-chloro-benzoyl)-2-[4-(cyclopropoxy)phenyl]-3-oxo-N-[rac-(1S)-1-[4-(difluoromethoxy)-2-fluoro-phenyl]ethyl]-6,8-dihydro-5H-imidazo[1,5-a]pyrazine-1-carboxamide | 1H NMR (400 MHz, Chloroform-d) δ 7.70 (d, J = 8.0 Hz, 1H), 7.59 (d, J = 1.6 Hz, 1H), 7.30-7.29 (m, 1H), 7.26-7.25 (m, 1H), 7.23-7.20 (m, 1H), 7.20-7.10 (m, 2H), 6.98-6.88 (m, 1H), 6.83-6.71 (m, 2H), 6.48 (m, 1H), 5.33 (d, J = 8.0 Hz, 1H), 5.15-4.88 (m, 3H), 4.21-3.60 (m, 5H), 1.15 (d, J = 6.8 Hz, 3H), 0.89-0.71 (m, 4H). |

| Compound # | Structure | Name | NMR |
|---|---|---|---|
| 315 | 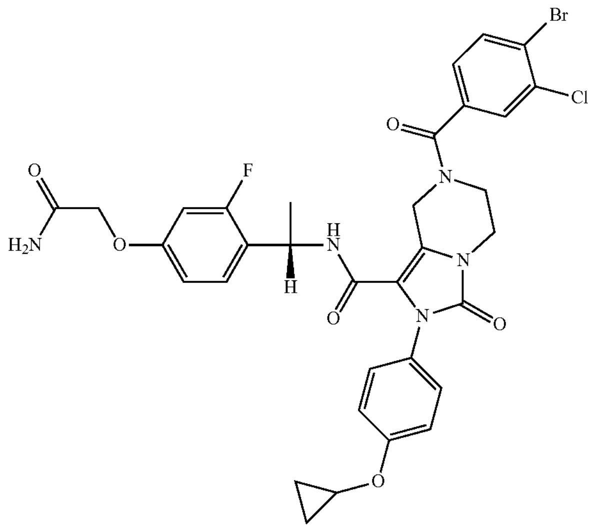 [SMILES: C[C@H](NC(=O)c1c2n(c(=O)n1-c1ccc(OC3CC3)cc1)CCN(C(=O)c1ccc(Br)c(Cl)c1)C2)c1ccc(OCC(N)=O)cc1F] | 7-(4-bromo-3-chloro-benzoyl)-2-[4-(cyclopropoxy)phenyl]-3-oxo-N-[rac-(1R)-1-[4-(2-amino-2-oxo-ethoxy)-2-fluoro-phenyl]ethyl]-6,8-dihydro-5H-imidazo[1,5-a]pyrazine-1-carboxamide | 1H NMR (400 MHz, Chloroform-d) δ 7.72 (d, J = 8.0 Hz, 1H), 7.61 (s, 1H), 7.29 (s, 1H), 7.32-7.19 (m, 1H), 7.28-7.24 (m, 1H), 7.16-7.14 (m, 2H), 6.91 (t, J = 8.6 Hz, 1H), 6.64-6.47 (m, 3H), 5.67 (s, 1H), 5.33 (d, J = 7.6 Hz, 1H), 5.04 (s, 3H), 4.47 (s, 2H), 3.99 (s, 2H), 3.90-3.73 (m, 3H), 1.18 (d, J = 6.9 Hz, 3H), 0.92-0.75 (m, 4H). |
| 316 | 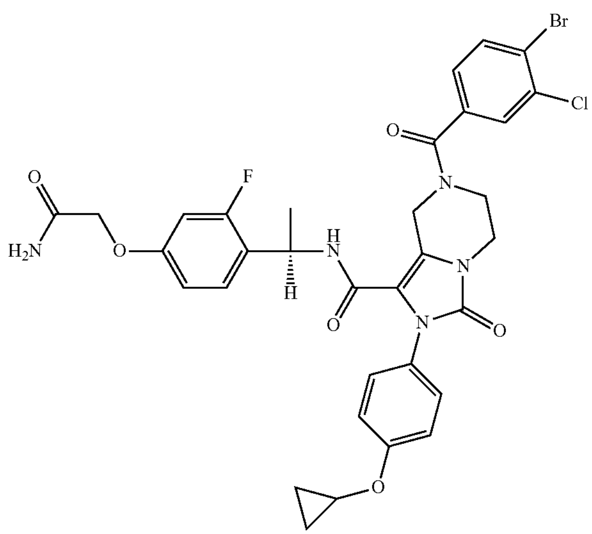 [SMILES: C[C@@H](NC(=O)c1c2n(c(=O)n1-c1ccc(OC3CC3)cc1)CCN(C(=O)c1ccc(Br)c(Cl)c1)C2)c1ccc(OCC(N)=O)cc1F] | 7-(4-bromo-3-chloro-benzoyl)-2-[4-(cyclopropoxy)phenyl]-3-oxo-N-[rac-(1S)-1-[4-(2-amino-2-oxo-ethoxy)-2-fluoro-phenyl]ethyl]-6,8-dihydro-5H-imidazo[1,5-a]pyrazine-1-carboxamide | 1H NMR (400 MHz, Chloroform-d) δ 7.72 (d, J = 8.0 Hz, 1H), 7.61 (s, 1H), 7.29 (s, 1H), 7.32-7.19 (m, 3H), 7.28-7.24 (m, 1H), 7.16-7.14 (m, 2H), 6.91 (t, J = 8.6 Hz, 1H), 6.64-6.53 (m, 2H ), 6.47 (s, 1H), 5.67 (s, 1H), 5.33 (d, J = 7.6 Hz, 1H), 5.04 (s, 3H), 4.47 (s, 2H), 3.99 (s, 2H), 3.90-3.73 (m, 3H), 1.18 (d, J = 6.9 Hz, 3H), 0.92-0.75 (m, 4H). |

TABLE A-continued
| Compound # | Structure | Name | NMR |
|---|---|---|---|
| 317 | 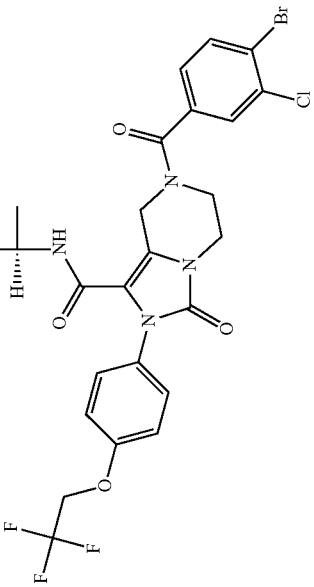 | 7-(4-bromo-3-chloro-benzoyl)-3-oxo-N-[rac-(1R)-1-[4-(difluoromethoxy)-2-fluoro-phenyl]ethyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.70 (d, J = 8.4 Hz, 1H), 7.59 (d, J = 1.6 Hz, 1H), 7.38-7.30 (m, 2H), 7.25-7.19 (m, 1H), 7.10-7.00 (m, 2H), 7.00-6.90 (m, 1H), 6.82-6.70 (m, 2H), 6.48 (m, 1H), 5.28 (d, J = 8.0 Hz, 1H), 5.18-4.90 (m, 3H), 4.49-4.30 (m, 2H), 4.13-3.60 (m, 4H), 1.19 (d, J = 6.8 Hz, 3H). |

TABLE A-continued
| Compound # | Structure | Name | NMR |
|---|---|---|---|
| 318 | 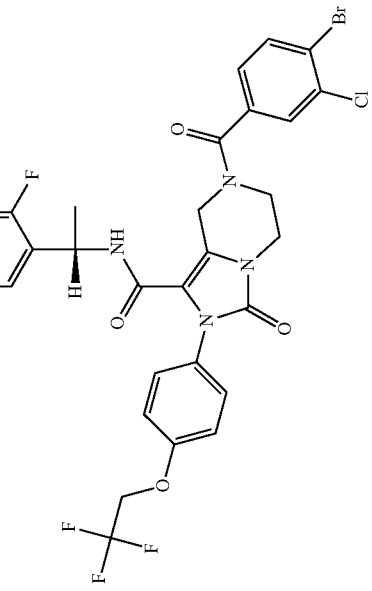 | 7-(4-bromo-3-chloro-benzoyl)-3-oxo-N-[rac-(1S)-1-[4-(difluoromethoxy)-2-fluoro-phenyl]ethyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.70 (d, J = 8.4 Hz, 1H), 7.59 (d, J = 1.6 Hz, 1H), 7.38-7.30 (m, 2H), 7.25-7.19 (m, 1H), 7.10-7.00 (m, 2H), 7.00-6.90 (m, 1H), 6.82-6.70 (m, 2H), 6.48 (m, 1H), 5.28 (d, J = 8.0 Hz, 1H), 5.18-4.90 (m, 3H), 4.49-4.30 (m, 2H), 3.13-3.60 (m, 4H), 1.19 (d, J = 6.8 Hz, 3H). |

TABLE A-continued
| Compound # | Structure | Name | NMR |
|---|---|---|---|
| 319 | 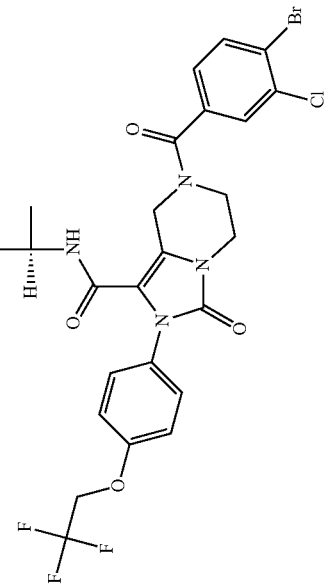 | 7-(4-bromo-3-chloro-benzoyl)-3-oxo-N-[rac-(1R)-1-[4-(2-amino-2-oxo-ethoxy)-2-fluoro-phenyl]ethyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.71 (d, J = 8.0 Hz, 1H), 7.59 (s, 1H), 7.38-7.29 (m, 2H), 7.22 (d, J = 8.2 Hz, 1H), 7.04 (d, J = 8.8 Hz, 2H), 6.92 (t, J = 8.2 Hz, 1H), 6.57-6.39 (m, 3H), 5.92 (s, 1H), 5.30 (d, J = 8.0 Hz, 1H), 5.04 (d, J = 7.2 Hz, 3H), 4.50-4.25 (m, 4H), 4.03 (s, 2H), 3.87 (s, 2H), 1.22 (d, J = 6.8 Hz, 3H). |

TABLE A-continued

| Compound # | Structure | Name | NMR |
|---|---|---|---|
| 320 | 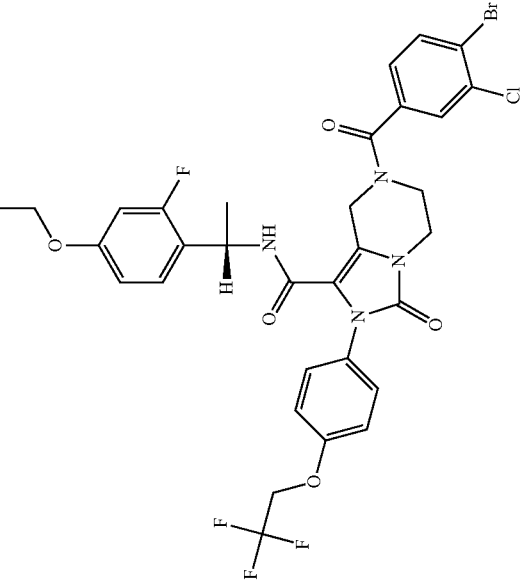 | 7-(4-bromo-3-chloro-benzoyl)-3-oxo-N-[rac-(1S)-1-[4-(2-amino-2-oxo-ethoxy)-2-fluoro-phenyl]ethyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.71 (d, J = 80 Hz, 1H), 7.59 (s, 1H), 7.38-7.29 (m, 2H), 7.22 (d, J = 8.2 Hz, 1H), 7.04 (d, J = 8.8 Hz, 2H), 6.92 (t, J = 8.2 Hz, 1H), 6.57-6.39 (m, 3H), 5.92 (s, 1H), 5.30 (d, J = 8.0 Hz, 1H), 5.04 (d, J = 7.2 Hz, 3H), 4.50-4.25 (m, 4H), 4.03 (s, 2H), 3.87 (s, 2H), 1.22 (d, J = 6.8 Hz, 3H). |
| 321 | 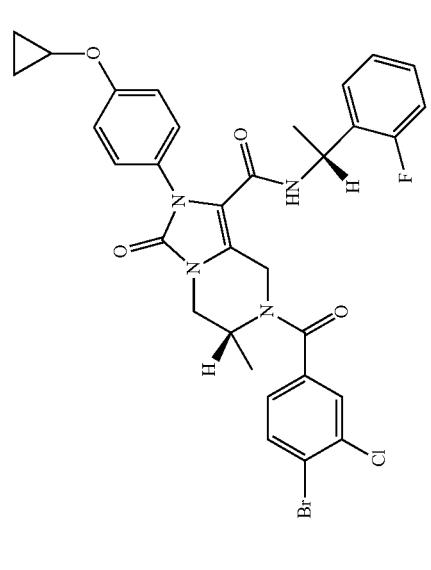 | (6RS)-7-(4-bromo-3-chloro-benzoyl)-2-[4-(cyclopropoxy)phenyl]-N-[(1R)-1-(2-fluorophenyl)ethyl]-6-methyl-3-oxo-6,8-dihydro-5H-imidazo[1,5-a]pyrazine-1-carboxamide | 1H NMR (400 MHz, Chloroform-d) δ 7.67 (d, J = 8.2 Hz, 1H), 7.55 (d, J = 2.0 Hz, 1H), 7.31-7.26 (m, 2H), 7.23-7.11 (m, 4H), 7.01 (td, J = 7.5, 1.2 Hz, 1H), 6.96-6.86 (m, 2H), 5.55-4.97 (m, 4H), 4.59 (m, 1H), 3.86 (d, J = 12.6 Hz, 1H), 3.80-3.63 (m, 2H), 1.39 (d, J = 7.0 Hz, 3H), 1.19 (d, J = 6.9 Hz, 3H), 0.89-0.73 (m, 4H). |

TABLE A-continued

| Compound # | Structure | Name | NMR |
|---|---|---|---|
| 322 | 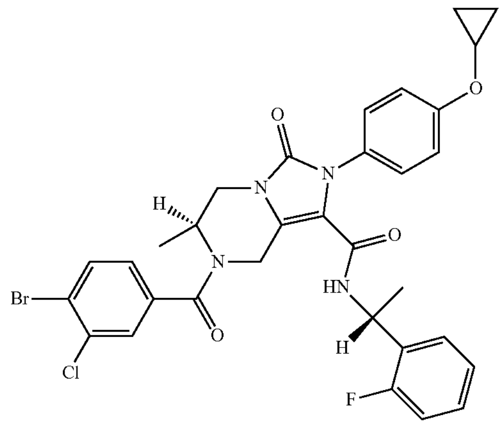 [SMILES: C[C@@H](NC(=O)c1c2n(c(=O)n1-c1ccc(OC3CC3)cc1)C[C@H](C)N(C(=O)c1ccc(Br)c(Cl)c1)C2)c1ccccc1F] | (6SR)-7-(4-bromo-3-chloro-benzoyl)-2-[4-(cyclopropoxy)phenyl]-N-[(1R)-1-(2-fluorophenyl)ethyl]-6-methyl-3-oxo-6,8-dihydro-5H-imidazo[1,5-a]pyrazine-1-carboxamide | 1H NMR (400 MHz, Chloroform-d) δ 7.67 (d, J = 8.2 Hz, 1H), 7.55 (d, J = 2.0 Hz, 1H), 7.31-7.26 (m, 2H), 7.23-7.11 (m, 4H), 7.01 (td, J = 7.5, 1.2 Hz, 1H), 6.96-6.86 (m, 2H), 5.55-4.97 (m, 4H), 4.59 (m, 1H), 3.86 (d, J = 12.6 Hz, 1H), 3.80-3.63 (m, 2H), 1.39 (d, J = 7.0 Hz, 3H), 1.19 (d, J = 6.9 Hz, 3H), 0.89-0.73 (m, 4H). |
| 323 | 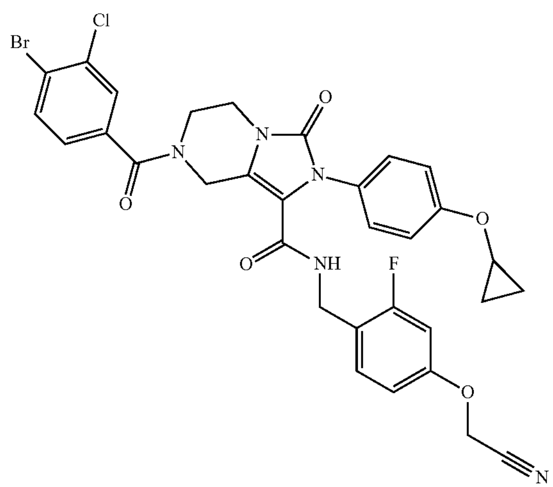 [SMILES: N#CCOc1ccc(CNC(=O)c2c3n(c(=O)n2-c2ccc(OC4CC4)cc2)CCN(C(=O)c2ccc(Br)c(Cl)c2)C3)c(F)c1] | 7-(4-bromo-3-chloro-benzoyl)-N-[[4-(cyanomethoxy)-2-fluoro-phenyl]methyl]-2-[4-(cyclopropoxy)phenyl]-3-oxo-6,8-dihydro-5H-imidazo[1,5-a]pyrazine-1-carboxamide | 1H NMR (400 MHz, DMSO-d6, 80° C.): 0.66-0.70 (m, 2H), 0.78-0.83 (m, 2H), 3.68 (t, J = 5.6 Hz, 2H), 3.81-3.87 (m, 3H), 4.23 (d, J = 5.5 Hz, 2H), 4.85 (s, 2H), 4.13 (s, 2H), 6.80 (dd, J = 8.6 Hz, 2.4 Hz, 1H), 6.89 (dd, J = 11.5 Hz, 2.5 Hz, 1H), 7.03-7.10 (m, 4H), 7.17-7.19 (m, 2H), 7.39 (dd, J = 8.2, 2.0 Hz, 1H), 7.74 (d, J = 1.8 Hz, 1H), 7.85 (d, J = 8.1 Hz, 1H). |

TABLE A-continued

| Compound # | Name | Structure | NMR |
|---|---|---|---|
| 324 | N-[[4-(2-amino-2-oxo-ethoxy)-2-fluoro-phenyl]methyl]-7-(4-bromo-3-chloro-benzoyl)-2-[4-(cyclopropoxy)phenyl]-3-oxo-6,8-dihydro-5H-imidazo[1,5-a]pyrazine-1-carboxamide | 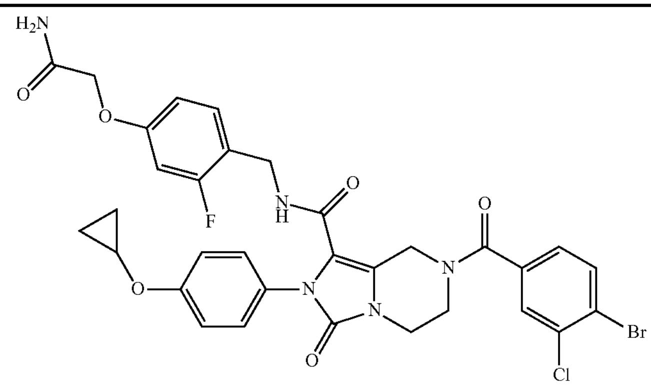 | 1H NMR (400 MHz, DMSO-d6, 80° C.): 0.65-0.71 (m, 2H), 0.77-0.84 (m, 2H), 3.68 (t, J = 5.4 Hz, 2H), 3.78-3.88 (m, 3H), 4.21 (d, J = 5.4 Hz, 2H), 4.43 (s, 2H), 4.85 (s, 2H), 6.70 (d, J = 8.3 Hz, 1H), 6.74 (d, J = 11.7 Hz, 1H), 6.96-7.08 (m, 4H), 7.11-7.29 (m, 4H), 7.39 (d, J = 8.4 Hz, 1H), 7.74 (s, 1H), 7.86 (d, J = 8.1 Hz, 1H). |
| 325 | 1-(5-benzylthiazol-2-yl)-7-(4-bromo-3-chloro-benzoyl)-2-(4-isopropoxyphenyl)-6,8-dihydro-5H-imidazo[1,5-a]pyrazin-3-one | 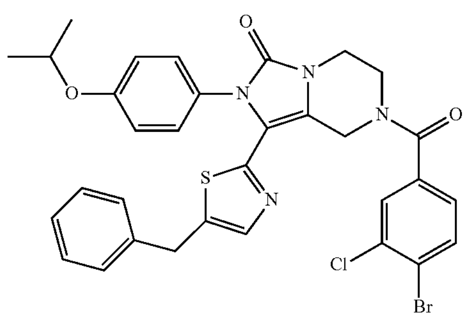 [SMILES: CC(C)Oc1ccc(-n2c(-c3ncc(Cc4ccccc4)s3)c3n(c2=O)CCN(C(=O)c2ccc(Br)c(Cl)c2)C3)cc1] | 1H-NMR (DMSO, 600 MHz, 80° C.): 1.31 (d, J = 6.0 Hz, 6H); 3.72 (t, J = 5.5 Hz, 2H); 3.86 (br. s., 2H); 4.04 (s, 2H); 4.63 (hept, J = 6.0 Hz, 1H); 4.94 (s, 2H); 6.97 (d, J = 8.6 Hz, 2H); 7.13 (d, J = 7.5 Hz, 2H); 7.17-7.22 (m, 3H); 7.24-7.28 (m, 2H); 7.37-7.42 (m, 1H); 7.49 (s, 1H); 7.73 (s, 1H); 7.84 (d, J = 8.2 Hz, 1H) ppm. |

| Compound # | Name | Structure | NMR |
|---|---|---|---|
| 326 | 7-(4-bromo-3-chloro-benzoyl)-N-[[4-(cyanomethoxy)-2-fluoro-phenyl]methyl]-3-oxo-2-[4-(2,2,2-trifluoroethoxy)phenyl]-6,8-dihydro-5H-imidazo[1,5-a]pyrazine-1-carboxamide | 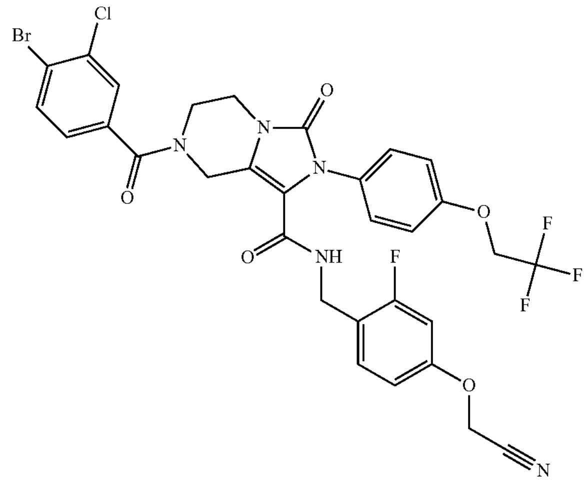 [SMILES: N#CCOc1ccc(CNC(=O)c2c3n(c(=O)n2-c2ccc(OCC(F)(F)F)cc2)CCN(C(=O)c2ccc(Br)c(Cl)c2)C3)c(F)c1] | 1H-NMR (DMSO, 600 MHz, 80° C.): 3.67 (t, J = 5.3 Hz, 2H); 3.80 (br. s., 2H); 4.24 (s, 2H); 4.74 (q, J = 8.8 Hz, 2H); 4.84 (s, 2H); 5.15 (s, 2H); 6.81 (d, J = 8.1 Hz, 1H); 6.91 (d, J = 11.6 Hz, 1H); 7.03-7.16 (br. s., 1H); 7.08 (d, J = 9.0 Hz, 2H); 7.21 (d, J = 9.0 Hz, 2H); 7.40 (dd, J = 8.2 Hz, 1.7 Hz, 1H); 7.54 (br. s., 1H); 7.76 (d, J = 1.6 Hz, 1H); 7.87 (d, J = 8.2 Hz, 1H) ppm. |
| 327 | 7-(4-bromo-3-chloro-benzoyl)-N-[[2-(4-fluoropyrazol-1-yl)phenyl]methyl]-3-oxo-2-[4-(2,2,2-trifluoroethoxy)phenyl]-6,8-dihydro-5H-imidazo[1,5-a]pyrazine-1-carboxamide | 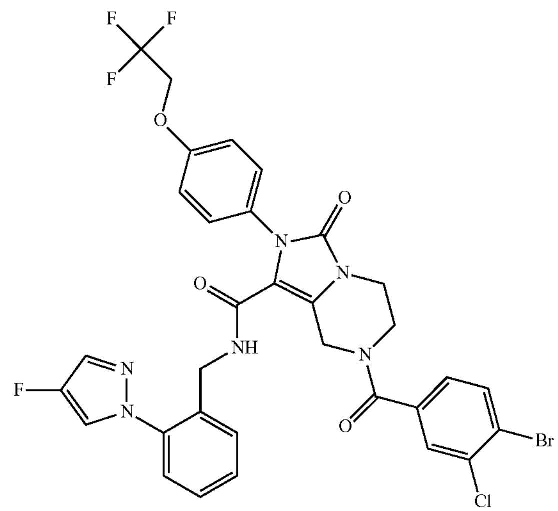 [SMILES: O=C(NCc1ccccc1-n1cc(F)cn1)c1c2n(c(=O)n1-c1ccc(OCC(F)(F)F)cc1)CCN(C(=O)c1ccc(Br)c(Cl)c1)C2] | 1H-NMR (DMSO, 600 MHz, 80° C.): 3.65-3.72 (m, 2H); 3.84 (s, 2H); 4.21 (d, J = 5.0 Hz, 2H); 4.70 (q, J = 8.8 Hz, 2H); 4.86 (s, 2H); 7.02-7.13 (m, 3H); 7.18-7.27 (m, 3H); 7.29-7.42 (m, 4H); 7.63 (s, 1H); 7.73 (s, 1H); 7.83 (d, J = 8.0 Hz, 1H); 8.06-8.14 (m, 1H) ppm |

TABLE A-continued

| Compound # | Structure | Name | NMR |
|---|---|---|---|
| 328 | 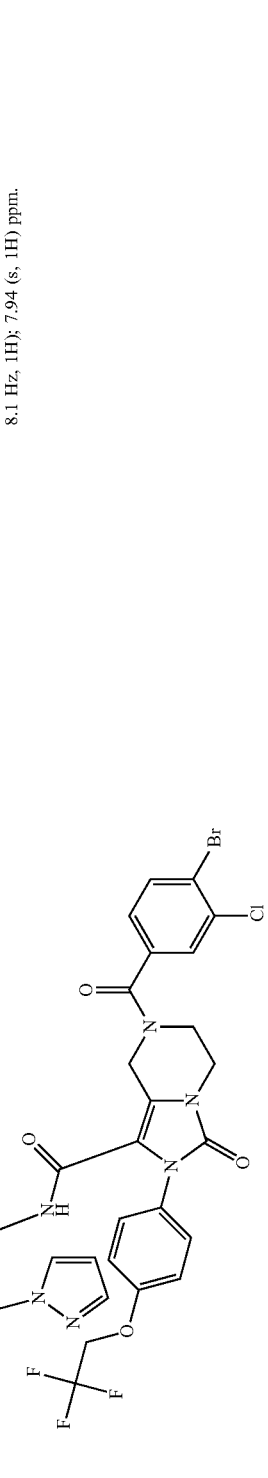 | N-[[4-(2-amino-2-oxo-ethoxy)-2-pyrazol-1-yl-phenyl]methyl]-7-(4-bromo-3-chloro-benzoyl)-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.67 (s, 2H); 3.82 (s, 2H); 4.13 (d, J = 4.9 Hz, 2H); 4.49 (s, 2H); 4.70 (q, J = 8.7 Hz, 2H); 4.86 (s, 2H); 6.45 (s, 1H); 6.94-6.98 (m, 2H); 7.00 (br. s, 1H); 7.08 (d, J = 8.3 Hz, 2H); 7.12 (br. s, 1H); 7.16-7.21 (m, 1H); 7.23 (d, J = 8.3 Hz, 2H); 7.39 (d, J = 8.1 Hz, 1H); 7.59 (s, 1H); 7.73 (s, 1H); 7.84 (d, J = 8.1 Hz, 1H); 7.94 (s, 1H) ppm. |
| 329 | 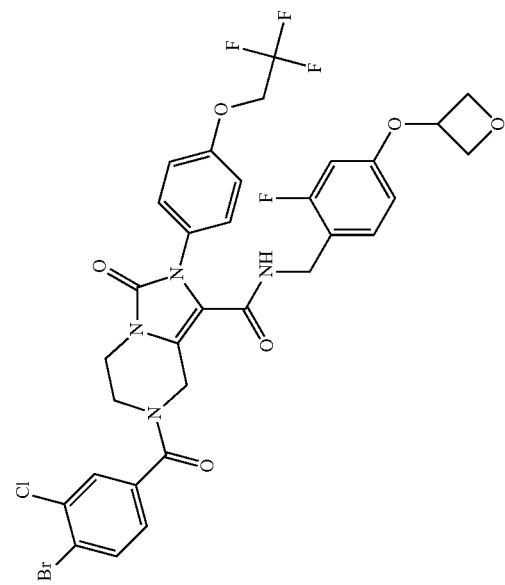 | 7-(4-bromo-3-chloro-benzoyl)-N-[[2-fluoro-4-(oxetan-3-yloxy)phenyl]methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 3.66-3.70 (m, 2H), 3.83 (s, 2H), 4.21 (d, J = 5.1 Hz, 2H), 4.54 (dd, J = 6.2 Hz, 5.7 Hz, 2H), 4.71 (q, J = 8.8 Hz, 2H), 4.83 (s, 2H), 4.91 (t, J = 6.4 Hz, 2H), 5.25-5.30 (m, 1H), 6.51-6.59 (m, 2H), 7.01 (t, J = 8.6 Hz, 1H), 7.07 (d, J = 8.3 Hz, 2H), 7.17 (br. s., 1H), 7.22 (d, J = 8.8 Hz, 2H), 7.39 (d, J = 7.8 Hz, 1H), 7.73 (s, 1H), 7.85 (d, J = 8.6 Hz, 1H) ppm. |

TABLE A-continued

| Compound # | Structure | Name | NMR |
|---|---|---|---|
| 330 | 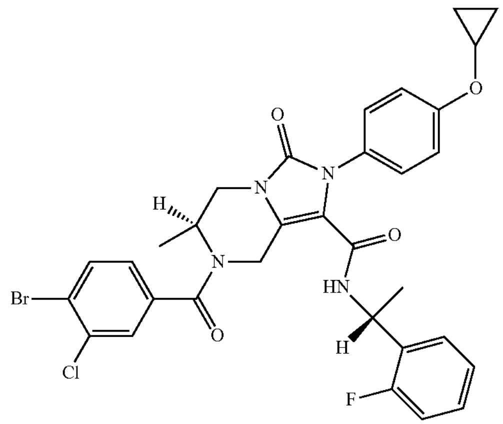 [SMILES: C[C@@H](NC(=O)c1c2n(c(=O)n1-c1ccc(OC3CC3)cc1)C[C@H](C)N(C(=O)c1ccc(Br)c(Cl)c1)C2)c1ccccc1F] | (6SR)-7-(4-bromo-3-chloro-benzoyl)-2-[4-(cyclopropoxy)phenyl]-6-methyl-3-oxo-N-[(1S)-1-phenylethyl]-6,8-dihydro-5H-imidazo[1,5-a]pyrazine-1-carboxamide | 1H NMR (400 MHz, Chloroform-d) δ 7.67 (d, J = 8.2 Hz, 1H), 7.56 (d, J = 2.0 Hz, 1H), 7.27 (d, J = 6.8 Hz, 2H), 7.22 (dd, J = 5.1, 2.0 Hz, 3H), 7.17 (dd, J = 8.2, 2.0 Hz, 1H), 7.16-7.10 (m, 2H), 6.92-6.80 (m, 2H), 5.07 (m, 4H), 4.61 (m, 1H), 3.86 (m, 1H), 3.79-3.62 (m, 2H), 1.40 (d, J = 7.0 Hz, 3H), 1.19 (d, J = 6.8 Hz, 3H), 0.90-0.72 (m, 4H). |
| 331 | 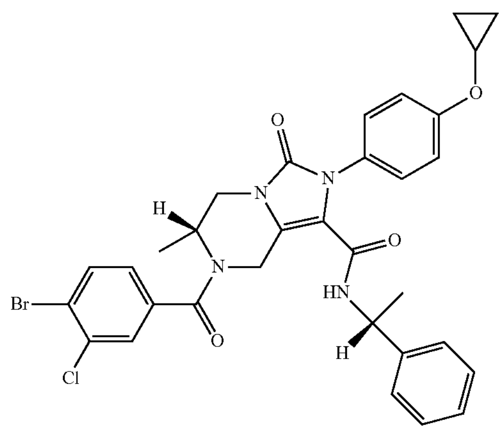 [SMILES: C[C@@H]1Cn2c(c(C(=O)N[C@H](C)c3ccccc3)n(-c3ccc(OC4CC4)cc3)c2=O)CN1C(=O)c1ccc(Br)c(Cl)c1] | (6RS)-7-(4-bromo-3-chloro-benzoyl)-2-[4-(cyclopropoxy)phenyl]-6-methyl-3-oxo-N-[(1S)-1-phenylethyl]-6,8-dihydro-5H-imidazo[1,5-a]pyrazine-1-carboxamide | 1H NMR (400 MHz, Chloroform-d) δ 7.71 (d, J = 8.2 Hz, 1H), 7.57 (d, J = 1.9 Hz, 1H), 7.30-7.26 (m, 2H), 7.25-7.17 (m, 4H), 7.16-7.11 (m, 2H), 6.89 (dd, J = 7.5, 2.0 Hz, 2H), 5.07 (m, 4H), 4.59 (m, 1H), 3.85 (m, 1H), 3.79-3.64 (m, 2H), 1.37 (d, J = 7.0 Hz, 3H), 1.16 (d, J = 6.9 Hz, 3H), 0.89-0.70 (m, 4H). |

| Compound # | Structure | Name | NMR |
|---|---|---|---|
| 332 | 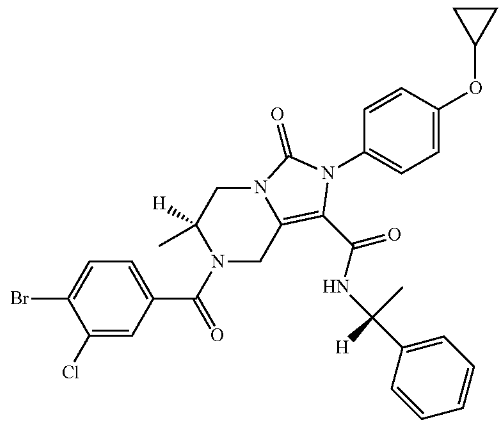 [SMILES: C[C@@H](NC(=O)c1c2n(c(=O)n1-c1ccc(OC3CC3)cc1)C[C@H](C)N(C(=O)c1ccc(Br)c(Cl)c1)C2)c1ccccc1] | (6SR)-7-(4-bromo-3-chloro-benzoyl)-2-[4-(cyclopropoxy)phenyl]-6-methyl-3-oxo-N-[(1R)-1-phenylethyl]-6,8-dihydro-5H-imidazo[1,5-a]pyrazine-1-carboxamide | 1H NMR (400 MHz, Chloroform-d) δ 7.71 (d, J = 8.2 Hz, 1H), 7.57 (d, J = 2.0 Hz, 1H), 7.28 (d, J = 6.7 Hz, 2H), 7.26-7.17 (m, 4H), 7.16-7.11 (m, 2H), 6.94-6.84 (m, 2H), 5.60-4.80 (m, 4H), 4.59 (m, 1H), 3.85 (d, J = 12.8 Hz, 1H), 3.79-3.62 (m, 2H), 1.37 (d, J = 7.0 Hz, 3H), 1.16 (d, J = 6.9 Hz, 3H), 0.88-0.73 (m, 4H). |
| 333 | 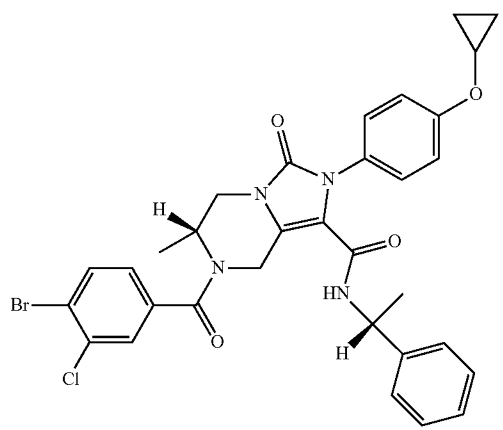 [SMILES: C[C@@H]1Cn2c(c(C(=O)N[C@H](C)c3ccccc3)n(-c3ccc(OC4CC4)cc3)c2=O)CN1C(=O)c1ccc(Br)c(Cl)c1] | (6RS)-7-(4-bromo-3-chloro-benzoyl)-2-[4-(cyclopropoxy)phenyl]-6-methyl-3-oxo-N-[(1R)-1-phenylethyl]-6,8-dihydro-5H-imidazo[1,5-a]pyrazine-1-carboxamide | 1H NMR (400 MHz, Chloroform-d) δ 7.67 (d, J = 8.2 Hz, 1H), 7.56 (d, J = 2.0 Hz, 1H), 7.28 (d, J = 2.1 Hz, 2H), 7.22 (dd, J = 5.1, 1.9 Hz, 3H), 7.17 (dd, J = 8.2, 2.0 Hz, 1H), 7.16-7.11 (m, 2H), 6.92-6.81 (m, 2H), 5.60-4.80 (m, 4H), 4.61 (m, 1H), 3.86 (m, 1H), 3.78-3.62 (m, 2H), 1.40 (d, J = 7.0 Hz, 3H), 1.19 (d, J = 6.8 Hz, 3H), 0.89-0.73 (m, 4H). |

| Compound # | Structure | Name | NMR |
|---|---|---|---|
| 334 | 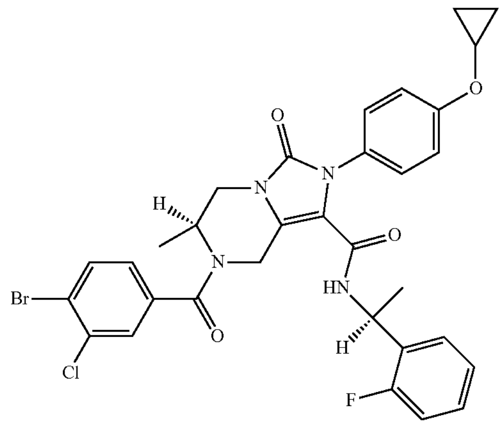 [SMILES: C[C@H](NC(=O)c1c2n(c(=O)n1-c1ccc(OC3CC3)cc1)C[C@H](C)N(C(=O)c1ccc(Br)c(Cl)c1)C2)c1ccccc1F] | (6SR)-7-(4-bromo-3-chloro-benzoyl)-2-[4-(cyclopropoxy)phenyl]-N-[(1S)-1-(2-fluorophenyl)ethyl]-6-methyl-3-oxo-6,8-dihydro-5H-imidazo[1,5-a]pyrazine-1-carboxamide | 1H NMR (400 MHz, Chloroform-d) δ 7.71 (d, J = 8.2 Hz, 1H), 7.57 (d, J = 1.9 Hz, 1H), 7.31-7.26 (m, 2H), 7.23-7.10 (m, 4H), 7.01 (td, J = 7.5, 1.2 Hz, 1H), 6.97-6.88 (m, 2H), 5.53-5.00 (m, 4H), 4.58 (m, 1H), 3.85 (m, 1H), 3.80-3.64 (m, 2H), 1.36 (d, J = 7.0 Hz, 3H), 1.18 (d, J = 6.9 Hz, 3H), 0.89-0.73 (m, 4H). |
| 335 | 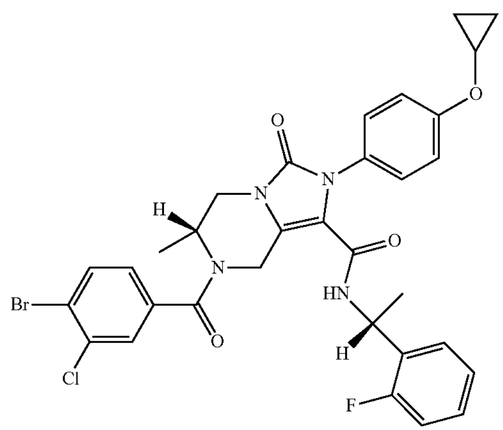 [SMILES: C[C@@H]1Cn2c(c(C(=O)N[C@H](C)c3ccccc3F)n(-c3ccc(OC4CC4)cc3)c2=O)CN1C(=O)c1ccc(Br)c(Cl)c1] | (6RS)-7-(4-bromo-3-chloro-benzoyl)-2-[4-(cyclopropoxy)phenyl]-N-[(1S)-1-(2-fluorophenyl)ethyl]-6-methyl-3-oxo-6,8-dihydro-5H-imidazo[1,5-a]pyrazine-1-carboxamide | 1H NMR (400 MHz, Chloroform-d) δ 7.71 (d, J = 8.2 Hz, 1H), 7.57 (d, J = 1.9 Hz, 1H), 73.1-7.26 (m, 2H), 7.23-7.10 (m, 4H), 7.01 (td, J = 7.5, 1.2 Hz, 1H), 6.97-6.88 (m, 2H), 5.53-5.00 (m, 4H), 4.58 (m, 1H), 3.85 (m, 1H), 3.80-3.64 (m, 2H), 1.36 (d, J = 7.0 Hz, 3H), 1.18 (d, J = 6.9 Hz, 3H), 0.89-0.73 (m, 4H). |

TABLE A-continued
| Compound # | Structure | Name | NMR |
|---|---|---|---|
| 336 | 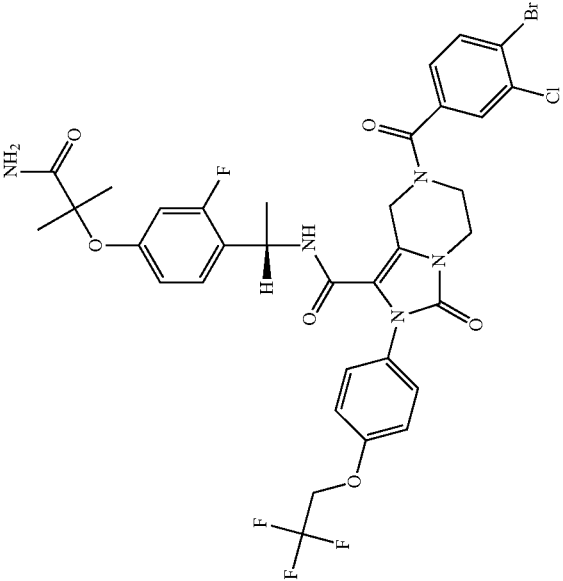 | 7-(4-bromo-3-chloro-benzoyl)-3-oxo-N-[rac-(1S)-1-[4-(2-amino-1,1-dimethyl-2-oxo-ethoxy)-2-fluoro-phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.71 (d, J = 7.8 Hz, 1H), 7.58 (s, 1H), 7.40-7.29 (m, 2H), 7.25-7.18 (m, 1H), 7.05 (d, J = 8.4 Hz, 2H), 6.96-6.79 (m, 1H), 6.71-6.59 (m, 3H), 6.29-5.70 (m, 1H), 5.31 (d, J = 7.5 Hz, 1H), 5.17-4.90 (m, 3H), 4.50-4.41 (m, 2H), 4.20-3.62 (m, 4H), 1.52 (s, 6H), 1.19 (d, J = 6.9 Hz, 3H). |

TABLE A-continued
| Compound # | Structure | Name | NMR |
|---|---|---|---|
| 337 | 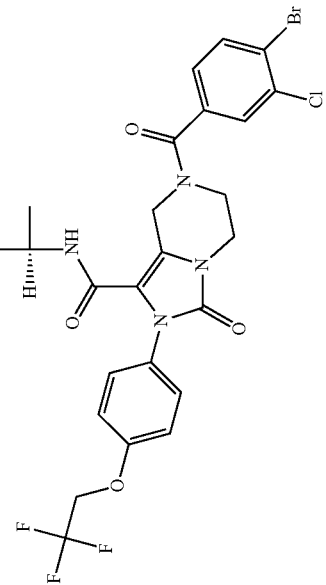 | 7-(4-bromo-3-chloro-benzoyl)-3-oxo-N-[rac-(1R)-1-[4-(2-amino-1,1-dimethyl-2-oxo-ethoxy)-2-fluoro-phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.71 (d, J = 8.4 Hz, 1H), 7.59 (s, 1H), 7.38-7.30 (m, 2H), 7.25-7.19 (m, 1H), 7.04 (d, J = 9.0 Hz, 2H), 65.95-6.80 (m, 1H), 6.67-6.38 (m, 3H), 5.42 (s, 1H), 5.31 (d, J = 7.8 Hz, 1H), 5.15-4.89 (m, 3H), 4.51-4.31 (m, 2H), 4.15-3.70 (m, 4H), 1.52 (s, 6H), 1.19 (d, J = 6.9 Hz, 3H). |

TABLE A-continued

| Compound # | Structure | Name | NMR |
|---|---|---|---|
| 338 | 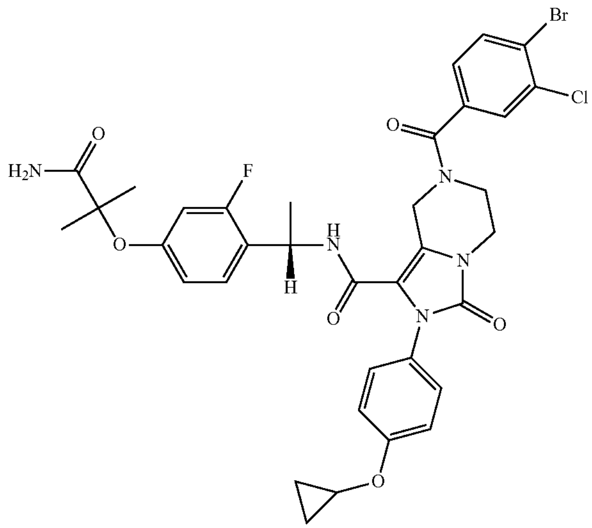 | 7-(4-bromo-3-chloro-benzoyl)-2-[4-(cyclopropoxy)phenyl]-3-oxo-N-[(1S)-1-[4-(2-amino-1,1-dimethyl-2-oxo-ethoxy)-2-fluoro-phenyl]ethyl]-6,8-dihydro-5H-imidazo[1,5-a]pyrazine-1-carboxamide | 1H NMR (300 MHz, Chloroform-d) δ 7.71 (d, J = 8.1 Hz, 1H), 7.59 (s, 1H), 7.29 (s, 1H), 7.25-7.20 (m, 2H), 7.18-7.08 (m, 2H), 6.91-6.81 (m, 1H), 6.71 (s, 1H), 6.65-6.50 (m, 2H), 6.36 (s, 1H), 5.37 (d, J = 8.0 Hz, 1H), 5.13 ˚C 4.92 (m, 3H), 4.35-3.57 (m, 5H), 1.53 (s, 6H), 1.17 (d, J = 6.9 Hz, 3H), 0.86-0.76 (m, 4H). |
| 339 | 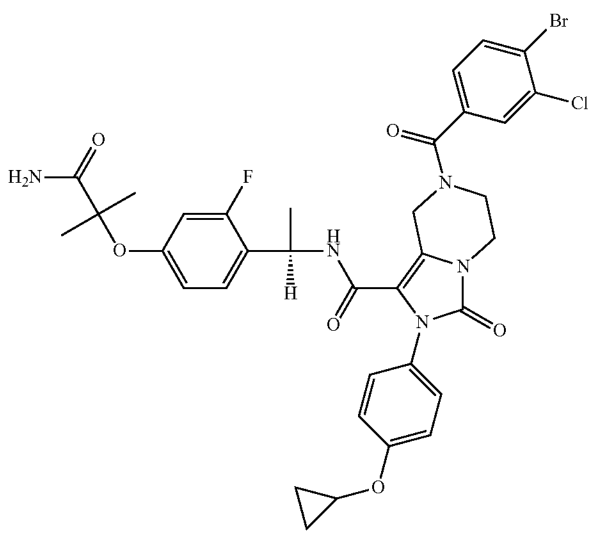 | 7-(4-bromo-3-chloro-benzoyl)-2-[4-(cyclopropoxy)phenyl]-3-oxo-N-[rac-(1R)-1-[4-(2-amino-1,1-dimethyl-2-oxo-ethoxy)-2-fluoro-phenyl]ethyl]-6,8-dihydro-5H-imidazo[1,5-a]pyrazine-1-carboxamide | 1H NMR (300 MHz, Chloroform-d) δ 7.71 (d, J = 8.1 Hz, 1H), 7.59 (s, 1H), 7.27 (s, 1H), 7.28-7.20 (m, 2H), 7.19-7.09 (m, 2H), 6.91–679 (m, 1H), 6.75-6.50 (m, 3H), 6.20 (s, 1H), 5.36 (d, J = 7.8 Hz, 1H), 5.12-4.90 (m, 3H), 4.35-3.55 (m, 5H), 1.53 (s, 6H), 1.16 (d, J = 6.9 Hz, 3H), 0.89-0.76 (m, 4H). |

TABLE A-continued

| Compound # | Structure | Name | NMR |
|---|---|---|---|
| 340 | 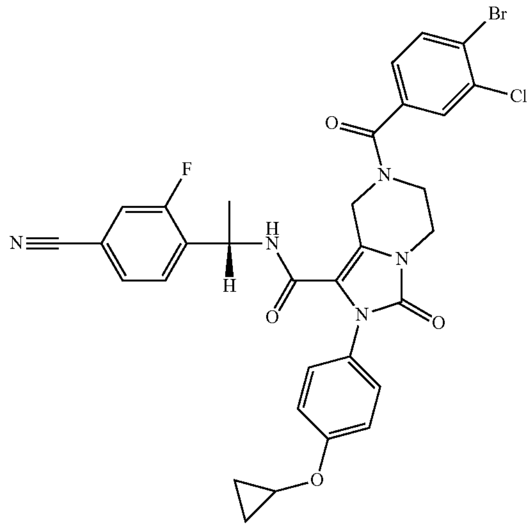 [SMILES: C[C@H](NC(=O)c1c2n(c(=O)n1-c1ccc(OC3CC3)cc1)CCN(C(=O)c1ccc(Br)c(Cl)c1)C2)c1ccc(C#N)cc1F] | 7-(4-bromo-3-chloro-benzoyl)-2-[4-(cyclopropoxy)phenyl]-3-oxo-N-[rac-(1S)-1-(4-cyano-2-fluoro-phenyl)ethyl]-6,8-dihydro-5H-imidazo[1,5-a]pyrazine-1-carboxamide | 1H NMR (400 MHz, Chloroform-d) δ 7.69 (d, J = 8.2 Hz, 1H), 7.58 (d, J = 1.9 Hz, 1H), 7.35 (dd, J = 7.9, 1.6 Hz, 1H), 7.32-7.27 (m, 2H), 7.23 (dd, J = 8.0, 1.8 Hz, 1H), 7.20 (d, J = 1.8 Hz, 2H), 7.18 (d, J = 2.0 Hz, 1H), 7.07 (d, J = 7.9 Hz, 1H), 5.32 (d, J = 7.6 Hz, 1H), 5.18-4.82 (m, 3H), 4.27-3.71 (m, 5H), 1.13 (d, J = 7.0 Hz, 3H), 0.92-0.72 (m, 4H). |
| 341 | 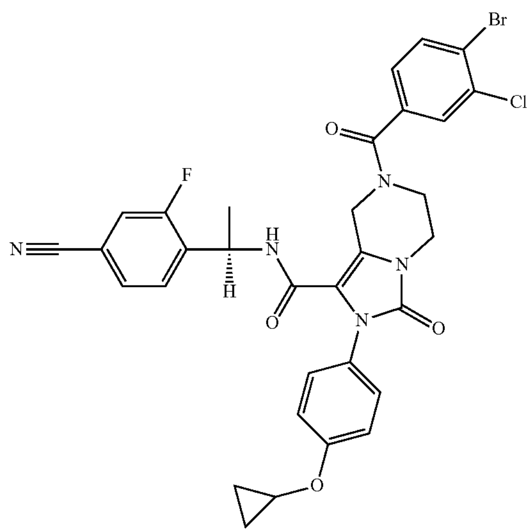 [SMILES: C[C@@H](NC(=O)c1c2n(c(=O)n1-c1ccc(OC3CC3)cc1)CCN(C(=O)c1ccc(Br)c(Cl)c1)C2)c1ccc(C#N)cc1F] | 7-(4-bromo-3-chloro-benzoyl)-2-[4-(cyclopropoxy)phenyl]-3-oxo-N-[rac-(1R)-1-(4-cyano-2-fluoro-phenyl)ethyl]-6,8-dihydro-5H-imidazo[1,5-a]pyrazine-1-carboxamide | 1H NMR (400 MHz, Chloroform-d) δ 7.69 (d, J = 8.2 Hz, 1H), 7.58 (d, J = 1.9 Hz, 1H), 7.35 (dd, J = 7.9, 1.6 Hz, 1H), 7.32-7.27 (m, 2H), 7.23 (dd, J = 8.0, 1.8 Hz, 1H), 7.20 (d, J = 1.8 Hz, 2H), 7.18 (d, J = 2.0 Hz, 1H), 7.07 (d, J = 7.9 Hz, 1H), 5.32 (d, J = 7.6 Hz, 1H), 5.18-4.82 (m, 3H), 4.27-3.71 (m, 5H), 1.13 (d, J = 7.0 Hz, 3H), 0.92-0.72 (m, 4H). |

TABLE A-continued

| Compound # | Structure | Name | NMR |
|---|---|---|---|
| 342 | 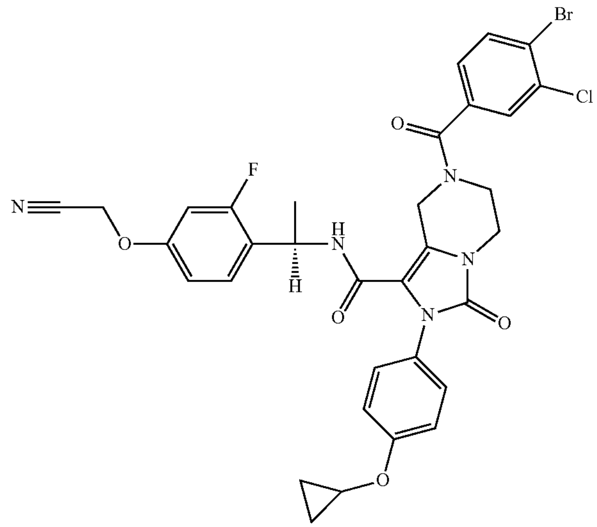 [SMILES: C[C@@H](NC(=O)c1c2n(c(=O)n1-c1ccc(OC3CC3)cc1)CCN(C(=O)c1ccc(Br)c(Cl)c1)C2)c1ccc(OCC#N)cc1F] | 7-(4-bromo-3-chloro-benzoyl)-2-[4-(cyclopropoxy)phenyl]-3-oxo-N-[rac-(1R)-1-[4-(cyanomethoxy)-2-fluoro-phenyl]ethyl]-6,8-dihdyro-5H-imidazo[1,5-a]pyrazine-1-carboxamide | 1H NMR (400 MHz, Chloroform-d) δ 7.71 (d, J = 8.4 Hz, 1H), 7.60 (s, 1H), 7.28 (s, 1H), 7.25-7.11 (m, 4H), 7.00-6.82 (m, 1H), 6.69-6.51 (m, 2H), 5.37 (s, 1H), 5.03 (s, 3H), 4.73 (s, 2H), 3.95-3.70 (m, 5H), 1.16 (d, J = 6.8 Hz, 3H), 0.86-0.79 (m, 4H). |
| 343 | 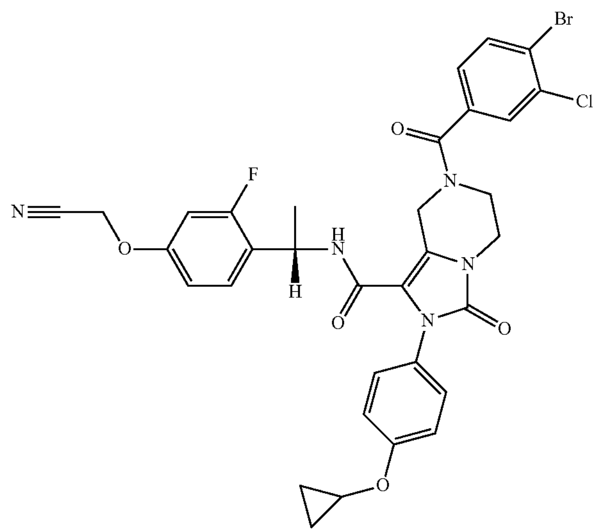 | 7-(4-bromo-3-chloro-benzoyl)-2-[4-(cyclopropoxy)phenyl]-3-oxo-N-[rac-(1S)-1-[4-(cyanomethoxy)-2-fluoro-phenyl]ethyl]-6,8-dihydro-5H-imidazo[1,5-a]pyrazine-1-carboxamide | 1H NMR (300 MHz, Chloroform-d) δ 7.71 (d, J = 8.1 Hz, 1H), 7.60 (s, 1H), 7.28 (s, 1H), 7.27-7.12 (m, 4H), 6.93 (t, J = 8.5 Hz, 1H), 6.67-6.57 (m, 2H), 5.41 (d, J = 8.1 Hz, 1H), 5.12-4.91 (m, 3H), 4.73 (s, 2H), 4.18 (s, 2H), 3.91-3.71 (m, 3H), 1.16 (d, J = 6.9 Hz, 3H), 0.89-0.76 (m, 4H). |

TABLE A-continued

| Compound # | Structure | Name | NMR |
|---|---|---|---|
| 344 | 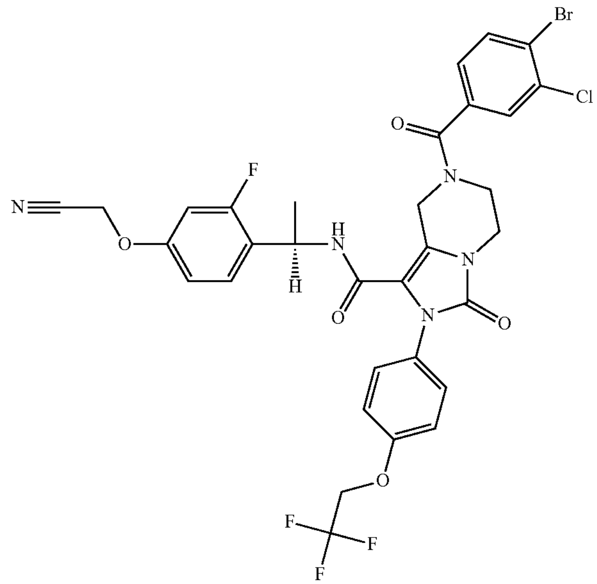 [SMILES: C[C@@H](NC(=O)c1c2n(c(=O)n1-c1ccc(OCC(F)(F)F)cc1)CCN(C(=O)c1ccc(Br)c(Cl)c1)C2)c1ccc(OCC#N)cc1F] | 7-(4-bromo-3-chloro-benzoyl)-3-oxo-N-[rac-(1R)-1-[4-(cyanomethoxy)-2-fluoro-phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.72 (d, J = 8.1 Hz, 1H), 7.60 (d, J = 1.5 Hz, 1H), 7.37-7.28 (m, 2H), 7.25-7.20 (m, 1H), 7.10-6.89 (m, 3H), 6.73-6.49 (m, 2H), 5.36 (d, J = 7.8 Hz, 1H), 5.18-4.91 (m, 3H), 4.73 (s, 2H), 4.50-4.35 (m, 2H), 4.11 (s, 2H), 3.85 (s, 2H), 1.20 (d, J = 6.9 Hz, 3H). |

TABLE A-continued
| Compound # | Structure | Name | NMR |
|---|---|---|---|
| 345 | 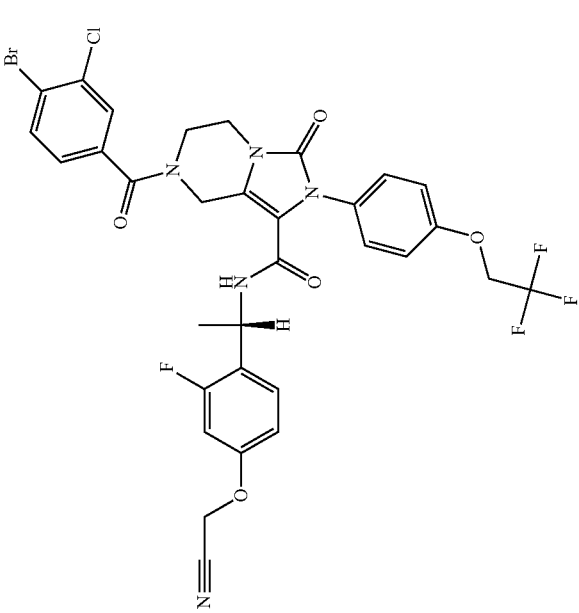 | 7-(4-bromo-3-chloro-benzoyl)-3-oxo-N-[rac-(1S)-1-[4-(cyanomethoxy)-2-fluoro-phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.60 (s, 1H), 7.36-7.29 (m, 2H), 7.25-7.20 (m, 1H), 7.09-7.02 (m, 2H), 7.00-6.89 (m, 1H), 6.71-6.53 (m, 2H), 5.36 (d, J = 8.1 Hz, 1H), 5.15-4.92 (m, 3H), 4.73 (s, 2H), 4.47-4.35 (m, 2H), 3.93 (s, 2H), 3.84 (s, 2H), 1.20 (d, J = 6.9 Hz, 3H). |

TABLE A-continued

| Compound # | Structure | Name | NMR |
|---|---|---|---|
| 346 | 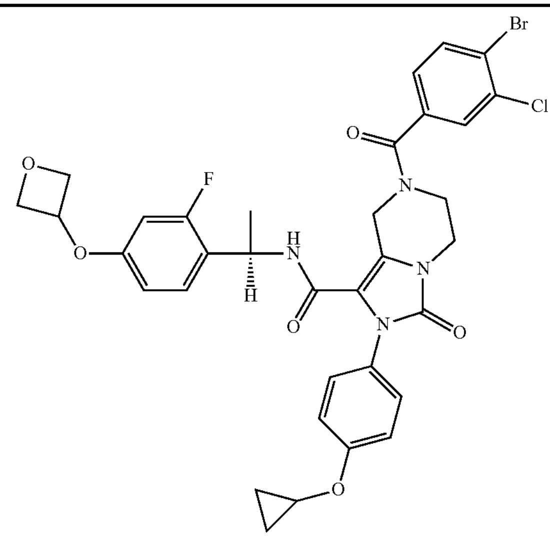 | 7-(4-bromo-3-chloro-benzoyl)-2-[4-(cyclopropoxy)phenyl]-3-oxo-N-[rac-(1R)-1-[2-fluoro-4-(oxetan-3-yloxy)phenyl]ethyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.61 (d, J = 1.9 Hz, 1H), 7.28-7.21 (m, 3H), 7.15 (d, J = 8.9 Hz, 2H), 6.85 (t, J = 8.5 Hz, 1H), 6.41-6.27 (m, 2H), 5.35 (d, J = 8.0 Hz, 1H), 5.20-4.96 (m, 6H), 4.74 (t, J = 6.2 Hz, 2H), 4.25-3.68 (m, 5H), 1.16 (d, J = 6.9 Hz, 3H), 0.97-0.74 (m, 4H). |
| 347 | 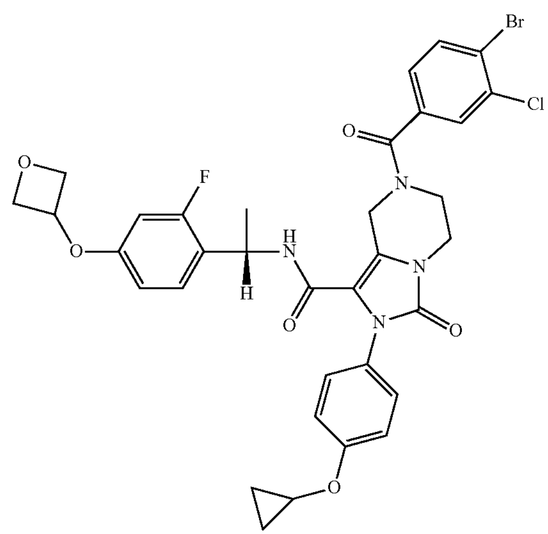 [SMILES: C[C@H](NC(=O)c1c2n(c(=O)n1-c1ccc(OC3CC3)cc1)CCN(C(=O)c1ccc(Br)c(Cl)c1)C2)c1ccc(OC2COC2)cc1F] | 7-(4-bromo-3-chloro-benzoyl)-2-[4-(cyclopropoxy)phenyl]-3-oxo-N-[rac-(1S)-1-[2-fluoro-4-(oxetan-3-yloxy)phenyl]ethyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.61 (d, J = 1.9 Hz, 1H), 7.28-7.21 (m, 3H), 7.15 (d, J = 8.9 Hz, 2H), 6.85 (t, J = 8.5 Hz, 1H), 6.41-6.27 (m, 2H), 5.35 (d, J = 8.0 Hz, 1H), 5.20-4.96 (m, 6H), 4.74 (t, J = 6.2 Hz, 2H), 4.25-3.68 (m, 5H), 1.16 (d, J = 6.9 Hz, 3H), 0.97-0.74 (m, 4H). |

| Compound # | Structure | Name | NMR |
|---|---|---|---|
| 348 | 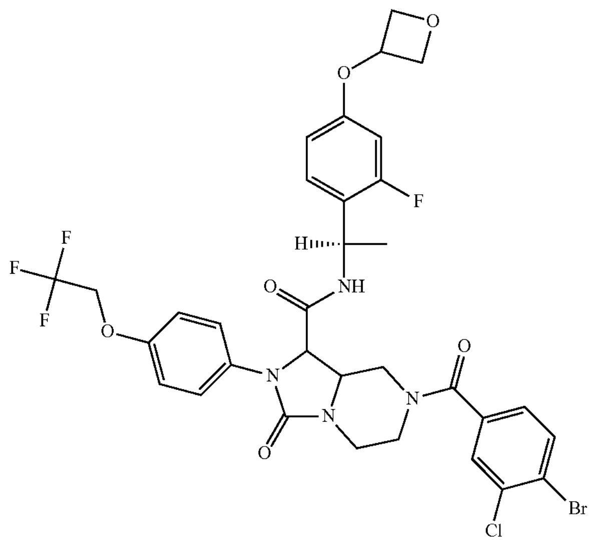 [SMILES: C[C@@H](NC(=O)C1C2CN(C(=O)c3ccc(Br)c(Cl)c3)CCN2C(=O)N1c1ccc(OCC(F)(F)F)cc1)c1ccc(OC2COC2)cc1F] | 7-(4-bromo-3-chloro-benzoyl)-3-oxo-N-[rac-(1R)-1-[2-fluoro-4-(oxetan-3-yloxy)phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.61 (d, J = 1.9 Hz, 1H), 7.33 (d, J = 8.8 Hz, 2H), 7.25 (dd, J = 8.3, 2.1 Hz, 1H), 7.05 (d, J = 8.8 Hz, 2H), 6.88 (t, J = 8.6 Hz, 1H), 6.40-6.26 (m, 2H), 5.30 (d, J = 8.1 Hz, 1H), 5.17-4.96 (m, 6H), 4.80-4.68 (m, 2H), 4.50-4.32 (m, 2H), 4.01-3.84 (m, 4H), 1.20 (d, J = 6.9 Hz, 3H). |
| 349 | 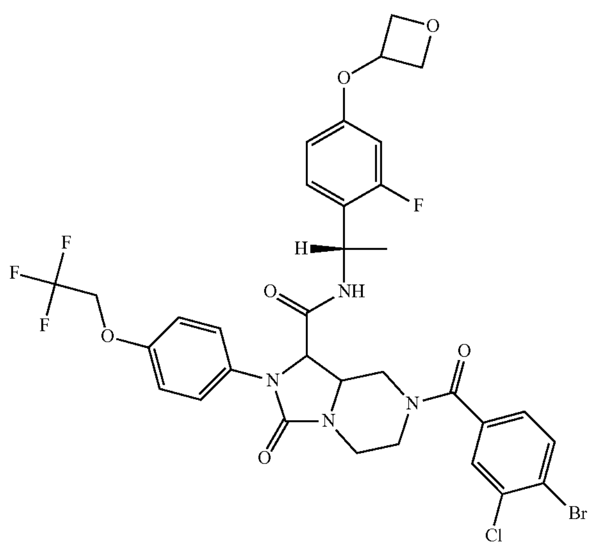 [SMILES: C[C@H](NC(=O)C1C2CN(C(=O)c3ccc(Br)c(Cl)c3)CCN2C(=O)N1c1ccc(OCC(F)(F)F)cc1)c1ccc(OC2COC2)cc1F] | 7-(4-bromo-3-chloro-benzoyl)-3-oxo-N-[rac-(1S)-1-[2-fluoro-4-(oxetan-3-yloxy)phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.72 (d, J = 8.2 Hz, 1H), 7.61 (d, J = 1.9 Hz, 1H), 7.33 (d, J = 8.8 Hz, 2H), 7.25 (dd, J = 8.3, 2.1 Hz, 1H), 7.05 (d, J = 8.8 Hz, 2H), 6.88 (t, J = 8.6 Hz, 1H), 6.40-6.26 (m, 2H), 5.30 (d, J = 8.1 Hz, 1H), 5.17-4.96 (m, 6H), 4.80-4.68 (m, 2H), 4.50-4.32 (m, 2H), 4.01-3.84 (m, 4H), 1.20 (d, J = 6.9 Hz, 3H). |

TABLE A-continued

| Compound # | Structure | Name | NMR |
|---|---|---|---|
| 350 | 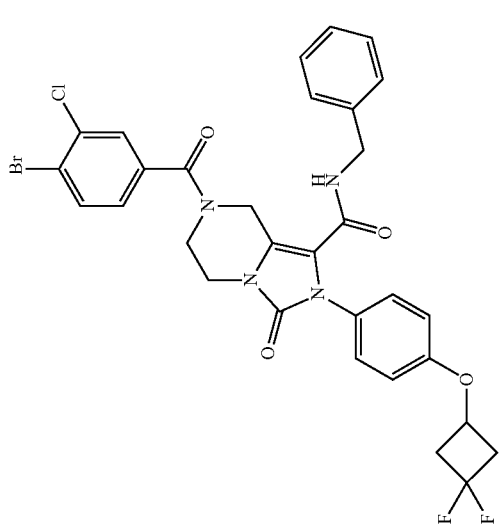 | N-benzyl-7-(4-bromo-3-chloro-benzoyl)-2-[4-(3,3-difluorocyclobutoxy)phenyl]-3-oxo-6,8-dihydro-5H-imidazo[1,5-a]pyrazine-1-carboxamide | 1H NMR (400 MHz, DMSO-d6, 80° C.): 2.67-2.74 (m, 2H), 3.14-3.25 (m, 2H), 3.68 (t, J = 5.4 Hz, 2H), 3.83 (t, J = 5.2 Hz, 2H), 4.25 (d, J = 5.6 Hz, 2H), 4.75-4.79 (m, 1H), 4.85 (s, 2H), 6.92 (d, J = 8.8 Hz, 2H), 7.05 (d, J = 6.9 Hz, 2H), 7.20-7.25 (m, 6H), 7.39 (dd, J = 8.0, 1.7 Hz, 1H), 7.74 (d, J = 1.4 Hz, 1H), 7.85 (d, J = 8.1 Hz, 1H). |
| 351 | 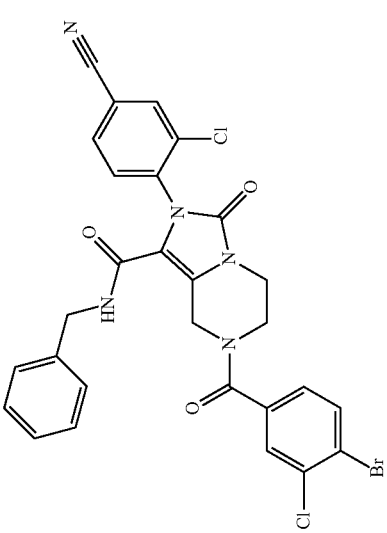 | N-benzyl-7-(4-bromo-3-chloro-benzoyl)-2-(2-chloro-4-cyano-phenyl)-3-oxo-6,8-dihydro-5H-imidazo[1,5-a]pyrazine-1-carboxamide | 1H-NMR (DMSO, 600 MHz, 80° C.): 3.91 (s, 2H); 4.03 (dd, J = 5.7 Hz, 5.1 Hz, 2H); 4.39 (d, J = 6.3 Hz, 2H); 4.99 (s, 2H); 7.18-7.24 (m, 1H); 7.25-7.32 (m, 4H); 7.40 (dd, J = 8.2 Hz, 1.2 Hz, 1H); 7.74 (s, 1H); 7.82-7.89 (m, 3H); 7.89-7.96 (m, 1H); 8.14 (s, 1H) ppm. |

TABLE A-continued

| Compound # | Name | NMR |
|---|---|---|
| 352 | N-benzyl-7-(4-bromo-3-chloro-benzoyl)-3-oxo-2-[2-(trifluoromethyl)-1H-indol-5-yl]-6,8-dihydro-5H-imidazo[1,5-a]pyrazine-1-carboxamide | 1H-NMR (DMSO, 600 MHz, 80° C.): 3.71 (t, J = 5.5 Hz, 2H); 3.86 (br. s, 2H); 4.19 (d, J = 5.8 Hz, 2H); 4.89 (s, 2H); 6.87-6.94 (m, 3H); 7.00 (s, 1H); 7.06-7.16 (m, 3H); 7.19 (dd, J = 8.8 Hz, 1.9 Hz, 1H); 7.41 (dd, J = 8.2 Hz, 1.9 Hz, 1H); 7.50 (d, J = 8.8 Hz, 1H); 7.62 (d, J = 1.7 Hz, 1H); 7.75 (d, J = 1.7 Hz, 1H); 7.86 (d, J = 8.2 Hz, 1H); 12.16 (br. s, 1H) ppm. |
| 353 | 7-(4-bromo-3-chloro-benzoyl)-N-[[2-fluoro-4-[rac-(1S)-2-amino-1-methyl-2-oxo-ethoxy]phenyl]methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 1.46 (d, J = 6.5 Hz, 3H), 3.65-3.72 (m, 2H), 3.79-3.87 (m, 2H), 4.22 (d, J = 5.8 Hz, 2H), 4.66 (q, J = 6.5 Hz, 1H), 4.73 (q, J = 8.8 Hz, 2H), 4.85 (s, 2H), 6.67-6.74 (m, 2H), 7.02 (t, J = 8.7 Hz, 1H), 7.09 (d, J = 8.9 Hz, 2H), 7.19 (br. s, 1H), 7.23 (d, J = 8.9 Hz, 2H), 6.92-7.30 (m, 2H), 7.40 (dd, J = 8.1 Hz, 1.5 Hz, 1H), 7.74 (d, J = 1.7 Hz, 1H), 7.86 (d, J = 8.2 Hz, 1H) ppm. |

| Compound # | Structure | Name | NMR |
|---|---|---|---|
| 354 | 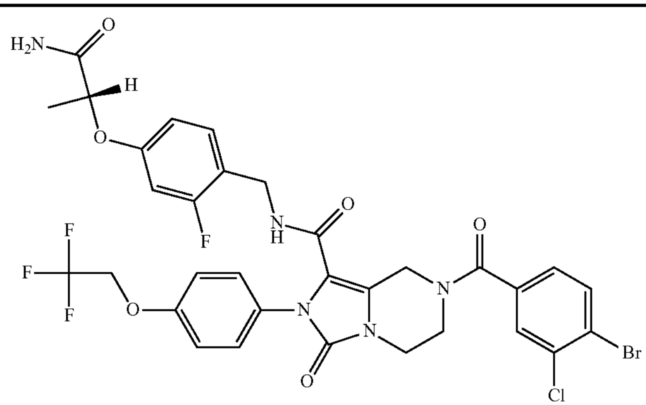 | 7-(4-bromo-3-chloro-benzoyl)-N-[[2-fluoro-4-[rac-(1R)-2-amino-1-methyl-2-oxo-ethoxy]phenyl]methyl]-3-oxo-2-[4-(2,2,2-trifluoroethoxy)phenyl]-6,8-dihydro-5H-imidazo[1,5-a]pyrazine-1-carboxamide | 1H-NMR (DMSO, 600 MHz, 80° C.): 1.46 (d, J = 6.5 Hz, 3H), 3.67-3.72 (m, 2H), 3.79-3.87 (m, 2H), 4.22 (d, J = 5.8 Hz, 2H), 4.66 (q, J = 6.5 Hz, 1H), 4.73 (q, J = 8.8 Hz, 2H), 4.85 (s, 2H), 6.67-6.73 (m, 2H), 7.02 (t, J = 8.7 Hz, 1H), 7.09 (d, J = 8.9 Hz, 2H), 7.18 (br. s. 1H), 7.23 (d, J = 8.9 Hz, 2H), 6.92-7.28 (m, 2H), 7.40 (dd, J = 8.1 Hz, 1.5 Hz, 1H), 7.74 (d, J = 1.7 Hz, 1H), 7.86 (d, J = 8.2 Hz, 1H) ppm. |
| 355 | 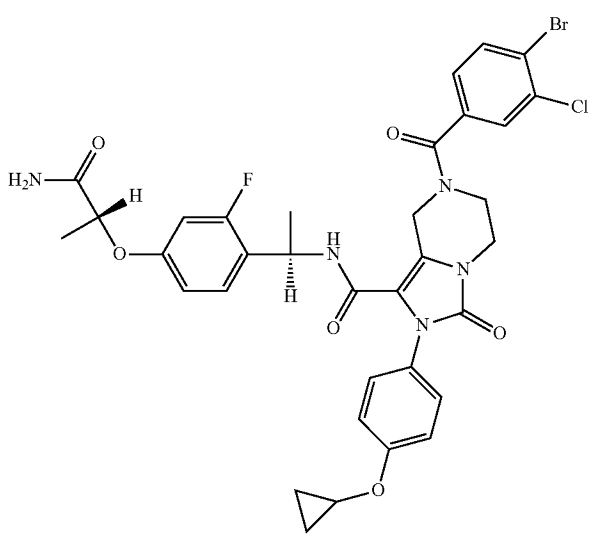 [SMILES: C[C@@H](Oc1ccc([C@@H](C)NC(=O)c2c3n(c(=O)n2-c2ccc(OC4CC4)cc2)CCN(C(=O)c2ccc(Br)c(Cl)c2)C3)c(F)c1)C(N)=O] | 7-(4-bromo-3-chloro-benzoyl)-2-[4-(cyclopropoxy)phenyl]-3-oxo-N-[rac-(1R)-1-[2-fluoro-4-[rac-(1R)-2-amino-1-methyl-2-oxo-ethoxy]phenyl]ethyl]-6,8-dihydro-5H-imidazo[1,5-a]pyrazine-1-carboxamide | 1H NMR (400 MHz, Chloroform-d) δ 7.70 (d, J = 8.4 Hz, 1H), 7.59 (s, 1H), 7.27 (s, 1H), 7.26-7.20 (m, 2H), 7.19-7.11 (m, 2H), 6.87 (s, 1H), 6.64-6.49 (m, 2H), 6.37 (s, 1H), 5.87 (s, 1H), 5.35 (d, J = 8.0 Hz, 1H), 5.02 (s, 3H), 4.69-4.55 (m, 1H), 4.01-3.65 (m, 5H), 1.59 (d, J = 6.8 Hz, 3H), 1.14 (d, J = 6.8 Hz, 3H), 0.88-0.80 (m, 4H). |

| Compound # | Structure | Name | NMR |
|---|---|---|---|
| 356 | 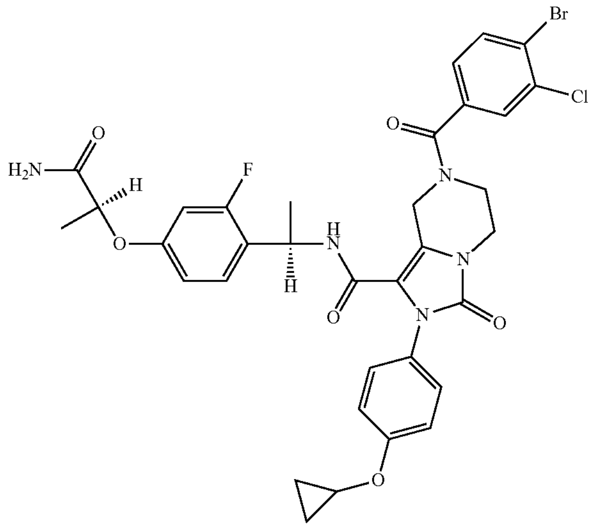 [SMILES: C[C@H](Oc1ccc([C@@H](C)NC(=O)c2c3n(c(=O)n2-c2ccc(OC4CC4)cc2)CCN(C(=O)c2ccc(Br)c(Cl)c2)C3)c(F)c1)C(N)=O] | 7-(4-bromo-3-chloro-benzoyl)-2-[4-(cyclopropoxy)phenyl]-3-oxo-N-[rac-(1R)-1-[2-fluoro-4-[rac-(1S)-2-amino-1-methyl-2-oxo-ethoxy]phenyl]ethyl]-6,8-dihydro-5H-imidazo[1,5-a]pyrazine-1-carboxamide | 1H NMR (400 MHz, Chloroform-d) δ 7.71 (d, J = 8.0 Hz, 1H), 7.59 (s, 1H), 7.26-7.20 (m, 3H), 7.12-7.08 (m, 2H), 6.86 (s, 1H), 6.61-6.47 (m, 2H), 6.34 (s, 1H), 5.55 (s, 1H), 5.31 (d, J = 8.0 Hz, 1H), 5.02 (s, 3H), 4.65-4.51 (m, 1H), 4.15-3.65 (m, 5H), 1.60 (d, J = 6.8 Hz, 3H), 1.16 (d, J = 6.8 Hz, 3H), 0.88-0.85 (m, 4H). |
| 357 | 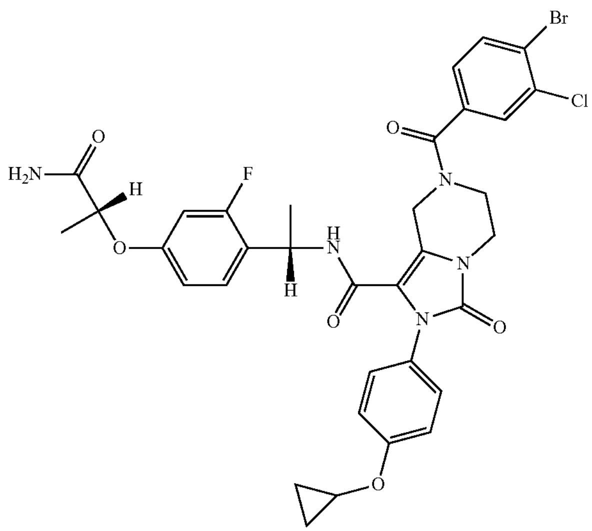 [SMILES: C[C@H](Oc1ccc([C@H](C)NC(=O)c2c3n(c(=O)n2-c2ccc(OC4CC4)cc2)CCN(C(=O)c2ccc(Br)c(Cl)c2)C3)c(F)c1)C(N)=O] | 7-(4-bromo-3-chloro-benzoyl)-2-[4-(cyclopropoxy)phenyl]-3-oxo-N-[rac-(1S)-1-[2-fluoro-4-[rac-(1R)-2-amino-1-methyl-2-oxo-ethoxy]phenyl]ethyl]-6,8-dihydro-5H-imidazo[1,5-a]pyrazine-1-carboxamide | 1H NMR (400 MHz, Chloroform-d) δ 7.69 (d, J = 8.2 Hz, 1H), 7.59 (d, J = 2.0 Hz, 1H), 7.27 (d, J = 2.2 Hz, 1H), 7.26-7.20 (m, 2H), 7.17-7.12 (m, 2H), 6.87 (s, 1H), 6.63-6.48 (m, 2H), 6.40 (s, 1H), 5.97 (s, 1H), 5.34 (d, J = 7.9 Hz, 1H), 5.02 (s, 3H), 4.61 (q, J = 6.8 Hz, 1H), 4.12-3.71 (m, 5H), 1.58 (d, J = 6.7 Hz, 3H), 1.13 (d, J = 6.9 Hz, 3H), 0.89-0.74 (m, 4H). |

TABLE A-continued
| Compound # | Structure | Name | NMR |
|---|---|---|---|
| 358 | 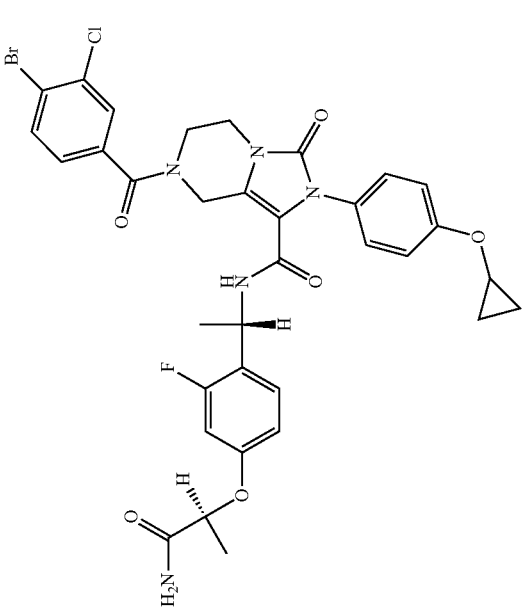 | 7-(4-bromo-3-chloro-benzoyl)-2-[4-(cyclopropoxy)phenyl]-3-oxo-N-[rac-(1S)-1-[2-fluoro-4-[rac-(1S)-2-amino-1-methyl-2-oxo-ethoxy]phenyl]ethyl]-6,8-dihydro-5H-imidazo[1,5-a]pyrazine-1-carboxamide | 1H NMR (400 MHz, Chloroform-d) δ 7.71 (d, J = 8.0 Hz, 1H), 7.59 (s, 1H), 7.26-7.20 (m, 3H), 7.12-7.08 (m, 2H), 6.86 (s, 1H), 6.61-6.47 (m, 2H), 6.34 (s, 1H), 5.55 (s, 1H), 5.31 (d, J = 8.0 Hz, 1H), 5.02 (s, 3H), 4.65-4.51 (m, 1H), 4.15-3.65 (m, 5H), 1.60 (d, J = 6.8 Hz, 3H), 1.16 (d, J = 6.8 Hz, 3H), 0.88-0.85 (m, 4H). |

TABLE A-continued
| Compound # | Structure | Name | NMR |
|---|---|---|---|
| 359 | 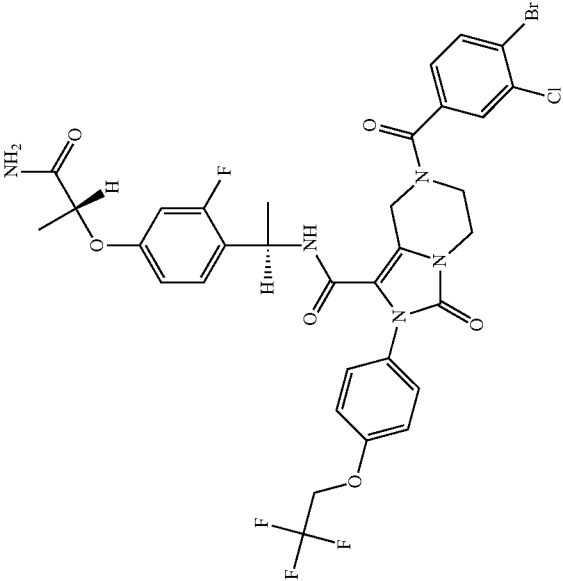 | 7-(4-bromo-3-chloro-benzoyl)-3-oxo-N-[rac-(1R)-1-[2-fluoro-4-[rac-(1R)-2-amino-1-methyl-2-oxo-ethoxy]phenyl]ethyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.71 (d, J = 8.4 Hz, 1H), 7.59 (d, J = 1.6 Hz, 1H), 7.39-7.30 (m, 2H), 7.24-7.20 (m, 1H), 7.10-7.00 (m, 2H), 6.91 (s, 1H), 6.60-6.48 (m, 2H), 6.25 (s, 1H), 5.43 (s, 1H), 5.30 (d, J = 8.0 Hz, 1H), 5.04 (s, 3H), 4.70-4.58 (m, 1H), 4.49-4.36 (m, 2H), 4.08-3.65 (m, 4H), 1.60 (d, J = 4.8 Hz, 3H), 1.17 (d, J = 6.8 Hz, 3H). |

TABLE A-continued
| Compound # | Structure | Name | NMR |
|---|---|---|---|
| 360 | 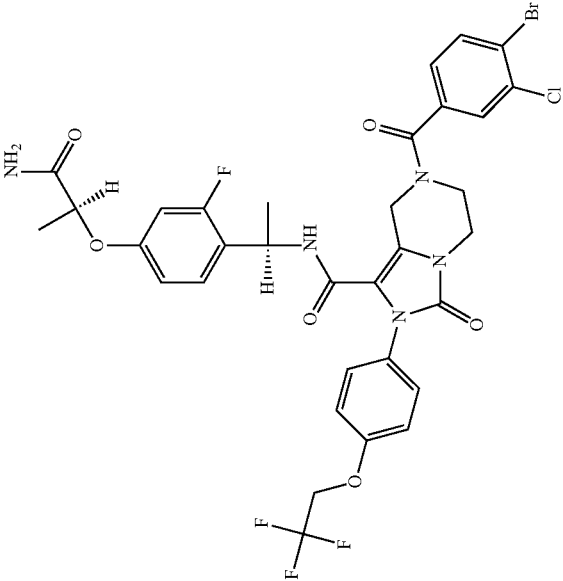 | 7-(4-bromo-3-chloro-benzoyl)-N-[rac-(1R)-1-[2-fluoro-4-[rac-(1S)-2-amino-1-methyl-2-oxo-ethoxy]phenyl]ethyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.71 (d, J = 8.4 Hz, 1H), 7.59 (d, J = 1.6 Hz, 1H), 7.39-7.30 (m, 2H), 7.24-7.20 (m, 1H), 7.10-7.00 (m, 2H), 6.91 (s, 1H), 6.60-6.48 (m, 2H), 6.25 (s, 1H), 5.43 (s, 1H), 5.30 (d, J = 8.0 Hz, 1H), 5.04 (s, 3H), 4.70-4.58 (m, 1H), 4.49-4.36 (m, 2H), 4.08-3.65 (m, 4H), 1.60 (d, J = 4.8 Hz, 3H), 1.17 (d, J = 6.8 Hz, 3H). |

TABLE A-continued
| Compound # | Structure | Name | NMR |
|---|---|---|---|
| 361 | 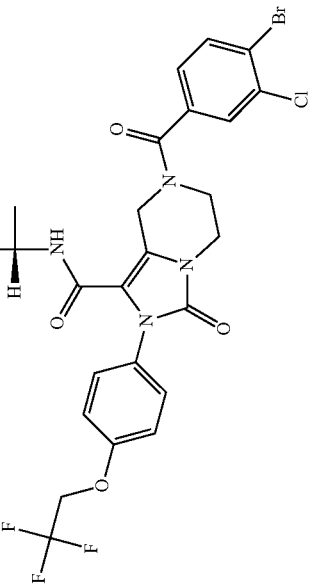 | 7-(4-bromo-3-chloro-benzoyl)-3-oxo-N-[rac-(1S)-1-[2-fluoro-4-[rac-(1R)-2-amino-1-methyl-2-oxo-ethoxy]phenyl]ethyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.71 (d, J = 8.4 Hz, 1H), 7.59 (d, J = 1.6 Hz, 1H), 7.39-7.30 (m, 2H), 7.24-7.20 (m, 1H), 7.10-7.00 (m, 2H), 6.91 (s, 1H), 6.60-6.48 (m, 2H), 6.25 (s, 1H), 5.43 (s, 1H), 5.30 (d, J = 8.0 Hz, 1H), 5.04 (s, 3H), 4.70-4.58 (m, 1H), 4.49-4.36 (m, 2H), 4.08-3.65 (m, 4H), 1.60 (d, J = 4.8 Hz, 3H), 1.17 (d, J = 6.8 Hz, 3H). |

TABLE A-continued

| Compound # | Structure | Name | NMR |
|---|---|---|---|
| 362 | 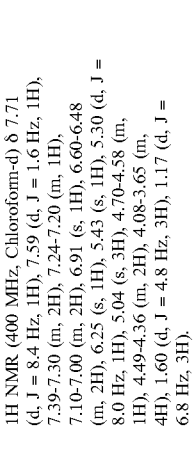 | 7-(4-bromo-3-chloro-benzoyl)-3-oxo-N-[rac-(1S)-1-[2-fluoro-4-[rac-(1S)-2-amino-1-methyl-2-oxo-ethoxy]phenyl]ethyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.71 (d, J = 8.4 Hz, 1H), 7.59 (d, J = 1.6 Hz, 1H), 7.39-7.30 (m, 2H), 7.24-7.20 (m, 1H), 7.10-7.00 (m, 2H), 6.91 (s, 1H), 6.60-6.48 (m, 2H), 6.25 (s, 1H), 5.43 (s, 1H), 5.30 (d, J = 8.0 Hz, 1H), 5.04 (s, 3H), 4.70-4.58 (m, 1H), 4.49-4.36 (m, 2H), 4.08-3.65 (m, 4H), 1.60 (d, J = 4.8 Hz, 3H), 1.17 (d, J = 6.8 Hz, 3H). |
| 363 | 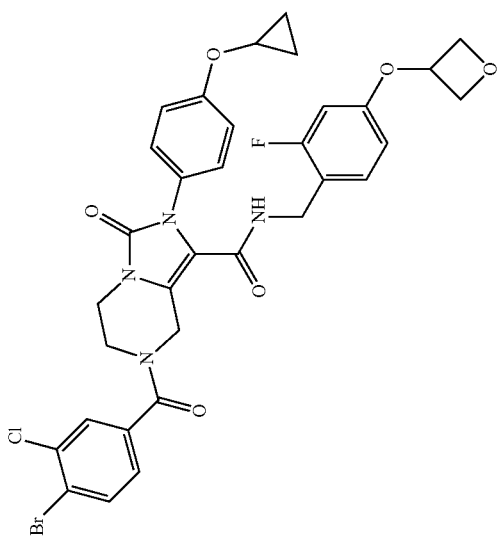 | 7-(4-bromo-3-chloro-benzoyl)-2-[4-(cyclopropoxy)phenyl]-N-[[2-fluoro-4-(oxetan-3-yloxy)phenyl]methyl]-3-oxo-6,8-dihydro-5H-imidazo[1,5-a]pyrazine-1-carboxamide | 1H NMR (400 MHz, DMSO-d6, 80° C.): 0.66-0.70 (m, 2H), 0.78-0.82 (m, 2H), 3.68 (t, J = 5.2 Hz, 2H), 3.80-3.87 (m, 3H), 4.20 (d, J = 4.8 Hz, 2H), 4.54 (t, J = 5.8 Hz, 2H), 4.84 (s, 2H), 4.92 (t, J = 6.5 Hz, 2H), 5.27 (quint, J = 5.3 Hz, 1H), 6.52 (d, J = 8.5 Hz, 1H), 6.57 (d, J = 11.8 Hz, 1H), 6.97-7.06 (m, 4H), 7.17-7.19 (m, 2H), 7.39 (d, J = 8.3 Hz, 1H), 7.74 (s, 1H), 7.85 (d, J = 8.1 Hz, 1H). |

| Compound # | Structure | Name | NMR |
|---|---|---|---|
| 364 | 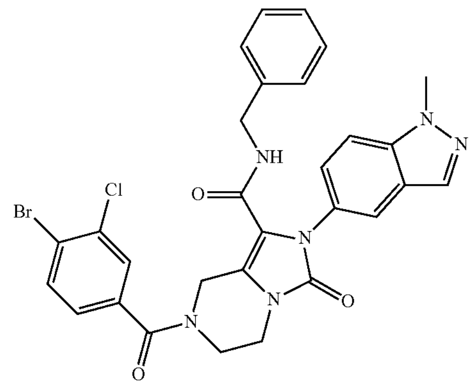 [SMILES: Cn1ncc2cc(-n3c(C(=O)NCc4ccccc4)c4n(c3=O)CCN(C(=O)c3ccc(Br)c(Cl)c3)C4)ccc21] | N-benzyl-7-(4-bromo-3-chloro-benzoyl)-2-(1-methylindazol-5-yl)-3-oxo-6,8-dihydro-5H-imidazo[1,5-a]pyrazine-1-carboxamide | 1H NMR (400 MHz, DMSO-d6, 80° C.): 3.71 (t, J = 5.4 Hz, 2H), 3.86 (m, J = 5.4 Hz, 2H), 4.07 (s, 3H), 4.21 (d, J = 5.5 Hz, 2H), 4.89 (s, 2H), 6.93 (d, J = 6.6 Hz, 2H), 7.11-7.19 (m, 4H), 6.26 (d, J = 8.9 Hz, 1H), 7.41 (d, J = 8.2 Hz, 1H), 7.61 (d, J = 8.9 Hz, 1H), 7.67 (s, 1H), 7.76 (s, 1H), 7.86 (d, J = 8.2 Hz, 1H), 8.04 (s, 1H). |
| 365 | 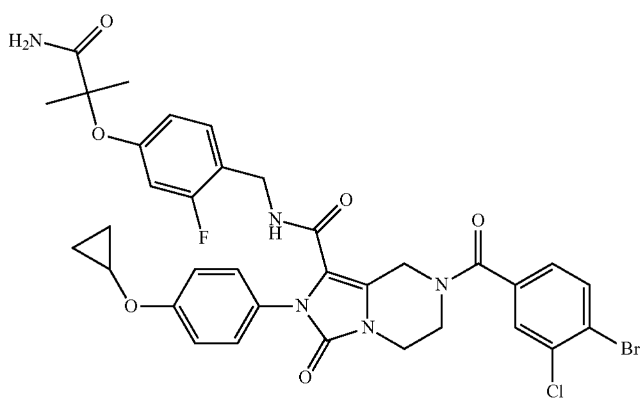 [SMILES: CC(C)(Oc1ccc(CNC(=O)c2c3n(c(=O)n2-c2ccc(OC4CC4)cc2)CCN(C(=O)c2ccc(Br)c(Cl)c2)C3)c(F)c1)C(N)=O] | N-[[4-(2-amino-1,1-dimethyl-2-oxo-ethoxy)-2-fluoro-phenyl]methyl]-7-(4-bromo-3-chloro-benzoyl)-2-[4-(cyclopropoxy)phenyl]-3-oxo-6,8-dihydro-5H-imidazo[1,5-a]pyrazine-1-carboxamide | 1H NMR (400 MHz, DMSO-d6, 80° C.): 0.66-0.72 (m, 2H), 0.79-0.84 (m, 2H), 1.45 (s, 6H), 3.68 (t, J = 5.0 Hz, 2H), 3.78-3.89 (m, 3H), 4.22 (d, J = 5.0 Hz, 2H), 4.85 (s, 2H), 6.64-6.69 (m, 2H) 6.96 (t, J = 8.3 Hz, 1H), 7.05-7.10 (m, 4H), 7.17-7.23 (m, 3H), 7.40 (d, J = 8.7 Hz, 1H), 7.75 (s, 1H), 7.86 (d, J = 8.7 Hz, 1H). |

TABLE A-continued

| Compound # | Structure | Name | NMR |
|---|---|---|---|
| 366 | 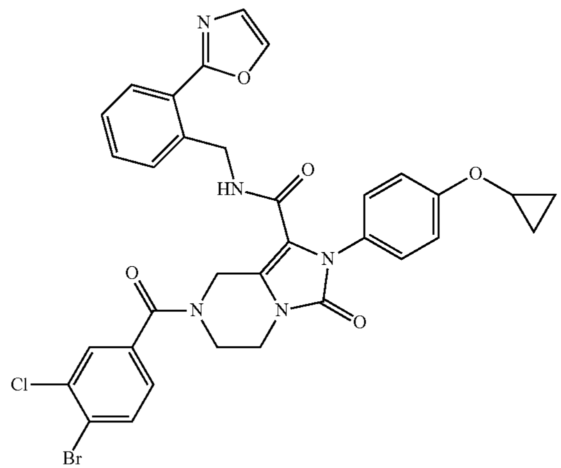 [SMILES: O=C(NCc1ccccc1-c1ncco1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-N-[(2-oxazol-2-yl)phenyl)methyl]-3-oxo-6,8-dihydro-5H-imidazo[1,5-a]pyrazine-1-carboxamide | 1H NMR (400 MHz, Chloroform-d) δ 7.92-7.89 (m, 1H), 7.75-7.57 (m, 3H), 7.50 (s, 1H), 7.42-7.35 (m, 2H), 7.22-7.18 (m, 1H), 7.12-7.00 (m, 3H), 6.93 (s, 1H), 6.88-6.78 (m, 2H), 4.98 (s, 2H), 4.57 (d, J = 5.2 Hz, 2H), 4.10-3.70 (m, 4H), 3.64 °C 3.60 (m, 1H), 0.81-0.71 (m, 4H). |
| 367 | 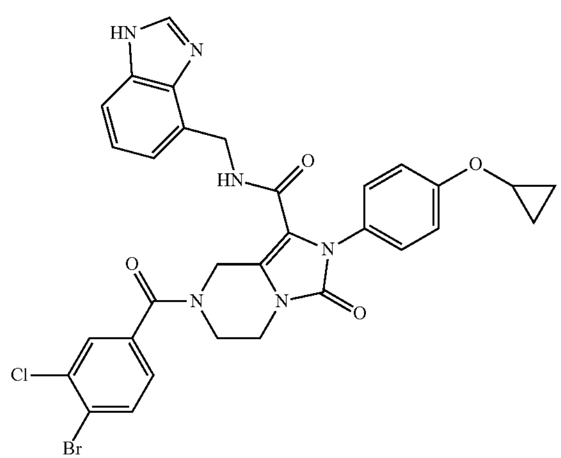 [SMILES: O=C(NCc1cccc2[nH]cnc12)c1c2n(c(=O)n1-c1ccc(OC3CC3)cc1)CCN(C(=O)c1ccc(Br)c(Cl)c1)C2] | N-(1H-benzoimidazol-4-ylmethyl)-7-(4-bromo-3-chloro-benzoyl)-2-[4-(cyclopropoxy)phenyl]-3-oxo-6,8-dihydro-5H-imidazo[1,5-a]pyrazine-1-carboxamide | 1H NMR (400 MHz, Chloroform-d) δ 7.96 (s, 1H), 7.74 (d, J = 8.0 Hz, 1H), 7.71-7.59 (m, 2H), 7.24 (s, 1H), 7.18-7.00 (m, 3H), 6.94 (d, J = 8.4 Hz, 2H), 6.85 (d, J = 7.2 Hz, 1H), 5.72 (s, 1H), 5.10 (s, 2H), 4.52 (s, 2H), 4.10-3.58 (m, 5H), 0.88-0.67 (m, 4H). |

TABLE A-continued

| Compound # | Structure | Name | NMR |
|---|---|---|---|
| 368 | 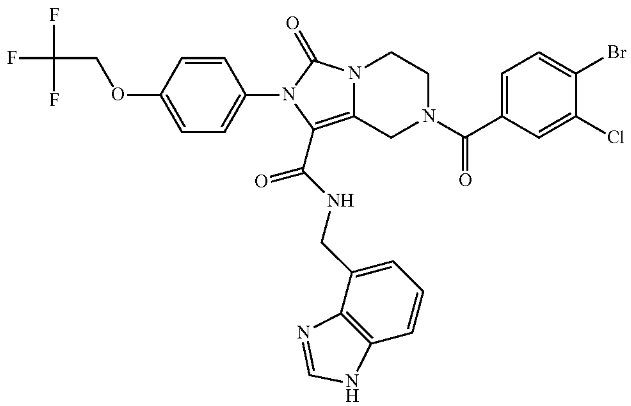 [SMILES: O=C(NCc1cccc2[nH]cnc12)c1c2n(c(=O)n1-c1ccc(OCC(F)(F)F)cc1)CCN(C(=O)c1ccc(Br)c(Cl)c1)C2] | N-(1H-benzimidazol-4-ylmethyl)-7-(4-bromo-3-chloro-benzoyl)-3-oxo-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 8.10-7.45 (m, 4H), 7.25 (d, J = 9.2 Hz, 1H), 7.19-7.00 (m, 3H), 6.98-6.59 (m, 3H), 5.08 (s, 2H), 4.55 (s, 2H), 4.27 (s, 2H), 4.11-3.65 (m, 4H). |
| 369 | 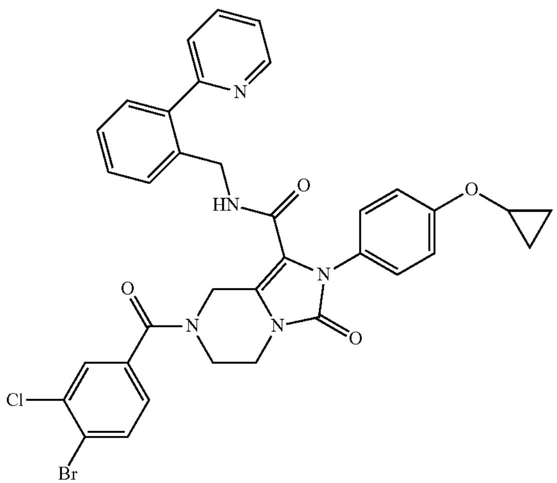 [SMILES: O=C(NCc1ccccc1-c1ccccn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-3-oxo-N-[[2-(2-pyridyl)phenyl]methyl]-6,8-dihydro-5H-imidazo[1,5-a]pyrazine-1-carboxamide | 1H NMR (300 MHz, Chloroform-d) δ 8.23 (s, 1H), 7.82-7.59 (m, 3H), 7.42 (d, J = 12.0 Hz, 5H), 7.27-7.04 (m, 5H), 6.79 (d, J = 8.6 Hz, 2H), 5.04 (s, 2H), 4.30 (d, J = 5.9 Hz, 2H), 4.06-3.75 (m, 4H), 3.53-3.42 (m, 1H), 0.77-0.46 (m, 4H). |

TABLE A-continued

| Compound # | Structure | Name | NMR |
|---|---|---|---|
| 370 | 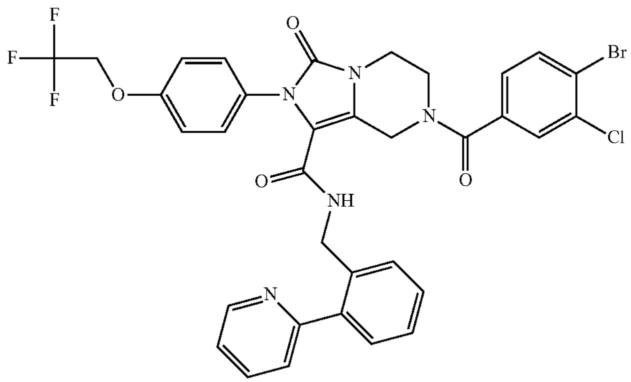 [SMILES: O=C(NCc1ccccc1-c1ccccn1)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-3-oxo-N-[[2-(2-pyridyl)phenyl]methyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 8.21 (s, 1H), 7.84-7.58 (m, 3H), 7.54-7.34 (m, 5H), 7.27-7.11 (m, 5H), 6.58 (d, J = 8.4 Hz, 2H), 5.04 (s, 2H), 4.29 (d, J = 5.9 Hz, 2H), 4.01 (q, J = 8.0 Hz, 4H), 3.84 (s, 2H). |
| 371 | 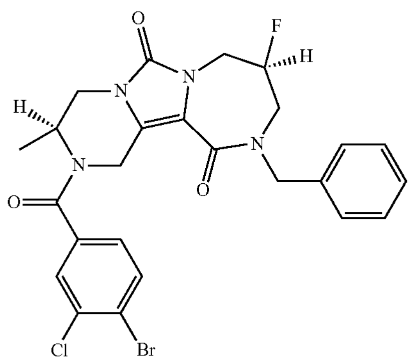 [SMILES: C[C@H]1Cn2c(c3n(c2=O)C[C@@H](F)CN(Cc2ccccc2)C3=O)CN1C(=O)c1ccc(Br)c(Cl)c1] | rac-(5S,11S)-13-benzyl-4-(4-bromo-3-chloro-benzoyl)-11-fluoro-5-methyl-4,7,9,13-tetrazatricyclo[7.5.0.0^2,7]tetradec-1-ene-8,14-dione | 1H NMR (400 MHz, Chloroform-d) δ 7.71 (d, J = 8.2 Hz, 1H), 7.55 (d, J = 2.0 Hz, 1H), 7.41-7.32 (m, 3H), 7.31-7.27 (m, 2H), 7.19 (dd, J = 8.2, 2.0 Hz, 1H), 5.60-4.85 (m, 3H), 4.62 (m, 1H), 4.40 (d, J = 6.7 Hz, 1H), 4.29 (d, J = 6.7 Hz, 1H), 4.19 (m, 1H), 4.07 (m, 1H), 3.84 (m, 2H), 3.65 (d, J = 13.1 Hz, 1H), 3.56-3.49 (m, 1H), 1.36 (d, J = 7.0 Hz, 3H). |

| Compound # | Structure | Name | NMR |
|---|---|---|---|
| 372 | 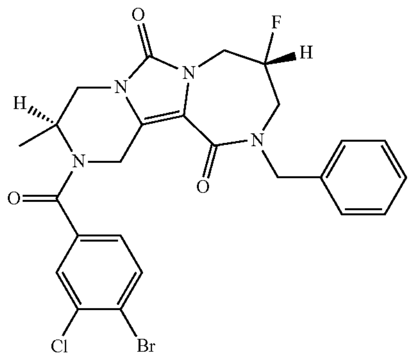 [SMILES: C[C@H]1Cn2c(c3n(c2=O)C[C@H](F)CN(Cc2ccccc2)C3=O)CN1C(=O)c1ccc(Br)c(Cl)c1] | rac-(5S,11R)-13-benzyl-4-(4-bromo-3-chloro-benzoyl)-11-fluoro-5-methyl-4,7,9,13-tetrazatricyclo[7.5.0.0^2,7]tetradec-1-ene-8,14-dione | 1H NMR (400 MHz, Chloroform-d) δ 7.71 (d, J = 8.2 Hz, 1H), 7.55 (d, J = 1.9 Hz, 1H), 7.39-7.31 (m, 3H), 7.27 (d, J = 1.9 Hz, 2H), 7.19 (dd, J = 8.2, 2.0 Hz, 1H), 5.65-4.85 (m, 3H), 4.57 (m, 1H), 4.41 (d, J = 6.4 Hz, 1H), 4.29 (d, J = 6.4 Hz, 1H), 4.14 (m, 2H), 3.83 (m, 2H), 3.73-3.64 (m, 1H), 3.60-3.50 (m, 1H), 1.32 (d, J = 7.0 Hz, 3H). |
| 373 | 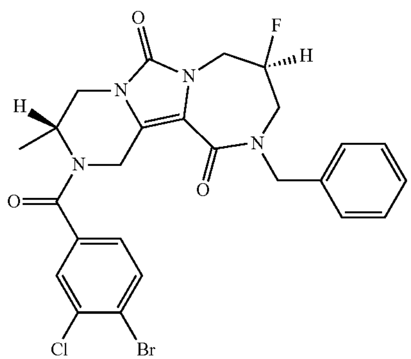 [SMILES: C[C@@H]1Cn2c(c3n(c2=O)C[C@@H](F)CN(Cc2ccccc2)C3=O)CN1C(=O)c1ccc(Br)c(Cl)c1] | rac-(5R,11S)-13-benzyl-4-(4-bromo-3-chloro-benzoyl)-11-fluoro-5-methyl-4,7,9,13-tetrazatricyclo[7.5.0.0^2,7]tetradec-1-ene-8,14-dione | 1H NMR (400 MHz, Chloroform-d) δ 7.71 (d, J = 8.2 Hz, 1H), 7.55 (d, J = 1.9 Hz, 1H), 7.39-7.31 (m, 3H), 7.27 (d, J = 1.9 Hz, 2H), 7.19 (dd, J = 8.2, 2.0 Hz, 1H), 5.65-4.85 (m, 3H), 4.57 (m, 1H), 4.41 (d, J = 6.4 Hz, 1H), 4.29 (d, J = 6.4 Hz, 1H), 4.14 (m, 2H), 3.83 (m, 2H), 3.73-3.64 (m, 1H), 3.60-3.50 (m, 1H), 1.32 (d, J = 7.0 Hz, 3H). |
| 374 | 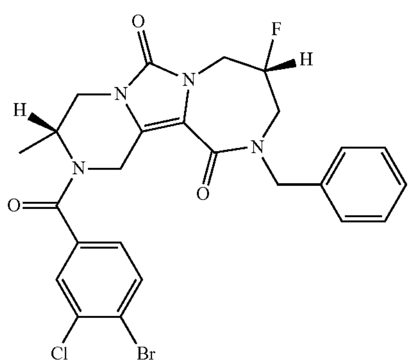 [SMILES: C[C@@H]1Cn2c(c3n(c2=O)C[C@H](F)CN(Cc2ccccc2)C3=O)CN1C(=O)c1ccc(Br)c(Cl)c1] | rac-(5R,11R)-13-benzyl-4-(4-bromo-3-chloro-benzoyl)-11-fluoro-5-methyl-4,7,9,13-tetrazatricyclo[7.5.0.0^2,7]tetradec-1-ene-8,14-dione | 1H NMR (400 MHz, Chloroform-d) δ 7.71 (d, J = 8.2 Hz, 1H), 7.55 (d, J = 2.0 Hz, 1H), 7.41-7.32 (m, 3H), 7.31-7.27 (m, 2H), 7.19 (dd, J = 8.2, 2.0 Hz, 1H), 5.60-4.85 (m, 3H), 4.62 (m, 1H), 4.40 (d, J = 6.7 Hz, 1H), 4.29 (d, J = 6.7 Hz, 1H), 4.19 (m, 1H), 4.07 (m, 1H), 3.84 (m, 2H), 3.65 (d, J = 13.1 Hz, 1H), 3.56-3.49 (m, 1H), 1.36 (d, J = 7.0 Hz, 3H). |

TABLE A-continued

| Compound # | Structure | Name | NMR |
|---|---|---|---|
| 375 | 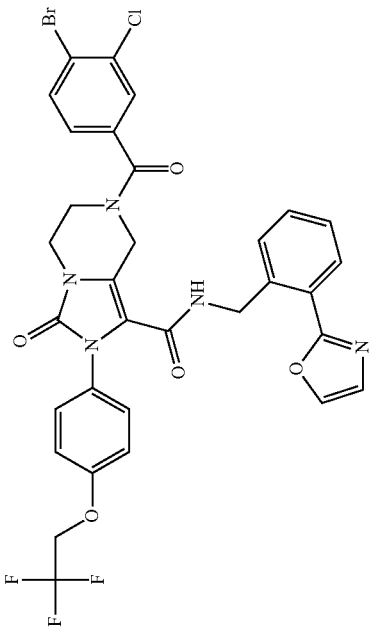 | 7-(4-bromo-3-chloro-benzoyl)-N-[[2-(2-oxazol-2-ylphenyl)methyl]-3-oxo-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.97-7.87 (m, 1H), 7.73-7.59 (m, 3H), 7.57-7.38 (m, 3H), 7.25-7.19 (m, 1H), 7.17-7.03 (m, 3H), 6.91 (s, 1H), 6.72-6.58 (m, 2H), 5.15 (s, 2H), 4.58 (d, J = 5.4 Hz, 2H), 4.30-4.15 (m, 2H), 4.14-3.65 (m, 4H). |
| 376 | 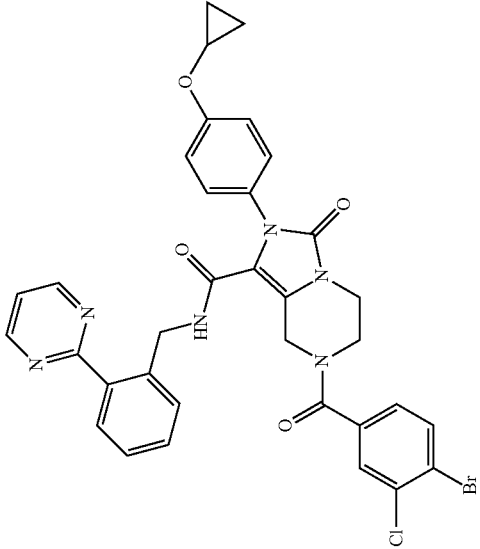 | 7-(4-bromo-3-chloro-benzoyl)-2-[4-(cyclopropoxy)phenyl]-3-oxo-N-[[2-pyrimidin-2-ylphenyl)methyl]-6,8-dihydro-5H-imidazo[1,5-a]pyrazine-1-carboxamide | 1H NMR (300 MHz, Chloroform-d) δ 8.60 (d, J = 4.9 Hz, 2H), 8.16-8.07 (m, 1H), 7.73 (d, J = 8.2 Hz, 1H), 7.64 (s, 1H), 7.45 (dd, J = 5.7, 3.5 Hz, 3H), 7.26 (dd, J = 8.2, 2.0 Hz, 1H), 7.18 (t, J = 4.9 Hz, 1H), 7.09 (d, J = 8.8 Hz, 2H), 6.99 (s, 1H), 6.73 (d, J = 8.7 Hz, 2H), 5.07 (s, 2H), 4.49 (d, J = 6.6 Hz, 2H), 3.94 (m, 4H), 3.46 (dt, J = 6.0, 3.1 Hz, 1H), 0.79-0.53 (m, 4H). |

TABLE A-continued

| Compound # | Structure | Name | NMR |
|---|---|---|---|
| 377 | 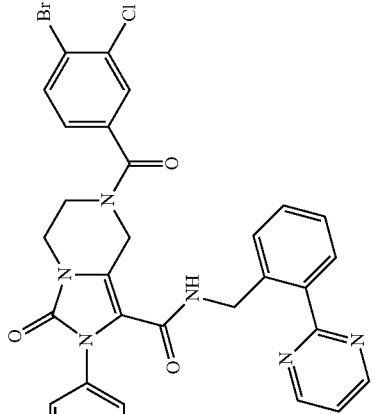 | 7-(4-bromo-3-chloro-benzoyl)-3-oxo-N-[(2-pyrimidin-2-yl)phenyl)methyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 8.59 (d, J = 4.9 Hz, 2H), 8.16 (dd, J = 6.1, 3.2 Hz, 1H), 7.74 (d, J = 8.2 Hz, 1H), 7.64 (d, J = 2.0 Hz, 1H), 7.56-7.43 (m, 3H), 7.26 (dd, J = 8.2, 2.0 Hz, 1H), 7.21-7.06 (m, 3H), 7.00 (s, 1H), 6.56 (d, J = 8.7 Hz, 2H), 5.06 (s, 2H), 4.50 (d, J = 5.6 Hz, 1H), 4.18-3.68 (m, 6H). |
| 378 | 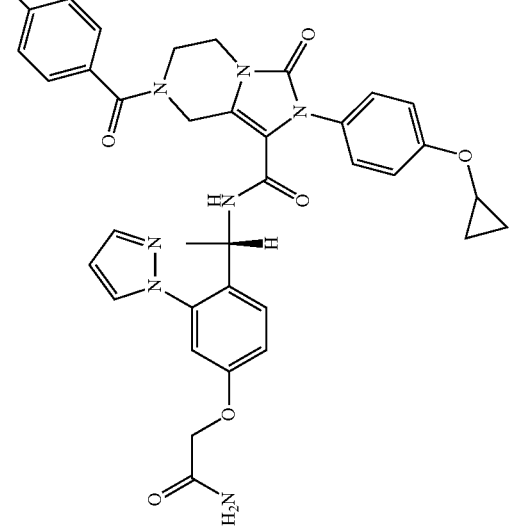 | 7-(4-bromo-3-chloro-benzoyl)-2-[4-(cyclopropoxy)phenyl]-3-oxo-N-[rac-(1S)-1-[4-(2-amino-2-oxo-ethoxy)-2-pyrazol-1-yl-phenyl]ethyl]-6,8-dihydro-5H-imidazo[1,5-a]pyrazine-1-carboxamide | 1H NMR (300 MHz, Chloroform-d) δ 7.81-7.51 (m, 4H), 7.30 (s, 1H), 7.24-7.17 (m, 1H), 7.15-6.94 (m, 3H), 6.91-6.75 (m, 2H), 6.67-6.40 (m, 2H), 6.10 (d, J = 7.4 Hz, 1H), 5.84 (s, 1H), 4.98 (s, 3H), 4.53 (s, 2H), 3.86 (m, 5H), 0.94-0.68 (m, 7H). |

TABLE A-continued

| Compound # | Structure | Name | NMR |
|---|---|---|---|
| 379 | 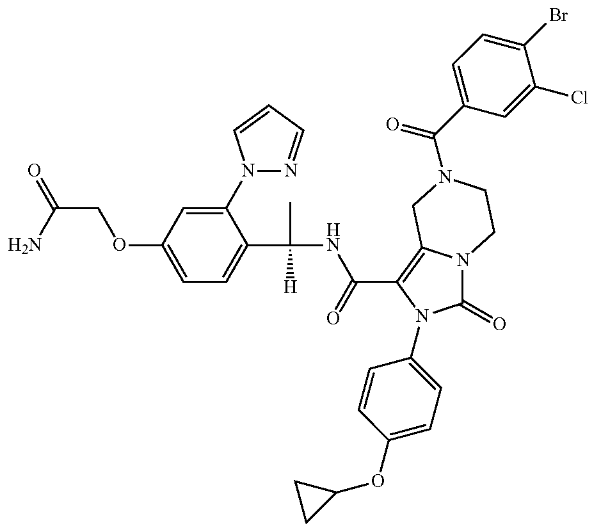 [SMILES: C[C@@H](NC(=O)c1c2n(c(=O)n1-c1ccc(OC3CC3)cc1)CCN(C(=O)c1ccc(Br)c(Cl)c1)C2)c1ccc(OCC(N)=O)cc1-n1cccn1] | 7-(4-bromo-3-chloro-benzoyl)-2-[4-(cyclopropoxy)phenyl]-3-oxo-N-[rac-(1R)-1-[4-(2-amino-2-oxo-ethoxy)-2-pyrazol-1-yl-phenyl]ethyl]-6,8-dihydro-5H-imidazo[1,5-a]pyrazine-1-carboxamide | 1H NMR (300 MHz, Chloroform-d) δ 7.81-7.51 (m, 4H), 7.30 (s, 1H), 7.24-7.17 (m, 1H), 7.15-6.94 (m, 3H), 6.91-6.75 (m, 2H), 6.67-6.40 (m, 2H), 6.10 (d, J = 7.4 Hz, 1H), 5.84 (s, 1H), 4.98 (s, 3H), 4.53 (s, 2H), 3.86 (m, 5H), 0.94-0.68 (m, 7H). |

TABLE A-continued
| Compound # | Structure | Name | NMR |
|---|---|---|---|
| 380 | 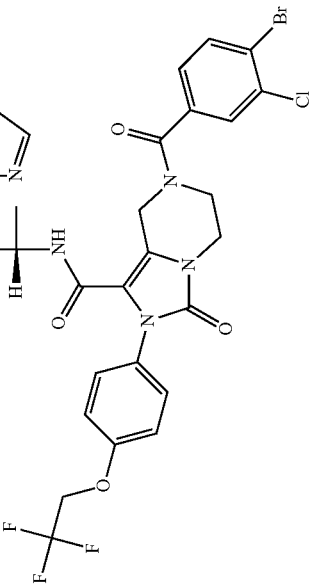 | 7-(4-bromo-3-chloro-benzoyl)-3-oxo-N-[rac-(1S)-1-[4-(2-amino-2-oxo-ethoxy)-2-pyrazol-1-yl-phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.68-7.48 (m, 4H), 7.35-7.29 (m, 2H), 7.23-7.03 (m, 2H), 6.98-6.76 (m, 4H), 6.68-6.40 (m, 3H), 5.76 (s, 1H), 5.15-4.85 (m, 3H), 4.53 (s, 2H), 4.39-4.22 (m, 2H), 4.12-3.74 (m, 4H), 0.90-0.70 (m, 3H). |

| Compound # | Structure | Name | NMR |
|---|---|---|---|
| 381 | 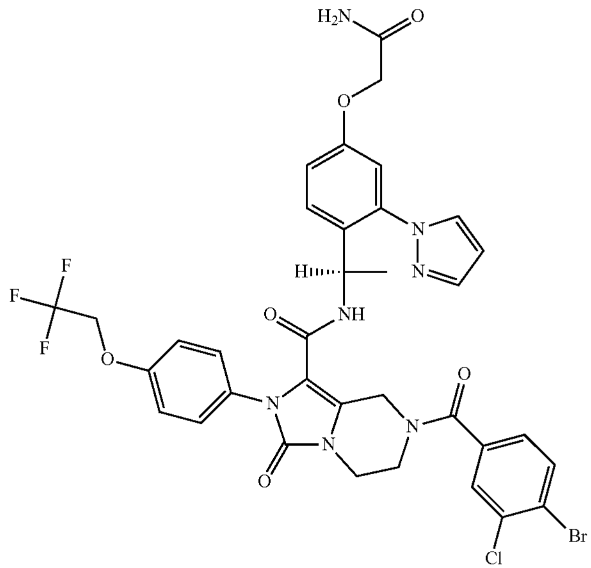 [SMILES: C[C@@H](NC(=O)c1c2n(c(=O)n1-c1ccc(OCC(F)(F)F)cc1)CCN(C(=O)c1ccc(Br)c(Cl)c1)C2)c1ccc(OCC(N)=O)cc1-n1cccn1] | 7-(4-bromo-3-chloro-benzoyl)-3-oxo-N-[rac-(1R)-1-[4-(2-amino-2-oxo-ethoxy)-2-pyrazol-1-yl-phenyl]ethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 7.68-7.48 (m, 4H), 7.35-7.29 (m, 2H), 7.23-7.03 (m, 2H), 6.98-6.76 (m, 4H), 6.68-6.40 (m, 3H), 5.76 (s, 1H), 5.15-4.85 (m, 3H), 4.53 (s, 2H), 4.39-4.22 (m, 2H), 4.12-3.74 (m, 4H), 0.90-0.70 (m, 3H). |
| 382 | 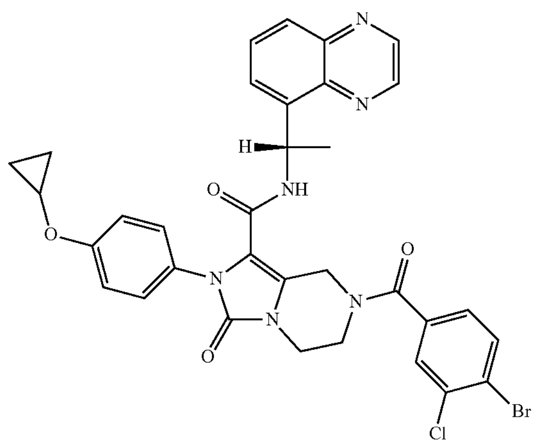 [SMILES: C[C@H](NC(=O)c1c2n(c(=O)n1-c1ccc(OC3CC3)cc1)CCN(C(=O)c1ccc(Br)c(Cl)c1)C2)c1cccc2nccnc12] | 7-(4-bromo-3-chloro-benzoyl)-2-[4-(cyclopropoxy)phenyl]-3-oxo-N-[rac-(1S)-1-quinoxalin-5-ylethyl]-6,8-dihydro-5H-imidazo[1,5-a]pyrazine-1-carboxamide | 1H NMR (300 MHz, Chloroform-d) δ 8.83 (d, J = 1.8 Hz, 1H), 8.52 (s, 1H), 8.01 (dd, J = 8.5, 1.4 Hz, 1H), 7.68 (dd, J = 14.9, 7.9 Hz, 2H), 7.61 (d, J = 2.0 Hz, 1H), 7.50 (d, J = 7.2 Hz, 2H), 7.27-7.20 (m, 3H), 6.98 (d, J = 8.8 Hz, 2H), 6.92 (d, J = 9.1 Hz, 1H), 5.75 (d, J = 9.1 Hz, 1H), 5.03 (s, 2H), 3.98 (s, 2H), 3.83 (s, 2H), 3.70-3.60 (m, 1H), 1.44 (d, J = 6.9 Hz, 3H), 0.90-0.68 (m, 4H). |

TABLE A-continued

| Compound # | Structure | Name | NMR |
|---|---|---|---|
| 383 | 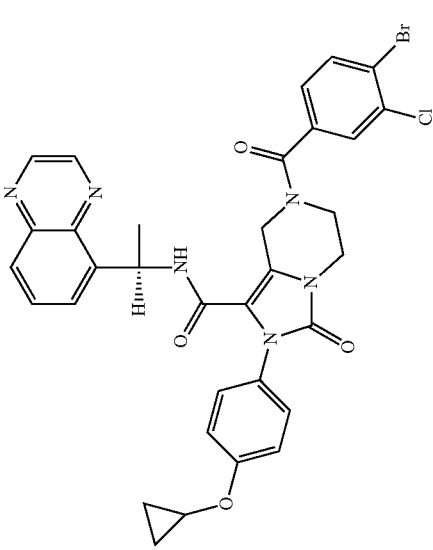 | 7-(4-bromo-3-chloro-benzoyl)-2-[4-(cyclopropoxy)phenyl]-3-oxo-N-[rac-(1R)-1-quinoxalin-5-ylethyl]-6,8-dihydro-5H-imidazo[1,5-a]pyrazine-1-carboxamide | 1H NMR (300 MHz, Chloroform-d) δ 8.83 (d, J = 1.8 Hz, 1H), 8.52 (s, 1H), 8.01 (dd, J = 8.5, 1.4 Hz, 1H), 7.68 (dd, J = 14.9, 7.9 Hz, 2H), 7.61 (d, J = 2.0 Hz, 1H), 7.50 (d, J = 7.2 Hz, 1H), 7.27-7.20 (m, 3H), 6.98 (d, J = 8.8 Hz, 2H), 6.92 (d, J = 9.1 Hz, 1H), 5.75 (d, J = 9.1 Hz, 1H), 5.03 (s, 2H), 3.98 (s, 2H), 3.83 (s, 2H), 3.70-3.60 (m, 1H), 1.44 (d, J = 6.9 Hz, 3H), 0.90-0.68 (m, 4H). |
| 384 | 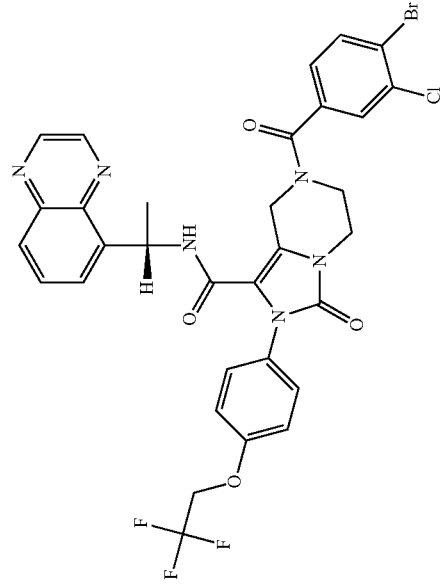 | 7-(4-bromo-3-chloro-benzoyl)-N-[rac-(1S)-1-quinoxalin-5-ylethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 8.82 (d, J = 1.8 Hz, 1H), 8.46 (s, 1H), 8.02 (d, J = 8.9 Hz, 1H), 7.70 (dd, J = 14.3, 8.1 Hz, 2H), 7.61 (d, J = 1.9 Hz, 1H), 7.54 (d, J = 7.1 Hz, 1H), 7.28-7.21 (m, 3H), 7.05 (s, 1H), 6.77 (d, J = 8.9 Hz, 2H), 5.71 (s, 1H), 5.03 (s, 2H), 4.41-4.17 (m, 2H), 4.00 (s, 2H), 3.82 (s, 2H), 1.48 (d, J = 6.9 Hz, 3H). |

| Compound # | Structure | Name | NMR |
|---|---|---|---|
| 385 | 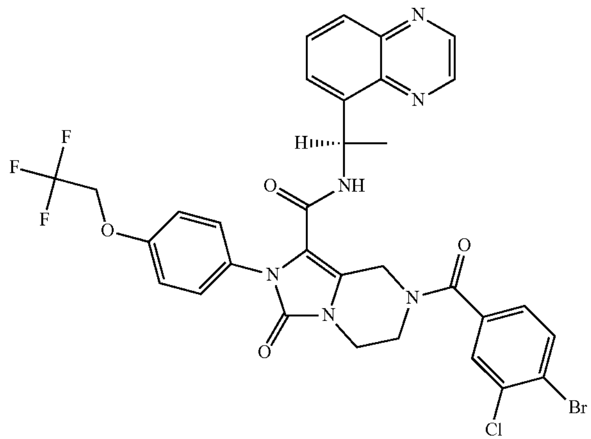 [SMILES: C[C@@H](NC(=O)c1c2n(c(=O)n1-c1ccc(OCC(F)(F)F)cc1)CCN(C(=O)c1ccc(Br)c(Cl)c1)C2)c1cccc2nccnc12] | 7-(4-bromo-3-chloro-benzoyl)-3-oxo-N-[rac-(1R)-1-quinoxalin-5-ylethyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 8.83 (d, J = 1.8 Hz, 1H), 8.46 (s, 1H), 8.02 (d, J = 8.2 Hz, 1H), 7.70 (dd, J = 14.2, 8.0 Hz, 2H), 7.61 (d, J = 1.9 Hz, 1H), 7.54 (d, J = 7.1 Hz, 1H), 7.27-7.21 (m, 3H), 7.05 (s, 1H), 6.77 (d, J = 8.9 Hz, 2H), 5.70 (s, 1H), 5.03 (s, 2H), 4.33-4.15 (m, 2H), 4.00 (s, 2H), 3.82 (s, 2H), 1.48 (d, J = 6.9 Hz, 3H). |
| 386 | 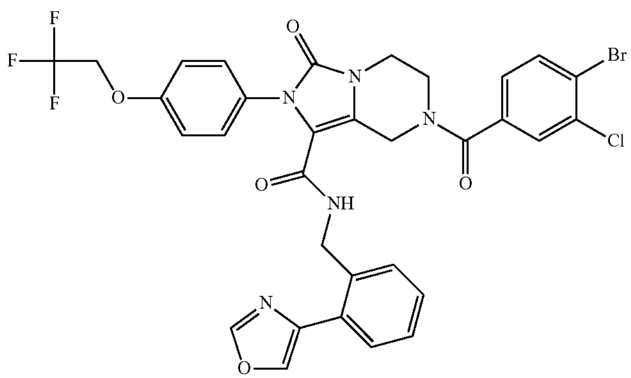 [SMILES: O=C(NCc1ccccc1-c1cocn1)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-N-[(2-oxazol-4-ylphenyl)methyl]-3-oxo-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.77 (s, 1H), 7.69 (d, J = 8.2 Hz, 2H), 7.60 (d, J = 2.0 Hz, 1H), 7.39 (dd, J = 5.5, 3.6 Hz, 2H), 7.31 (dd, J = 5.7, 3.3 Hz, 2H), 7.21 (dd, J = 8.2, 2.0 Hz, 1H), 7.19-7.12 (m, 2H), 6.84 (br, 1H), 6.73 (d, J = 8.5 Hz, 2H), 5.01 (s, 2H), 4.37 (s, 2H), 4.22 (q, J = 8.0 Hz, 2H), 4.15-3.60 (m, 4H). |

| Compound # | Structure | Name | NMR |
|---|---|---|---|
| 387 | 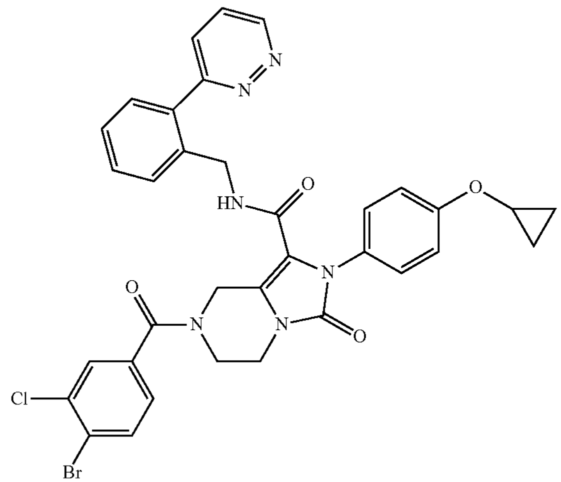 [SMILES: O=C(NCc1ccccc1-c1cccnn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-3-oxo-N-[(2-pyridazin-3-ylphenyl)methyl]-6,8-dihydro-5H-imidazo[1,5-a]pyrazine-1-carboxamide | 1H NMR (300 MHz, Chloroform-d) δ 9.14 (dd, J = 4.8, 1.8 Hz, 1H), 7.72-7.54 (m, 4H), 7.43 (m, 4H), 7.16-7.09 (m, 3H), 6.95-6.70 (m, 3H), 5.02 (s, 2H), 4.33 (s, 2H), 4.05-3.85 (m, 4H), 3.48 (dt, J = 5.9, 3.1 Hz, 1H), 0.75-0.53 (m, 4H). |
| 388 | 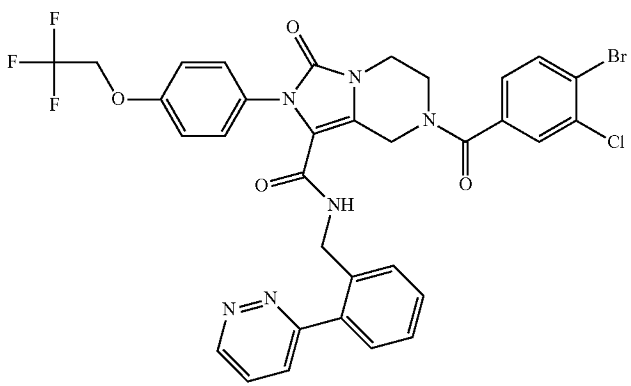 [SMILES: O=C(NCc1ccccc1-c1cccnn1)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-3-oxo-N-[(2-pyridazin-3-ylphenyl)methyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 9.12 (dd, J = 4.9, 1.8 Hz, 1H), 7.72-7.36 (m, 8H), 7.27-7.12 (m, 3H), 7.02 (t, J = 6.2 Hz, 1H), 6.58 (d, J = 8.9 Hz, 2H), 5.02 (s, 2H), 4.31 (d, J = 5.5 Hz, 2H), 4.18-3.71 (m, 6H). |

TABLE A-continued

| Compound # | Structure | Name | NMR |
|---|---|---|---|
| 389 | 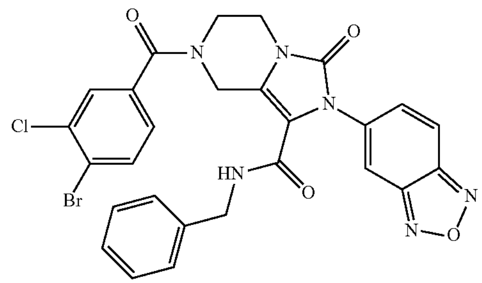 [SMILES: O=C(NCc1ccccc1)c1c2n(c(=O)n1-c1ccc3nonc3c1)CCN(C(=O)c1ccc(Br)c(Cl)c1)C2] | 2-(2,1,3-benzoxadiazol-5-yl)-N-benzyl-7-(4-bromo-3-chloro-benzoyl)-3-oxo-6,8-dihydro-5H-imidazo[1,5-a]pyrazine-1-carboxamide | 1H-NMR (DMSO, 600 MHz, 80° C.): 3.74 (t, J = 5.5 Hz, 2H); 3.81-3.91 (m, 2H); 4.31 (d, J = 5.8 Hz, 2H); 4.91 (s, 2H); 7.09-7.18 (m, 2H); 7.18-7.27 (m, 3H); 7.40 (dd, J = 8.0 Hz, 1.9 Hz, 1H); 7.46 (dd, J = 9.5 Hz, 1.6 Hz, 1H); 7.75 (d, J = 1.9 Hz, 1H); 7.79-7.83 (m, 1H); 7.85 (d, J = 8.0 Hz, 1H); 8.0 (d, J = 9.5 Hz, 1H); 8.04 (br. s, 1H) ppm. |
| 390 | 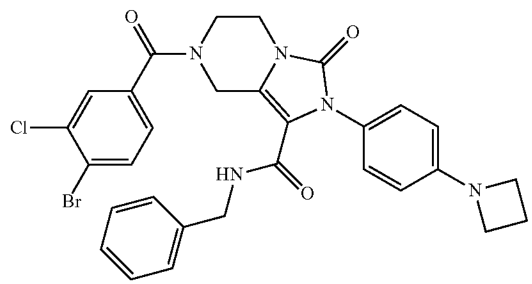 [SMILES: O=C(NCc1ccccc1)c1c2n(c(=O)n1-c1ccc(N3CCC3)cc1)CCN(C(=O)c1ccc(Br)c(Cl)c1)C2] | 2-[4-(azetidin-1-yl)phenyl]-N-benzyl-7-(4-bromo-3-chloro-benzoyl)-3-oxo-6,8-dihydro-5H-imidazo[1,5-a]pyrazine-1-carboxamide | 1H NMR (400 MHz, DMSO-d6, 80°C): 2.35 (quint., J = 7.3 Hz, 2H), 3.67 (t, J = 5.5 Hz, 2H), 3.84 (t, J = 7.1 Hz, 6H), 4.23 (d, J = 5.5 Hz, 2H), 4.86 (s, 2H), 6.39 (d, J = 8.3 Hz, 2H), 6.77 (br s, 1H), 7.01 (d, J = 6.5 Hz, 2H), 7.06 (d, J = 8.3 Hz, 2H), 7.21-7.28 (m, 3H), 7.39 (d, J = 8.1 Hz, 1H), 7.74 (s, 1H), 7.85 (d, J = 8.1 Hz, 1H). |
| 391 | 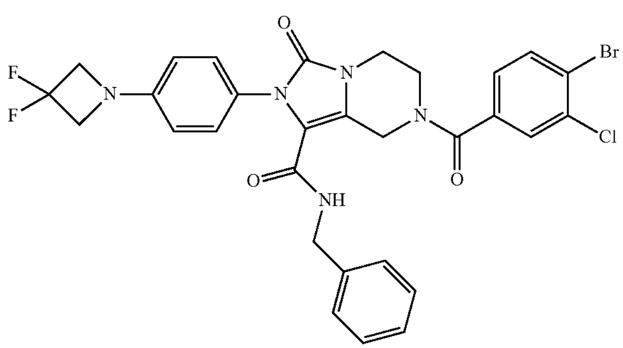 [SMILES: O=C(NCc1ccccc1)c1c2n(c(=O)n1-c1ccc(N3CC(F)(F)C3)cc1)CCN(C(=O)c1ccc(Br)c(Cl)c1)C2] | N-benzyl-7-(4-bromo-3-chloro-benzoyl)-2-[4-(3,3-difluoroazetidin-1-yl)phenyl]-3-oxo-6,8-dihydro-5H-imidazo[1,5-a]pyrazine-1-carboxamide | 1H NMR (400 MHz, DMSO-d6, 80° C.): 3.68 (t, J = 5.0 Hz, 2H), 3.83 (br s, 2H), 4.23-4.31 (m, 6H), 4.86 (s, 2H), 6.57 (d, J = 8.0 Hz, 2H), 6.99 (br s, 1H) 7.03 (d, J = 6.9 Hz, 2H), 7.14 (d, J = 7.7 Hz, 2H), 7.19-7.27 (m, 3H), 7.39 (d, J = 7.7 Hz, 1H), 7.74 (s, 1H), 7.85 (d, J = 8.2 Hz, 1H). |

TABLE A-continued

| Compound # | Name | Structure | NMR |
|---|---|---|---|
| 392 | N-benzyl-7-(4-bromo-3-chloro-benzoyl)-2-[4-(3,3-difluoropyrrolidin-1-yl)phenyl]-3-oxo-6,8-dihydro-5H-imidazo[1,5-a]pyrazine-1-carboxamide | 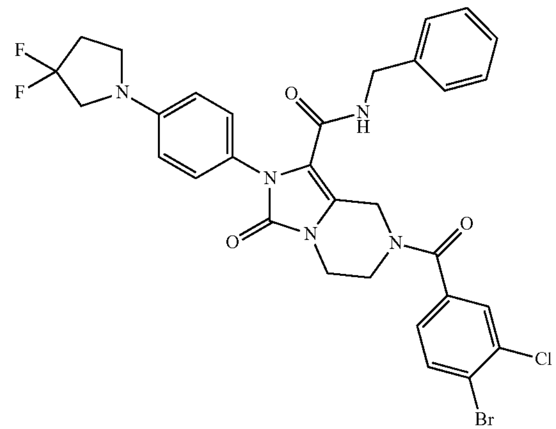 [SMILES: O=C(NCc1ccccc1)c1c2n(c(=O)n1-c1ccc(N3CCC(F)(F)C3)cc1)CCN(C(=O)c1ccc(Br)c(Cl)c1)C2] | 1H NMR (400 MHz, DMSO-d6, 80° C.): 2.52-2.60 (m, 2H), 3.50 (t, J = 7.1 Hz, 2H), 3.66-3.72 (m, 4H), 3.84 (br s, 2H), 4.23 (d, J = 5.6 Hz, 2H), 4.86 (s, 2H), 6.62 (d, J = 8.9 Hz, 2H), 6.86 (br s, 1H), 7.00 (d, J = 6.3 Hz, 2H), 7.12 (d, J = 8.8 Hz, 2H), 7.19-7.23 (m, 3H), 7.40 (dd, J = 8.2, 2.0 Hz, 1H), 7.74 (d, J = 1.8 Hz, 1H), 7.85 (d, J = 8.1 Hz, 1H). |
| 393 | N-benzyl-7-(4-bromo-3-chloro-benzoyl)-3-oxo-2-[4-(2,2,2-trifluoro-1,1-dimethyl-ethoxy)phenyl]-6,8-dihydro-5H-imidazo[1,5-a]pyrazine-1-carboxamide | 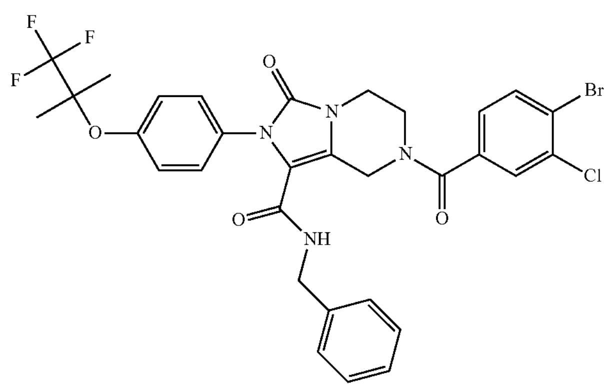 [SMILES: CC(C)(Oc1ccc(-n2c(C(=O)NCc3ccccc3)c3n(c2=O)CCN(C(=O)c2ccc(Br)c(Cl)c2)C3)cc1)C(F)(F)F] | 1H NMR (400 MHz, DMSO-d6, 80° C.): 1.44 (s, 6H), 3.70 (t, J = 5.0 Hz, 2H), 3.84 (br s, 2H), 4.27 (d, J = 5.6 Hz, 2H), 4.87 (s, 2H), 7.08-7.11 (m, 4H), 7.20-7.28 (m, 5H), 7.40 (d, J = 8.1 Hz, 1H), 7.44 (br s, 1H), 7.75 (s, 1H), 7.86 (td, J = 7.9 Hz, 1H) |

TABLE A-continued

| Compound # | Structure | Name | NMR |
|---|---|---|---|
| 394 | 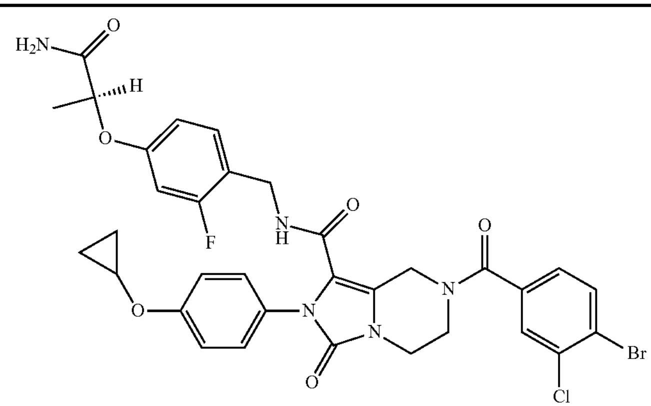 | 7-(4-bromo-3-chloro-benzoyl)-2-[4-(cyclopropoxy)phenyl]-N-[[2-fluoro-4-[rac-(1S)-2-amino-1-methyl-2-oxo-ethoxy]phenyl]methyl]-3-oxo-6,8-dihydro-5H-imidazo[1,5-a]pyrazine-1-carboxamide | 1H NMR (400 MHz, DMSO-d6, 80° C.): 0.67-0.71 (m, 2H), 0.80-0.84 (m, 2H), 1.46 (d, J = 6.6 Hz, 3H), 3.68 (t, J = 5.3 Hz, 2H), 3.80-3.87 (m, 3H), 4.21 (d, J = 5.2 Hz, 2H), 4.65 (q, J = 6.7 Hz, 1H), 4.86 (s, 2H), 6.67-6.72 (m, 2H), 6.98-7.20 (m, 8H), 7.40 (d, J = 8.2 Hz, 1H), 7.75 (s, 1H), 7.87 (d, J = 8.2 Hz, 1H). |
| 395 | 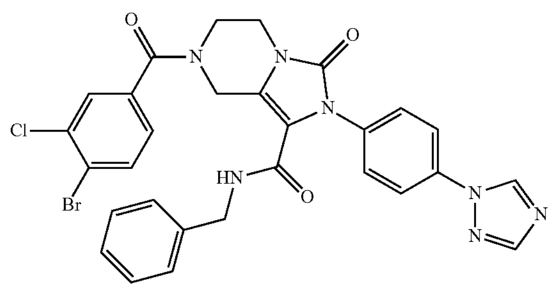 [SMILES: O=C(NCc1ccccc1)c1c2n(c(=O)n1-c1ccc(-n3cncn3)cc1)CCN(C(=O)c1ccc(Br)c(Cl)c1)C2] | N-benzyl-7-(4-bromo-3-chloro-benzoyl)-3-oxo-2-[4-(1,2,4-triazol-1-yl)phenyl]-6,8-dihydro-5H-imidazo[1,5-a]pyrazine-1-carboxamide | 1H NMR (400 MHz, DMSO-d6, 80° C.): 3.72 (t, J = 5.4 Hz, 2H), 3.85 (br s, 2H), 4.29 (d, J = 5.8 Hz, 2H), 4.87 (s, 2H), 7.10 (d, J = 6.7 Hz, 2H), 7.16-7.24 (m, 3H), 7.40 (d, J = 8.4 Hz, 1H), 7.44 (d, J = 8.3 Hz, 2H), 7.75 (s, 2H), 7.85-7.87 (m, 3H), 8.21 (s, 1H), 9.19 (s, 1H). |
| 396 | 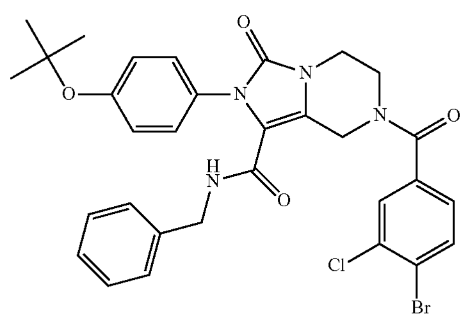 [SMILES: CC(C)(C)Oc1ccc(-n2c(C(=O)NCc3ccccc3)c3n(c2=O)CCN(C(=O)c2ccc(Br)c(Cl)c2)C3)cc1] | N-benzyl-7-(4-bromo-3-chloro-benzoyl)-2-(4-tert-butoxyphenyl)-3-oxo-6,8-dihydro-5H-imidazo[1,5-a]pyrazine-1-carboxamide | 1H-NMR (DMSO, 600 MHz, 80° C.): 1.34 (s, 9H), 3.70 (dd, J = 5.4 Hz, 4.9 Hz, 2H), 3.85 (br.s., 2H), 4.26 (d, J = 5.8 Hz, 2H), 4.87 (s, 2H), 6.99 (d, J = 9.0 Hz, 2H), 7.08 (d, J = 6.7 Hz, 2H), 7.11-7.17 (m, 1H), 7.18-7.28 (m, 5H), 7.40 (dd, J = 8.4 Hz, 1.7 Hz, 1H), 7.75 (d, J = 1.4 Hz, 1H), 7.85 (d, J = 8.3 Hz, 1H) ppm. |

TABLE A-continued

| Compound # | Structure | Name | NMR |
|---|---|---|---|
| 397 | 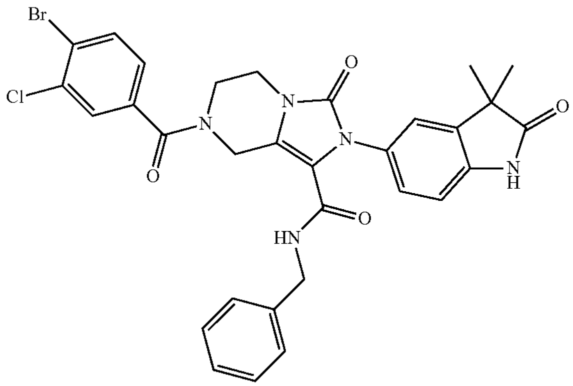 [SMILES: CC1(C)C(=O)Nc2ccc(-n3c(C(=O)NCc4ccccc4)c4n(c3=O)CCN(C(=O)c3ccc(Br)c(Cl)c3)C4)cc21] | N-benzyl-7-(4-bromo-3-chloro-benzoyl)-2-(3,3-dimethyl-2-oxo-indolin-5-yl)-3-oxo-6,8-dihydro-5H-imidazo[1,5-a]pyrazine-1-carboxamide | 1H-NMR (DMSO, 600 MHz, 80° C.): 1.20 (s, 6H), 3.70 (dd, J = 5.9 Hz, 5.0 Hz, 2H), 3.85 (br.s., 2H), 4.24 (d, J = 5.4 Hz, 2H), 4.87 (s, 2H), 6.86 (br. s., 1H), 6.90 (d, J = 7.9 Hz, 1H), 6.97-7.03 (m, 2H), 7.13 (dd, J = 8.1 Hz, 1.9 Hz, 1H), 7.15-7.25 (m, 4H), 7.40 (dd, J = 8.3 Hz, 1.6 Hz, 1H), 7.75 (d, J = 1.8 Hz, 1H), 7.86 (d, J = 8.2 Hz, 1H), 10.15 (s, 1H) ppm. |
| 398 | 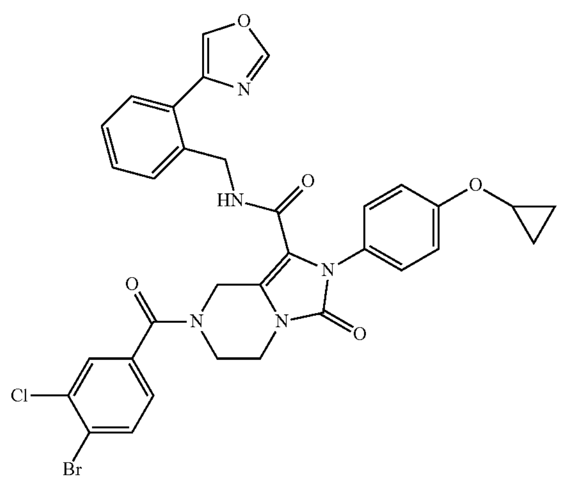 [SMILES: O=C(NCc1ccccc1-c1cocn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropxy)phenyl]-N-[(2-oxazol-4-ylphenyl)methyl]-3-oxo-6,8-dihydro-5H-imidazo[1,5-a]pyrazine-1-carboxamide | 1H NMR (400 MHz, Chloroform-d) δ 7.76-7.56 (m, 4H), 7.49-7.35 (m, 2H), 7.33-7.27 (m, 2H), 7.23-7.18 (m, 1H), 7.18-7.11 (m, 2H), 6.98-6.87 (m, 2H), 6.77 (s, 1H), 5.01 (s, 2H), 4.37 (s, 2H), 4.02 (s, 2H), 3.80 (s, 2H), 3.69-3.49 (m, 1H), 0.82-0.62 (m, 4H). |

TABLE A-continued

| Compound # | Structure | Name | NMR |
|---|---|---|---|
| 399 | 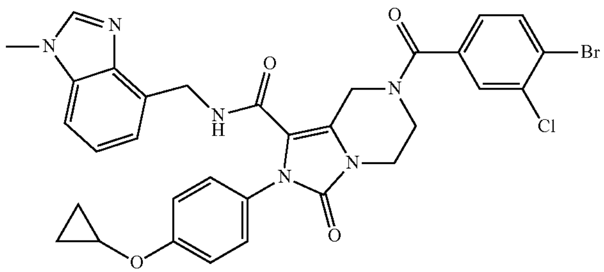 [SMILES: Cn1cnc2c(CNC(=O)c3c4n(c(=O)n3-c3ccc(OC5CC5)cc3)CCN(C(=O)c3ccc(Br)c(Cl)c3)C4)cccc21] | 7-(4-bromo-3-chloro-benzoyl)-2-[4-(cyclopropoxy)phenyl]-N-[(1-methylbenzimidazol-4-yl)methyl]-3-oxo-6,8-dihydro-5H-imidazo[1,5-a]pyrazine-1-carboxamide | 1H NMR (400 MHz, Chloroform-d) δ 7.76-7.50 (m, 3H), 7.28-7.18 (m, 5H), 6.97 (s, 1H), 6.80 (d, J = 8.3 Hz, 2H), 6.41-5.93 (s, 1H), 5.15 (s, 2H), 4.73 (s, 2H), 4.15 (s, 2H), 3.84 (s, 5H), 3.58 (s, 1H), 0.85-0.59 (m, 4H). |
| 400 | 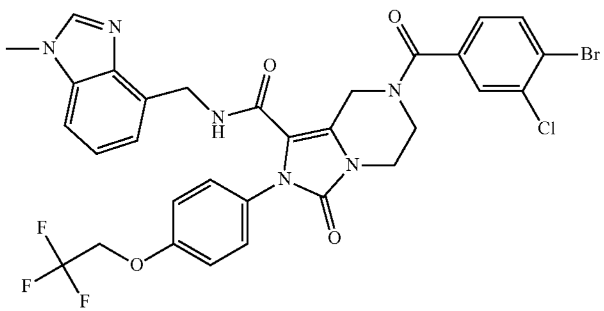 [SMILES: Cn1cnc2c(CNC(=O)c3c4n(c(=O)n3-c3ccc(OCC(F)(F)F)cc3)CCN(C(=O)c3ccc(Br)c(Cl)c3)C4)cccc21] | 7-(4-bromo-3-chloro-benzoyl)-N-[(1-methylbenzimidazol-4-yl)methyl]-3-oxo-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 7.85-7.53 (m, 3H), 7.38-7.52 (m, 1H), 7.19-7.26 (m, 2H), 7.14 (d, J = 8.4 Hz, 2H), 7.04 (s, 1H), 6.55-6.80 (m, 2H), 4.60-5.20 (m, 4H), 4.21 (q, J = 8.1 Hz, 2H), 4.15-3.96 (s, 1H), 3.96-3.60 (m, 6H). |
| 401 | 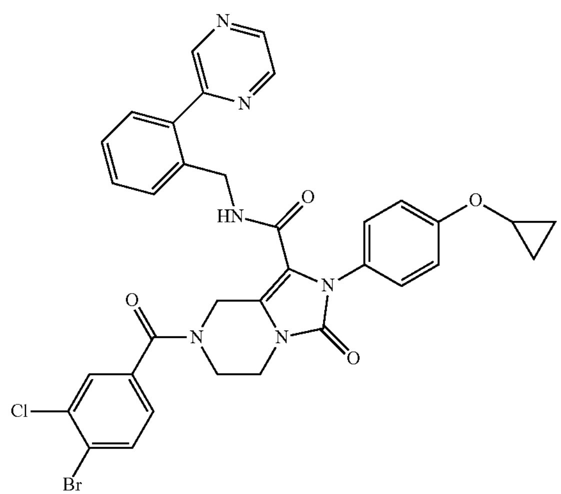 [SMILES: O=C(NCc1ccccc1-c1cnccn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-3-oxo-N-[(2-pyrazin-2-ylphenyl)methyl]-6,8-dihydro-5H-imidazo[1,5-a]pyrazine-1-carboxamide | 1H NMR (300 MHz, Chloroform-d) δ 8.75 (s, 1H), 8.50 (s, 1H), 8.20 (s, 1H), 7.72 (d, J = 8.4 Hz, 1H), 7.61 (s, 1H), 7.54-7.40 (m, 4H), 7.26-7.20 (m, 1H), 7.19-7.08 (m, 2H), 6.90-6.74 (m, 2H), 6.60 (s, 1H), 5.03 (s, 2H), 4.28 (s, 2H), 4.01 (s, 2H), 3.81 (s, 2H), 3.48-3.44 (m, 1H), 0.75-0.65 (m, 2H), 0.62-0.49 (m, 2H). |

TABLE A-continued

| Compound # | Structure | Name | NMR |
|---|---|---|---|
| 402 | 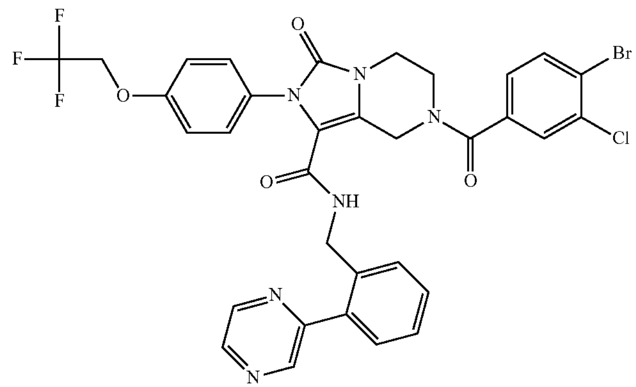 [SMILES: O=C(NCc1ccccc1-c1cnccn1)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-3-oxo-N-[(2-pyrazin-2-yl)phenyl)methyl]-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 8.75 (s, 1H), 8.50 (d, J = 2.1 Hz, 1H), 8.19 (s, 1H), 7.72 (d, J = 8.4 Hz, 1H), 7.60 (s, 1H), 7.54-7.40 (m, 4H), 7.26-7.12 (m, 3H), 6.65 (d, J = 8.7 Hz, 3H), 5.02 (s, 2H), 4.28 (d, J = 3.3 Hz, 2H), 4.17-3.91 (m, 4H), 3.81 (s, 2H). |
| 403 | 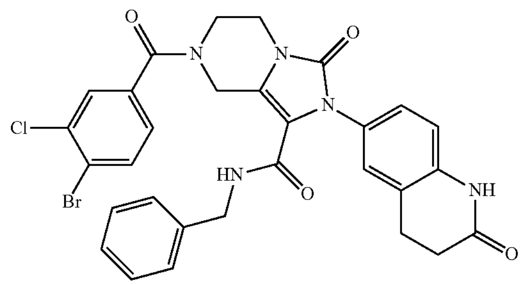 [SMILES: O=C1CCc2cc(-n3c(C(=O)NCc4ccccc4)c4n(c3=O)CCN(C(=O)c3ccc(Br)c(Cl)c3)C4)ccc2N1] | N-benzyl-7-(4-bromo-3-chloro-benzoyl)-3-oxo-2-(2-oxo-3,4-dihydro-1H-quinolin-6-yl)-6,8-dihydro-5H-imidazo[1,5-a]pyrazine-1-carboxamide | 1H-NMR (DMSO, 600 MHz, 80° C.): 2.43 (dd, J = 7.6 Hz, 7.2 Hz, 2H); 2.84 (dd, J = 7.6 Hz, 7.2 Hz, 2H); 3.68 (dd, J = 5.8 Hz, 5.6 Hz, 2H); 3.80-3.88 (m, 2H); 4.26 (d, J = 5.7 Hz, 2H); 4.86 (s, 2H); 6.90 (d, J = 8.4 Hz, 1H); 6.99-7.11 (m, 5H); 7.17-7.27 (m, 3H); 7.39 (dd, J = 8.2 Hz, 1.9 Hz, 1H); 7.74 (d, J = 1.8 Hz, 1H); 7.85 (d, J = 8.2 Hz, 1H); 9.88 (s, 1H) ppm. |
| 404 | 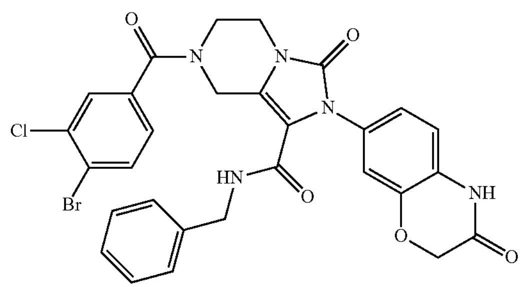 [SMILES: O=C1COc2cc(-n3c(C(=O)NCc4ccccc4)c4n(c3=O)CCN(C(=O)c3ccc(Br)c(Cl)c3)C4)ccc2N1] | N-benzyl-7-(4-bromo-3-chloro-benzoyl)-3-oxo-2-(3-oxo-4H-1,4-benzoxazin-7-yl)-6,8-dihydro-5H-imidazo[1,5-a]pyrazine-1-carboxamide | 1H-NMR (DMSO, 600 MHz, 80° C.): 3.68 (t, J = 5.5 Hz, 2H); 3.83 (s, 2H); 4.27 (d, J = 5.5 Hz, 2H); 4.55 (s, 2H); 4.84 (s, 2H); 6.84 (dd, J = 8.2 Hz, 2.2 Hz, 1H); 6.88 (d, J = 1.6 Hz, 1H); 6.92 (d, J = 8.2 Hz, 1H); 7.07 (d, J = 7.0 Hz, 2H); 7.18-7.32 (m, 4H); 7.39 (dd, J = 8.1 Hz, 1.6 Hz, 1H); 7.73 (d, J = 1.6 Hz, 1H); 7.84 (d, J = 8.1 Hz, 1H); 10.52 (s, 1H) ppm. |

TABLE A-continued

| Compound # | Structure | Name | NMR |
|---|---|---|---|
| 405 | 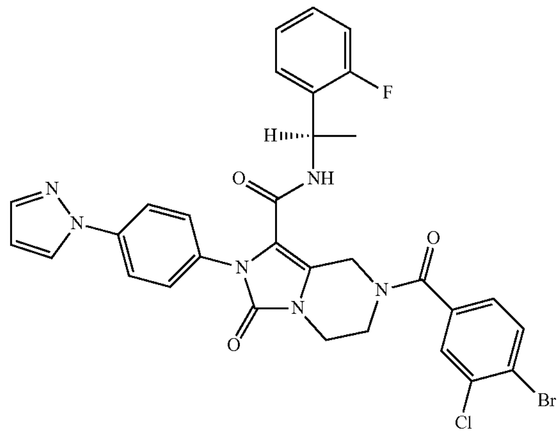 [SMILES: C[C@@H](NC(=O)c1c2n(c(=O)n1-c1ccc(-n3cccn3)cc1)CCN(C(=O)c1ccc(Br)c(Cl)c1)C2)c1ccccc1F] | 7-(4-bromo-3-chloro-benzoyl)-3-oxo-2-(4-pyrazol-1-ylphenyl)-N-[rac-(1R)-1-(2-fluorophenyl)ethyl]-6,8-dihydro-5H-imidazo[1,5-a]pyrazine-1-carboxamide | 1H-NMR (DMSO, 600 MHz, 80° C.): 1.28 (d, J = 6.8 Hz, 3H), 3.69-3.76 (m, 2H), 3.81-3.93 (m, 2H), 4.85 (s, 2H), 5.10-5.19 (m, 1H), 6.55 (dd, J = 1.8 Hz, 1.7 Hz, 1H), 6.99-7.07 (m, 2H), 7.12-7.18 (m, 1H), 7.19-7.25 (m, 1H), 7.32-7.44 (m, 4H), 7.73-7.77 (m, 2H), 7.82-7.88 (m, 3H), 8.39 (d, J = 2.4 Hz, 1H) ppm. |
| 406 | 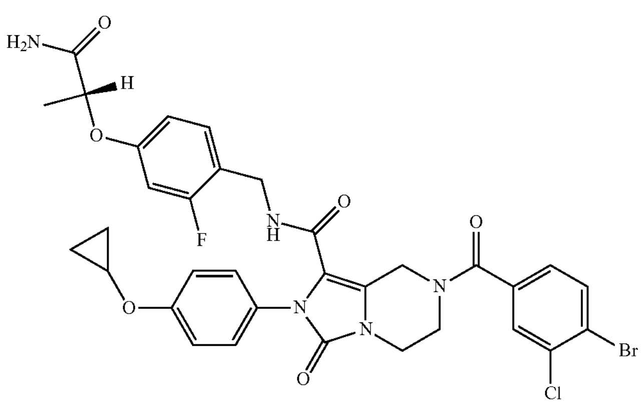 [SMILES: C[C@@H](Oc1ccc(CNC(=O)c2c3n(c(=O)n2-c2ccc(OC4CC4)cc2)CCN(C(=O)c2ccc(Br)c(Cl)c2)C3)c(F)c1)C(N)=O] | 7-(4-bromo-3-chloro-benzoyl)-2-[4-(cyclopropoxy)phenyl]-N-[[2-fluoro-4-[rac-(1R)-2-amino-1-methyl-2-oxo-ethoxy]phenyl]methyl]-3-oxo-6,8-dihydro-5H-imidazo[1,5-a]pyrazine-1-carboxamide | 1H NMR (400 MHz, DMSO-d6, 80° C.): 0.66-0.70 (m, 2H), 0.79-0.83 (m, 2H), 1.44 (d, J = 6.6 Hz, 3H), 3.67 (t, J = 5.8 Hz, 2H), 3.80-3.87 (m, 3H), 4.20 (d, J = 5.5 Hz, 2H), 4.64 (q, J = 6.6 Hz, 1H), 4.85 (s, 2H), 6.66-6.71 (m, 2H), 6.97-7.02 (m, 2H), 7.05 (d, J = 8.9 Hz, 3H), 7.18 (d, J = 8.8 Hz, 3H), 7.39 (dd, J = 8.1, 1.9 Hz, 1H), 7.74 (d, J = 1.8 Hz, 1H), 7.85 (d, J = 8.3 Hz, 1H). |

| Compound # | Structure | Name | NMR |
|---|---|---|---|
| 407 | 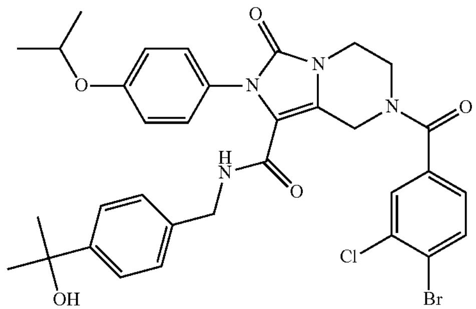 [SMILES: CC(C)Oc1ccc(-n2c(C(=O)NCc3ccc(C(C)(C)O)cc3)c3n(c2=O)CCN(C(=O)c2ccc(Br)c(Cl)c2)C3)cc1] | 7-(4-bromo-3-chloro-benzoyl)-N-[[4-(1-hydroxy-1-methyl-ethyl)phenyl]methyl]-2-(4-isopropoxyphenyl)-3-oxo-6,8-dihydro-5H-imidazo[1,5-a]pyrazine-1-carboxamide | 1H NMR (400 MHz, DMSO-d6, 80° C.): 1.30 (d, J = 6.0 Hz, 6H), 1.43 (s, 6H), 3.68 (t, J = 5.8 Hz, 2H), 3.83 (t, J = 5.3 Hz, 2H), 4.22 (d, J = 5.6 Hz, 2H), 4.56-4.63 (m, 2H), 4.87 (s, 2H), 6.92-6.96 (m, 4H), 7.10 (br s, 1H), 7.18 (d, J = 8.9 Hz, 1H), 7.34 (d, J = 8.3 Hz, 2H), 7.40 (dd, J = 8.2, 2.0 Hz, 1H), 7.75 (d, J = 1.9 Hz, 1H), 7.86 (d, J = 8.3 Hz, 1H). |
| 408 | 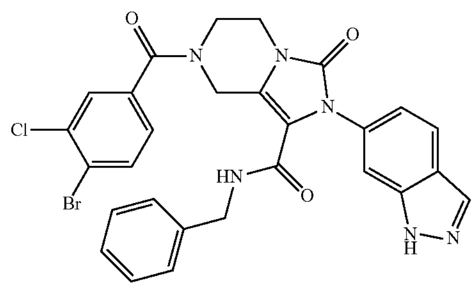 [SMILES: O=C(NCc1ccccc1)c1c2n(c(=O)n1-c1ccc3cn[nH]c3c1)CCN(C(=O)c1ccc(Br)c(Cl)c1)C2] | N-benzyl-7-(4-bromo-3-chloro-benzoyl)-2-(1H-indazol-6-yl)-3-oxo-6,8-dihydro-5H-imidazo[1,5-a]pyrazine-1-carboxamide | 1H-NMR (DMSO, 600 MHz, 80° C.): 3.72 (dd, J = 5.7 Hz, 5.5 Hz, 2H); 3.81-3.91 (m, 2H); 4.23 (d, J = 5.8 Hz, 2H); 4.88 (s, 2H); 6.92-7.01 (m, 3H); 7.10-7.19 (m, 3H); 7.30-7.37 (m, 1H); 7.40 (dd, J = 8.2 Hz, 1.9 Hz, 1H); 7.52 (s, 1H); 7.75 (dd, J = 5.2 Hz, 3.2 Hz, 2H); 7.85 (d, J = 8.2 Hz, 1H); 8.08 (s, 1H); 12.92 (s, 1H) ppm. |
| 409 | 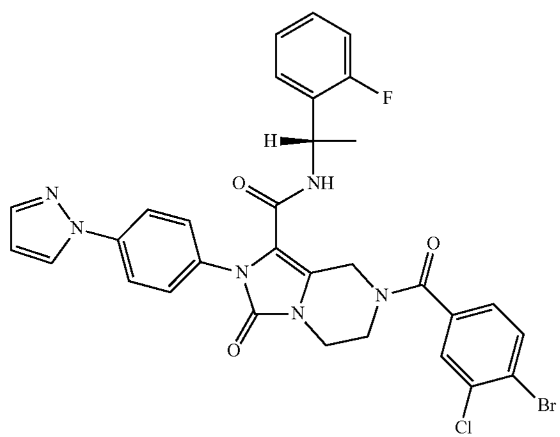 [SMILES: C[C@H](NC(=O)c1c2n(c(=O)n1-c1ccc(-n3cccn3)cc1)CCN(C(=O)c1ccc(Br)c(Cl)c1)C2)c1ccccc1F] | 7-(4-bromo-3-chloro-benzoyl)-3-oxo-2-(4-pyrazol-1-ylphenyl)-N-[rac-(1S)-1-(2-fluorophenyl)ethyl]-6,8-dihydro-5H-imidazo[1,5-a]pyrazine-1-carboxamide | 1H-NMR (DMSO, 600 MHz, 80° C.): 1.28 (d, J = 6.8 Hz, 3H), 3.69-3.76 (m, 2H), 3.81-3.93 (m, 2H), 4.85 (s, 2H), 5.10-5.19 (m, 1H), 6.55 (dd, J = 1.8 Hz, 1.7 Hz, 1H), 6.99-7.07 (m, 2H), 7.12-7.18 (m, 1H), 7.19-7.25 (m, 1H), 7.32-7.44 (m, 4H), 7.73-7.77 (m, 2H), 7.82-7.88 (m, 3H), 8.39 (d, J = 2.4 Hz, 1H) ppm. |

TABLE A-continued

| Compound # | Structure | Name | NMR |
|---|---|---|---|
| 410 | 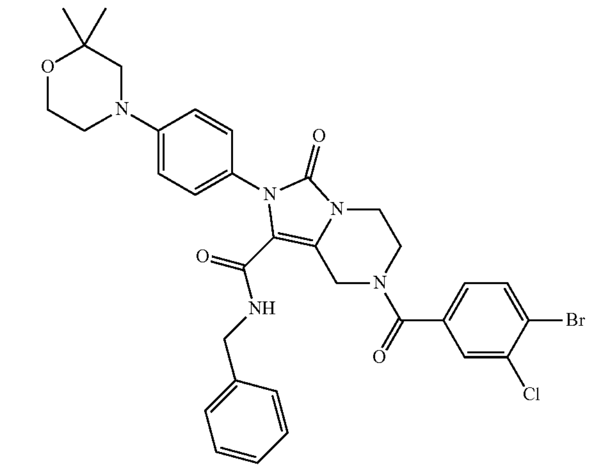 [SMILES: CC1(C)CN(c2ccc(-n3c(C(=O)NCc4ccccc4)c4n(c3=O)CCN(C(=O)c3ccc(Br)c(Cl)c3)C4)cc2)CCO1] | N-benzyl-7-(4-bromo-3-chlorobenzoyl)-2-[4-(2,2-dimethylmorpholin-4-yl)phenyl]-3-oxo-6,8-dihydro-5H-imidazo[1,5-a]pyrazine-1-carboxamide | 1H NMR (400 MHz, DMSO-d6, 80° C.): 1.26 (s, 6H), 2.98 (s, 2H), 3.09 (t, J = 4.5 Hz, 2H), 3.68 (t, J = 5.2 Hz, 2H), 3.78 (t, J = 4.5 Hz, 2H), 3.83 (br s, 2H), 4.24 (d, J = 5.4 Hz, 2H), 4.86 (s, 2H), 6.91 (d, J = 8.2 Hz, 2H), 6.97 (br s, 1H), 7.02 (d, J = 6.4 Hz, 2H), 7.12 (d, J = 8.2 Hz, 2H), 7.19-7.25 (m, 3H), 7.40 (d, J = 8.2 Hz, 1H), 7.74 (s, 1H), 7.85 (d, J = 8.2 Hz, 1H). |
| 411 | 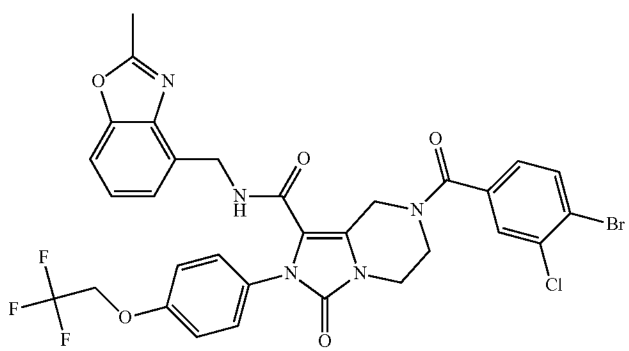 [SMILES: Cc1nc2c(CNC(=O)c3c4n(c(=O)n3-c3ccc(OCC(F)(F)F)cc3)CCN(C(=O)c3ccc(Br)c(Cl)c3)C4)cccc2o1] | 7-(4-bromo-3-chloro-benzoyl)-N-[(2-methyl-1,3-benzoxazol-4-yl)methyl]-3-oxo-2-[4-(2,2,2-trifluoroethoxy)phenyl]-6,8-dihydro-5H-imidazo[1,5-a]pyrazine-1-carboxamide | 1H NMR (400 MHz, DMSO-d6, 80° C.): 2.60 (s, 3H), 3.68 (t, J = 5.4 Hz, 2H), 3.82 (br s, 2H), 4.57 (d, J = 5.5 Hz, 2H), 4.70 (d, J = 8.7 Hz, 2H), 4.87 (s, 2H), 6.98 (d, J = 7.4 Hz, 1H), 7.04 (d, J = 8.7 Hz, 2H), 7.20 (d, J = 7.9 Hz, 1H), 7.24 (d, J = 8.7 Hz, 2H), 7.34 (br s, 1H), 7.38 (d, J = 8.2 Hz, 1H), 7.47 (d, J = 8.2 Hz, 1H), 7.74 (s, 1H), 7.83 (d, J = 8.3 Hz, 1H). |

TABLE A-continued

| Compound # | Structure | Name | NMR |
|---|---|---|---|
| 412 | 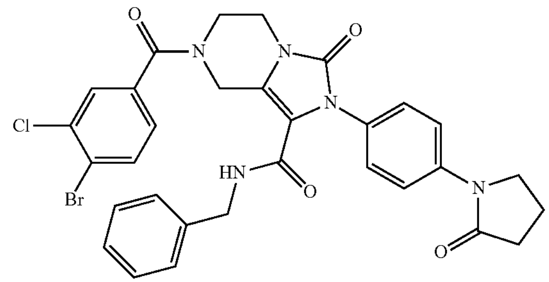 [SMILES: O=C(NCc1ccccc1)c1c2n(c(=O)n1-c1ccc(N3CCCC3=O)cc1)CCN(C(=O)c1ccc(Br)c(Cl)c1)C2] | N-benzyl-7-(4-bromo-3-chloro-benzoyl)-3-oxo-2-[4-(2-oxopyrrolidin-1-yl)phenyl]-6,8-dihydro-5H-imidazo[1,5-a]pyrazine-1-carboxamide | 1H NMR (400 MHz, DMSO-d6, 80° C.): 2.11 (quint, J = 7.5 Hz, 2H), 2.55 (m, 2H), 3.06 (t, J = 5.5 Hz, 2H), 3.83-3.86 (m, 4H), 4.26 (d, J = 5.5 Hz, 2H), 4.85 (s, 2H), 7.06 (d, J = 6.6 Hz, 2H), 7.19-7.28 (m, 5H), 7.40 (dd, J = 8.2 Hz, 1.6 Hz, 1H), 7.43 (brs, 1H), 7.68 (d, J = 8.8 Hz, 2H), 7.75 (d, J = 1.6 Hz, 1H), 7.85 (d, J = 8.5 Hz, 1H) |
| 413 | 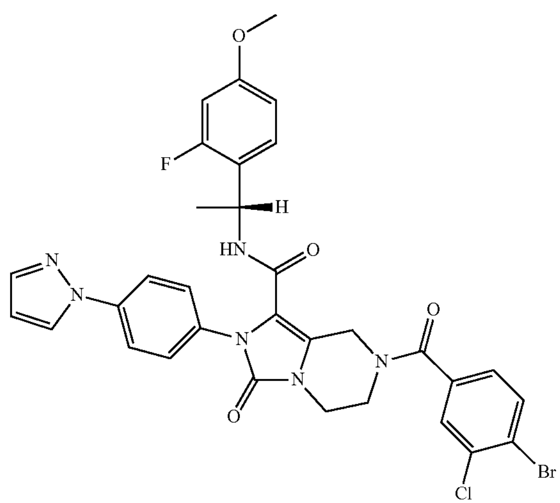 [SMILES: COc1ccc([C@@H](C)NC(=O)c2c3n(c(=O)n2-c2ccc(-n4cccn4)cc2)CCN(C(=O)c2ccc(Br)c(Cl)c2)C3)c(F)c1] | 7-(4-bromo-3-chloro-benzoyl)-3-oxo-2-(4-pyrazol-1-ylphenyl)-N-[rac-(1R)-1-(2-fluoro-4-methoxy-phenyl)ethyl]-6,8-dihydro-5H-imidazo[1,5-a]pyrazine-1-carboxamide | 1H-NMR (DMSO, 600 MHz, 80° C.): 1.25 (d, J = 7.2 Hz, 3H), 3.70-3.74 (m, 5H), 3.81-3.93 (m, 2H), 4.85 (s, 2H), 5.03-5.10 (m, 1H), 6.56 (dd, J = 2.1 Hz, 1.9 Hz, 1H), 6.58-6.65 (m, 2H), 7.01 (dd, J = 8.9 Hz, 8.1 Hz, 1H), 7.26-7.31 (m, 1H), 7.38 (d, J = 8.8 Hz, 2H), 7.41 (dd, J = 8.2 Hz, 1.7 Hz, 1H), 7.76 (s, 2H), 7.82-7.88 (m, 3H), 8.41 (d, J = 2.5 Hz, 1H) ppm. |

| Compound # | Structure | Name | NMR |
|---|---|---|---|
| 414 | 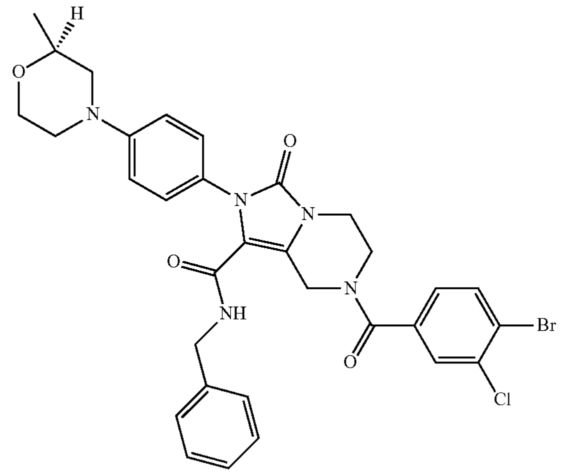 [SMILES: C[C@H]1CN(c2ccc(-n3c(C(=O)NCc4ccccc4)c4n(c3=O)CCN(C(=O)c3ccc(Br)c(Cl)c3)C4)cc2)CCO1] | N-benzyl-7-(4-bromo-3-chlorobenzoyl)-3-oxo-2-[4-[rac-(2S)-2-methylmorpholin-4-yl]phenyl]-6,8-dihydro-5H-imidazo[1,5-a]pyrazine-1-carboxamide | 1H-NMR (DMSO, 600 MHz, 80° C.): 1.19 (d, J = 6.3 Hz, 3H), 2.38-2.43 (m, 1H), 2.73 (td, J = 11.7 Hz, 3.5 Hz, 1H), 3.46-3.50 (m, 1H), 3.54-3.58 (m, 1H), 3.62-3.70 (m, 4H), 3.84 (br. s., 2H), 3.93 (ddd, J = 11.3 Hz, 3.2 Hz, 1.6 Hz, 1H), 4.24 (d, J = 5.2 Hz, 2H), 4.86 (s, 2H), 6.93 (d, J = 9.8 Hz, 3H), 7.02 (d, J = 7.7 Hz, 2H), 7.14 (d, J = 8.8 Hz, 2H), 7.19-7.26 (m, 3H), 7.39 (dd, J = 8.1 Hz, 1.8 Hz, 1H), 7.74 (d, J = 1.7 Hz, 1H), 7.85 (d, J = 8.2 Hz, 1H) ppm. |
| 415 | 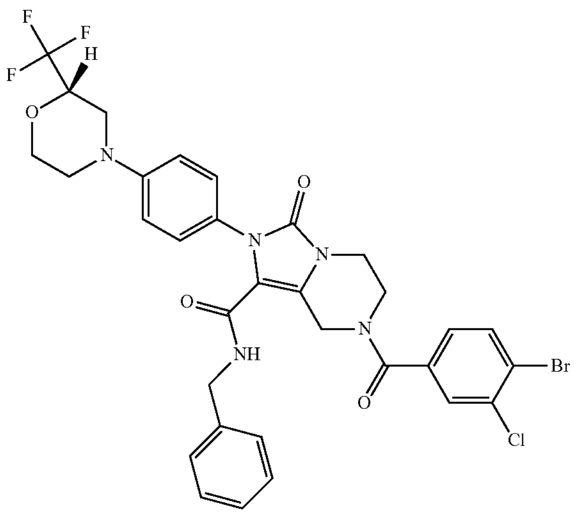 [SMILES: O=C(NCc1ccccc1)c1c2n(c(=O)n1-c1ccc(N3CCO[C@H](C(F)(F)F)C3)cc1)CCN(C(=O)c1ccc(Br)c(Cl)c1)C2] | N-benzyl-7-(4-bromo-3-chlorobenzoyl)-2-[4-(2,2-difluoro-1λ²-fluora-8-oxa-5-azaspiro[2.5]octan-5-yl)phenyl]-3-oxo-6,8-dihydro-5H-imidazo[1,5-a]pyrazine-1-carboxamide | 1H-NMR (DMSO, 600 MHz, 80° C.): 2.83 (t, J = 11.0 Hz, 1H), 2.89 (td, J = 11.6 Hz, 2.8 Hz, 1H), 3.55 (d, J = 13.3 Hz, 1H), 3.67-3.73 (m, 3H), 3.78-3.88 (m, 3H), 4.11 (m, 1H), 4.25 (d, J = 6.1 Hz, 2H), 4.28-4.34 (m, 1H), 4.87 (s, 2H), 7.01 (d, J = 8.8 Hz, 2H), 7.05 (d, J = 7.2 Hz, 3H), 7.18 (d, J = 8.3 Hz, 2H), 7.20-7.27 (m, 3H), 7.40 (dd, J = 8.3 Hz, 1.6 Hz, 1H), 7.75 (d, J = 1.3 Hz, 1H), 7.86 (d, J = 8.3 Hz, 1H) ppm. |

TABLE A-continued

| Compound # | Structure | Name | NMR |
|---|---|---|---|
| 416 | 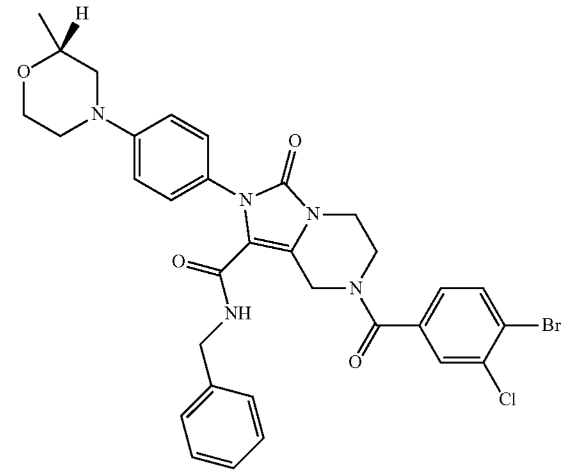 [SMILES: C[C@@H]1CN(c2ccc(-n3c(C(=O)NCc4ccccc4)c4n(c3=O)CCN(C(=O)c3ccc(Br)c(Cl)c3)C4)cc2)CCO1] | N-benzyl-7-(4-bromo-3-chlorobenzoyl)-3-oxo-2-[4-[rac-(2R)-2-methylmorpholin-4-yl]phenyl]-6,8-dihydro-5H-imidazo[1,5-a]pyrazine-1-carboxamide | 1H-NMR (DMSO, 600 MHz, 80° C.): 1.19 (d, J = 6.3 Hz, 3H), 2.38-2.43 (m, 1H), 2.73 (td, J = 11.7 Hz, 3.5 Hz, 1H), 3.46-3.50 (m, 1H), 3.54-3.58 (m, 1H), 3.62-3.70 (m, 4H), 3.84 (br. s., 2H), 3.93 (ddd, J = 11.3 Hz, 3.2 Hz, 1.6 Hz, 1H), 4.24 (d, J = 5.2 Hz, 2H), 4.86 (s, 2H), 6.93 (d, J = 9.8 Hz, 3H), 7.02 (d, J = 7.7 Hz, 2H), 7.14 (d, J = 8.8 Hz, 2H), 7.19-7.26 (m, 3H), 7.39 (dd, J = 8.1 Hz, 1.8 Hz, 1H), 7.74 (d, J = 1.7 Hz, 1H), 7.85 (d, J = 8.2 Hz, 1H) ppm. |
| 417 | 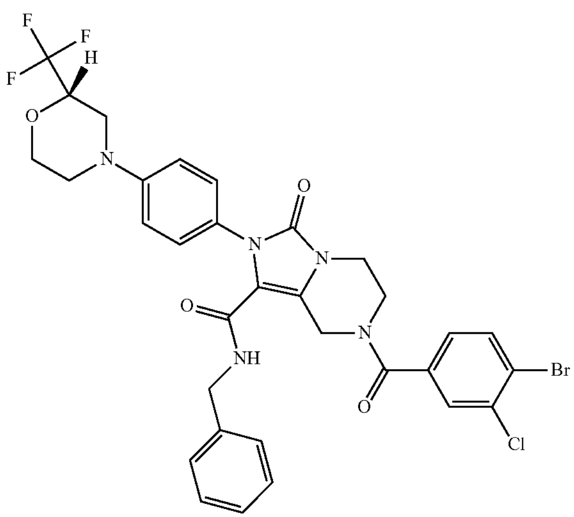 [SMILES: O=C(NCc1ccccc1)c1c2n(c(=O)n1-c1ccc(N3CCO[C@H](C(F)(F)F)C3)cc1)CCN(C(=O)c1ccc(Br)c(Cl)c1)C2] | N-benzyl-7-(4-bromo-3-chlorobenzoyl)-3-oxo-2-[4-[rac-(2S)-2-(trifluoromethyl)morpholin-4-yl]phenyl]-6,8-dihydro-5H-imidazo[1,5-a]pyrazine-1-carboxamide | 1H-NMR (DMSO, 600 MHz, 80° C.): 2.83 (t, J = 11.0 Hz, 1H), 2.89 (td, J = 11.6 Hz, 2.8 Hz, 1H), 3.55 (d, J = 13.3 Hz, 1H), 3.67-3.73 (m, 3H), 3.78-3.88 (m, 3H), 4.11 (m, 1H), 4.25 (d, J = 6.1 Hz, 2H), 4.28-4.34 (m, 1H), 4.87 (s, 2H), 7.01 (d, J = 8.8 Hz, 2H), 7.05 (d, J = 7.2 Hz, 3H), 7.18 (d, J = 8.3 Hz, 2H), 7.20-7.27 (m, 3H), 7.40 (dd, J = 8.3 Hz, 1.6 Hz, 1H), 7.75 (d, J = 1.3 Hz, 1H), 7.86 (d, J = 8.3 Hz, 1H) ppm. |

TABLE A-continued

| Compound # | Structure | Name | NMR |
|---|---|---|---|
| 418 | 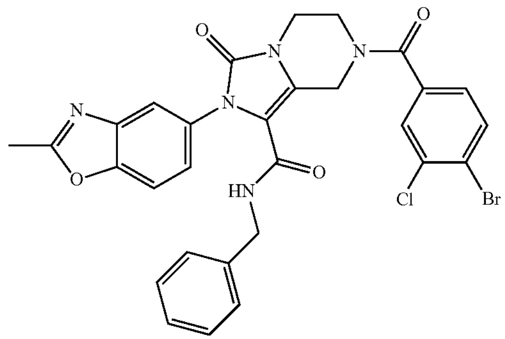 | N-benzyl-7-(4-bromo-3-chlorobenzoyl)-2-(2-methyl-1,3-benzoxazol-5-yl)-3-oxo-6,8-dihydro-5H-imidazo[1,5-a]pyrazine-1-carboxamide | 1H NMR (400 MHz, DMSO-d6, 80° C.): 2.64 (s, 3H), 3.71 (t, J = 5.4 Hz, 2H), 3.85 (t, J = 5.4 Hz, 2H), 4.23 (d, J = 5.6 Hz, 2H), 4.87 (s, 2H), 7.00 (br s, 2H), 7.18 (d, J = 2.8 Hz, 3H), 7.22 (dd, J = 8.6 Hz, 1.7 Hz, 1H), 7.39-7.43 (m, 2H), 7.55 (d, J = 1.7 Hz, 1H), 7.63 (d, J = 8.6 Hz, 1H), 7.75 (d, J = 1.4 Hz, 1H), 7.86 (d, J = 8.3 Hz, 1H). |
| 419 | 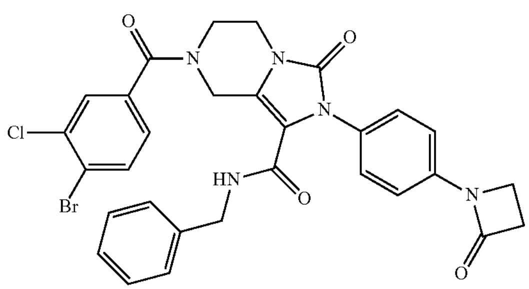 [SMILES: O=C(NCc1ccccc1)c1c2n(c(=O)n1-c1ccc(N3CCC3=O)cc1)CCN(C(=O)c1ccc(Br)c(Cl)c1)C2] | N-benzyl-7-(4-bromo-3-chlorobenzoyl)-3-oxo-2-[4-(2-oxoazetidin-1-yl)phenyl]-6,8-dihydro-5H-imidazo[1,5-a]pyrazine-1-carboxamide | 1H NMR (400 MHz, DMSO-d6, 80° C.): 3.12 (t, J = 4.6 Hz, 2H), 3.65 (t, J = 4.5 Hz, 2H), 3.69 (t, J = 5.5 Hz, 2H), 3.83 (t, J = 4.7 Hz, 2H), 4.25 (d, J = 5.8 Hz, 2H), 4.85 (s, 2H), 7.06 (d, J = 6.3 Hz, 2H), 7.21-7.26 (m, 5H), 7.34-7.41 (m, 4H), 7.75 (d, J = 1.4 Hz, 1H), 7.85 (d, J = 8.2 Hz, 1H) |

TABLE A-continued

| Compound # | Structure | Name | NMR |
|---|---|---|---|
| 420 | 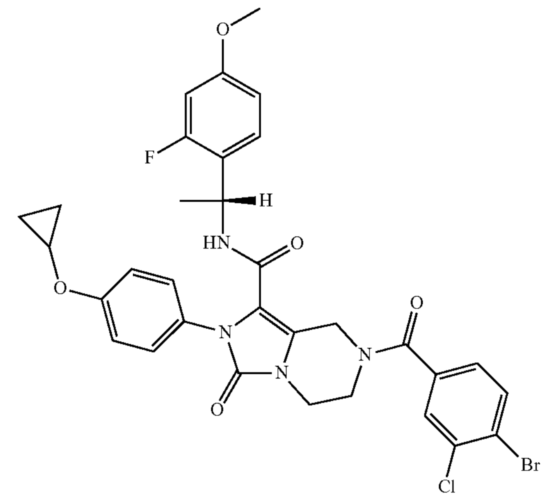 [SMILES: COc1ccc([C@@H](C)NC(=O)c2c3n(c(=O)n2-c2ccc(OC4CC4)cc2)CCN(C(=O)c2ccc(Br)c(Cl)c2)C3)c(F)c1] | 7-(4-bromo-3-chloro-benzoyl)-2-[4-(cyclopropoxy)phenyl]-3-oxo-N-[rac-(1R)-1-(2-fluoro-4-methoxy-phenyl)ethyl]-6,8-dihydro-5H-imidazo[1,5-a]pyrazine-1-carboxamide | 1H-NMR (DMSO, 600 MHz, 80° C.): 0.67-0.72 (m, 2H), 0.79-0.84 (m, 2H), 1.20 (d, J = 6.6 Hz, 3H), 3.66-3.72 (m, 2H), 3.77 (s, 3H), 3.80-3.91 (m, 3H), 4.85 (s, 2H), 5.00-5.07 (m, 1H), 6.64-6.73 (m, 3H), 6.98 (t, J = 9.1 Hz, 1H), 7.09 (d, J = 8.8 Hz, 2H), 7.22 (d, J = 8.8 Hz, 2H), 7.40 (dd, J = 8.2 Hz, 2.0 Hz, 1H), 7.74 (d, J = 2.0 Hz, 1H), 7.85 (d, J = 8.2 Hz, 1H) ppm. |
| 421 | 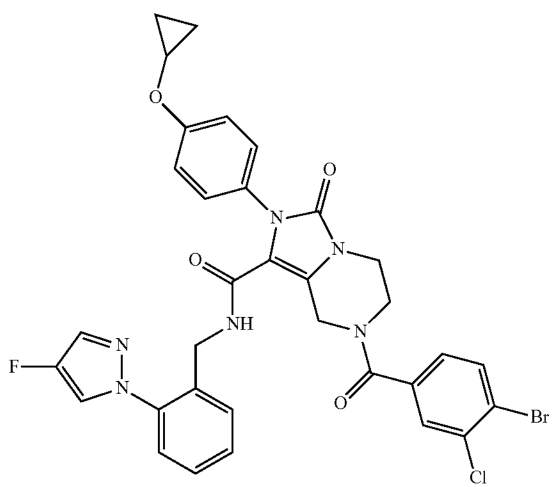 [SMILES: O=C(NCc1ccccc1-n1cc(F)cn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-N-[[2-(4-fluoropyrazol-1-yl)phenyl]methyl]-3-oxo-6,8-dihydro-5H-imidazo[1,5-a]pyrazine-1-carboxamide | 1H-NMR (DMSO, 600 MHz, 80° C.): 0.64-0.69 (m, 2H), 0.77-0.82 (m, 2H), 3.65-3.71 (m, 2H), 3.80-3.87 (m, 3H), 4.21 (d, J = 5.9 Hz, 2H), 4.86 (s, 2H), 6.95 (br.s., 1H), 7.06 (d, J = 8.8 Hz, 2H), 7.18-7.23 (m, 3H), 7.32-7.36 (m, 2H), 7.37-7.42 (m, 2H), 7.63 (d, J = 4.1 Hz, 1H), 7.73 (d, J = 1.8 Hz, 1H), 7.83 (d, J = 8.1 Hz, 1H), 8.09 (d, J = 4.4 Hz, 1H) ppm. |

TABLE A-continued

| Compound # | Structure | Name | NMR |
|---|---|---|---|
| 422 | 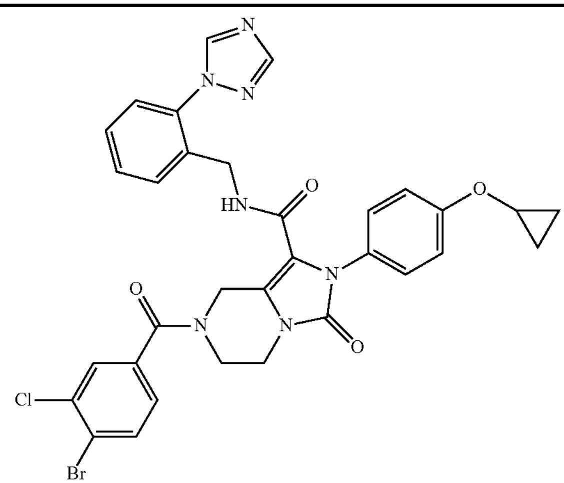 | 7-(4-bromo-3-chloro-benzoyl)-2-[4-(cyclopropoxy)phenyl]-3-oxo-N-[[2-(1,2,4-triazol-1-yl)phenyl]methyl]-6,8-dihydro-5H-imidazo[1,5-a]pyrazine-1-carboxamide | 1H-NMR (DMSO, 600 MHz, 80° C.): 0.62-0.70 (m, 2H), 0.76-0.83 (m, 2H), 3.68 (dd, J = 5.5 Hz, 5.2 Hz, 2H), 3.75-3.92 (m, 3H), 4.17 (d, J = 5.7 Hz, 2H), 4.85 (s, 2H), 7.06 (d, J = 8.8 Hz, 3H), 7.19 (d, J = 8.8 Hz, 2H), 7.22-7.30 (m, 1H), 7.35-7.50 (m, 4H), 7.73 (d, J = 1.8 Hz, 1H), 7.84 (d, J = 8.2 Hz, 1H), 8.08 (s, 1H), 8.73 (s, 1H) ppm. |
| 423 | 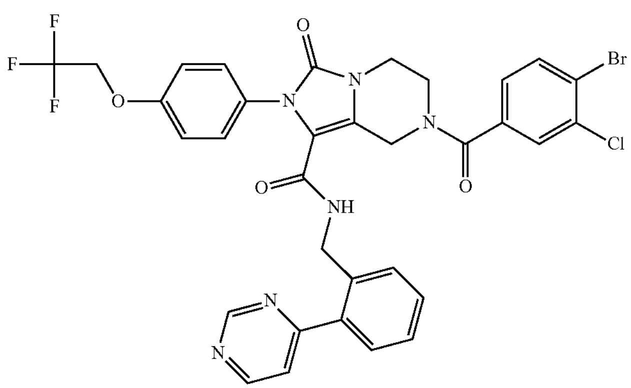 [SMILES: O=C(NCc1ccccc1-c1ccncn1)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-3-oxo-N-[(2-pyrimidin-4-yl)phenyl)methyl]-2-[4-(2,2,2-trifluoroethoxy)phenyl]-6,8-dihydro-5H-imidazo[1,5-a]pyrazine-1-carboxamide | 1H NMR (400 MHz, Chloroform-d) δ 8.86-8.71 (m, 2H), 7.71 (d, J = 8.2 Hz, 1H), .61 (d, J = 1.9 Hz, 1H), 7.48 (tt, J = 9.1, 4.2 Hz, 5H), 7.23 (dd, J = 8.2, 2.0 Hz, 1H), 7.16-7.06 (m, 2H), 6.95 (s,1H), 6.55 (d, J = 8.5 Hz, 2H), 5.02 (s, 2H), 4.34 (s, 2H), 4.14-3.72 (m, 6H). |

| Compound # | Structure | Name | NMR |
|---|---|---|---|
| 424 | 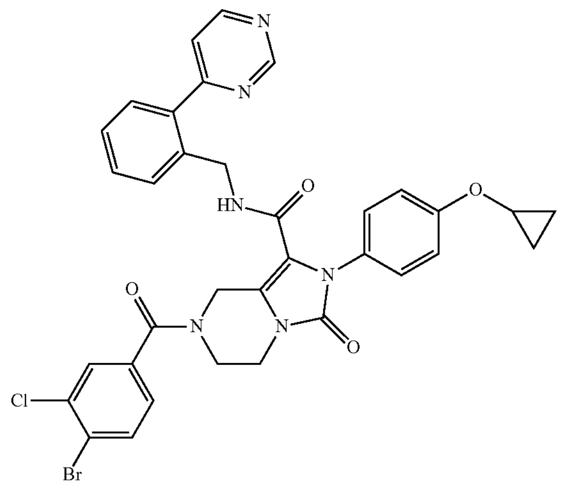 [SMILES: O=C(NCc1ccccc1-c1ccncn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-3-oxo-N-[(2-pyrimidin-4-ylphenyl)methyl]-6,8-dihydro-5H-imidazo[1,5-a]pyrazine-1-carboxamide | 1H NMR (400 MHz, Chloroform-d) δ 8.84-8.71 (m, 2H), 7.70 (d, J = 8.2 Hz, 1H), 7.61 (s, 1H), 7.57-7.37 (m, 5H), 7.23 (dd, J = 8.2, 2.0 Hz, 1H), 7.16-7.06 (m, 2H), 6.83 (m, 3H), 5.02 (s, 2H), 4.34 (s, 2H), 4.05-3.85 (m, 4H), 3.48 (dt, J = 6.1, 3.1 Hz, 1H), 0.71 (dt, J = 7.8, 5.8 Hz, 2H), 0.60 (d, J = 7.3 Hz, 2H). |
| 425 | 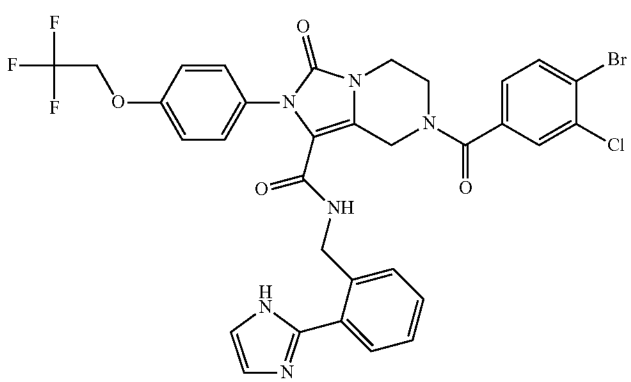 [SMILES: O=C(NCc1ccccc1-c1ncc[nH]1)c1c2n(c(=O)n1-c1ccc(OCC(F)(F)F)cc1)CCN(C(=O)c1ccc(Br)c(Cl)c1)C2] | 7-(4-bromo-3-chloro-benzoyl)-N-[[2-(1H-imidazol-2-yl)phenyl]methyl]-3-oxo-2-[4-(2,2,2-trifluoroethoxy)phenyl]-6,8-dihydro-5H-imidazo[1,5-a]pyrazine-1-carboxamide | 1H NMR (300 MHz, Chloroform-d) δ 8.05-7.65 (m, 2H), 7.65-7.52 (m, 2H), 7.50-7.30 (m, 4H), 7.25-7.15 (m, 4H), 7.01 (d, J = 8.5 Hz, 3H), 5.02 (s, 2H), 4.46 (q, J = 8.0 Hz, 2H), 4.20-3.50 (m, 6H). |

TABLE A-continued

| Compound # | Structure | Name | NMR |
|---|---|---|---|
| 426 | 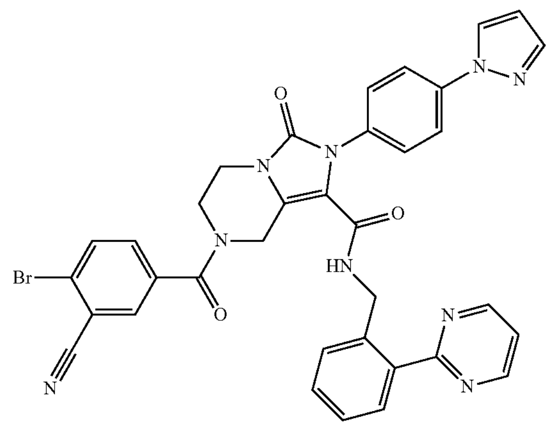 [SMILES: N#Cc1cc(C(=O)N2CCn3c(c(C(=O)NCc4ccccc4-c4ncccn4)n(-c4ccc(-n5cccn5)cc4)c3=O)C2)ccc1Br] | 7-(4-bromo-3-cyano-benzoyl)-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide | 1H-NMR (DMSO, 600 MHz, 80° C.): 3.71 (dd, J = 5.8 Hz, 5.1 Hz, 2H), 3.85 (s, 2H), 4.54 (d, J = 5.7 Hz, 2H), 4.89 (s, 2H), 6.54 (t, J = 2.1 Hz, 1H), 7.24-7.34 (m, 5H), 7.35-7.42 (m, 2H), 7.68 (d, J = 8.8 Hz, 2H), 7.72-7.76 (m, 2H), 7.89-7.92 (m, 1H), 7.95 (d, J = 8.4 Hz, 1H), 8.05 (d, J = 2.1 Hz, 1H), 8.28 (d, J = 2.5 Hz, 1H), 8.74 (d, J = 4.9 Hz, 2H) ppm. |
| 427 | 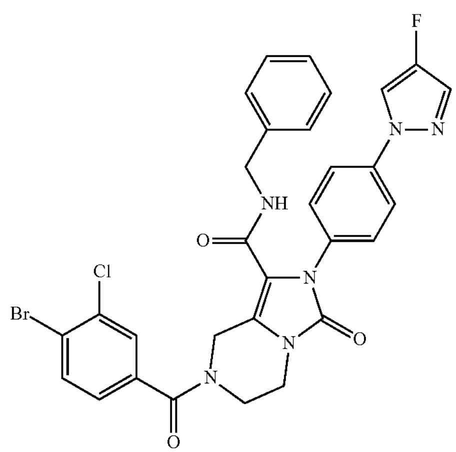 [SMILES: O=C(NCc1ccccc1)c1c2n(c(=O)n1-c1ccc(-n3cc(F)cn3)cc1)CCN(C(=O)c1ccc(Br)c(Cl)c1)C2] | N-benzyl-7-(4-bromo-3-chloro-benzoyl)-2-[4-(4-fluoropyrazol-1-yl)phenyl]-3-oxo-6,8-dihydro-5H-imidazo[1,5-a]pyrazine-1-carboxamide | 1H-NMR (DMSO-d6, 600 MHz, 80° C.): 3.71 (dd, J = 5.2 Hz, 5.2 Hz, 2H), 3.84 (s, 2H), 4.28 (d, J = 5.4 Hz, 2H), 4.86 (s, 2H), 7.09 (d, J = 7.0 Hz, 2H), 7.15-7.30 (m, 3H), 7.30-7.47 (m, 3H), 7.59 (br. s, 1H), 7.74 (s, 1H), 7.76-7.83 (m, 3H), 7.85 (d, J = 8.2 Hz, 1H), 8.56 (d, J = 3.8 Hz, 1H) ppm. |

TABLE A-continued

| Compound # | Name | Structure | NMR |
|---|---|---|---|
| 428 | N-[[4-(2-amino-1,1-dimethyl-2-oxo-ethoxy)-2-fluoro-phenyl]methyl]-7-(4-bromo-3-chloro-benzoyl)-3-oxo-2-[4-(2,2,2-trifluoroethoxy)phenyl]-6,8-dihydro-5H-imidazo[1,5-a]pyrazine-1-carboxamide | 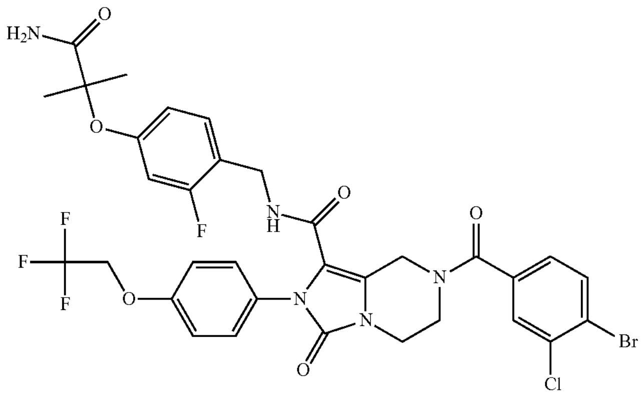 [SMILES: CC(C)(Oc1ccc(CNC(=O)c2c3n(c(=O)n2-c2ccc(OCC(F)(F)F)cc2)CCN(C(=O)c2ccc(Br)c(Cl)c2)C3)c(F)c1)C(N)=O] | 1H-NMR (DMSO-d6, 600 MHz, 80° C.): 1.46 (s, 6H), 3.68 (dd, J = 5.6 Hz, 5.6 Hz, 2H), 3.78-3.88 (m, 2H), 4.23 (d, J = 5.7 Hz, 2H), 4.72 (q, J = 8.8 Hz, 2H), 4.85 (s, 2H), 6.68 (d, J = 9.9 Hz, 2H), 6.99 (t, J = 8.5 Hz, 1H), 7.05 (br. s, 2H), 7.08 (d, J = 9.0 Hz, 2H), 7.23 (d, J = 9.0 Hz, 3H), 7.39 (dd, J = 8.1 Hz, 1.8 Hz, 1H), 7.74 (d, J = 1.8 Hz, 1H), 7.86 (d, J = 8.3 Hz, 1H) ppm. |
| 429 | 7-(4-bromo-3-chloro-benzoyl)-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide | 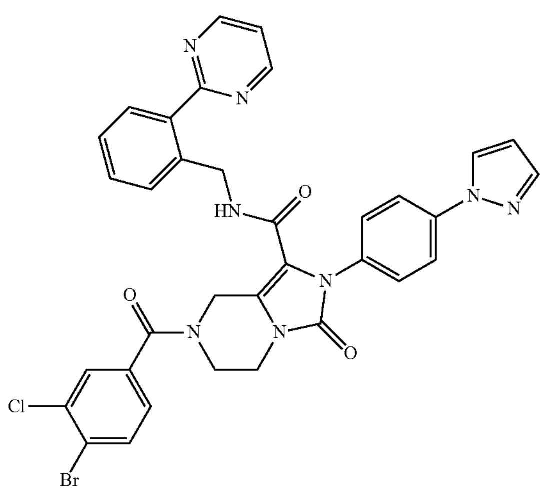 [SMILES: O=C(NCc1ccccc1-c1ncccn1)c1c2n(c(=O)n1-c1ccc(-n3cccn3)cc1)CCN(C(=O)c1ccc(Br)c(Cl)c1)C2] | 1H-NMR (DMSO, 600 MHz, 80° C.): 3.70 (dd, J = 5.6 Hz, 5.2 Hz, 2H), 3.85 (br. s., 2H), 4.53 (d, J = 5.9 Hz, 2H), 4.89 (s, 2H), 6.53 (dd, J = 2.1 Hz, 1.8 Hz, 1H), 7.26 (br. s., 1H), 7.28-7.32 (m, 4H), 7.34-7.40 (m, 3H), 7.67 (d, J = 8.4 Hz, 2H), 7.73 (d, J = 1.6 Hz, 2H), 7.83 (d, J = 8.3 Hz, 1H), 7.88-7.92 (m, 1H), 8.27 (d, J = 2.5 Hz, 1H), 8.73 (d, J = 4.8 Hz, 2H) ppm. |

TABLE A-continued

| Compound # | Structure | Name | NMR |
|---|---|---|---|
| 430 | 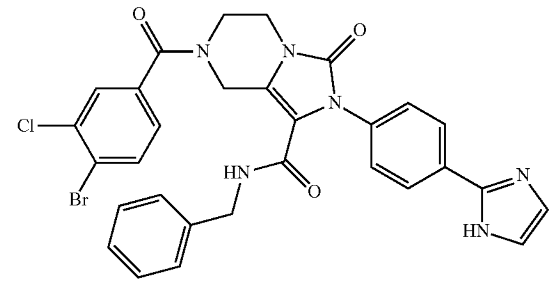 [SMILES: O=C(NCc1ccccc1)c1c2n(c(=O)n1-c1ccc(-c3ncc[nH]3)cc1)CCN(C(=O)c1ccc(Br)c(Cl)c1)C2] | N-benzyl-7-(4-bromo-3-chloro-benzoyl)-2-[4-(1H-imidazol-2-yl)phenyl]-3-oxo-6,8-dihydro-5H-imidazo[1,5-a]pyrazine-1-carboxamide | 1H NMR (400 MHz, DMSO-d6, 80° C.): 3.71 (t, J = 5.4 Hz, 2H), 3.85 (t, J = 5.4 Hz, 2H), 4.28 (d, J = 5.7 Hz, 2H), 4.87 (s, 2H), 7.05-7.09 (m, 3H), 7.16-7.23 (m, 4H), 7.33 (d, J = 8.5 Hz, 2H), 7.40 (dd, J = 8.2 Hz, 1.7 Hz, 1H), 7.62 (br s, 1H), 7.75 (d, J = 1.6 Hz, 1H), 7.85 (d, J = 8.2 Hz, 1H), 7.96 (d, J = 8.5 Hz, 2H), 12.32 (s, 1H). |
| 431 | 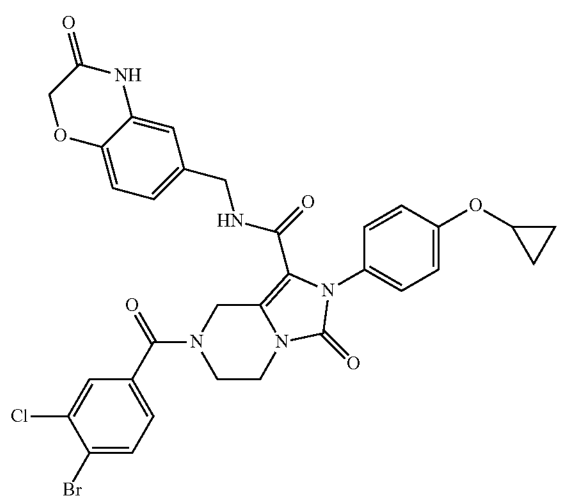 [SMILES: O=C1COc2ccc(CNC(=O)c3c4n(c(=O)n3-c3ccc(OC5CC5)cc3)CCN(C(=O)c3ccc(Br)c(Cl)c3)C4)cc2N1] | 7-(4-bromo-3-chloro-benzoyl)-2-[4-(cyclopropoxy)phenyl]-3-oxo-N-[(3-oxo-4H-1,4-benzoxazin-6-yl)methyl]-6,8-dihydro-5H-imidazo[1,5-a]pyrazine-1-carboxamide | 1H-NMR (DMSO, 600 MHz, 80° C.): 0.63-0.69 (m, 2H), 0.75-0.82 (m, 2H), 3.68 (dd, J = 5.8 Hz, 5.4 Hz, 2H), 3.80-3.86 (m, 3H), 4.15 (d, J = 5.5 Hz, 2H), 4.51 (s, 2H), 4.86 (s, 2H), 6.58 (d, J = 7.3 Hz, 1H), 6.71 (s, 1H), 6.79 (d, J = 8.2 Hz, 1H), 7.05 (d, J = 8.8 Hz, 2H), 7.09 (br. s., 1H), 7.19 (d, J = 8.8 Hz, 2H), 7.40 (dd, J = 8.3 Hz, 1.6 Hz, 1H), 7.74 (d, J = 1.7 Hz, 1H), 7.85 (d, J = 8.5 Hz, 1H), 10.40 (s, 1H) ppm. |

TABLE A-continued

| Compound # | Structure | Name | NMR |
|---|---|---|---|
| 432 | 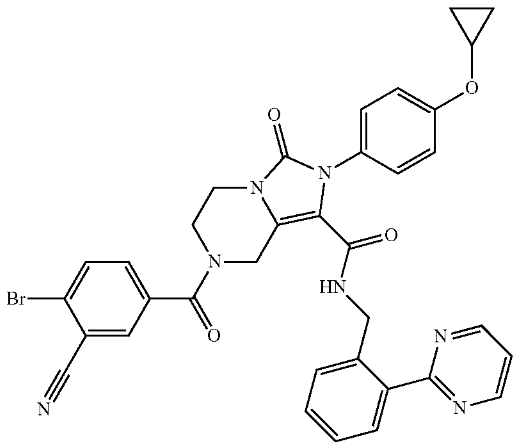 [SMILES: N#Cc1cc(C(=O)N2CCn3c(c(C(=O)NCc4ccccc4-c4ncccn4)n(-c4ccc(OC5CC5)cc4)c3=O)C2)ccc1Br] | 7-(4-bromo-3-cyano-benzoyl)-2-[4-(cyclopropoxy)phenyl]-3-oxo-N-[(2-pyrimidin-2-ylphenyl)methyl]-6,8-dihydro-5H-imidazo[1,5-a]pyrazine-1-carboxamide | 1H-NMR (DMSO, 600 MHz, 80° C.): 0.56-0.61 (m, 2H), 0.73-0.78 (m, 2H), 3.65-3.69 (m, 2H), 3.70-3.74 (m, 1H), 3.82 (br. s., 2H), 4.50 (d, J = 5.6 Hz, 2H), 4.88 (s, 2H), 6.90 (d, J = 8.6 Hz, 2H), 7.03-7.08 (m, 1H), 7.12 (d, J = 8.6 Hz, 2H), 7.25-7.31 (m, 1H), 7.38-7.44 (m, 3H), 7.73 (dd, J = 8.4 Hz, 1.7 Hz, 1H), 7.93-7.99 (m, 2H), 8.05 (d, J = 1.7 Hz, 1H), 8.79 (d, J = 4.9 Hz, 2H) ppm. |
| 433 | 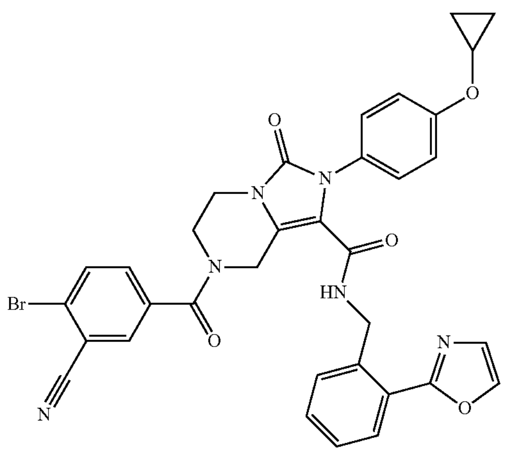 [SMILES: N#Cc1cc(C(=O)N2CCn3c(c(C(=O)NCc4ccccc4-c4ncco4)n(-c4ccc(OC5CC5)cc4)c3=O)C2)ccc1Br] | 7-(4-bromo-3-cyano-benzoyl)-2-[4-(cyclopropoxy)phenyl]-N-[(2-oxazol-2-ylphenyl)methyl]-3-oxo-6,8-dihydro-5H-imidazo[1,5-a]pyrazine-1-carboxamide | 1H-NMR (DMSO, 600 MHz, 80° C.): 0.64-0.72 (m, 2H), 0.77-0.85 (m, 2H), 3.67 (dd, J = 5.5 Hz, 5.1 Hz, 2H), 3.82 (m, 3H), 4.61 (d, J = 5.7 Hz, 2H), 4.87 (s, 2H), 6.98 (d, J = 8.7 Hz, 2H), 7.13 (d, J = 87 Hz, 3H), 7.25 (s, 1H), 7.27-7.32 (m, 1H), 7.42 (quint, J = 6.8 Hz, 2H), 7.73 (dd, J = 7.0 Hz, 1.4 Hz, 1H), 7.89 (dd, J = 8.3 Hz, 1.7 Hz, 1H), 7.96 (d, J = 8.5 Hz, 1H), 8.05 (d, J = 1.7 Hz, 1H), 8.13 (s, 1H) ppm. |

TABLE A-continued

| Compound # | Structure | Name | NMR |
|---|---|---|---|
| 434 | 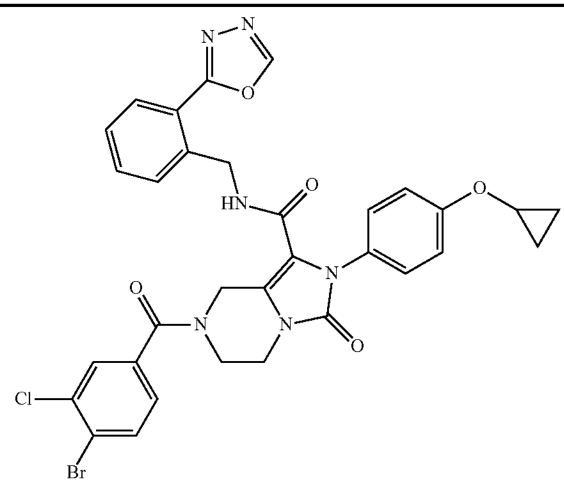 | 7-(4-bromo-3-chloro-benzoyl)-2-[4-(cyclopropoxy)phenyl]-N-[[2-(1,3,4-oxadiazol-2-yl)phenyl]methyl]-3-oxo-6,8-dihydro-5H-imidazo[1,5-a]pyrazine-1-carboxamide | 1H-NMR (DMSO, 600 MHz, 80° C.): 0.62-0.72 (m, 2H), 0.79-0.84 (m, 2H), 3.68 (dd, J = 5.7 Hz, 5.3 Hz, 2H), 3.79-3.89 (m, 3H), 4.64 (d, J = 5.8 Hz, 2H), 4.87 (s, 2H), 6.99 (d, J = 8.9 Hz, 2H), 7.15 (d, J = 8.9 Hz, 2H), 7.10-7.16 (m, 1H), 7.30-7.34 (m, 1H), 7.40 (dd, J = 8.2 Hz, 1.6 Hz, 1H), 7.48-7.55 (m, 2H), 7.75 (d, J = 1.6 Hz, 1H), 7.85 (d, J = 8.2 Hz, 1H), 7.88-7.92 (m, 1H), 9.23 (s, 1H) ppm. |
| 435 | 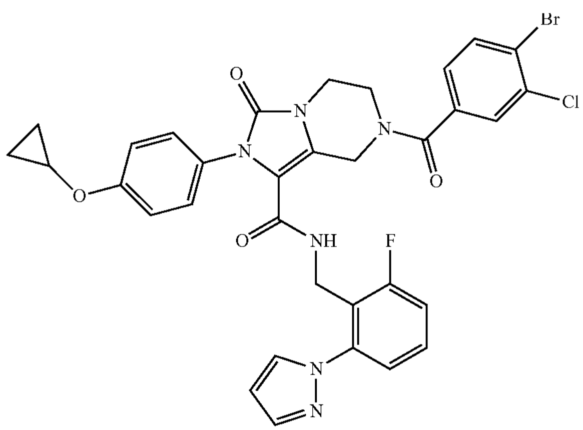 [SMILES: O=C(NCc1c(F)cccc1-n1cccn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-N-[(2-fluoro-6-pyrazol-1-yl-phenyl)methyl]-3-oxo-6,8-dihydro-5H-imidazo[1,5-a]pyrazine-1-carboxamide | 1H-NMR (DMSO, 600 MHz, 80° C.): 0.59-0.65 (m, 2H), 0.74-0.79 (m, 2H), 3.63-3.69 (m, 2H), 3.75-3.80 (m, 1H), 3.83 (br.s., 2H), 4.24 (d, J = 4.9 Hz, 2H), 4.84 (s, 2H), 6.46-6.49 (m, 1H), 6.65 (br. s., 1H), 6.96 (d, J = 8.5 Hz, 2H), 7.14 (d, J = 8.9 Hz, 2H), 7.20-7.26 (m, 2H), 7.38 (dd, J = 8.0 Hz, 1.3 Hz, 1H), 7.44-7.50 (m, 1H), 7.62 (s, 1H), 7.72 (d, J = 1.6 Hz, 1H), 7.83 (d, J = 8.0 Hz, 1H), 7.96 (d, J = 1.9 Hz, 1H) ppm. |

TABLE A-continued

| Compound # | Structure | Name | NMR |
|---|---|---|---|
| 436 | 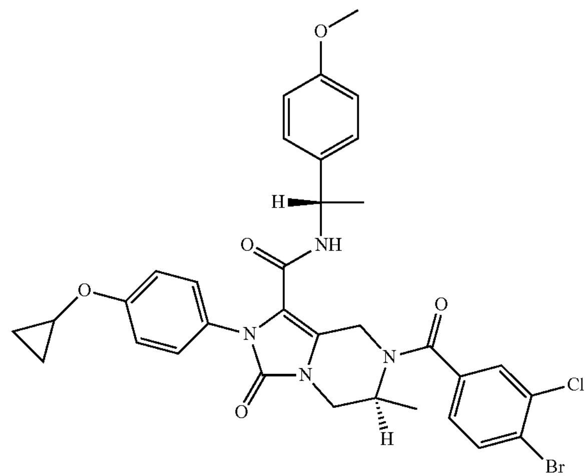 [SMILES: COc1ccc([C@H](C)NC(=O)c2c3n(c(=O)n2-c2ccc(OC4CC4)cc2)C[C@H](C)N(C(=O)c2ccc(Br)c(Cl)c2)C3)cc1] | (6SR)-7-(4-bromo-3-chloro-benzoyl)-2-[4-(cyclopropoxy)phenyl]-N-[(1S)-1-(4-methoxyphenyl)ethyl]-6-methyl-3-oxo-6,8-dihydro-5H-imidazo[1,5-a]pyrazine-1-carboxamide | 1H NMR (300 MHz, Chloroform-d) δ 7.73 (d, J = 8.2 Hz, 1H), 7.59 (d, J = 2.0 Hz, 1H), 7.29-7.08 (m, 6H), 6.90-6.73 (m, 4H), 5.32 (s, 1H), 5.16 (d, J = 7.5 Hz, 1H), 4.90 (d, J = 7.7 Hz, 1H), 4.61 (d, J = 19.3 Hz, 1H), 3.94-3.61 (m, 6H), 1.39 (d, J = 7.0 Hz, 3H), 1.17 (d, J = 6.9 Hz, 3H), 0.89-0.75 (m, 4H). |
| 437 | 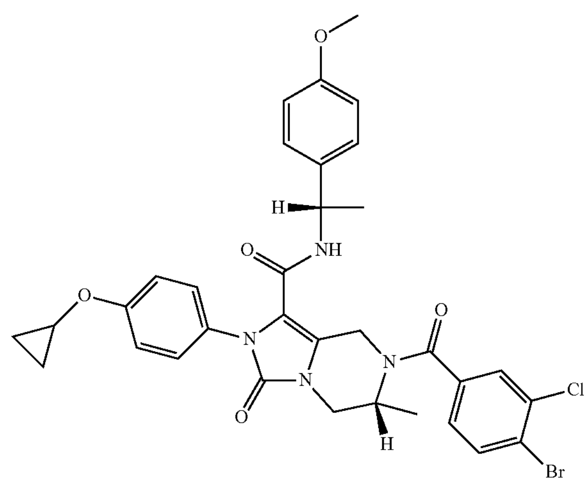 [SMILES: COc1ccc([C@H](C)NC(=O)c2c3n(c(=O)n2-c2ccc(OC4CC4)cc2)C[C@@H](C)N(C(=O)c2ccc(Br)c(Cl)c2)C3)cc1] | (6RS)-7-(4-bromo-3-chloro-benzoyl)-2-[4-(cyclopropoxy)phenyl]-N-[(1S)-1-(4-methoxyphenyl)ethyl]-6-methyl-3-oxo-6,8-dihydro-5H-imidazo[1,5-a]pyrazine-1-carboxamide | 1H NMR (300 MHz, Chloroform-d) δ 7.73 (d, J = 8.2 Hz, 1H), 7.59 (d, J = 2.0 Hz, 1H), 7.29-7.08 (m, 6H), 6.90-6.73 (m, 4H), 5.32 (s, 1H), 5.16 (d, J = 7.5 Hz, 1H), 4.90 (d, J = 7.7 Hz, 1H), 4.61 (d, J = 19.3 Hz, 1H), 3.94-3.61 (m, 6H), 1.39 (d, J = 7.0 Hz, 3H), 1.17 (d, J = 6.9 Hz, 3H), 0.89-0.75 (m, 4H). |

TABLE A-continued

| Compound # | Structure | Name | NMR |
|---|---|---|---|
| 438 | 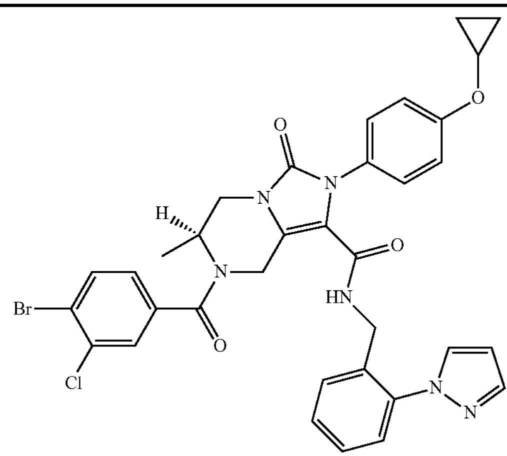 | rac-(6S)-7-(4-bromo-3-chlorobenzoyl)-2-[4-(cyclopropoxy)phenyl]-6-methyl-3-oxo-N-[(2-pyrazol-1-ylphenyl)methyl]-6,8-dihydro-5H-imidazo[1,5-a]pyrazine-1-carboxamide | 1H NMR (400 MHz, Chloroform-d) δ 7.69 (d, J = 8.2 Hz, 1H), 7.58 (dd, J = 15.3, 2.2 Hz, 2H), 7.49 (s, 1H), 7.42-7.28 (m, 3H), 7.23-7.14 (m, 4H), 7.00-6.93 (m, 2H), 6.70 (s, 1H), 6.37 (t, J = 2.2 Hz, 1H), 5.21 (s, 2H), 4.61 (s, 1H), 4.20 (s, 2H), 3.84 (d, J = 12.9 Hz, 1H), 3.71-3.59 (m, 2H), 1.38 (d, J = 7.0 Hz, 3H), 0.81-0.64 (m, 4H). |
| 439 | 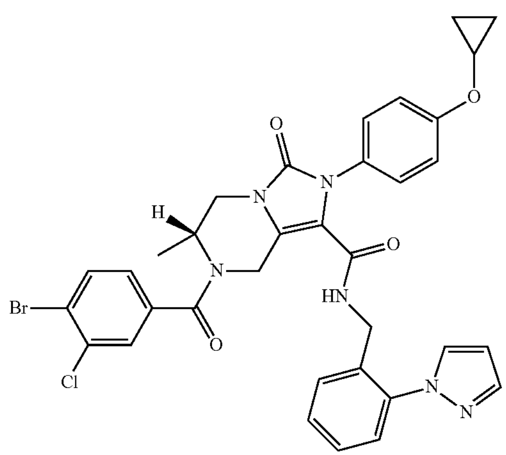 [SMILES: C[C@@H]1Cn2c(c(C(=O)NCc3ccccc3-n3cccn3)n(-c3ccc(OC4CC4)cc3)c2=O)CN1C(=O)c1ccc(Br)c(Cl)c1] | rac-(6R)-7-(4-bromo-3-chlorobenzoyl)-2-[4-(cyclopropoxy)phenyl]-6-methyl-3-oxo-N-[(2-pyrazol-1-ylphenyl)methyl]-6,8-dihydro-5H-imidazo[1,5-a]pyrazine-1-carboxamide | 1H NMR (400 MHz, Chloroform-d) δ 7.69 (d, J = 8.2 Hz, 1H), 7.58 (dd, J = 15.3, 2.2 Hz, 2H), 7.49 (s, 1H), 7.42-7.28 (m, 3H), 7.23-7.14 (m, 4H), 7.00-6.93 (m, 2H), 6.70 (s, 1H), 6.37 (t, J = 2.2 Hz, 1H), 5.21 (s, 2H), 4.61 (s, 1H), 4.20 (s, 2H), 3.84 (d, J = 12.9 Hz, 1H), 3.71-3.59 (m, 2H), 1.38 (d, J = 7.0 Hz, 3H), 0.81-0.64 (m, 4H). |

TABLE A-continued

| Compound # | Structure | Name | NMR |
|---|---|---|---|
| 440 | 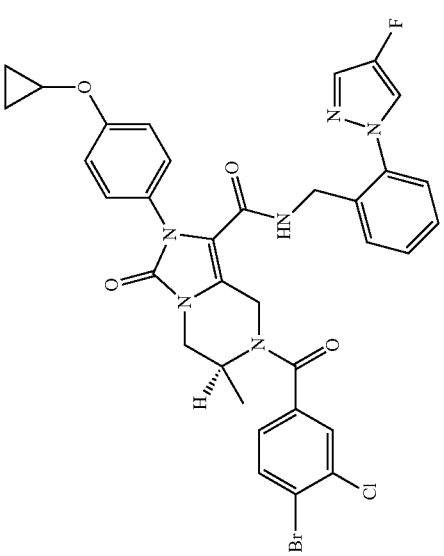 | rac-(6S)-7-(4-bromo-3-chloro-benzoyl)-2-[4-(cyclopropoxy)phenyl]-N-[[2-(4-fluoropyrazol-1-yl)phenyl]methyl]-6-methyl-3-oxo-6,8-dihydro-5H-imidazo[1,5-a]pyrazine-1-carboxamide | 1H NMR (400 MHz, Chloroform-d) δ 7.70 (d, J = 8.2 Hz, 1H), 7.58-7.45 (m, 3H), 7.38-7.32 (m, 2H), 7.24-7.13 (m, 5H), 6.98 (d, J = 8.8 Hz, 2H), 6.42 (s, 1H), 5.34 (s, 1H), 4.58 (m, 1H), 4.22 (d, J = 5.6 Hz, 2H), 3.84 (d, J = 12.8 Hz, 1H), 3.66 (tt, J = 6.0, 3.0 Hz, 2H), 1.38 (d, J = 7.0 Hz, 3H), 0.87-0.61 (m, 4H). |
| 441 | 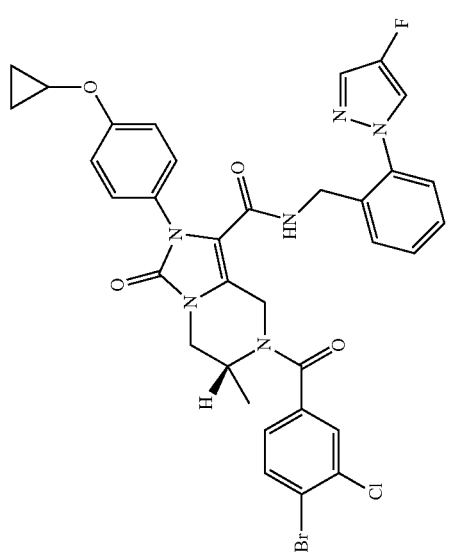 | rac-(6R)-7-(4-bromo-3-chloro-benzoyl)-2-[4-(cyclopropoxy)phenyl]-N-[[2-(4-fluoropyrazol-1-yl)phenyl]methyl]-6-methyl-3-oxo-6,8-dihydro-5H-imidazo[1,5-a]pyrazine-1-carboxamide | 1H NMR (400 MHz, Chloroform-d) δ 7.70 (d, J = 8.2 Hz, 1H), 7.58-7.45 (m, 3H), 7.38-7.32 (m, 2H), 7.24-7.13 (m, 5H), 6.98 (d, J = 8.8 Hz, 2H), 6.42 (s, 1H), 5.34 (s, 1H), 4.58 (m, 1H), 4.22 (d, J = 5.6 Hz, 2H), 3.84 (d, J = 12.8 Hz, 1H), 3.66 (tt, J = 6.0, 3.0 Hz, 2H), 1.38 (d, J = 7.0 Hz, 3H), 0.87-0.61 (m, 4H). |

| Compound # | Structure | Name | NMR |
|---|---|---|---|
| 442 | 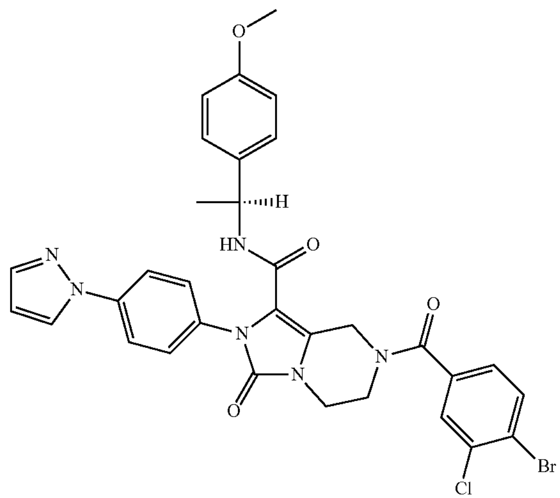 [SMILES: COc1ccc([C@H](C)NC(=O)c2c3n(c(=O)n2-c2ccc(-n4cccn4)cc2)CCN(C(=O)c2ccc(Br)c(Cl)c2)C3)cc1] | 7-(4-bromo-3-chloro-benzoyl)-N-[(1S)-1-(4-methoxyphenyl)ethyl]-3-oxo-2-(4-pyrazol-1-ylphenyl)-6,8-dihydro-5H-imidazo[1,5-a]pyrazine-1-carboxamide | 1H NMR (400 MHz, Chloroform-d) δ 7.93 (d, J = 2.4 Hz, 1H), 7.82-7.69 (m, 4H), 7.61 (s, 1H), 7.40 (d, J = 8.8 Hz, 2H), 7.25-7.20 (m, 1H), 6.80 (d, J = 8.0 Hz, 2H), 6.64 (d, J = 8.8 Hz, 2H), 6.54 (t, J = 2.2 Hz, 1H), 5.17-4.80 (m, 4H), 4.18-3.71 (m, 4H), 3.66 (s, 3H), 1.21 (d, J = 6.4 Hz, 3H). |
| 443 | 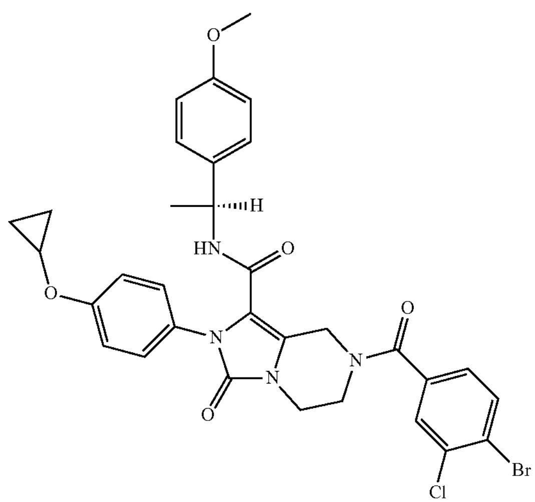 [SMILES: COc1ccc([C@H](C)NC(=O)c2c3n(c(=O)n2-c2ccc(OC4CC4)cc2)CCN(C(=O)c2ccc(Br)c(Cl)c2)C3)cc1] | 7-(4-bromo-3-chloro-benozyl)-2-[4-(cyclopropoxy)phenyl]-N-[(1S)-1-(4-methoxyphenyl)ethyl]-3-oxo-6,8-dihydro-5H-imidazo[1,5-a]pyrazine-1-carboxamide | 1H NMR (400 MHz, Chloroform-d) δ 7.70 (d, J = 8.0 Hz, 1H), 7.60 (s, 1H), 7.25-7.20 (m, 3H), 7.16-7.08 (m, 2H), 6.89-6.70 (m, 4H), 5.22-4.75 (m, 4H), 4.19-3.90 (m, 2H), 3.89-3.70 (m, 6H), 1.16 (d, J = 6.4 Hz, 3H), 0.89-0.71 (m, 4H). |

TABLE A-continued

| Compound # | Structure | Name | NMR |
|---|---|---|---|
| 444 | 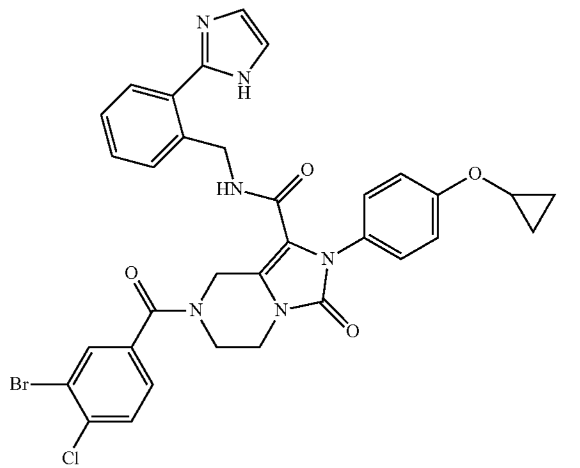 [SMILES: O=C(NCc1ccccc1-c1ncc[nH]1)c1c2n(c(=O)n1-c1ccc(OC3CC3)cc1)CCN(C(=O)c1ccc(Cl)c(Br)c1)C2] | 7-(4-bromo-3-chloro-benzoyl)-2-[4-(cyclopropoxy)phenyl]-N-[[2-(1H-imidazol-2-yl)phenyl]methyl]-3-oxo-6,8-dihydro-5H-imidazo[1,5-a]pyrazine-1-carboxamide | 1H NMR (400 MHz, Chloroform-d) δ 7.75-7.37 (m, 4H), 7.37-7.27 (m, 2H), 7.23-6.88 (m, 8H), 5.00 (s, 2H), 4.30-4.16 (m, 2H), 4.08-3.59 (m, 5H), 0.86-0.69 (m, 4H). |
| 445 | 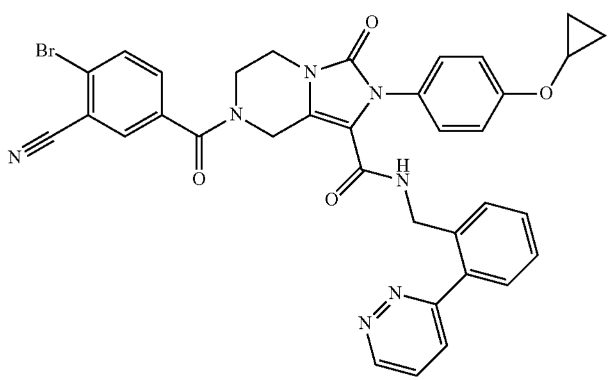 [SMILES: N#Cc1cc(C(=O)N2CCn3c(c(C(=O)NCc4ccccc4-c4cccnn4)n(-c4ccc(OC5CC5)cc4)c3=O)C2)ccc1Br] | 7-(4-bromo-3-cyano-benzoyl)-2-[4-(cyclopropoxy)phenyl]-3-oxo-N-[(2-pyridazin-3-yl)phenyl)methyl]-6,8-dihydro-5H-imidazo[1,5-a]pyrazine-1-carboxamide | 1H-NMR (DMSO, 600 MHz, 80° C.): 0.61-0.66 (m, 2H), 0.76-0.81 (m, 2H), 3.69 (dd, J = 5.8 Hz, 5.2 Hz, 2H), 3.77-3.88 (m, 3H), 4.32 (d, J = 5.9 Hz, 2H), 4.85 (s, 2H), 7.00 (d, J = 8.7 Hz, 2H), 7.16 (d, J = 8.7 Hz, 3H), 7.23 (d, J = 6.9 Hz, 1H), 7.38-7.48 (m, 3H), 7.72-7.81 (m, 3H), 7.95 (d, J = 8.3 Hz, 1H), 8.06 (d, J = 2.2 Hz, 1H), 9.21 (dd, J = 5.0 Hz, 1.7 Hz, 1H) ppm |

| Compound # | Structure | Name | NMR |
|---|---|---|---|
| 446 | 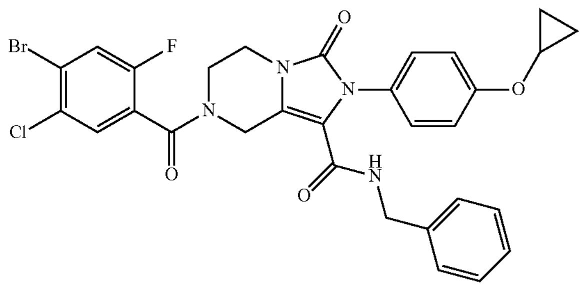 [SMILES: O=C(NCc1ccccc1)c1c2n(c(=O)n1-c1ccc(OC3CC3)cc1)CCN(C(=O)c1cc(Cl)c(Br)cc1F)C2] | N-benzyl-7-(4-bromo-5-chloro-2-fluoro-benzoyl)-2-[4-(cyclopropoxy)phenyl]-3-oxo-6,8-dihydro-5H-imidazo[1,5-a]pyrazine-1-carboxamide | 600 MHz, 100° C., DMSO-d6 0.67-0.70 (m, 2H), 0.8 (q, J = 6.3 Hz, 2H), 3.67 (s, 2H), 3.67-3.96 (m, 3H), 4.26 (s, 2H), 4.87 (s, 2H), 7.06 (d, J = 8.1 Hz, 4H), 7.19-7.28 (m, 5H), 7.79 (d, J = 6.4 Hz, 1H), 7.84 (d, J = 8.8 Hz, 1H) |
| 447 | 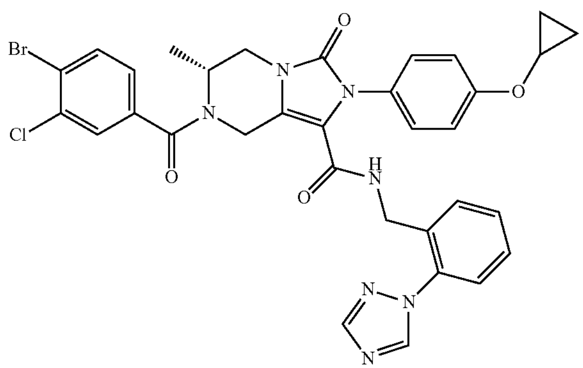 [SMILES: C[C@@H]1Cn2c(c(C(=O)NCc3ccccc3-n3cncn3)n(-c3ccc(OC4CC4)cc3)c2=O)CN1C(=O)c1ccc(Br)c(Cl)c1] | rac-(6R)-7-(4-bromo-3-chloro-benzoyl)-2-[4-(cyclopropoxy)phenyl]-6-methyl-3-oxo-N-[[2-(1,2,4-triazol-1-yl)phenyl]methyl]-6,8-dihydro-5H-imidazo[1,5-a]pyrazine-1-carboxamide | 1H NMR (300 MHz, Chloroform-d) δ 8.34 (s, 1H), 7.86 (s, 1H), 7.73 (d, J = 8.2 Hz, 1H), 7.62-7.53 (m, 2H), 7.5-7.39 (m, 2H), 7.27-7.18 (m, 3H), 7.04 (d, J = 8.7 Hz, 2H), 6.36 (s, 1H), 5.43 (s, 1H), 4.61 (d, J = 19.1 Hz, 1H), 4.20 (d, J = 5.5 Hz, 2H), 3.86 (d, J = 12.8 Hz, 1H), 3.70 (dq, J = 5.9, 3.4 Hz, 2H), 2.08 (s, 1H), 1.40 (d, J = 6.9 Hz, 3H), 0.97-0.58 (m, 4H) |
| 448 | 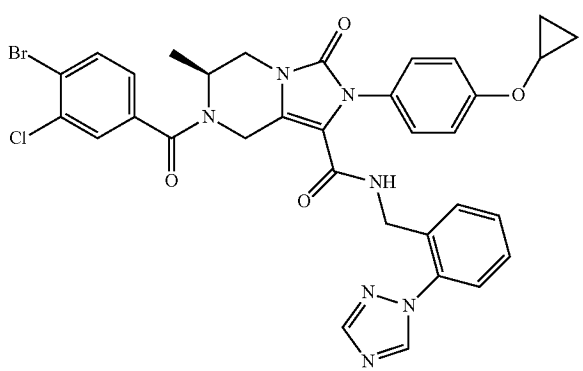 [SMILES: C[C@H]1Cn2c(c(C(=O)NCc3ccccc3-n3cncn3)n(-c3ccc(OC4CC4)cc3)c2=O)CN1C(=O)c1ccc(Br)c(Cl)c1] | rac-(6S)-7-(4-bromo-3-chloro-benzoyl)-2-[4-(cyclopropoxy)phenyl]-6-methyl-3-oxo-N-[[2-(1,2,4-triazol-1-yl)phenyl]methyl]-6,8-dihydro-5H-imidazo[1,5-a]pyrazine-1-carboxamide | 1H NMR (300 MHz, Chloroform-d) δ 8.35 (s, 1H), 7.86 (s, 1H), 7.73 (d, J = 8.2 Hz, 1H), 7.59 (d, J = 1.9 Hz, 2H), 7.49-7.39 (m, 2H), 7.27-7.17 (m, 3H), 7.05 (d, J = 8.6 Hz, 2H), 6.36 (s, 1H), 5.22 (s, 1H), 4.61 (d, J = 19.0 Hz, 1H), 4.20 (d, J = 5.3 Hz, 2H), 3.86 (d, J = 12.8 Hz, 1H), 3.69 (dd, J = 7.4, 4.4 Hz, 2H), 2.10 (s, 1H), 1.40 (d, J = 6.9 Hz, 3H), 0.97-0.58 (m, 4H) |

| Compound # | Structure | Name | NMR |
|---|---|---|---|
| 449 | 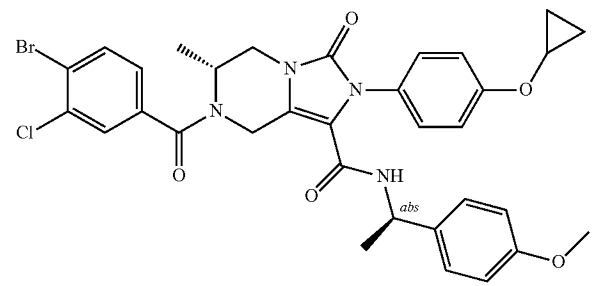 [SMILES: COc1ccc([C@@H](C)NC(=O)c2c3n(c(=O)n2-c2ccc(OC4CC4)cc2)C[C@@H](C)N(C(=O)c2ccc(Br)c(Cl)c2)C3)cc1] | (6RS)-7-(4-bromo-3-chloro-benzoyl)-2-[4-(cyclopropoxy)phenyl]-N-[(1R)-1-(4-methoxyphenyl)ethyl]-6-methyl-3-oxo-6,8-dihydro-5H-imidazo[1,5-a]pyrazine-1-carboxamide | 1H NMR (300 MHz, Chloroform-d) δ 7.73 (d, J = 8.2 Hz, 1H), 7.59 (d, J = 1.9 Hz, 1H), 7.27-7.09 (m, 4H), 6.89-6.73 (m, 4H), 5.43 (s, 1H), 5.16 (d, J = 7.4 Hz, 1H), 4.96-4.81 (m, 1H), 4.62 (d, J = 19.4 Hz, 1H), 3.93-3.62 (m, 7H), 1.39 (d, J = 7.0 Hz, 3H), 1.17 (d, J = 6.9 Hz, 4H), 0.91-0.76 (m, 4H) |
| 450 | 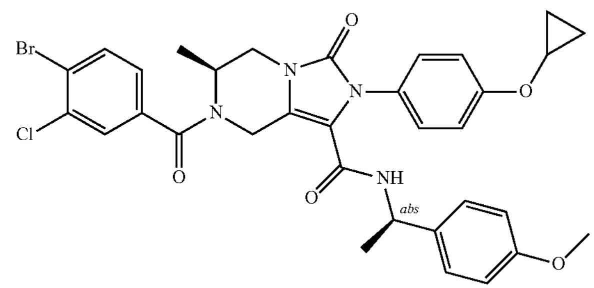 [SMILES: COc1ccc([C@@H](C)NC(=O)c2c3n(c(=O)n2-c2ccc(OC4CC4)cc2)C[C@H](C)N(C(=O)c2ccc(Br)c(Cl)c2)C3)cc1] | (6SR)-7-(4-bromo-3-chloro-benzoyl)-2-[4-(cyclopropoxy)phenyl]-N-[(1R)-1-(4-methoxyphenyl)ethyl]-6-methyl-3-oxo-6,8-dihydro-5H-imidazo[1,5-a]pyrazine-1-carboxamide | 1H NMR (300 MHz, Chloroform-d) δ 7.71 (d, J = 8.2 Hz, 1H), 7.58 (d, J = 1.9 Hz, 1H), 7.36 (s, 1H), 7.28-7.08 (m, 4H), 6.80 (q, J = 8.5 Hz, 4H), 5.44 (s, 1H), 5.15 (d, J = 7.3 Hz, 1H), 4.97-4.82 (m, 1H), 4.63 (d, J = 19.1 Hz, 1H), 3.94-3.64 (m, 6H), 1.42 (d, J = 7.0 Hz, 3H), 1.30-1.15 (m, 3H), 0.83 (dt, J = 12.9, 3.4 Hz, 4H) |
| 451 | 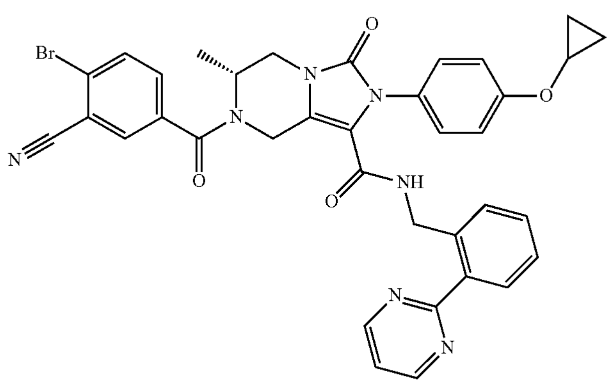 [SMILES: C[C@@H]1Cn2c(c(C(=O)NCc3ccccc3-c3ncccn3)n(-c3ccc(OC4CC4)cc3)c2=O)CN1C(=O)c1ccc(Br)c(C#N)c1] | rac-(6R)-7-(4-bromo-3-cyano-benzoyl)-2-[4-(cyclopropoxy)phenyl]-6-methyl-3-oxo-N-[(2-pyrimidin-2-yl)phenyl)methyl]-6,8-dihydro-5H-imidazo[1,5-a]pyrazine-1-carboxamide | 1H NMR (300 MHz, Chloroform-d) δ 8.59 (d, J = 4.9 Hz, 2H), 8.19-8.06 (m, 1H), 7.86-7.75 (m, 2H), 7.61-7.42 (m, 4H), 7.21-7.00 (m, 4H), 6.72 (d, J = 8.8 Hz, 2H), 5.28 (s, 2H), 4.78-4.35 (m, 3H), 3.88 (d, J = 12.8 Hz, 1H), 3.73 (d, J = 11.8 Hz, 1H), 3.44 (dt, J = 6.0, 3.0 Hz, 1H), 1.43 (d, J = 7.0 Hz, 3H), 0.72 (d, J = 6.1 Hz, 2H), 0.62-0.49 (m, 2H) |

TABLE A-continued

| Compound # | Structure | Name | NMR |
|---|---|---|---|
| 452 | 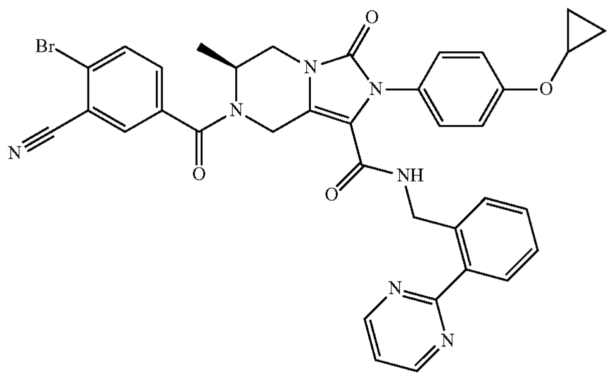 [SMILES: C[C@H]1Cn2c(c(C(=O)NCc3ccccc3-c3ncccn3)n(-c3ccc(OC4CC4)cc3)c2=O)CN1C(=O)c1ccc(Br)c(C#N)c1] | rac-(6S)-7-(4-bromo-3-cyano-benzoyl)-2-[4-(cyclopropoxy)phenyl]-6-methyl-3-oxo-N-[(2-pyrimidin-2-yl)phenyl)methyl]-6,8-dihydro-5H-imidazo[1,5-a]pyrazine-1-carboxamide | 1H NMR (300 MHz, Chloroform-d) δ 8.59 (d, J = 4.9 Hz, 2H), 8.18-8.07 (m, 1H), 7.88-7.76 (m, 2H), 7.61-7.40 (m, 4H), 7.23-6.99 (m, 4H), 6.72 (d, J = 8.8 Hz, 2H), 5.28 (s, 2H), 4.69 (d, J = 18.8 Hz, 1H), 4.57 (dd, J = 13.6, 6.0 Hz, 1H), 4.43 (dd, J = 13.5, 5.4 Hz, 1H), 3.88 (d, J = 12.8 Hz, 1H), 3.73 (d, J = 11.8 Hz, 1H), 3.44 (dt, J = 6.0, 3.0 Hz, 1H), 1.43 (d, J = 7.0 Hz, 3H), 0.72 (d, J = 6.1 Hz, 2H), 0.62-0.42 (m, 2H) |
| 453 | 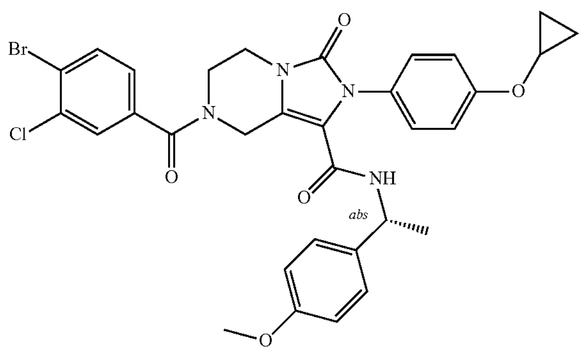 [SMILES: COc1ccc([C@@H](C)NC(=O)c2c3n(c(=O)n2-c2ccc(OC4CC4)cc2)CCN(C(=O)c2ccc(Br)c(Cl)c2)C3)cc1] | 7-(4-bromo-3-chloro-benzoyl)-2-[4-(cyclopropoxy)phenyl]-N-[(1R)-1-(4-methoxyphenyl)ethyl]-3-oxo-6,8-dihydro-5H-imidazo[1,5-a]pyrazine-1-carboxamide | 1H NMR (400 MHz, Chloroform-d) δ 7.70 (d, J = 8.4 Hz, 1H), 7.60 (s, 1H), 7.25-7.19 (m, 3H), 7.14-7.00 (m, 2H), 6.90-6.69 (m, 4H), 5.20-5.09 (m, 1H), 5.09-4.75 (m, 3H), 4.22-3.90 (m, 2H), 3.90-3.70 (m, 6H), 1.16 (d, J = 6.8 Hz, 3H), 0.88-0.73 (m, 4H) |
| 454 | 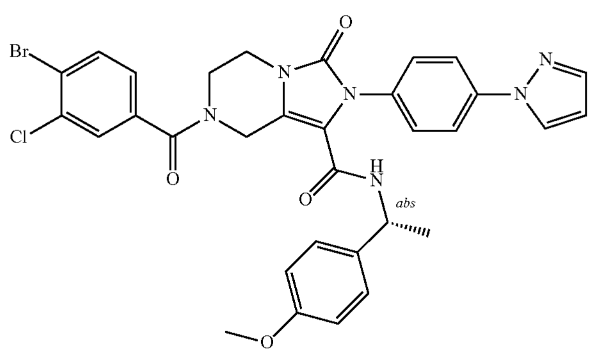 [SMILES: COc1ccc([C@@H](C)NC(=O)c2c3n(c(=O)n2-c2ccc(-n4cccn4)cc2)CCN(C(=O)c2ccc(Br)c(Cl)c2)C3)cc1] | 7-(4-bromo-3-chloro-benzoyl)-N-[(1R)-1-(4-methoxyphenyl)ethyl]-3-oxo-2-(4-pyrazol-1-ylphenyl)-6,8-dihydro-5H-imidazo[1,5-a]pyrazine-1-carboxamide | 1H NMR (400 MHz, Chloroform-d) δ 7.93 (d, J = 2.4 Hz, 1H), 7.83-7.75 (m, 3H), 7.71 (d, J = 8.4 Hz, 1H), 7.61 (d, J = 1.2 Hz, 1H), 7.40 (d, J = 8.8 Hz, 2H), 7.25-7.18 (m, 1H), 6.80 (d, J = 8.0 Hz, 2H), 6.64 (d, J = 8.8 Hz, 2H), 6.54 (t, J = 2.0 Hz, 1H), 5.15-4.80 (m, 4H), 4.20-3.70 (m, 4H), 3.66 (s, 3H), 1.21 (d, J = 6.4 Hz, 3H) |

TABLE A-continued

| Compound # | Structure | Name | NMR |
|---|---|---|---|
| 455 | 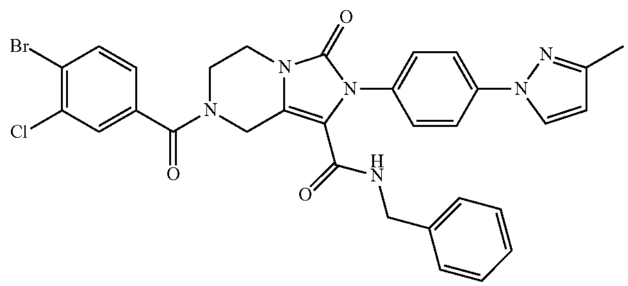 [SMILES: Cc1ccn(-c2ccc(-n3c(C(=O)NCc4ccccc4)c4n(c3=O)CCN(C(=O)c3ccc(Br)c(Cl)c3)C4)cc2)n1] | N-benzyl-7-(4-bromo-3-chloro-benzoyl)-2-[4-(3-methylpyrazol-1-yl)phenyl]-3-oxo-6,8-dihydro-5H-imidazo[1,5-a]pyrazine-1-carboxamide | 1H NMR (400 MHz, DMSO-d6, 80° C.): 2.30 (s, 3H), 3.71 (t, J = 5.8 Hz, 2H), 3.85 (t, J = 4.8 Hz, 2H), 4.27 (d, J = 5.8 Hz, 2H), 4.87 (s, 2H), 6.34 (d, J = 2.4 Hz, 1H), 7.08 (d, J = 6.8 Hz, 2H), 7.20-7.23 (m, 3H), 7.33-7.37 (m, 2H), 7.40 (dd, J = 8.3, 1.9 Hz, 1H), 7.58 (br s, 1H), 7.75 (d, J = 1.9 Hz, 1H), 7.79 (d, J = 8.8 Hz, 2H), 7.85 (d, J = 8.3 Hz, 1H), 8.27 (d, J = 2.4 Hz, 1H) |
| 456 | 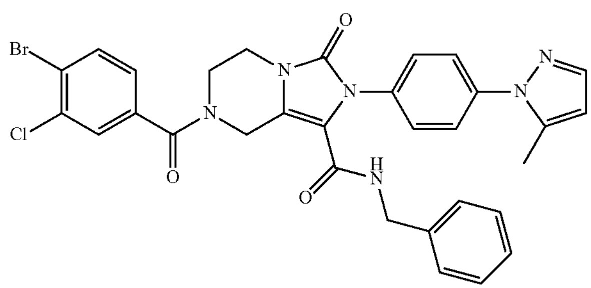 [SMILES: Cc1ccnn1-c1ccc(-n2c(C(=O)NCc3ccccc3)c3n(c2=O)CCN(C(=O)c2ccc(Br)c(Cl)c2)C3)cc1] | N-benzyl-7-(4-bromo-3-chloro-benzoyl)-2-[4-(5-methylpyrazol-1-yl)phenyl]-3-oxo-6,8-dihydro-5H-imidazo[1,5-a]pyrazine-1-carboxamide | 1H NMR (400 MHz, DMSO-d6, 80° C.): 2.35 (s, 3H), 3.72 (t, J = 5.6 Hz, 2H), 3.85 (t, J = 5.5 Hz, 2H), 4.28 (d, J = 5.8 Hz, 2H), 4.88 (s, 2H), 6.27 s, 1H), 7.10-7.12 (m, 2H), 7.12-7.27 (m, 3H), 7.39-7.41 (m, 3H), 7.53-7.56 (m, 3H), 7.75 (d, J = 1.9 Hz, 2H), 7.85 (d, J = 8.1 Hz, 1H). |
| 457 | 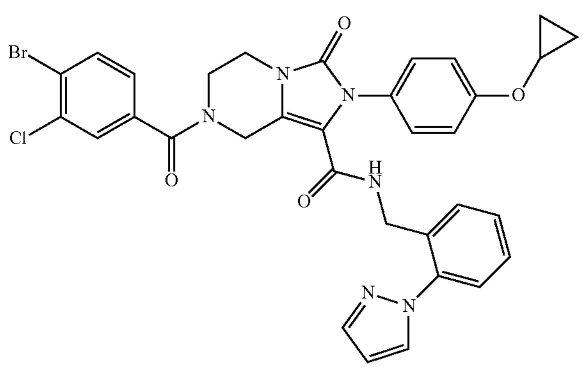 [SMILES: O=C(NCc1ccccc1-n1cccn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-3-oxo-N-[(2-pyrazol-1-yl)phenyl)methyl]-6,8-dihydro-5H-imidazo[1,5-a]pyrazine-1-carboxamide | 1H-NMR (DMSO, 600 MHz, 80° C.): 0.65-0.69 (m, 2H), 0.77-0.83 (m, 2H), 3.68 (dd, J = 5.5 Hz, 4.9 Hz, 2H), 3.80-3.89 (m, 3H), 4.19 (d, J = 6.0 Hz, 2H), 4.87 (s, 2H), 6.48 (dd, J = 2.1 Hz, 2.0 Hz, 1H), 7.05-7.11 (m, 3H), 7.18-7.24 (m, 3H), 7.30-7.37 (m, 2H), 7.38-7.43 (m, 2H), 7.61 (d, J = 1.4 Hz, 1H), 7.75 (d, J = 1.9 Hz, 1H), 7.85 (d, J = 8.2 Hz, 1H), 7.96 (d, J = 2.3 Hz, 1H) ppm |

TABLE A-continued

| Compound # | Structure | Name | NMR |
|---|---|---|---|
| 458 | 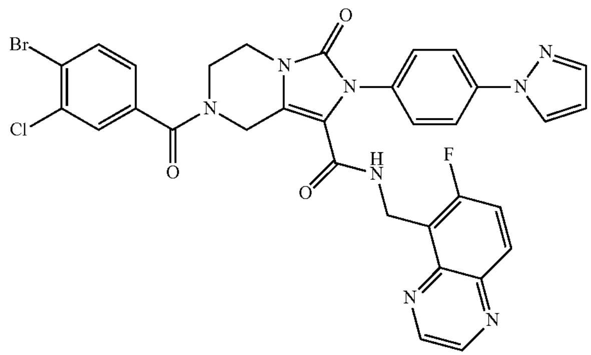 [SMILES: O=C(NCc1c(F)ccc2nccnc12)c1c2n(c(=O)n1-c1ccc(-n3cccn3)cc1)CCN(C(=O)c1ccc(Br)c(Cl)c1)C2] | 7-(4-bromo-3-chloro-benzoyl)-N-[(6-fluoroquinoxalin-5-yl)methyl]-3-oxo-2-(4-pyrazol-1-ylphenyl)-6,8-dihydro-5H-imidazo[1,5-a]pyrazine-1-carboxamide | 1H-NMR (DMSO-d6, 600 MHz, 80° C.): 3.63-3.70 (m, 2H), 3.80 (br. s, 2H), 4.82 (s, 2H), 4.88 (d, J = 4.5 Hz, 2H), 6.58 (s, 1H), 7.11 (br. s, 1H), 7.27 (d, J = 8.4 Hz, 2H), 7.37 (d, J = 8.1 Hz, 1H), 7.62-7.70 (m, 3H), 7.73 (s, 1H), 7.78 (s, 1H), 7.84 (d, J = 8.1 Hz, 1H), 8.01 (dd, J = 8.9 Hz, 5.9 Hz, 1H), 8.35 (s, 1H), 8.72 (s, 1H), 8.76 (s, 1H) ppm |
| 459 | 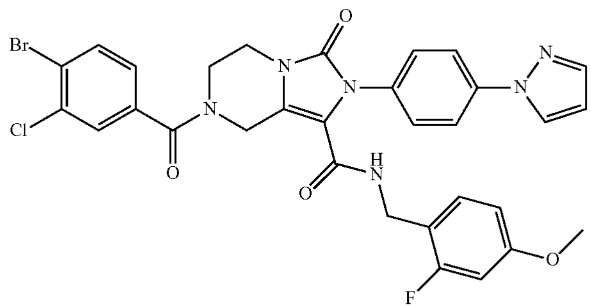 [SMILES: COc1ccc(CNC(=O)c2c3n(c(=O)n2-c2ccc(-n4cccn4)cc2)CCN(C(=O)c2ccc(Br)c(Cl)c2)C3)c(F)c1] | 7-(4-bromo-3-chloro-benzoyl)-N-[(2-fluoro-4-methoxy-phenyl)methyl]-3-oxo-2-(4-pyrazol-1-ylphenyl)-6,8-dihydro-5H-imidazo[1,5-a]pyrazine-1-carboxamide | 1H-NMR (DMSO, 600 MHz, 80° C.): 3.70-3.74 (m, 5H), 3.85 (br. s., 2H), 4.24 (d, J = 5.6 Hz, 2H), 4.86 (s, 2H), 6.56 (dd, J = 2.1 Hz, 2.1 Hz, 1H), 6.61 (dd, J = 8.7 Hz, 2.2 Hz, 1H), 6.66 (dd, J = 12.3 Hz, 1.8 Hz, 1H), 7.00 (dd, J = 8.3 Hz, 8.3 Hz, 1H), 7.36 (d, J = 8.7 Hz, 2H), 7.41 (dd, J = 8.3 Hz, 1.7 Hz, 1H), 7.48 (br. s., 1H), 7.76 (s, 2H), 7.82-7.88 (m, 3H), 8.42 (d, J = 2.2 Hz, 1H) ppm |
| 460 | 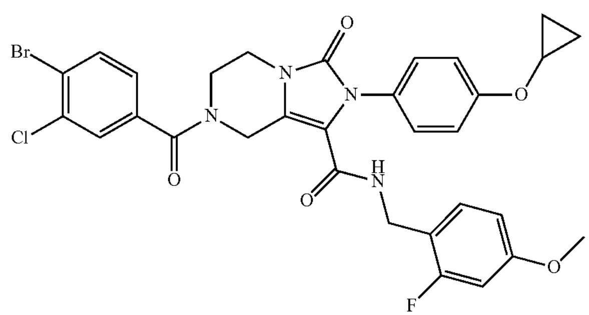 [SMILES: COc1ccc(CNC(=O)c2c3n(c(=O)n2-c2ccc(OC4CC4)cc2)CCN(C(=O)c2ccc(Br)c(Cl)c2)C3)c(F)c1] | 7-(4-bromo-3-chloro-benzoyl)-2-[4-(cyclopropoxy)phenyl]-N-[(2-fluoro-4-methoxy-phenyl)methyl]-3-oxo-6,8-dihydro-5H-imidazo[1,5-a]pyrazine-1-carboxamide | 1H-NMR (DMSO, 600 MHz, 80° C.): 0.65-0.70 (m, 2H), 0.78-0.83 (m, 2H), 3.68 (dd, J = 5.4 Hz, 5.2 Hz, 2H), 3.77 (s, 3H), 3.79-3.87 (m, 2H), 4.20 (d, J = 5.0 Hz, 2H), 4.84 (s, 2H), 6.65 (dd, J = 8.3 Hz, 2.2 Hz, 1H), 6.69 (dd, J = 12.1 Hz, 2.1 Hz, 1H), 6.93-7.09 (m, 4H), 7.18 (d, J = 9.0 Hz, 2H), 7.40 (dd, J = 8.2 Hz, 1.8 Hz, 1H), 7.74 (d, J = 1.6 Hz, 1H), 7.86 (d, J = 8.2 Hz, 1H) ppm |

| Compound # | Structure | Name | NMR |
|---|---|---|---|
| 461 | 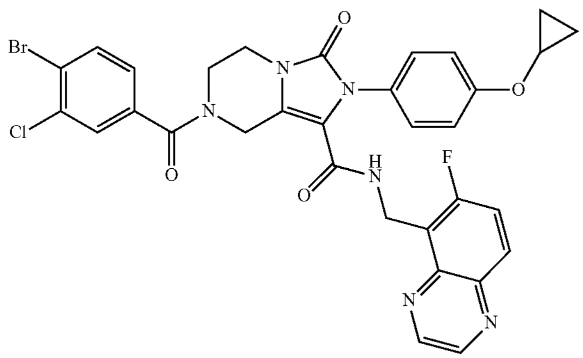 [SMILES: O=C(NCc1c(F)ccc2nccnc12)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-N-[(6-fluoroquinoxalin-5-yl)methyl]-3-oxo-6,8-dihydro-5H-imidazo[1,5-a]pyrazine-1-carboxamide | 1H-NMR (DMSO, 600 MHz, 80° C.): 0.61-0.67 (m, 2H), 0.76-0.82 (m, 2H), 3.64 (dd, J = 5.4 Hz, 5.1 Hz, 2H), 3.72-3.77 (m, 1H), 3.80 (br.s., 2H), 4.79-4.88 (m, 4H), 6.76 (br. s., 1H), 6.85 (d, J = 8.9 Hz, 2H), 7.08 (d, J = 8.7 Hz, 2H), 7.37 (dd, J = 8.2 Hz, 1.8 Hz, 1H), 7.69-7.74 (m, 2H), 7.84 (d, J = 8.0 Hz, 1H), 8.10 (dd, J = 9.3 Hz, 5.7 Hz, 1H), 8.85 (s, 1H), 8.94 (d, J = 1.6 Hz, 1H) ppm. |
| 462 | 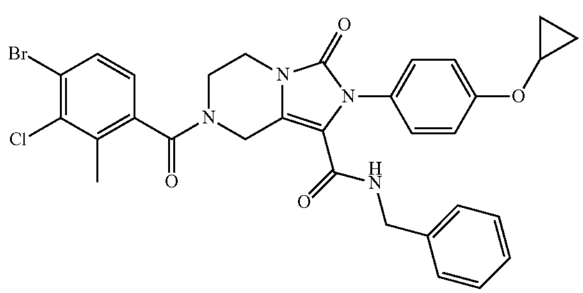 [SMILES: Cc1c(C(=O)N2CCn3c(c(C(=O)NCc4ccccc4)n(-c4ccc(OC5CC5)cc4)c3=O)C2)ccc(Br)c1Cl] | N-benzyl-7-(4-bromo-3-chloro-2-methyl-benzoyl)-2-[4-(cyclopropoxy)phenyl]-3-oxo-6,8-dihydro-5H-imidazo[1,5-a]pyrazine-1-carboxamide | 600 MHz, 100° C., DMSO-d6 0.68 (m, 2H), 0.8 (d, J = 6.4 Hz, 2H), 2.37 (s, 3H), 3.61 (br s, 2H), 3.85 (m, J = 3.1 Hz, 1H), 4.28 (br s, 2H), 4.54 (br s, 2H), 5.01 (br s, 2H), 7.06 (m, J = 8.7 Hz, 5H), 7.22 (m, 6H), 7.69 (d, J = 8.3 Hz, 1H) ppm. |

TABLE A-continued

| Compound # | Structure | Name | NMR |
|---|---|---|---|
| 463 | 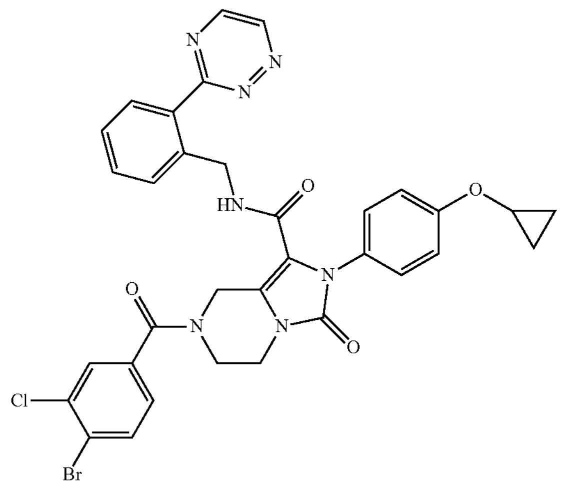 [SMILES: O=C(NCc1ccccc1-c1nccnn1)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-3-oxo-N-[[2-(1,2,4-triazin-3-yl)phenyl]methyl]-6,8-dihydro-5H-imidazo[1,5-a]pyrazine-1-carboxamide | 1H NMR (400 MHz, Chloroform-d) δ ppm 9.13 (d, J = 2.4 Hz, 1H), 8.53 (d, J = 2.4 Hz, 1H), 8.32-8.11 (m, 1H), 7.71 (d, J = 8.2 Hz, 1H), 7.64-7.58 (m, 1H), 7.56-7.43 (m, 3H), 7.23 (dd, J = 8.2, 2.0 Hz, 1H), 7.09-6.99 (m, 2H), 6.67 (d, J = 8.8 Hz, 3H), 5.02 (s, 2H), 4.51 (d, J = 5.6 Hz, 2H), 3.92 (d, J = 90.8 Hz, 4H), 3.43 (dt, J = 6.0, 3.2 Hz, 1H), 0.78-0.65 (m, 2H), 0.59 (q, J = 3.4 Hz, 2H) |
| 464 | 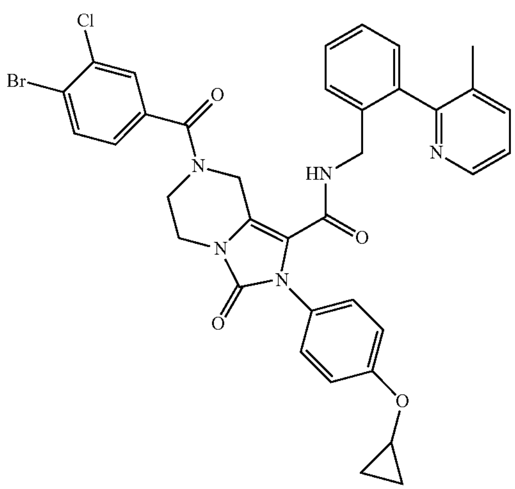 [SMILES: Cc1cccnc1-c1ccccc1CNC(=O)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-N-[[2-(3-methyl-2-pyridyl)phenyl]methyl]-3-oxo-6,8-dihydro-5H-imidazo[1,5-a]pyrazine-1-carboxamide | 1H NMR (400 MH, Chloroform-d) δ ppm 8.19 (s, 1H), 7.74-7.48 (m, 3H), 7.35-7.28 (m, 2H), 7.26-7.07 (m, 6H), 6.91 (d, J = 88 Hz, 2H), 6.19 (s, 1H), 4.97 (s, 2H), 3.93 (d, J = 86.5 Hz, 6H), 3.59 (dq, J = 6.0, 3.0 Hz, 1H), 2.10 (s, 3H), 0.82-0.54 (m, 4H) |

TABLE A-continued

| Compound # | Structure | Name | NMR |
|---|---|---|---|
| 465 | 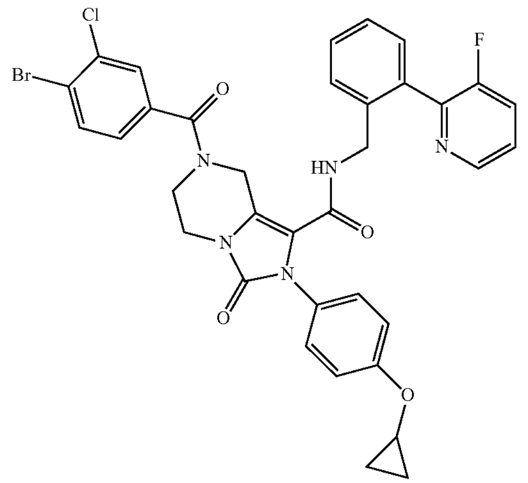 [SMILES: O=C(NCc1ccccc1-c1ncccc1F)c1c2n(c(=O)n1-c1ccc(OC3CC3)cc1)CCN(C(=O)c1ccc(Br)c(Cl)c1)C2] | 7-(4-bromo-3-chloro-benzoyl)-2-[4-(cyclopropoxy)phenyl]-N-[[2-(3-fluoro-2-pyridyl)phenyl]methyl]-3-oxo-6,8-dihydro-5H-imidazo[1,5-a]pyrazine-1-carboxamide | 1H NMR (400 MHz, Chloroform-d) δ ppm 8.15 (s, 1H), 7.70 (d, J = 8.2 Hz, 1H), 7.64-7.56 (m, 1H), 7.53-7.29 (m, 5H), 7.26-7.08 (m, 4H), 6.84 (d, J = 8.4 Hz, 2H), 6.37 (s, 1H), 5.00 (s, 2H), 4.00 (d, J = 147.2 Hz, 6H), 3.53 (dt, J = 6.3, 3.2 Hz, 1H), 0.71 (dt, J = 7.7, 5.7 Hz, 2H), 0.59 (s, 2H). |
| 466 | 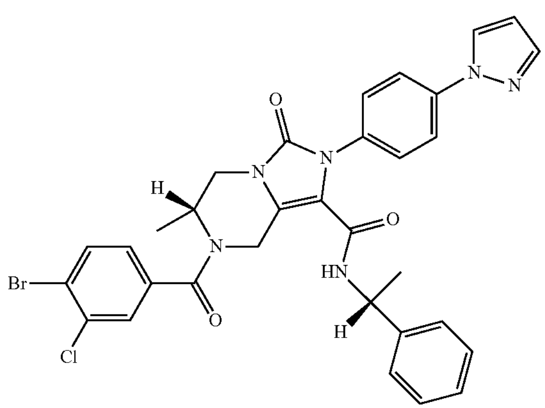 [SMILES: C[C@@H]1Cn2c(c(C(=O)N[C@H](C)c3ccccc3)n(-c3ccc(-n4cccn4)cc3)c2=O)CN1C(=O)c1ccc(Br)c(Cl)c1] | (6RS)-7-(4-bromo-3-chloro-benzoyl)-6-methyl-3-oxo-N-[(1R)-1-phenylethyl]-2-(4-pyrazol-1-ylphenyl)-6,8-dihydro-5H-imidazo[1,5-a]pyrazine-1-carboxamide | 1H NMR (300 MHz, Chloroform-d) δ 7.96 (d, J = 2.6 Hz, 1H), 7.85-7.77 (m, 3H), 7.72 (d, J = 8.2 Hz, 1H), 7.59 (d, J = 1.9 Hz, 1H), 7.45 (d, J = 8.7 Hz, 2H), 7.21 (dd, J = 8.2, 2.0 Hz, 1H), 7.16-7.10 (m, 3H), 6.90 (s, 2H), 6.57 (t, J = 2.1 Hz, 1H), 5.48 (s, 1H), 5.14 (d, J = 7.3 Hz, 1H), 4.97 (t, J = 6.9 Hz, 1H), 4.63 (d, J = 19.1 Hz, 1H), 3.89 (d, J = 12.8 Hz, 1H), 3.73 (d, J = 13.5 Hz, 1H), 1.43 (d, J = 7.0 Hz, 3H), 1.26 (d, J = 6.8 Hz, 3H) |

TABLE A-continued

| Compound # | Structure | Name | NMR |
|---|---|---|---|
| 467 | 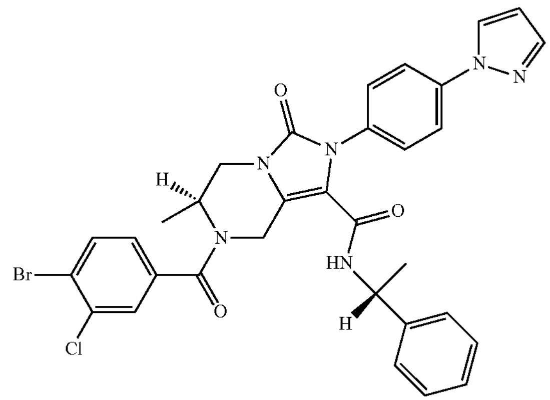 [SMILES: C[C@@H](NC(=O)c1c2n(c(=O)n1-c1ccc(-n3cccn3)cc1)C[C@H](C)N(C(=O)c1ccc(Br)c(Cl)c1)C2)c1ccccc1] | (6SR)-7-(4-bromo-3-chloro-benzoyl)-6-methyl-3-oxo-N-[(1R)-1-phenylethyl]-2-(4-pyrazol-1-ylphenyl)-6,8-dihydro-5H-imidazo[1,5-a]pyrazine-1-carboxamide | 1H NMR (300 MHz, Chloroform-d) δ 7.96 (d, J = 2.6 Hz, 1H), 7.85-7.63 (m, 4H), 7.60 (d, J = 1.9 Hz, 1H), 7.44 (d, J = 8.6 Hz, 2H), 7.23-7.09 (m, 4H), 6.96-6.88 (m, 2H), 6.57 (t, J = 2.1 Hz, 1H), 5.48 (s, 1H), 5.14 (d J = 7.6 Hz, 1H), 4.98 (t, J = 7.0 Hz, 1H), 4.65 (s, 1H), 3.88 (d, J = 12.7 Hz, 1H), 3.79-3.68 (m, 1H), 1.41 (d, J = 6.9 Hz, 3H), 1.25 (t, J = 6.6 Hz, 3H) |
| 468 | 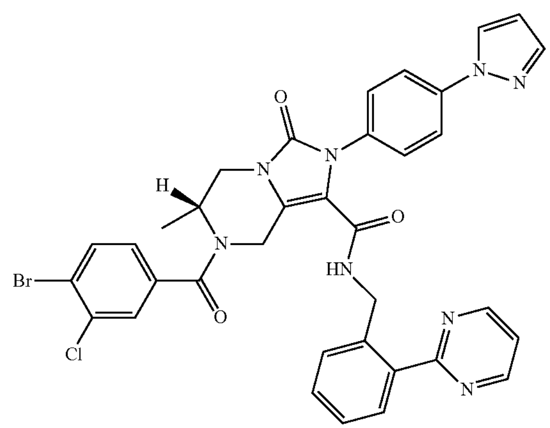 [SMILES: C[C@@H]1Cn2c(c(C(=O)NCc3ccccc3-c3ncccn3)n(-c3ccc(-n4cccn4)cc3)c2=O)CN1C(=O)c1ccc(Br)c(Cl)c1] | rac-(6R)-7-(4-bromo-3-chloro-benzoyl)-6-methyl-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide | 1H NMR (400 MHz, Chloroform-d) δ 8.43 (d, J = 4.9 Hz, 2H), 8.06-7.97 (m, 1H), 7.77-7.58 (m, 4H), 7.52 (d, J = 7.2 Hz, 1H), 7.43 (pd, J = 7.3, 1.8 Hz, 2H), 7.32 (d, J = 8.6 Hz, 2H), 7.24-7.17 (m, 3H), 7.13 (s, 1H), 6.99 (t, J = 4.9 Hz, 1H), 6.44 (dd, J = 2.5, 1.7 Hz, 1H), 5.36 (s, 2H), 4.72-4.52 (m, 2H), 4.42 (dd, J = 13.4, 5.9 Hz, 1H), 3.84 (d, J = 12.8 Hz, 1H), 3.70 (d, J = 13.1 Hz, 1H), 1.39 (d, J = 7.0 Hz, 3H) |

TABLE A-continued

| Compound # | Structure | Name | NMR |
|---|---|---|---|
| 469 | 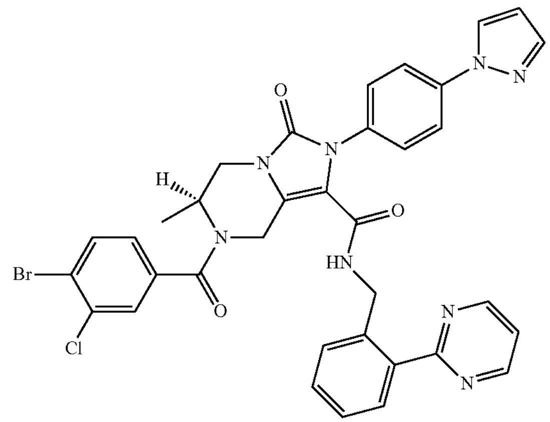 [SMILES: C[C@H]1Cn2c(c(C(=O)NCc3ccccc3-c3ncccn3)n(-c3ccc(-n4cccn4)cc3)c2=O)CN1C(=O)c1ccc(Br)c(Cl)c1] | rac-(6S)-7-(4-bromo-3-chlorobenzoyl)-6-methyl-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide | 1H NMR (400 MHz, Chloroform-d) δ 8.43 (d, J = 4.9 Hz, 2H), 8.07-7.95 (m, 1H), 7.75-7.57 (m, 4H), 7.52 (d, J = 7.4 Hz, 1H), 7.47-7.38 (m, 2H), 7.32 (d, J = 8.5 Hz, 2H), 7.23-7.17 (m, 3H), 7.13 (s, 1H), 6.99 (t, J = 4.9 Hz, 1H), 6.44 (t, J = 2.1 Hz, 1H), 5.36 (s, 2H), 4.71-4.51 (m, 2H), 4.42 (dd, J = 13.5, 5.9 Hz, 1H), 3.84 (d, J = 12.8 Hz, 1H), 3.70 (d, J = 12.8 Hz, 1H), 1.39 (d, J = 7.0 Hz, 3H) |
| 470 | 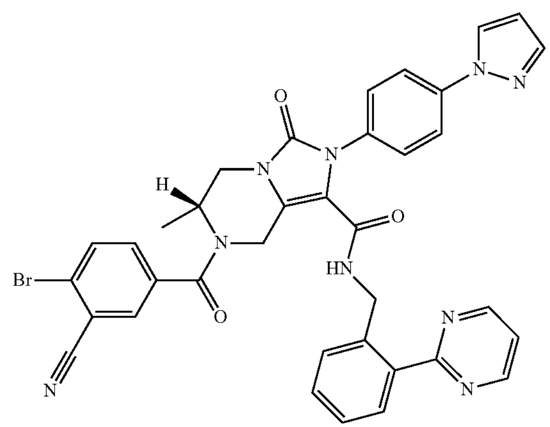 [SMILES: C[C@@H]1Cn2c(c(C(=O)NCc3ccccc3-c3ncccn3)n(-c3ccc(-n4cccn4)cc3)c2=O)CN1C(=O)c1ccc(Br)c(C#N)c1] | rac-(6R)-7-(4-bromo-3-cyanobenzoyl)-6-methyl-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide | 1H NMR (300 MHz, Chloroform-d) δ 8.45 (d, J = 4.9 Hz, 2H), 8.09-8.00 (m, 1H), 7.88-7.77 (m, 2H), 7.68 (dd, J = 14.2, 2.1 Hz, 2H), 7.62-7.39 (m, 4H), 7.34 (d, J = 8.7 Hz, 2H), 7.23 (d, J = 8.8 Hz, 2H), 7.15 (s, 1H), 7.02 (t, J = 4.9 Hz, 1H), 6.47 (t, J = 2.1 Hz, 1H), 5.25 (s, 2H), 4.73 (s, 1H), 4.59 (d, J = 10.5 Hz, 1H), 4.44 (d, J = 12.6 Hz, 1H), 3.89 (d, J = 12.8 Hz, 1H), 3.74 (d, J = 8.3 Hz, 1H), 1.44 (d, J = 6.9 Hz, 3H) |

| Compound # | Structure | Name | NMR |
|---|---|---|---|
| 471 | 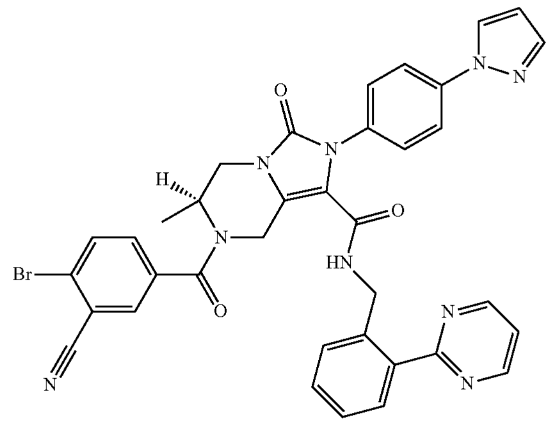 [SMILES: C[C@H]1Cn2c(c(C(=O)NCc3ccccc3-c3ncccn3)n(-c3ccc(-n4cccn4)cc3)c2=O)CN1C(=O)c1ccc(Br)c(C#N)c1] | rac-(6S)-7-(4-bromo-3-cyano-benzoyl)-6-methyl-3-oxo-2-(4-pyrazol-1-ylphenyl)-N-[(2-pyrimidin-2-yl)phenyl)methyl]-6,8-dihydro-5H-imidazo[1,5-a]pyrazine-1-carboxamide | 1H NMR (300 MHz, Chloroform-d) δ 8.45 (d, J = 4.9 Hz, 2H), 8.09-8.00 (m, 1H), 7.88-7.77 (m, 2H), 7.68 (dd, J = 14.2, 2.1 Hz, 2H), 7.62-7.39 (m, 4H), 7.34 (d, J = 8.7 Hz, 2H), 7.23 (d, J = 8.8 Hz, 2H), 7.15 (s, 1H), 7.02 (t, J = 4.9 Hz, 1H), 6.47 (t, J = 2.1 Hz, 1H), 5.25 (s, 2H), 4.73 (s, 1H), 4.59 (d, J = 10.5 Hz, 1H), 4.44 (d, J = 12.6 Hz, 1H), 3.89 (d, J = 12.8 Hz, 1H), 3.74 (d, J = 8.3 Hz, 1H), 1.44 (d, J = 6.9 Hz, 3H). |
| 472 | 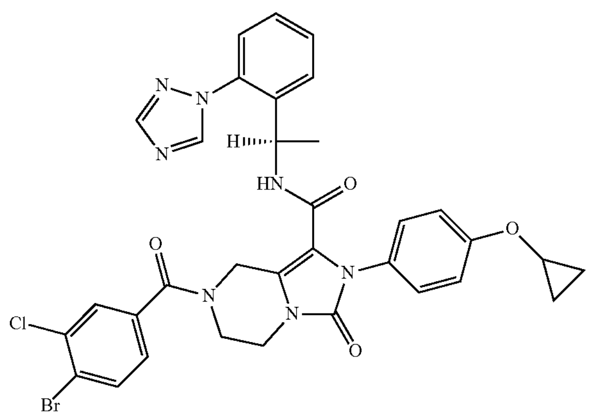 [SMILES: C[C@@H](NC(=O)c1c2n(c(=O)n1-c1ccc(OC3CC3)cc1)CCN(C(=O)c1ccc(Br)c(Cl)c1)C2)c1ccccc1-n1cncn1] | 7-(4-bromo-3-chloro-benzoyl)-2-[4-(cyclopropoxy)phenyl]-3-oxo-N-[rac-(1R)-1-[2-(1,2,4-triazol-1-yl)phenyl]ethyl]-6,8-dihydro-5H-imidazo[1,5-a]pyrazine-1-carboxamide | 1H NMR (400 MHz, Chloroform-d) δ 8.48 (s, 1H), 8.08 (s, 1H), 7.71 (d, J = 8.0 Hz, 1H), 7.60 (d, J = 2.0 Hz, 1H), 7.44-7.37 (m, 2H), 7.34-7.31 (m, 2H), 7.26-7.18 (m, 4H), 7.01 (d, J = 7.6 Hz, 1H), 5.57 (d, J = 7.2 Hz, 1H), 4.96 (s, 2H), 4.88-4.82 (m, 1H), 4.00 (s, 2H), 3.83-3.77 (m, 3H), 0.97 (d, J = 6.4 Hz, 3H), 0.89-0.78 (m, 4H) |

TABLE A-continued

| Compound # | Name | NMR |
|---|---|---|
| 473 | 7-(4-bromo-3-chloro-benzoyl)-2-[4-(cyclopropoxy)phenyl]-3-oxo-N-[(1S)-1-[2-(1,2,4-triazol-1-yl)phenyl]ethyl]-6,8-dihydro-5H-imidazo[1,5-a]pyrazine-1-carboxamide | 1H NMR (400 MHz, Chloroform-d) δ 8.43 (s, 1H), 8.06 (s, 1H), 7.70 (d, J = 8.4 Hz, 1H), 7.60 (d, J = 2.0 Hz, 1H), 7.43-7.36 (m, 2H), 7.34-7.31 (m, 2H), 7.26-7.18 (m, 4H), 7.00 (d, J = 7.6 Hz, 1H), 5.58 (d, J = 7.2 Hz, 1H), 4.96 (s, 2H), 4.90-4.83 (m, 1H), 4.00 (s, 2H), 3.83-3.77 (m, 3H), 0.97 (d, J = 6.8 Hz, 3H), 0.89-0.84 (m, 2H), 0.82-0.78 (m, 2H) |
| 474 | 7-(4-bromo-3-chloro-benzoyl)-3-oxo-2-(4-pyrazol-1-ylphenyl)-N-[rac-(1R)-1-[2-(1,2,4-triazol-1-yl)phenyl]ethyl]-6,8-dihydro-5H-imidazo[1,5-a]pyrazine-1-carboxamide | 1H NMR (400 MHz, Chloroform-d) δ 8.35 (s, 1H), 8.03 (s, 1H), 7.93 С 7.92 (m, 1H), 7.78 С 7.70 (m, 4H), 7.60 (d, J = 4.0 Hz, 1H), 7.48 С 7.44 (m, 2H), 7.37 С 7.30 (m, 2H), 7.24 С 7.21 (m, 1H), 7.17 С 7.09 (m, 2H), 6.54 С 6.53 (m, 1H), 5.94 (d, J = 8.0 Hz, 1H), 5.01 С 4.97 (m, 3H), 4.00 (s, 2H), 3.84 (s, 2H), 0.98 (d, J = 8.0 Hz, 3H) |

TABLE A-continued

| Compound # | Structure | Name | NMR |
|---|---|---|---|
| 475 | 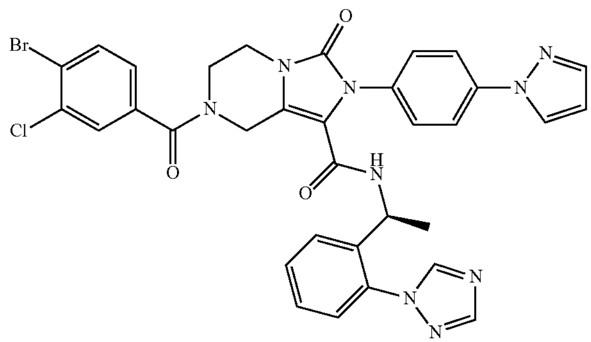 [SMILES: C[C@H](NC(=O)c1c2n(c(=O)n1-c1ccc(-n3cccn3)cc1)CCN(C(=O)c1ccc(Br)c(Cl)c1)C2)c1ccccc1-n1cncn1] | 7-(4-bromo-3-chloro-benzoyl)-3-oxo-2-(4-pyrazol-1-ylphenyl)-N-[rac-(1S)-1-[2-(1,2,4-triazol-1-yl)phenyl]ethyl]-6,8-dihydro-5H-imidazo[1,5-a]pyrazine-1-carboxamide | 1H NMR (400 MHz, Chloroform-d) δ 8.34 (s, 1H), 8.03 (s, 1H), 7.93 C 7.92 (m, 1H), 7.78 C 7.70 (m, 4H), 7.60 (d, J = 2.0 Hz, 1H), 7.47 C 7.44 (m, 2H), 7.37 C 7.30 (m, 2H), 7.24 C 7.21 (m, 1H), 7.16 C 7.09 (m, 2H), 6.54 (m, 1H), 5.95 (d, J = 8.0 Hz, 1H), 5.01 C 4.97 (m, 3H), 3.99 (s, 2H), 3.83 (s, 2H), 0.98 (d, J = 4.0 Hz, 3H). |
| 476 | 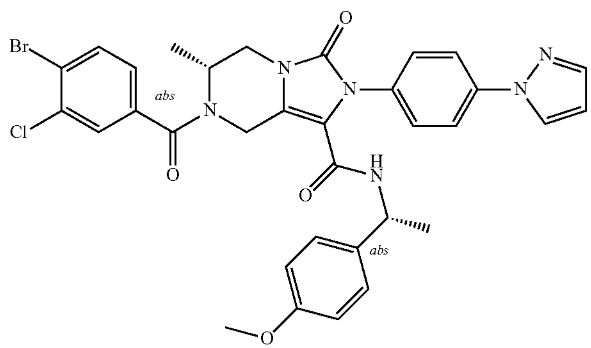 [SMILES: COc1ccc([C@@H](C)NC(=O)c2c3n(c(=O)n2-c2ccc(-n4cccn4)cc2)C[C@@H](C)N(C(=O)c2ccc(Br)c(Cl)c2)C3)cc1] | (6R)-7-(4-bromo-3-chloro-benzoyl)-N-[(1R)-1-(4-methoxyphenyl)ethyl]-6-methyl-3-oxo-2-(4-pyrazol-1-ylphenyl)-6,8-dihydro-5H-imidazo[1,5-a]pyrazine-1-carboxamide | 1H NMR (300 MHz, Chloroform-d) δ 7.96 (d, J = 2.5 Hz, 1H), 7.84-7.73 (m, 4H), 7.59 (d, J = 1.9 Hz, 1H), 7.44 (d, J = 8.6 Hz, 2H), 7.22 (dd, J = 8.2, 2.0 Hz, 1H), 6.82 (d, J = 8.3 Hz, 2H), 6.66 (d, J = 8.5 Hz, 2H), 6.60-6.53 (m, 1H), 5.38 (s, 1H), 5.10 (d, J = 7.3 Hz, 1H), 4.97-4.87 (m, 1H), 4.67 (s, 1H), 3.89 (d, J = 12.8 Hz, 1H), 3.84-3.68 (s, 4H), 1.43 (d, J = 7.0 Hz, 3H), 1.31-1.21 (m, 3H) |
| 477 | 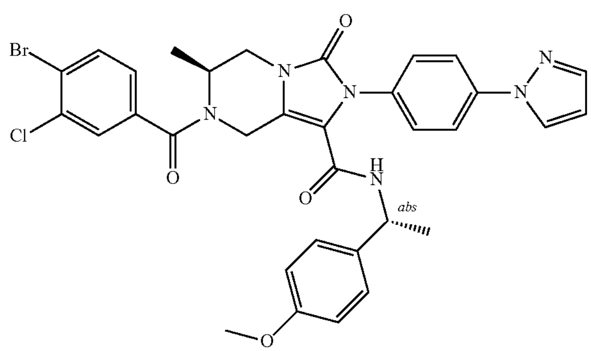 [SMILES: COc1ccc([C@@H](C)NC(=O)c2c3n(c(=O)n2-c2ccc(-n4cccn4)cc2)C[C@H](C)N(C(=O)c2ccc(Br)c(Cl)c2)C3)cc1] | (6SR)-7-(4-bromo-3-chloro-benzoyl)-N-[(1R)-1-(4-methoxyphenyl)ethyl]-6-methyl-3-oxo-2-(4-pyrazol-1-ylphenyl)-6,8-dihydro-5H-imidazo[1,5-a]pyrazine-1-carboxamide | 1H NMR (300 MHz, Chloroform-d) δ 7.96 (d, J = 2.6 Hz, 1H), 7.85-7.71 (m, 4H), 7.60 (d, J = 1.9 Hz, 1H), 7.43 (d, J = 8.5 Hz, 2H), 7.23 (dd, J = 8.2, 2.0 Hz, 1H), 6.84 (d, J = 8.5 Hz, 2H), 6.68 (d, J = 8.6 Hz, 2H), 6.61-6.54 (m, 1H), 5.38 (s, 1H), 5.02 (dd, J = 44.1, 7.3 Hz, 2H), 4.63 (d, J = 19.0 Hz, 1H), 3.87 (d, J = 12.8 Hz, 1H), 3.69 (s, 4H), 1.41 (d, J = 7.0 Hz, 3H), 1.23 (d, J = 6.8 Hz, 3H) |

TABLE A-continued

| Compound # | Structure | Name | NMR |
|---|---|---|---|
| 478 | 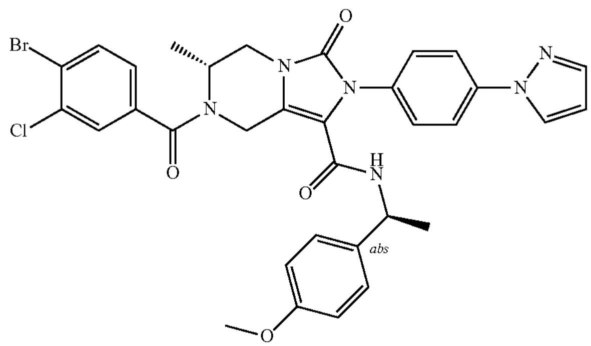 [SMILES: COc1ccc([C@H](C)NC(=O)c2c3n(c(=O)n2-c2ccc(-n4cccn4)cc2)C[C@@H](C)N(C(=O)c2ccc(Br)c(Cl)c2)C3)cc1] | (6RS)-7-(4-bromo-3-chloro-benzoyl)-N-[(1S)-1-(4-methoxyphenyl)ethyl]-6-methyl-3-oxo-2-(4-pyrazol-1-ylphenyl)-6,8-dihydro-5H-imidazo[1,5-a]pyrazine-1-carboxamide | 1H NMR (300 MHz, Chloroform-d) δ 7.96 (d, J = 2.6 Hz, 1H), 7.85-7.71 (m, 4H), 7.60 (d, J = 1.8 Hz, 1H), 7.43 (d, J = 8.4 Hz, 2H), 7.23 (dd, J = 8.2, 1.9 Hz, 1H), 6.84 (d, J = 8.5 Hz, 2H), 6.68 (d, J = 8.6 Hz, 2H), 6.57 (t, J = 2.1 Hz, 1H), 5.35 (s, 1H), 5.09 (d, J = 7.5 Hz, 1H), 4.94 (s, 1H), 4.63 (d, J = 19.0 Hz, 1H), 3.87 (d, J = 12.8 Hz, 1H), 3.69 (s, 4H), 1.41 (d, J = 6.9 Hz, 3H), 1.23 (d, J = 6.7 Hz, 3H) |
| 479 | 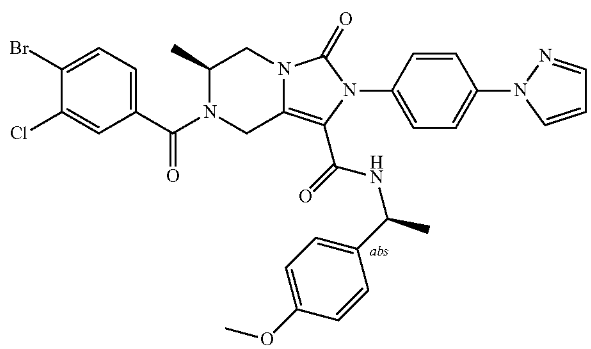 [SMILES: COc1ccc([C@H](C)NC(=O)c2c3n(c(=O)n2-c2ccc(-n4cccn4)cc2)C[C@H](C)N(C(=O)c2ccc(Br)c(Cl)c2)C3)cc1] | (6SR)-7-(4-bromo-3-chloro-benzoyl)-N-[(1S)-1-(4-methoxyphenyl)ethyl]-6-methyl-3-oxo-2-(4-pyrazol-1-ylphenyl)-6,8-dihydro-5H-imidazo[1,5-a]pyrazine-1-carboxamide | 1H NMR (300 MHz, Chloroform-d) δ 7.96 (d, J = 2.5 Hz, 1H), 7.84-7.69 (m, 4H), 7.60 (d, J = 1.8 Hz, 1H), 7.44 (d, J = 8.4 Hz, 2H), 7.22 (dd, J = 8.2, 2.0 Hz, 1H), 6.82 (d, J = 8.2 Hz, 2H), 6.66 (d, J = 8.4 Hz, 2H), 6.57 (t, J = 2.1 Hz, 1H), 5.35 (s, 1H), 5.09 (d, J = 7.4 Hz, 1H), 4.98-4.82 (m, 1H), 4.64 (d, J = 19.0 Hz, 1H), 3.89 (d, J = 12.8 Hz, 1H), 3.69 (s, 4H), 1.43 (d, J = 7.0 Hz, 3H), 1.26 (d, J = 6.8 Hz, 3H) |
| 480 | 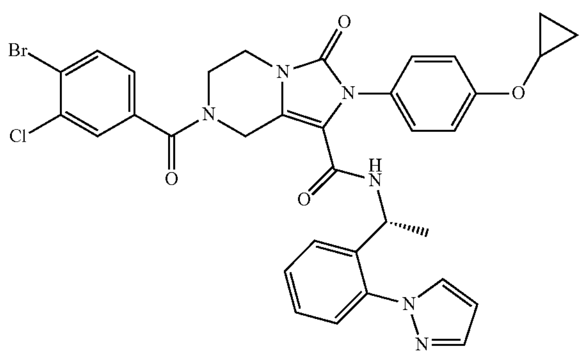 [SMILES: C[C@@H](NC(=O)c1c2n(c(=O)n1-c1ccc(OC3CC3)cc1)CCN(C(=O)c1ccc(Br)c(Cl)c1)C2)c1ccccc1-n1cccn1] | 7-(4-bromo-3-chloro-benzoyl)-2-[4-(cyclopropoxy)phenyl]-3-oxo-N-[rac-(1R)-1-(2-pyrazol-1-ylphenyl)ethyl]-6,8-dihydro-5H-imidazo[1,5-a]pyrazine-1-carboxamide | 1H NMR (300 MHz, Chloroform-d) δ 7.79 C 7.55 (m, 4H), 7.40 C 7.31 (m, 3H), 7.26 C 7.18 (m, 2H), 7.15 C 6.99 (m, 3H), 6.44 (s, 1H), 6.24 (d, J = 9.0 Hz, 1H), 5.15 C 4.85 (m, 3H), 4.20 C 3.65 (m, 5H), 0.99 C 0.65 (m, 8H) |

| Compound # | Structure | Name | NMR |
|---|---|---|---|
| 481 | 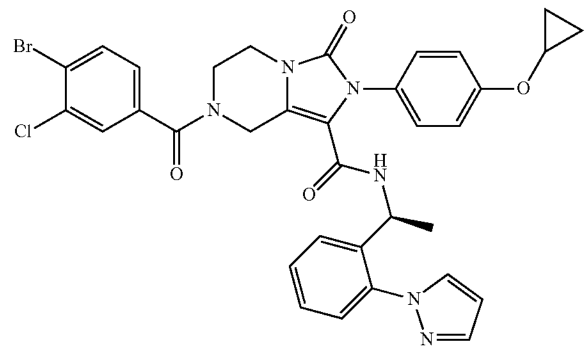 [SMILES: C[C@H](NC(=O)c1c2n(c(=O)n1-c1ccc(OC3CC3)cc1)CCN(C(=O)c1ccc(Br)c(Cl)c1)C2)c1ccccc1-n1cccn1] | 7-(4-bromo-3-chloro-benzoyl)-2-[4-(cyclopropoxy)phenyl]-3-oxo-N-[rac-(1S)-1-(2-pyrazol-1-ylphenyl)ethyl]-6,8-dihydro-5H-imidazo[1,5-a]pyrazine-1-carboxamide | 1H NMR (300 MHz, Chloroform-d) δ 7.79 C 7.55 (m, 4H), 7.40 C 7.31 (m, 3H), 7.26 C 7.18 (m, 2H), 7.15 C 6.99 (m, 3H), 6.44 (s, 1H), 6.24 (d, J = 9.0 Hz, 1H), 5.15 C 4.85 (m, 3H), 4.20 C 3.65 (m, 5H), 0.99 C 0.65 (m, 8H). |
| 482 | 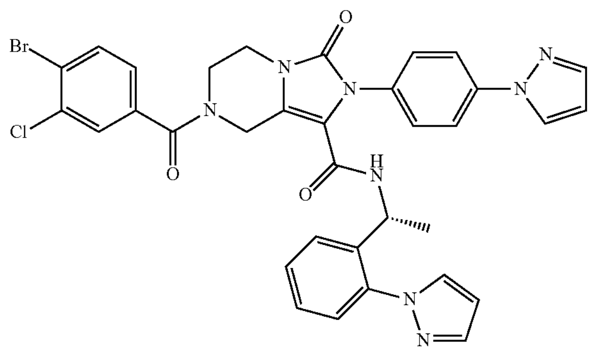 [SMILES: C[C@@H](NC(=O)c1c2n(c(=O)n1-c1ccc(-n3cccn3)cc1)CCN(C(=O)c1ccc(Br)c(Cl)c1)C2)c1ccccc1-n1cccn1] | 7-(4-bromo-3-chloro-benzoyl)-3-oxo-2-(4-pyrazol-1-ylphenyl)-N-[rac-(1R)-1-(2-pyrazol-1-ylphenyl)ethyl]-6,8-dihydro-5H-imidazo[1,5-a]pyrazine-1-carboxamide | 1H NMR (300 MHz, Chloroform-d) δ 7.85 (s, 1H), 7.78 (s, 1H), 7.72 C 7.50 (m, 6H), 7.48 C 7.38 (m, 2H), 7.29 C 7.16 (m, 3H), 7.13 C 6.99 (m, 2H), 6.51 (s, 1H), 6.40 (s, 1H), 5.19 (s, 1H), 5.00 (s, 2H), 4.29 C 3.68 (m, 4H), 0.84 (d, J = 6.9 Hz, 3H) |
| 483 | 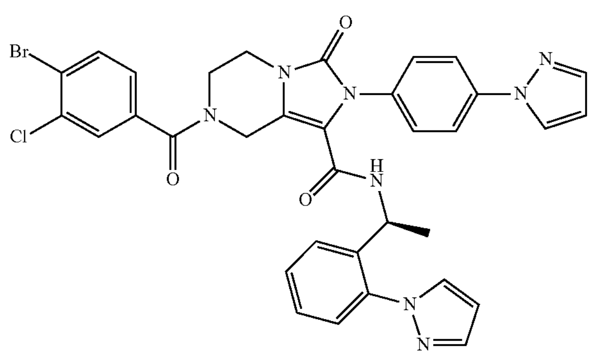 [SMILES: C[C@H](NC(=O)c1c2n(c(=O)n1-c1ccc(-n3cccn3)cc1)CCN(C(=O)c1ccc(Br)c(Cl)c1)C2)c1ccccc1-n1cccn1] | 7-(4-bromo-3-chloro-benzoyl)-3-oxo-2-(4-pyrazol-1-ylphenyl)-N-[rac-(1S)-1-(2-pyrazol-1-ylphenyl)ethyl]-6,8-dihydro-5H-imidazo[1,5-a]pyrazine-1-carboxamide | 1H NMR (300 MHz, Chloroform-d) δ 7.85 (s, 1H), 7.78 (s, 1H), 7.72 C 7.50 (m, 6H), 7.48 C 7.38 (m, 2H), 7.29 C 7.16 (m, 3H), 7.13 C 6.99 (m, 2H), 6.51 (s, 1H), 6.40 (s, 1H), 5.19 (s, 1H), 5.00 (s, 2H), 4.29 C 3.68 (m, 4H), 0.84 (d, J = 6.9 Hz, 3H) |

Example A

HBV-DNA Antiviral Assay Using HepG2.2.15 Cells

The following assay procedure describes the HBV antiviral assay. This assay uses HepG2.2.15 cells, which have been transfected with HBV genome, and extracellular HBV DNA quantification as endpoint. Cell viability is assessed in parallel by measuring the intracellular ATP content using the CellTiter-Glo© reagent from Promega.

On day 0, HepG2.2.15 cells were seeded in 96-well plates at a density of $6.0 \times 10^4$ cells/well (0.1 mL/well). The cells were incubated at 37° C. and 5% $CO_2$.

On day 1, the test articles were diluted and added to cell culture wells (8 concentrations, 4-fold dilution, in duplicate). GLS4, Tenofovir and Sorafenib were used as reference compounds. 100 µL of culture medium containing the compounds was added to the plate, and the final total volume per well was 200 µL. The final concentration of DMSO in the culture medium was 0.5%. The plate map of compound treatment is shown below. The cells were cultured at 37° C. and 5% $CO_2$ for 3 days. The plate map of compound treatment is shown in FIG. 1.

On day 4, the plates were refreshed with culture media with compounds.

On day 7, cell viability was assessed using the CellTiter-Glo, and the cell culture supernatants were collected for determination of HBV DNA by qPCR.

HBV DNA quantification by qPCR

Extracellular DNA was isolated with QIAamp 96 DNA Blood Kit per the manufacturer's manual. HBV DNA was then quantified by qPCR with HBV specific primers and probes as specified in Table 1 using the FastStart Universal MasterMix from Roche on an ABI-7900HT. The PCR cycle program consisted of 95° C. for 10 min, followed by 40 cycles at 95° C. for 15 sec and 60° C. for 1 min.

TABLE 1

HBV DNA Primers and Probe

| Items | Name | Sequence (5'→3') |
|---|---|---|
| HBV Primer | HBV-forward | GTGTCTGCGGCGTTTTATCA (SEQ ID NO: 1) |
| | HBV-reverse | GACAAACGGGCAACATACCTT (SEQ ID NO: 2) |
| HBV Probe | HBV probe | FAM-CCTCTKCATCCTGCTGCTATGCCTCATC-TAMRA (SEQ ID NO: 3) |

A DNA standard was prepared by dilution of the pAAV2 HBV1.3 plasmid with concentrations ranging from 10 to $1 \times 10^7$ copies/µL and used to generate a standard curve by plotting Ct value vs. the concentration of the HBV plasmid DNA standard. The quantity of HBV DNA in each sample was determined by interpolating from the standard curve.

Cell Viability

After harvest of the supernatants, the cell viability was detected by CellTiter-Glo® according to the manufacturer's manual. In brief, 50 µL of fresh cell culture medium was added to the culture plates, followed by addition of 50 µL CellTiter-Glo into each well. The plates were incubated at room temperature for 10 mins. The luminescence signal was collected on a BioTek Synergy 2 plate reader.

Data Analysis

Cell viability was calculated as follows: % Cell viability= (luminescence value of test sample−average luminescence value of blank)/(average luminescence value of 0.5% DMSO control−average luminescence of blank)×100%. HBV DNA inhibition was calculated as follows: 100-(HBV DNA copy number of test sample−HBV DNA copy number of ETV)/HBV DNA copy number of 0.5% DMSO control−HBV DNA copy number of ETV)×100%. The $CC_{50}$, $EC_{50}$ and $EC_{90}$ values were determined by dose-response curves fitted by GraphPad Prism using "log (agonist) vs. response—Variable slope".

Compounds of Formula (I) are active against HBV as shown in Table 2, where 'A' indicates an $EC_{50} \leq 100$ nM, 'B' indicates an $EC_{50} > 100$ nM and $\leq 500$ nM, 'C' indicates an $EC_{50} > 500$ nM and $\leq 5000$ nM, and 'D' indicates an $EC_{50} > 5000$ nM.

TABLE 2

| Compound | $EC_{50}$ |
|---|---|
| 1 | D |
| 2 | C |
| 3 | B |
| 4 | A |
| 5 | D |
| 6 | D |
| 7 | D |
| 8 | D |
| 9 | B |
| 10 | C |
| 11 | B |
| 12 | D |
| 13 | C |
| 14 | D |
| 16 | C |
| 17 | D |
| 18 | D |
| 19 | D |
| 20 | D |
| 463 | B |
| 464 | C |
| 465 | B |
| 466 | C |
| 467 | B |
| 468 | B |
| 469 | A |
| 470 | B |
| 471 | C |
| 472 | C |
| 473 | D |

Example B

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using ATPlite (Perkin Elmer).

On day 0, HepG2.117 cells (which are maintained in routine cell culture with doxycycline present in the medium at a final concentration of 1 µg/mL) were seeded in 96-well plates (white with clear bottom) at a density of $2.0 \times 10^4$ cells/well (0.1 mL/well) in medium without doxycycline to induce pgRNA transcription and subsequent formation of HBV particles. The cells were incubated at 37° C. and 5% $CO_2$.

On day 1, medium was removed from each well, the test articles were diluted in culture medium without doxycycline and 100 µL was added to cell culture wells (9 concentrations, 4-fold dilution). For each plate, 6 untreated (merely DMSO) wells were included. The final concentration of DMSO in the culture medium was 2%. Each plate was prepared in duplicate (one for HBV DNA extraction, one for ATPlite measurement). The cells were incubated at 37° C. and 5% $CO_2$ for 3 days.

On day 4, cell viability was assessed using ATPlite and cell lysates were prepared for HBV DNA extraction and subsequent quantification by qPCR.

HBV DNA Quantification by qPCR

Medium was removed from each well and 100 μL of 0.33% NP-40 in $H_2O$ was added to each well. Plates were sealed, incubated at 4° C. for 5 mins, vortexed extensively and centrifuged briefly. Next, 35 μL of lysate was added to 65 μL QuickExtract DNA Extraction Solution (Epicentre) in a PCR plate for each well. PCR plate was incubated at 65° C. for 6 mins, 98° C. for 2 mins and finally cooled to 4° C. HBV DNA was then quantified by qPCR with HBV-specific primers and probes as specified in Table 3 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 3

HBV DNA Primers and Probe for HepG2.117 assay

| Items | Name | Sequence (5'→3') |
|---|---|---|
| HBV Primer | HBV-forward | GTGTCTGCGGCGTTTTATCA (SEQ ID NO: 4) |
|  | HBV-reverse | GACAAACGGGCAACATACCTT (SEQ ID NO: 5) |
| HBV Probe | HBV probe | FAM/CCTCTKCAT/ZEN/CCT GCTGCTATGCCTCATC/3IABkFQ/ (SEQ ID NO: 6) |

A DNA standard was prepared by dilution of an IDT gBlock corresponding to the amplicon with concentrations ranging from 10^2 to 10^8 copies/input (i.e. per 4 μL) and used to generate a standard curve by plotting Cq values vs. HBV DNA standard concentration. The quantity of HBV DNA in each sample was determined by interpolating from the standard curve.

Cell Viability

Using the other plates, the cell viability was quantified by ATPlite according to the manufacturer's manual. In brief, 50 μL of cell lysis solution was added to the culture plates and shaken for 5', followed by addition of 50 μL substrate into each well and further shaking. The plates were incubated at room temperature for 10 mins and luminescence signal was subsequently measured on a VarioSkan Lux (ThermoFisher) plate reader.

Data Analysis

Cell viability was calculated as follows: % Cell viability= (luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir was required due to the excellent dynamic window of this assay. The $CC_{50}$, $EC_{50}$ and $EC_{90}$ values were determined by dose-response curves fitted by GraphPad Prism using "log (agonist) vs. response—Variable slope".

As shown in Table 4, compounds of Formula (I) are active against HBV, where 'A' indicates an $EC_{50} \leq 100$ nM, 'B' indicates an $EC_{50} > 100$ nM and <500 nM, 'C' indicates an $EC_5 > 500$ nM and <5000 nM, and 'D' indicates an $EC_{50} > 5000$ nM.

TABLE 4

| Compound | $EC_{50}$ |
|---|---|
| 15 | D |
| 21 | C |
| 22 | C |
| 23 | C |
| 24 | B |
| 25 | D |
| 26 | C |
| 27 | C |
| 28 | C |
| 29 | C |
| 30 | D |
| 31 | D |
| 32 | B |
| 33 | B |
| 34 | C |
| 35 | D |
| 36 | D |
| 37 | C |
| 38 | C |
| 39 | B |
| 40 | B |
| 41 | C |
| 42 | C |
| 43 | C |
| 44 | C |
| 45 | C |
| 46 | D |
| 47 | D |
| 48 | C |
| 49 | D |
| 50 | D |
| 51 | C |
| 52 | C |
| 53 | D |
| 54 | C |
| 55 | C |
| 56 | B |
| 57 | D |
| 58 | D |
| 59 | C |
| 60 | B |
| 61 | C |
| 62 | C |
| 63 | C |
| 64 | D |
| 66 | C |
| 67 | C |
| 68 | C |
| 69 | B |
| 70 | C |
| 71 | D |
| 72 | C |
| 73 | A |
| 74 | D |
| 75 | C |
| 76 | C |
| 77 | D |
| 78 | D |
| 79 | C |
| 80 | D |
| 81 | D |
| 82 | B |
| 83 | D |
| 84 | D |
| 85 | C |
| 86 | C |
| 87 | D |
| 88 | C |
| 89 | C |
| 90 | C |
| 91 | C |
| 92 | C |
| 93 | D |

TABLE 4-continued

| Compound | EC$_{50}$ |
|---|---|
| 94 | D |
| 95 | D |
| 96 | D |
| 97 | C |
| 98 | C |
| 99 | C |
| 100 | B |
| 101 | C |
| 102 | C |
| 103 | C |
| 104 | D |
| 105 | D |
| 106 | D |
| 107 | C |
| 108 | D |
| 109 | B |
| 110 | C |
| 111 | D |
| 112 | D |
| 113 | C |
| 114 | B |
| 115 | B |
| 116 | B |
| 117 | D |
| 118 | B |
| 119 | B |
| 120 | C |
| 121 | C |
| 122 | C |
| 123 | B |
| 124 | C |
| 125 | B |
| 126 | D |
| 127 | C |
| 128 | B |
| 129 | C |
| 130 | B |
| 131 | D |
| 132 | B |
| 133 | D |
| 134 | D |
| 135 | C |
| 136 | B |
| 137 | B |
| 138 | D |
| 139 | B |
| 140 | C |
| 141 | B |
| 142 | B |
| 143 | A |
| 144 | C |
| 145 | B |
| 146 | B |
| 147 | B |
| 148 | B |
| 149 | C |
| 150 | B |
| 151 | B |
| 152 | B |
| 153 | B |
| 154 | B |
| 155 | B |
| 156 | B |
| 157 | D |
| 158 | B |
| 160 | C |
| 161 | A |
| 162 | B |
| 163 | C |
| 164 | C |
| 165 | B |
| 166 | B |
| 167 | A |
| 168 | B |
| 169 | C |
| 170 | B |
| 171 | D |
| 173 | D |

TABLE 4-continued

| Compound | EC$_{50}$ |
|---|---|
| 174 | C |
| 175 | C |
| 176 | B |
| 178 | C |
| 179 | B |
| 180 | C |
| 181 | B |
| 182 | B |
| 183 | C |
| 184 | B |
| 185 | B |
| 186 | C |
| 188 | C |
| 189 | C |
| 190 | C |
| 191 | C |
| 192 | D |
| 193 | B |
| 194 | B |
| 195 | C |
| 196 | D |
| 197 | D |
| 198 | C |
| 199 | B |
| 200 | B |
| 201 | B |
| 202 | B |
| 203 | B |
| 204 | D |
| 205 | C |
| 206 | D |
| 207 | D |
| 208 | B |
| 209 | B |
| 210 | B |
| 211 | C |
| 212 | B |
| 213 | D |
| 214 | B |
| 215 | D |
| 216 | D |
| 217 | C |
| 218 | A |
| 219 | C |
| 220 | D |
| 221 | D |
| 222 | D |
| 223 | D |
| 224 | D |
| 225 | D |
| 226 | D |
| 227 | C |
| 228 | B |
| 229 | A |
| 230 | B |
| 231 | A |
| 232 | D |
| 233 | B |
| 234 | B |
| 235 | B |
| 236 | B |
| 237 | C |
| 238 | B |
| 239 | C |
| 240 | D |
| 241 | D |
| 242 | D |
| 243 | B |
| 244 | B |
| 245 | A |
| 246 | B |
| 247 | D |
| 248 | B |
| 249 | B |
| 250 | B |
| 251 | B |
| 252 | B |
| 253 | B |

TABLE 4-continued

| Compound | EC$_{50}$ |
|---|---|
| 254 | D |
| 255 | B |
| 256 | B |
| 257 | C |
| 258 | A |
| 259 | B |
| 260 | C |
| 261 | B |
| 262 | B |
| 263 | C |
| 264 | C |
| 265 | C |
| 266 | B |
| 268 | B |
| 269 | D |
| 270 | C |
| 271 | B |
| 272 | B |
| 273 | C |
| 274 | D |
| 275 | D |
| 276 | B |
| 277 | A |
| 278 | B |
| 279 | B |
| 280 | B |
| 281 | C |
| 282 | C |
| 283 | C |
| 284 | C |
| 285 | C |
| 286 | C |
| 287 | C |
| 288 | B |
| 289 | B |
| 290 | C |
| 291 | C |
| 292 | C |
| 293 | C |
| 294 | D |
| 295 | B |
| 296 | C |
| 297 | B |
| 298 | C |
| 299 | C |
| 301 | C |
| 302 | B |
| 303 | C |
| 304 | A |
| 305 | B |
| 306 | B |
| 307 | C |
| 308 | C |
| 309 | C |
| 310 | B |
| 311 | B |
| 312 | C |
| 313 | B |
| 314 | B |
| 315 | C |
| 316 | A |
| 317 | C |
| 318 | B |
| 319 | C |
| 320 | B |
| 321 | C |
| 322 | B |
| 323 | B |
| 324 | B |
| 325 | D |
| 326 | B |
| 327 | A |
| 328 | C |
| 329 | B |
| 330 | B |
| 331 | C |
| 332 | B |
| 333 | C |
| 334 | B |
| 335 | C |
| 336 | B |
| 337 | B |
| 338 | B |
| 339 | B |
| 340 | B |
| 341 | C |
| 342 | B |
| 343 | B |
| 344 | C |
| 345 | B |
| 346 | B |
| 347 | B |
| 348 | C |
| 349 | B |
| 350 | C |
| 351 | D |
| 352 | C |
| 353 | C |
| 354 | C |
| 355 | C |
| 356 | B |
| 357 | B |
| 358 | A |
| 359 | C |
| 360 | C |
| 361 | B |
| 362 | B |
| 363 | B |
| 364 | B |
| 365 | A |
| 366 | A |
| 367 | B |
| 368 | C |
| 369 | A |
| 370 | A |
| 371 | A |
| 372 | B |
| 373 | B |
| 374 | B |
| 375 | B |
| 376 | A |
| 377 | A |
| 378 | D |
| 379 | D |
| 380 | D |
| 381 | D |
| 382 | A |
| 383 | B |
| 384 | B |
| 385 | B |
| 386 | B |
| 387 | A |
| 388 | A |
| 389 | C |
| 390 | B |
| 391 | B |
| 392 | B |
| 393 | C |
| 394 | B |
| 395 | C |
| 396 | B |
| 397 | C |
| 398 | A |
| 399 | B |
| 400 | B |
| 401 | A |
| 402 | A |
| 403 | C |
| 404 | C |
| 405 | A |
| 406 | B |
| 407 | A |
| 408 | B |
| 409 | C |
| 410 | B |
| 411 | B |

TABLE 4-continued

| Compound | EC$_{50}$ |
|---|---|
| 412 | B |
| 413 | A |
| 414 | B |
| 415 | B |
| 416 | B |
| 417 | B |
| 418 | B |
| 419 | C |
| 420 | A |
| 421 | A |
| 422 | A |
| 423 | A |
| 424 | A |
| 425 | A |
| 426 | B |
| 427 | B |
| 428 | B |
| 429 | A |
| 430 | C |
| 431 | C |
| 432 | B |
| 433 | B |
| 434 | A |
| 435 | A |
| 436 | A |
| 437 | C |
| 438 | A |
| 439 | B |
| 440 | A |
| 441 | B |
| 442 | B |
| 443 | B |
| 444 | A |
| 445 | B |
| 446 | D |
| 447 | B |
| 448 | A |
| 449 | C |
| 450 | A |
| 451 | B |
| 452 | A |
| 453 | B |
| 454 | B |
| 455 | B |
| 456 | C |
| 457 | A |
| 458 | B |
| 459 | B |
| 460 | B |
| 461 | A |
| 462 | C |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

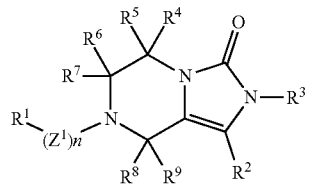

(I)

wherein:

n is 1;

$Z^1$ is —C(=O)—, —NH—C(=O)—, —OCH$_2$C(=O)—, —CH=CHC(=O)— or —CH(CF$_3$)—;

$R^1$ is selected from the group consisting of an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl);

$R^2$ is selected from the group consisting of —C(=O)NR$^{10}$R$^{11}$ an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl);

$R^3$ is selected from the group consisting of hydrogen, an unsubstituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); or $R^2$ and $R^3$ are taken together along with the atoms to which $R^2$ and $R^3$ are each attached to form an optionally substituted 6, 7 or 8 membered monocyclic heterocyclyl or an optionally substituted 9 to 14 membered spirocyclic heterocyclyl;

$R^4$ and $R^5$ are independently selected from the group consisting of hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl ($C_{1-4}$ alkyl), an optionally substituted heteroaryl($C_{1-4}$ alkyl) and an optionally substituted heterocyclyl($C_{1-4}$ alkyl);

$R^6$ and $R^7$ are independently selected from the group consisting of hydrogen, halogen, an unsubstituted $C_{1-4}$ alkyl, an unsubstituted $C_{1-4}$ haloalkyl, an optionally substituted $C_{3-4}$ cycloalkyl, an optionally substituted aryl, an optionally substituted heteroaryl, an optionally substituted heterocyclyl, an optionally substituted aryl ($C_{1-4}$ alkyl), an optionally substituted heteroaryl($C_{1-4}$ alkyl) and an optionally substituted heterocyclyl($C_{1-4}$ alkyl); or $R^4$ and $R^5$ are taken together along with the carbon to which $R^4$ and $R^5$ are attached to form an optionally substituted monocyclic $C_{3-6}$ cycloalkyl or an optionally substituted 3 to 6 member monocyclic heterocyclyl; or $R^6$ and $R^7$ are taken together along with the carbon to which $R^6$ and $R^7$ are attached to form an optionally substituted monocyclic $C_{3-6}$ cycloalkyl or an optionally substituted 3 to 6 member monocyclic heterocyclyl; or $R^4$ and $R^6$ are taken together along with the carbons to which $R^4$ and $R^6$ are each attached to form an optionally monocyclic $C_{5-7}$ cycloalkyl or an optionally substituted 5 to 7 member monocyclic heterocyclyl; or $R^5$ and $R^7$ are taken together along with the carbons to which $R^5$ and $R^7$ are each attached to form an optionally monocyclic $C_{5-7}$ cycloalkyl or an optionally substituted 5 to 7 member monocyclic heterocyclyl;

$R^8$ and $R^9$ are independently selected from the group consisting of hydrogen, an unsubstituted $C_{1-4}$ alkyl and an unsubstituted $C_{1-4}$ haloalkyl; or $R^8$ and $R^9$ are taken together along with the carbon to which $R^8$ and $R^9$ are attached to form an optionally substituted monocyclic $C_{3-4}$ cycloalkyl, an optionally substituted oxetane or an optionally substituted thietane; and $R^{10}$ and $R^{11}$ are independently selected from the group consisting of hydrogen, an optionally substituted $C_{1-8}$ alkyl, an optionally substituted $C_{2-6}$ alkenyl, an optionally substituted $C_{2-6}$ alkynyl, an optionally substituted $C_{3-8}$ cycloalkyl, an optionally substituted $C_{3-10}$ cycloalkenyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); or $R^{10}$ and $R^{11}$ are taken together along with the nitrogen to which $R^{10}$ and $R^{11}$ are attached to form an optionally substituted 4 to 8 member monocyclic heterocyclyl or an optionally substituted 7 to 12 member bicyclic heterocyclyl.

2. The compound of claim 1, wherein $Z^1$ is —C(=O)—.

3. The compound of claim 1, wherein $R^1$ is an optionally substituted aryl.

4. The compound of claim 3, wherein $R^1$ is an optionally substituted phenyl.

5. The compound of claim 1, wherein $R^1$ is substituted with one or more substituents independently selected from the group consisting of deuterium, halogen, cyano, an unsubstituted $C_{1-6}$ alkyl, an unsubstituted $C_{1-6}$ haloalkyl, an unsubstituted $C_{1-6}$ alkoxy, an unsubstituted $C_{1-6}$ haloalkoxy, an unsubstituted acyl, an unsubstituted C-amido, an unsubstituted sulfonyl, an unsubstituted amino, a mono-substituted amine and a di-substituted amine.

6. The compound of claim 1, wherein $R^2$ is —C(=O) $NR^{10}R^{11}$.

7. The compound of claim 6, wherein $R^{10}$ is hydrogen or an optionally substituted $C_{1-4}$ alkyl.

8. The compound of claim 7, wherein $R^{11}$ is an optionally substituted $C_{1-8}$ alkyl or an optionally substituted aryl($C_{1-4}$ alkyl).

9. The compound of claim 8, wherein $R^{11}$ is a substituted benzyl.

10. The compound of claim 7, wherein $R^{11}$ is an optionally substituted heteroaryl($C_{1-4}$ alkyl).

11. The compound of claim 7, wherein $R^{11}$ is an optionally substituted heterocyclyl($C_{1-4}$ alkyl).

12. The compound of claim 9, wherein $R^{11}$ is substituted with one or more substituents selected from the group consisting of halogen, cyano, an unsubstituted $C_{1-4}$ alkyl, an unsubstituted $C_{3-6}$ cycloalkyl, an unsubstituted $C_{1-4}$ alkoxy, an unsubstituted $C_{1-4}$ hydroxyalkyl, an unsubstituted $C_{1-4}$ alkoxyalkyl, an unsubstituted $C_{1-4}$ haloalkyl, an unsubstituted $C_{1-4}$ haloalkoxy, an unsubstituted acyl, an unsubstituted C-carboxy, an unsubstituted C-amido, an unsubstituted C-carboxy($C_{1-3}$ alkyl), —O—(an unsubstituted $C_{1-4}$ alkyl)—(an unsubstituted C-carboxy), an unsubstituted C-amido($C_{1-3}$ alkyl), —O—($C_{1-3}$ alkyl)—O—(an unsubstituted C-amido), —O—(an unsubstituted $C_{1-4}$ alkyl)—NH (an unsubstituted $C_{1-4}$ alkyl), —O—(an unsubstituted $C_{1-4}$ alkyl)—N(an unsubstituted $C_{1-4}$ alkyl)$_2$, an unsubstituted —O—(an unsubstituted $C_{1-4}$ alkyl)—CN, an unsubstituted sulfonyl, an unsubstituted monocyclic 5-6 membered heteroaryl, a halogen-substituted monocyclic 5-6 membered heteroaryl, an unsubstituted $C_{1-4}$ alkyl substituted monocyclic 5-6 membered heteroaryl, an optionally substituted aryl($C_{1-4}$ alkyl), an unsubstituted monocyclic 5-6 membered heterocyclyl, a halogen-substituted monocyclic 5-6 membered heterocyclyl and an unsubstituted $C_{1-4}$ alkyl substituted monocyclic 5-6 membered heterocyclyl.

13. The compound of claim 9, wherein the (—CH$_2$— of the substituted benzyl is substituted with a substituent selected form the group consisting of an unsubstituted $C_{1-4}$ alkyl, an unsubstituted $C_{3-4}$ cycloalkyl, an unsubstituted $C_{1-4}$ haloalkyl, an unsubstituted $C_{1-4}$ hydroxyalkyl and

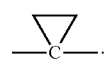

14. The compound of claim 1, wherein $R^2$ is an optionally substituted heteroaryl.

15. The compound of claim 1, wherein $R^3$ is an optionally substituted aryl.

16. The compound of claim 15, wherein $R^3$ is an unsubstituted or a substituted phenyl.

17. The compound of claim 1, wherein $R^3$ is an optionally substituted heteroaryl.

18. The compound of claim 1, wherein $R^3$ is an optionally substituted heterocyclyl.

19. The compound of claim 1, wherein $R^2$ and $R^3$ are taken together along with the atoms to which $R^2$ and $R^3$ are each attached to form an optionally substituted 6, 7 or 8 membered monocyclic heterocyclyl.

20. The compound of claim 19, wherein $R^2$ and $R^3$ are taken together along with the atoms to which $R^2$ and $R^3$ are each attached to form:

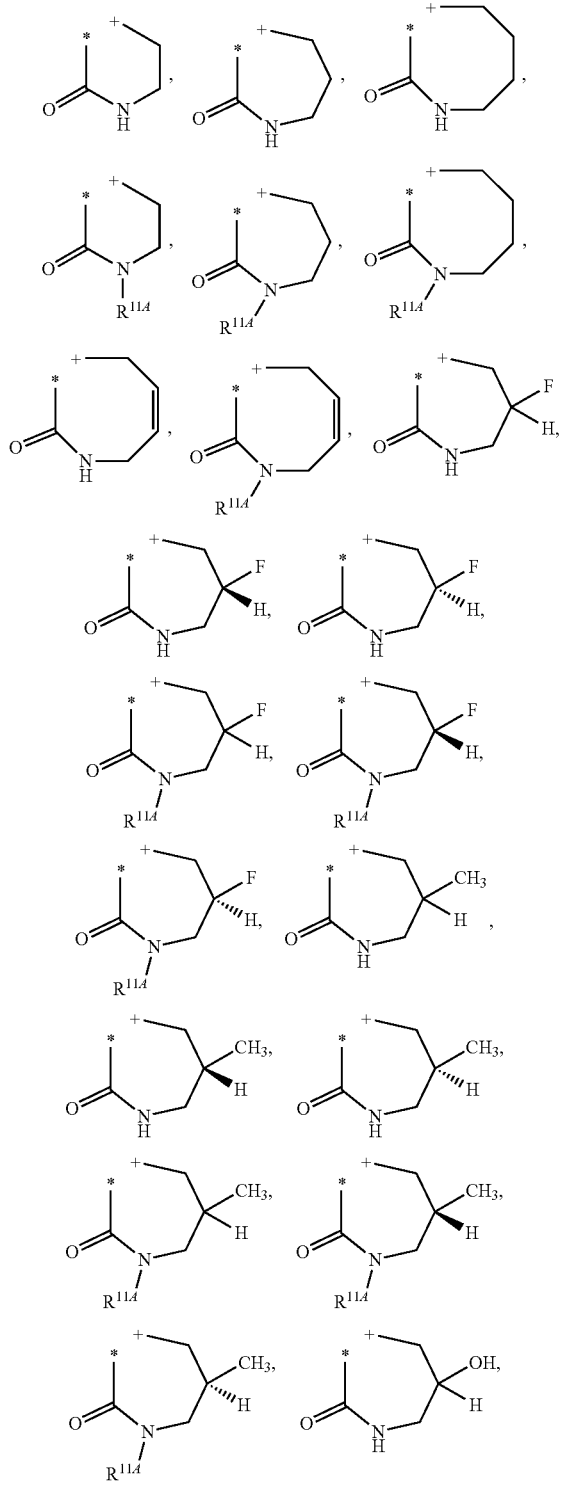
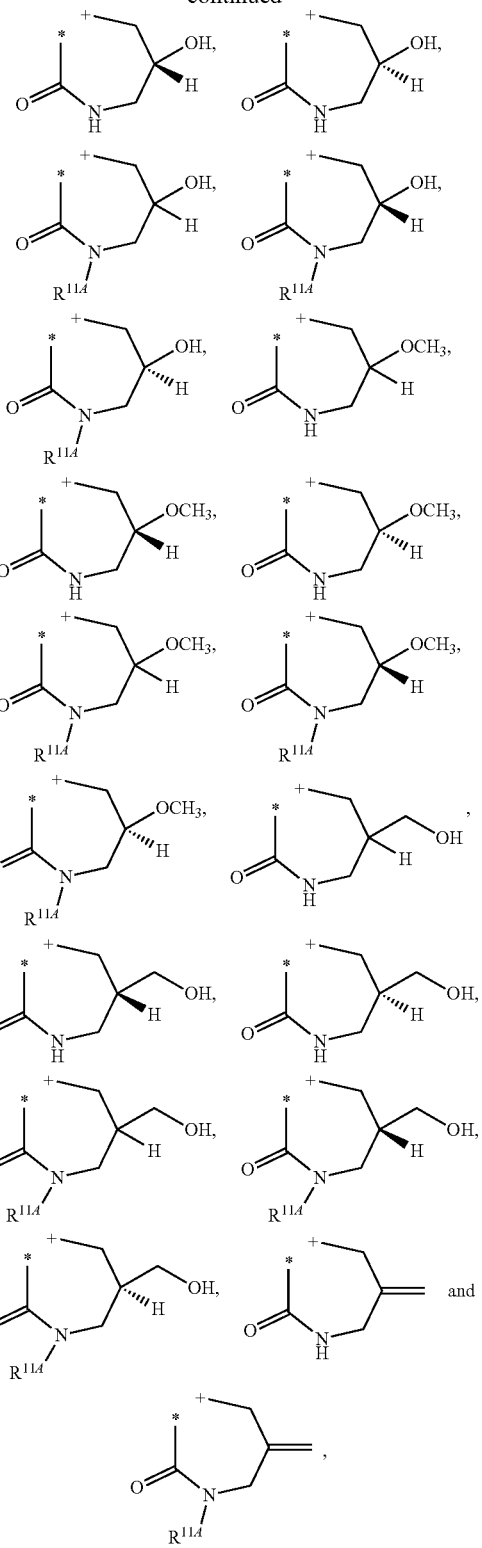

where "+" indicates the point of attachment to the nitrogen of $R^3$ and "*" indicates the point of attachment to carbon of $R^2$; and $R^{11A}$ is $R^{11}$.

21. The compound of claim 20, wherein $R^{11A}$ is hydrogen, an unsubstituted or a substituted $C_{1-4}$ alkyl or an unsubstituted or a substituted aryl($C_{1-4}$ alkyl).

22. The compound of claim 1, wherein $R^4$ is hydrogen; $R^5$ is hydrogen; $R^6$ is hydrogen; $R^7$ is hydrogen; $R^8$ is hydrogen; and $R^9$ is hydrogen.

23. The compound of claim 1, wherein the compound is selected from Formula (Ib), Formula (Ic), Formula (Ie), Formula (If) and Formula (Ig):

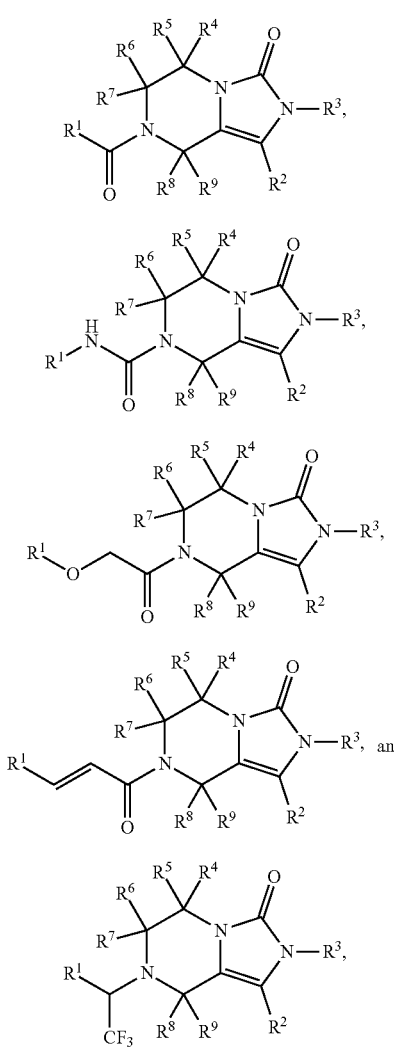

or a pharmaceutically acceptable salt of any of the foregoing.

24. The compound of claim 1, wherein the compound is selected from Formula (Ij), Formula (Ik), Formula (Im), Formula (In), Formula (Io) and Formula (Ip):

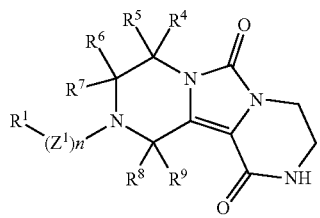

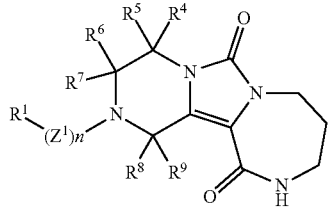

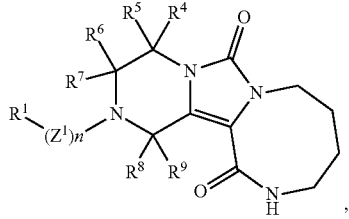

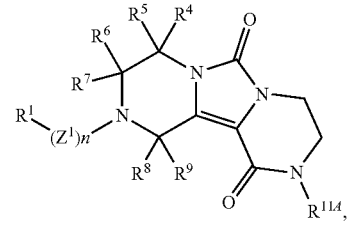

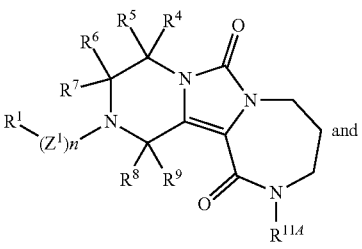

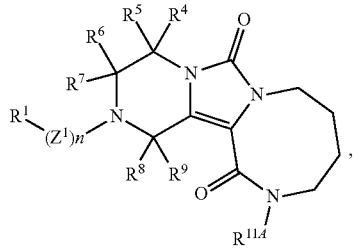

or a pharmaceutically acceptable salt of any of the foregoing, wherein the piperazinone ring of Formula (Ij), the diazepanone ring of Formula (Ik), the diazocanone ring of Formula (Im), the piperazinone ring of Formula (In), the diazepanone ring of Formula (Io), the diazocanone ring of Formula (Ip) is each unsubstituted or substituted 1, 2 or 3 times with a moiety independently selected from the group consisting of halogen, an unsubstituted $C_{1-4}$ alkyl, an unsubstituted $C_{2-4}$ alkenyl, hydroxy, an unsubstituted $C_{1-4}$ alkoxy, an unsubstituted $C_{1-4}$ hydroxyalkyl, an unsubstituted $C_{3-6}$ cycloalkyl($C_{1-3}$)alkyl and an unsubstituted or a substituted aryl($C_1$ alkyl).

25. A compound selected from the group consisting of:
12-benzyl-N-(3-chloro-4-fluoro-phenyl)-8,13-dioxo-4,7,9,12-tetrazatricyclo[7.4.0.0^2,7]tridec-1-ene-4-carboxamide, N-(3-chloro-4-fluoro-phenyl)-12-[(4-methoxyphenyl)methyl]-8,13-dioxo-4,7,9,12-tetrazatricyclo[7.4.0.0^2,7]tridec-1-ene-4-carboxamide, 12-(4-bromo-3-fluoro-benzoyl)-4-[(4-methoxyphenyl)methyl]-4,7,9,12-tetrazatricyclo[7.4.0.0^2,7]tridec-1-ene-3,8-dione, 12-(4-bromo-3-chloro-benzoyl)-4-[(4-methoxyphenyl)methyl]-4,7,9,12-tetrazatricyclo[7.4.0.0^2,7]tridec-1-ene-3,8-dione, 12-(4-bromobenzoyl)-4-[(4-methoxyphenyl)methyl]-4,7,9,12-tetrazatricyclo[7.4.0.0^2,7]tridec-1-ene-3,8-dione, 7-(4-bromo-3-chloro-benzoyl)-2-(3-methoxyphenyl)-N-[(4-methoxyphenyl)methyl]-3-oxo-6,8-dihydro-5H-imidazo[1,5-a]pyrazine-1-carboxamide, N-benzyl-7-(4-bromo-3-chloro-benzoyl)-2-(4-fluorophenyl)-3-oxo-6,8-dihydro-5H-imidazo[1,5-a]pyrazine-1-carboxamide, N-benzyl-7-(4-bromo-3-chloro-benzoyl)-2-(3-fluorophenyl)-3-oxo-6,8-dihydro-5H-imidazo[1,5-a]pyrazine-1-carboxamide, N-benzyl-7-(4-bromo-3-chloro-benzoyl)-2-(4-methoxyphenyl)-3-oxo-6,8-dihydro-5H-imidazo[1,5-a]pyrazine-1-carboxamide, N-benzyl-7-(4-bromo-3-chloro-benzoyl)-2-(4-carbamoylphenyl)-3-oxo-6,8-dihydro-5H-imidazo[1,5-a]pyrazine-1-carboxamide, N-benzyl-7-(4-bromo-3-chloro-benzoyl)-2-(4-chlorophenyl)-3-oxo-6,8-dihydro-5H-imidazo[1,5-a]pyrazine-1-carboxamide, N-benzyl-7-(4-bromo-3-chloro-benzoyl)-N-methyl-3-oxo-2-phenyl-6,8-dihydro-5H-imidazo[1,5-a]pyrazine-1-carboxamide, 7-(4-bromo-3-chloro-benzoyl)-3-oxo-2-phenyl-N-(2-phenylethyl)-6,8-dihydro-5H-imidazo[1,5-a]pyrazine-1-carboxamide, N-benzyl-7-(4-bromo-3-chloro-benzoyl)-2-(3-chlorophenyl)-3-oxo-6,8-dihydro-5H-imidazo[1,5-a]pyrazine-1-carboxamide 7-(4-bromo-3-chloro-benzoyl)-N-(1-methyl-1-phenyl-ethyl)-3-oxo-2-phenyl-6,8-dihydro-5H-imidazo[1,5-a]pyrazine-1-carboxamide, 7-(4-bromo-3-chloro-benzoyl)-3-oxo-2-phenyl-N-(1-phenylcyclopropyl)-6,8-dihydro-5H-imidazo[1,5-a]pyrazine-1-carboxamide, 7-(4-bromo-3-chloro-benzoyl)-N-[(3,4-dimethoxyphenyl)methyl]-3-oxo-2-phenyl-6,8-dihydro-5H-imidazo[1,5-a]pyrazine-1-carboxamide, 7-(4-bromo-3-chloro-benzoyl)-N-[(3-methoxyphenyl)methyl]-3-oxo-2-phenyl-6,8-dihydro-5H-imidazo[1,5-a]pyrazine-1-carboxamide, N-benzyl-7-(3,4-dichlorobenzoyl)-3-oxo-2-phenyl-6,8-dihydro-5H-imidazo[1,5-a]pyrazine-1-carboxamide, N-benzyl-7-(4-bromo-3-chloro-benzoyl)-2-(3-carbamoylphenyl)-3-oxo-6,8-dihydro-5H-imidazo[1,5-a]pyrazine-1-carboxamide, N-benzyl-7-(4-bromo-3-chloro-benzoyl)-2-[4-(methylcarbamoyl)phenyl]-3-oxo-6,8-dihydro-5H-imidazo[1,5-a]pyrazine-1-carboxamide, 7-(4-bromo-3-chloro-benzoyl)-3-oxo-2-phenyl-N-[rac-(1R)-1-phenylethyl]-6,8-dihydro-5H-imidazo[1,5-a]pyrazine-1-carboxamide, 7-(4-bromo-3-chloro-benzoyl)-3-oxo-2-phenyl-N-[rac-(1S)-1-phenylethyl]-6,8-dihydro-5H-imidazo[1,5-a]pyrazine-1-carboxamide, 7-(4-bromo-3-chloro-benzoyl)-N-[(4-methoxy-2-methyl-phenyl)methyl]-3-oxo-2-phenyl-6,8-dihydro-5H-imidazo[1,5-a]pyrazine-1-carboxamide, 7-(4-bromo-3-chloro-benzoyl)-N-[(2-fluoro-4-methoxyphenyl)methyl]-3-oxo-2-phenyl-6,8-dihydro-5H-imidazo[1,5-a]pyrazine-1-carboxamide, N-benzyl-7-(4-bromo-3-chloro-benzoyl)-2-(3-methoxyphenyl)-3-oxo-6,8-dihydro-5H-imidazo[1,5-a]pyrazine-1-carboxamide, N-benzyl-7-(4-bromo-3-chloro-benzoyl)-2-(2-chlorophenyl)-3-oxo-6,8-dihydro-5H-imidazo[1,5-a]pyrazine-1-carboxamide, N-benzyl-7-(4-bromo-3-chloro-benzoyl)-2-(4-cyanophenyl)-3-oxo-6,8-dihydro-5H-imidazo[1,5-a]pyrazine-1-carboxamide, N-benzyl-7-(4-bromo-3-chloro-benzoyl)-2-(3-cyanophenyl)-3-oxo-6,8-dihydro-5H-imidazo[1,5-a]pyrazine-1-carboxamide, N-benzyl-7-(4-bromo-3-chloro-benzoyl)-2-(4-methylsulfonylphenyl)-3-oxo-6,8-dihydro-5H-imidazo[1,5-a]pyrazine-1-carboxamide, N-benzyl-7-(4-bromo-3-chloro-benzoyl)-2-(3-methylsulfonylphenyl)-3-oxo-6,8-dihydro-5H-imidazo[1,5-a]pyrazine-1-carboxamide, N-benzyl-7-(4-bromo-3-chloro-benzoyl)-3-oxo-2-(3-sulfamoylphenyl)-6,8-dihydro-5H-imidazo[1,5-a]pyrazine-1-carboxamide, N-benzyl-7-(4-bromo-3-chloro-benzoyl)-2-[3-(methylcarbamoyl)phenyl]-3-oxo-6,8-dihydro-5H-imidazo[1,5-a]pyrazine-1-carboxamide, N-benzyl-7-(3,4-dichlorobenzoyl)-3-oxo-2-(3-pyridyl)-6,8-dihydro-5H-imidazo[1,5-a]pyrazine-1-carboxamide, N-benzyl-2-(3-chloro-4-methoxy-phenyl)-7-(3,4-dichlorobenzoyl)-3-oxo-6,8-dihydro-5H-imidazo[1,5-a]pyrazine-1-carboxamide, N-benzyl-7-(3,4-dichlorobenzoyl)-2-(4-ethoxyphenyl)-3-oxo-6,8-dihydro-5H-imidazo[1,5-a]pyrazine-1-carboxamide, N-benzyl-7-(3,4-dichlorobenzoyl)-2-(4-isopropoxyphenyl)-3-oxo-6,8-dihydro-5H-imidazo[1,5-a]pyrazine-1-carboxamide, 7-(3,4-dichlorobenzoyl)-2-(4-methoxyphenyl)-3-oxo-N-(pyridazin-4-ylmethyl)-6,8-dihydro-5H-imidazo[1,5-a]pyrazine-1-carboxamide, N-benzyl-7-(3,4-dichlorobenzoyl)-2-(4-methoxyphenyl)-3-oxo-6,8-dihydro-5H-imidazo[1,5-a]pyrazine-1-carboxamide, N-benzyl-2-(4-methoxyphenyl)-7-(4-methyl-1H-indole-2-carbonyl)-3-oxo-6,8-dihydro-5H-imidazo[1,5-a]pyrazine-1-carboxamide, N-benzyl-7-(4-chloro-1H-indole-2-carbonyl)-2-(4-methoxyphenyl)-3-oxo-6,8-dihydro-5H-imidazo[1,5-a]pyrazine-1-carboxamide, 7-(3,4-dichlorobenzoyl)-2-(4-methoxyphenyl)-3-oxo-N-(4-pyridylmethyl)-6,8-dihydro-5H-imidazo[1,5-a]pyrazine-1-carboxamide, 7-(3,4-dichlorobenzoyl)-N-isobutyl-2-(4-methoxyphenyl)-3-oxo-6,8-dihydro-5H-imidazo[1,5-a]pyrazine-1-carboxamide, N-benzyl-2-(2-chloro-4-methoxy-phenyl)-7-(3,4-dichlorobenzoyl)-3-oxo-6,8-dihydro-5H-imidazo[1,5-a]pyrazine-1-carboxamide, 7-(4-bromo-3-chloro-benzoyl)-N-[(4-fluorophenyl)methyl]-2-(4-methoxyphenyl)-3-oxo-6,8-dihydro-5H-imidazo[1,5-a]pyrazine-1-carboxamide, 7-(3,4-dichlorobenzoyl)-N-[(4-fluorophenyl)methyl]-2-(4-methoxyphenyl)-3-oxo-6,8-dihydro-5H-imidazo[1,5-a]pyrazine-1-carboxamide, 7-(4-bromo-3-chloro-benzoyl)-N-[(3-cyanophenyl)methyl]-2-(4-methoxyphenyl)-3-oxo-6,8-dihydro-5H-imidazo[1,5-a]pyrazine-1-carboxamide, N-[(3-cyanophenyl)methyl]-7-(3,4-dichlorobenzoyl)-2-(4-methoxyphenyl)-3-oxo-6,8-dihydro-5H-imidazo[1,5-a]pyrazine-1-carboxamide, 7-(3,4-dichlorobenzoyl)-2-(4-methoxyphenyl)-3-oxo-N-(3-pyridylmethyl)-6,8-dihydro-5H-imidazo[1,5-a]pyrazine-1-carboxamide, N-(benzothiophen-5-ylmethyl)-7-(3,4-dichlorobenzoyl)-2-(4-methoxyphenyl)-3-oxo-6,8-dihydro-5H-imidazo[1,5-a]pyrazine-1-carboxamide, N-(benzofuran-5-ylmethyl)-7-(3,4-dichlorobenzoyl)-2-(4-methoxyphenyl)-3-oxo-6,8-dihydro-5H-imidazo[1,5-a]pyrazine-1-carboxamide, 7-(3,4-dichlorobenzoyl)-2-(4-methoxyphenyl)-N-[(2-methyl-1,3-benzoxazol-5-yl)methyl]-3-oxo-6,8-dihydro-5H-imidazo[1,5-a]pyrazine-1-carboxamide, 7-(3,4-dichlorobenzoyl)-2-(4-methoxyphenyl)-3-oxo-N-[rac-(1R)-1-phenylethyl]-6,8-dihydro-5H-imidazo[1,5-a]pyrazine-1-carboxamide, 7-(4-bromo-3-chloro-benzoyl)-2-(4-methoxyphenyl)-3-oxo-N-[rac-(1S)-1-phenylethyl]-6,8-dihydro-5H-imidazo[1,5-a]pyrazine-1-carboxamide, 7-(3,4-dichlorobenzoyl)-2-(4-methoxyphenyl)-3-oxo-N-[rac-(1S)-1-phenylethyl]-6,8-dihydro-5H-imidazo[1,5-a]pyrazine-1-carboxamide, N-benzyl-7-(4-bromo-3-chloro-benzoyl)-3-oxo-2-(4-sulfamoylphenyl)-6,8-dihydro-5H-imidazo[1,5-a]pyrazine-1-carboxamide, 7-(4-bromo-3-chloro-benzoyl)-2-(4-methoxyphenyl)-3-oxo-N-[rac-(1R)-1-(4-methoxyphenyl)ethyl]-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1S)-1-(4-methoxyphenyl)ethyl]-6,8-dihydro-5H-imidazo [1,5-a]pyrazine-1-carboxamide, 7-(3,4-dichlorobenzoyl)-2-(4-methoxyphenyl)-1-phenyl-6,8-dihydro-5H-imidazo [1,5-a]pyrazin-3-one, 7-(4-bromo-3-chloro-benzoyl)-2-(4-methoxyphenyl)-3-oxo-N-[rac-(1R)-indan-1-yl]-6,8-dihydro-5H-imidazo[1,5-a]pyrazine-1-carboxamide, 7-(4-bromo-3-chloro-benzoyl)-2-(4-methoxyphenyl)-3-oxo-N-[rac-(1S)-indan-1-yl]-6,8-dihydro-5H-imidazo[1,5-a]pyrazine-1-carboxamide, N-benzyl-7-(3,4-dichlorobenzoyl)-2-[4-methoxy-2-(trifluoromethyl)phenyl]-3-oxo-6,8-dihydro-5H-imidazo[1,5-a]pyrazine-1-carboxamide, N-benzyl-7-(3,4-dichlorobenzoyl)-3-oxo-2-(2-pyridyl)-6,8-dihydro-5H-imidazo [1,5-a]pyrazine-1-carboxamide, N-benzyl-7-(3,4-dichlorobenzoyl)-2-(2-fluoro-4-methoxy-phenyl)-3-oxo-6,8-dihydro-5H-imidazo[1,5-a]pyrazine-1-carboxamide, N-benzyl-2-(2-cyano-4-methoxy-phenyl)-7-(3,4-dichlorobenzoyl)-3-oxo-6,8-dihydro-5H-imidazo[1,5-a]pyrazine-1-carboxamide, N-benzyl-7-(3,4-dichlorobenzoyl)-2-(6-methoxy-3-pyridyl)-3-oxo-6,8-dihydro-5H-imidazo[1,5-a]pyrazine-1-carboxamide, 7-(4-bromo-3-chloro-benzoyl)-2-(4-methoxyphenyl)-3-oxo-N-[rac-(1R)-1-phenylethyl]-6,8-dihydro-5H-imidazo [1,5-a]pyrazine-1-carboxamide, 7-(3,4-dichlorobenzoyl)-2-(4-methoxyphenyl)-3-oxo-N-phenyl-6,8-dihydro-5H-imidazo[1,5-a]pyrazine-1-carboxamide, N-[(4-cyanophenyl)methyl]-7-(3,4-dichlorobenzoyl)-2-(4-methoxyphenyl)-3-oxo-6,8-dihydro-5H-imidazo [1,5-a]pyrazine-1-carboxamide, N-[(2-chloro-4-methoxy-phenyl)methyl]-7-(3,4-dichlorobenzoyl)-2-(4-methoxyphenyl)-3-oxo-6,8-dihydro-5H-imidazo [1,5-a]pyrazine-1-carboxamide, 1-(5-benzyloxazol-2-yl)-7-(4-bromo-3-chloro-benzoyl)-2-(4-methoxyphenyl)-6,8-dihydro-5H-imidazo [1,5-a]pyrazin-3-one, N-benzyl-7-(3,4-dichlorobenzoyl)-2-(4-methoxy-2-methyl-phenyl)-3-oxo-6,8-dihydro-5H-imidazo[1,5-a]pyrazine-1-carboxamide, 2-(1,3-benzodioxol-5-yl)-N-benzyl-7-(3,4-dichlorobenzoyl)-3-oxo-6,8-dihydro-5H-imidazo[1,5-a]pyrazine-1-carboxamide, 7-(3,4-dichlorobenzoyl)-N-[(4-methoxy-3-methyl-phenyl)methyl]-2-(4-methoxyphenyl)-3-oxo-6,8-dihydro-5H-imidazo [1,5-a]pyrazine-1-carboxamide, 7-(3,4-dichlorobenzoyl)-N-[(3-methoxy-4-methyl-phenyl)methyl]-2-(4-methoxyphenyl)-3-oxo-6,8-dihydro-5H-imidazo [1,5-a]pyrazine-1-carboxamide, 7-(3,4-dichlorobenzoyl)-N-(2,3-dihydro-1,4-benzodioxin-6-ylmethyl)-2-(4-methoxyphenyl)-3-oxo-6,8-dihydro-5H-imidazo[1,5-a]pyrazine-1-carboxamide, 7-(3,4-dichlorobenzoyl)-2-(4-methoxyphenyl)-3-oxo-N-(6-quinolylmethyl)-6,8-dihydro-5H-imidazo [1,5-a]pyrazine-1-carboxamide, 7-(3,4-dichlorobenzoyl)-2-(4-methoxyphenyl)-3-oxo-N-[(2-oxo-1,3-dihydrobenzimidazol-5-yl)methyl]-6,8-dihydro-5H-imidazo [1,5-a]pyrazine-1-carboxamide, 7-(3,4-dichlorobenzoyl)-2-(4-methoxyphenyl)-3-oxo-N-[rac-(1S)-1-cyclopropylethyl]-6,8-dihydro-5H-imidazo [1,5-a]pyrazine-1-carboxamide, 7-(3,4-dichlorobenzoyl)-2-(4-methoxyphenyl)-3-oxo-N-[rac-(1R)-1-cyclopropylethyl]-6,8-dihydro-5H-imidazo [1,5-a]pyrazine-1-carboxamide, N-benzyl-7-(3,4-dichlorobenzoyl)-2-(2,6-dichloro-4-methoxy-phenyl)-3-oxo-6,8-dihydro-5H-imidazo [1,5-a]pyrazine-1-carboxamide, rac-(11R)-13-benzyl-4-(4-bromo-3-chloro-benzoyl)-11-methyl-4,7,9,13-tetrazatricyclo [7 0.5 0.0.0^2,7]tetradec-1-ene-8,14-dione, rac-(11S)-13-benzyl-4-(4-bromo-3-chloro-benzoyl)-11-methyl-4,7,9,13-tetrazatricyclo [7 0.5.0.0^2,7]tetradec-1-ene-8,14-dione, 7-(4-bromo-3-chloro-benzoyl)-2-(4-methoxyphenyl)-3-oxo-N-[rac-(1R)-5-methoxyindan-1-yl]-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1S)-5-methoxyindan-1-yl]-6,8-dihydro-5H-imidazo [1,5-a]pyrazine-1-carboxamide, 7-(4-bromo-3-chloro-benzoyl)-N-[(4-chloro-3-methoxy-phenyl)methyl]-2-(4-methoxyphenyl)-3-oxo-6,8-dihydro-5H-imidazo[1,5-a]pyrazine-1-carboxamide, N-[(4-chloro-3-methoxy-phenyl)methyl]-7-(3,4-dichlorobenzoyl)-2-(4-methoxyphenyl)-3-oxo-6,8-dihydro-5H-imidazo [1,5-a]pyrazine-1-carboxamide, 7-(3,4-dichlorobenzoyl)-N-[(4-fluoro-3-methoxy-phenyl)methyl]-2-(4-methoxyphenyl)-3-oxo-6,8-dihydro-5H-imidazo [1,5-a]pyrazine-1-carboxamide, N-[(4-carbamoylphenyl)methyl]-7-(3,4-dichlorobenzoyl)-2-(4-methoxyphenyl)-3-oxo-6,8-dihydro-5H-imidazo [1,5-a]pyrazine-1-carboxamide, N-(cyclopropylmethyl)-7-(3,4-dichlorobenzoyl)-2-(4-methoxyphenyl)-3-oxo-6,8-dihydro-5H-imidazo [1,5-a]pyrazine-1-carboxamide, 7-(3,4-dichlorobenzoyl)-N-[1-(hydroxymethyl)cyclopropyl]-2-(4-methoxyphenyl)-3-oxo-6,8-dihydro-5H-imidazo [1,5-a]pyrazine-1-carboxamide, 7-(3,4-dichlorobenzoyl)-N-(1H-indazol-5-ylmethyl)-2-(4-methoxyphenyl)-3-oxo-6,8-dihydro-5H-imidazo [1,5-a]pyrazine-1-carboxamide, N-benzyl-7-(6,7-dichloroquinazolin-4-yl)-2-(4-methoxyphenyl)-3-oxo-6,8-dihydro-5H-imidazo[1,5-a]pyrazine-1-carboxamide, 13-benzyl-4-(4-bromo-3-chloro-benzoyl)-11-methylene-4,7,9,13-tetrazatricyclo [7 0.5.0.0^2,7]tetradec-1-ene-8,14-dione, N-benzyl-7-(4-bromo-3-chloro-benzoyl)-2-(5-methoxy-2-pyridyl)-3-oxo-6,8-dihydro-5H-imidazo[1,5-a]pyrazine-1-carboxamide, 7-(3,4-dichlorobenzoyl)-N-[1-(methoxymethyl)cyclopropyl]-2-(4-methoxyphenyl)-N-methyl-3-oxo-6,8-dihydro-5H-imidazo [1,5-a]pyrazine-1-carboxamide, 7-(4-bromo-3-chloro-benzoyl)-2-methyl-3-oxo-N-[rac-(1S)-1-phenylethyl]-6,8-dihydro-5H-imidazo [1,5-a]pyrazine-1-carboxamide, 7-(4-bromo-3-chloro-benzoyl)-2-methyl-3-oxo-N-[rac-(1R)-1-phenylethyl]-6,8-dihydro-5H-imidazo [1,5-a]pyrazine-1-carboxamide, 7-(4-bromo-3-chloro-benzoyl)-2-(4-methoxyphenyl)-N-[(2-methoxyphenyl)methyl]-3-oxo-6,8-dihydro-5H-imidazo [1,5-a]pyrazine-1-carboxamide, 7-(3,4-dichlorobenzoyl)-2-(4-methoxyphenyl)-N-[(2-methoxyphenyl)methyl]-3-oxo-6,8-dihydro-5H-imidazo [1,5-a]pyrazine-1-carboxamide, 7-(4-bromo-3-chloro-benzoyl)-N-[(4-fluoro-2-methylphenyl)methyl]-2-(4-methoxyphenyl)-3-oxo-6,8-dihydro-5H-imidazo[1,5-a]pyrazine-1-carboxamide, N-benzyl-7-(7-chloroquinazolin-4-yl)-2-(4-methoxyphenyl)-3-oxo-6,8-dihydro-5H-imidazo[1,5-a]pyrazine-1-carboxamide, 7-(4-bromo-3-chloro-benzoyl)-2-(4-isopropoxyphenyl)-3-oxo-N-[rac-(1R)-1-phenylethyl]-6,8-dihydro-5H-imidazo [1,5-a]pyrazine-1-carboxamide, 7-(4-bromo-3-chloro-benzoyl)-2-(4-isopropoxyphenyl)-3-oxo-N-[rac-(1S)-1-phenylethyl]-6,8-dihydro-5H-imidazo [1,5-a]pyrazine-1-carboxamide, 2-(benzofuran-5-yl)-N-benzyl-7-(3,4-dichlorobenzoyl)-3-oxo-6,8-dihydro-5H-imidazo[1,5-a]pyrazine-1-carboxamide, N-benzyl-7-(3,4-dichlorobenzoyl)-2-[4-(difluoromethoxy)phenyl]-3-oxo-6,8-dihydro-5H-imidazo[1,5-a]pyrazine-1-carboxamide, N-benzyl-7-(3,4-dichlorobenzoyl)-3-oxo-2-(p-tolyl)-6,8-dihydro-5H-imidazo [1,5-a]pyrazine-1-carboxamide, N-benzyl-7-(4-bromo-3-chloro-benzoyl)-3-oxo-2-(p-tolyl)-6,8-dihydro-5H-imidazo [1,5-a]pyrazine-1-carboxamide, N-benzyl-7-(3,4-dichlorobenzoyl)-2-(4-methoxy-3-methyl-phenyl)-3-oxo-6,8-dihydro-5H-imidazo[1,5-a]pyrazine-1-carboxamide, 7-(4-bromo-3-chloro-benzoyl)-N-[(3-fluorophenyl)methyl]-2-(4-methoxyphenyl)-3-oxo-6,8-dihydro-5H-imidazo [1,5-a]pyrazine-1-carboxamide, N-[(3-carbamoylphenyl)methyl]-7-(3,4-dichlorobenzoyl)-2-(4-methoxyphenyl)-3-oxo-6,8-dihydro-5H-imidazo [1,5-a]pyrazine-1-carboxamide, 7-(4-bromo-3-chloro-benzoyl)-3-oxo-N-[rac-(1S)-1-phenylethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1R)-1-phenylethyl]-2-[4-(2,2,2-trifluoroethoxy)phenyl]-6,8-dihydro-5H-imidazo [1,5-a]pyrazine-1-carboxamide, 7-(3,4-dichlorobenzoyl)-2-(4-isopropoxyphenyl)-3-oxo-N-[rac-(1S)-1-phenylethyl]-6,8-dihydro-5H-imidazo [1,5-a]pyrazine-1-carboxamide, 7-(3,4-dichlorobenzoyl)-2-(4-isopropoxyphenyl)-3-oxo-N-[rac-(1R)-1-phenylethyl]-6,8-dihydro-5H-imidazo [1,5-a]pyrazine-1-carboxamide, N-benzyl-7-(3,4-dichlorobenzoyl)-3-oxo-2-[4-(trifluoromethoxy)phenyl]-6,8-dihydro-5H-imidazo[1,5-a]pyrazine-1-carboxamide, (11Z)-4-(4-bromo-3-chloro-benzoyl)-14-[(4-methoxyphenyl)methyl]-4,7,9,14-tetrazatricyclo [7 0.6.0.0^2,7]pentadeca-1,11-diene-8,15-dione, 4-(4-bromo-3-chloro-benzoyl)-13-(cyclopropylmethyl)-4,7,9,13-tetrazatricyclo [7 0.5.0.0^2,7]tetradec-1-ene-8,14-dione, 4-(4-bromo-3-chloro-benzoyl)-13-isobutyl-4,7,9,13-tetrazatricyclo [7 0.5.0.0^2,7]tetradec-1-ene-8,14-dione, 4-(4-bromo-3-chloro-benzoyl)-14-[(4-methoxyphenyl)methyl]-4,7,9,14-tetrazatricyclo [7 0.6.0.0^2,7]pentadec-1-ene-8,15-dione, 7-(4-bromo-3-chloro-benzoyl)-2-[4-(cyclobutoxy)phenyl]-3-oxo-N-[rac-(1S)-1-phenylethyl]-6,8-dihydro-5H-imidazo [1,5-a]pyrazine-1-carboxamide, 7-(4-bromo-3-chloro-benzoyl)-2-[4-(cyclobutoxy)phenyl]-3-oxo-N-[rac-(1R)-1-phenylethyl]-6,8-dihydro-5H-imidazo [1,5-a]pyrazine-1-carboxamide, N-benzyl-7-(3,4-dichlorobenzoyl)-3-oxo-2-pyrimidin-2-yl-6,8-dihydro-5H-imidazo [1,5-a]pyrazine-1-carboxamide, 7-(4-bromo-3-chloro-benzoyl)-N-[(4-chlorophenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-2-(4-methoxyphenyl)-3-oxo-N-[[4-(trifluoromethyl)phenyl]methyl]-6,8-dihydro-5H-imidazo[1,5-a]pyrazine-1-carboxamide, 7-(4-bromo-3-chloro-benzoyl)-N-[1-(4-fluorophenyl)ethyl]-2-(4-methoxyphenyl)-3-oxo-6,8-dihydro-5H-imidazo [1,5-a]pyrazine-1-carboxamide, 7-(4-bromo-3-chloro-benzoyl)-N-[(4-isopropylphenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-N-[(2,4-dimethoxyphenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1R)-2-hydroxy-1-phenyl-ethyl]-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1R)-1-(4-bromophenyl)ethyl]-6,8-dihydro-5H-imidazo [1,5-a]pyrazine-1-carboxamide, rac-(11R)-13-benzyl-4-(4-bromo-3-chloro-benzoyl)-11-(hydroxymethyl)-4,7,9,13-tetrazatricyclo [7 0.5.0.0^2,7]tetradec-1-ene-8,14-dione, rac-(11S)-13-benzyl-4-(4-bromo-3-chloro-benzoyl)-11-(hydroxymethyl)-4,7,9,13-tetrazatricyclo [7 0.5.0.0^2,7]tetradec-1-ene-8,14-dione, 7-(4-bromo-3-chloro-benzoyl)-N-[[4-(difluoromethoxy)phenyl]methyl]-2-(4-methoxyphenyl)-3-oxo-6,8-dihydro-5H-imidazo [1,5-a]pyrazine-1-carboxamide, 7-(4-bromo-3-chloro-benzoyl)-2-(4-methoxyphenyl)-3-oxo-N-[rac-(R)-cyclopropyl(phenyl)methyl]-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1R)-1-phenylpropyl]-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1S)-1-phenylpropyl]-6,8-dihydro-5H-imidazo [1,5-a]pyrazine-1-carboxamide, 7-(4-bromo-3-chloro-benzoyl)-2-(4-methoxyphenyl)-3-oxo-N-[[3-(trifluoromethyl)phenyl] methyl]-6,8-dihydro-5H-imidazo [1,5-a]pyrazine-1-carboxamide, 7-(4-bromo-3-chloro-benzoyl)-N-[(3,5-dimethoxyphenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-N-[(2-cyanophenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-N-[(3-methoxy-2-methyl-phenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-N-[(4-isopropoxyphenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-2-(4-methoxyphenyl)-3-oxo-N-(pyrimidin-2-ylmethyl)-6,8-dihydro-5H-imidazo [1,5-a]pyrazine-1-carboxamide, 7-(4-bromo-3-chloro-benzoyl)-2-(4-methoxyphenyl)-3-oxo-N-[[4-(trifluoromethoxy)phenyl]methyl]-6,8-dihydro-5H-imidazo[1,5-a]pyrazine-1-carboxamide, rac-(2R)-2- [[7-(4-bromo-3-chloro-benzoyl)-2-(4-methoxyphenyl)-3-oxo-6,8-dihydro-5H-imidazo[1,5-a]pyrazine-1-carbonyl] amino]-2-phenyl-acetic acid, 7-(4-bromo-3-chloro-benzoyl)-2-(4-methoxyphenyl)-3-oxo-N-[rac-(1S)-2-methyl-1-phenyl-propyl]-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1R)-1-(2-fluorophenyl)ethyl]-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1S)-1-(2-fluorophenyl)ethyl]-6,8-dihydro-5H-imidazo [1,5-a]pyrazine-1-carboxamide, 7-(4-bromo-3-chloro-benzoyl)-2-(4-cyanophenyl)-N-[(4-methoxy-2-methyl-phenyl)methyl]-3-oxo-6,8-dihydro-5H-imidazo [1,5-a]pyrazine-1-carboxamide, 7-(4-bromo-3-chloro-benzoyl)-2-(4-cyanophenyl)-N-[(2-fluoro-4-methoxy-phenyl)methyl]-3-oxo-6,8-dihydro-5H-imidazo [1,5-a]pyrazine-1-carboxamide, methyl 3- [[[7-(4-bromo-3-chloro-benzoyl)-2-(4-methoxyphenyl)-3-oxo-6,8-dihydro-5H-imidazo[1,5-a]pyrazine-1-carbonyl] amino] methyl]benzoate, 7-(4-bromo-3-chloro-benzoyl)-2-(4-methoxyphenyl)-3-oxo-N-(8-quinolylmethyl)-6,8-dihydro-5H-imidazo [1,5-a]pyrazine-1-carboxamide, 7-(4-bromo-3-chloro-benzoyl)-2-(4-methoxyphenyl)-3-oxo-N-[(2-pyrazol-1-ylphenyl)methyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-phenylethyl]-6,8-dihydro-5H-imidazo [1,5-a]pyrazine-1-carboxamide, 7-(4-bromo-3-chloro-benzoyl)-2-[4-(oxetan-3-yloxy)phenyl]-3-oxo-N-[rac-(1S)-1-phenylethyl]-6,8-dihydro-5H-imidazo [1,5-a]pyrazine-1-carboxamide, 7-(4-bromo-3-chloro-benzoyl)-2-[4-(oxetan-3-yloxy)phenyl]-3-oxo-N-[rac-(1R)-1-phenylethyl]-6,8-dihydro-5H-imidazo [1,5-a]pyrazine-1-carboxamide, 7-(4-bromo-3-chloro-benzoyl)-2-(4-methoxyphenyl)-3-oxo-N-(pyrazin-2-ylmethyl)-6,8-dihydro-5H-imidazo [1,5-a]pyrazine-1-carboxamide, 7-(4-bromo-3-chloro-benzoyl)-3-oxo-N-[rac-(1R)-1-phenylethyl]-2,5,6,8-tetrahydroimidazo [1,5-a]pyrazine-1-carboxamide, 1-(5-benzyl-1,3,4-oxadiazol-2-yl)-7-(3,4-dichlorobenzoyl)-2-(4-methoxyphenyl)-6,8-dihydro-5H-imidazo [1,5-a]pyrazin-3-one, rac-(11R)-13-benzyl-4-(4-bromo-3-chloro-benzoyl)-11-hydroxy-4,7,9,13-tetrazatricyclo [7 0.5.0.0^2,7]tetradec-1-ene-8,14-dione, rac-(11S)-13-benzyl-4-(4-bromo-3-chloro-benzoyl)-11-hydroxy-4,7,9,13-tetrazatricyclo [7 0.5.0.0^2,7]tetradec-1-ene-8,14-dione, 7-(4-bromo-3-chloro-benzoyl)-2-(4-methoxyphenyl)-3-oxo-N-[rac-(S)-cyclopropyl(phenyl)methyl]-6,8-dihydro-5H-imidazo [1,5-a]pyrazine-1-carboxamide, rac-(2S)-2- [[7-(4-bromo-3-chloro-benzoyl)-2-(4-methoxyphenyl)-3-oxo-6,8-dihydro-5H-imidazo[1,5-a]pyrazine-1-carbonyl] amino]-2-phenyl-acetic acid, 7-(4-bromo-3-chloro-benzoyl)-2-(4-methoxyphenyl)-3-oxo-N-[rac-(1R)-2-methyl-1-phenyl-propyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-phenylethyl]-6,8-dihydro-5H-imidazo [1,5-a]pyrazine-1-carboxamide, 7-(4-bromo-3-chloro-benzoyl)-N-[(4-cyanophenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-N-[(2-fluorophenyl)methyl]-2-(4-methoxyphenyl)-3-oxo-6,8-dihydro-5H-imidazo [1,5-a]pyrazine-1-carboxamide, N-(1,3-benzodioxol-5-ylmethyl)-7-(4-bromo-3-chloro-benzoyl)-2-(4-methoxyphenyl)-3-oxo-6,8-dihydro-5H-imidazo [1,5-a]pyrazine-1-carboxamide, N-[[4-(2-amino-2-oxo-ethyl)phenyl]methyl]-7-(4-bromo-3-chloro-benzoyl)-2-(4-methoxyphenyl)-3-oxo-6,8-dihydro-5H-imidazo [1,5-a]pyrazine-1-carboxamide, N-benzyl-7-(4-bromo-3-chloro-benzoyl)-2-(4-isopropoxyphenyl)-3-oxo-6,8-dihydro-5H-imidazo[1,5-a]pyrazine-1-carboxamide, 7-(4-bromo-3-chloro-benzoyl)-2-(4-isopropoxyphenyl)-N-[(4-methoxyphenyl)methyl]-3-oxo-6,8-dihydro-5H-imidazo [1,5-a]pyrazine-1-carboxamide, 7-(4-bromo-3-chloro-benzoyl)-N-[(3-ethylsulfonylphenyl)methyl]-2-(4-isopropoxyphenyl)-3-oxo-6,8-dihydro-5H-imidazo [1,5-a]pyrazine-1-carboxamide, N-benzyl-7-(4-chloro-6-fluoro-1H-indole-2-carbonyl)-2-(4-methoxyphenyl)-3-oxo-6,8-dihydro-5H-imidazo [1,5-a]pyrazine-1-carboxamide, 7-(4-bromo-3-chloro-benzoyl)-3-oxo-N-[rac-(1R)-1-phenylethyl]-2,5,6,8-tetrahydroimidazo [1,5-a]pyrazine-1-carboxamide, 7-(4-bromo-3-chloro-benzoyl)-2-cyclopropyl-3-oxo-N-[rac-(1R)-1-phenylethyl]-6,8-dihydro-5H-imidazo [1,5-a]pyrazine-1-carboxamide, 7-(4-bromo-3-chloro-benzoyl)-2-cyclopropyl-3-oxo-N-[rac-(1S)-1-phenylethyl]-6,8-dihydro-5H-imidazo [1,5-a]pyrazine-1-carboxamide, 7-(4-bromo-3-chloro-benzoyl)-2-(4-methoxyphenyl)-3-oxo-N-(2-pyridylmethyl)-6,8-dihydro-5H-imidazo[1,5-a]pyrazine-1-carboxamide, 7-(4-bromo-3-chloro-benzoyl)-2-(4-methoxyphenyl)-3-oxo-N-[(6-oxo-1H-pyridin-3-yl)methyl]-6,8-dihydro-5H-imidazo[1,5-a]pyrazine-1-carboxamide, rac-(11R)-4-(4-bromo-3-chloro-benzoyl)-11-hydroxy-13-[(4-methoxyphenyl)methyl]-4,7,9,13-tetrazatricyclo [7.5.0.0^2,7]tetradec-1-ene-8,14-dione, rac-(11S)-4-(4-bromo-3-chloro-benzoyl)-11-hydroxy-13-[(4-methoxyphenyl)methyl]-4,7,9,13-tetrazatricyclo[7.5.0.0^2,7]tetradec-1-ene-8,14-dione, N-benzyl-7-(4-bromo-3-chloro-benzoyl)-3-oxo-2-phenyl-6,8-dihydro-5H-imidazo[1,5-a]pyrazine-1-carboxamide, ethyl 2-[4-[[[7-(4-bromo-3-chloro-benzoyl)-2-(4-methoxyphenyl)-3-oxo-6,8-dihydro-5H-imidazo[1,5-a]pyrazine-1-carbonyl]amino]methyl]phenyl]acetate, 7-(4-bromo-3-chloro-benzoyl)-2-(4-isopropoxyphenyl)-1-(5-phenyloxazol-2-yl)-6,8-dihydro-5H-imidazo[1,5-a]pyrazin-3-one, rac-(6R)-N-benzyl-7-(4-bromo-3-chloro-benzoyl)-2-(4-methoxyphenyl)-6-methyl-3-oxo-6,8-dihydro-5H-imidazo[1,5-a]pyrazine-1-carboxamide, rac-(6S)-N-benzyl-7-(4-bromo-3-chloro-benzoyl)-2-(4-methoxyphenyl)-6-methyl-3-oxo-6,8-dihydro-5H-imidazo[1,5-a]pyrazine-1-carboxamide, rac-(11R)-13-benzyl-4-(4-bromo-3-chloro-benzoyl)-11-fluoro-4,7,9,13-tetrazatricyclo[7.5.0.0^2,7]tetradec-1-ene-8,14-dione, rac-(11S)-13-benzyl-4-(4-bromo-3-chloro-benzoyl)-11-fluoro-4,7,9,13-tetrazatricyclo[7.5.0.0^2,7]tetradec-1-ene-8,14-dione, (11RS)-4-(4-bromo-3-chloro-benzoyl)-11-hydroxy-13-[(1R)-1-phenylethyl]-4,7,9,13-tetrazatricyclo[7.5.0.0^2,7]tetradec-1-ene-8,14-dione, (11SR)-4-(4-bromo-3-chloro-benzoyl)-11-hydroxy-13-[(1R)-1-phenylethyl]-4,7,9,13-tetrazatricyclo[7.5.0.0^2,7]tetradec-1-ene-8,14-dione, 2-[4-[[[7-(4-bromo-3-chloro-benzoyl)-2-(4-methoxyphenyl)-3-oxo-6,8-dihydro-5H-imidazo[1,5-a]pyrazine-1-carbonyl]amino]methyl]phenoxy]acetic acid, N-[[4-(2-amino-2-oxo-ethoxy)phenyl]methyl]-7-(4-bromo-3-chloro-benzoyl)-2-(4-methoxyphenyl)-3-oxo-6,8-dihydro-5H-imidazo[1,5-a]pyrazine-1-carboxamide, 7-(4-bromo-3-chloro-benzoyl)-2-(4-methoxyphenyl)-3-oxo-N-[rac-(1R)-2-amino-2-oxo-1-phenyl-ethyl]-6,8-dihydro-5H-imidazo[1,5-a]pyrazine-1-carboxamide, 7-(4-bromo-3-chloro-benzoyl)-2-(4-methoxyphenyl)-3-oxo-N-[rac-(1S)-2-amino-2-oxo-1-phenyl-ethyl]-6,8-dihydro-5H-imidazo[1,5-a]pyrazine-1-carboxamide, 7-(4-bromo-3-chloro-benzoyl)-2-(4-methoxyphenyl)-3-oxo-N-[rac-(1R)-2,2,2-trifluoro-1-phenyl-ethyl]-6,8-dihydro-5H-imidazo[1,5-a]pyrazine-1-carboxamide, 7-(4-bromo-3-chloro-benzoyl)-2-(4-methoxyphenyl)-3-oxo-N-[rac-(1S)-2,2,2-trifluoro-1-phenyl-ethyl]-6,8-dihydro-5H-imidazo[1,5-a]pyrazine-1-carboxamide, 7-(4-bromo-3-chloro-benzoyl)-N-[(2-cyclopropyl-4-methoxy-phenyl)methyl]-2-(4-methoxyphenyl)-3-oxo-6,8-dihydro-5H-imidazo[1,5-a]pyrazine-1-carboxamide, 7-(4-bromo-3-chloro-benzoyl)-N-[(4-cyano-3-methoxy-phenyl)methyl]-2-(4-isopropoxyphenyl)-3-oxo-6,8-dihydro-5H-imidazo[1,5-a]pyrazine-1-carboxamide, 7-(4-bromo-3-chloro-benzoyl)-N-[(4-cyano-2-fluoro-phenyl)methyl]-2-(4-isopropoxyphenyl)-3-oxo-6,8-dihydro-5H-imidazo[1,5-a]pyrazine-1-carboxamide, N-benzyl-7-[2-(2-chlorophenoxy)acetyl]-2-(4-isopropoxyphenyl)-3-oxo-6,8-dihydro-5H-imidazo[1,5-a]pyrazine-1-carboxamide, N-benzyl-7-(4-bromo-3-chloro-benzoyl)-2-(1H-indol-5-yl)-3-oxo-6,8-dihydro-5H-imidazo[1,5-a]pyrazine-1-carboxamide, 2-[4-[[[7-(4-bromo-3-chloro-benzoyl)-2-(4-methoxyphenyl)-3-oxo-6,8-dihydro-5H-imidazo[1,5-a]pyrazine-1-carbonyl]amino]methyl]phenyl]acetic acid, N-benzyl-[(E)-3-(2-chlorophenyl)prop-2-enoyl]-2-(4-isopropoxyphenyl)-3-oxo-6,8-dihydro-5H-imidazo [1,5-a]pyrazine-1-carboxamide, N-benzyl-7-(4-bromo-3-cyano-benzoyl)-2-(4-isopropoxyphenyl)-3-oxo-6,8-dihydro-5H-imidazo[1,5-a]pyrazine-1-carboxamide, 7-(4-bromo-3-chloro-benzoyl)-N-[(2-fluoro-4-methoxyphenyl)methyl]-2-(4-isopropoxyphenyl)-3-oxo-6,8-dihydro-5H-imidazo [1,5-a]pyrazine-1-carboxamide, N-(1H-benzimidazol-5-ylmethyl)-7-(4-bromo-3-chloro-benzoyl)-2-(4-isopropoxyphenyl)-3-oxo-6,8-dihydro-5H-imidazo [1,5-a]pyrazine-1-carboxamide, N-(benzofuran-5-ylmethyl)-7-(4-bromo-3-chloro-benzoyl)-2-(4-isopropoxyphenyl)-3-oxo-6,8-dihydro-5H-imidazo [1,5-a]pyrazine-1-carboxamide, 7-(4-bromo-3-chloro-benzoyl)-N-[[4-(hydroxymethyl)phenyl]methyl]-2-(4-isopropoxyphenyl)-3-oxo-6,8-dihydro-5H-imidazo [1,5-a]pyrazine-1-carboxamide, 7-(4-bromo-3-chloro-benzoyl)-N-[(2-carbamoylphenyl)methyl]-2-(4-isopropoxyphenyl)-3-oxo-6,8-dihydro-5H-imidazo [1,5-a]pyrazine-1-carboxamide, N-benzyl-7-(6-bromopyridine-3-carbonyl)-2-(4-isopropoxyphenyl)-3-oxo-6,8-dihydro-5H-imidazo [1,5-a]pyrazine-1-carboxamide, N-benzyl-7-(4-chlorobenzothiophene-2-carbonyl)-2-(4-isopropoxyphenyl)-3-oxo-6,8-dihydro-5H-imidazo [1,5-a]pyrazine-1-carboxamide, N-benzyl-7-(4-bromo-3-methyl-benzoyl)-2-(4-isopropoxyphenyl)-3-oxo-6,8-dihydro-5H-imidazo[1,5-a]pyrazine-1-carboxamide, N-benzyl-7-[(E)-3-(2,3-dichlorophenyl)prop-2-enoyl]-2-(4-isopropoxyphenyl)-3-oxo-6,8-dihydro-5H-imidazo [1,5-a]pyrazine-1-carboxamide, 7-(4-bromo-3-chloro-benzoyl)-2-(4-isopropoxyphenyl)-N-[(4-methylsulfonylphenyl)methyl]-3-oxo-6,8-dihydro-5H-imidazo [1,5-a]pyrazine-1-carboxamide, 7-(4-bromo-3-chloro-benzoyl)-N-[(2,4-dimethoxyphenyl)methyl]-2-(4-isopropoxyphenyl)-3-oxo-6,8-dihydro-5H-imidazo [1,5-a]pyrazine-1-carboxamide, 7-(4-bromo-3-chloro-benzoyl)-N-[(2,4-dimethoxyphenyl)methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-(8-quinolylmethyl)-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[(2-pyrazol-1-ylphenyl)methyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-(4-isopropoxyphenyl)-N-[(1-methyl-6-oxo-3-pyridyl)methyl]-3-oxo-6,8-dihydro-5H-imidazo [1,5-a]pyrazine-1-carboxamide, 7-(4-bromo-3-chloro-benzoyl)-2-(4-isopropoxyphenyl)-3-oxo-N-[rac-(1R)-1-(4-cyanophenyl)ethyl]-6,8-dihydro-5H-imidazo [1,5-a]pyrazine-1-carboxamide, 7-(4-bromo-3-chloro-benzoyl)-2-(4-isopropoxyphenyl)-3-oxo-N-[rac-(1S)-1-(4-cyanophenyl)ethyl]-6,8-dihydro-5H-imidazo [1,5-a]pyrazine-1-carboxamide, 7-(4-bromo-3-chloro-benzoyl)-2-(4-isopropoxyphenyl)-3-oxo-N-[rac-(1S)-1-(2-fluoro-4-methoxy-phenyl)ethyl]-6,8-dihydro-5H-imidazo [1,5-a]pyrazine-1-carboxamide, 7-(4-bromo-3-chloro-benzoyl)-N-[(4-cyano-2-methoxy-phenyl)methyl]-2-(4-isopropoxyphenyl)-3-oxo-6,8-dihydro-5H-imidazo [1,5-a]pyrazine-1-carboxamide, (11RS)-4-(4-bromo-3-chloro-benzoyl)-11-hydroxy-13-[(1S)-1-phenylethyl]-4,7,9,13-tetrazatricyclo [7 0.5.0.0^2,7]tetradec-1-ene-8,14-dione, (11SR)-4-(4-bromo-3-chloro-benzoyl)-11-hydroxy-13-[(1S)-1-phenylethyl]-4,7,9,13-tetrazatricyclo [7 0.5.0.0^2,7]tetradec-1-ene-8,14-dione, 13-benzyl-4-(4-bromo-3-chloro-benzoyl)spiro [4,7,9,13-tetrazatricyclo [7 0.5.0.0^2,7]tetradec-1-ene-11,3'-oxetane]-8,14-dione, N-benzyl-2-(4-isopropoxyphenyl)-3-oxo-7-[rac-(1R)-1-(4-bromo-3-chloro-phenyl)-2,2,2-trifluoro-ethyl]-6,8-dihydro-5H-imidazo [1,5-a]pyrazine-1-carboxamide, N-benzyl-2-(4-isopropoxyphenyl)-3-oxo-7-[rac-(1S)-1-(4-bromo-3-chloro-phenyl)-2,2,2-trifluoro-ethyl]-6,8-dihydro-5H-imidazo [1,5-a]pyrazine-1-carboxamide, N-benzyl-7-[(E)-3-(3,4-dichlorophenyl)prop-2-enoyl]-2-(4-isopropoxyphenyl)-3-oxo-6,8-dihydro-5H-imidazo [1,5-a]pyrazine-1-carboxamide, 7-(4-bromo-3-chloro-benzoyl)-N-[[4-(difluoromethyl)phenyl]methyl]-2-(4-isopropoxyphenyl)-3-oxo-6,8-dihydro-5H-imidazo [1,5-a]pyrazine-1-carboxamide, 7-(4-bromo-3-chloro-benzoyl)-N-[(2-fluoro-4-methoxy-phenyl)methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-(4-isopropoxyphenyl)-3-oxo-N-[rac-(1R)-1-(2-fluoro-4-methoxy-phenyl)ethyl]-6,8-dihydro-5H-imidazo [1,5-a]pyrazine-1-carboxamide, 7-(4-bromo-3-chloro-benzoyl)-N-[(4-methoxy-2-methyl-phenyl)methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-(4-methoxycyclohexyl)-3-oxo-N-[rac-(1S)-1-phenylethyl]-6,8-dihydro-5H-imidazo [1,5-a]pyrazine-1-carboxamide, 2-(benzothiophen-5-yl)-N-benzyl-7-(4-bromo-3-chloro-benzoyl)-3-oxo-6,8-dihydro-5H-imidazo[1,5-a]pyrazine-1-carboxamide, 7-(4-bromo-3-chloro-benzoyl)-N-[(4-cyano-2-methoxy-phenyl)methyl]-3-oxo-2-[4-(2,2,2-trifluoroethoxy)phenyl]-6,8-dihydro-5H-imidazo [1,5-a]pyrazine-1-carboxamide, N-benzyl-7-(4-bromo-3-chloro-benzoyl)-2-[4-(2-methoxyethoxy)phenyl]-3-oxo-6,8-dihydro-5H-imidazo [1,5-a]pyrazine-1-carboxamide, 7-(4-bromo-3-chloro-benzoyl)-N-[(2-ethyl-4-methoxy-phenyl)methyl]-2-(4-methoxyphenyl)-3-oxo-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1S)-2,2-difluoro-1-phenyl-ethyl]-6,8-dihydro-5H-imidazo [1,5-a]pyrazine-1-carboxamide, 7-(4-bromo-3-chloro-benzoyl)-2-(4-methoxyphenyl)-3-oxo-N-[rac-(1R)-2,2-difluoro-1-phenyl-ethyl]-6,8-dihydro-5H-imidazo [1,5-a]pyrazine-1-carboxamide, 7-(4-bromo-3-chloro-benzoyl)-2-(4-methoxycyclohexyl)-3-oxo-N-[rac-(1R)-1-phenylethyl]-6,8-dihydro-5H-imidazo [1,5-a]pyrazine-1-carboxamide, 7-(4-bromo-3-chloro-benzoyl)-2-(4-isopropoxyphenyl)-N-[(6-methoxybenzofuran-5-yl)methyl]-3-oxo-6,8-dihydro-5H-imidazo [1,5-a]pyrazine-1-carboxamide, N-benzyl-7-(4-bromo-3-chloro-benzoyl)-2-(2-methyl-benzofuran-6-yl)-3-oxo-6,8-dihydro-5H-imidazo [1,5-a]pyrazine-1-carboxamide, N-benzyl-7-(4-bromo-3-chloro-benzoyl)-2-(4-cyano-3-methyl-phenyl)-3-oxo-6,8-dihydro-5H-imidazo [1,5-a]pyrazine-1-carboxamide, 7-(4-bromo-3-chloro-benzoyl)-N-[(4-methoxy-2-pyrazol-1-yl-phenyl)methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-N-[(2-methoxy-6-methyl-phenyl)methyl]-3-oxo-2-[4-(2,2,2-trifluoroethoxy)phenyl]-6,8-dihydro-5H-imidazo [1,5-a]pyrazine-1-carboxamide, N-benzyl-7-(4-bromo-3-chloro-benzoyl)-2-[4-(2,2-difluoroethoxy)phenyl]-3-oxo-6,8-dihydro-5H-imidazo [1,5-a]pyrazine-1-carboxamide, N-benzyl-7-(4-bromo-3-chloro-benzoyl)-2-(1-methylindol-5-yl)-3-oxo-6,8-dihydro-5H-imidazo[1,5-a]pyrazine-1-carboxamide, 7-(4-bromo-3-chloro-benzoyl)-3-oxo-N-[rac-(1R)-1-(2-fluorophenyl)ethyl]-2-[4-(2,2,2-trifluoroethoxy)phenyl]-6,8-dihydro-5H-imidazo[1,5-a]pyrazine-1-carboxamide, 7-(4-bromo-3-chloro-benzoyl)-N-[(2-imidazol-1-ylphenyl)methyl]-3-oxo-2-[4-(2,2,2-trifluoroethoxy)phenyl]-6,8-dihydro-5H-imidazo[1,5-a]pyrazine-1-carboxamide, 7-(4-bromo-3-chloro-benzoyl)-3-oxo-N-[rac-(1S)-1-(2-fluorophenyl)ethyl]-2-[4-(2,2,2-trifluoroethoxy)phenyl]-6,8-dihydro-5H-imidazo[1,5-a]pyrazine-1-carboxamide, N-benzyl-7-(4-bromo-3-chloro-benzoyl)-2-[4-(cyanomethoxy)phenyl]-3-oxo-6,8-dihydro-5H-imidazo[1,5-a]pyrazine-1-carboxamide, 7-(4-bromo-3-chloro-benzoyl)-N-[[2-(difluoromethoxy)-4-methoxy-phenyl]methyl]-3-oxo-2-[4-(2,2,2-trifluoroethoxy)phenyl]-6,8-dihydro-5H-imidazo[1,5-a]pyrazine-1-carboxamide, 7-(4-bromo-3-chloro-benzoyl)-3-oxo-N-[(4-pyrazol-1-ylphenyl)methyl]-2-[4-(2,2,2-trifluoroethoxy)phenyl]-6,8-dihydro-5H-imidazo[1,5-a]pyrazine-1-carboxamide, 7-(4-bromo-3-chloro-benzoyl)-N-[(4-imidazol-1-ylphenyl)methyl]-3-oxo-2-[4-(2,2,2-trifluoroethoxy)phenyl]-6,8-dihydro-5H-imidazo[1,5-a]pyrazine-1-carboxamide, 1-(5-benzyl-1,3,4-oxadiazol-2-yl)-7-(4-bromo-3-chloro-benzoyl)-2-(4-isopropoxyphenyl)-6,8-dihydro-5H-imidazo[1,5-a]pyrazin-3-one, N-benzyl-7-(4-bromo-3-chloro-benzoyl)-2-(4-methylsulfanylphenyl)-3-oxo-6,8-dihydro-5H-imidazo[1,5-a]pyrazine-1-carboxamide, N-benzyl-7-(4-bromo-3-chloro-benzoyl)-3-oxo-2-(4-pyrazol-1-ylphenyl)-6,8-dihydro-5H-imidazo[1,5-a]pyrazine-1-carboxamide, N-benzyl-7-(4-bromo-3-chloro-benzoyl)-2-(4-isobutoxyphenyl)-3-oxo-6,8-dihydro-5H-imidazo[1,5-a]pyrazine-1-carboxamide, N-benzyl-7-(4-bromo-3-chloro-benzoyl)-2-[4-(2-hydroxyethoxy)phenyl]-3-oxo-6,8-dihydro-5H-imidazo [1,5-a]pyrazine-1-carboxamide, 2-[4-[1-(benzylcarbamoyl)-7-(4-bromo-3-chloro-benzoyl)-3-oxo-6,8-dihydro-5H-imidazo[1,5-a]pyrazin-2-yl]phenoxy]acetic acid, 7-(4-bromo-3-chloro-benzoyl)-2-(4-methoxyphenyl)-1-(2-pyridyl)-6,8-dihydro-5H-imidazo[1,5-a]pyrazin-3-one, N-benzyl-7-(4-bromo-3-chloro-benzoyl)-2-(3-methyl-benzofuran-5-yl)-3-oxo-6,8-dihydro-5H-imidazo[1,5-a]pyrazine-1-carboxamide, 7-(4-bromo-3-chloro-benzoyl)-3-oxo-N-(quinoxalin-5-ylmethyl)-2-[4-(2,2,2-trifluoroethoxy)phenyl]-6,8-dihydro-5H-imidazo[1,5-a]pyrazine-1-carboxamide, N-benzyl-7-(4-bromo-3-chloro-benzoyl)-2-(4-morpholinophenyl)-3-oxo-6,8-dihydro-5H-imidazo[1,5-a]pyrazine-1-carboxamide, rac-(6S)-N-benzyl-7-(4-bromo-3-chloro-benzoyl)-6-cyclopropyl-2-(4-methoxyphenyl)-3-oxo-6,8-dihydro-5H-imidazo[1,5-a]pyrazine-1-carboxamide, rac-(6R)-N-benzyl-7-(4-bromo-3-chloro-benzoyl)-6-cyclopropyl-2-(4-methoxyphenyl)-3-oxo-6,8-dihydro-5H-imidazo[1,5-a]pyrazine-1-carboxamide, 1-(4-benzyl-2-pyridyl)-7-(4-bromo-3-chloro-benzoyl)-2-(4-methoxyphenyl)-6,8-dihydro-5H-imidazo[1,5-a]pyrazin-3-one, N-benzyl-7-(4-bromo-3-chloro-benzoyl)-3-oxo-2-[4-[rac-(1R)-2,2,2-trifluoro-1-methylethoxy]phenyl]-6,8-dihydro-5H-imidazo[1,5-a]pyrazine-1-carboxamide, N-benzyl-7-(4-bromo-3-chloro-benzoyl)-3-oxo-2-[4-[rac-(1S)-2,2,2-trifluoro-1-methylethoxy]phenyl]-6,8-dihydro-5H-imidazo[1,5-a]pyrazine-1-carboxamide, 7-(4-bromo-3-chloro-benzoyl)-N-[[2-fluoro-4-(trifluoromethoxy)phenyl]methyl]-3-oxo-2-[4-(2,2,2-trifluoroethoxy)phenyl]-6,8-dihydro-5H-imidazo[1,5-a]pyrazine-1-carboxamide, 2-[4-(2-amino-2-oxo-ethoxy)phenyl]-N-benzyl-7-(4-bromo-3-chloro-benzoyl)-3-oxo-6,8-dihydro-5H-imidazo [1,5-a]pyrazine-1-carboxamide, 7-(4-bromo-3-chloro-benzoyl)-N-[[4-(difluoromethoxy)-2-fluoro-phenyl]methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-N-[(4-cyano-2-fluoro-phenyl)methyl]-3-oxo-2-[4-(2,2,2-trifluoroethoxy)phenyl]-6,8-dihydro-5H-imidazo [1,5-a]pyrazine-1-carboxamide, rac-(11R)-4-(4-bromo-3-chloro-benzoyl)-13-[(2-fluoro-4-methoxy-phenyl)methyl]-11-hydroxy-4,7,9,13-tetrazatricyclo [7 0.5.0.0^2,7]tetradec-1-ene-8,14-dione, rac-(11S)-4-(4-bromo-3-chloro-benzoyl)-13-[(2-fluoro-4-methoxy-phenyl)methyl]-11-hydroxy-4,7,9,13-tetrazatricyclo [7 0.5.0.0^2,7]tetradec-1-ene-8,14-dione, 7-(4-bromo-3-chloro-benzoyl)-2-[4-(cyclopropoxy)phenyl]-3-oxo-N-[rac-(1R)-1-[2-fluoro-4-(trifluoromethoxy)phenyl] ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-[2-fluoro-4-(trifluoromethoxy)phenyl] ethyl]-6,8-dihydro-5H-imidazo [1,5-a]pyrazine-1-carboxamide, 7-(4-bromo-3-chloro-benzoyl)-3-oxo-N-[rac-(1R)-1-[2-fluoro-4-(trifluoroethoxy)phenyl]ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1S)-1-[2-fluoro-4-(trifluoroethoxy)phenyl]ethyl]-2-[4-(2,2,2-trifluoroethoxy)phenyl]-6,8-dihydro-5H-imidazo [1,5-a]pyrazine-1-carboxamide, 4- [[[7-(4-bromo-3-chloro-benzoyl)-2-(4-isopropoxyphenyl)-3-oxo-6,8-dihydro-5H-imidazo[1,5-a]pyrazine-1-carbonyl] amino]methyl]benzoic acid, 7-(4-bromo-3-chloro-benzoyl)-N-[(6-methylbenzofuran-5-yl)methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-N-[[2-fluoro-4-(trifluoromethoxy)phenyl] methyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[[4-(difluoromethoxy)-2-fluoro-phenyl] methyl]-3-oxo-6,8-dihydro-5H-imidazo [1,5-a]pyrazine-1-carboxamide, N-benzyl-7-(4-bromo-3-chloro-benzoyl)-2-(1H-indazol-5-yl)-3-oxo-6,8-dihydro-5H-imidazo[1,5-a]pyrazine-1-carboxamide, 7-(4-bromo-3-chloro-benzoyl)-3-oxo-N-[rac-(1R)-1-(4-cyano-2-fluoro-phenyl)ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1S)-1-(4-cyano-2-fluoro-phenyl)ethyl]-2-[4-(2,2,2-trifluoroethoxy)phenyl]-6,8-dihydro-5H-imidazo [1,5-a]pyrazine-1-carboxamide, rac-(6R)-N-benzyl-7-(4-bromo-3-chloro-benzoyl)-2-[4-(cyclopropoxy)phenyl]-6-methyl-3-oxo-6,8-dihydro-5H-imidazo [1,5-a]pyrazine-1-carboxamide, rac-(6S)-N-benzyl-7-(4-bromo-3-chloro-benzoyl)-2-[4-(cyclopropoxy)phenyl]-6-methyl-3-oxo-6,8-dihydro-5H-imidazo [1,5-a]pyrazine-1-carboxamide, N-[[4-(2-amino-2-oxo-ethoxy)-2-fluoro-phenyl] methyl]-7-(4-bromo-3-chloro-benzoyl)-3-oxo-2-[4-(2,2,2-trifluoroethoxy)phenyl]-6,8-dihydro-5H-imidazo [1,5-a] pyrazine-1-carboxamide, 7-(4-bromo-3-chloro-benzoyl)-3-oxo-N-[[2-(1,2,4-triazol-1-yl)phenyl]methyl]-2-[4-(2,2,2-trifluoroethoxy) phenyl]-6,8-dihydro-5H-imidazo [1,5-a]pyrazine-1-carboxamide, 7-(4-bromo-3-chloro-benzoyl)-N-[(2-chloro-6-fluoro-phenyl)methyl]-2-[4-(cyclopropoxy)phenyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[(2,6-difluorophenyl)methyl]-3-oxo-6,8-dihydro-5H-imidazo [1,5-a]pyrazine-1-carboxamide, 7-(4-bromo-3-chloro-benzoyl)-N-[(4-cyano-2-fluoro-phenyl)methyl]-2-[4-(cyclopropoxy)phenyl]-3-oxo-6,8-dihydro-5H-imidazo [1,5-a]pyrazine-1-carboxamide, 1-(3-benzyl-2-pyridyl)-7-(4-bromo-3-chloro-benzoyl)-2-(4-methoxyphenyl)-6,8-dihydro-5H-imidazo [1,5-a] pyrazin-3-one, rac-(11R)-13-benzyl-4-(4-bromo-3-chloro-benzoyl)-11-methoxy-4,7,9,13-tetrazatricyclo [7 0.5.0.0^2,7]tetradec-1-ene-8,14-dione, rac-(11S)-13-benzyl-4-(4-bromo-3-chloro-benzoyl)-11-methoxy-4,7,9,13-tetrazatricyclo [7 0.5.0.0^2,7]tetradec-1-ene-8,14-dione, N-benzyl-7-(4-bromo-3-chloro-benzoyl)-2-[4-(methylamino)phenyl]-3-oxo-6,8-dihydro-5H-imidazo [1,5-a] pyrazine-1-carboxamide, N-benzyl-7-(4-bromo-3-chloro-benzoyl)-2-(4-imidazol-1-ylphenyl)-3-oxo-6,8-dihydro-5H-imidazo [1,5-a] pyrazine-1-carboxamide, 7-(4-bromo-3-chloro-benzoyl)-2-[4-(cyclopropoxy)phenyl]-3-oxo-N-[rac-(1R)-1-[4-(difluoromethoxy)-2-fluoro-phenyl] ethyl]-6,8-dihydro-5H-imidazo [1,5-a] pyrazine-1-carboxamide, 7-(4-bromo-3-chloro-benzoyl)-2-[4-(cyclopropoxy)phenyl]-3-oxo-N-[rac-(1S)-1-[4-(difluoromethoxy)-2-fluoro-phenyl] ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-[4-(2-amino-2-oxo-ethoxy)-2-fluoro-phenyl] ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-[4-(2-amino-2-oxo-ethoxy)-2-fluoro-phenyl] ethyl]-6,8-dihydro-5H-imidazo [1,5-a]pyrazine-1-carboxamide, 7-(4-bromo-3-chloro-benzoyl)-3-oxo-N-[rac-(1R)-1-[4-(difluoromethoxy)-2-fluoro-phenyl]ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1S)-1-[4-(difluoromethoxy)-2-fluoro-phenyl]ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1R)-1-[4-(2-amino-2-oxo-ethoxy)-2-fluoro-phenyl]ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1S)-1-[4-(2-amino-2-oxo-ethoxy)-2-fluoro-phenyl]ethyl]-2-[4-(2,2,2-trifluoroethoxy)phenyl]-6,8-dihydro-5H-imidazo [1,5-a]pyrazine-1-carboxamide, (6RS)-7-(4-bromo-3-chloro-benzoyl)-2-[4-(cyclopropoxy)phenyl]-N-[(1R)-1-(2-fluorophenyl)ethyl]-6-methyl-3-oxo-6,8-dihydro-5H-imidazo [1,5-a]pyrazine-1-carboxamide, (6SR)-7-(4-bromo-3-chloro-benzoyl)-2-[4-(cyclopropoxy)phenyl]-N-[(1R)-1-(2-fluorophenyl)ethyl]-6-methyl-3-oxo-6,8-dihydro-5H-imidazo[1,5-a]pyrazine-1-carboxamide, 7-(4-bromo-3-chloro-benzoyl)-N-[[4-(cyanomethoxy)-2-fluoro-phenyl]methyl]-2-[4-(cyclopropoxy)phenyl]-3-oxo-6,8-dihydro-5H-imidazo [1,5-a]pyrazine-1-carboxamide, N-[[4-(2-amino-2-oxo-ethoxy)-2-fluoro-phenyl] methyl]-7-(4-bromo-3-chloro-benzoyl)-2-[4-(cyclopropoxy)phenyl]-3-oxo-6,8-dihydro-5H-imidazo [1,5-a]pyrazine-1-carboxamide, 1-(5-benzylthiazol-2-yl)-7-(4-bromo-3-chloro-benzoyl)-2-(4-isopropoxyphenyl)-6,8-dihydro-5H-imidazo [1,5-a]pyrazin-3-one, 7-(4-bromo-3-chloro-benzoyl)-N-[[4-(cyanomethoxy)-2-fluoro-phenyl]methyl]-3-oxo-2-[4-(2,2,2-trifluoroethoxy)phenyl]-6,8-dihydro-5H-imidazo [1,5-a]pyrazine-1-carboxamide 7-(4-bromo-3-chloro-benzoyl)-N-[[2-(4-fluoropyrazol-1-yl)phenyl]methyl]-3-oxo-2-[4-(2,2,2-trifluoroethoxy)phenyl]-6,8-dihydro-5H-imidazo [1,5-a]pyrazine-1-carboxamide, N-[[4-(2-amino-2-oxo-ethoxy)-2-pyrazol-1-yl-phenyl]methyl]-7-(4-bromo-3-chloro-benzoyl)-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-N-[[2-fluoro-4-(oxetan-3-yloxy)phenyl]methyl]-3-oxo-2-[4-(2,2,2-trifluoroethoxy)phenyl]-6,8-dihydro-5H-imidazo [1,5-a]pyrazine-1-carboxamide, (6SR)-7-(4-bromo-3-chloro-benzoyl)-2-[4-(cyclopropoxy)phenyl]-6-methyl-3-oxo-N-[(1S)-1-phenyl-ethyl]-6,8-dihydro-5H-imidazo [1,5-a]pyrazine-1-carboxamide, (6RS)-7-(4-bromo-3-chloro-benzoyl)-2-[4-(cyclopropoxy)phenyl]-6-methyl-3-oxo-N-[(1S)-1-phenyl-ethyl]-6,8-dihydro-5H-imidazo [1,5-a]pyrazine-1-carboxamide, (6SR)-7-(4-bromo-3-chloro-benzoyl)-2-[4-(cyclopropoxy)phenyl]-6-methyl-3-oxo-N-[(1R)-1-phenyl-ethyl]-6,8-dihydro-5H-imidazo [1,5-a]pyrazine-1-carboxamide, (6RS)-7-(4-bromo-3-chloro-benzoyl)-2-[4-(cyclopropoxy)phenyl]-6-methyl-3-oxo-N-[(1R)-1-phenyl-ethyl]-6,8-dihydro-5H-imidazo [1,5-a]pyrazine-1-carboxamide, (6SR)-7-(4-bromo-3-chloro-benzoyl)-2-[4-(cyclopropoxy)phenyl]-N-[(1S)-1-(2-fluorophenyl)ethyl]-6-methyl-3-oxo-6,8-dihydro-5H-imidazo [1,5-a]pyrazine-1-carboxamide, (6RS)-7-(4-bromo-3-chloro-benzoyl)-2-[4-(cyclopropoxy)phenyl]-N-[(1S)-1-(2-fluorophenyl)ethyl]-6-methyl-3-oxo-6,8-dihydro-5H-imidazo [1,5-a]pyrazine-1-carboxamide, 7-(4-bromo-3-chloro-benzoyl)-3-oxo-N-[rac-(1S)-1-[4-(2-amino-1,1-dimethyl-2-oxo-ethoxy)-2-fluoro-phenyl] ethyl]-2-[4-(2,2,2-trifluoroethoxy)phenyl]-6,8-dihydro-5H-imidazo [ 1,5-a]pyrazine-1-carboxamide, 7-(4-bromo-3-chloro-benzoyl)-3-oxo-N-[rac-(1R)-1-[4-(2-amino-1,1-dimethyl-2-oxo-ethoxy)-2-fluoro-phenyl] ethyl]-2-[4-(2,2,2-trifluoroethoxy)phenyl]-6,8-dihydro-5H-imidazo [ 1,5-a]pyrazine-1-carboxamide, 7-(4-bromo-3-chloro-benzoyl)-2-[4-(cyclopropoxy)phenyl]-3-oxo-N-[rac-(1S)-1-[4-(2-amino-1,1-dimethyl-2-oxo-ethoxy)-2-fluoro-phenyl]ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-[4-(2-amino-1,1-dimethyl-2-oxo-ethoxy)-2-fluoro-phenyl]ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-(4-cyano-2-fluoro-phenyl)ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-(4-cyano-2-fluoro-phenyl)ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-[4-(cyanomethoxy)-2-fluoro-phenyl] ethyl]-6,8-dihydro-5H-imidazo [1,5-a] pyrazine-1-carboxamide, 7-(4-bromo-3-chloro-benzoyl)-2-[4-(cyclopropoxy)phenyl]-3-oxo-N-[rac-(1S)-1-[4-(cyanomethoxy)-2-fluoro-phenyl] ethyl]-6,8-dihydro-5H-imidazo [1,5-a] pyrazine-1-carboxamide, 7-(4-bromo-3-chloro-benzoyl)-3-oxo-N-[rac-(1R)-1-[4-(cyanomethoxy)-2-fluoro-phenyl]ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1S)-1-[4-(cyanomethoxy)-2-fluoro-phenyl]ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-[2-fluoro-4-(oxetan-3-yloxy)phenyl]ethyl]-6,8-dihydro-5H-imidazo [1,5-a] pyrazine-1-carboxamide, 7-(4-bromo-3-chloro-benzoyl)-2-[4-(cyclopropoxy)phenyl]-3-oxo-N-[rac-(1S)-1-[2-fluoro-4-(oxetan-3-yloxy)phenyl]ethyl]-6,8-dihydro-5H-imidazo [1,5-a]pyrazine-1-carboxamide, 7-(4-bromo-3-chloro-benzoyl)-3-oxo-N-[rac-(1R)-1-[2-fluoro-4-(oxetan-3-yloxy)phenyl]ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1S)-1-[2-fluoro-4-(oxetan-3-yloxy)phenyl] ethyl]-2-[4-(2,2,2-trifluoroethoxy)phenyl]-6,8-dihydro-5H-imidazo [1,5-a]pyrazine-1-carboxamide, N-benzyl-7-(4-bromo-3-chloro-benzoyl)-2-[4-(3,3-difluorocyclobutoxy)phenyl]-3-oxo-6,8-dihydro-5H-imidazo [1,5-a]pyrazine-1-carboxamide, N-benzyl-7-(4-bromo-3-chloro-benzoyl)-2-(2-chloro-4-cyano-phenyl)-3-oxo-6,8-dihydro-5H-imidazo[1,5-a]pyrazine-1-carboxamide, N-benzyl-7-(4-bromo-3-chloro-benzoyl)-3-oxo-2-[2-(trifluoromethyl)-1H-indol-5-yl]-6,8-dihydro-5H-imidazo [1,5-a]pyrazine-1-carboxamide, 7-(4-bromo-3-chloro-benzoyl)-N-[[2-fluoro-4- [rac-(1S)-2-amino-1-methyl-2-oxo-ethoxy]phenyl]methyl]-3-oxo-2-[4-(2,2,2-trifluoroethoxy)phenyl]-6,8-dihydro-5H-imidazo [ 1,5-a]pyrazine-1-carboxamide, 7-(4-bromo-3-chloro-benzoyl)-N-[[2-fluoro-4-[rac-(1R)-2-amino-1-methyl-2-oxo-ethoxy]phenyl]methyl]-3-oxo-2-[4-(2,2,2-trifluoroethoxy)phenyl]-6,8-dihydro-5H-imidazo [ 1,5-a]pyrazine-1-carboxamide, 7-(4-bromo-3-chloro-benzoyl)-2-[4-(cyclopropoxy)phenyl]-3-oxo-N-[rac-(1R)-1-[2-fluoro-4- [rac-(1R)-2-amino-1-methyl-2-oxo-ethoxy]phenyl]ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-[2-fluoro-4- [rac-(1S)-2-amino-1-methyl-2-oxo-ethoxy]phenyl]ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-[2-fluoro-4- [rac-(1R)-2-amino-1-methyl-2-oxo-ethoxy]phenyl]ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-[2-fluoro-4- [rac-(1S)-2-amino-1-methyl-2-oxo-ethoxy]phenyl]ethyl]-6,8-dihydro-5H-imidazo [1,5-a]pyrazine-1-carboxamide, 7-(4-bromo-3-chloro-benzoyl)-3-oxo-N-[rac-(1R)-1-[2-fluoro-4- [rac-(1R)-2-amino-1-methyl-2-oxo-ethoxy]phenyl] ethyl]-2-[4-(2,2,2-trifluoroethoxy)phenyl]-6,8-dihydro-5H-imidazo[1,5-a]pyrazine-1-carboxamide, 7-(4-bromo-3-chloro-benzoyl)-3-oxo-N-[rac-(1R)-1-[2-fluoro-4-[rac-(1S)-2-amino-1-methyl-2-oxo-ethoxy] phenyl] ethyl]-2-[4-(2,2,2-trifluoroethoxy)phenyl]-6,8-dihydro-5H-imidazo[1,5-a]pyrazine-1-carboxamide, 7-(4-bromo-3-chloro-benzoyl)-3-oxo-N-[rac-(1S)-1-[2-fluoro-4- [rac-(1R)-2-amino-1-methyl-2-oxo-ethoxy] phenyl] ethyl]-2-[4-(2,2,2-trifluoroethoxy)phenyl]-6,8-dihydro-5H-imidazo[1,5-a]pyrazine-1-carboxamide, 7-(4-bromo-3-chloro-benzoyl)-3-oxo-N-[rac-(1S)-1-[2-fluoro-4- [rac-(1S)-2-amino-1-methyl-2-oxo-ethoxy] phenyl] ethyl]-2-[4-(2,2,2-trifluoroethoxy)phenyl]-6,8-dihydro-5H-imidazo[1,5-a]pyrazine-1-carboxamide, 7-(4-bromo-3-chloro-benzoyl)-2-[4-(cyclopropoxy)phenyl]-N-[[2-fluoro-4-(oxetan-3-yloxy)phenyl]methyl]-3-oxo-6,8-dihydro-5H-imidazo [1,5-a]pyrazine-1-carboxamide N-benzyl-7-(4-bromo-3-chloro-benzoyl)-2-(1-methylindazol-5-yl)-3-oxo-6,8-dihydro-5H-imidazo[1,5-a]pyrazine-1-carboxamide, N-[[4-(2-amino-1,1-dimethyl-2-oxo-ethoxy)-2-fluorophenyl] methyl]-7-(4-bromo-3-chloro-benzoyl)-2-[4-(cyclopropoxy)phenyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[(2-oxazol-2-ylphenyl)methyl]-3-oxo-6,8-dihydro-5H-imidazo [1,5-a]pyrazine-1-carboxamide, N-(1H-benzimidazol-4-ylmethyl)-7-(4-bromo-3-chloro-benzoyl)-2-[4-(cyclopropoxy)phenyl]-3-oxo-6,8-dihydro-5H-imidazo [1,5-a]pyrazine-1-carboxamide, N-(1H-benzimidazol-4-ylmethyl)-7-(4-bromo-3-chloro-benzoyl)-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[[2-(2-pyridyl)phenyl]methyl]-6,8-dihydro-5H-imidazo [1,5-a]pyrazine-1-carboxamide, 7-(4-bromo-3-chloro-benzoyl)-3-oxo-N-[[2-(2-pyridyl) phenyl]methyl]-2-[4-(2,2,2-trifluoroethoxy)phenyl]-6,8-dihydro-5H-imidazo [1,5-a]pyrazine-1-carboxamide, rac-(5S,11S)-13-benzyl-4-(4-bromo-3-chloro-benzoyl)-11-fluoro-5-methyl-4,7,9,13-tetrazatricyclo [7 0.5.0.0^2,7]tetradec-1-ene-8,14-dione, rac-(5S,11R)-13-benzyl-4-(4-bromo-3-chloro-benzoyl)-11-fluoro-5-methyl-4,7,9,13-tetrazatricyclo [7 0.5.0.0^2,7]tetradec-1-ene-8,14-dione, rac-(5R,11S)-13-benzyl-4-(4-bromo-3-chloro-benzoyl)-11-fluoro-5-methyl-4,7,9,13-tetrazatricyclo [7 0.5.0.0^2,7]tetradec-1-ene-8,14-dione, rac-(5R,11R)-13-benzyl-4-(4-bromo-3-chloro-benzoyl)-11-fluoro-5-methyl-4,7,9,13-tetrazatricyclo [7 0.5.0.0^2,7]tetradec-1-ene-8,14-dione, 7-(4-bromo-3-chloro-benzoyl)-N-[(2-oxazol-2-ylphenyl) methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[(2-pyrimidin-2-ylphenyl)methyl]-6,8-dihydro-5H-imidazo [1,5-a]pyrazine-1-carboxamide, 7-(4-bromo-3-chloro-benzoyl)-3-oxo-N-[(2-pyrimidin-2-ylphenyl)methyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-[4-(2-amino-2-oxo-ethoxy)-2-pyrazol-1-yl-phenyl] ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-[4-(2-amino-2-oxo-ethoxy)-2-pyrazol-1-yl-phenyl] ethyl]-6,8-dihydro-5H-imidazo [1,5-a]pyrazine-1-carboxamide, 7-(4-bromo-3-chloro-benzoyl)-3-oxo-N-[rac-(1S)-1-[4-(2-amino-2-oxo-ethoxy)-2-pyrazol-1-yl-phenyl]ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1R)-1-[4-(2-amino-2-oxo-ethoxy)-2-pyrazol-1-yl-phenyl] ethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-quinoxalin-5-ylethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-quinoxalin-5-ylethyl]-6,8-dihydro-5H-imidazo [1,5-a]pyrazine-1-carboxamide, 7-(4-bromo-3-chloro-benzoyl)-3-oxo-N-[rac-(1S)-1-quinoxalin-5-ylethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-3-oxo-N-[rac-(1R)-1-quinoxalin-5-ylethyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-N-[(2-oxazol-4-ylphenyl)methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[(2-pyridazin-3-ylphenyl)methyl]-6,8-dihydro-5H-imidazo [1,5-a]pyrazine-1-carboxamide, 7-(4-bromo-3-chloro-benzoyl)-3-oxo-N-[(2-pyridazin-3-ylphenyl)methyl]-2-[4-(2,2,2-trifluoroethoxy)phenyl]-6,8-dihydro-5H-imidazo [1,5-a]pyrazine-1-carboxamide, 2-(2,1,3-benzoxadiazol-5-yl)-N-benzyl-7-(4-bromo-3-chloro-benzoyl)-3-oxo-6,8-dihydro-5H-imidazo [1,5-a]pyrazine-1-carboxamide, 2-[4-(azetidin-1-yl)phenyl]-N-benzyl-7-(4-bromo-3-chloro-benzoyl)-3-oxo-6,8-dihydro-5H-imidazo [1,5-a]pyrazine-1-carboxamide, N-benzyl-7-(4-bromo-3-chloro-benzoyl)-2-[4-(3,3-difluoroazetidin-1-yl)phenyl]-3-oxo-6,8-dihydro-5H-imidazo [1,5-a]pyrazine-1-carboxamide, N-benzyl-7-(4-bromo-3-chloro-benzoyl)-2-[4-(3,3-difluoropyrrolidin-1-yl)phenyl]-3-oxo-6,8-dihydro-5H-imidazo [1,5-a]pyrazine-1-carboxamide, N-benzyl-7-(4-bromo-3-chloro-benzoyl)-3-oxo-2-[4-(2,2,2-trifluoro-1,1-dimethyl-ethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-N-[[2-fluoro-4- [rac-(1S)-2-amino-1-methyl-2-oxo-ethoxy]phenyl]methyl]-3-oxo-6,8-dihydro-5H-imidazo [ 1,5-a]pyrazine-1-carboxamide, N-benzyl-7-(4-bromo-3-chloro-benzoyl)-3-oxo-2-[4-(1,2,4-triazol-1-yl)phenyl]-6,8-dihydro-5H-imidazo [1,5-a]pyrazine-1-carboxamide, N-benzyl-7-(4-bromo-3-chloro-benzoyl)-2-(4-tert-butoxyphenyl)-3-oxo-6,8-dihydro-5H-imidazo[1,5-a]pyrazine-1-carboxamide, N-benzyl-7-(4-bromo-3-chloro-benzoyl)-2-(3,3-dimethyl-2-oxo-indolin-5-yl)-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[(2-oxazol-4-ylphenyl)methyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[(1-methylbenzimidazol-4-yl)methyl]-3-oxo-6,8-dihydro-5H-imidazo [1,5-a]pyrazine-1-carboxamide, 7-(4-bromo-3-chloro-benzoyl)-N-[(1-methylbenzimidazol-4-yl)methyl]-3-oxo-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[(2-pyrazin-2-ylphenyl)methyl]-6,8-dihydro-5H-imidazo [1,5-a]pyrazine-1-carboxamide, 7-(4-bromo-3-chloro-benzoyl)-3-oxo-N-[(2-pyrazin-2-ylphenyl)methyl]-2-[4-(2,2,2-trifluoroethoxy)phenyl]-6,8-dihydro-5H-imidazo [1,5-a]pyrazine-1-carboxamide, N-benzyl-7-(4-bromo-3-chloro-benzoyl)-3-oxo-2-(2-oxo-3,4-dihydro-1H-quinolin-6-yl)-6,8-dihydro-5H-imidazo [1,5-a]pyrazine-1-carboxamide, N-benzyl-7-(4-bromo-3-chloro-benzoyl)-3-oxo-2-(3-oxo-4H-1,4-benzoxazin-7-yl)-6,8-dihydro-5H-imidazo [1,5-a]pyrazine-1-carboxamide, 7-(4-bromo-3-chloro-benzoyl)-3-oxo-2-(4-pyrazol-1-ylphenyl)-N-[rac-(1R)-1-(2-fluorophenyl)ethyl]-6,8-dihydro-5H-imidazo [1,5-a]pyrazine-1-carboxamide, 7-(4-bromo-3-chloro-benzoyl)-2-[4-(cyclopropoxy)phenyl]-N-[[2-fluoro-4- [rac-(1R)-2-amino-1-methyl-2-oxo-ethoxy]phenyl]methyl]-3-oxo-6,8-dihydro-5H-imidazo [ 1,5-a]pyrazine-1-carboxamide, 7-(4-bromo-3-chloro-benzoyl)-N-[[4-(1-hydroxy-1-methyl-ethyl)phenyl]methyl]-2-(4-isopropoxyphenyl)-3-oxo-6,8-dihydro-5H-imidazo [1,5-a]pyrazine-1-carboxamide, N-benzyl-7-(4-bromo-3-chloro-benzoyl)-2-(1H-indazol-6-yl)-3-oxo-6,8-dihydro-5H-imidazo[1,5-a]pyrazine-1-carboxamide, 7-(4-bromo-3-chloro-benzoyl)-3-oxo-2-(4-pyrazol-1-ylphenyl)-N-[rac-(1S)-1-(2-fluorophenyl)ethyl]-6,8-dihydro-5H-imidazo [1,5-a]pyrazine-1-carboxamide, N-benzyl-7-(4-bromo-3-chloro-benzoyl)-2-[4-(2,2-dimethylmorpholin-4-yl)phenyl]-3-oxo-6,8-dihydro-5H-imidazo [1,5-a]pyrazine-1-carboxamide, 7-(4-bromo-3-chloro-benzoyl)-N-[(2-methyl-1,3-benzoxazol-4-yl)methyl]-3-oxo-2-[4-(2,2,2-trifluoroethoxy)phenyl]-6,8-dihydro-5H-imidazo [1,5-a]pyrazine-1-carboxamide, N-benzyl-7-(4-bromo-3-chloro-benzoyl)-3-oxo-2-[4-(2-oxopyrrolidin-1-yl)phenyl]-6,8-dihydro-5H-imidazo [1,5-a]pyrazine-1-carboxamide, 7-(4-bromo-3-chloro-benzoyl)-3-oxo-2-(4-pyrazol-1-ylphenyl)-N-[rac-(1R)-1-(2-fluoro-4-methoxy-phenyl)ethyl]-6,8-dihydro-5H-imidazo [1,5-a]pyrazine-1-carboxamide, N-benzyl-7-(4-bromo-3-chloro-benzoyl)-3-oxo-2- [4-[rac-(2S)-2-methylmorpholin-4-yl]phenyl]-6,8-dihydro-5H-imidazo [1,5-a]pyrazine-1-carboxamide, N-benzyl-7-(4-bromo-3-chloro-benzoyl)-2-[4-(2,2-difluoro-1λ^2-fluora-8-oxa-5-azaspiro [2.5] octan-5-yl)phenyl]-3-oxo-6,8-dihydro-5H-imidazo [1,5-a]pyrazine-1-carboxamide, N-benzyl-7-(4-bromo-3-chloro-benzoyl)-3-oxo-2- [4-[rac-(2R)-2-methylmorpholin-4-yl]phenyl]-6,8-dihydro-5H-imidazo [1,5-a]pyrazine-1-carboxamide, N-benzyl-7-(4-bromo-3-chloro-benzoyl)-3-oxo-2- [4-[rac-(2S)-2-(trifluoromethyl)morpholin-4-yl]phenyl]-6,8-dihydro-5H-imidazo [1,5-a]pyrazine-1-carboxamide, N-benzyl-7-(4-bromo-3-chloro-benzoyl)-2-(2-methyl-1,3-benzoxazol-5-yl)-3-oxo-6,8-dihydro-5H-imidazo [1,5-a]pyrazine-1-carboxamide, N-benzyl-7-(4-bromo-3-chloro-benzoyl)-3-oxo-2-[4-(2-oxoazetidin-1-yl)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-(2-fluoro-4-methoxy-phenyl)ethyl]-6,8-dihydro-5H-imidazo [1,5-a]pyrazine-1-carboxamide, 7-(4-bromo-3-chloro-benzoyl)-2-[4-(cyclopropoxy)phenyl]-N-[[2-(4-fluoropyrazol-1-yl)phenyl]methyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[ [2-(1,2,4-triazol-1-yl)phenyl]methyl]-6,8-dihydro-5H-imidazo [1,5-a]pyrazine-1-carboxamide, 7-(4-bromo-3-chloro-benzoyl)-3-oxo-N-[(2-pyrimidin-4-ylphenyl)methyl]-2-[4-(2,2,2-trifluoroethoxy)phenyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[(2-pyrimidin-4-ylphenyl)methyl]-6,8-dihydro-5H-imidazo [1,5-a]pyrazine-1-carboxamide, 7-(4-bromo-3-chloro-benzoyl)-N-[ [2-(1H-imidazol-2-yl)phenyl]methyl]-3-oxo-2-[4-(2,2,2-trifluoroethoxy)phenyl]-6,8-dihydro-5H-imidazo [1,5-a]pyrazine-1-carboxamide, 7-(4-bromo-3-cyano-benzoyl)-3-oxo-2-(4-pyrazol-1-ylphenyl)-N-[(2-pyrimidin-2-ylphenyl)methyl]-6,8-dihydro-5H-imidazo [1,5-a]pyrazine-1-carboxamide, N-benzyl-7-(4-bromo-3-chloro-benzoyl)-2-[4-(4-fluoropyrazol-1-yl)phenyl]-3-oxo-6,8-dihydro-5H-imidazo [1,5-a]pyrazine-1-carboxamide, N-[[4-(2-amino-1,1-dimethyl-2-oxo-ethoxy)-2-fluorophenyl]methyl]-7-(4-bromo-3-chloro-benzoyl)-3-oxo-2-[4-(2,2,2-trifluoroethoxy)phenyl]-6,8-dihydro-5H-imidazo [ 1,5-a]pyrazine-1-carboxamide, 7-(4-bromo-3-chloro-benzoyl)-3-oxo-2-(4-pyrazol-1-ylphenyl)-N-[(2-pyrimidin-2-ylphenyl)methyl]-6,8-dihydro-5H-imidazo [1,5-a]pyrazine-1-carboxamide, N-benzyl-7-(4-bromo-3-chloro-benzoyl)-2-[4-(1H-imidazol-2-yl)phenyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[(3-oxo-4H-1,4-benzoxazin-6-yl)methyl]-6,8-dihydro-5H-imidazo [1,5-a]pyrazine-1-carboxamide, 7-(4-bromo-3-cyano-benzoyl)-2-[4-(cyclopropoxy)phenyl]-3-oxo-N-[(2-pyrimidin-2-ylphenyl)methyl]-6,8-dihydro-5H-imidazo [1,5-a]pyrazine-1-carboxamide, 7-(4-bromo-3-cyano-benzoyl)-2-[4-(cyclopropoxy)phenyl]-N-[(2-oxazol-2-ylphenyl)methyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[[2-(1,3,4-oxadiazol-2-yl)phenyl]methyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[(2-fluoro-6-pyrazol-1-yl-phenyl)methyl]-3-oxo-6,8-dihydro-5H-imidazo [1,5-a]pyrazine-1-carboxamide, (6SR)-7-(4-bromo-3-chloro-benzoyl)-2-[4-(cyclopropoxy)phenyl]-N-[(1S)-1-(4-methoxyphenyl)ethyl]-6-methyl-3-oxo-6,8-dihydro-5H-imidazo [1,5-a]pyrazine-1-carboxamide, (6RS)-7-(4-bromo-3-chloro-benzoyl)-2-[4-(cyclopropoxy)phenyl]-N-[(1S)-1-(4-methoxyphenyl)ethyl]-6-methyl-3-oxo-6,8-dihydro-5H-imidazo [1,5-a]pyrazine-1-carboxamide, rac-(6S)-7-(4-bromo-3-chloro-benzoyl)-2-[4-(cyclopropoxy)phenyl]-6-methyl-3-oxo-N-[(2-pyrazol-1-ylphenyl)methyl]-6,8-dihydro-5H-imidazo [1,5-a]pyrazine-1-carboxamide, rac-(6R)-7-(4-bromo-3-chloro-benzoyl)-2-[4-(cyclopropoxy)phenyl]-6-methyl-3-oxo-N-[(2-pyrazol-1-ylphenyl)methyl]-6,8-dihydro-5H-imidazo [1,5-a]pyrazine-1-carboxamide, rac-(6S)-7-(4-bromo-3-chloro-benzoyl)-2-[4-(cyclopropoxy)phenyl]-N-[[2-(4-fluoropyrazol-1-yl)phenyl]methyl]-6-methyl-3-oxo-6,8-dihydro-5H-imidazo [ 1,5-a]pyrazine-1-carboxamide, rac-(6R)-7-(4-bromo-3-chloro-benzoyl)-2-[4-(cyclopropoxy)phenyl]-N-[[2-(4-fluoropyrazol-1-yl)phenyl]methyl]-6-methyl-3-oxo-6,8-dihydro-5H-imidazo [ 1,5-a]pyrazine-1-carboxamide, 7-(4-bromo-3-chloro-benzoyl)-N-[(1S)-1-(4-methoxyphenyl)ethyl]-3-oxo-2-(4-pyrazol-1-ylphenyl)-6,8-dihydro-5H-imidazo [1,5-a]pyrazine-1-carboxamide, 7-(4-bromo-3-chloro-benzoyl)-2-[4-(cyclopropoxy)phenyl]-N-[(1S)-1-(4-methoxyphenyl)ethyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[[2-(1H-imidazol-2-yl)phenyl]methyl]-3-oxo-6,8-dihydro-5H-imidazo [1,5-a]pyrazine-1-carboxamide, 7-(4-bromo-3-cyano-benzoyl)-2-[4-(cyclopropoxy)phenyl]-3-oxo-N-[(2-pyridazin-3-ylphenyl)methyl]-6,8-dihydro-5H-imidazo [1,5-a]pyrazine-1-carboxamide, N-benzyl-7-(4-bromo-5-chloro-2-fluoro-benzoyl)-2-[4-(cyclopropoxy)phenyl]-3-oxo-6,8-dihydro-5H-imidazo [1,5-a]pyrazine-1-carboxamide, rac-(6R)-7-(4-bromo-3-chloro-benzoyl)-2-[4-(cyclopropoxy)phenyl]-6-methyl-3-oxo-N-[ [2-(1,2,4-triazol-1-yl)phenyl]methyl]-6,8-dihydro-5H-imidazo [ 1,5-a]pyrazine-1-carboxamide, rac-(6S)-7-(4-bromo-3-chloro-benzoyl)-2-[4-(cyclopropoxy)phenyl]-6-methyl-3-oxo-N-[ [2-(1,2,4-triazol-1-yl)phenyl]methyl]-6,8-dihydro-5H-imidazo [1,5-a]pyrazine-1-carboxamide, (6RS)-7-(4-bromo-3-chloro-benzoyl)-2-[4-(cyclopropoxy)phenyl]-N-[(1R)-1-(4-methoxyphenyl)ethyl]-6-methyl-3-oxo-6,8-dihydro-5H-imidazo [1,5-a]pyrazine-1-carboxamide, (6SR)-7-(4-bromo-3-chloro-benzoyl)-2-[4-(cyclopropoxy)phenyl]-N-[(1R)-1-(4-methoxyphenyl)ethyl]-6-methyl-3-oxo-6,8-dihydro-5H-imidazo [1,5-a]pyrazine-1-carboxamide, rac-(6R)-7-(4-bromo-3-cyano-benzoyl)-2-[4-(cyclopropoxy)phenyl]-6-methyl-3-oxo-N-[(2-pyrimidin-2-ylphenyl)methyl]-6,8-dihydro-5H-imidazo [1,5-a]pyrazine-1-carboxamide, rac-(6S)-7-(4-bromo-3-cyano-benzoyl)-2-[4-(cyclopropoxy)phenyl]-6-methyl-3-oxo-N-[(2-pyrimidin-2-ylphenyl)methyl]-6,8-dihydro-5H-imidazo [1,5-a]pyrazine-1-carboxamide, 7-(4-bromo-3-chloro-benzoyl)-2-[4-(cyclopropoxy)phenyl]-N-[(1R)-1-(4-methoxyphenyl)ethyl]-3-oxo-6,8-dihydro-5H-imidazo [1,5-a]pyrazine-1-carboxamide, 7-(4-bromo-3-chloro-benzoyl)-N-[(1R)-1-(4-methoxyphenyl)ethyl]-3-oxo-2-(4-pyrazol-1-ylphenyl)-6,8-dihydro-5H-imidazo [1,5-a]pyrazine-1-carboxamide, N-benzyl-7-(4-bromo-3-chloro-benzoyl)-2-[4-(3-methylpyrazol-1-yl)phenyl]-3-oxo-6,8-dihydro-5H-imidazo [1,5-a]pyrazine-1-carboxamide, N-benzyl-7-(4-bromo-3-chloro-benzoyl)-2-[4-(5-methylpyrazol-1-yl)phenyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[(2-pyrazol-1-ylphenyl)methyl]-6,8-dihydro-5H-imidazo [1,5-a]pyrazine-1-carboxamide, 7-(4-bromo-3-chloro-benzoyl)-N-[(6-fluoroquinoxalin-5-yl)methyl]-3-oxo-2-(4-pyrazol-1-ylphenyl)-6,8-dihydro-5H-imidazo [1,5-a]pyrazine-1-carboxamide, 7-(4-bromo-3-chloro-benzoyl)-N-[(2-fluoro-4-methoxyphenyl)methyl]-3-oxo-2-(4-pyrazol-1-ylphenyl)-6,8-dihydro-5H-imidazo [1,5-a]pyrazine-1-carboxamide, 7-(4-bromo-3-chloro-benzoyl)-2-[4-(cyclopropoxy)phenyl]-N-[(2-fluoro-4-methoxy-phenyl)methyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[(6-fluoroquinoxalin-5-yl)methyl]-3-oxo-6,8-dihydro-5H-imidazo [1,5-a]pyrazine-1-carboxamide, N-benzyl-7-(4-bromo-3-chloro-2-methyl-benzoyl)-2-[4-(cyclopropoxy)phenyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[ [2-(1,2,4-triazin-3-yl)phenyl] methyl]-6,8-dihydro-5H-imidazo [1,5-a]pyrazine-1-carboxamide, 7-(4-bromo-3-chloro-benzoyl)-2-[4-(cyclopropoxy)phenyl]-N-[[2-(3-methyl-2-pyridyl)phenyl]methyl]-3-oxo-6,8-dihydro-5H-imidazo [1,5-a]pyrazine-1-carboxamide, 7-(4-bromo-3-chloro-benzoyl)-2-[4-(cyclopropoxy)phenyl]-N-[[2-(3-fluoro-2-pyridyl)phenyl]methyl]-3-oxo-6,8-dihydro-5H-imidazo [1,5-a]pyrazine-1-carboxamide, (6RS)-7-(4-bromo-3-chloro-benzoyl)-6-methyl-3-oxo-N-[(1R)-1-phenylethyl]-2-(4-pyrazol-1-ylphenyl)-6,8-dihydro-5H-imidazo [1,5-a]pyrazine-1-carboxamide, (6SR)-7-(4-bromo-3-chloro-benzoyl)-6-methyl-3-oxo-N-[(1R)-1-phenylethyl]-2-(4-pyrazol-1-ylphenyl)-6,8-dihydro-5H-imidazo [1,5-a]pyrazine-1-carboxamide, rac-(6R)-7-(4-bromo-3-chloro-benzoyl)-6-methyl-3-oxo-2-(4-pyrazol-1-ylphenyl)-N-[(2-pyrimidin-2-ylphenyl)methyl]-6,8-dihydro-5H-imidazo [1,5-a]pyrazine-1-carboxamide, rac-(6S)-7-(4-bromo-3-chloro-benzoyl)-6-methyl-3-oxo-2-(4-pyrazol-1-ylphenyl)-N-[(2-pyrimidin-2-ylphenyl)methyl]-6,8-dihydro-5H-imidazo [1,5-a]pyrazine-1-carboxamide, rac-(6R)-7-(4-bromo-3-cyano-benzoyl)-6-methyl-3-oxo-2-(4-pyrazol-1-ylphenyl)-N-[(2-pyrimidin-2-ylphenyl)methyl]-6,8-dihydro-5H-imidazo [1,5-a]pyrazine-1-carboxamide, rac-(6S)-7-(4-bromo-3-cyano-benzoyl)-6-methyl-3-oxo-2-(4-pyrazol-1-ylphenyl)-N-[(2-pyrimidin-2-ylphenyl)methyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-[2-(1,2,4-triazol-1-yl)phenyl]ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-[2-(1,2,4-triazol-1-yl)phenyl] ethyl]-6,8-dihydro-5H-imidazo [1,5-a]pyrazine-1-carboxamide, 7-(4-bromo-3-chloro-benzoyl)-3-oxo-2-(4-pyrazol-1-ylphenyl)-N-[rac-(1R)-1-[2-(1,2,4-triazol-1-yl)phenyl]ethyl]-6,8-dihydro-5H-imidazo [1,5-a]pyrazine-1-carboxamide, 7-(4-bromo-3-chloro-benzoyl)-3-oxo-2-(4-pyrazol-1-ylphenyl)-N-[rac-(1S)-1-[2-(1,2,4-triazol-1-yl)phenyl]ethyl]-6,8-dihydro-5H-imidazo [1,5-a]pyrazine-1-carboxamide, (6R)-7-(4-bromo-3-chloro-benzoyl)-N-[(1R)-1-(4-methoxyphenyl)ethyl]-6-methyl-3-oxo-2-(4-pyrazol-1-ylphenyl)-6,8-dihydro-5H-imidazo [1,5-a]pyrazine-1-carboxamide, (6SR)-7-(4-bromo-3-chloro-benzoyl)-N-[(1R)-1-(4-methoxyphenyl)ethyl]-6-methyl-3-oxo-2-(4-pyrazol-1-ylphenyl)-6,8-dihydro-5H-imidazo [1,5-a]pyrazine-1-carboxamide, (6RS)-7-(4-bromo-3-chloro-benzoyl)-N-[(1S)-1-(4-methoxyphenyl)ethyl]-6-methyl-3-oxo-2-(4-pyrazol-1-ylphenyl)-6,8-dihydro-5H-imidazo [1,5-a]pyrazine-1-carboxamide, (6SR)-7-(4-bromo-3-chloro-benzoyl)-N-[(1S)-1-(4-methoxyphenyl)ethyl]-6-methyl-3-oxo-2-(4-pyrazol-1-ylphenyl)-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1R)-1-(2-pyrazol-1-ylphenyl)ethyl]-6,8-dihydro-5H-imidazo [1,5-a]pyrazine-1-carboxamide, 7-(4-bromo-3-chloro-benzoyl)-2-[4-(cyclopropoxy)phenyl]-3-oxo-N-[rac-(1S)-1-(2-pyrazol-1-ylphenyl)ethyl]-6,8-dihydro-5H-imidazo [1,5-a]pyrazine-1-carboxamide, 7-(4-bromo-3-chloro-benzoyl)-3-oxo-2-(4-pyrazol-1-ylphenyl)-N-[rac-(1R)-1-(2-pyrazol-1-ylphenyl)ethyl]-6,8-dihydro-5H-imidazo [1,5-a]pyrazine-1-carboxamide, 7-(4-bromo-3-chloro-benzoyl)-3-oxo-2-(4-pyrazol-1-ylphenyl)-N-[rac-(1S)-1-(2-pyrazol-1-ylphenyl)ethyl]-6,8-dihydro-5H-imidazo [1,5-a]pyrazine-1-carboxamide, N-(3-chloro-4-fluorophenyl)-6,12-dioxo-1,3,4,8,9,10,11,12-octahydro-2H,6H-pyrazino [1',2':3,4]imidazo [1,5-a] [1,4]diazepine-2-carboxamide, N-(3-chloro-4-fluorophenyl)-11-methyl-6,12-dioxo-1,3,4,8,9,10,11,12-octahydro-2H,6H-pyrazino [1',2':3,4] imidazo [1,5-a] [1,4]diazepine-2-carboxamide, 11-benzyl-N-(3-chloro-4-fluorophenyl)-6,12-dioxo-1,3,4,8,9,10,11,12-octahydro-2H,6H-pyrazino [1',2':3,4] imidazo [1,5-a] [1,4]diazepine-2-carboxamide, N-(3-chloro-4-fluorophenyl)-11-(4-methoxybenzyl)-6,12-dioxo-1,3,4,8,9,10,11,12-octahydro-2H,6H-pyrazino [1',2':3,4]imidazo [1,5-a] [1,4] diazepine-2-carboxamide, 4-(4-bromobenzoyl)-4,7,9,13-tetraazatricyclo [7 0.5 0.0.0ˆ[2,7]] tetradec-1-ene-8,14-dione, 2-(4-bromo-3-fluorobenzoyl)-1,2,3,4,8,9,10,11-octahydro-6H,12H-pyrazino [1',2':3,4]imidazo [1,5-a] [1,4] diazepine-6,12-dione, 2-(4-bromo-3-chlorobenzoyl)-1,2,3,4,8,9,10,11-octahydro-6H,12H-pyrazino [1',2':3,4]imidazo [1,5-a] [1,4] diazepine-6,12-dione, 2-(4-bromo-3-chlorobenzoyl)-11-methyl-1,2,3,4,8,9,10,11-octahydro-6H,12H-pyrazino [1',2':3,4]imidazo [1,5-a] [1,4]diazepine-6,12-dione, 2-(4-bromo-3-chlorobenzoyl)-11-(4-methoxybenzyl)-1,2,3,4,8,9,10,11-octahydro-6H,12H-pyrazino [1',2':3,4] imidazo [1,5-a] [1,4]diazepine-6,12-dione, $N^7$-(3-chloro-4-fluorophenyl)-3-oxo-2-phenyl-N1-(propan-2-yl)-2H,3H,5H,6H,7H,8H-imidazo[1,5-a]pyrazine-1,7-dicarboxamide, $N^7$-(3-chloro-4-fluorophenyl)-N1-[(4-methoxyphenyl)methyl]-3-oxo-2-phenyl-2H,3H,5H,6H,7H,8H-imidazo [1,5-a]pyrazine-1,7-dicarboxamide, 7-(4-bromo-3-chlorobenzoyl)-3-oxo-2-phenyl-N-(propan-2-yl)-2H,3H,5H,6H,7H,8H-imidazo[1,5-a]pyrazine-1-carboxamide, 7-(4-bromo-3-chlorobenzoyl)-N-[(4-methoxyphenyl)methyl]-3-oxo-2-phenyl-2H,3H,5H,6H,7H,8H-imidazo [1,5-a]pyrazine-1-carboxamide, 2-benzyl-7-(4-bromo-3-chlorobenzoyl)-N-[(4-methoxyphenyl)methyl]-3-oxo-2H,3H,5H,6H,7H,8H-imidazo [1,5-a]pyrazine-1-carboxamide, 7-(4-bromo-3-chlorobenzoyl)-N-[(4-methoxyphenyl)methyl]-3-oxo-2-(2-phenylethyl)-5H,6H,8H-imidazo[1,5-a]pyrazine-1-carboxamide and 13-benzyl-4-(4-bromo-3-chlorobenzoyl)-11-fluoro-4,7,9,13-tetraazatricyclo [7 0.5 0.0.0^[2,7]] tetradec-1-ene-8,14-dione, or a pharmaceutically acceptable salt of any of the foregoing.

26. A pharmaceutical composition comprising an effective amount of a compound of claim 1, or a pharmaceutically acceptable salt thereof, and excipient.

27. A method for treating hepatitis B in a subject comprising administering to the subject in need thereof an effective amount of a compound of claim 1, or a pharmaceutically acceptable salt thereof, suffering from hepatitis B.

28. The method of claim 27 further comprising treating hepatitis D in a subject suffering from hepatitis D.

29. The method of claim 27, further comprising administering an additional agent selected from the group consisting of recombinant interferon alpha 2b, IFN-α, PEG-IFN-α-2a, lamivudine, telbivudine, adefovir dipivoxil, clevudine, entecavir, tenofovir alafenamide and tenofovir disoproxil.

30. The compound of claim 1, wherein $Z^1$ is —NH—C(=O)—.

* * * * *